US009684001B2

(12) United States Patent
Ralhan et al.

(10) Patent No.: US 9,684,001 B2
(45) Date of Patent: Jun. 20, 2017

(54) BIOMARKERS FOR HEAD-AND-NECK CANCERS AND PRECANCERS

(71) Applicants: Ranju Ralhan, Thornhill (CA); Paul G. Walfish, Toronto (CA)

(72) Inventors: Ranju Ralhan, Thornhill (CA); Paul G. Walfish, Toronto (CA)

( * ) Notice: Subject to any disclaimer, the term of this patent is extended or adjusted under 35 U.S.C. 154(b) by 0 days.

(21) Appl. No.: 14/028,287

(22) Filed: Sep. 16, 2013

(65) Prior Publication Data

US 2014/0080138 A1    Mar. 20, 2014

Related U.S. Application Data

(63) Continuation-in-part of application No. 12/866,567, filed as application No. PCT/CA2009/000154 on Feb. 6, 2009, now Pat. No. 8,921,053.

(51) Int. Cl.
*G01N 33/68* (2006.01)
*G01N 33/574* (2006.01)

(52) U.S. Cl.
CPC ... *G01N 33/6893* (2013.01); *G01N 33/57407* (2013.01); *G01N 2333/4727* (2013.01); *G01N 2333/5759* (2013.01)

(58) Field of Classification Search
CPC ........................................................ A61K 39/00
See application file for complete search history.

(56) References Cited

U.S. PATENT DOCUMENTS

| | | |
|---|---|---|
| 2007/0264644 A1 | 11/2007 | Showe |
| 2008/0226554 A1 | 9/2008 | Colgan |
| 2010/0172838 A1 | 7/2010 | Siu |

FOREIGN PATENT DOCUMENTS

| | | |
|---|---|---|
| WO | WO 2007/038402 | 4/2007 |
| WO | WO 2008/096374 | 8/2008 |

OTHER PUBLICATIONS

Tockman et al (Cancer Res., 1992, 52:2711s-2718s).*
Banerjee et al (Molecular Cancer Therapeutics, 2005, 4: 865-875).*
Bloching et al (Oral Oncology, 2000, 36: 550-555).*
Tripathi et al (PLoS One, 2011, 6(5): e19213, pp. 1-10).*
Tripathi et al (PLoS One, 2010, 5(8): e11939, pp. 1-10).*
Arora et al., "Identification of differentially expressed genes in oral squamous cell carcinoma", Molecular Carcinogenesis, 42(2):97-108 (Feb. 2005).
De Bree et al., "Clinical imaging of head and neck cancer with technetium-99m-labeled monoclonal antibody E48 IgG or F(ab')-2", Journal of Nuclear Medicine, 35(5):775-83 (May 1994).
Koike, "Identification of differentially expressed proteins in oral squamous cell carcinoma using a global proteomic approach", International Journal of Oncology, 27(1):59-67 (Jul. 2005).

Lin et al., "Chromosome 3q29 and 8q22.3 amplifications in head and neck squamous cell carcinoma (HNSCC) imply the roles of transferring receptor (Tfr) and 14-3-3 zeta in HNSCC tumorigenesis", Proceedings of the American Association for Cancer Research Annual Meeting: 48:269 (Apr. 2007).
Matta et al., "Over-expression of 14-3-3 zeta is an early event in oral cancer", BMC Cancer, 7(1):169 (Sep. 2007).
Roesch-Ely, "Proteomic analysis reveals successive aberrations in protein expression from healthy mucosa to invasive head and neck cancer", Oncogene, 26(1):54-64 (Jan. 4, 2007).
Sudha, "Global proteomic analysis distinguishes biologic differences in head and neck squamous carcinoma", Laboratory Investigations, 87(8):775-766 (Aug. 2007).
Tockman et al.. "Considerations in Bringing a Cancer Biomarker to Clinical Application", Cancer Res., 1992, 52:2711s-2718s.
Zhou et al., "Reciprocal Negative Regulation between S100A7/psoriasin and beta-catenin signaling plays an important role in tumor progession of squamous cell carcinoma of oral cavity", Oncogene, 2008, 27(25): Abstract.
Alberts et al., Molecular Biology of the Cell, 3rd Edition, 1994, p. 465.
Greenbaum et al., "Comparing protein abundance and mRNA expression levels on a genomic scale", Genome Biology, 2003, vol. 4, issue 9, pp. 117.1-117.8.
Emberley et al., "Psoriasin (S100A7) Expression is Associated with Poor Outcome in Estrogen Receptor-negative Invasive Breast Cancer", Clin Cancer Res. 2003, 9:2627-2631.
Emberley et al., "S100A7 (Psoriasin) Expression is Associated with Aggressive Features and Alteration of Jab1 in Ductal Carcinoma in situ of the Breast", Breast Cancer Res. 2004, 6 R308-R315.
Kaur et al., "S100A7 Overexpression is a Predictive Marker for High Risk of Malignant Transformation in Oral Dysplasia", International Journal of Cancer, 134, 1379-1388 (2014).
PCT International Search Report for PCT/CA2009/00154 dated Jun. 3, 2009.
Supplementary European Search Report dated Aug. 4, 2011 issued in corresponding EP patent application No. 09707708.
Fukuzawa, H. et al, "Transcription promoter activity of the human S100A7 gene in oral squamous cell carcinoma cell lines", Biochimica et Biophysica Acta . Gene Structure and Expression, Elsevier, Amsterdam, NL, vol. 1759, No. 3-4, p. 171-176.

(Continued)

*Primary Examiner* — Sean Aeder
(74) *Attorney, Agent, or Firm* — Santosh K. Chari; Blake, Cassels & Graydon LLP

(57) ABSTRACT

The invention provides markers and methods for detecting head-and-neck precancers, (including OPLs), cancers and related disease conditions in a subject. The invention also provides localization and imaging methods for head-and-neck precancers (including OPLs) and cancers, along with kits for carrying out methods of the invention. The invention further provides therapeutic applications for head-and-neck precancers (including OPLs) and cancers which employ head-and-neck precancer and cancer markers, and binding agents for the markers. Methods of identifying a subject having oral dysplasia that is at high risk of malignant transformation are provided.

6 Claims, 42 Drawing Sheets

(56) References Cited

OTHER PUBLICATIONS

Ralhan, R. et al, "Discovery and Verification of Head-and-neck Cancer Biomarkers by Differential Protein Expression Analysis Using iTRAQ Labeling, Multidimensional Liquid Chromatography, and Tandem Mass Spectrometry", Molecular & Cellular Proteomics, vol. 7, No. 6, p. 1162-1173.

Noemi Moubayed et al, "Psoriasin (S100A7) is significantly up-regulated in human epithelial skin tumours", Journal of Cancer Research and Clinical Oncology, Springer, Berlin, DE, vol. 133, No. 4, p. 253-261.

European Search Report dated Oct. 26, 2015 issued in corresponding EP patent application No. 15169256.

Frasor et al., "Gene expression preferentially regulated by tamoxifen in breast cancer cells and correlations with clinical outcome", Cancer Res., 66(14), pp. 7334-7340, Jul. 15, 2006.

\* cited by examiner (SEQ ID NO: 376)

| Residue | b | y |
|---|---|---|
| A | 216.1466 | 1647.8064 |
| A | 287.1836 | 1432.6872 |
| E | 416.2252 | 1361.6301 |
| E | 545.2688 | 1232.5875 |
| E | 674.3113 | 1103.5449 |
| D | 789.3383 | 974.5023 |
| E | 918.3809 | 859.4754 |
| A | 989.4180 | 730.4328 |
| D | 1104.4449 | 659.3957 |
| P | 1201.4977 | 544.3687 |
| K[IT4] | 1473.6947 | 447.3160 |
| R | 1629.7958 | 175.1190 |

FIGURE 19B

| Residue | b | y |
|---|---|---|
| V | 244.1778 | 1124.5969 |
| G | 301.1992 | |
| Y | 464.2625 | 824.4950 |
| V | 563.3310 | |
| S | 650.3630 | |
| G | 707.3845 | |
| W | 893.4638 | |
| G | 950.4852 | |
| R | 1106.5863 | |

FIGURE 19C (A) (i) Mild dysplasia (ii) Moderate Dysplasia (iii) Severe Dysplasia (B)

(a)

(b)

SEQUENCE LISTING

<160> NUMBER OF SEQ ID NOS: 763

<210> SEQ ID NO 1
<211> LENGTH: 146
<212> TYPE: PRT
<213> ORGANISM: HUMAN

<400> SEQUENCE: 1

Met Ala Gly Glu Leu Thr Pro Glu Glu Ala Gln Tyr Lys Lys Ala
1               5                   10                  15

Phe Ser Ala Val Asp Thr Asp Gly Asn Gly Thr Ile Asn Ala Gln Glu
                20                  25                  30

Leu Gly Ala Ala Leu Lys Ala Thr Gly Lys Asn Leu Ser Glu Ala Gln
            35                  40                  45

Leu Arg Lys Leu Ile Ser Glu Val Asp Ser Asp Gly Asp Gly Glu Ile
        50                  55                  60

Ser Phe Gln Glu Phe Leu Thr Ala Ala Arg Lys Ala Arg Ala Gly Leu
65                  70                  75                  80

Glu Asp Leu Gln Val Ala Phe Arg Ala Phe Asp Gln Asp Gly Asp Gly
                85                  90                  95

His Ile Thr Val Asp Glu Leu Arg Arg Ala Met Ala Gly Leu Gly Gln
                100                 105                 110

Pro Leu Pro Gln Glu Glu Leu Asp Ala Met Ile Arg Glu Ala Asp Val
            115                 120                 125

Asp Gln Asp Gly Arg Val Asn Tyr Glu Glu Phe Ala Arg Met Leu Ala
        130                 135                 140

Gln Glu
145

<210> SEQ ID NO 2
<211> LENGTH: 1689
<212> TYPE: PRT
<213> ORGANISM: HUMAN

<400> SEQUENCE: 2

Met Gly Ser Lys Arg Arg Arg Ala Thr Ser Pro Ser Ser Ser Val Ser
1               5                   10                  15

Gly Asp Phe Asp Asp Gly His His Ser Val Ser Thr Pro Gly Pro Ser
                20                  25                  30

Arg Lys Arg Arg Arg Leu Ser Asn Leu Pro Thr Val Asp Pro Ile Ala
            35                  40                  45

```
Val Cys His Glu Leu Tyr Asn Thr Ile Arg Asp Tyr Lys Asp Glu Gln
     50                  55                  60
Gly Arg Leu Leu Cys Glu Leu Phe Ile Arg Ala Pro Lys Arg Arg Asn
 65                  70                  75                  80
Gln Pro Asp Tyr Tyr Glu Val Val Ser Gln Pro Ile Asp Leu Met Lys
                     85                  90                  95
Ile Gln Gln Lys Leu Lys Met Glu Glu Tyr Asp Asp Val Asn Leu Leu
                100                 105                 110
Thr Ala Asp Phe Gln Leu Leu Phe Asn Asn Ala Lys Ser Tyr Tyr Lys
                115                 120                 125
Pro Asp Ser Pro Glu Tyr Lys Ala Ala Cys Lys Leu Trp Asp Leu Tyr
130                 135                 140
Leu Arg Thr Arg Asn Glu Phe Val Gln Lys Gly Glu Ala Asp Asp Glu
145                 150                 155                 160
Asp Asp Asp Glu Asp Gly Gln Asp Asn Gln Gly Thr Val Thr Glu Gly
                165                 170                 175
Ser Ser Pro Ala Tyr Leu Lys Glu Ile Leu Glu Gln Leu Leu Glu Ala
                180                 185                 190
Ile Val Val Ala Thr Asn Pro Ser Gly Arg Leu Ile Ser Glu Leu Phe
                195                 200                 205
Gln Lys Leu Pro Ser Lys Val Gln Tyr Pro Asp Tyr Tyr Ala Ile Ile
                210                 215                 220
Lys Glu Pro Ile Asp Leu Lys Thr Ile Ala Gln Arg Ile Gln Asn Gly
225                 230                 235                 240
Ser Tyr Lys Ser Ile His Ala Met Ala Lys Asp Ile Asp Leu Leu Ala
                245                 250                 255
Lys Asn Ala Lys Thr Tyr Asn Glu Pro Gly Ser Gln Val Phe Lys Asp
                260                 265                 270
Ala Asn Ser Ile Lys Lys Ile Phe Tyr Met Lys Lys Ala Glu Ile Glu
                275                 280                 285
His His Glu Met Ala Lys Ser Ser Leu Arg Met Arg Thr Pro Ser Asn
                290                 295                 300
Leu Ala Ala Ala Arg Leu Thr Gly Pro Ser His Ser Lys Gly Ser Leu
305                 310                 315                 320
Gly Glu Glu Arg Asn Pro Thr Ser Lys Tyr Tyr Arg Asn Lys Arg Ala
                325                 330                 335
Val Gln Gly Gly Arg Leu Ser Ala Ile Thr Met Ala Leu Gln Tyr Gly
                340                 345                 350
Ser Glu Ser Glu Glu Asp Ala Ala Leu Ala Ala Ala Arg Tyr Glu Glu
                355                 360                 365
Gly Glu Ser Glu Ala Glu Ser Ile Thr Ser Phe Met Asp Val Ser Asn
                370                 375                 380
Pro Phe Tyr Gln Leu Tyr Asp Thr Val Arg Ser Cys Arg Asn Asn Gln
385                 390                 395                 400
Gly Gln Leu Ile Ala Glu Pro Phe Tyr His Leu Pro Ser Lys Lys Lys
                405                 410                 415
Tyr Pro Asp Tyr Tyr Gln Gln Ile Lys Met Pro Ile Ser Leu Gln Gln
                420                 425                 430
Ile Arg Thr Lys Leu Lys Asn Gln Glu Tyr Glu Thr Leu Asp His Leu
                435                 440                 445
Glu Cys Asp Leu Asn Leu Met Phe Glu Asn Ala Lys Arg Tyr Asn Val
450                 455                 460
```

-continued

```
Pro Asn Ser Ala Ile Tyr Lys Arg Val Leu Lys Leu Gln Gln Val Met
465                 470                 475                 480

Gln Ala Lys Lys Glu Leu Ala Arg Arg Asp Asp Ile Glu Asp Gly
            485                 490                 495

Asp Ser Met Ile Ser Ser Ala Thr Ser Asp Thr Gly Ser Ala Lys Arg
            500                 505                 510

Lys Ser Lys Lys Asn Ile Arg Lys Gln Arg Met Lys Ile Leu Phe Asn
            515                 520                 525

Val Val Leu Glu Ala Arg Glu Pro Gly Ser Gly Arg Arg Leu Cys Asp
            530                 535                 540

Leu Phe Met Val Lys Pro Ser Lys Lys Asp Tyr Pro Asp Tyr Tyr Lys
545                 550                 555                 560

Ile Ile Leu Glu Pro Met Asp Leu Lys Ile Ile Glu His Asn Ile Arg
                    565                 570                 575

Asn Asp Lys Tyr Ala Gly Glu Glu Gly Met Ile Glu Asp Met Lys Leu
                580                 585                 590

Met Phe Arg Asn Ala Arg His Tyr Asn Glu Glu Gly Ser Gln Val Tyr
            595                 600                 605

Asn Asp Ala His Ile Leu Glu Lys Leu Leu Lys Glu Lys Arg Lys Glu
            610                 615                 620

Leu Gly Pro Leu Pro Asp Asp Asp Met Ala Ser Pro Lys Leu Lys
625                 630                 635                 640

Leu Ser Arg Lys Ser Gly Ile Ser Pro Lys Ser Lys Tyr Met Thr
                645                 650                 655

Pro Met Gln Gln Lys Leu Asn Glu Val Tyr Glu Ala Val Lys Asn Tyr
            660                 665                 670

Thr Asp Lys Arg Gly Arg Arg Leu Ser Ala Ile Phe Leu Arg Leu Pro
            675                 680                 685

Ser Arg Ser Glu Leu Pro Asp Tyr Tyr Leu Thr Ile Lys Lys Pro Met
            690                 695                 700

Asp Met Glu Lys Ile Arg Ser His Met Met Ala Asn Lys Tyr Gln Asp
705                 710                 715                 720

Ile Asp Ser Met Val Glu Asp Phe Val Met Met Phe Asn Asn Ala Cys
                725                 730                 735

Thr Tyr Asn Glu Pro Glu Ser Leu Ile Tyr Lys Asp Ala Leu Val Leu
            740                 745                 750

His Lys Val Leu Leu Glu Thr Arg Arg Asp Leu Glu Gly Asp Glu Asp
            755                 760                 765

Ser His Val Pro Asn Val Thr Leu Leu Ile Gln Glu Leu Ile His Asn
            770                 775                 780

Leu Phe Val Ser Val Met Ser His Gln Asp Asp Glu Gly Arg Cys Tyr
785                 790                 795                 800

Ser Asp Ser Leu Ala Glu Ile Pro Ala Val Asp Pro Asn Phe Pro Asn
            805                 810                 815

Lys Pro Pro Leu Thr Phe Asp Ile Ile Arg Lys Asn Val Glu Asn Asn
            820                 825                 830

Arg Tyr Arg Arg Leu Asp Leu Phe Gln Glu His Met Phe Glu Val Leu
            835                 840                 845

Glu Arg Ala Arg Arg Met Asn Arg Thr Asp Ser Glu Ile Tyr Glu Asp
            850                 855                 860

Ala Val Glu Leu Gln Gln Phe Phe Ile Lys Ile Arg Asp Glu Leu Cys
865                 870                 875                 880

Lys Asn Gly Glu Ile Leu Leu Ser Pro Ala Leu Ser Tyr Thr Thr Lys
```

885                 890                 895
His Leu His Asn Asp Val Glu Lys Glu Arg Lys Glu Lys Leu Pro Lys
                900                 905                 910

Glu Ile Glu Glu Asp Lys Leu Lys Arg Glu Glu Lys Arg Glu Ala
            915                 920                 925

Glu Lys Ser Glu Asp Ser Ser Gly Ala Ala Gly Leu Ser Gly Leu His
        930                 935                 940

Arg Thr Tyr Ser Gln Asp Cys Ser Phe Lys Asn Ser Met Tyr His Val
945                 950                 955                 960

Gly Asp Tyr Val Tyr Val Glu Pro Ala Glu Ala Asn Leu Gln Pro His
                965                 970                 975

Ile Val Cys Ile Glu Arg Leu Trp Glu Asp Ser Ala Gly Glu Lys Trp
            980                 985                 990

Leu Tyr Gly Cys Trp Phe Tyr Arg Pro Asn Glu Thr Phe His Leu Ala
        995                 1000                1005

Thr Arg Lys Phe Leu Glu Lys Glu Val Phe Lys Ser Asp Tyr Tyr
    1010                1015                1020

Asn Lys Val Pro Val Ser Lys Ile Leu Gly Lys Cys Val Val Met
    1025                1030                1035

Phe Val Lys Glu Tyr Phe Lys Leu Cys Pro Glu Asn Phe Arg Asp
    1040                1045                1050

Glu Asp Val Phe Val Cys Glu Ser Arg Tyr Ser Ala Lys Thr Lys
    1055                1060                1065

Ser Phe Lys Lys Ile Lys Leu Trp Thr Met Pro Ile Ser Ser Val
    1070                1075                1080

Arg Phe Val Pro Arg Asp Val Pro Leu Pro Val Val Arg Val Ala
    1085                1090                1095

Ser Val Phe Ala Asn Ala Asp Lys Gly Asp Asp Glu Lys Asn Thr
    1100                1105                1110

Asp Asn Ser Glu Asp Ser Arg Ala Glu Asp Asn Phe Asn Leu Glu
    1115                1120                1125

Lys Glu Lys Glu Asp Val Pro Val Glu Met Ser Asn Gly Glu Pro
    1130                1135                1140

Gly Cys His Tyr Phe Glu Gln Leu His Tyr Asn Asp Met Trp Leu
    1145                1150                1155

Lys Val Gly Asp Cys Val Phe Ile Lys Ser His Gly Leu Val Arg
    1160                1165                1170

Pro Arg Val Gly Arg Ile Glu Lys Val Trp Val Arg Asp Gly Ala
    1175                1180                1185

Ala Tyr Phe Tyr Gly Pro Ile Phe Ile His Pro Glu Glu Thr Glu
    1190                1195                1200

His Glu Pro Thr Lys Met Phe Tyr Lys Lys Glu Val Phe Leu Ser
    1205                1210                1215

Asn Leu Glu Glu Thr Cys Pro Met Thr Cys Ile Leu Gly Lys Cys
    1220                1225                1230

Ala Val Leu Ser Phe Lys Asp Phe Leu Ser Cys Arg Pro Thr Glu
    1235                1240                1245

Ile Pro Glu Asn Asp Ile Leu Leu Cys Glu Ser Arg Tyr Asn Glu
    1250                1255                1260

Ser Asp Lys Gln Met Lys Lys Phe Lys Gly Leu Lys Arg Phe Ser
    1265                1270                1275

Leu Ser Ala Lys Val Val Asp Asp Glu Ile Tyr Tyr Phe Arg Lys
    1280                1285                1290

-continued

```
Pro Ile Val Pro Gln Lys Glu Pro Ser Pro Leu Leu Glu Lys Lys
    1295                1300                1305

Ile Gln Leu Leu Glu Ala Lys Phe Ala Glu Leu Glu Gly Gly Asp
    1310                1315                1320

Asp Asp Ile Glu Glu Met Gly Glu Glu Asp Ser Glu Val Ile Glu
    1325                1330                1335

Pro Pro Ser Leu Pro Gln Leu Gln Thr Pro Leu Ala Ser Glu Leu
    1340                1345                1350

Asp Leu Met Pro Tyr Thr Pro Pro Gln Ser Thr Pro Lys Ser Ala
    1355                1360                1365

Lys Gly Ser Ala Lys Lys Glu Gly Ser Lys Arg Lys Ile Asn Met
    1370                1375                1380

Ser Gly Tyr Ile Leu Phe Ser Ser Glu Met Arg Ala Val Ile Lys
    1385                1390                1395

Ala Gln His Pro Asp Tyr Ser Phe Gly Glu Leu Ser Arg Leu Val
    1400                1405                1410

Gly Thr Glu Trp Arg Asn Leu Glu Thr Ala Lys Lys Ala Glu Tyr
    1415                1420                1425

Glu Glu Arg Ala Ala Lys Val Ala Glu Gln Gln Glu Arg Glu Arg
    1430                1435                1440

Ala Ala Gln Gln Gln Gln Pro Ser Ala Ser Pro Arg Ala Gly Thr
    1445                1450                1455

Pro Val Gly Ala Leu Met Gly Val Val Pro Pro Thr Pro Met
    1460                1465                1470

Gly Met Leu Asn Gln Gln Leu Thr Pro Val Ala Gly Met Met Gly
    1475                1480                1485

Gly Tyr Pro Pro Gly Leu Pro Pro Leu Gln Gly Pro Val Asp Gly
    1490                1495                1500

Leu Val Ser Met Gly Ser Met Gln Pro Leu His Pro Gly Gly Pro
    1505                1510                1515

Pro Pro His His Leu Pro Pro Gly Val Pro Gly Leu Pro Gly Ile
    1520                1525                1530

Pro Pro Pro Gly Val Met Asn Gln Gly Val Ala Pro Met Val Gly
    1535                1540                1545

Thr Pro Ala Pro Gly Gly Ser Pro Tyr Gly Gln Gln Val Gly Val
    1550                1555                1560

Leu Gly Pro Pro Gly Gln Gln Ala Pro Pro Tyr Pro Gly Pro
    1565                1570                1575

His Pro Ala Gly Pro Pro Val Ile Gln Gln Pro Thr Thr Pro Met
    1580                1585                1590

Phe Val Ala Pro Pro Lys Thr Gln Arg Leu Leu His Ser Glu
    1595                1600                1605

Ala Tyr Leu Lys Tyr Ile Glu Gly Leu Ser Ala Glu Ser Asn Ser
    1610                1615                1620

Ile Ser Lys Trp Asp Gln Thr Leu Ala Ala Arg Arg Arg Asp Val
    1625                1630                1635

His Leu Ser Lys Glu Gln Glu Ser Arg Leu Pro Ser His Trp Leu
    1640                1645                1650

Lys Ser Lys Gly Ala His Thr Thr Met Ala Asp Ala Leu Trp Arg
    1655                1660                1665

Leu Arg Asp Leu Met Leu Arg Asp Thr Leu Asn Ile Arg Gln Ala
    1670                1675                1680
```

```
Tyr Asn Leu Glu Asn Val
    1685

<210> SEQ ID NO 3
<211> LENGTH: 268
<212> TYPE: PRT
<213> ORGANISM: HUMAN

<400> SEQUENCE: 3

Met Ala Val Asn Val Tyr Ser Thr Ser Val Thr Ser Asp Asn Leu Ser
1               5                   10                  15

Arg His Asp Met Leu Ala Trp Ile Asn Glu Ser Leu Gln Leu Asn Leu
            20                  25                  30

Thr Lys Ile Glu Gln Leu Cys Ser Gly Ala Ala Tyr Cys Gln Phe Met
        35                  40                  45

Asp Met Leu Phe Pro Gly Ser Ile Ala Leu Lys Lys Val Lys Phe Gln
    50                  55                  60

Ala Lys Leu Glu His Glu Tyr Ile Gln Asn Phe Lys Ile Leu Gln Ala
65                  70                  75                  80

Gly Phe Lys Arg Met Gly Val Asp Lys Ile Ile Pro Val Asp Lys Leu
                85                  90                  95

Val Lys Gly Lys Phe Gln Asp Asn Phe Glu Phe Val Gln Trp Phe Lys
            100                 105                 110

Lys Phe Phe Asp Ala Asn Tyr Asp Gly Lys Asp Tyr Asp Pro Val Ala
        115                 120                 125

Ala Arg Gln Gly Gln Glu Thr Ala Val Ala Pro Ser Leu Val Ala Pro
    130                 135                 140

Ala Leu Asn Lys Pro Lys Lys Pro Leu Thr Ser Ser Ser Ala Ala Pro
145                 150                 155                 160

Gln Arg Pro Ile Ser Thr Gln Arg Thr Ala Ala Ala Pro Lys Ala Gly
                165                 170                 175

Pro Gly Val Val Arg Lys Asn Pro Gly Val Gly Asn Gly Asp Asp Glu
            180                 185                 190

Ala Ala Glu Leu Met Gln Gln Val Asn Val Leu Lys Leu Thr Val Glu
        195                 200                 205

Asp Leu Glu Lys Glu Arg Asp Phe Tyr Phe Gly Lys Leu Arg Asn Ile
    210                 215                 220

Glu Leu Ile Cys Gln Glu Asn Glu Gly Glu Asn Asp Pro Val Leu Gln
225                 230                 235                 240

Arg Ile Val Asp Ile Leu Tyr Ala Thr Asp Glu Gly Phe Val Ile Pro
                245                 250                 255

Asp Glu Gly Gly Pro Gln Glu Glu Gln Glu Glu Tyr
            260                 265

<210> SEQ ID NO 4
<211> LENGTH: 261
<212> TYPE: PRT
<213> ORGANISM: HUMAN

<400> SEQUENCE: 4

Met Ala Ser Pro Asp Trp Gly Tyr Asp Asp Lys Asn Gly Pro Glu Gln
1               5                   10                  15

Trp Ser Lys Leu Tyr Pro Ile Ala Asn Gly Asn Asn Gln Ser Pro Val
            20                  25                  30

Asp Ile Lys Thr Ser Glu Thr Lys His Asp Thr Ser Leu Lys Pro Ile
        35                  40                  45
```

```
Ser Val Ser Tyr Asn Pro Ala Thr Ala Lys Glu Ile Ile Asn Val Gly
 50                  55                  60

His Ser Phe His Val Asn Phe Glu Asp Asn Asp Asn Arg Ser Val Leu
 65                  70                  75                  80

Lys Gly Gly Pro Phe Ser Asp Ser Tyr Arg Leu Phe Gln Phe His Phe
                 85                  90                  95

His Trp Gly Ser Thr Asn Glu His Gly Ser Glu His Thr Val Asp Gly
                100                 105                 110

Val Lys Tyr Ser Ala Glu Leu His Val Ala His Trp Asn Ser Ala Lys
            115                 120                 125

Tyr Ser Ser Leu Ala Glu Ala Ala Ser Lys Ala Asp Gly Leu Ala Val
130                 135                 140

Ile Gly Val Leu Met Lys Val Gly Glu Ala Asn Pro Lys Leu Gln Lys
145                 150                 155                 160

Val Leu Asp Ala Leu Gln Ala Ile Lys Thr Lys Gly Lys Arg Ala Pro
                165                 170                 175

Phe Thr Asn Phe Asp Pro Ser Thr Leu Leu Pro Ser Ser Leu Asp Phe
                180                 185                 190

Trp Thr Tyr Pro Gly Ser Leu Thr His Pro Pro Leu Tyr Glu Ser Val
            195                 200                 205

Thr Trp Ile Ile Cys Lys Glu Ser Ile Ser Val Ser Ser Glu Gln Leu
210                 215                 220

Ala Gln Phe Arg Ser Leu Leu Ser Asn Val Glu Gly Asp Asn Ala Val
225                 230                 235                 240

Pro Met Gln His Asn Asn Arg Pro Thr Gln Pro Leu Lys Gly Arg Thr
                245                 250                 255

Val Arg Ala Ser Phe
                260

<210> SEQ ID NO 5
<211> LENGTH: 233
<212> TYPE: PRT
<213> ORGANISM: HUMAN

<400> SEQUENCE: 5

Met Leu Asn Leu Leu Leu Ala Leu Pro Val Leu Ala Ser Arg Ala
 1               5                  10                  15

Tyr Ala Ala Pro Ala Pro Gly Gln Ala Leu Gln Arg Val Gly Ile Val
                 20                  25                  30

Gly Gly Gln Glu Ala Pro Arg Ser Lys Trp Pro Trp Gln Val Ser Leu
             35                  40                  45

Arg Val Arg Asp Arg Tyr Trp Met His Phe Cys Gly Gly Ser Leu Ile
 50                  55                  60

His Pro Gln Trp Val Leu Thr Ala Ala His Cys Val Gly Pro Asp Val
 65                  70                  75                  80

Lys Asp Leu Ala Ala Leu Arg Val Gln Leu Arg Glu Gln His Leu Tyr
                 85                  90                  95

Tyr Gln Asp Gln Leu Leu Pro Val Ser Arg Ile Ile Val His Pro Gln
                100                 105                 110

Phe Tyr Thr Ala Gln Ile Gly Ala Asp Ile Ala Leu Leu Glu Leu Glu
            115                 120                 125

Glu Pro Val Asn Val Ser Ser His Val His Thr Val Thr Leu Pro Pro
130                 135                 140

Ala Ser Glu Thr Phe Pro Pro Gly Met Pro Cys Trp Val Thr Gly Trp
145                 150                 155                 160
```

```
Gly Asp Val Asp Asn Asp Glu Arg Leu Pro Pro Pro Phe Pro Leu Lys
                165                 170                 175

Gln Val Lys Val Pro Ile Met Glu Asn His Ile Cys Asp Ala Lys Tyr
            180                 185                 190

His Leu Gly Ala Tyr Thr Gly Asp Asp Val Arg Ile Val Arg Asp Asp
        195                 200                 205

Met Leu Cys Ala Gly Asn Thr Arg Arg Asp Ser Cys Gln Val Ala Thr
    210                 215                 220

Ala Pro His Thr Phe Pro Ala Pro Ser
225                 230

<210> SEQ ID NO 6
<211> LENGTH: 136
<212> TYPE: PRT
<213> ORGANISM: HUMAN

<400> SEQUENCE: 6

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 7
<211> LENGTH: 627
<212> TYPE: PRT
<213> ORGANISM: HUMAN

<400> SEQUENCE: 7

Met Ala Thr Thr Gln Ile Ser Lys Asp Glu Leu Asp Glu Leu Lys Glu
1               5                   10                  15

Ala Phe Ala Lys Val Asp Leu Asn Ser Asn Gly Phe Ile Cys Asp Tyr
            20                  25                  30

Glu Leu His Glu Leu Phe Lys Glu Ala Asn Met Pro Leu Pro Gly Tyr
        35                  40                  45

Lys Val Arg Glu Ile Ile Gln Lys Leu Met Leu Asp Gly Asp Arg Asn
    50                  55                  60

Lys Asp Gly Lys Ile Ser Phe Asp Glu Phe Val Tyr Ile Phe Gln Glu
65                  70                  75                  80

Val Lys Ser Ser Asp Ile Ala Lys Thr Phe Arg Lys Ala Ile Asn Arg
                85                  90                  95

Lys Glu Gly Ile Cys Ala Leu Gly Gly Thr Ser Glu Leu Ser Ser Glu
            100                 105                 110
```

-continued

Gly Thr Gln His Ser Tyr Ser Glu Glu Lys Tyr Ala Phe Val Asn
            115                 120                 125

Trp Ile Asn Lys Ala Leu Glu Asn Asp Pro Asp Cys Arg His Val Ile
130                 135                 140

Pro Met Asn Pro Asn Thr Asp Asp Leu Phe Lys Ala Val Gly Asp Gly
145                 150                 155                 160

Ile Val Leu Cys Lys Met Ile Asn Leu Ser Val Pro Asp Thr Ile Asp
                165                 170                 175

Glu Arg Ala Ile Asn Lys Lys Leu Thr Pro Phe Ile Ile Gln Glu
            180                 185                 190

Asn Leu Asn Leu Ala Leu Asn Ser Ala Ser Ala Ile Gly Cys His Val
            195                 200                 205

Val Asn Ile Gly Ala Glu Asp Leu Arg Ala Gly Lys Pro His Leu Val
            210                 215                 220

Leu Gly Leu Leu Trp Gln Ile Ile Lys Ile Gly Leu Phe Ala Asp Ile
225                 230                 235                 240

Glu Leu Ser Arg Asn Glu Ala Leu Ala Ala Leu Leu Arg Asp Gly Glu
                245                 250                 255

Thr Leu Glu Glu Leu Met Lys Leu Ser Pro Glu Glu Leu Leu Leu Arg
            260                 265                 270

Trp Ala Asn Phe His Leu Glu Asn Ser Gly Trp Gln Lys Ile Asn Asn
            275                 280                 285

Phe Ser Ala Asp Ile Lys Asp Ser Lys Ala Tyr Phe His Leu Leu Asn
            290                 295                 300

Gln Ile Ala Pro Lys Gly Gln Lys Gly Glu Pro Arg Ile Asp Ile
305                 310                 315                 320

Asn Met Ser Gly Phe Asn Glu Thr Asp Asp Leu Lys Arg Ala Glu Ser
                325                 330                 335

Met Leu Gln Gln Ala Asp Lys Leu Gly Cys Arg Gln Phe Val Thr Pro
            340                 345                 350

Ala Asp Val Val Ser Gly Asn Pro Lys Leu Asn Leu Ala Phe Val Ala
            355                 360                 365

Asn Leu Phe Asn Lys Tyr Pro Ala Leu Thr Lys Pro Glu Asn Gln Asp
            370                 375                 380

Ile Asp Trp Thr Leu Leu Glu Gly Glu Thr Arg Glu Glu Arg Thr Phe
385                 390                 395                 400

Arg Asn Trp Met Asn Ser Leu Gly Val Asn Pro His Val Asn His Leu
                405                 410                 415

Tyr Ala Asp Leu Gln Asp Ala Leu Val Ile Leu Gln Leu Tyr Glu Arg
            420                 425                 430

Ile Lys Val Pro Val Asp Trp Ser Lys Val Asn Lys Pro Pro Tyr Pro
            435                 440                 445

Lys Leu Gly Ala Asn Met Lys Lys Leu Glu Asn Cys Asn Tyr Ala Val
            450                 455                 460

Glu Leu Gly Lys His Pro Ala Lys Phe Ser Leu Val Gly Ile Gly Gly
465                 470                 475                 480

Gln Asp Leu Asn Asp Gly Asn Gln Thr Leu Thr Leu Ala Leu Val Trp
                485                 490                 495

Gln Leu Met Arg Arg Tyr Thr Leu Asn Val Leu Glu Asp Leu Gly Asp
            500                 505                 510

Gly Gln Lys Ala Asn Asp Asp Ile Ile Val Asn Trp Val Asn Arg Thr
            515                 520                 525

```
Leu Ser Glu Ala Gly Lys Ser Thr Ile Gln Ser Phe Lys Asp Lys
    530                 535                 540

Thr Ile Ser Ser Leu Ala Val Val Asp Leu Ile Asp Ala Ile Gln
545                 550                 555                 560

Pro Gly Cys Ile Asn Tyr Asp Leu Val Lys Ser Gly Asn Leu Thr Glu
                565                 570                 575

Asp Asp Lys His Asn Asn Ala Lys Tyr Ala Val Ser Met Ala Arg Arg
            580                 585                 590

Ile Gly Ala Arg Val Tyr Ala Leu Pro Glu Asp Leu Val Glu Val Lys
            595                 600                 605

Pro Lys Met Val Met Thr Val Phe Ala Cys Leu Met Gly Arg Gly Met
    610                 615                 620

Lys Arg Val
625

<210> SEQ ID NO 8
<211> LENGTH: 103
<212> TYPE: PRT
<213> ORGANISM: HUMAN

<400> SEQUENCE: 8

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 9
<211> LENGTH: 165
<212> TYPE: PRT
<213> ORGANISM: HUMAN

<400> SEQUENCE: 9

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110
```

```
Phe Ile Cys Thr Ala Lys Thr Glu Trp Leu Asp Gly Lys His Val Val
            115                 120                 125

Phe Gly Lys Val Lys Glu Gly Met Asn Ile Val Glu Ala Met Glu Arg
        130                 135                 140

Phe Gly Ser Arg Asn Gly Lys Thr Ser Lys Lys Ile Thr Ile Ala Asp
145                 150                 155                 160

Cys Gly Gln Leu Glu
                165

<210> SEQ ID NO 10
<211> LENGTH: 189
<212> TYPE: PRT
<213> ORGANISM: HUMAN

<400> SEQUENCE: 10

Met Arg Leu Ser Leu Pro Leu Leu Leu Leu Leu Gly Ala Trp Ala
1               5                   10                  15

Ile Pro Gly Gly Leu Gly Asp Arg Ala Pro Leu Thr Ala Thr Ala Pro
                20                  25                  30

Gln Leu Asp Asp Glu Glu Met Tyr Ser Ala His Met Pro Ala His Leu
            35                  40                  45

Arg Cys Asp Ala Cys Arg Ala Val Ala Tyr Gln Met Trp Gln Asn Leu
        50                  55                  60

Ala Lys Ala Glu Thr Lys Leu His Thr Ser Asn Ser Gly Gly Arg Arg
65                  70                  75                  80

Glu Leu Ser Glu Leu Val Tyr Thr Asp Val Leu Asp Arg Ser Cys Ser
                85                  90                  95

Arg Asn Trp Gln Asp Tyr Gly Val Arg Glu Val Asp Gln Val Lys Arg
            100                 105                 110

Leu Thr Gly Pro Gly Leu Ser Glu Gly Pro Glu Pro Ser Ile Ser Val
        115                 120                 125

Met Val Thr Gly Gly Pro Trp Pro Thr Arg Leu Ser Arg Thr Cys Leu
    130                 135                 140

His Tyr Leu Gly Glu Phe Gly Glu Asp Gln Ile Tyr Glu Ala His Gln
145                 150                 155                 160

Gln Gly Arg Gly Ala Leu Glu Ala Leu Leu Cys Gly Pro Gln Gly
                165                 170                 175

Ala Cys Ser Glu Lys Val Ser Ala Thr Arg Glu Glu Leu
            180                 185

<210> SEQ ID NO 11
<211> LENGTH: 332
<212> TYPE: PRT
<213> ORGANISM: HUMAN

<400> SEQUENCE: 11

Met Ala Thr Leu Lys Asp Gln Leu Ile Tyr Asn Leu Leu Lys Glu Glu
1               5                   10                  15

Gln Thr Pro Gln Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
        50                  55                  60

Leu Gln His Gly Ser Leu Phe Leu Arg Thr Pro Lys Ile Val Ser Gly
65                  70                  75                  80
```

-continued

```
Lys Asp Tyr Asn Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asn Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Met Asn Val Ala Gly
        195                 200                 205

Val Ser Leu Lys Thr Leu His Pro Asp Leu Gly Thr Asp Lys Asp Lys
    210                 215                 220

Glu Gln Trp Lys Glu Val His Lys Gln Val Val Glu Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Val Ser Thr Met Ile Lys Gly Leu Tyr Gly Ile Lys Asp Asp Val Phe
        275                 280                 285

Leu Ser Val Pro Cys Ile Leu Gly Gln Asn Gly Ile Ser Asp Leu Val
    290                 295                 300

Lys Val Thr Leu Thr Ser Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 12
<211> LENGTH: 338
<212> TYPE: PRT
<213> ORGANISM: HUMAN

<400> SEQUENCE: 12

Met Ser Leu Ser Ala Phe Thr Leu Phe Leu Ala Leu Ile Gly Gly Thr
1               5                   10                  15

Ser Gly Gln Tyr Tyr Asp Tyr Asp Phe Pro Leu Ser Ile Tyr Gly Gln
            20                  25                  30

Ser Ser Pro Asn Cys Ala Pro Glu Cys Asn Cys Pro Glu Ser Tyr Pro
        35                  40                  45

Ser Ala Met Tyr Cys Asp Glu Leu Lys Leu Lys Ser Val Pro Met Val
    50                  55                  60

Pro Pro Gly Ile Lys Tyr Leu Tyr Leu Arg Asn Asn Gln Ile Asp His
65                  70                  75                  80

Ile Asp Glu Lys Ala Phe Glu Asn Val Thr Asp Leu Gln Trp Leu Ile
                85                  90                  95

Leu Asp His Asn Leu Leu Glu Asn Ser Lys Ile Lys Gly Arg Val Phe
            100                 105                 110

Ser Lys Leu Lys Gln Leu Lys Lys Leu His Ile Asn His Asn Asn Leu
        115                 120                 125
```

```
Thr Glu Ser Val Gly Pro Leu Pro Lys Ser Leu Glu Asp Leu Gln Leu
    130                 135                 140

Thr His Asn Lys Ile Thr Lys Leu Gly Ser Phe Glu Gly Leu Val Asn
145                 150                 155                 160

Leu Thr Phe Ile His Leu Gln His Asn Arg Leu Lys Glu Asp Ala Val
                165                 170                 175

Ser Ala Ala Phe Lys Gly Leu Lys Ser Leu Glu Tyr Leu Asp Leu Ser
            180                 185                 190

Phe Asn Gln Ile Ala Arg Leu Pro Ser Gly Leu Pro Val Ser Leu Leu
        195                 200                 205

Thr Leu Tyr Leu Asp Asn Asn Lys Ile Ser Asn Ile Pro Asp Glu Tyr
    210                 215                 220

Phe Lys Arg Phe Asn Ala Leu Gln Tyr Leu Arg Leu Ser His Asn Glu
225                 230                 235                 240

Leu Ala Asp Ser Gly Ile Pro Gly Asn Ser Phe Asn Val Ser Ser Leu
                245                 250                 255

Val Glu Leu Asp Leu Ser Tyr Asn Lys Leu Lys Asn Ile Pro Thr Val
            260                 265                 270

Asn Glu Asn Leu Glu Asn Tyr Tyr Leu Glu Val Asn Gln Leu Glu Lys
        275                 280                 285

Phe Asp Ile Lys Ser Phe Cys Lys Ile Leu Gly Pro Leu Ser Tyr Ser
    290                 295                 300

Lys Ile Lys His Leu Arg Leu Asp Gly Asn Arg Ile Ser Glu Thr Ser
305                 310                 315                 320

Leu Pro Pro Asp Met Tyr Glu Cys Leu Arg Val Ala Asn Glu Val Thr
                325                 330                 335

Leu Asn

<210> SEQ ID NO 13
<211> LENGTH: 101
<212> TYPE: PRT
<213> ORGANISM: HUMAN

<400> SEQUENCE: 13

Met Ser Asn Thr Gln Ala Glu Arg Ser Ile Ile Gly Met Ile Asp Met
1               5                   10                  15

Phe His Lys Tyr Thr Arg Arg Asp Asp Lys Ile Asp Lys Pro Ser Leu
            20                  25                  30

Leu Thr Met Met Lys Glu Asn Phe Pro Asn Phe Leu Ser Ala Cys Asp
        35                  40                  45

Lys Lys Gly Thr Asn Tyr Leu Ala Asp Val Phe Glu Lys Lys Asp Lys
    50                  55                  60

Asn Glu Asp Lys Lys Ile Asp Phe Ser Glu Phe Leu Ser Leu Leu Gly
65                  70                  75                  80

Asp Ile Ala Thr Asp Tyr His Lys Gln Ser His Gly Ala Ala Pro Cys
                85                  90                  95

Ser Gly Gly Ser Gln
            100

<210> SEQ ID NO 14
<211> LENGTH: 198
<212> TYPE: PRT
<213> ORGANISM: HUMAN

<400> SEQUENCE: 14
```

```
Met Ala Ser Gly Asn Ala Arg Ile Gly Lys Pro Ala Pro Asp Phe Lys
1               5                   10                  15

Ala Thr Ala Val Val Asp Gly Ala Phe Lys Glu Val Lys Leu Ser Asp
            20                  25                  30

Tyr Lys Gly Lys Tyr Val Val Leu Phe Phe Tyr Pro Leu Asp Phe Thr
        35                  40                  45

Phe Val Cys Pro Thr Glu Ile Ile Ala Phe Ser Asn Arg Ala Glu Asp
    50                  55                  60

Phe Arg Lys Leu Gly Cys Glu Val Leu Gly Val Ser Val Asp Ser Gln
65                  70                  75                  80

Phe Thr His Leu Ala Trp Ile Asn Thr Pro Arg Lys Glu Gly Gly Leu
                85                  90                  95

Gly Pro Leu Asn Ile Pro Leu Leu Ala Asp Val Thr Arg Arg Leu Ser
            100                 105                 110

Glu Asp Tyr Gly Val Leu Lys Thr Asp Glu Gly Ile Ala Tyr Arg Gly
        115                 120                 125

Leu Phe Ile Ile Asp Gly Lys Gly Val Leu Arg Gln Ile Thr Val Asn
    130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175

Lys Pro Gly Ser Asp Thr Ile Lys Pro Asn Val Asp Asp Ser Lys Glu
            180                 185                 190

Tyr Phe Ser Lys His Asn
        195

<210> SEQ ID NO 15
<211> LENGTH: 140
<212> TYPE: PRT
<213> ORGANISM: HUMAN

<400> SEQUENCE: 15

Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Thr Glu Glu Lys Tyr Gln Glu Ala Leu Ala Lys Gly Arg Phe Gln Ala
65                  70                  75                  80

Glu Arg Arg Glu Ala Val Pro Gly Arg Gly Asp Pro Glu Pro Gly Pro
                85                  90                  95

Pro Ile Arg Thr Gly Leu Ser Val Glu Glu Asn Ser Leu Arg Ile Cys
            100                 105                 110

Thr Gly Ser Glu Phe Ser Arg His Asp Ser Leu Ser Phe Lys His Met
        115                 120                 125

Val Tyr Leu Ile Val Glu Gly Val Pro Arg Trp Val
    130                 135                 140

<210> SEQ ID NO 16
<211> LENGTH: 418
<212> TYPE: PRT
<213> ORGANISM: HUMAN
```

<400> SEQUENCE: 16

```
Met Pro Ser Ser Val Ser Trp Gly Ile Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
```

```
                       405                 410                 415

Gln Lys

<210> SEQ ID NO 17
<211> LENGTH: 332
<212> TYPE: PRT
<213> ORGANISM: HUMAN

<400> SEQUENCE: 17

Met Gly Ala Gln Phe Ser Lys Thr Ala Ala Lys Gly Glu Ala Ala Ala
1               5                   10                  15

Glu Arg Pro Gly Glu Ala Ala Val Ala Ser Ser Pro Ser Lys Ala Asn
            20                  25                  30

Gly Gln Glu Asn Gly His Val Lys Val Asn Gly Asp Ala Ser Pro Ala
        35                  40                  45

Ala Ala Glu Ser Gly Ala Lys Glu Glu Leu Gln Ala Asn Gly Ser Ala
    50                  55                  60

Pro Ala Ala Asp Lys Glu Glu Pro Ala Ala Gly Ser Gly Ala Ala
65                  70                  75                  80

Ser Pro Ser Ala Ala Glu Lys Gly Glu Pro Ala Ala Ala Ala Pro
                85                  90                  95

Glu Ala Gly Ala Ser Pro Val Glu Lys Glu Ala Pro Ala Glu Gly Glu
            100                 105                 110

Ala Ala Glu Pro Gly Ser Pro Thr Ala Ala Glu Gly Glu Ala Ala Ser
        115                 120                 125

Ala Ala Ser Ser Thr Ser Ser Pro Lys Ala Glu Asp Gly Ala Thr Pro
    130                 135                 140

Ser Pro Ser Asn Glu Thr Pro Lys Lys Lys Lys Arg Phe Ser Phe
145                 150                 155                 160

Lys Lys Ser Phe Lys Leu Ser Gly Phe Ser Phe Lys Lys Asn Lys Lys
                165                 170                 175

Glu Ala Gly Glu Gly Gly Glu Ala Glu Ala Pro Ala Ala Glu Gly Gly
            180                 185                 190

Lys Asp Glu Ala Ala Gly Gly Ala Ala Ala Ala Ala Glu Ala Gly
        195                 200                 205

Ala Ala Ser Gly Glu Gln Ala Ala Pro Gly Glu Glu Ala Ala Ala
    210                 215                 220

Gly Glu Glu Gly Ala Ala Gly Gly Asp Ser Gln Glu Ala Lys Pro Gln
225                 230                 235                 240

Glu Ala Ala Val Ala Pro Glu Lys Pro Pro Ala Ser Asp Glu Thr Lys
                245                 250                 255

Ala Ala Glu Glu Pro Ser Lys Val Glu Glu Lys Lys Ala Glu Glu Ala
            260                 265                 270

Gly Ala Ser Ala Ala Ala Cys Glu Ala Pro Ser Ala Ala Gly Leu Val
        275                 280                 285

Cys Pro Arg Arg Gly Gly Ser Pro Arg Gly Ala Arg Gly Arg Arg
    290                 295                 300

Ser Leu Asn Gln Ala Cys Ala Ala Pro Ser Gln Glu Ala Gln Pro Glu
305                 310                 315                 320

Cys Ser Pro Glu Ala Pro Pro Ala Glu Ala Ala Glu
                325                 330

<210> SEQ ID NO 18
<211> LENGTH: 803
<212> TYPE: PRT
```

<213> ORGANISM: HUMAN

<400> SEQUENCE: 18

```
Met Arg Ala Leu Trp Val Leu Gly Leu Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
            35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
                100                 105                 110

Asp Lys Ile Arg Leu Ile Ser Leu Thr Asp Glu Asn Ala Leu Ser Gly
            115                 120                 125

Asn Glu Glu Leu Thr Val Lys Ile Lys Cys Asp Lys Glu Lys Asn Leu
130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
                180                 185                 190

Gly Gln Phe Gly Val Gly Phe Tyr Ser Ala Phe Leu Val Ala Asp Lys
            195                 200                 205

Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
                260                 265                 270

Gln Phe Ile Asn Phe Pro Ile Tyr Val Trp Ser Ser Lys Thr Glu Thr
            275                 280                 285

Val Glu Glu Pro Met Glu Glu Glu Ala Ala Lys Glu Glu Lys Glu
    290                 295                 300

Glu Ser Asp Asp Glu Ala Ala Val Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
                340                 345                 350

Asp Glu Tyr Lys Ala Phe Tyr Lys Ser Phe Ser Lys Glu Ser Asp Asp
            355                 360                 365

Pro Met Ala Tyr Ile His Phe Thr Ala Glu Gly Glu Val Thr Phe Lys
    370                 375                 380

Ser Ile Leu Phe Val Pro Thr Ser Ala Pro Arg Gly Leu Phe Asp Glu
385                 390                 395                 400
```

```
Tyr Gly Ser Lys Lys Ser Asp Tyr Ile Lys Leu Tyr Val Arg Arg Val
            405                 410                 415
Phe Ile Thr Asp Asp Phe His Asp Met Met Pro Lys Tyr Leu Asn Phe
            420                 425                 430
Val Lys Gly Val Val Asp Ser Asp Asp Leu Pro Leu Asn Val Ser Arg
            435                 440                 445
Glu Thr Leu Gln Gln His Lys Leu Leu Lys Val Ile Arg Lys Lys Leu
            450                 455                 460
Val Arg Lys Thr Leu Asp Met Ile Lys Lys Ile Ala Asp Asp Lys Tyr
465                 470                 475                 480
Asn Asp Thr Phe Trp Lys Glu Phe Gly Thr Asn Ile Lys Leu Gly Val
                    485                 490                 495
Ile Glu Asp His Ser Asn Arg Thr Arg Leu Ala Lys Leu Leu Arg Phe
                500                 505                 510
Gln Ser Ser His His Pro Thr Asp Ile Thr Ser Leu Asp Gln Tyr Val
            515                 520                 525
Glu Arg Met Lys Glu Lys Gln Asp Lys Ile Tyr Phe Met Ala Gly Ser
            530                 535                 540
Ser Arg Lys Glu Ala Glu Ser Ser Pro Phe Val Glu Arg Leu Leu Lys
545                 550                 555                 560
Lys Gly Tyr Glu Val Ile Tyr Leu Thr Glu Pro Val Asp Glu Tyr Cys
                    565                 570                 575
Ile Gln Ala Leu Pro Glu Phe Asp Gly Lys Arg Phe Gln Asn Val Ala
                580                 585                 590
Lys Glu Gly Val Lys Phe Asp Glu Ser Glu Lys Thr Lys Glu Ser Arg
                595                 600                 605
Glu Ala Val Glu Lys Glu Phe Glu Pro Leu Leu Asn Trp Met Lys Asp
            610                 615                 620
Lys Ala Leu Lys Asp Lys Ile Glu Lys Ala Val Val Ser Gln Arg Leu
625                 630                 635                 640
Thr Glu Ser Pro Cys Ala Leu Val Ala Ser Gln Tyr Gly Trp Ser Gly
                    645                 650                 655
Asn Met Glu Arg Ile Met Lys Ala Gln Ala Tyr Gln Thr Gly Lys Asp
                660                 665                 670
Ile Ser Thr Asn Tyr Tyr Ala Ser Gln Lys Lys Thr Phe Glu Ile Asn
            675                 680                 685
Pro Arg His Pro Leu Ile Arg Asp Met Leu Arg Arg Ile Lys Glu Asp
            690                 695                 700
Glu Asp Asp Lys Thr Val Leu Asp Leu Ala Val Val Leu Phe Glu Thr
705                 710                 715                 720
Ala Thr Leu Arg Ser Gly Tyr Leu Leu Pro Asp Thr Lys Ala Tyr Gly
                    725                 730                 735
Asp Arg Ile Glu Arg Met Leu Arg Leu Ser Leu Asn Ile Asp Pro Asp
                740                 745                 750
Ala Lys Val Glu Glu Pro Glu Glu Pro Glu Glu Thr Ala Glu
            755                 760                 765
Asp Thr Thr Glu Asp Thr Glu Gln Asp Glu Asp Glu Met Asp Val
            770                 775                 780
Gly Thr Asp Glu Glu Glu Glu Thr Ala Lys Glu Ser Thr Ala Glu Lys
785                 790                 795                 800
Asp Glu Leu

<210> SEQ ID NO 19
```

-continued

```
<211> LENGTH: 111
<212> TYPE: PRT
<213> ORGANISM: HUMAN

<400> SEQUENCE: 19

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
                20                  25                  30

Ala Pro Ala Asn Gly Asn Ala Glu Asn Glu Glu Asn Gly Glu Gln Glu
            35                  40                  45

Ala Asp Asn Glu Val Asp Glu Glu Glu Glu Gly Gly Glu Glu Glu
50                  55                  60

Glu Glu Glu Glu Glu Gly Asp Gly Glu Glu Asp Gly Asp Glu Asp
65                  70                  75                  80

Glu Glu Ala Glu Ser Ala Thr Gly Lys Arg Ala Ala Glu Asp Asp Glu
                85                  90                  95

Asp Asp Asp Val Asp Thr Lys Lys Gln Lys Thr Asp Glu Asp Asp
                100                 105                 110

<210> SEQ ID NO 20
<211> LENGTH: 126
<212> TYPE: PRT
<213> ORGANISM: HUMAN

<400> SEQUENCE: 20

Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
                20                  25                  30

Ser Arg Lys Glu Ser Tyr Ser Ile Tyr Val Tyr Lys Val Leu Lys Gln
            35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
                100                 105                 110

Ser Glu Gly Thr Lys Ala Val Thr Lys Tyr Thr Ser Ser Lys
            115                 120                 125

<210> SEQ ID NO 21
<211> LENGTH: 294
<212> TYPE: PRT
<213> ORGANISM: HUMAN

<400> SEQUENCE: 21

Met Glu Asp Ser Met Asp Met Asp Met Ser Pro Leu Arg Pro Gln Asn
1               5                   10                  15

Tyr Leu Phe Gly Cys Glu Leu Lys Ala Asp Lys Asp Tyr His Phe Lys
                20                  25                  30

Val Asp Asn Asp Glu Asn Glu His Gln Leu Ser Leu Arg Thr Val Ser
            35                  40                  45

Leu Gly Ala Gly Ala Lys Asp Glu Leu His Ile Val Glu Ala Glu Ala
    50                  55                  60
```

-continued

```
Met Asn Tyr Glu Gly Ser Pro Ile Lys Val Thr Leu Ala Thr Leu Lys
 65                  70                  75                  80

Met Ser Val Gln Pro Thr Val Ser Leu Gly Gly Phe Glu Ile Thr Pro
                 85                  90                  95

Pro Val Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu
        115                 120                 125

Glu Glu Glu Asp Val Lys Leu Leu Ser Ile Ser Gly Lys Arg Ser Ala
130                 135                 140

Pro Gly Gly Ser Lys Val Pro Gln Lys Lys Val Lys Leu Ala Ala
145                 150                 155                 160

Asp Glu Asp Asp Asp Asp Asp Glu Asp Asp Asp Glu Asp Asp
                165                 170                 175

Asp Gly Asp Asp Phe Asp Asp Glu Glu Ala Glu Glu Lys Ala Pro Val
            180                 185                 190

Lys Lys Ser Ile Arg Asp Thr Pro Ala Lys Asn Ala Gln Lys Ser Asn
        195                 200                 205

Gln Asn Gly Lys Asp Ser Lys Pro Ser Ser Thr Pro Arg Ser Lys Gly
    210                 215                 220

Gln Glu Ser Phe Lys Lys Gln Glu Lys Thr Pro Lys Thr Pro Lys Gly
225                 230                 235                 240

Pro Ser Ser Val Glu Asp Ile Lys Ala Lys Met Gln Ala Ser Ile Glu
                245                 250                 255

Lys Gly Gly Ser Leu Pro Lys Val Glu Ala Lys Phe Ile Asn Cys Val
            260                 265                 270

Lys Asn Cys Phe Arg Met Thr Asp Gln Glu Ala Ile Gln Asp Leu Trp
        275                 280                 285

Gln Trp Arg Lys Ser Leu
    290

<210> SEQ ID NO 22
<211> LENGTH: 531
<212> TYPE: PRT
<213> ORGANISM: HUMAN

<400> SEQUENCE: 22

Met Ser Lys Pro His Ser Glu Ala Gly Thr Ala Phe Ile Gln Thr Gln
  1               5                  10                  15

Gln Leu His Ala Ala Met Ala Asp Thr Phe Leu Glu His Met Cys Arg
                 20                  25                  30

Leu Asp Ile Asp Ser Pro Pro Ile Thr Ala Arg Asn Thr Gly Ile Ile
            35                  40                  45

Cys Thr Ile Gly Pro Ala Ser Arg Ser Val Glu Thr Leu Lys Glu Met
        50                  55                  60

Ile Lys Ser Gly Met Asn Val Ala Arg Leu Asn Phe Ser His Gly Thr
 65                  70                  75                  80

His Glu Tyr His Ala Glu Thr Ile Lys Asn Val Arg Thr Ala Thr Glu
                 85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
130                 135                 140
```

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
            165                 170                 175

Asp Asp Gly Leu Ile Ser Leu Gln Val Lys Gln Lys Gly Ala Asp Phe
        180                 185                 190

Leu Val Thr Glu Val Glu Asn Gly Gly Ser Leu Gly Ser Lys Lys Gly
    195                 200                 205

Val Asn Leu Pro Gly Ala Ala Val Asp Leu Pro Ala Val Ser Glu Lys
210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
        355                 360                 365

Asp Tyr Pro Leu Glu Ala Val Arg Met Gln His Leu Ile Ala Arg Glu
    370                 375                 380

Ala Glu Ala Ala Ile Tyr His Leu Gln Leu Phe Glu Glu Leu Arg Arg
385                 390                 395                 400

Leu Ala Pro Ile Thr Ser Asp Pro Thr Glu Ala Thr Ala Val Gly Ala
                405                 410                 415

Val Glu Ala Ser Phe Lys Cys Cys Ser Gly Ala Ile Ile Val Leu Thr
            420                 425                 430

Lys Ser Gly Arg Ser Ala His Gln Val Ala Arg Tyr Arg Pro Arg Ala
        435                 440                 445

Pro Ile Ile Ala Val Thr Arg Asn Pro Gln Thr Ala Arg Gln Ala His
    450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
                485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
        515                 520                 525

Pro Val Pro
530

<210> SEQ ID NO 23
<211> LENGTH: 248

```
<212> TYPE: PRT
<213> ORGANISM: HUMAN

<400> SEQUENCE: 23

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Gly Ala Val Glu Lys
            20                  25                  30

Gly Glu Glu Leu Ser Cys Glu Glu Arg Asn Leu Leu Ser Val Ala Tyr
        35                  40                  45

Lys Asn Val Val Gly Gly Gln Arg Ala Ala Trp Arg Val Leu Ser Ser
50                  55                  60

Ile Glu Gln Lys Ser Asn Glu Glu Gly Ser Glu Glu Lys Gly Pro Glu
65                  70                  75                  80

Val Arg Glu Tyr Arg Glu Lys Val Glu Thr Glu Leu Gln Gly Val Cys
                85                  90                  95

Asp Thr Val Leu Gly Leu Leu Asp Ser His Leu Ile Lys Glu Ala Gly
            100                 105                 110

Asp Ala Glu Ser Arg Val Phe Tyr Leu Lys Met Lys Gly Asp Tyr Tyr
        115                 120                 125

Arg Tyr Leu Ala Glu Val Ala Thr Gly Asp Asp Lys Lys Arg Ile Ile
130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
210                 215                 220

Asp Asn Leu Thr Leu Trp Thr Ala Asp Asn Ala Gly Glu Glu Gly Gly
225                 230                 235                 240

Glu Ala Pro Gln Glu Pro Gln Ser
                245

<210> SEQ ID NO 24
<211> LENGTH: 245
<212> TYPE: PRT
<213> ORGANISM: HUMAN

<400> SEQUENCE: 24

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95
```

```
Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
210                 215                 220

Leu Thr Leu Trp Thr Ser Asp Thr Gln Gly Asp Glu Ala Glu Ala Gly
225                 230                 235                 240

Glu Gly Gly Glu Asn
                245

<210> SEQ ID NO 25
<211> LENGTH: 463
<212> TYPE: PRT
<213> ORGANISM: HUMAN

<400> SEQUENCE: 25

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
            20                  25                  30

Phe Lys Arg Ser Arg Asn Thr Asp Glu Met Val Glu Leu Arg Ile Leu
        35                  40                  45

Leu Gln Ser Lys Asn Ala Gly Ala Val Ile Gly Lys Gly Gly Lys Asn
    50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Gly Leu
            100                 105                 110

Gln Leu Pro Ser Pro Thr Ala Thr Ser Gln Leu Pro Leu Glu Ser Asp
        115                 120                 125

Ala Val Glu Cys Leu Asn Tyr Gln His Tyr Lys Gly Ser Asp Phe Asp
    130                 135                 140

Cys Glu Leu Arg Leu Leu Ile His Gln Ser Leu Ala Gly Gly Ile Ile
145                 150                 155                 160

Gly Val Lys Gly Ala Lys Ile Lys Glu Leu Arg Glu Asn Thr Gln Thr
                165                 170                 175

Thr Ile Lys Leu Phe Gln Glu Cys Cys Pro His Ser Thr Asp Arg Val
            180                 185                 190

Val Leu Ile Gly Gly Lys Pro Asp Arg Val Val Glu Cys Ile Lys Ile
        195                 200                 205

Ile Leu Asp Leu Ile Ser Glu Ser Pro Ile Lys Gly Arg Ala Gln Pro
    210                 215                 220
```

```
Tyr Asp Pro Asn Phe Tyr Asp Glu Thr Tyr Asp Tyr Gly Gly Phe Thr
225                 230                 235                 240

Met Met Phe Asp Asp Arg Arg Gly Arg Pro Val Gly Phe Pro Met Arg
            245                 250                 255

Gly Arg Gly Gly Phe Asp Arg Met Pro Pro Gly Arg Gly Gly Arg Pro
        260                 265                 270

Met Pro Pro Ser Arg Arg Asp Tyr Asp Asp Met Ser Pro Arg Arg Gly
    275                 280                 285

Pro Pro Pro Pro Pro Gly Arg Gly Gly Gly Ser Arg Ala
290                 295                 300

Arg Asn Leu Pro Leu Pro Pro Pro Pro Arg Gly Gly Asp Leu
305                 310                 315                 320

Met Ala Tyr Asp Arg Arg Gly Arg Pro Gly Asp Arg Tyr Asp Gly Met
                325                 330                 335

Val Gly Phe Ser Ala Asp Glu Thr Trp Asp Ser Ala Ile Asp Thr Trp
            340                 345                 350

Ser Pro Ser Glu Trp Gln Met Ala Tyr Glu Pro Gln Gly Gly Ser Gly
        355                 360                 365

Tyr Asp Tyr Ser Tyr Ala Gly Arg Gly Ser Tyr Gly Asp Leu Gly
    370                 375                 380

Gly Pro Ile Ile Thr Thr Gln Val Thr Ile Pro Lys Asp Leu Ala Gly
385                 390                 395                 400

Ser Ile Ile Gly Lys Gly Gly Gln Arg Ile Lys Gln Ile Arg His Glu
                405                 410                 415

Ser Gly Ala Ser Ile Lys Ile Asp Glu Pro Leu Glu Gly Ser Glu Asp
            420                 425                 430

Arg Ile Ile Thr Ile Thr Gly Thr Gln Asp Gln Ile Gln Asn Ala Gln
        435                 440                 445

Tyr Leu Leu Gln Asn Ser Val Lys Gln Tyr Ser Gly Lys Phe Phe
    450                 455                 460

<210> SEQ ID NO 26
<211> LENGTH: 63
<212> TYPE: PRT
<213> ORGANISM: HUMAN

<400> SEQUENCE: 26

Arg Arg Arg Thr Gly Leu Arg Lys Lys Lys Lys Leu Pro Arg Met
1               5                   10                  15

Glu Arg Arg Lys Met Lys Gly Lys Lys Lys Asp Glu Glu Glu Glu
                20                  25                  30

Glu Asp Asp Glu Gly Pro Ala Leu Lys Arg Ala Ala Glu Glu Glu Asp
            35                  40                  45

Glu Ala Asp Pro Lys Arg Gln Lys Thr Glu Asn Gly Ala Ser Ala
    50                  55                  60

<210> SEQ ID NO 27
<211> LENGTH: 98
<212> TYPE: PRT
<213> ORGANISM: HUMAN

<400> SEQUENCE: 27

Met Met Cys Gly Ala Pro Ser Ala Thr Gln Pro Ala Thr Ala Glu Thr
1               5                   10                  15

Gln His Ile Ala Asp Gln Val Arg Ser Gln Leu Glu Glu Lys Glu Asn
                20                  25                  30
```

```
Lys Lys Phe Pro Val Phe Lys Ala Val Ser Phe Lys Ser Gln Val Val
            35                  40                  45

Ala Gly Thr Asn Tyr Phe Ile Lys Val His Val Gly Asp Glu Asp Phe
 50                      55                  60

Val His Leu Arg Val Phe Gln Ser Leu Pro His Glu Asn Lys Pro Leu
 65                  70                  75                  80

Thr Leu Ser Asn Tyr Gln Thr Asn Lys Ala Lys His Asp Glu Leu Thr
                 85                  90                  95

Tyr Phe

<210> SEQ ID NO 28
<211> LENGTH: 281
<212> TYPE: PRT
<213> ORGANISM: HUMAN

<400> SEQUENCE: 28

Met Ser Arg Ile Ser Gln Met Thr Ala Ala Arg Ser Pro Pro Arg Leu
 1               5                  10                  15

His Met Ala Met Trp Ser Thr Arg Phe Ala Thr Ser Val Arg Thr Asn
            20                  25                  30

Ala Val Gln Arg Ile Leu Gly Gly His Leu Asp Ala Lys Gly Ser Phe
        35                  40                  45

Pro Trp Gln Ala Lys Met Val Ser His Asn Leu Thr Thr Gly Ala
 50                  55                  60

Thr Leu Ile Asn Glu Gln Trp Leu Leu Thr Thr Ala Lys Asn Leu Phe
 65                  70                  75                  80

Leu Asn His Ser Glu Asn Ala Thr Ala Lys Asp Ile Ala Pro Thr Leu
                 85                  90                  95

Thr Leu Tyr Val Gly Lys Lys Gln Leu Val Glu Ile Glu Lys Val Val
                100                 105                 110

Leu His Pro Asn Tyr Ser Gln Val Asp Ile Gly Leu Ile Lys Leu Lys
            115                 120                 125

Gln Lys Val Ser Val Asn Glu Arg Val Met Pro Ile Cys Leu Pro Ser
        130                 135                 140

Lys Asp Tyr Ala Glu Val Gly Arg Val Gly Tyr Val Ser Gly Trp Gly
145                 150                 155                 160

Arg Asn Ala Asn Phe Lys Phe Thr Asp His Leu Lys Tyr Val Met Leu
                165                 170                 175

Pro Val Ala Asp Gln Asp Gln Cys Ile Arg His Tyr Glu Gly Ser Thr
            180                 185                 190

Val Pro Glu Lys Lys Thr Pro Lys Ser Pro Val Gly Val Gln Pro Ile
        195                 200                 205

Leu Asn Glu His Thr Phe Cys Ala Gly Met Ser Lys Tyr Gln Glu Asp
    210                 215                 220

Thr Cys Tyr Gly Asp Ala Gly Ser Ala Phe Ala Val His Asp Leu Glu
225                 230                 235                 240

Glu Asp Thr Trp Tyr Ala Thr Gly Ile Leu Ser Phe Asp Lys Ser Cys
                245                 250                 255

Ala Val Ala Glu Tyr Gly Val Tyr Val Lys Val Thr Ser Ile Gln Asp
            260                 265                 270

Trp Val Gln Lys Thr Ile Ala Glu Asn
        275                 280

<210> SEQ ID NO 29
```

<211> LENGTH: 135
<212> TYPE: PRT
<213> ORGANISM: HUMAN

<400> SEQUENCE: 29

Met Ala Thr Val Gln Gln Leu Glu Gly Arg Trp Arg Leu Val Asp Ser
1               5                   10                  15

Lys Gly Phe Asp Glu Tyr Met Lys Glu Leu Gly Val Gly Ile Ala Leu
            20                  25                  30

Arg Lys Met Gly Ala Met Ala Lys Pro Asp Cys Ile Ile Thr Cys Asp
        35                  40                  45

Gly Lys Asn Leu Thr Ile Lys Thr Glu Ser Thr Leu Lys Thr Thr Gln
    50                  55                  60

Phe Ser Cys Thr Leu Gly Glu Lys Phe Glu Glu Thr Thr Ala Asp Gly
65                  70                  75                  80

Arg Lys Thr Gln Thr Val Cys Asn Phe Thr Asp Gly Ala Leu Val Gln
            85                  90                  95

His Gln Glu Trp Asp Gly Lys Glu Ser Thr Ile Thr Arg Lys Leu Lys
        100                 105                 110

Asp Gly Lys Leu Val Val Glu Cys Val Met Asn Asn Val Thr Cys Thr
    115                 120                 125

Arg Ile Tyr Glu Lys Val Glu
    130             135

<210> SEQ ID NO 30
<211> LENGTH: 470
<212> TYPE: PRT
<213> ORGANISM: HUMAN

<400> SEQUENCE: 30

Met Asp Trp Thr Trp Arg Phe Leu Phe Val Val Ala Ala Ala Thr Ser
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Asp Ser Phe
        35                  40                  45

Asn Ser Leu Ala Ile Asn Trp Val Arg Gln Ala Pro Gly Gln Gly Leu
    50                  55                  60

Glu Trp Met Gly Gly Ile Ile Pro Ile Phe Gly Thr Thr Asn Tyr Ala
65                  70                  75                  80

Gln Arg Phe Gln Gly Arg Val Thr Phe Thr Ala Asp Glu Ser Thr Gly
            85                  90                  95

Arg Ala Tyr Met Glu Leu Thr Ser Leu Arg Ser Glu Asp Thr Ala Val
        100                 105                 110

Tyr Tyr Cys Ala Ser Arg Phe Ile Ser Glu Thr Asn Phe Cys Phe Lys
    115                 120                 125

Phe Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
    195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 31
<211> LENGTH: 105
<212> TYPE: PRT
<213> ORGANISM: HUMAN

<400> SEQUENCE: 31

Met Ala Lys Ile Ser Ser Pro Thr Glu Thr Glu Arg Cys Ile Glu Ser
1               5                   10                  15

Leu Ile Ala Val Phe Gln Lys Tyr Ala Gly Lys Asp Gly Tyr Asn Tyr
            20                  25                  30

Thr Leu Ser Lys Thr Glu Phe Leu Ser Phe Met Asn Thr Glu Leu Ala
        35                  40                  45

Ala Phe Thr Lys Asn Gln Lys Asp Pro Gly Val Leu Asp Arg Met Met
    50                  55                  60

Lys Lys Leu Asp Thr Asn Ser Asp Gly Gln Leu Asp Phe Ser Glu Phe
65                  70                  75                  80

Leu Asn Leu Ile Gly Gly Leu Ala Met Ala Cys His Asp Ser Phe Leu
                85                  90                  95

Lys Ala Val Pro Ser Gln Lys Arg Thr

<210> SEQ ID NO 32
<211> LENGTH: 233
<212> TYPE: PRT
<213> ORGANISM: HUMAN

<400> SEQUENCE: 32

Met Ala Trp Thr Pro Leu Leu Pro Leu Leu Thr Phe Cys Thr Val
1               5                   10                  15

Ser Glu Ala Ser Tyr Glu Leu Thr Gln Pro Pro Ser Val Ser Val
            20                  25                  30

Ser Pro Gly Gln Thr Ala Arg Ile Thr Cys Ser Gly Asp Ala Leu Pro Lys
            35                  40                  45

Lys Tyr Ala Tyr Trp Tyr Gln Gln Lys Ser Gly Gln Thr Pro Val Leu
50                  55                  60

Val Ile Tyr Asp Asp Thr Glu Arg Pro Ser Gly Ile Pro Glu Arg Phe
65                  70                  75                  80

Ser Gly Ser Ser Ser Gly Thr Val Ala Thr Leu Thr Leu Ser Gly Ala
                85                  90                  95

Gln Val Glu Asp Glu Ala Asp Tyr Tyr Cys Tyr Ser Ser Asp Ser Ser
            100                 105                 110

Gly Asn His Trp Val Phe Gly Gly Gly Thr Lys Leu Thr Val Leu Gly
            115                 120                 125

Gln Pro Lys Ala Ala Pro Ser Val Thr Leu Phe Pro Pro Ser Ser Glu
130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
            195                 200                 205

His Arg Ser Tyr Ser Cys Gln Val Thr His Glu Gly Ser Thr Val Glu
        210                 215                 220

Lys Thr Val Ala Pro Thr Glu Cys Ser
225                 230

<210> SEQ ID NO 33
<211> LENGTH: 286
<212> TYPE: PRT
<213> ORGANISM: HUMAN

<400> SEQUENCE: 33

Met Ser Glu Glu Gln Phe Gly Gly Thr Gly Arg Arg His Ala Asn Gly
1               5                   10                  15

Gly Gly Arg Arg Ser Ala Gly Asp Glu Glu Gly Ala Met Val Ala Ala
            20                  25                  30

Thr Gln Gly Ala Ala Ala Ala Arg Glu Ala Asp Ala Gly Pro Gly Ala
            35                  40                  45

Glu Pro Arg Leu Glu Ala Pro Lys Gly Ser Ala Glu Ser Glu Gly Ala
        50                  55                  60

Lys Ile Asp Ala Ser Lys Asn Glu Glu Asp Glu Gly Lys Met Phe Ile
65                  70                  75                  80

Gly Gly Leu Ser Trp Asp Thr Thr Lys Lys Asp Leu Lys Asp Tyr Phe

```
                        85                  90                  95
Ser Lys Phe Gly Glu Val Val Asp Cys Thr Leu Lys Leu Asp Pro Ile
            100                 105                 110

Thr Gly Arg Ser Arg Gly Phe Gly Phe Val Leu Phe Lys Glu Ser Glu
            115                 120                 125

Ser Val Asp Lys Val Met Asp Gln Lys Glu His Lys Leu Asn Gly Lys
            130                 135                 140

Val Ile Asp Pro Lys Arg Ala Lys Ala Met Lys Thr Lys Glu Pro Val
145                 150                 155                 160

Lys Lys Ile Phe Val Gly Gly Leu Ser Pro Asp Thr Pro Glu Glu Lys
                    165                 170                 175

Ile Arg Glu Tyr Phe Gly Gly Phe Gly Glu Val Glu Ser Ile Glu Leu
                180                 185                 190

Pro Met Asp Asn Lys Thr Asn Lys Arg Arg Gly Phe Cys Phe Ile Thr
            195                 200                 205

Phe Lys Glu Glu Glu Pro Val Lys Lys Ile Met Glu Lys Lys Tyr His
            210                 215                 220

Asn Val Gly Leu Ser Lys Cys Glu Ile Lys Val Ala Met Ser Lys Glu
225                 230                 235                 240

Gln Tyr Gln Gln Gln Gln Trp Gly Ser Arg Gly Gly Phe Ala Gly
                    245                 250                 255

Arg Ala Arg Gly Glu Phe Arg Asn Ser Ser Glu Ala Gly Glu Gly Leu
                260                 265                 270

Glu Leu Pro Pro Asn Ser Ile His Cys Trp Gln Leu Ser Val
            275                 280                 285

<210> SEQ ID NO 34
<211> LENGTH: 372
<212> TYPE: PRT
<213> ORGANISM: HUMAN

<400> SEQUENCE: 34

Met Ser Lys Ser Glu Ser Pro Lys Glu Pro Glu Gln Leu Arg Lys Leu
1               5                   10                  15

Phe Ile Gly Gly Leu Ser Phe Glu Thr Thr Asp Glu Ser Leu Arg Ser
                20                  25                  30

His Phe Glu Gln Trp Gly Thr Leu Thr Asp Cys Val Val Met Arg Asp
            35                  40                  45

Pro Asn Thr Lys Arg Ser Arg Gly Phe Gly Phe Val Thr Tyr Ala Thr
        50                  55                  60

Val Glu Glu Val Asp Ala Ala Met Asn Ala Arg Pro His Lys Val Asp
65                  70                  75                  80

Gly Arg Val Val Glu Pro Lys Arg Ala Val Ser Arg Glu Asp Ser Gln
                    85                  90                  95

Arg Pro Gly Ala His Leu Thr Val Lys Lys Ile Phe Val Gly Gly Ile
            100                 105                 110

Lys Glu Asp Thr Glu Glu His His Leu Arg Asp Tyr Phe Glu Gln Tyr
            115                 120                 125

Gly Lys Ile Glu Val Ile Glu Ile Met Thr Asp Arg Gly Ser Gly Lys
            130                 135                 140

Lys Arg Gly Phe Ala Phe Val Thr Phe Asp Asp His Asp Ser Val Asp
145                 150                 155                 160

Lys Ile Val Ile Gln Lys Tyr His Thr Val Asn Gly His Asn Cys Glu
                    165                 170                 175
```

Val Arg Lys Ala Leu Ser Lys Gln Glu Met Ala Ser Ala Ser Ser
            180                 185                 190

Gln Arg Gly Arg Ser Gly Ser Gly Asn Phe Gly Gly Gly Arg Gly Gly
        195                 200                 205

Gly Phe Gly Gly Asn Asp Asn Phe Gly Arg Gly Gly Asn Phe Ser Gly
    210                 215                 220

Arg Gly Gly Phe Gly Gly Ser Arg Gly Gly Gly Tyr Gly Gly Ser
225                 230                 235                 240

Gly Asp Gly Tyr Asn Gly Phe Gly Asn Asp Gly Gly Tyr Gly Gly
                245                 250                 255

Gly Pro Gly Tyr Ser Gly Gly Ser Arg Gly Tyr Gly Ser Gly Gly Gln
            260                 265                 270

Gly Tyr Gly Asn Gln Gly Ser Gly Tyr Gly Gly Ser Gly Ser Tyr Asp
            275                 280                 285

Ser Tyr Asn Asn Gly Gly Gly Arg Gly Phe Gly Gly Gly Ser Gly Ser
        290                 295                 300

Asn Phe Gly Gly Gly Gly Ser Tyr Asn Asp Phe Gly Asn Tyr Asn Asn
305                 310                 315                 320

Gln Ser Ser Asn Phe Gly Pro Met Lys Gly Gly Asn Phe Gly Gly Arg
                325                 330                 335

Ser Ser Gly Pro Tyr Gly Gly Gly Gly Gln Tyr Phe Ala Lys Pro Arg
            340                 345                 350

Asn Gln Gly Gly Tyr Gly Gly Ser Ser Ser Ser Ser Ser Tyr Gly Ser
            355                 360                 365

Gly Arg Arg Phe
    370

<210> SEQ ID NO 35
<211> LENGTH: 205
<212> TYPE: PRT
<213> ORGANISM: HUMAN

<400> SEQUENCE: 35

Met Thr Glu Arg Arg Val Pro Phe Ser Leu Leu Arg Gly Pro Ser Trp
1               5                   10                  15

Asp Pro Phe Arg Asp Trp Tyr Pro His Ser Arg Leu Phe Asp Gln Ala
            20                  25                  30

Phe Gly Leu Pro Arg Leu Pro Glu Glu Trp Ser Gln Trp Leu Gly Gly
        35                  40                  45

Ser Ser Trp Pro Gly Tyr Val Arg Pro Leu Pro Pro Ala Ala Ile Glu
50                  55                  60

Ser Pro Ala Val Ala Ala Pro Ala Tyr Ser Arg Ala Leu Ser Arg Gln
65                  70                  75                  80

Leu Ser Ser Gly Val Ser Glu Ile Arg His Thr Ala Asp Arg Trp Arg
                85                  90                  95

Val Ser Leu Asp Val Asn His Phe Ala Pro Asp Glu Leu Thr Val Lys
            100                 105                 110

Thr Lys Asp Gly Val Val Glu Ile Thr Gly Lys His Glu Glu Arg Gln
        115                 120                 125

Asp Glu His Gly Tyr Ile Ser Arg Cys Phe Thr Arg Lys Tyr Thr Leu
    130                 135                 140

Pro Pro Gly Val Asp Pro Thr Gln Val Ser Ser Ser Leu Ser Pro Glu
145                 150                 155                 160

Gly Thr Leu Thr Val Glu Ala Pro Met Pro Lys Leu Ala Thr Gln Ser
                165                 170                 175

Asn Glu Ile Thr Ile Pro Val Thr Phe Glu Ser Arg Ala Gln Leu Gly
            180                 185                 190

Gly Pro Glu Ala Ala Lys Ser Asp Glu Thr Ala Ala Lys
            195                 200                 205

<210> SEQ ID NO 36
<211> LENGTH: 166
<212> TYPE: PRT
<213> ORGANISM: HUMAN

<400> SEQUENCE: 36

Met Ala Ser Gly Val Ala Val Ser Asp Gly Val Ile Lys Val Phe Asn
1               5                   10                  15

Asp Met Lys Val Arg Lys Ser Ser Thr Pro Glu Glu Val Lys Lys Arg
            20                  25                  30

Lys Lys Ala Val Leu Phe Cys Leu Ser Glu Asp Lys Lys Asn Ile Ile
            35                  40                  45

Leu Glu Glu Gly Lys Glu Ile Leu Val Gly Asp Val Gly Gln Thr Val
        50                  55                  60

Asp Asp Pro Tyr Ala Thr Phe Val Lys Met Leu Pro Asp Lys Asp Cys
65                  70                  75                  80

Arg Tyr Ala Leu Tyr Asp Ala Thr Tyr Glu Thr Lys Glu Ser Lys Lys
                85                  90                  95

Glu Asp Leu Val Phe Ile Phe Trp Ala Pro Glu Ser Ala Pro Leu Lys
            100                 105                 110

Ser Lys Met Ile Tyr Ala Ser Ser Lys Asp Ala Ile Lys Lys Lys Leu
            115                 120                 125

Thr Gly Ile Lys His Glu Leu Gln Ala Asn Cys Tyr Glu Glu Val Lys
        130                 135                 140

Asp Arg Cys Thr Leu Ala Glu Lys Leu Gly Gly Ser Ala Val Ile Ser
145                 150                 155                 160

Leu Glu Gly Lys Pro Leu
                165

<210> SEQ ID NO 37
<211> LENGTH: 335
<212> TYPE: PRT
<213> ORGANISM: HUMAN

<400> SEQUENCE: 37

Met Gly Lys Val Lys Val Gly Val Asn Gly Phe Gly Arg Ile Gly Arg
1               5                   10                  15

Leu Val Thr Arg Ala Ala Phe Asn Ser Gly Lys Val Asp Ile Val Ala
            20                  25                  30

Ile Asn Asp Pro Phe Ile Asp Leu Asn Tyr Met Val Tyr Met Phe Gln
            35                  40                  45

Tyr Asp Ser Thr His Gly Lys Phe His Gly Thr Val Lys Ala Glu Asn
        50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
            100                 105                 110

Gln Gly Gly Ala Lys Arg Val Ile Ile Ser Ala Pro Ser Ala Asp Ala
            115                 120                 125

```
Pro Met Phe Val Met Gly Val Asn His Glu Lys Tyr Asp Asn Ser Leu
    130                 135                 140

Lys Ile Ile Ser Asn Ala Ser Cys Thr Thr Asn Cys Leu Ala Pro Leu
145                 150                 155                 160

Ala Lys Val Ile His Asp Asn Phe Gly Ile Val Glu Gly Leu Met Thr
                165                 170                 175

Thr Val His Ala Ile Thr Ala Thr Gln Lys Thr Val Asp Gly Pro Ser
            180                 185                 190

Gly Lys Leu Trp Arg Asp Gly Arg Gly Ala Leu Gln Asn Ile Ile Pro
        195                 200                 205

Ala Ser Thr Gly Ala Ala Lys Ala Val Gly Lys Val Ile Pro Glu Leu
    210                 215                 220

Asp Gly Lys Leu Thr Gly Met Ala Phe Arg Val Pro Thr Ala Asn Val
225                 230                 235                 240

Ser Val Val Asp Leu Thr Cys Arg Leu Glu Lys Pro Ala Lys Tyr Asp
                245                 250                 255

Asp Ile Lys Lys Val Val Lys Gln Ala Ser Glu Gly Pro Leu Lys Gly
            260                 265                 270

Ile Leu Gly Tyr Thr Glu His Gln Val Val Ser Ser Asp Phe Asn Ser
        275                 280                 285

Asp Thr His Ser Ser Thr Phe Asp Ala Gly Ala Gly Ile Ala Leu Asn
    290                 295                 300

Asp His Phe Val Lys Leu Ile Ser Trp Tyr Asp Asn Glu Phe Gly Tyr
305                 310                 315                 320

Ser Asn Arg Val Val Asp Leu Met Ala His Met Ala Ser Lys Glu
                325                 330                 335

<210> SEQ ID NO 38
<211> LENGTH: 152
<212> TYPE: PRT
<213> ORGANISM: HUMAN

<400> SEQUENCE: 38

Met Ala Asn Leu Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Ala Met Lys Phe Leu Arg Ala Ser Glu Glu His Leu
        35                  40                  45

Lys Gln His Tyr Ile Asp Leu Lys Asp Arg Pro Phe Phe Pro Gly Leu
    50                  55                  60

Val Lys Tyr Met Asn Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Lys Ser Ala Glu Lys
        115                 120                 125

Glu Ile Ser Leu Trp Phe Lys Pro Glu Glu Leu Val Asp Tyr Lys Ser
    130                 135                 140

Cys Ala His Asp Trp Val Tyr Glu
145                 150
```

<210> SEQ ID NO 39
<211> LENGTH: 858
<212> TYPE: PRT
<213> ORGANISM: HUMAN

<400> SEQUENCE: 39

```
Met Val Asn Phe Thr Val Asp Gln Ile Arg Ala Ile Met Asp Lys Lys
1               5                   10                  15

Ala Asn Ile Arg Asn Met Ser Val Ile Ala His Val Asp His Gly Lys
            20                  25                  30

Ser Thr Leu Thr Asp Ser Leu Val Cys Lys Ala Gly Ile Ile Ala Ser
        35                  40                  45

Ala Arg Ala Gly Glu Thr Arg Phe Thr Asp Thr Arg Lys Asp Glu Gln
    50                  55                  60

Glu Arg Cys Ile Thr Ile Lys Ser Thr Ala Ile Ser Leu Phe Tyr Glu
65                  70                  75                  80

Leu Ser Glu Asn Asp Leu Asn Phe Ile Lys Gln Ser Lys Asp Gly Ala
                85                  90                  95

Gly Phe Leu Ile Asn Leu Ile Asp Ser Pro Gly His Val Asp Phe Ser
            100                 105                 110

Ser Glu Val Thr Ala Ala Leu Arg Val Thr Asp Gly Ala Leu Val Val
        115                 120                 125

Val Asp Cys Val Ser Gly Val Cys Val Gln Thr Glu Thr Val Leu Arg
    130                 135                 140

Gln Ala Ile Ala Glu Arg Ile Lys Pro Val Leu Met Met Asn Lys Met
145                 150                 155                 160

Asp Arg Ala Leu Leu Glu Leu Gln Leu Glu Pro Glu Glu Leu Tyr Gln
                165                 170                 175

Thr Phe Gln Arg Ile Val Glu Asn Val Asn Val Ile Ile Ser Thr Tyr
            180                 185                 190

Gly Glu Gly Glu Ser Gly Pro Met Gly Asn Ile Met Ile Asp Pro Val
        195                 200                 205

Leu Gly Thr Val Gly Phe Gly Ser Gly Leu His Gly Trp Ala Phe Thr
    210                 215                 220

Leu Lys Gln Phe Ala Glu Met Tyr Val Ala Lys Phe Ala Ala Lys Gly
225                 230                 235                 240

Glu Gly Gln Leu Gly Pro Ala Glu Arg Ala Lys Lys Val Glu Asp Met
                245                 250                 255

Met Lys Lys Leu Trp Gly Asp Arg Tyr Phe Asp Pro Ala Asn Gly Lys
            260                 265                 270

Phe Ser Lys Ser Ala Thr Ser Pro Glu Gly Lys Lys Leu Pro Arg Thr
        275                 280                 285

Phe Cys Gln Leu Ile Leu Asp Pro Ile Phe Lys Val Phe Asp Ala Ile
    290                 295                 300

Met Asn Phe Lys Lys Glu Glu Thr Ala Lys Leu Ile Glu Lys Leu Asp
305                 310                 315                 320

Ile Lys Leu Asp Ser Glu Asp Lys Asp Lys Glu Gly Lys Pro Leu Leu
                325                 330                 335

Lys Ala Val Met Arg Arg Trp Leu Pro Ala Gly Asp Ala Leu Leu Gln
            340                 345                 350

Met Ile Thr Ile His Leu Pro Ser Pro Val Thr Ala Gln Lys Tyr Arg
        355                 360                 365

Cys Glu Leu Leu Tyr Glu Gly Pro Pro Asp Asp Glu Ala Ala Met Gly
    370                 375                 380
```

```
Ile Lys Ser Cys Asp Pro Lys Gly Pro Leu Met Tyr Ile Ser Lys
385                 390                 395                 400

Met Val Pro Thr Ser Asp Lys Gly Arg Phe Tyr Ala Phe Gly Arg Val
            405                 410                 415

Phe Ser Gly Leu Val Ser Thr Gly Leu Lys Val Arg Ile Met Gly Pro
        420                 425                 430

Asn Tyr Thr Pro Gly Lys Lys Glu Asp Leu Tyr Leu Lys Pro Ile Gln
            435                 440                 445

Arg Thr Ile Leu Met Met Gly Arg Tyr Val Glu Pro Ile Glu Asp Val
    450                 455                 460

Pro Cys Gly Asn Ile Val Gly Leu Val Gly Val Asp Gln Phe Leu Val
465                 470                 475                 480

Lys Thr Gly Thr Ile Thr Thr Phe Glu His Ala His Asn Met Arg Val
            485                 490                 495

Met Lys Phe Ser Val Ser Pro Val Val Arg Val Ala Val Glu Ala Lys
            500                 505                 510

Asn Pro Ala Asp Leu Pro Lys Leu Val Glu Gly Leu Lys Arg Leu Ala
            515                 520                 525

Lys Ser Asp Pro Met Val Gln Cys Ile Ile Glu Glu Ser Gly Glu His
530                 535                 540

Ile Ile Ala Gly Ala Gly Glu Leu His Leu Glu Ile Cys Leu Lys Asp
545                 550                 555                 560

Leu Glu Glu Asp His Ala Cys Ile Pro Ile Lys Lys Ser Asp Pro Val
                565                 570                 575

Val Ser Tyr Arg Glu Thr Val Ser Glu Glu Ser Asn Val Leu Cys Leu
            580                 585                 590

Ser Lys Ser Pro Asn Lys His Asn Arg Leu Tyr Met Lys Ala Arg Pro
            595                 600                 605

Phe Pro Asp Gly Leu Ala Glu Asp Ile Asp Lys Gly Glu Val Ser Ala
            610                 615                 620

Arg Gln Glu Leu Lys Gln Arg Ala Arg Tyr Leu Ala Glu Lys Tyr Glu
625                 630                 635                 640

Trp Asp Val Ala Glu Ala Arg Lys Ile Trp Cys Phe Gly Pro Asp Gly
                645                 650                 655

Thr Gly Pro Asn Ile Leu Thr Asp Ile Thr Lys Gly Val Gln Tyr Leu
            660                 665                 670

Asn Glu Ile Lys Asp Ser Val Val Ala Gly Phe Gln Trp Ala Thr Lys
            675                 680                 685

Glu Gly Ala Leu Cys Glu Glu Asn Met Arg Gly Val Arg Phe Asp Val
            690                 695                 700

His Asp Val Thr Leu His Ala Asp Ala Ile His Arg Gly Gly Gly Gln
705                 710                 715                 720

Ile Ile Pro Thr Ala Arg Arg Cys Leu Tyr Ala Ser Val Leu Thr Ala
                725                 730                 735

Gln Pro Arg Leu Met Glu Pro Ile Tyr Leu Val Glu Ile Gln Cys Pro
            740                 745                 750

Glu Gln Val Val Gly Gly Ile Tyr Gly Val Leu Asn Arg Lys Arg Gly
                755                 760                 765

His Val Phe Glu Glu Ser Gln Val Ala Gly Thr Pro Met Phe Val Val
            770                 775                 780

Lys Ala Tyr Leu Pro Val Asn Glu Ser Phe Gly Phe Thr Ala Asp Leu
785                 790                 795                 800

Arg Ser Asn Thr Gly Gly Gln Ala Phe Pro Gln Cys Val Phe Asp His
```

```
                        805                 810                 815
Trp Gln Ile Leu Pro Gly Asp Pro Phe Asp Asn Ser Ser Arg Pro Ser
                    820                 825                 830

Gln Val Val Ala Glu Thr Arg Lys Arg Lys Gly Leu Lys Glu Gly Ile
                835                 840                 845

Pro Ala Leu Asp Asn Phe Leu Asp Lys Leu
            850                 855
```

<210> SEQ ID NO 40
<211> LENGTH: 187
<212> TYPE: PRT
<213> ORGANISM: HUMAN

<400> SEQUENCE: 40

```
Met Pro Val Asp Leu Ser Lys Trp Ser Gly Pro Leu Ser Leu Gln Glu
1               5                   10                  15

Val Asp Glu Gln Pro Gln His Pro Leu His Val Thr Tyr Ala Gly Ala
            20                  25                  30

Ala Val Asp Glu Leu Gly Lys Val Leu Thr Pro Thr Gln Val Lys Asn
        35                  40                  45

Arg Pro Thr Ser Ile Ser Trp Asp Gly Leu Asp Ser Gly Lys Leu Tyr
    50                  55                  60

Thr Leu Val Leu Thr Asp Pro Asp Ala Pro Ser Arg Lys Asp Pro Lys
65                  70                  75                  80

Tyr Arg Glu Trp His His Phe Leu Val Val Asn Met Lys Gly Asn Asp
                85                  90                  95

Ile Ser Ser Gly Thr Val Leu Ser Asp Tyr Val Gly Ser Gly Pro Pro
            100                 105                 110

Lys Gly Thr Gly Leu His Arg Tyr Val Trp Leu Val Tyr Glu Gln Asp
        115                 120                 125

Arg Pro Leu Lys Cys Asp Glu Pro Ile Leu Ser Asn Arg Ser Gly Asp
    130                 135                 140

His Arg Gly Lys Phe Lys Val Ala Ser Phe Arg Lys Lys Tyr Glu Leu
145                 150                 155                 160

Arg Ala Pro Val Ala Gly Thr Cys Tyr Gln Ala Glu Trp Asp Asp Tyr
                165                 170                 175

Val Pro Lys Leu Tyr Glu Gln Leu Ser Gly Lys
            180                 185
```

<210> SEQ ID NO 41
<211> LENGTH: 149
<212> TYPE: PRT
<213> ORGANISM: HUMAN

<400> SEQUENCE: 41

```
Met Ala Asp Gln Leu Thr Glu Glu Gln Val Thr Glu Phe Lys Glu Ala
1               5                   10                  15

Phe Ser Leu Phe Asp Lys Asp Gly Asp Gly Cys Ile Thr Thr Arg Glu
            20                  25                  30

Leu Gly Thr Val Met Arg Ser Leu Gly Gln Asn Pro Thr Glu Ala Glu
        35                  40                  45

Leu Arg Asp Met Met Ser Glu Ile Asp Arg Asp Gly Asn Gly Thr Val
    50                  55                  60

Asp Phe Pro Glu Phe Leu Gly Met Met Ala Arg Lys Met Lys Asp Thr
65                  70                  75                  80

Asp Asn Glu Glu Glu Ile Arg Glu Ala Phe Arg Val Phe Asp Lys Asp
```

```
                    85                  90                  95
Gly Asn Gly Phe Val Ser Ala Ala Glu Leu Arg His Val Met Thr Arg
                100                 105                 110

Leu Gly Glu Lys Leu Ser Asp Glu Glu Val Asp Glu Met Ile Arg Ala
            115                 120                 125

Ala Asp Thr Asp Gly Asp Gly Gln Val Asn Tyr Glu Glu Phe Val Arg
        130                 135                 140

Val Leu Val Ser Lys
145

<210> SEQ ID NO 42
<211> LENGTH: 19
<212> TYPE: PRT
<213> ORGANISM: HUMAN

<400> SEQUENCE: 42

Ala Phe Leu Ala Ser Pro Glu Tyr Val Asn Leu Pro Ile Asn Gly Asn
1               5                   10                  15

Gly Lys Gln

<210> SEQ ID NO 43
<211> LENGTH: 19
<212> TYPE: PRT
<213> ORGANISM: HUMAN

<400> SEQUENCE: 43

Asp Gln Gln Glu Ala Ala Leu Val Asp Met Val Asn Asp Gly Val Glu
1               5                   10                  15

Asp Leu Arg

<210> SEQ ID NO 44
<211> LENGTH: 16
<212> TYPE: PRT
<213> ORGANISM: HUMAN

<400> SEQUENCE: 44

Phe Gln Asp Gly Asp Leu Thr Leu Tyr Gln Ser Asn Thr Ile Leu Arg
1               5                   10                  15

<210> SEQ ID NO 45
<211> LENGTH: 11
<212> TYPE: PRT
<213> ORGANISM: HUMAN

<400> SEQUENCE: 45

Met Leu Leu Ala Asp Gln Gly Gln Ser Trp Lys
1               5                   10

<210> SEQ ID NO 46
<211> LENGTH: 11
<212> TYPE: PRT
<213> ORGANISM: HUMAN

<400> SEQUENCE: 46

Pro Pro Tyr Thr Val Val Tyr Phe Pro Val Arg
1               5                   10

<210> SEQ ID NO 47
<211> LENGTH: 26
<212> TYPE: PRT
<213> ORGANISM: HUMAN
```

```
<400> SEQUENCE: 47

Thr Leu Gly Leu Tyr Gly Lys Asp Gln Gln Glu Ala Ala Leu Val Asp
1               5                   10                  15

Met Val Asn Asp Gly Val Glu Asp Leu Arg
            20                  25

<210> SEQ ID NO 48
<211> LENGTH: 9
<212> TYPE: PRT
<213> ORGANISM: HUMAN

<400> SEQUENCE: 48

Asp Gln Leu Ile Tyr Asn Leu Leu Lys
1               5

<210> SEQ ID NO 49
<211> LENGTH: 8
<212> TYPE: PRT
<213> ORGANISM: HUMAN

<400> SEQUENCE: 49

Phe Ile Ile Pro Asn Val Val Lys
1               5

<210> SEQ ID NO 50
<211> LENGTH: 14
<212> TYPE: PRT
<213> ORGANISM: HUMAN

<400> SEQUENCE: 50

Gly Glu Met Met Asp Leu Gln His Gly Ser Leu Phe Leu Arg
1               5                   10

<210> SEQ ID NO 51
<211> LENGTH: 9
<212> TYPE: PRT
<213> ORGANISM: HUMAN

<400> SEQUENCE: 51

Leu Val Ile Ile Thr Ala Gly Ala Arg
1               5

<210> SEQ ID NO 52
<211> LENGTH: 11
<212> TYPE: PRT
<213> ORGANISM: HUMAN

<400> SEQUENCE: 52

Gln Val Val Glu Ser Ala Tyr Glu Val Ile Lys
1               5                   10

<210> SEQ ID NO 53
<211> LENGTH: 12
<212> TYPE: PRT
<213> ORGANISM: HUMAN

<400> SEQUENCE: 53

Val Ile Gly Ser Gly Cys Asn Leu Asp Ser Ala Arg
1               5                   10

<210> SEQ ID NO 54
<211> LENGTH: 10
<212> TYPE: PRT
<213> ORGANISM: HUMAN
```

<400> SEQUENCE: 54

Val Thr Leu Thr Ser Glu Glu Glu Ala Arg
1               5                   10

<210> SEQ ID NO 55
<211> LENGTH: 8
<212> TYPE: PRT
<213> ORGANISM: HUMAN

<400> SEQUENCE: 55

Ala Val Leu Thr Ile Asp Glu Lys
1               5

<210> SEQ ID NO 56
<211> LENGTH: 16
<212> TYPE: PRT
<213> ORGANISM: HUMAN

<400> SEQUENCE: 56

Asp Thr Glu Glu Glu Asp Phe His Val Asp Gln Val Thr Thr Val Lys
1               5                   10                  15

<210> SEQ ID NO 57
<211> LENGTH: 8
<212> TYPE: PRT
<213> ORGANISM: HUMAN

<400> SEQUENCE: 57

Phe Leu Glu Asn Glu Asp Arg Arg
1               5

<210> SEQ ID NO 58
<211> LENGTH: 15
<212> TYPE: PRT
<213> ORGANISM: HUMAN

<400> SEQUENCE: 58

Gly Thr Glu Ala Ala Gly Ala Met Phe Leu Glu Ala Ile Pro Met
1               5                   10                  15

<210> SEQ ID NO 59
<211> LENGTH: 22
<212> TYPE: PRT
<213> ORGANISM: HUMAN

<400> SEQUENCE: 59

Gly Thr Glu Ala Ala Gly Ala Met Phe Leu Glu Ala Ile Pro Met Ser
1               5                   10                  15

Ile Pro Pro Glu Val Lys
            20

<210> SEQ ID NO 60
<211> LENGTH: 15
<212> TYPE: PRT
<213> ORGANISM: HUMAN

<400> SEQUENCE: 60

Leu Gln His Leu Glu Asn Glu Leu Thr His Asp Ile Ile Thr Lys
1               5                   10                  15

<210> SEQ ID NO 61
<211> LENGTH: 10
<212> TYPE: PRT

```
<213> ORGANISM: HUMAN

<400> SEQUENCE: 61

Ser Val Leu Gly Gln Leu Gly Ile Thr Lys
1               5                   10

<210> SEQ ID NO 62
<211> LENGTH: 15
<212> TYPE: PRT
<213> ORGANISM: HUMAN

<400> SEQUENCE: 62

Thr Asp Thr Ser His His Asp Gln Asp His Pro Thr Phe Asn Lys
1               5                   10                  15

<210> SEQ ID NO 63
<211> LENGTH: 18
<212> TYPE: PRT
<213> ORGANISM: HUMAN

<400> SEQUENCE: 63

Val Phe Ser Asn Gly Ala Asp Leu Ser Gly Val Thr Glu Glu Ala Pro
1               5                   10                  15

Leu Lys

<210> SEQ ID NO 64
<211> LENGTH: 22
<212> TYPE: PRT
<213> ORGANISM: HUMAN

<400> SEQUENCE: 64

Cys Gly Ala Pro Ser Ala Thr Gln Pro Ala Thr Ala Glu Thr Gln His
1               5                   10                  15

Ile Ala Asp Gln Val Arg
            20

<210> SEQ ID NO 65
<211> LENGTH: 21
<212> TYPE: PRT
<213> ORGANISM: HUMAN

<400> SEQUENCE: 65

Gly Ala Pro Ser Ala Thr Gln Pro Ala Thr Ala Glu Thr Gln His Ile
1               5                   10                  15

Ala Asp Gln Val Arg
            20

<210> SEQ ID NO 66
<211> LENGTH: 24
<212> TYPE: PRT
<213> ORGANISM: HUMAN

<400> SEQUENCE: 66

Met Met Cys Gly Ala Pro Ser Ala Thr Gln Pro Ala Thr Ala Glu Thr
1               5                   10                  15

Gln His Ile Ala Asp Gln Val Arg
            20

<210> SEQ ID NO 67
<211> LENGTH: 19
<212> TYPE: PRT
<213> ORGANISM: HUMAN
```

-continued

```
<400> SEQUENCE: 67

Pro Ser Ala Thr Gln Pro Ala Thr Ala Glu Thr Gln His Ile Ala Asp
1               5                   10                  15

Gln Val Arg

<210> SEQ ID NO 68
<211> LENGTH: 12
<212> TYPE: PRT
<213> ORGANISM: HUMAN

<400> SEQUENCE: 68

Ser Gln Val Val Ala Gly Thr Asn Tyr Phe Ile Lys
1               5                   10

<210> SEQ ID NO 69
<211> LENGTH: 12
<212> TYPE: PRT
<213> ORGANISM: HUMAN

<400> SEQUENCE: 69

Val His Val Gly Asp Glu Asp Phe Val His Leu Arg
1               5                   10

<210> SEQ ID NO 70
<211> LENGTH: 8
<212> TYPE: PRT
<213> ORGANISM: HUMAN

<400> SEQUENCE: 70

Ala Leu Tyr Glu Ala Gly Glu Arg
1               5

<210> SEQ ID NO 71
<211> LENGTH: 11
<212> TYPE: PRT
<213> ORGANISM: HUMAN

<400> SEQUENCE: 71

Asp Ile Thr Ser Asp Thr Ser Gly Asp Phe Arg
1               5                   10

<210> SEQ ID NO 72
<211> LENGTH: 16
<212> TYPE: PRT
<213> ORGANISM: HUMAN

<400> SEQUENCE: 72

Gly Leu Gly Thr Asp Glu Asp Thr Leu Ile Glu Ile Leu Ala Ser Arg
1               5                   10                  15

<210> SEQ ID NO 73
<211> LENGTH: 14
<212> TYPE: PRT
<213> ORGANISM: HUMAN

<400> SEQUENCE: 73

Gly Thr Asp Val Asn Val Phe Asn Thr Ile Leu Thr Thr Arg
1               5                   10

<210> SEQ ID NO 74
<211> LENGTH: 13
<212> TYPE: PRT
<213> ORGANISM: HUMAN
```

<400> SEQUENCE: 74

Gly Val Asp Glu Ala Thr Ile Ile Asp Ile Leu Thr Lys
1               5                   10

<210> SEQ ID NO 75
<211> LENGTH: 15
<212> TYPE: PRT
<213> ORGANISM: HUMAN

<400> SEQUENCE: 75

Lys Gly Thr Asp Val Asn Val Phe Asn Thr Ile Leu Thr Thr Arg
1               5                   10                  15

<210> SEQ ID NO 76
<211> LENGTH: 8
<212> TYPE: PRT
<213> ORGANISM: HUMAN

<400> SEQUENCE: 76

Asn Ala Leu Leu Ser Leu Ala Lys
1               5

<210> SEQ ID NO 77
<211> LENGTH: 17
<212> TYPE: PRT
<213> ORGANISM: HUMAN

<400> SEQUENCE: 77

Gln Ala Trp Phe Ile Glu Asn Glu Glu Gln Glu Tyr Val Gln Thr Val
1               5                   10                  15

Lys

<210> SEQ ID NO 78
<211> LENGTH: 11
<212> TYPE: PRT
<213> ORGANISM: HUMAN

<400> SEQUENCE: 78

Thr Pro Ala Gln Phe Asp Ala Asp Glu Leu Arg
1               5                   10

<210> SEQ ID NO 79
<211> LENGTH: 13
<212> TYPE: PRT
<213> ORGANISM: HUMAN

<400> SEQUENCE: 79

Ala Ala Glu Asp Asp Glu Asp Asp Val Asp Thr Lys
1               5                   10

<210> SEQ ID NO 80
<211> LENGTH: 14
<212> TYPE: PRT
<213> ORGANISM: HUMAN

<400> SEQUENCE: 80

Ala Ala Glu Asp Asp Glu Asp Asp Val Asp Thr Lys Lys
1               5                   10

<210> SEQ ID NO 81
<211> LENGTH: 10
<212> TYPE: PRT
<213> ORGANISM: HUMAN

```
<400> SEQUENCE: 81

Glu Val Val Glu Glu Ala Glu Asn Gly Arg
1               5                   10

<210> SEQ ID NO 82
<211> LENGTH: 11
<212> TYPE: PRT
<213> ORGANISM: HUMAN

<400> SEQUENCE: 82

Lys Glu Val Val Glu Glu Ala Glu Asn Gly Arg
1               5                   10

<210> SEQ ID NO 83
<211> LENGTH: 14
<212> TYPE: PRT
<213> ORGANISM: HUMAN

<400> SEQUENCE: 83

Ser Asp Ala Ala Val Asp Thr Ser Ser Glu Ile Thr Thr Lys
1               5                   10

<210> SEQ ID NO 84
<211> LENGTH: 13
<212> TYPE: PRT
<213> ORGANISM: HUMAN

<400> SEQUENCE: 84

Asp Phe Glu Pro Ser Leu Gly Pro Val Cys Pro Phe Arg
1               5                   10

<210> SEQ ID NO 85
<211> LENGTH: 15
<212> TYPE: PRT
<213> ORGANISM: HUMAN

<400> SEQUENCE: 85

Asp Leu Pro Pro Asp Thr Thr Leu Leu Asp Leu Gln Asn Asn Lys
1               5                   10                  15

<210> SEQ ID NO 86
<211> LENGTH: 8
<212> TYPE: PRT
<213> ORGANISM: HUMAN

<400> SEQUENCE: 86

Glu Leu His Leu Asp Asn Asn Lys
1               5

<210> SEQ ID NO 87
<211> LENGTH: 11
<212> TYPE: PRT
<213> ORGANISM: HUMAN

<400> SEQUENCE: 87

Val Ser Pro Gly Ala Phe Thr Pro Leu Val Lys
1               5                   10

<210> SEQ ID NO 88
<211> LENGTH: 9
<212> TYPE: PRT
<213> ORGANISM: HUMAN

<400> SEQUENCE: 88
```

-continued

```
Ala Asp Leu Ser Glu Ala Ala Asn Arg
1               5

<210> SEQ ID NO 89
<211> LENGTH: 16
<212> TYPE: PRT
<213> ORGANISM: HUMAN

<400> SEQUENCE: 89

Asp Gly Gln Val Ile Asn Glu Thr Ser Gln His His Asp Asp Leu Glu
1               5                   10                  15

<210> SEQ ID NO 90
<211> LENGTH: 9
<212> TYPE: PRT
<213> ORGANISM: HUMAN

<400> SEQUENCE: 90

Asp Asn Leu Ala Glu Asp Ile Met Arg
1               5

<210> SEQ ID NO 91
<211> LENGTH: 11
<212> TYPE: PRT
<213> ORGANISM: HUMAN

<400> SEQUENCE: 91

Glu Glu Ala Glu Asn Thr Leu Gln Ser Phe Arg
1               5                   10

<210> SEQ ID NO 92
<211> LENGTH: 10
<212> TYPE: PRT
<213> ORGANISM: HUMAN

<400> SEQUENCE: 92

Glu Lys Leu Gln Glu Met Leu Gln Arg
1               5                   10

<210> SEQ ID NO 93
<211> LENGTH: 19
<212> TYPE: PRT
<213> ORGANISM: HUMAN

<400> SEQUENCE: 93

Glu Met Glu Glu Asn Phe Ala Val Glu Ala Ala Asn Tyr Gln Asp Thr
1               5                   10                  15

Ile Gly Arg

<210> SEQ ID NO 94
<211> LENGTH: 15
<212> TYPE: PRT
<213> ORGANISM: HUMAN

<400> SEQUENCE: 94

Glu Thr Asn Leu Asp Ser Leu Pro Leu Val Asp Thr His Ser Lys
1               5                   10                  15

<210> SEQ ID NO 95
<211> LENGTH: 9
<212> TYPE: PRT
<213> ORGANISM: HUMAN

<400> SEQUENCE: 95
```

```
Glu Tyr Gln Asp Leu Leu Asn Val Lys
1               5

<210> SEQ ID NO 96
<211> LENGTH: 10
<212> TYPE: PRT
<213> ORGANISM: HUMAN

<400> SEQUENCE: 96

Phe Ala Asp Leu Ser Glu Ala Ala Asn Arg
1               5                   10

<210> SEQ ID NO 97
<211> LENGTH: 10
<212> TYPE: PRT
<213> ORGANISM: HUMAN

<400> SEQUENCE: 97

Ile Leu Leu Ala Glu Leu Glu Gln Leu Lys
1               5                   10

<210> SEQ ID NO 98
<211> LENGTH: 14
<212> TYPE: PRT
<213> ORGANISM: HUMAN

<400> SEQUENCE: 98

Ile Ser Leu Pro Leu Pro Asn Phe Ser Ser Leu Asn Leu Arg
1               5                   10

<210> SEQ ID NO 99
<211> LENGTH: 9
<212> TYPE: PRT
<213> ORGANISM: HUMAN

<400> SEQUENCE: 99

Lys Leu Leu Glu Gly Glu Glu Ser Arg
1               5

<210> SEQ ID NO 100
<211> LENGTH: 10
<212> TYPE: PRT
<213> ORGANISM: HUMAN

<400> SEQUENCE: 100

Leu Gly Asp Leu Tyr Glu Glu Glu Met Arg
1               5                   10

<210> SEQ ID NO 101
<211> LENGTH: 8
<212> TYPE: PRT
<213> ORGANISM: HUMAN

<400> SEQUENCE: 101

Leu Leu Glu Gly Glu Glu Ser Arg
1               5

<210> SEQ ID NO 102
<211> LENGTH: 19
<212> TYPE: PRT
<213> ORGANISM: HUMAN

<400> SEQUENCE: 102

Leu Leu Gln Asp Ser Val Asp Phe Ser Leu Ala Asp Ala Ile Asn Thr
1               5                   10                  15
```

```
Glu Phe Lys

<210> SEQ ID NO 103
<211> LENGTH: 9
<212> TYPE: PRT
<213> ORGANISM: HUMAN

<400> SEQUENCE: 103

Leu Gln Asp Glu Ile Gln Asn Met Lys
1               5

<210> SEQ ID NO 104
<211> LENGTH: 14
<212> TYPE: PRT
<213> ORGANISM: HUMAN

<400> SEQUENCE: 104

Leu Gln Asp Glu Ile Gln Asn Met Lys Glu Glu Met Ala Arg
1               5                   10

<210> SEQ ID NO 105
<211> LENGTH: 8
<212> TYPE: PRT
<213> ORGANISM: HUMAN

<400> SEQUENCE: 105

Leu Gln Glu Glu Met Leu Gln Arg
1               5

<210> SEQ ID NO 106
<211> LENGTH: 13
<212> TYPE: PRT
<213> ORGANISM: HUMAN

<400> SEQUENCE: 106

Asn Leu Asp Ser Leu Pro Leu Val Asp Thr His Ser Lys
1               5                   10

<210> SEQ ID NO 107
<211> LENGTH: 10
<212> TYPE: PRT
<213> ORGANISM: HUMAN

<400> SEQUENCE: 107

Asn Leu Gln Glu Ala Glu Glu Trp Tyr Lys
1               5                   10

<210> SEQ ID NO 108
<211> LENGTH: 10
<212> TYPE: PRT
<213> ORGANISM: HUMAN

<400> SEQUENCE: 108

Gln Asp Val Asp Asn Ala Ser Leu Ala Arg
1               5                   10

<210> SEQ ID NO 109
<211> LENGTH: 9
<212> TYPE: PRT
<213> ORGANISM: HUMAN

<400> SEQUENCE: 109

Gln Gln Tyr Glu Ser Val Ala Ala Lys
1               5
```

```
<210> SEQ ID NO 110
<211> LENGTH: 9
<212> TYPE: PRT
<213> ORGANISM: HUMAN

<400> SEQUENCE: 110

Gln Val Asp Gln Leu Thr Asn Asp Lys
1               5

<210> SEQ ID NO 111
<211> LENGTH: 13
<212> TYPE: PRT
<213> ORGANISM: HUMAN

<400> SEQUENCE: 111

Gln Val Gln Ser Leu Thr Cys Glu Val Asp Ala Leu Lys
1               5                   10

<210> SEQ ID NO 112
<211> LENGTH: 10
<212> TYPE: PRT
<213> ORGANISM: HUMAN

<400> SEQUENCE: 112

Arg Gln Val Asp Gln Leu Thr Asn Asp Lys
1               5                   10

<210> SEQ ID NO 113
<211> LENGTH: 13
<212> TYPE: PRT
<213> ORGANISM: HUMAN

<400> SEQUENCE: 113

Thr Asn Glu Lys Val Glu Leu Gln Glu Leu Asn Asp Arg
1               5                   10

<210> SEQ ID NO 114
<211> LENGTH: 9
<212> TYPE: PRT
<213> ORGANISM: HUMAN

<400> SEQUENCE: 114

Val Glu Leu Gln Glu Leu Asn Asp Arg
1               5

<210> SEQ ID NO 115
<211> LENGTH: 14
<212> TYPE: PRT
<213> ORGANISM: HUMAN

<400> SEQUENCE: 115

Val Glu Val Glu Arg Asp Asn Leu Ala Glu Asp Ile Met Arg
1               5                   10

<210> SEQ ID NO 116
<211> LENGTH: 24
<212> TYPE: PRT
<213> ORGANISM: HUMAN

<400> SEQUENCE: 116

Ala Tyr Glu Glu Asp Tyr Gly Ser Ser Leu Glu Glu Asp Ile Gln Ala
1               5                   10                  15

Asp Thr Ser Gly Tyr Leu Glu Arg
```

20

<210> SEQ ID NO 117
<211> LENGTH: 11
<212> TYPE: PRT
<213> ORGANISM: HUMAN

<400> SEQUENCE: 117

Glu Gly Val Ile Ile Glu Ile Leu Ala Ser Arg
1               5                   10

<210> SEQ ID NO 118
<211> LENGTH: 15
<212> TYPE: PRT
<213> ORGANISM: HUMAN

<400> SEQUENCE: 118

Gly Ile Gly Thr Asn Glu Gln Ala Ile Ile Asp Val Leu Thr Lys
1               5                   10                  15

<210> SEQ ID NO 119
<211> LENGTH: 11
<212> TYPE: PRT
<213> ORGANISM: HUMAN

<400> SEQUENCE: 119

Asn Ala Leu Leu Ser Leu Val Gly Ser Asp Pro
1               5                   10

<210> SEQ ID NO 120
<211> LENGTH: 16
<212> TYPE: PRT
<213> ORGANISM: HUMAN

<400> SEQUENCE: 120

Ser Ser Ser His Phe Asn Pro Asp Pro Asp Ala Glu Thr Leu Tyr Lys
1               5                   10                  15

<210> SEQ ID NO 121
<211> LENGTH: 15
<212> TYPE: PRT
<213> ORGANISM: HUMAN

<400> SEQUENCE: 121

Thr Leu Ser Ser Met Ile Met Glu Asp Thr Ser Gly Asp Tyr Lys
1               5                   10                  15

<210> SEQ ID NO 122
<211> LENGTH: 25
<212> TYPE: PRT
<213> ORGANISM: HUMAN

<400> SEQUENCE: 122

Ala Glu Gly Ser Asp Val Ala Asn Ala Val Leu Asp Gly Ala Asp Cys
1               5                   10                  15

Ile Met Leu Ser Gly Glu Thr Ala Lys
            20                  25

<210> SEQ ID NO 123
<211> LENGTH: 8
<212> TYPE: PRT
<213> ORGANISM: HUMAN

<400> SEQUENCE: 123

```
Ala Pro Ile Ile Ala Val Thr Arg
1               5

<210> SEQ ID NO 124
<211> LENGTH: 16
<212> TYPE: PRT
<213> ORGANISM: HUMAN

<400> SEQUENCE: 124

Glu Ala Glu Ala Ala Ile Tyr His Leu Gln Leu Phe Glu Glu Leu Arg
1               5                   10                  15

<210> SEQ ID NO 125
<211> LENGTH: 17
<212> TYPE: PRT
<213> ORGANISM: HUMAN

<400> SEQUENCE: 125

Glu Ala Glu Ala Ala Ile Tyr His Leu Gln Leu Phe Glu Glu Leu Arg
1               5                   10                  15

Arg

<210> SEQ ID NO 126
<211> LENGTH: 15
<212> TYPE: PRT
<213> ORGANISM: HUMAN

<400> SEQUENCE: 126

Phe Asp Glu Ile Leu Glu Ala Ser Asp Gly Ile Met Val Ala Arg
1               5                   10                  15

<210> SEQ ID NO 127
<211> LENGTH: 18
<212> TYPE: PRT
<213> ORGANISM: HUMAN

<400> SEQUENCE: 127

Gly Ala Asp Phe Leu Val Thr Glu Val Glu Asn Gly Gly Ser Leu Gly
1               5                   10                  15

Ser Lys

<210> SEQ ID NO 128
<211> LENGTH: 11
<212> TYPE: PRT
<213> ORGANISM: HUMAN

<400> SEQUENCE: 128

Gly Asp Leu Gly Ile Glu Ile Pro Ala Glu Lys
1               5                   10

<210> SEQ ID NO 129
<211> LENGTH: 9
<212> TYPE: PRT
<213> ORGANISM: HUMAN

<400> SEQUENCE: 129

Gly Asp Tyr Pro Leu Glu Ala Val Arg
1               5

<210> SEQ ID NO 130
<211> LENGTH: 10
<212> TYPE: PRT
<213> ORGANISM: HUMAN
```

```
<400> SEQUENCE: 130

Gly Ser Gly Thr Ala Glu Val Glu Leu Lys
1               5                   10

<210> SEQ ID NO 131
<211> LENGTH: 17
<212> TYPE: PRT
<213> ORGANISM: HUMAN

<400> SEQUENCE: 131

Gly Val Asn Leu Pro Gly Ala Ala Val Asp Leu Pro Ala Val Ser Glu
1               5                   10                  15

Lys

<210> SEQ ID NO 132
<211> LENGTH: 13
<212> TYPE: PRT
<213> ORGANISM: HUMAN

<400> SEQUENCE: 132

Ile Tyr Val Asp Asp Gly Leu Ile Ser Leu Gln Val Lys
1               5                   10

<210> SEQ ID NO 133
<211> LENGTH: 9
<212> TYPE: PRT
<213> ORGANISM: HUMAN

<400> SEQUENCE: 133

Lys Ala Ser Asp Val His Glu Val Arg
1               5

<210> SEQ ID NO 134
<211> LENGTH: 22
<212> TYPE: PRT
<213> ORGANISM: HUMAN

<400> SEQUENCE: 134

Leu Ala Pro Ile Thr Ser Asp Pro Thr Glu Ala Thr Ala Val Gly Ala
1               5                   10                  15

Val Glu Ala Ser Phe Lys
            20

<210> SEQ ID NO 135
<211> LENGTH: 11
<212> TYPE: PRT
<213> ORGANISM: HUMAN

<400> SEQUENCE: 135

Leu Asp Ile Asp Ser Pro Pro Ile Thr Ala Arg
1               5                   10

<210> SEQ ID NO 136
<211> LENGTH: 13
<212> TYPE: PRT
<213> ORGANISM: HUMAN

<400> SEQUENCE: 136

Asn Thr Gly Ile Ile Cys Thr Ile Gly Pro Ala Ser Arg
1               5                   10

<210> SEQ ID NO 137
<211> LENGTH: 16
```

```
<212> TYPE: PRT
<213> ORGANISM: HUMAN

<400> SEQUENCE: 137

Arg Phe Asp Glu Ile Leu Glu Ala Ser Asp Gly Ile Met Val Ala Arg
1               5                   10                  15

<210> SEQ ID NO 138
<211> LENGTH: 23
<212> TYPE: PRT
<213> ORGANISM: HUMAN

<400> SEQUENCE: 138

Thr Ala Thr Glu Ser Phe Ala Ser Asp Pro Ile Leu Tyr Arg Pro Val
1               5                   10                  15

Ala Val Ala Leu Asp Thr Lys
            20

<210> SEQ ID NO 139
<211> LENGTH: 9
<212> TYPE: PRT
<213> ORGANISM: HUMAN

<400> SEQUENCE: 139

Val Asn Phe Ala Met Asn Val Gly Lys
1               5

<210> SEQ ID NO 140
<211> LENGTH: 9
<212> TYPE: PRT
<213> ORGANISM: HUMAN

<400> SEQUENCE: 140

Phe Ala Phe Gln Ala Glu Val Asn Arg
1               5

<210> SEQ ID NO 141
<211> LENGTH: 14
<212> TYPE: PRT
<213> ORGANISM: HUMAN

<400> SEQUENCE: 141

Gly Val Val Asp Ser Asp Asp Leu Pro Leu Asn Val Ser Arg
1               5                   10

<210> SEQ ID NO 142
<211> LENGTH: 9
<212> TYPE: PRT
<213> ORGANISM: HUMAN

<400> SEQUENCE: 142

Ile Tyr Phe Met Ala Gly Ser Ser Arg
1               5

<210> SEQ ID NO 143
<211> LENGTH: 10
<212> TYPE: PRT
<213> ORGANISM: HUMAN

<400> SEQUENCE: 143

Leu Gly Val Ile Glu Asp His Ser Asn Arg
1               5                   10

<210> SEQ ID NO 144
```

```
<211> LENGTH: 19
<212> TYPE: PRT
<213> ORGANISM: HUMAN

<400> SEQUENCE: 144

Leu Ile Ser Leu Thr Asp Glu Asn Ala Leu Ser Gly Asn Glu Glu Leu
1               5                   10                  15

Thr Val Lys

<210> SEQ ID NO 145
<211> LENGTH: 14
<212> TYPE: PRT
<213> ORGANISM: HUMAN

<400> SEQUENCE: 145

Asn Leu Leu His Val Thr Asp Thr Gly Val Gly Met Thr Arg
1               5                   10

<210> SEQ ID NO 146
<211> LENGTH: 8
<212> TYPE: PRT
<213> ORGANISM: HUMAN

<400> SEQUENCE: 146

Ala Leu Glu Leu Glu Gln Glu Arg
1               5

<210> SEQ ID NO 147
<211> LENGTH: 10
<212> TYPE: PRT
<213> ORGANISM: HUMAN

<400> SEQUENCE: 147

Ala Leu Thr Ser Glu Leu Ala Asn Ala Arg
1               5                   10

<210> SEQ ID NO 148
<211> LENGTH: 10
<212> TYPE: PRT
<213> ORGANISM: HUMAN

<400> SEQUENCE: 148

Ala Pro Asp Phe Val Phe Tyr Ala Pro Arg
1               5                   10

<210> SEQ ID NO 149
<211> LENGTH: 10
<212> TYPE: PRT
<213> ORGANISM: HUMAN

<400> SEQUENCE: 149

Ala Gln Gln Glu Leu Glu Glu Gln Thr Arg
1               5                   10

<210> SEQ ID NO 150
<211> LENGTH: 8
<212> TYPE: PRT
<213> ORGANISM: HUMAN

<400> SEQUENCE: 150

Glu Ala Leu Leu Gln Ala Ser Arg
1               5

<210> SEQ ID NO 151
```

```
<211> LENGTH: 8
<212> TYPE: PRT
<213> ORGANISM: HUMAN

<400> SEQUENCE: 151

Glu Lys Glu Glu Leu Met Glu Arg
1               5

<210> SEQ ID NO 152
<211> LENGTH: 17
<212> TYPE: PRT
<213> ORGANISM: HUMAN

<400> SEQUENCE: 152

Phe Tyr Pro Glu Asp Val Ser Glu Glu Leu Ile Gln Asp Ile Thr Gln
1               5                   10                  15

Arg

<210> SEQ ID NO 153
<211> LENGTH: 9
<212> TYPE: PRT
<213> ORGANISM: HUMAN

<400> SEQUENCE: 153

Ile Gly Phe Pro Trp Ser Glu Ile Arg
1               5

<210> SEQ ID NO 154
<211> LENGTH: 9
<212> TYPE: PRT
<213> ORGANISM: HUMAN

<400> SEQUENCE: 154

Ile Gln Val Trp His Glu Glu His Arg
1               5

<210> SEQ ID NO 155
<211> LENGTH: 8
<212> TYPE: PRT
<213> ORGANISM: HUMAN

<400> SEQUENCE: 155

Ile Ser Gln Leu Glu Met Ala Arg
1               5

<210> SEQ ID NO 156
<211> LENGTH: 11
<212> TYPE: PRT
<213> ORGANISM: HUMAN

<400> SEQUENCE: 156

Lys Ala Gln Gln Glu Leu Glu Glu Gln Thr Arg
1               5                   10

<210> SEQ ID NO 157
<211> LENGTH: 16
<212> TYPE: PRT
<213> ORGANISM: HUMAN

<400> SEQUENCE: 157

Lys Thr Gln Glu Gln Leu Ala Leu Glu Met Ala Glu Leu Thr Ala Arg
1               5                   10                  15

<210> SEQ ID NO 158
```

```
<211> LENGTH: 8
<212> TYPE: PRT
<213> ORGANISM: HUMAN

<400> SEQUENCE: 158

Gln Leu Phe Asp Gln Val Val Lys
1               5

<210> SEQ ID NO 159
<211> LENGTH: 27
<212> TYPE: PRT
<213> ORGANISM: HUMAN

<400> SEQUENCE: 159

Thr Ala Met Ser Thr Pro His Val Ala Glu Pro Ala Glu Asn Glu Gln
1               5                   10                  15

Asp Glu Gln Asp Glu Asn Gly Ala Glu Ala Ser
            20                  25

<210> SEQ ID NO 160
<211> LENGTH: 12
<212> TYPE: PRT
<213> ORGANISM: HUMAN

<400> SEQUENCE: 160

Thr Ala Asn Asp Met Ile His Ala Glu Asn Met Arg
1               5                   10

<210> SEQ ID NO 161
<211> LENGTH: 15
<212> TYPE: PRT
<213> ORGANISM: HUMAN

<400> SEQUENCE: 161

Thr Gln Glu Gln Leu Ala Leu Glu Met Ala Glu Leu Thr Ala Arg
1               5                   10                  15

<210> SEQ ID NO 162
<211> LENGTH: 19
<212> TYPE: PRT
<213> ORGANISM: HUMAN

<400> SEQUENCE: 162

Val Thr Thr Met Asp Ala Glu Leu Glu Phe Ala Ile Gln Pro Asn Thr
1               5                   10                  15

Thr Gly Lys

<210> SEQ ID NO 163
<211> LENGTH: 9
<212> TYPE: PRT
<213> ORGANISM: HUMAN

<400> SEQUENCE: 163

Glu Leu Pro Ser Phe Val Gly Glu Lys
1               5

<210> SEQ ID NO 164
<211> LENGTH: 16
<212> TYPE: PRT
<213> ORGANISM: HUMAN

<400> SEQUENCE: 164

Glu Leu Pro Ser Phe Val Gly Glu Lys Val Asp Glu Glu Gly Leu Lys
1               5                   10                  15
```

<210> SEQ ID NO 165
<211> LENGTH: 11
<212> TYPE: PRT
<213> ORGANISM: HUMAN

<400> SEQUENCE: 165

Gly Thr Asn Tyr Leu Ala Asp Val Phe Glu Lys
1               5                   10

<210> SEQ ID NO 166
<211> LENGTH: 12
<212> TYPE: PRT
<213> ORGANISM: HUMAN

<400> SEQUENCE: 166

Gly Thr Asn Tyr Leu Ala Asp Val Phe Glu Lys Lys
1               5                   10

<210> SEQ ID NO 167
<211> LENGTH: 11
<212> TYPE: PRT
<213> ORGANISM: HUMAN

<400> SEQUENCE: 167

Ser Ile Ile Gly Met Ile Asp Met Phe His Lys
1               5                   10

<210> SEQ ID NO 168
<211> LENGTH: 12
<212> TYPE: PRT
<213> ORGANISM: HUMAN

<400> SEQUENCE: 168

Ala Asp Leu His Thr Leu Ser Glu Asp Ser Tyr Lys
1               5                   10

<210> SEQ ID NO 169
<211> LENGTH: 24
<212> TYPE: PRT
<213> ORGANISM: HUMAN

<400> SEQUENCE: 169

Asp Asn Leu Thr Leu Trp Thr Ala Asp Asn Ala Gly Glu Glu Gly Gly
1               5                   10                  15

Glu Ala Pro Gln Glu Pro Gln Ser
            20

<210> SEQ ID NO 170
<211> LENGTH: 10
<212> TYPE: PRT
<213> ORGANISM: HUMAN

<400> SEQUENCE: 170

Asp Ser Thr Leu Ile Met Gln Leu Leu Arg
1               5                   10

<210> SEQ ID NO 171
<211> LENGTH: 8
<212> TYPE: PRT
<213> ORGANISM: HUMAN

<400> SEQUENCE: 171

Glu Glu Lys Gly Pro Glu Val Arg

```
1               5

<210> SEQ ID NO 172
<211> LENGTH: 9
<212> TYPE: PRT
<213> ORGANISM: HUMAN

<400> SEQUENCE: 172

Glu Met Pro Pro Thr Asn Pro Ile Arg
1               5

<210> SEQ ID NO 173
<211> LENGTH: 14
<212> TYPE: PRT
<213> ORGANISM: HUMAN

<400> SEQUENCE: 173

Gly Ala Val Glu Lys Gly Glu Glu Leu Ser Cys Glu Glu Arg
1               5                   10

<210> SEQ ID NO 174
<211> LENGTH: 9
<212> TYPE: PRT
<213> ORGANISM: HUMAN

<400> SEQUENCE: 174

Gly Glu Glu Leu Ser Cys Glu Glu Arg
1               5

<210> SEQ ID NO 175
<211> LENGTH: 7
<212> TYPE: PRT
<213> ORGANISM: HUMAN

<400> SEQUENCE: 175

Leu Ala Glu Gln Ala Glu Arg
1               5

<210> SEQ ID NO 176
<211> LENGTH: 8
<212> TYPE: PRT
<213> ORGANISM: HUMAN

<400> SEQUENCE: 176

Asn Leu Leu Ser Val Ala Tyr Lys
1               5

<210> SEQ ID NO 177
<211> LENGTH: 11
<212> TYPE: PRT
<213> ORGANISM: HUMAN

<400> SEQUENCE: 177

Ser Ala Tyr Gln Glu Ala Met Asp Ile Ser Lys
1               5                   10

<210> SEQ ID NO 178
<211> LENGTH: 12
<212> TYPE: PRT
<213> ORGANISM: HUMAN

<400> SEQUENCE: 178

Ser Ala Tyr Gln Glu Ala Met Asp Ile Ser Lys Lys
1               5                   10
```

```
<210> SEQ ID NO 179
<211> LENGTH: 14
<212> TYPE: PRT
<213> ORGANISM: HUMAN

<400> SEQUENCE: 179

Ser Asn Glu Glu Gly Ser Glu Glu Lys Gly Pro Glu Val Arg
1               5                   10

<210> SEQ ID NO 180
<211> LENGTH: 19
<212> TYPE: PRT
<213> ORGANISM: HUMAN

<400> SEQUENCE: 180

Thr Thr Phe Asp Glu Ala Met Ala Asp Leu His Thr Leu Ser Glu Asp
1               5                   10                  15

Ser Tyr Lys

<210> SEQ ID NO 181
<211> LENGTH: 8
<212> TYPE: PRT
<213> ORGANISM: HUMAN

<400> SEQUENCE: 181

Val Leu Ser Ser Ile Glu Gln Lys
1               5

<210> SEQ ID NO 182
<211> LENGTH: 9
<212> TYPE: PRT
<213> ORGANISM: HUMAN

<400> SEQUENCE: 182

Tyr Glu Asp Met Ala Ala Phe Met Lys
1               5

<210> SEQ ID NO 183
<211> LENGTH: 11
<212> TYPE: PRT
<213> ORGANISM: HUMAN

<400> SEQUENCE: 183

Tyr Leu Ala Glu Val Ala Thr Gly Asp Asp Lys
1               5                   10

<210> SEQ ID NO 184
<211> LENGTH: 9
<212> TYPE: PRT
<213> ORGANISM: HUMAN

<400> SEQUENCE: 184

Ile Ser Ser Pro Thr Glu Thr Glu Arg
1               5

<210> SEQ ID NO 185
<211> LENGTH: 16
<212> TYPE: PRT
<213> ORGANISM: HUMAN

<400> SEQUENCE: 185

Thr Glu Phe Leu Ser Phe Met Asn Thr Glu Leu Ala Ala Phe Thr Lys
1               5                   10                  15
```

<210> SEQ ID NO 186
<211> LENGTH: 17
<212> TYPE: PRT
<213> ORGANISM: HUMAN

<400> SEQUENCE: 186

Gly Asp Thr Ala Asn Glu Ile Gly Gln Val Leu His Phe Glu Asn Val
1               5                   10                  15
Lys

<210> SEQ ID NO 187
<211> LENGTH: 19
<212> TYPE: PRT
<213> ORGANISM: HUMAN

<400> SEQUENCE: 187

Val Cys Leu Glu Ile Thr Glu Asp Gly Gly Asp Ser Ile Glu Val Pro
1               5                   10                  15
Gly Ala Arg

<210> SEQ ID NO 188
<211> LENGTH: 8
<212> TYPE: PRT
<213> ORGANISM: HUMAN

<400> SEQUENCE: 188

Phe Asn Ala Leu Gln Tyr Leu Arg
1               5

<210> SEQ ID NO 189
<211> LENGTH: 10
<212> TYPE: PRT
<213> ORGANISM: HUMAN

<400> SEQUENCE: 189

Ile Ser Asn Ile Pro Asp Glu Tyr Phe Lys
1               5                   10

<210> SEQ ID NO 190
<211> LENGTH: 21
<212> TYPE: PRT
<213> ORGANISM: HUMAN

<400> SEQUENCE: 190

Asn Ile Pro Thr Val Asn Glu Asn Leu Glu Asn Tyr Tyr Leu Glu Val
1               5                   10                  15
Asn Gln Leu Glu Lys
                20

<210> SEQ ID NO 191
<211> LENGTH: 10
<212> TYPE: PRT
<213> ORGANISM: HUMAN

<400> SEQUENCE: 191

Asn Asn Gln Ile Asp His Ile Asp Glu Lys
1               5                   10

<210> SEQ ID NO 192
<211> LENGTH: 11
<212> TYPE: PRT
<213> ORGANISM: HUMAN

```
<400> SEQUENCE: 192

Ser Leu Glu Asp Leu Gln Leu Thr His Asn Lys
1               5                   10

<210> SEQ ID NO 193
<211> LENGTH: 14
<212> TYPE: PRT
<213> ORGANISM: HUMAN

<400> SEQUENCE: 193

Ser Leu Glu Tyr Leu Asp Leu Ser Phe Asn Gln Ile Ala Arg
1               5                   10

<210> SEQ ID NO 194
<211> LENGTH: 13
<212> TYPE: PRT
<213> ORGANISM: HUMAN

<400> SEQUENCE: 194

Ala Ala Leu Val Val Asp Asn Gly Ser Gly Met Cys Lys
1               5                   10

<210> SEQ ID NO 195
<211> LENGTH: 10
<212> TYPE: PRT
<213> ORGANISM: HUMAN

<400> SEQUENCE: 195

Ala Gly Phe Ala Gly Asp Asp Ala Pro Arg
1               5                   10

<210> SEQ ID NO 196
<211> LENGTH: 19
<212> TYPE: PRT
<213> ORGANISM: HUMAN

<400> SEQUENCE: 196

Ala Leu Asp Phe Glu Gln Glu Met Ala Thr Ala Ala Ser Ser Ser
1               5                   10                  15

Leu Glu Lys

<210> SEQ ID NO 197
<211> LENGTH: 9
<212> TYPE: PRT
<213> ORGANISM: HUMAN

<400> SEQUENCE: 197

Ala Val Phe Pro Ser Ile Val Gly Arg
1               5

<210> SEQ ID NO 198
<211> LENGTH: 11
<212> TYPE: PRT
<213> ORGANISM: HUMAN

<400> SEQUENCE: 198

Ala Val Phe Pro Ser Ile Val Gly Arg Pro Arg
1               5                   10

<210> SEQ ID NO 199
<211> LENGTH: 17
<212> TYPE: PRT
<213> ORGANISM: HUMAN
```

<400> SEQUENCE: 199

Asp Asp Asp Ile Ala Ala Leu Val Val Asp Asn Gly Ser Gly Met Cys
1               5                   10                  15
Lys

<210> SEQ ID NO 200
<211> LENGTH: 10
<212> TYPE: PRT
<213> ORGANISM: HUMAN

<400> SEQUENCE: 200

Asp Glu Ser Gly Pro Ser Ile Val His Arg
1               5                   10

<210> SEQ ID NO 201
<211> LENGTH: 8
<212> TYPE: PRT
<213> ORGANISM: HUMAN

<400> SEQUENCE: 201

Asp Leu Thr Asp Tyr Leu Met Lys
1               5

<210> SEQ ID NO 202
<211> LENGTH: 21
<212> TYPE: PRT
<213> ORGANISM: HUMAN

<400> SEQUENCE: 202

Asp Leu Tyr Ala Asn Thr Val Leu Ser Gly Gly Thr Thr Met Tyr Pro
1               5                   10                  15
Gly Ile Ala Asp Arg
            20

<210> SEQ ID NO 203
<211> LENGTH: 11
<212> TYPE: PRT
<213> ORGANISM: HUMAN

<400> SEQUENCE: 203

Asp Ser Tyr Val Gly Asp Glu Ala Gln Ser Lys
1               5                   10

<210> SEQ ID NO 204
<211> LENGTH: 12
<212> TYPE: PRT
<213> ORGANISM: HUMAN

<400> SEQUENCE: 204

Asp Ser Tyr Val Gly Asp Glu Ala Gln Ser Lys Arg
1               5                   10

<210> SEQ ID NO 205
<211> LENGTH: 11
<212> TYPE: PRT
<213> ORGANISM: HUMAN

<400> SEQUENCE: 205

Glu Ile Thr Ala Leu Ala Pro Ser Thr Met Lys
1               5                   10

<210> SEQ ID NO 206
<211> LENGTH: 9

```
<212> TYPE: PRT
<213> ORGANISM: HUMAN

<400> SEQUENCE: 206

Gly Phe Ala Gly Asp Asp Ala Pro Arg
1               5

<210> SEQ ID NO 207
<211> LENGTH: 10
<212> TYPE: PRT
<213> ORGANISM: HUMAN

<400> SEQUENCE: 207

Gly Tyr Ser Phe Thr Thr Thr Ala Glu Arg
1               5                   10

<210> SEQ ID NO 208
<211> LENGTH: 11
<212> TYPE: PRT
<213> ORGANISM: HUMAN

<400> SEQUENCE: 208

His Gln Gly Val Met Val Gly Met Gly Gln Lys
1               5                   10

<210> SEQ ID NO 209
<211> LENGTH: 11
<212> TYPE: PRT
<213> ORGANISM: HUMAN

<400> SEQUENCE: 209

Ile Trp His His Thr Phe Tyr Asn Glu Leu Arg
1               5                   10

<210> SEQ ID NO 210
<211> LENGTH: 22
<212> TYPE: PRT
<213> ORGANISM: HUMAN

<400> SEQUENCE: 210

Lys Asp Leu Tyr Ala Asn Thr Val Leu Ser Gly Gly Thr Thr Met Tyr
1               5                   10                  15

Pro Gly Ile Ala Asp Arg
            20

<210> SEQ ID NO 211
<211> LENGTH: 23
<212> TYPE: PRT
<213> ORGANISM: HUMAN

<400> SEQUENCE: 211

Leu Cys Tyr Val Ala Leu Asp Phe Glu Gln Glu Met Ala Thr Ala Ala
1               5                   10                  15

Ser Ser Ser Ser Leu Glu Lys
            20

<210> SEQ ID NO 212
<211> LENGTH: 10
<212> TYPE: PRT
<213> ORGANISM: HUMAN

<400> SEQUENCE: 212

Leu Leu Thr Glu Ala Pro Leu Asn Pro Lys
1               5                   10
```

```
<210> SEQ ID NO 213
<211> LENGTH: 13
<212> TYPE: PRT
<213> ORGANISM: HUMAN

<400> SEQUENCE: 213

Gln Glu Tyr Asp Glu Ser Gly Pro Ser Ile Val His Arg
1               5                   10

<210> SEQ ID NO 214
<211> LENGTH: 13
<212> TYPE: PRT
<213> ORGANISM: HUMAN

<400> SEQUENCE: 214

Ser Gly Gly Thr Thr Met Tyr Pro Gly Ile Ala Asp Arg
1               5                   10

<210> SEQ ID NO 215
<211> LENGTH: 16
<212> TYPE: PRT
<213> ORGANISM: HUMAN

<400> SEQUENCE: 215

Ser Tyr Glu Leu Pro Asp Gly Gln Val Ile Thr Ile Gly Asn Glu Arg
1               5                   10                  15

<210> SEQ ID NO 216
<211> LENGTH: 9
<212> TYPE: PRT
<213> ORGANISM: HUMAN

<400> SEQUENCE: 216

Thr Ala Leu Ala Pro Ser Thr Met Lys
1               5

<210> SEQ ID NO 217
<211> LENGTH: 8
<212> TYPE: PRT
<213> ORGANISM: HUMAN

<400> SEQUENCE: 217

Thr Glu Ala Pro Leu Asn Pro Lys
1               5

<210> SEQ ID NO 218
<211> LENGTH: 22
<212> TYPE: PRT
<213> ORGANISM: HUMAN

<400> SEQUENCE: 218

Thr Thr Gly Ile Val Met Asp Ser Gly Asp Gly Val Thr His Thr Val
1               5                   10                  15

Pro Ile Tyr Glu Gly Tyr
            20

<210> SEQ ID NO 219
<211> LENGTH: 26
<212> TYPE: PRT
<213> ORGANISM: HUMAN

<400> SEQUENCE: 219

Thr Thr Gly Ile Val Met Asp Ser Gly Asp Gly Val Thr His Thr Val
```

```
                1               5                   10                  15
Pro Ile Tyr Glu Gly Tyr Ala Leu Pro His
            20                  25

<210> SEQ ID NO 220
<211> LENGTH: 29
<212> TYPE: PRT
<213> ORGANISM: HUMAN

<400> SEQUENCE: 220

Thr Thr Gly Ile Val Met Asp Ser Gly Asp Gly Val Thr His Thr Val
1               5                   10                  15

Pro Ile Tyr Glu Gly Tyr Ala Leu Pro His Ala Ile Leu
            20                  25

<210> SEQ ID NO 221
<211> LENGTH: 20
<212> TYPE: PRT
<213> ORGANISM: HUMAN

<400> SEQUENCE: 221

Val Ala Leu Asp Phe Glu Gln Glu Met Ala Thr Ala Ala Ser Ser Ser
1               5                   10                  15

Ser Leu Glu Lys
            20

<210> SEQ ID NO 222
<211> LENGTH: 8
<212> TYPE: PRT
<213> ORGANISM: HUMAN

<400> SEQUENCE: 222

Val Ala Pro Glu Glu His Pro Val
1               5

<210> SEQ ID NO 223
<211> LENGTH: 9
<212> TYPE: PRT
<213> ORGANISM: HUMAN

<400> SEQUENCE: 223

Val Ala Pro Glu Glu His Pro Val Leu
1               5

<210> SEQ ID NO 224
<211> LENGTH: 10
<212> TYPE: PRT
<213> ORGANISM: HUMAN

<400> SEQUENCE: 224

Val Ala Pro Glu Glu His Pro Val Leu Leu
1               5                   10

<210> SEQ ID NO 225
<211> LENGTH: 18
<212> TYPE: PRT
<213> ORGANISM: HUMAN

<400> SEQUENCE: 225

Val Ala Pro Glu Glu His Pro Val Leu Leu Thr Glu Ala Pro Leu Asn
1               5                   10                  15

Pro Lys
```

<210> SEQ ID NO 226
<211> LENGTH: 15
<212> TYPE: PRT
<213> ORGANISM: HUMAN

<400> SEQUENCE: 226

Val Leu Ser Gly Gly Thr Thr Met Tyr Pro Gly Ile Ala Asp Arg
1               5                   10                  15

<210> SEQ ID NO 227
<211> LENGTH: 16
<212> TYPE: PRT
<213> ORGANISM: HUMAN

<400> SEQUENCE: 227

Tyr Pro Ile Glu His Gly Ile Val Thr Asn Trp Asp Asp Met Glu Lys
1               5                   10                  15

<210> SEQ ID NO 228
<211> LENGTH: 10
<212> TYPE: PRT
<213> ORGANISM: HUMAN

<400> SEQUENCE: 228

Asp Ala Val Thr Tyr Thr Glu His Ala Lys
1               5                   10

<210> SEQ ID NO 229
<211> LENGTH: 12
<212> TYPE: PRT
<213> ORGANISM: HUMAN

<400> SEQUENCE: 229

Asp Asn Ile Gln Gly Ile Thr Lys Pro Ala Ile Arg
1               5                   10

<210> SEQ ID NO 230
<211> LENGTH: 10
<212> TYPE: PRT
<213> ORGANISM: HUMAN

<400> SEQUENCE: 230

Ile Ser Gly Leu Ile Tyr Glu Glu Thr Arg
1               5                   10

<210> SEQ ID NO 231
<211> LENGTH: 12
<212> TYPE: PRT
<213> ORGANISM: HUMAN

<400> SEQUENCE: 231

Thr Val Thr Ala Met Asp Val Val Tyr Ala Leu Lys
1               5                   10

<210> SEQ ID NO 232
<211> LENGTH: 8
<212> TYPE: PRT
<213> ORGANISM: HUMAN

<400> SEQUENCE: 232

Val Phe Leu Glu Asn Val Ile Arg
1               5

<210> SEQ ID NO 233

```
<211> LENGTH: 16
<212> TYPE: PRT
<213> ORGANISM: HUMAN

<400> SEQUENCE: 233

Ala Phe Asp Gln Asp Gly Asp Gly His Ile Thr Val Asp Glu Leu Arg
1               5                   10                  15

<210> SEQ ID NO 234
<211> LENGTH: 23
<212> TYPE: PRT
<213> ORGANISM: HUMAN

<400> SEQUENCE: 234

Ala Phe Ser Ala Val Asp Thr Asp Gly Asn Gly Thr Ile Asn Ala Gln
1               5                   10                  15

Glu Leu Gly Ala Ala Leu Lys
            20

<210> SEQ ID NO 235
<211> LENGTH: 11
<212> TYPE: PRT
<213> ORGANISM: HUMAN

<400> SEQUENCE: 235

Ala Gly Leu Glu Asp Leu Gln Val Ala Phe Arg
1               5                   10

<210> SEQ ID NO 236
<211> LENGTH: 19
<212> TYPE: PRT
<213> ORGANISM: HUMAN

<400> SEQUENCE: 236

Ala Met Ala Gly Leu Gly Gln Pro Leu Pro Gln Glu Glu Leu Asp Ala
1               5                   10                  15

Met Ile Arg

<210> SEQ ID NO 237
<211> LENGTH: 8
<212> TYPE: PRT
<213> ORGANISM: HUMAN

<400> SEQUENCE: 237

Asn Leu Ser Glu Ala Gln Leu Arg
1               5

<210> SEQ ID NO 238
<211> LENGTH: 8
<212> TYPE: PRT
<213> ORGANISM: HUMAN

<400> SEQUENCE: 238

Val Asn Tyr Glu Glu Phe Ala Arg
1               5

<210> SEQ ID NO 239
<211> LENGTH: 11
<212> TYPE: PRT
<213> ORGANISM: HUMAN

<400> SEQUENCE: 239

Glu Lys Leu Glu Ala Thr Ile Asn Glu Leu Val
1               5                   10
```

<210> SEQ ID NO 240
<211> LENGTH: 13
<212> TYPE: PRT
<213> ORGANISM: HUMAN

<400> SEQUENCE: 240

Thr Ala Phe Gln Glu Ala Leu Asp Ala Ala Gly Asp Lys
1               5                   10

<210> SEQ ID NO 241
<211> LENGTH: 9
<212> TYPE: PRT
<213> ORGANISM: HUMAN

<400> SEQUENCE: 241

Val Gly Glu Phe Ser Gly Ala Asn Lys
1               5

<210> SEQ ID NO 242
<211> LENGTH: 11
<212> TYPE: PRT
<213> ORGANISM: HUMAN

<400> SEQUENCE: 242

Glu Gly Met Asn Ile Val Glu Ala Met Glu Arg
1               5                   10

<210> SEQ ID NO 243
<211> LENGTH: 9
<212> TYPE: PRT
<213> ORGANISM: HUMAN

<400> SEQUENCE: 243

Phe Glu Asp Glu Asn Phe Ile Leu Lys
1               5

<210> SEQ ID NO 244
<211> LENGTH: 14
<212> TYPE: PRT
<213> ORGANISM: HUMAN

<400> SEQUENCE: 244

Ile Ile Pro Gly Phe Met Cys Gln Gly Gly Asp Phe Thr Arg
1               5                   10

<210> SEQ ID NO 245
<211> LENGTH: 10
<212> TYPE: PRT
<213> ORGANISM: HUMAN

<400> SEQUENCE: 245

Ile Thr Ile Ala Asp Cys Gly Gln Leu Glu
1               5                   10

<210> SEQ ID NO 246
<211> LENGTH: 11
<212> TYPE: PRT
<213> ORGANISM: HUMAN

<400> SEQUENCE: 246

Lys Ile Thr Ile Ala Asp Cys Gly Gln Leu Glu
1               5                   10

```
<210> SEQ ID NO 247
<211> LENGTH: 15
<212> TYPE: PRT
<213> ORGANISM: HUMAN

<400> SEQUENCE: 247

Ser Ile Tyr Gly Glu Lys Phe Glu Asp Glu Asn Phe Ile Leu Lys
1               5                   10                  15

<210> SEQ ID NO 248
<211> LENGTH: 18
<212> TYPE: PRT
<213> ORGANISM: HUMAN

<400> SEQUENCE: 248

Val Asn Pro Thr Val Phe Phe Asp Ile Ala Val Asp Gly Glu Pro Leu
1               5                   10                  15

Gly Arg

<210> SEQ ID NO 249
<211> LENGTH: 9
<212> TYPE: PRT
<213> ORGANISM: HUMAN

<400> SEQUENCE: 249

Val Ser Phe Glu Leu Phe Ala Asp Lys
1               5

<210> SEQ ID NO 250
<211> LENGTH: 11
<212> TYPE: PRT
<213> ORGANISM: HUMAN

<400> SEQUENCE: 250

Glu Ile Ala Gln Asp Phe Lys Thr Asp Leu Arg
1               5                   10

<210> SEQ ID NO 251
<211> LENGTH: 9
<212> TYPE: PRT
<213> ORGANISM: HUMAN

<400> SEQUENCE: 251

Ser Ala Pro Ala Thr Gly Gly Val Lys
1               5

<210> SEQ ID NO 252
<211> LENGTH: 23
<212> TYPE: PRT
<213> ORGANISM: HUMAN

<400> SEQUENCE: 252

Asp Asn Leu Thr Leu Trp Thr Ser Asp Thr Gln Gly Asp Glu Ala Glu
1               5                   10                  15

Ala Gly Glu Gly Gly Glu Asn
            20

<210> SEQ ID NO 253
<211> LENGTH: 10
<212> TYPE: PRT
<213> ORGANISM: HUMAN

<400> SEQUENCE: 253

Asp Ser Thr Leu Ile Met Gln Leu Leu Arg
```

```
1               5                   10
```

<210> SEQ ID NO 254
<211> LENGTH: 9
<212> TYPE: PRT
<213> ORGANISM: HUMAN

<400> SEQUENCE: 254

```
Glu Met Gln Pro Thr His Pro Ile Arg
1               5
```

<210> SEQ ID NO 255
<211> LENGTH: 18
<212> TYPE: PRT
<213> ORGANISM: HUMAN

<400> SEQUENCE: 255

```
Gly Ile Val Asp Gln Ser Gln Gln Ala Tyr Gln Glu Ala Phe Glu Ile
1               5                   10                  15

Ser Lys
```

<210> SEQ ID NO 256
<211> LENGTH: 19
<212> TYPE: PRT
<213> ORGANISM: HUMAN

<400> SEQUENCE: 256

```
Gly Ile Val Asp Gln Ser Gln Gln Ala Tyr Gln Glu Ala Phe Glu Ile
1               5                   10                  15

Ser Lys Lys
```

<210> SEQ ID NO 257
<211> LENGTH: 7
<212> TYPE: PRT
<213> ORGANISM: HUMAN

<400> SEQUENCE: 257

```
Leu Ala Glu Gln Ala Glu Arg
1               5
```

<210> SEQ ID NO 258
<211> LENGTH: 9
<212> TYPE: PRT
<213> ORGANISM: HUMAN

<400> SEQUENCE: 258

```
Met Asp Lys Asn Glu Leu Val Gln Lys
1               5
```

<210> SEQ ID NO 259
<211> LENGTH: 8
<212> TYPE: PRT
<213> ORGANISM: HUMAN

<400> SEQUENCE: 259

```
Asn Leu Leu Ser Val Ala Tyr Lys
1               5
```

<210> SEQ ID NO 260
<211> LENGTH: 14
<212> TYPE: PRT
<213> ORGANISM: HUMAN

<400> SEQUENCE: 260

```
Ser Val Thr Glu Gln Gly Ala Glu Leu Ser Asn Glu Glu Arg
1               5                  10
```

<210> SEQ ID NO 261
<211> LENGTH: 19
<212> TYPE: PRT
<213> ORGANISM: HUMAN

<400> SEQUENCE: 261

```
Thr Ala Phe Asp Glu Ala Ile Ala Glu Leu Asp Thr Leu Ser Glu Glu
1               5                  10                  15

Ser Tyr Lys
```

<210> SEQ ID NO 262
<211> LENGTH: 8
<212> TYPE: PRT
<213> ORGANISM: HUMAN

<400> SEQUENCE: 262

```
Val Val Ser Ser Ile Glu Gln Lys
1               5
```

<210> SEQ ID NO 263
<211> LENGTH: 9
<212> TYPE: PRT
<213> ORGANISM: HUMAN

<400> SEQUENCE: 263

```
Tyr Asp Asp Met Ala Ala Cys Met Lys
1               5
```

<210> SEQ ID NO 264
<211> LENGTH: 12
<212> TYPE: PRT
<213> ORGANISM: HUMAN

<400> SEQUENCE: 264

```
Tyr Leu Ala Glu Val Ala Ala Gly Asp Asp Lys Lys
1               5                  10
```

<210> SEQ ID NO 265
<211> LENGTH: 13
<212> TYPE: PRT
<213> ORGANISM: HUMAN

<400> SEQUENCE: 265

```
Glu Leu Ser Glu Leu Val Tyr Thr Asp Val Leu Asp Arg
1               5                  10
```

<210> SEQ ID NO 266
<211> LENGTH: 8
<212> TYPE: PRT
<213> ORGANISM: HUMAN

<400> SEQUENCE: 266

```
Asn Trp Gln Asp Tyr Gly Val Arg
1               5
```

<210> SEQ ID NO 267
<211> LENGTH: 22
<212> TYPE: PRT
<213> ORGANISM: HUMAN

<400> SEQUENCE: 267

Thr Cys Leu His Tyr Leu Gly Glu Phe Gly Glu Asp Gln Ile Tyr Glu
1               5                   10                  15

Ala His Gln Gln Gly Arg
            20

<210> SEQ ID NO 268
<211> LENGTH: 14
<212> TYPE: PRT
<213> ORGANISM: HUMAN

<400> SEQUENCE: 268

Ala Ser Ala Glu Thr Val Asp Pro Ala Ser Leu Trp Glu Tyr
1               5                   10

<210> SEQ ID NO 269
<211> LENGTH: 18
<212> TYPE: PRT
<213> ORGANISM: HUMAN

<400> SEQUENCE: 269

Asp Val Pro Trp Gly Val Asp Ser Leu Ile Thr Leu Ala Phe Gln Asp
1               5                   10                  15

Gln Arg

<210> SEQ ID NO 270
<211> LENGTH: 10
<212> TYPE: PRT
<213> ORGANISM: HUMAN

<400> SEQUENCE: 270

Phe Leu Ile Val Ala His Asp Asp Gly Arg
1               5                   10

<210> SEQ ID NO 271
<211> LENGTH: 10
<212> TYPE: PRT
<213> ORGANISM: HUMAN

<400> SEQUENCE: 271

Lys Val Thr Gly Thr Leu Asp Ala Asn Arg
1               5                   10

<210> SEQ ID NO 272
<211> LENGTH: 14
<212> TYPE: PRT
<213> ORGANISM: HUMAN

<400> SEQUENCE: 272

Tyr Leu Ala Ala Asp Lys Asp Gly Asn Val Thr Cys Glu Arg
1               5                   10

<210> SEQ ID NO 273
<211> LENGTH: 10
<212> TYPE: PRT
<213> ORGANISM: HUMAN

<400> SEQUENCE: 273

Asp Asp Met Leu Cys Ala Gly Asn Thr Arg
1               5                   10

<210> SEQ ID NO 274
<211> LENGTH: 15
<212> TYPE: PRT

<213> ORGANISM: HUMAN

<400> SEQUENCE: 274

Glu Gln His Leu Tyr Tyr Gln Asp Gln Leu Leu Pro Val Ser Arg
1               5                   10                  15

<210> SEQ ID NO 275
<211> LENGTH: 9
<212> TYPE: PRT
<213> ORGANISM: HUMAN

<400> SEQUENCE: 275

Ile Val Gly Gly Gln Glu Ala Pro Arg
1               5

<210> SEQ ID NO 276
<211> LENGTH: 12
<212> TYPE: PRT
<213> ORGANISM: HUMAN

<400> SEQUENCE: 276

Val Pro Ile Met Glu Asn His Ile Cys Asp Ala Lys
1               5                   10

<210> SEQ ID NO 277
<211> LENGTH: 12
<212> TYPE: PRT
<213> ORGANISM: HUMAN

<400> SEQUENCE: 277

Tyr His Leu Gly Ala Tyr Thr Gly Asp Asp Val Arg
1               5                   10

<210> SEQ ID NO 278
<211> LENGTH: 15
<212> TYPE: PRT
<213> ORGANISM: HUMAN

<400> SEQUENCE: 278

Ala Met Gly Ile Met Asn Ser Phe Val Asn Asp Ile Phe Glu Arg
1               5                   10                  15

<210> SEQ ID NO 279
<211> LENGTH: 9
<212> TYPE: PRT
<213> ORGANISM: HUMAN

<400> SEQUENCE: 279

Leu Leu Leu Pro Gly Glu Leu Ala Lys
1               5

<210> SEQ ID NO 280
<211> LENGTH: 11
<212> TYPE: PRT
<213> ORGANISM: HUMAN

<400> SEQUENCE: 280

Gln Val His Pro Asp Thr Gly Ile Ser Ser Lys
1               5                   10

<210> SEQ ID NO 281
<211> LENGTH: 11
<212> TYPE: PRT
<213> ORGANISM: HUMAN

<400> SEQUENCE: 281

Ala Ala Glu Glu Pro Ser Lys Val Glu Glu Lys
1               5                   10

<210> SEQ ID NO 282
<211> LENGTH: 27
<212> TYPE: PRT
<213> ORGANISM: HUMAN

<400> SEQUENCE: 282

Glu Ala Pro Ala Glu Gly Glu Ala Ala Glu Pro Gly Ser Pro Thr Ala
1               5                   10                  15

Ala Glu Gly Glu Ala Ala Ser Ala Ala Ser Ser
            20                  25

<210> SEQ ID NO 283
<211> LENGTH: 9
<212> TYPE: PRT
<213> ORGANISM: HUMAN

<400> SEQUENCE: 283

Gly Pro Ser Ser Val Glu Asp Ile Lys
1               5

<210> SEQ ID NO 284
<211> LENGTH: 7
<212> TYPE: PRT
<213> ORGANISM: HUMAN

<400> SEQUENCE: 284

Val Thr Leu Ala Thr Leu Lys
1               5

<210> SEQ ID NO 285
<211> LENGTH: 8
<212> TYPE: PRT
<213> ORGANISM: HUMAN

<400> SEQUENCE: 285

Ala Leu Pro Ala Pro Ile Glu Lys
1               5

<210> SEQ ID NO 286
<211> LENGTH: 9
<212> TYPE: PRT
<213> ORGANISM: HUMAN

<400> SEQUENCE: 286

Asp Tyr Phe Pro Glu Pro Val Thr Val
1               5

<210> SEQ ID NO 287
<211> LENGTH: 14
<212> TYPE: PRT
<213> ORGANISM: HUMAN

<400> SEQUENCE: 287

Phe Asn Trp Tyr Val Asp Gly Val Glu Val His Asn Ala Lys
1               5                   10

<210> SEQ ID NO 288
<211> LENGTH: 22
<212> TYPE: PRT
<213> ORGANISM: HUMAN

<400> SEQUENCE: 288

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 289
<211> LENGTH: 12
<212> TYPE: PRT
<213> ORGANISM: HUMAN

<400> SEQUENCE: 289

Gly Pro Ser Val Phe Pro Leu Ala Pro Ser Ser Lys
1               5                   10

<210> SEQ ID NO 290
<211> LENGTH: 10
<212> TYPE: PRT
<213> ORGANISM: HUMAN

<400> SEQUENCE: 290

Asn Gln Val Ser Leu Thr Cys Leu Val Lys
1               5                   10

<210> SEQ ID NO 291
<211> LENGTH: 12
<212> TYPE: PRT
<213> ORGANISM: HUMAN

<400> SEQUENCE: 291

Gln Val Gln Leu Val Gln Ser Gly Ala Glu Val Lys
1               5                   10

<210> SEQ ID NO 292
<211> LENGTH: 14
<212> TYPE: PRT
<213> ORGANISM: HUMAN

<400> SEQUENCE: 292

Ser Thr Ser Gly Gly Thr Ala Ala Leu Gly Cys Leu Val Lys
1               5                   10

<210> SEQ ID NO 293
<211> LENGTH: 26
<212> TYPE: PRT
<213> ORGANISM: HUMAN

<400> SEQUENCE: 293

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25

<210> SEQ ID NO 294
<211> LENGTH: 19
<212> TYPE: PRT
<213> ORGANISM: HUMAN

<400> SEQUENCE: 294

Thr Pro Glu Val Thr Cys Val Val Val Asp Val Ser His Glu Asp Pro
1               5                   10                  15

Glu Val Lys

-continued

<210> SEQ ID NO 295
<211> LENGTH: 17
<212> TYPE: PRT
<213> ORGANISM: HUMAN

<400> SEQUENCE: 295

Thr Thr Pro Pro Val Leu Asp Ser Asp Gly Ser Phe Phe Leu Tyr Ser
1               5                   10                  15

Lys

<210> SEQ ID NO 296
<211> LENGTH: 16
<212> TYPE: PRT
<213> ORGANISM: HUMAN

<400> SEQUENCE: 296

Val Val Ser Val Leu Thr Val Leu His Gln Asp Trp Leu Asn Gly Lys
1               5                   10                  15

<210> SEQ ID NO 297
<211> LENGTH: 8
<212> TYPE: PRT
<213> ORGANISM: HUMAN

<400> SEQUENCE: 297

Ala Val Leu Thr Ile Asp Glu Lys
1               5

<210> SEQ ID NO 298
<211> LENGTH: 16
<212> TYPE: PRT
<213> ORGANISM: HUMAN

<400> SEQUENCE: 298

Asp Thr Glu Glu Glu Asp Phe His Val Asp Gln Val Thr Thr Val Lys
1               5                   10                  15

<210> SEQ ID NO 299
<211> LENGTH: 10
<212> TYPE: PRT
<213> ORGANISM: HUMAN

<400> SEQUENCE: 299

Leu Ser Ile Thr Gly Thr Tyr Asp Leu Lys
1               5                   10

<210> SEQ ID NO 300
<211> LENGTH: 21
<212> TYPE: PRT
<213> ORGANISM: HUMAN

<400> SEQUENCE: 300

Gly Ala Pro Ser Ala Thr Gln Pro Ala Thr Ala Glu Thr Gln His Ile
1               5                   10                  15

Ala Asp Gln Val Arg
            20

<210> SEQ ID NO 301
<211> LENGTH: 24
<212> TYPE: PRT
<213> ORGANISM: HUMAN

<400> SEQUENCE: 301

```
Met Met Cys Gly Ala Pro Ser Ala Thr Gln Pro Ala Thr Ala Glu Thr
1               5                   10                  15

Gln His Ile Ala Asp Gln Val Arg
            20
```

<210> SEQ ID NO 302
<211> LENGTH: 12
<212> TYPE: PRT
<213> ORGANISM: HUMAN

<400> SEQUENCE: 302

```
Ser Gln Val Val Ala Gly Thr Asn Tyr Phe Ile Lys
1               5                   10
```

<210> SEQ ID NO 303
<211> LENGTH: 21
<212> TYPE: PRT
<213> ORGANISM: HUMAN

<400> SEQUENCE: 303

```
Val Phe Gln Ser Leu Pro His Glu Asn Lys Pro Leu Thr Leu Ser Asn
1               5                   10                  15

Tyr Gln Thr Asn Lys
            20
```

<210> SEQ ID NO 304
<211> LENGTH: 13
<212> TYPE: PRT
<213> ORGANISM: HUMAN

<400> SEQUENCE: 304

```
Ala Ala Glu Asp Asp Glu Asp Asp Val Asp Thr Lys
1               5                   10
```

<210> SEQ ID NO 305
<211> LENGTH: 14
<212> TYPE: PRT
<213> ORGANISM: HUMAN

<400> SEQUENCE: 305

```
Ala Ala Glu Asp Asp Glu Asp Asp Val Asp Thr Lys Lys
1               5                   10
```

<210> SEQ ID NO 306
<211> LENGTH: 10
<212> TYPE: PRT
<213> ORGANISM: HUMAN

<400> SEQUENCE: 306

```
Glu Val Val Glu Glu Ala Glu Asn Gly Arg
1               5                   10
```

<210> SEQ ID NO 307
<211> LENGTH: 14
<212> TYPE: PRT
<213> ORGANISM: HUMAN

<400> SEQUENCE: 307

```
Arg Ala Ala Glu Asp Asp Glu Asp Asp Val Asp Thr Lys
1               5                   10
```

<210> SEQ ID NO 308
<211> LENGTH: 14

```
<212> TYPE: PRT
<213> ORGANISM: HUMAN

<400> SEQUENCE: 308

Ser Asp Ala Ala Val Asp Thr Ser Ser Glu Ile Thr Thr Lys
1               5                   10

<210> SEQ ID NO 309
<211> LENGTH: 16
<212> TYPE: PRT
<213> ORGANISM: HUMAN

<400> SEQUENCE: 309

Asp Asp Glu Val Asp Val Asp Gly Thr Val Glu Glu Asp Leu Gly Lys
1               5                   10                  15

<210> SEQ ID NO 310
<211> LENGTH: 10
<212> TYPE: PRT
<213> ORGANISM: HUMAN

<400> SEQUENCE: 310

Glu Phe Glu Pro Leu Leu Asn Trp Met Lys
1               5                   10

<210> SEQ ID NO 311
<211> LENGTH: 8
<212> TYPE: PRT
<213> ORGANISM: HUMAN

<400> SEQUENCE: 311

Glu Val Glu Glu Asp Glu Tyr Lys
1               5

<210> SEQ ID NO 312
<211> LENGTH: 9
<212> TYPE: PRT
<213> ORGANISM: HUMAN

<400> SEQUENCE: 312

Phe Ala Phe Gln Ala Glu Val Asn Arg
1               5

<210> SEQ ID NO 313
<211> LENGTH: 11
<212> TYPE: PRT
<213> ORGANISM: HUMAN

<400> SEQUENCE: 313

Lys Glu Ala Glu Ser Ser Pro Phe Val Glu Arg
1               5                   10

<210> SEQ ID NO 314
<211> LENGTH: 10
<212> TYPE: PRT
<213> ORGANISM: HUMAN

<400> SEQUENCE: 314

Leu Gly Val Ile Glu Asp His Ser Asn Arg
1               5                   10

<210> SEQ ID NO 315
<211> LENGTH: 19
<212> TYPE: PRT
<213> ORGANISM: HUMAN
```

```
<400> SEQUENCE: 315

Leu Ile Ser Leu Thr Asp Glu Asn Ala Leu Ser Gly Asn Glu Glu Leu
1               5                   10                  15

Thr Val Lys

<210> SEQ ID NO 316
<211> LENGTH: 24
<212> TYPE: PRT
<213> ORGANISM: HUMAN

<400> SEQUENCE: 316

Thr Asp Asp Glu Val Val Gln Arg Glu Glu Ala Ile Gln Leu Asp
1               5                   10                  15

Gly Leu Asn Ala Ser Gln Ile Arg
                20

<210> SEQ ID NO 317
<211> LENGTH: 16
<212> TYPE: PRT
<213> ORGANISM: HUMAN

<400> SEQUENCE: 317

Thr Val Leu Asp Leu Ala Val Val Leu Phe Glu Thr Ala Thr Leu Arg
1               5                   10                  15

<210> SEQ ID NO 318
<211> LENGTH: 13
<212> TYPE: PRT
<213> ORGANISM: HUMAN

<400> SEQUENCE: 318

Val Phe Ile Thr Asp Asp Phe His Asp Met Met Pro Lys
1               5                   10

<210> SEQ ID NO 319
<211> LENGTH: 17
<212> TYPE: PRT
<213> ORGANISM: HUMAN

<400> SEQUENCE: 319

Ala Ala Asp Thr Asp Gly Asp Gly Gln Val Asn Tyr Glu Glu Phe Val
1               5                   10                  15

Arg

<210> SEQ ID NO 320
<211> LENGTH: 13
<212> TYPE: PRT
<213> ORGANISM: HUMAN

<400> SEQUENCE: 320

Ala Asp Gln Leu Thr Glu Glu Gln Val Thr Glu Phe Lys
1               5                   10

<210> SEQ ID NO 321
<211> LENGTH: 11
<212> TYPE: PRT
<213> ORGANISM: HUMAN

<400> SEQUENCE: 321

Leu Ser Asp Glu Glu Val Asp Glu Met Ile Arg
1               5                   10
```

```
<210> SEQ ID NO 322
<211> LENGTH: 12
<212> TYPE: PRT
<213> ORGANISM: HUMAN

<400> SEQUENCE: 322

Ser Leu Gly Gln Asn Pro Thr Glu Ala Glu Leu Arg
1               5                   10

<210> SEQ ID NO 323
<211> LENGTH: 16
<212> TYPE: PRT
<213> ORGANISM: HUMAN

<400> SEQUENCE: 323

Val Phe Asp Lys Asp Gly Asn Gly Phe Val Ser Ala Ala Glu Leu Arg
1               5                   10                  15

<210> SEQ ID NO 324
<211> LENGTH: 20
<212> TYPE: PRT
<213> ORGANISM: HUMAN

<400> SEQUENCE: 324

Gly Asn Asp Ile Ser Ser Gly Thr Val Leu Ser Asp Tyr Val Gly Ser
1               5                   10                  15

Gly Pro Pro Lys
            20

<210> SEQ ID NO 325
<211> LENGTH: 14
<212> TYPE: PRT
<213> ORGANISM: HUMAN

<400> SEQUENCE: 325

Leu Tyr Thr Leu Val Leu Thr Asp Pro Asp Ala Pro Ser Arg
1               5                   10

<210> SEQ ID NO 326
<211> LENGTH: 8
<212> TYPE: PRT
<213> ORGANISM: HUMAN

<400> SEQUENCE: 326

Val Leu Thr Pro Thr Gln Val Lys
1               5

<210> SEQ ID NO 327
<211> LENGTH: 11
<212> TYPE: PRT
<213> ORGANISM: HUMAN

<400> SEQUENCE: 327

Gly Thr Asn Tyr Leu Ala Asp Val Phe Glu Lys
1               5                   10

<210> SEQ ID NO 328
<211> LENGTH: 20
<212> TYPE: PRT
<213> ORGANISM: HUMAN

<400> SEQUENCE: 328

Lys Ile Asp Phe Ser Glu Phe Leu Ser Leu Leu Gly Asp Ile Ala Thr
1               5                   10                  15
```

-continued

Asp Tyr His Lys
        20

<210> SEQ ID NO 329
<211> LENGTH: 13
<212> TYPE: PRT
<213> ORGANISM: HUMAN

<400> SEQUENCE: 329

Gln Ser His Gly Ala Ala Pro Cys Ser Gly Gly Ser Gln
1               5                   10

<210> SEQ ID NO 330
<211> LENGTH: 11
<212> TYPE: PRT
<213> ORGANISM: HUMAN

<400> SEQUENCE: 330

Ser Ile Ile Gly Met Ile Asp Met Phe His Lys
1               5                   10

<210> SEQ ID NO 331
<211> LENGTH: 10
<212> TYPE: PRT
<213> ORGANISM: HUMAN

<400> SEQUENCE: 331

Asp Ser Thr Leu Ile Met Gln Leu Leu Arg
1               5                   10

<210> SEQ ID NO 332
<211> LENGTH: 24
<212> TYPE: PRT
<213> ORGANISM: HUMAN

<400> SEQUENCE: 332

Glu Lys Val Glu Thr Glu Leu Gln Gly Val Cys Asp Thr Val Leu Gly
1               5                   10                  15

Leu Leu Asp Ser His Leu Ile Lys
            20

<210> SEQ ID NO 333
<211> LENGTH: 28
<212> TYPE: PRT
<213> ORGANISM: HUMAN

<400> SEQUENCE: 333

Glu Lys Val Glu Thr Glu Leu Gln Gly Val Cys Asp Thr Val Leu Gly
1               5                   10                  15

Leu Leu Asp Ser His Leu Ile Lys Glu Ala Gly Asp
            20                  25

<210> SEQ ID NO 334
<211> LENGTH: 9
<212> TYPE: PRT
<213> ORGANISM: HUMAN

<400> SEQUENCE: 334

Glu Met Pro Pro Thr Asn Pro Ile Arg
1               5

<210> SEQ ID NO 335
<211> LENGTH: 14

-continued

<212> TYPE: PRT
<213> ORGANISM: HUMAN

<400> SEQUENCE: 335

Gly Ala Val Glu Lys Gly Glu Glu Leu Ser Cys Glu Glu Arg
1               5                   10

<210> SEQ ID NO 336
<211> LENGTH: 9
<212> TYPE: PRT
<213> ORGANISM: HUMAN

<400> SEQUENCE: 336

Gly Glu Glu Leu Ser Cys Glu Glu Arg
1               5

<210> SEQ ID NO 337
<211> LENGTH: 10
<212> TYPE: PRT
<213> ORGANISM: HUMAN

<400> SEQUENCE: 337

Gly Ser Glu Glu Lys Gly Pro Glu Val Arg
1               5                   10

<210> SEQ ID NO 338
<211> LENGTH: 7
<212> TYPE: PRT
<213> ORGANISM: HUMAN

<400> SEQUENCE: 338

Leu Ala Glu Gln Ala Glu Arg
1               5

<210> SEQ ID NO 339
<211> LENGTH: 8
<212> TYPE: PRT
<213> ORGANISM: HUMAN

<400> SEQUENCE: 339

Asn Leu Leu Ser Val Ala Tyr Lys
1               5

<210> SEQ ID NO 340
<211> LENGTH: 12
<212> TYPE: PRT
<213> ORGANISM: HUMAN

<400> SEQUENCE: 340

Ser Ala Tyr Gln Glu Ala Met Asp Ile Ser Lys Lys
1               5                   10

<210> SEQ ID NO 341
<211> LENGTH: 14
<212> TYPE: PRT
<213> ORGANISM: HUMAN

<400> SEQUENCE: 341

Ser Asn Glu Glu Gly Ser Glu Glu Lys Gly Pro Glu Val Arg
1               5                   10

<210> SEQ ID NO 342
<211> LENGTH: 19
<212> TYPE: PRT
<213> ORGANISM: HUMAN

<400> SEQUENCE: 342

Thr Thr Phe Asp Glu Ala Met Ala Asp Leu His Thr Leu Ser Glu Asp
1               5                   10                  15
Ser Tyr Lys

<210> SEQ ID NO 343
<211> LENGTH: 22
<212> TYPE: PRT
<213> ORGANISM: HUMAN

<400> SEQUENCE: 343

Val Glu Thr Glu Leu Gln Gly Val Cys Asp Thr Val Leu Gly Leu Leu
1               5                   10                  15
Asp Ser His Leu Ile Lys
            20

<210> SEQ ID NO 344
<211> LENGTH: 8
<212> TYPE: PRT
<213> ORGANISM: HUMAN

<400> SEQUENCE: 344

Val Leu Ser Ser Ile Glu Gln Lys
1               5

<210> SEQ ID NO 345
<211> LENGTH: 9
<212> TYPE: PRT
<213> ORGANISM: HUMAN

<400> SEQUENCE: 345

Tyr Glu Asp Met Ala Ala Phe Met Lys
1               5

<210> SEQ ID NO 346
<211> LENGTH: 11
<212> TYPE: PRT
<213> ORGANISM: HUMAN

<400> SEQUENCE: 346

Tyr Leu Ala Glu Val Ala Thr Gly Asp Asp Lys
1               5                   10

<210> SEQ ID NO 347
<211> LENGTH: 10
<212> TYPE: PRT
<213> ORGANISM: HUMAN

<400> SEQUENCE: 347

Ala Gly Phe Ala Gly Asp Asp Ala Pro Arg
1               5                   10

<210> SEQ ID NO 348
<211> LENGTH: 9
<212> TYPE: PRT
<213> ORGANISM: HUMAN

<400> SEQUENCE: 348

Ala Val Phe Pro Ser Ile Val Gly Arg
1               5

<210> SEQ ID NO 349

```
<211> LENGTH: 11
<212> TYPE: PRT
<213> ORGANISM: HUMAN

<400> SEQUENCE: 349

Ala Val Phe Pro Ser Ile Val Gly Arg Pro Arg
1               5                   10

<210> SEQ ID NO 350
<211> LENGTH: 17
<212> TYPE: PRT
<213> ORGANISM: HUMAN

<400> SEQUENCE: 350

Asp Asp Asp Ile Ala Ala Leu Val Val Asp Asn Gly Ser Gly Met Cys
1               5                   10                  15

Lys

<210> SEQ ID NO 351
<211> LENGTH: 21
<212> TYPE: PRT
<213> ORGANISM: HUMAN

<400> SEQUENCE: 351

Asp Leu Tyr Ala Asn Thr Val Leu Ser Gly Gly Thr Thr Met Tyr Pro
1               5                   10                  15

Gly Ile Ala Asp Arg
            20

<210> SEQ ID NO 352
<211> LENGTH: 11
<212> TYPE: PRT
<213> ORGANISM: HUMAN

<400> SEQUENCE: 352

Asp Ser Tyr Val Gly Asp Glu Ala Gln Ser Lys
1               5                   10

<210> SEQ ID NO 353
<211> LENGTH: 12
<212> TYPE: PRT
<213> ORGANISM: HUMAN

<400> SEQUENCE: 353

Asp Ser Tyr Val Gly Asp Glu Ala Gln Ser Lys Arg
1               5                   10

<210> SEQ ID NO 354
<211> LENGTH: 11
<212> TYPE: PRT
<213> ORGANISM: HUMAN

<400> SEQUENCE: 354

Glu Ile Thr Ala Leu Ala Pro Ser Thr Met Lys
1               5                   10

<210> SEQ ID NO 355
<211> LENGTH: 10
<212> TYPE: PRT
<213> ORGANISM: HUMAN

<400> SEQUENCE: 355

Gly Tyr Ser Phe Thr Thr Thr Ala Glu Arg
1               5                   10
```

<210> SEQ ID NO 356
<211> LENGTH: 11
<212> TYPE: PRT
<213> ORGANISM: HUMAN

<400> SEQUENCE: 356

His Gln Gly Val Met Val Gly Met Gly Gln Lys
1               5                   10

<210> SEQ ID NO 357
<211> LENGTH: 7
<212> TYPE: PRT
<213> ORGANISM: HUMAN

<400> SEQUENCE: 357

Ile Ile Ala Pro Pro Glu Arg
1               5

<210> SEQ ID NO 358
<211> LENGTH: 11
<212> TYPE: PRT
<213> ORGANISM: HUMAN

<400> SEQUENCE: 358

Ile Trp His His Thr Phe Tyr Asn Glu Leu Arg
1               5                   10

<210> SEQ ID NO 359
<211> LENGTH: 23
<212> TYPE: PRT
<213> ORGANISM: HUMAN

<400> SEQUENCE: 359

Leu Cys Tyr Val Ala Leu Asp Phe Glu Gln Glu Met Ala Thr Ala Ala
1               5                   10                  15

Ser Ser Ser Ser Leu Glu Lys
            20

<210> SEQ ID NO 360
<211> LENGTH: 29
<212> TYPE: PRT
<213> ORGANISM: HUMAN

<400> SEQUENCE: 360

Leu Asp Leu Ala Gly Arg Asp Leu Thr Asp Tyr Leu Met Lys Ile Leu
1               5                   10                  15

Thr Glu Arg Gly Tyr Ser Phe Thr Thr Thr Ala Glu Phe
            20                  25

<210> SEQ ID NO 361
<211> LENGTH: 13
<212> TYPE: PRT
<213> ORGANISM: HUMAN

<400> SEQUENCE: 361

Gln Glu Tyr Asp Glu Ser Gly Pro Ser Ile Val His Arg
1               5                   10

<210> SEQ ID NO 362
<211> LENGTH: 16
<212> TYPE: PRT
<213> ORGANISM: HUMAN

-continued

<400> SEQUENCE: 362

Ser Tyr Glu Leu Pro Asp Gly Gln Val Ile Thr Ile Gly Asn Glu Arg
1               5                   10                  15

<210> SEQ ID NO 363
<211> LENGTH: 8
<212> TYPE: PRT
<213> ORGANISM: HUMAN

<400> SEQUENCE: 363

Thr Glu Ala Pro Leu Asn Pro Lys
1               5

<210> SEQ ID NO 364
<211> LENGTH: 29
<212> TYPE: PRT
<213> ORGANISM: HUMAN

<400> SEQUENCE: 364

Thr Thr Gly Ile Val Met Asp Ser Gly Asp Gly Val Thr His Thr Val
1               5                   10                  15

Pro Ile Tyr Glu Gly Tyr Ala Leu Pro His Ala Ile Leu
            20                  25

<210> SEQ ID NO 365
<211> LENGTH: 10
<212> TYPE: PRT
<213> ORGANISM: HUMAN

<400> SEQUENCE: 365

Val Ala Pro Glu Glu His Pro Val Leu Leu
1               5                   10

<210> SEQ ID NO 366
<211> LENGTH: 18
<212> TYPE: PRT
<213> ORGANISM: HUMAN

<400> SEQUENCE: 366

Val Ala Pro Glu Glu His Pro Val Leu Leu Thr Glu Ala Pro Leu Asn
1               5                   10                  15

Pro Lys

<210> SEQ ID NO 367
<211> LENGTH: 16
<212> TYPE: PRT
<213> ORGANISM: HUMAN

<400> SEQUENCE: 367

Tyr Pro Ile Glu His Gly Ile Val Thr Asn Trp Asp Asp Met Glu Lys
1               5                   10                  15

<210> SEQ ID NO 368
<211> LENGTH: 9
<212> TYPE: PRT
<213> ORGANISM: HUMAN

<400> SEQUENCE: 368

Asp Leu Ala Gly Ser Ile Ile Gly Lys
1               5

<210> SEQ ID NO 369
<211> LENGTH: 11

```
<212> TYPE: PRT
<213> ORGANISM: HUMAN

<400> SEQUENCE: 369

Ile Asp Glu Pro Leu Glu Gly Ser Glu Asp Arg
1               5                   10

<210> SEQ ID NO 370
<211> LENGTH: 16
<212> TYPE: PRT
<213> ORGANISM: HUMAN

<400> SEQUENCE: 370

Ile Leu Ser Ile Ser Ala Asp Ile Glu Thr Ile Gly Glu Ile Leu Lys
1               5                   10                  15

<210> SEQ ID NO 371
<211> LENGTH: 9
<212> TYPE: PRT
<213> ORGANISM: HUMAN

<400> SEQUENCE: 371

Ala Thr Val Gln Gln Leu Glu Gly Arg
1               5

<210> SEQ ID NO 372
<211> LENGTH: 9
<212> TYPE: PRT
<213> ORGANISM: HUMAN

<400> SEQUENCE: 372

Glu Leu Gly Val Gly Ile Ala Leu Arg
1               5

<210> SEQ ID NO 373
<211> LENGTH: 9
<212> TYPE: PRT
<213> ORGANISM: HUMAN

<400> SEQUENCE: 373

Phe Glu Glu Thr Thr Ala Asp Gly Arg
1               5

<210> SEQ ID NO 374
<211> LENGTH: 7
<212> TYPE: PRT
<213> ORGANISM: HUMAN

<400> SEQUENCE: 374

Gly Phe Asp Glu Tyr Met Lys
1               5

<210> SEQ ID NO 375
<211> LENGTH: 20
<212> TYPE: PRT
<213> ORGANISM: HUMAN

<400> SEQUENCE: 375

Thr Thr Gln Phe Ser Cys Thr Leu Gly Glu Lys Phe Glu Glu Thr Thr
1               5                   10                  15

Ala Asp Gly Arg
            20

<210> SEQ ID NO 376
```

```
<211> LENGTH: 12
<212> TYPE: PRT
<213> ORGANISM: HUMAN

<400> SEQUENCE: 376

Ala Ala Glu Glu Glu Asp Glu Ala Asp Pro Lys Arg
1               5                   10

<210> SEQ ID NO 377
<211> LENGTH: 8
<212> TYPE: PRT
<213> ORGANISM: HUMAN

<400> SEQUENCE: 377

Gly Phe Gly Phe Val Leu Phe Lys
1               5

<210> SEQ ID NO 378
<211> LENGTH: 9
<212> TYPE: PRT
<213> ORGANISM: HUMAN

<400> SEQUENCE: 378

Val Gly Tyr Val Ser Gly Trp Gly Arg
1               5

<210> SEQ ID NO 379
<211> LENGTH: 10
<212> TYPE: PRT
<213> ORGANISM: HUMAN

<400> SEQUENCE: 379

Asp Ser Thr Leu Ile Met Gln Leu Leu Arg
1               5                   10

<210> SEQ ID NO 380
<211> LENGTH: 18
<212> TYPE: PRT
<213> ORGANISM: HUMAN

<400> SEQUENCE: 380

Gly Ile Val Asp Gln Ser Gln Gln Ala Tyr Gln Glu Ala Phe Glu Ile
1               5                   10                  15

Ser Lys

<210> SEQ ID NO 381
<211> LENGTH: 7
<212> TYPE: PRT
<213> ORGANISM: HUMAN

<400> SEQUENCE: 381

Leu Ala Glu Gln Ala Glu Arg
1               5

<210> SEQ ID NO 382
<211> LENGTH: 8
<212> TYPE: PRT
<213> ORGANISM: HUMAN

<400> SEQUENCE: 382

Asn Leu Leu Ser Val Ala Tyr Lys
1               5

<210> SEQ ID NO 383
```

```
<211> LENGTH: 14
<212> TYPE: PRT
<213> ORGANISM: HUMAN

<400> SEQUENCE: 383

Ser Val Thr Glu Gln Gly Ala Glu Leu Ser Asn Glu Glu Arg
1               5                   10

<210> SEQ ID NO 384
<211> LENGTH: 19
<212> TYPE: PRT
<213> ORGANISM: HUMAN

<400> SEQUENCE: 384

Thr Ala Phe Asp Glu Ala Ile Ala Glu Leu Asp Thr Leu Ser Glu Glu
1               5                   10                  15

Ser Tyr Lys

<210> SEQ ID NO 385
<211> LENGTH: 8
<212> TYPE: PRT
<213> ORGANISM: HUMAN

<400> SEQUENCE: 385

Val Val Ser Ser Ile Glu Gln Lys
1               5

<210> SEQ ID NO 386
<211> LENGTH: 12
<212> TYPE: PRT
<213> ORGANISM: HUMAN

<400> SEQUENCE: 386

Tyr Leu Ala Glu Val Ala Ala Gly Asp Asp Lys Lys
1               5                   10

<210> SEQ ID NO 387
<211> LENGTH: 10
<212> TYPE: PRT
<213> ORGANISM: HUMAN

<400> SEQUENCE: 387

Ala Gly Val Glu Thr Thr Thr Pro Ser Lys
1               5                   10

<210> SEQ ID NO 388
<211> LENGTH: 11
<212> TYPE: PRT
<213> ORGANISM: HUMAN

<400> SEQUENCE: 388

Asp Thr Glu Arg Pro Ser Gly Ile Pro Glu Arg
1               5                   10

<210> SEQ ID NO 389
<211> LENGTH: 19
<212> TYPE: PRT
<213> ORGANISM: HUMAN

<400> SEQUENCE: 389

Ser Tyr Glu Leu Thr Gln Pro Pro Ser Val Ser Val Ser Pro Gly Gln
1               5                   10                  15

Thr Ala Arg
```

<210> SEQ ID NO 390
<211> LENGTH: 15
<212> TYPE: PRT
<213> ORGANISM: HUMAN

<400> SEQUENCE: 390

Ser Tyr Ser Cys Gln Val Thr His Glu Gly Ser Thr Val Glu Lys
1               5                   10                  15

<210> SEQ ID NO 391
<211> LENGTH: 22
<212> TYPE: PRT
<213> ORGANISM: HUMAN

<400> SEQUENCE: 391

Ala Gln Pro Val Gln Val Ala Glu Gly Ser Glu Pro Asp Gly Phe Trp
1               5                   10                  15

Glu Ala Leu Gly Gly Lys
            20

<210> SEQ ID NO 392
<211> LENGTH: 18
<212> TYPE: PRT
<213> ORGANISM: HUMAN

<400> SEQUENCE: 392

Thr Pro Ser Ala Ala Tyr Leu Trp Val Gly Thr Gly Ala Ser Glu Ala
1               5                   10                  15

Glu Lys

<210> SEQ ID NO 393
<211> LENGTH: 10
<212> TYPE: PRT
<213> ORGANISM: HUMAN

<400> SEQUENCE: 393

Ala Gly Ala His Leu Gln Gly Gly Ala Lys
1               5                   10

<210> SEQ ID NO 394
<211> LENGTH: 15
<212> TYPE: PRT
<213> ORGANISM: HUMAN

<400> SEQUENCE: 394

Gly Ala Leu Gln Asn Ile Ile Pro Ala Ser Thr Gly Ala Ala Lys
1               5                   10                  15

<210> SEQ ID NO 395
<211> LENGTH: 7
<212> TYPE: PRT
<213> ORGANISM: HUMAN

<400> SEQUENCE: 395

Leu Thr Gly Met Ala Phe Arg
1               5

<210> SEQ ID NO 396
<211> LENGTH: 8
<212> TYPE: PRT
<213> ORGANISM: HUMAN

<400> SEQUENCE: 396

Gln Ala Ser Glu Gly Pro Leu Lys
1               5

<210> SEQ ID NO 397
<211> LENGTH: 8
<212> TYPE: PRT
<213> ORGANISM: HUMAN

<400> SEQUENCE: 397

Thr Val Asp Gly Pro Ser Gly Lys
1               5

<210> SEQ ID NO 398
<211> LENGTH: 8
<212> TYPE: PRT
<213> ORGANISM: HUMAN

<400> SEQUENCE: 398

Val Ile Pro Glu Leu Asp Gly Lys
1               5

<210> SEQ ID NO 399
<211> LENGTH: 14
<212> TYPE: PRT
<213> ORGANISM: HUMAN

<400> SEQUENCE: 399

Val Pro Thr Ala Asn Val Ser Val Val Asp Leu Thr Cys Arg
1               5                   10

<210> SEQ ID NO 400
<211> LENGTH: 12
<212> TYPE: PRT
<213> ORGANISM: HUMAN

<400> SEQUENCE: 400

Val Val Asp Leu Met Ala His Met Ala Ser Lys Glu
1               5                   10

<210> SEQ ID NO 401
<211> LENGTH: 18
<212> TYPE: PRT
<213> ORGANISM: HUMAN

<400> SEQUENCE: 401

Gly Ala Asp Phe Leu Val Thr Glu Val Glu Asn Gly Gly Ser Leu Gly
1               5                   10                  15

Ser Lys

<210> SEQ ID NO 402
<211> LENGTH: 8
<212> TYPE: PRT
<213> ORGANISM: HUMAN

<400> SEQUENCE: 402

Ala Pro Ile Ile Ala Val Thr Arg
1               5

<210> SEQ ID NO 403
<211> LENGTH: 11
<212> TYPE: PRT
<213> ORGANISM: HUMAN

<400> SEQUENCE: 403

-continued

Gly Asp Leu Gly Ile Glu Ile Pro Ala Glu Lys
1               5                   10

<210> SEQ ID NO 404
<211> LENGTH: 9
<212> TYPE: PRT
<213> ORGANISM: HUMAN

<400> SEQUENCE: 404

Gly Asp Tyr Pro Leu Glu Ala Val Arg
1               5

<210> SEQ ID NO 405
<211> LENGTH: 8
<212> TYPE: PRT
<213> ORGANISM: HUMAN

<400> SEQUENCE: 405

Ile Glu Asn His Glu Gly Val Arg
1               5

<210> SEQ ID NO 406
<211> LENGTH: 9
<212> TYPE: PRT
<213> ORGANISM: HUMAN

<400> SEQUENCE: 406

Lys Ala Ser Asp Val His Glu Val Arg
1               5

<210> SEQ ID NO 407
<211> LENGTH: 11
<212> TYPE: PRT
<213> ORGANISM: HUMAN

<400> SEQUENCE: 407

Leu Asp Ile Asp Ser Pro Pro Ile Thr Ala Arg
1               5                   10

<210> SEQ ID NO 408
<211> LENGTH: 13
<212> TYPE: PRT
<213> ORGANISM: HUMAN

<400> SEQUENCE: 408

Asn Thr Gly Ile Ile Cys Thr Ile Gly Pro Ala Ser Arg
1               5                   10

<210> SEQ ID NO 409
<211> LENGTH: 10
<212> TYPE: PRT
<213> ORGANISM: HUMAN

<400> SEQUENCE: 409

Ala Gln Leu Gly Gly Pro Glu Ala Ala Lys
1               5                   10

<210> SEQ ID NO 410
<211> LENGTH: 17
<212> TYPE: PRT
<213> ORGANISM: HUMAN

<400> SEQUENCE: 410

Leu Ala Thr Gln Ser Asn Glu Ile Thr Ile Pro Val Thr Phe Glu Ser
1               5                   10                  15

Arg

<210> SEQ ID NO 411
<211> LENGTH: 9
<212> TYPE: PRT
<213> ORGANISM: HUMAN

<400> SEQUENCE: 411

Gln Asp Glu His Gly Tyr Ile Ser Arg
1               5

<210> SEQ ID NO 412
<211> LENGTH: 10
<212> TYPE: PRT
<213> ORGANISM: HUMAN

<400> SEQUENCE: 412

Gln Leu Ser Ser Gly Val Ser Glu Ile Arg
1               5                   10

<210> SEQ ID NO 413
<211> LENGTH: 16
<212> TYPE: PRT
<213> ORGANISM: HUMAN

<400> SEQUENCE: 413

Val Ser Leu Asp Val Asn His Phe Ala Pro Asp Glu Leu Thr Val Lys
1               5                   10                  15

<210> SEQ ID NO 414
<211> LENGTH: 13
<212> TYPE: PRT
<213> ORGANISM: HUMAN

<400> SEQUENCE: 414

Glu Asp Ser Gln Arg Pro Gly Ala His Leu Thr Val Lys
1               5                   10

<210> SEQ ID NO 415
<211> LENGTH: 11
<212> TYPE: PRT
<213> ORGANISM: HUMAN

<400> SEQUENCE: 415

Ser Glu Ser Pro Lys Glu Pro Glu Gln Leu Arg
1               5                   10

<210> SEQ ID NO 416
<211> LENGTH: 10
<212> TYPE: PRT
<213> ORGANISM: HUMAN

<400> SEQUENCE: 416

Gly Glu Gly Gln Leu Gly Pro Ala Glu Arg
1               5                   10

<210> SEQ ID NO 417
<211> LENGTH: 8
<212> TYPE: PRT
<213> ORGANISM: HUMAN

<400> SEQUENCE: 417

Ser Asp Pro Val Val Ser Tyr Arg
1               5

```
<210> SEQ ID NO 418
<211> LENGTH: 16
<212> TYPE: PRT
<213> ORGANISM: HUMAN

<400> SEQUENCE: 418

Asp Asp Glu Val Asp Val Asp Gly Thr Val Glu Glu Asp Leu Gly Lys
1               5                   10                  15

<210> SEQ ID NO 419
<211> LENGTH: 10
<212> TYPE: PRT
<213> ORGANISM: HUMAN

<400> SEQUENCE: 419

Glu Phe Glu Pro Leu Leu Asn Trp Met Lys
1               5                   10

<210> SEQ ID NO 420
<211> LENGTH: 8
<212> TYPE: PRT
<213> ORGANISM: HUMAN

<400> SEQUENCE: 420

Glu Val Glu Glu Asp Glu Tyr Lys
1               5

<210> SEQ ID NO 421
<211> LENGTH: 9
<212> TYPE: PRT
<213> ORGANISM: HUMAN

<400> SEQUENCE: 421

Phe Ala Phe Gln Ala Glu Val Asn Arg
1               5

<210> SEQ ID NO 422
<211> LENGTH: 11
<212> TYPE: PRT
<213> ORGANISM: HUMAN

<400> SEQUENCE: 422

Lys Glu Ala Glu Ser Ser Pro Phe Val Glu Arg
1               5                   10

<210> SEQ ID NO 423
<211> LENGTH: 10
<212> TYPE: PRT
<213> ORGANISM: HUMAN

<400> SEQUENCE: 423

Leu Gly Val Ile Glu Asp His Ser Asn Arg
1               5                   10

<210> SEQ ID NO 424
<211> LENGTH: 19
<212> TYPE: PRT
<213> ORGANISM: HUMAN

<400> SEQUENCE: 424

Leu Ile Ser Leu Thr Asp Glu Asn Ala Leu Ser Gly Asn Glu Glu Leu
1               5                   10                  15

Thr Val Lys
```

<210> SEQ ID NO 425
<211> LENGTH: 24
<212> TYPE: PRT
<213> ORGANISM: HUMAN

<400> SEQUENCE: 425

Thr Asp Asp Glu Val Val Gln Arg Glu Glu Ala Ile Gln Leu Asp
1               5                   10                  15

Gly Leu Asn Ala Ser Gln Ile Arg
            20

<210> SEQ ID NO 426
<211> LENGTH: 16
<212> TYPE: PRT
<213> ORGANISM: HUMAN

<400> SEQUENCE: 426

Thr Val Leu Asp Leu Ala Val Val Leu Phe Glu Thr Ala Thr Leu Arg
1               5                   10                  15

<210> SEQ ID NO 427
<211> LENGTH: 13
<212> TYPE: PRT
<213> ORGANISM: HUMAN

<400> SEQUENCE: 427

Val Phe Ile Thr Asp Asp Phe His Asp Met Met Pro Lys
1               5                   10

<210> SEQ ID NO 428
<211> LENGTH: 8
<212> TYPE: PRT
<213> ORGANISM: HUMAN

<400> SEQUENCE: 428

Gly Leu Val Gly Glu Ile Ile Lys
1               5

<210> SEQ ID NO 429
<211> LENGTH: 10
<212> TYPE: PRT
<213> ORGANISM: HUMAN

<400> SEQUENCE: 429

Asn Ile Ile His Gly Ser Asp Ser Val Lys
1               5                   10

<210> SEQ ID NO 430
<211> LENGTH: 12
<212> TYPE: PRT
<213> ORGANISM: HUMAN

<400> SEQUENCE: 430

Ala Ser Gly Val Ala Val Ser Asp Gly Val Ile Lys
1               5                   10

<210> SEQ ID NO 431
<211> LENGTH: 9
<212> TYPE: PRT
<213> ORGANISM: HUMAN

<400> SEQUENCE: 431

Ile Ser Ser Pro Thr Glu Thr Glu Arg

<210> SEQ ID NO 432
<211> LENGTH: 10
<212> TYPE: PRT
<213> ORGANISM: HUMAN

<400> SEQUENCE: 432

Asn Gln Lys Asp Pro Gly Val Leu Asp Arg
1               5                   10

<210> SEQ ID NO 433
<211> LENGTH: 10
<212> TYPE: PRT
<213> ORGANISM: HUMAN

<400> SEQUENCE: 433

Ala Thr Ala Val Val Asp Gly Ala Phe Lys
1               5                   10

<210> SEQ ID NO 434
<211> LENGTH: 8
<212> TYPE: PRT
<213> ORGANISM: HUMAN

<400> SEQUENCE: 434

Gly Leu Phe Ile Leu Asp Gly Lys
1               5

<210> SEQ ID NO 435
<211> LENGTH: 18
<212> TYPE: PRT
<213> ORGANISM: HUMAN

<400> SEQUENCE: 435

Lys Glu Gly Gly Leu Gly Pro Leu Asn Ile Pro Leu Leu Ala Asp Val
1               5                   10                  15

Thr Arg

<210> SEQ ID NO 436
<211> LENGTH: 9
<212> TYPE: PRT
<213> ORGANISM: HUMAN

<400> SEQUENCE: 436

Leu Ser Glu Asp Tyr Gly Val Leu Lys
1               5

<210> SEQ ID NO 437
<211> LENGTH: 11
<212> TYPE: PRT
<213> ORGANISM: HUMAN

<400> SEQUENCE: 437

Gln Ile Thr Val Asn Asp Leu Pro Val Gly Arg
1               5                   10

<210> SEQ ID NO 438
<211> LENGTH: 8
<212> TYPE: PRT
<213> ORGANISM: HUMAN

<400> SEQUENCE: 438

Thr Asp Glu Gly Ile Ala Tyr Arg

```
1               5

<210> SEQ ID NO 439
<211> LENGTH: 7
<212> TYPE: PRT
<213> ORGANISM: HUMAN

<400> SEQUENCE: 439

Thr Leu Val Val His Glu Lys
1               5

<210> SEQ ID NO 440
<211> LENGTH: 15
<212> TYPE: PRT
<213> ORGANISM: HUMAN

<400> SEQUENCE: 440

Ala Met Gly Ile Met Asn Ser Phe Val Asn Asp Ile Phe Glu Arg
1               5                   10                  15

<210> SEQ ID NO 441
<211> LENGTH: 9
<212> TYPE: PRT
<213> ORGANISM: HUMAN

<400> SEQUENCE: 441

Leu Leu Leu Pro Gly Glu Leu Ala Lys
1               5

<210> SEQ ID NO 442
<211> LENGTH: 11
<212> TYPE: PRT
<213> ORGANISM: HUMAN

<400> SEQUENCE: 442

Gln Val His Pro Asp Thr Gly Ile Ser Ser Lys
1               5                   10

<210> SEQ ID NO 443
<211> LENGTH: 11
<212> TYPE: PRT
<213> ORGANISM: HUMAN

<400> SEQUENCE: 443

Ala Ala Glu Glu Pro Ser Lys Val Glu Glu Lys
1               5                   10

<210> SEQ ID NO 444
<211> LENGTH: 15
<212> TYPE: PRT
<213> ORGANISM: HUMAN

<400> SEQUENCE: 444

Ala Glu Asp Gly Ala Thr Pro Ser Pro Ser Asn Glu Thr Pro Lys
1               5                   10                  15

<210> SEQ ID NO 445
<211> LENGTH: 16
<212> TYPE: PRT
<213> ORGANISM: HUMAN

<400> SEQUENCE: 445

Ala Glu Asp Gly Ala Thr Pro Ser Pro Ser Asn Glu Thr Pro Lys Lys
1               5                   10                  15
```

```
<210> SEQ ID NO 446
<211> LENGTH: 14
<212> TYPE: PRT
<213> ORGANISM: HUMAN

<400> SEQUENCE: 446

Ala Val Ala Pro Glu Lys Pro Pro Ala Ser Asp Glu Thr Lys
1               5                   10

<210> SEQ ID NO 447
<211> LENGTH: 17
<212> TYPE: PRT
<213> ORGANISM: HUMAN

<400> SEQUENCE: 447

Glu Ala Gly Glu Gly Gly Glu Ala Glu Ala Pro Ala Ala Glu Gly Gly
1               5                   10                  15

Lys

<210> SEQ ID NO 448
<211> LENGTH: 27
<212> TYPE: PRT
<213> ORGANISM: HUMAN

<400> SEQUENCE: 448

Glu Ala Pro Ala Glu Gly Glu Ala Ala Glu Pro Gly Ser Pro Thr Ala
1               5                   10                  15

Ala Glu Gly Glu Ala Ala Ser Ala Ala Ser Ser
            20                  25

<210> SEQ ID NO 449
<211> LENGTH: 27
<212> TYPE: PRT
<213> ORGANISM: HUMAN

<400> SEQUENCE: 449

Glu Glu Leu Gln Ala Asn Gly Ser Ala Pro Ala Ala Asp Lys Glu Glu
1               5                   10                  15

Pro Ala Ala Ala Gly Ser Gly Ala Ala Ser Pro
            20                  25

<210> SEQ ID NO 450
<211> LENGTH: 19
<212> TYPE: PRT
<213> ORGANISM: HUMAN

<400> SEQUENCE: 450

Gly Glu Ala Ala Ala Glu Arg Pro Gly Glu Ala Ala Val Ala Ser Ser
1               5                   10                  15

Pro Ser Lys

<210> SEQ ID NO 451
<211> LENGTH: 18
<212> TYPE: PRT
<213> ORGANISM: HUMAN

<400> SEQUENCE: 451

Gly Glu Pro Ala Ala Ala Ala Pro Glu Ala Gly Ala Ser Pro Val
1               5                   10                  15

Glu Lys
```

<210> SEQ ID NO 452
<211> LENGTH: 26
<212> TYPE: PRT
<213> ORGANISM: HUMAN

<400> SEQUENCE: 452

Gly Ser Ala Pro Ala Ala Asp Lys Glu Pro Ala Ala Gly Ser
1               5                   10                  15

Gly Ala Ala Ser Pro Ser Ala Ala Glu Lys
            20                  25

<210> SEQ ID NO 453
<211> LENGTH: 15
<212> TYPE: PRT
<213> ORGANISM: HUMAN

<400> SEQUENCE: 453

Val Asn Gly Asp Ala Ser Pro Ala Ala Ala Glu Ser Gly Ala Lys
1               5                   10                  15

<210> SEQ ID NO 454
<211> LENGTH: 19
<212> TYPE: PRT
<213> ORGANISM: HUMAN

<400> SEQUENCE: 454

Ala Phe Leu Ala Ser Pro Glu Tyr Val Asn Leu Pro Ile Asn Gly Asn
1               5                   10                  15

Gly Lys Gln

<210> SEQ ID NO 455
<211> LENGTH: 20
<212> TYPE: PRT
<213> ORGANISM: HUMAN

<400> SEQUENCE: 455

Ala Leu Pro Gly Gln Leu Lys Pro Phe Glu Thr Leu Leu Ser Gln Asn
1               5                   10                  15

Gln Gly Gly Lys
            20

<210> SEQ ID NO 456
<211> LENGTH: 10
<212> TYPE: PRT
<213> ORGANISM: HUMAN

<400> SEQUENCE: 456

Ala Ser Cys Leu Tyr Gly Gln Leu Pro Lys
1               5                   10

<210> SEQ ID NO 457
<211> LENGTH: 16
<212> TYPE: PRT
<213> ORGANISM: HUMAN

<400> SEQUENCE: 457

Phe Gln Asp Gly Asp Leu Thr Leu Tyr Gln Ser Asn Thr Ile Leu Arg
1               5                   10                  15

<210> SEQ ID NO 458
<211> LENGTH: 9
<212> TYPE: PRT
<213> ORGANISM: HUMAN

<400> SEQUENCE: 458

Gly Pro Ser Ser Val Glu Asp Ile Lys
1               5

<210> SEQ ID NO 459
<211> LENGTH: 21
<212> TYPE: PRT
<213> ORGANISM: HUMAN

<400> SEQUENCE: 459

Met Ser Val Gln Pro Thr Val Ser Leu Gly Gly Phe Glu Ile Thr Pro
1               5                   10                  15

Pro Val Val Leu Arg
            20

<210> SEQ ID NO 460
<211> LENGTH: 14
<212> TYPE: PRT
<213> ORGANISM: HUMAN

<400> SEQUENCE: 460

Met Thr Asp Gln Glu Ala Ile Gln Asp Leu Trp Gln Trp Arg
1               5                   10

<210> SEQ ID NO 461
<211> LENGTH: 11
<212> TYPE: PRT
<213> ORGANISM: HUMAN

<400> SEQUENCE: 461

Ala Ser Leu Glu Asn Ser Leu Glu Glu Thr Lys
1               5                   10

<210> SEQ ID NO 462
<211> LENGTH: 9
<212> TYPE: PRT
<213> ORGANISM: HUMAN

<400> SEQUENCE: 462

Asp Ala Glu Glu Trp Phe Phe Thr Lys
1               5

<210> SEQ ID NO 463
<211> LENGTH: 19
<212> TYPE: PRT
<213> ORGANISM: HUMAN

<400> SEQUENCE: 463

Ile Leu Thr Ala Thr Val Asp Asn Ala Asn Val Leu Leu Gln Ile Asp
1               5                   10                  15

Asn Ala Arg

<210> SEQ ID NO 464
<211> LENGTH: 11
<212> TYPE: PRT
<213> ORGANISM: HUMAN

<400> SEQUENCE: 464

Lys Val Val Ser Thr His Glu Gln Val Leu Arg
1               5                   10

<210> SEQ ID NO 465
<211> LENGTH: 10

-continued

```
<212> TYPE: PRT
<213> ORGANISM: HUMAN

<400> SEQUENCE: 465

Val Val Ser Thr His Glu Gln Val Leu Arg
1               5                   10

<210> SEQ ID NO 466
<211> LENGTH: 21
<212> TYPE: PRT
<213> ORGANISM: HUMAN

<400> SEQUENCE: 466

Ala Thr Leu Lys Asp Gln Leu Ile Tyr Asn Leu Leu Lys Glu Glu Gln
1               5                   10                  15

Thr Pro Gln Asn Lys
            20

<210> SEQ ID NO 467
<211> LENGTH: 9
<212> TYPE: PRT
<213> ORGANISM: HUMAN

<400> SEQUENCE: 467

Asp Gln Leu Ile Tyr Asn Leu Leu Lys
1               5

<210> SEQ ID NO 468
<211> LENGTH: 17
<212> TYPE: PRT
<213> ORGANISM: HUMAN

<400> SEQUENCE: 468

Asp Gln Leu Ile Tyr Asn Leu Leu Lys Glu Glu Gln Thr Pro Gln Asn
1               5                   10                  15

Lys

<210> SEQ ID NO 469
<211> LENGTH: 7
<212> TYPE: PRT
<213> ORGANISM: HUMAN

<400> SEQUENCE: 469

Phe Ile Ile Pro Asn Trp Lys
1               5

<210> SEQ ID NO 470
<211> LENGTH: 14
<212> TYPE: PRT
<213> ORGANISM: HUMAN

<400> SEQUENCE: 470

Gly Glu Met Met Asp Leu Gln His Gly Ser Leu Phe Leu Arg
1               5                   10

<210> SEQ ID NO 471
<211> LENGTH: 11
<212> TYPE: PRT
<213> ORGANISM: HUMAN

<400> SEQUENCE: 471

Lys Ser Ala Asp Thr Leu Trp Gly Ile Gln Lys
1               5                   10
```

<210> SEQ ID NO 472
<211> LENGTH: 9
<212> TYPE: PRT
<213> ORGANISM: HUMAN

<400> SEQUENCE: 472

Leu Val Ile Ile Thr Ala Gly Ala Arg
1               5

<210> SEQ ID NO 473
<211> LENGTH: 11
<212> TYPE: PRT
<213> ORGANISM: HUMAN

<400> SEQUENCE: 473

Gln Val Val Glu Ser Ala Tyr Glu Val Ile Lys
1               5                   10

<210> SEQ ID NO 474
<211> LENGTH: 10
<212> TYPE: PRT
<213> ORGANISM: HUMAN

<400> SEQUENCE: 474

Arg Val His Pro Val Ser Thr Met Ile Lys
1               5                   10

<210> SEQ ID NO 475
<211> LENGTH: 10
<212> TYPE: PRT
<213> ORGANISM: HUMAN

<400> SEQUENCE: 475

Ser Ala Asp Thr Leu Trp Gly Ile Gln Lys
1               5                   10

<210> SEQ ID NO 476
<211> LENGTH: 16
<212> TYPE: PRT
<213> ORGANISM: HUMAN

<400> SEQUENCE: 476

Thr Leu His Pro Asp Leu Gly Thr Asp Lys Asp Lys Glu Gln Trp Lys
1               5                   10                  15

<210> SEQ ID NO 477
<211> LENGTH: 9
<212> TYPE: PRT
<213> ORGANISM: HUMAN

<400> SEQUENCE: 477

Val His Pro Val Ser Thr Met Ile Lys
1               5

<210> SEQ ID NO 478
<211> LENGTH: 12
<212> TYPE: PRT
<213> ORGANISM: HUMAN

<400> SEQUENCE: 478

Val Ile Gly Ser Gly Cys Asn Leu Asp Ser Ala Arg
1               5                   10

<210> SEQ ID NO 479

-continued

<210> SEQ ID NO 479 (implied)
<211> LENGTH: 10
<212> TYPE: PRT
<213> ORGANISM: HUMAN

<400> SEQUENCE: 479

Val Thr Leu Thr Ser Glu Glu Glu Ala Arg
1               5                   10

<210> SEQ ID NO 480
<211> LENGTH: 10
<212> TYPE: PRT
<213> ORGANISM: HUMAN

<400> SEQUENCE: 480

Ala Ser Pro Asp Trp Gly Tyr Asp Asp Lys
1               5                   10

<210> SEQ ID NO 481
<211> LENGTH: 18
<212> TYPE: PRT
<213> ORGANISM: HUMAN

<400> SEQUENCE: 481

Ala Ser Pro Asp Trp Gly Tyr Asp Asp Lys Asn Gly Pro Glu Gln Trp
1               5                   10                  15

Ser Lys

<210> SEQ ID NO 482
<211> LENGTH: 19
<212> TYPE: PRT
<213> ORGANISM: HUMAN

<400> SEQUENCE: 482

Glu Ile Ile Asn Val Gly His Ser Phe His Val Asn Phe Glu Asp Asn
1               5                   10                  15

Asp Asn Arg

<210> SEQ ID NO 483
<211> LENGTH: 9
<212> TYPE: PRT
<213> ORGANISM: HUMAN

<400> SEQUENCE: 483

Gly Gly Pro Phe Ser Asp Ser Tyr Arg
1               5

<210> SEQ ID NO 484
<211> LENGTH: 10
<212> TYPE: PRT
<213> ORGANISM: HUMAN

<400> SEQUENCE: 484

His Asp Thr Ser Leu Lys Pro Ile Ser Val
1               5                   10

<210> SEQ ID NO 485
<211> LENGTH: 18
<212> TYPE: PRT
<213> ORGANISM: HUMAN

<400> SEQUENCE: 485

His Asp Thr Ser Leu Lys Pro Ile Ser Val Ser Tyr Asn Pro Ala Thr
1               5                   10                  15

Ala Lys

<210> SEQ ID NO 486
<211> LENGTH: 16
<212> TYPE: PRT
<213> ORGANISM: HUMAN

<400> SEQUENCE: 486

Leu Tyr Pro Ile Ala Asn Gly Asn Asn Gln Ser Pro Val Asp Ile Lys
1               5                   10                  15

<210> SEQ ID NO 487
<211> LENGTH: 13
<212> TYPE: PRT
<213> ORGANISM: HUMAN

<400> SEQUENCE: 487

Ser Ala Glu Leu His Val Ala His Trp Asn Ser Ala Lys
1               5                   10

<210> SEQ ID NO 488
<211> LENGTH: 25
<212> TYPE: PRT
<213> ORGANISM: HUMAN

<400> SEQUENCE: 488

Ser Leu Leu Ser Asn Val Glu Gly Asp Asn Ala Val Pro Met Gln His
1               5                   10                  15

Asn Asn Arg Pro Thr Gln Pro Leu Lys
            20                  25

<210> SEQ ID NO 489
<211> LENGTH: 9
<212> TYPE: PRT
<213> ORGANISM: HUMAN

<400> SEQUENCE: 489

Ser Ser Glu Gln Leu Ala Gln Phe Arg
1               5

<210> SEQ ID NO 490
<211> LENGTH: 9
<212> TYPE: PRT
<213> ORGANISM: HUMAN

<400> SEQUENCE: 490

Val Leu Asp Ala Leu Gln Ala Ile Lys
1               5

<210> SEQ ID NO 491
<211> LENGTH: 14
<212> TYPE: PRT
<213> ORGANISM: HUMAN

<400> SEQUENCE: 491

Tyr Ser Ala Glu Leu His Val Ala His Trp Asn Ser Ala Lys
1               5                   10

<210> SEQ ID NO 492
<211> LENGTH: 10
<212> TYPE: PRT
<213> ORGANISM: HUMAN

<400> SEQUENCE: 492

Tyr Ser Ser Leu Ala Glu Ala Ala Ser Lys
1               5                   10

<210> SEQ ID NO 493
<211> LENGTH: 16
<212> TYPE: PRT
<213> ORGANISM: HUMAN

<400> SEQUENCE: 493

Asp Thr Glu Glu Glu Asp Phe His Val Asp Gln Val Thr Thr Val Lys
1               5                   10                  15

<210> SEQ ID NO 494
<211> LENGTH: 10
<212> TYPE: PRT
<213> ORGANISM: HUMAN

<400> SEQUENCE: 494

Glu Asp Pro Gln Gly Asp Ala Ala Gln Lys
1               5                   10

<210> SEQ ID NO 495
<211> LENGTH: 15
<212> TYPE: PRT
<213> ORGANISM: HUMAN

<400> SEQUENCE: 495

Gly Thr Glu Ala Ala Gly Ala Met Phe Leu Glu Ala Ile Pro Met
1               5                   10                  15

<210> SEQ ID NO 496
<211> LENGTH: 10
<212> TYPE: PRT
<213> ORGANISM: HUMAN

<400> SEQUENCE: 496

Lys Leu Ser Ser Trp Val Leu Leu Met Lys
1               5                   10

<210> SEQ ID NO 497
<211> LENGTH: 10
<212> TYPE: PRT
<213> ORGANISM: HUMAN

<400> SEQUENCE: 497

Leu Gly Met Phe Asn Ile Gln His Cys Lys
1               5                   10

<210> SEQ ID NO 498
<211> LENGTH: 15
<212> TYPE: PRT
<213> ORGANISM: HUMAN

<400> SEQUENCE: 498

Leu Gln His Leu Glu Asn Glu Leu Thr His Asp Ile Ile Thr Lys
1               5                   10                  15

<210> SEQ ID NO 499
<211> LENGTH: 10
<212> TYPE: PRT
<213> ORGANISM: HUMAN

<400> SEQUENCE: 499

Leu Ser Ile Thr Gly Thr Tyr Asp Leu Lys
1               5                   10

<210> SEQ ID NO 500
<211> LENGTH: 10
<212> TYPE: PRT
<213> ORGANISM: HUMAN

<400> SEQUENCE: 500

Leu Val Asp Lys Phe Leu Glu Asp Val Lys
1               5                   10

<210> SEQ ID NO 501
<211> LENGTH: 18
<212> TYPE: PRT
<213> ORGANISM: HUMAN

<400> SEQUENCE: 501

Val Phe Ser Asn Gly Ala Asp Leu Ser Gly Val Thr Glu Glu Ala Pro
1               5                   10                  15

Leu Lys

<210> SEQ ID NO 502
<211> LENGTH: 16
<212> TYPE: PRT
<213> ORGANISM: HUMAN

<400> SEQUENCE: 502

Ala Ala Tyr Leu Gln Glu Thr Gly Lys Pro Leu Asp Glu Thr Leu Lys
1               5                   10                  15

<210> SEQ ID NO 503
<211> LENGTH: 17
<212> TYPE: PRT
<213> ORGANISM: HUMAN

<400> SEQUENCE: 503

Ala Ala Tyr Leu Gln Glu Thr Gly Lys Pro Leu Asp Glu Thr Leu Lys
1               5                   10                  15

Lys

<210> SEQ ID NO 504
<211> LENGTH: 8
<212> TYPE: PRT
<213> ORGANISM: HUMAN

<400> SEQUENCE: 504

Ala Leu Tyr Glu Ala Gly Glu Arg
1               5

<210> SEQ ID NO 505
<211> LENGTH: 12
<212> TYPE: PRT
<213> ORGANISM: HUMAN

<400> SEQUENCE: 505

Cys Ala Thr Ser Lys Pro Ala Phe Phe Ala Glu Lys
1               5                   10

<210> SEQ ID NO 506
<211> LENGTH: 11
<212> TYPE: PRT
<213> ORGANISM: HUMAN

<400> SEQUENCE: 506

```
Asp Ile Thr Ser Asp Thr Ser Gly Asp Phe Arg
1               5                   10
```

<210> SEQ ID NO 507
<211> LENGTH: 24
<212> TYPE: PRT
<213> ORGANISM: HUMAN

<400> SEQUENCE: 507

```
Gly Gly Pro Gly Ser Ala Val Ser Pro Tyr Pro Thr Phe Asn Pro Ser
1               5                   10                  15

Ser Asp Val Ala Ala Leu His Lys
            20
```

<210> SEQ ID NO 508
<211> LENGTH: 16
<212> TYPE: PRT
<213> ORGANISM: HUMAN

<400> SEQUENCE: 508

```
Gly Leu Gly Thr Asp Glu Asp Thr Leu Ile Glu Ile Leu Ala Ser Arg
1               5                   10                  15
```

<210> SEQ ID NO 509
<211> LENGTH: 14
<212> TYPE: PRT
<213> ORGANISM: HUMAN

<400> SEQUENCE: 509

```
Gly Thr Asp Val Asn Val Phe Asn Thr Ile Leu Thr Thr Arg
1               5                   10
```

<210> SEQ ID NO 510
<211> LENGTH: 13
<212> TYPE: PRT
<213> ORGANISM: HUMAN

<400> SEQUENCE: 510

```
Gly Val Asp Glu Ala Thr Ile Ile Asp Ile Leu Thr Lys
1               5                   10
```

<210> SEQ ID NO 511
<211> LENGTH: 15
<212> TYPE: PRT
<213> ORGANISM: HUMAN

<400> SEQUENCE: 511

```
Lys Gly Thr Asp Val Asn Val Phe Asn Thr Ile Leu Thr Thr Arg
1               5                   10                  15
```

<210> SEQ ID NO 512
<211> LENGTH: 8
<212> TYPE: PRT
<213> ORGANISM: HUMAN

<400> SEQUENCE: 512

```
Asn Ala Leu Leu Ser Leu Ala Lys
1               5
```

<210> SEQ ID NO 513
<211> LENGTH: 16
<212> TYPE: PRT
<213> ORGANISM: HUMAN

<400> SEQUENCE: 513

Ser Glu Asp Phe Gly Val Asn Glu Asp Leu Ala Asp Ser Asp Ala Arg
1               5                   10                  15

<210> SEQ ID NO 514
<211> LENGTH: 9
<212> TYPE: PRT
<213> ORGANISM: HUMAN

<400> SEQUENCE: 514

Ser Glu Ile Asp Met Asn Asp Ile Lys
1               5

<210> SEQ ID NO 515
<211> LENGTH: 11
<212> TYPE: PRT
<213> ORGANISM: HUMAN

<400> SEQUENCE: 515

Thr Pro Ala Gln Phe Asp Ala Asp Glu Leu Arg
1               5                   10

<210> SEQ ID NO 516
<211> LENGTH: 9
<212> TYPE: PRT
<213> ORGANISM: HUMAN

<400> SEQUENCE: 516

Asp Gly Val Val Glu Ile Thr Gly Lys
1               5

<210> SEQ ID NO 517
<211> LENGTH: 28
<212> TYPE: PRT
<213> ORGANISM: HUMAN

<400> SEQUENCE: 517

Lys Tyr Thr Leu Pro Pro Gly Val Asp Pro Thr Gln Val Ser Ser Ser
1               5                   10                  15

Leu Ser Pro Glu Gly Thr Leu Thr Val Glu Ala Pro
            20                  25

<210> SEQ ID NO 518
<211> LENGTH: 17
<212> TYPE: PRT
<213> ORGANISM: HUMAN

<400> SEQUENCE: 518

Leu Ala Thr Gln Ser Asn Glu Ile Thr Ile Pro Val Thr Phe Glu Ser
1               5                   10                  15

Arg

<210> SEQ ID NO 519
<211> LENGTH: 9
<212> TYPE: PRT
<213> ORGANISM: HUMAN

<400> SEQUENCE: 519

Gln Asp Glu His Gly Tyr Ile Ser Arg
1               5

<210> SEQ ID NO 520
<211> LENGTH: 10
<212> TYPE: PRT

```
<213> ORGANISM: HUMAN

<400> SEQUENCE: 520

Gln Leu Ser Ser Gly Val Ser Glu Ile Arg
1               5                   10

<210> SEQ ID NO 521
<211> LENGTH: 11
<212> TYPE: PRT
<213> ORGANISM: HUMAN

<400> SEQUENCE: 521

Thr Lys Asp Gly Val Val Glu Ile Thr Gly Lys
1               5                   10

<210> SEQ ID NO 522
<211> LENGTH: 16
<212> TYPE: PRT
<213> ORGANISM: HUMAN

<400> SEQUENCE: 522

Val Ser Leu Asp Val Asn His Phe Ala Pro Asp Glu Leu Thr Val Lys
1               5                   10                  15

<210> SEQ ID NO 523
<211> LENGTH: 13
<212> TYPE: PRT
<213> ORGANISM: HUMAN

<400> SEQUENCE: 523

Ala Ala Glu Asp Asp Glu Asp Asp Val Asp Thr Lys
1               5                   10

<210> SEQ ID NO 524
<211> LENGTH: 14
<212> TYPE: PRT
<213> ORGANISM: HUMAN

<400> SEQUENCE: 524

Ala Ala Glu Asp Asp Glu Asp Asp Val Asp Thr Lys Lys
1               5                   10

<210> SEQ ID NO 525
<211> LENGTH: 10
<212> TYPE: PRT
<213> ORGANISM: HUMAN

<400> SEQUENCE: 525

Glu Val Val Glu Glu Ala Glu Asn Gly Arg
1               5                   10

<210> SEQ ID NO 526
<211> LENGTH: 15
<212> TYPE: PRT
<213> ORGANISM: HUMAN

<400> SEQUENCE: 526

Glu Val Val Glu Glu Ala Glu Asn Gly Arg Asp Ala Pro Ala Asn
1               5                   10                  15

<210> SEQ ID NO 527
<211> LENGTH: 11
<212> TYPE: PRT
<213> ORGANISM: HUMAN
```

<400> SEQUENCE: 527

Lys Glu Val Val Glu Glu Ala Glu Asn Gly Arg
1               5                   10

<210> SEQ ID NO 528
<211> LENGTH: 14
<212> TYPE: PRT
<213> ORGANISM: HUMAN

<400> SEQUENCE: 528

Ser Asp Ala Ala Val Asp Thr Ser Ser Glu Ile Thr Thr Lys
1               5                   10

<210> SEQ ID NO 529
<211> LENGTH: 15
<212> TYPE: PRT
<213> ORGANISM: HUMAN

<400> SEQUENCE: 529

Asp Leu Pro Pro Asp Thr Thr Leu Leu Asp Leu Gln Asn Asn Lys
1               5                   10                  15

<210> SEQ ID NO 530
<211> LENGTH: 11
<212> TYPE: PRT
<213> ORGANISM: HUMAN

<400> SEQUENCE: 530

Asn Leu His Ala Leu Ile Leu Val Asn Asn Lys
1               5                   10

<210> SEQ ID NO 531
<211> LENGTH: 13
<212> TYPE: PRT
<213> ORGANISM: HUMAN

<400> SEQUENCE: 531

Ser Ser Gly Ile Glu Asn Gly Ala Phe Gln Gly Met Lys
1               5                   10

<210> SEQ ID NO 532
<211> LENGTH: 11
<212> TYPE: PRT
<213> ORGANISM: HUMAN

<400> SEQUENCE: 532

Val Ser Pro Gly Ala Phe Thr Pro Leu Val Lys
1               5                   10

<210> SEQ ID NO 533
<211> LENGTH: 14
<212> TYPE: PRT
<213> ORGANISM: HUMAN

<400> SEQUENCE: 533

Val Val Gln Cys Ser Asp Leu Gly Leu Asp Lys Val Pro Lys
1               5                   10

<210> SEQ ID NO 534
<211> LENGTH: 9
<212> TYPE: PRT
<213> ORGANISM: HUMAN

<400> SEQUENCE: 534

Ala Asp Leu Ser Glu Ala Ala Asn Arg
1               5

<210> SEQ ID NO 535
<211> LENGTH: 16
<212> TYPE: PRT
<213> ORGANISM: HUMAN

<400> SEQUENCE: 535

Asp Gly Gln Val Ile Asn Glu Thr Ser Gln His His Asp Asp Leu Glu
1               5                   10                  15

<210> SEQ ID NO 536
<211> LENGTH: 9
<212> TYPE: PRT
<213> ORGANISM: HUMAN

<400> SEQUENCE: 536

Asp Asn Leu Ala Glu Asp Ile Met Arg
1               5

<210> SEQ ID NO 537
<211> LENGTH: 11
<212> TYPE: PRT
<213> ORGANISM: HUMAN

<400> SEQUENCE: 537

Glu Glu Ala Glu Asn Thr Leu Gln Ser Phe Arg
1               5                   10

<210> SEQ ID NO 538
<211> LENGTH: 10
<212> TYPE: PRT
<213> ORGANISM: HUMAN

<400> SEQUENCE: 538

Glu Lys Leu Gln Glu Met Leu Gln Arg
1               5                   10

<210> SEQ ID NO 539
<211> LENGTH: 19
<212> TYPE: PRT
<213> ORGANISM: HUMAN

<400> SEQUENCE: 539

Glu Met Glu Glu Asn Phe Ala Val Glu Ala Ala Asn Tyr Gln Asp Thr
1               5                   10                  15

Ile Gly Arg

<210> SEQ ID NO 540
<211> LENGTH: 15
<212> TYPE: PRT
<213> ORGANISM: HUMAN

<400> SEQUENCE: 540

Glu Thr Asn Leu Asp Ser Leu Pro Leu Val Asp Thr His Ser Lys
1               5                   10                  15

<210> SEQ ID NO 541
<211> LENGTH: 9
<212> TYPE: PRT
<213> ORGANISM: HUMAN

<400> SEQUENCE: 541

```
Glu Tyr Gln Asp Leu Leu Asn Val Lys
1               5

<210> SEQ ID NO 542
<211> LENGTH: 10
<212> TYPE: PRT
<213> ORGANISM: HUMAN

<400> SEQUENCE: 542

Phe Ala Asp Leu Ser Glu Ala Ala Asn Arg
1               5                   10

<210> SEQ ID NO 543
<211> LENGTH: 10
<212> TYPE: PRT
<213> ORGANISM: HUMAN

<400> SEQUENCE: 543

Ile Leu Leu Ala Glu Leu Glu Gln Leu Lys
1               5                   10

<210> SEQ ID NO 544
<211> LENGTH: 14
<212> TYPE: PRT
<213> ORGANISM: HUMAN

<400> SEQUENCE: 544

Ile Leu Leu Ala Glu Leu Glu Gln Leu Lys Gly Gln Gly Lys
1               5                   10

<210> SEQ ID NO 545
<211> LENGTH: 14
<212> TYPE: PRT
<213> ORGANISM: HUMAN

<400> SEQUENCE: 545

Ile Ser Leu Pro Leu Pro Asn Phe Ser Ser Leu Asn Leu Arg
1               5                   10

<210> SEQ ID NO 546
<211> LENGTH: 9
<212> TYPE: PRT
<213> ORGANISM: HUMAN

<400> SEQUENCE: 546

Lys Leu Leu Glu Gly Glu Glu Ser Arg
1               5

<210> SEQ ID NO 547
<211> LENGTH: 13
<212> TYPE: PRT
<213> ORGANISM: HUMAN

<400> SEQUENCE: 547

Lys Val Glu Ser Leu Gln Glu Glu Ile Ala Phe Leu Lys
1               5                   10

<210> SEQ ID NO 548
<211> LENGTH: 14
<212> TYPE: PRT
<213> ORGANISM: HUMAN

<400> SEQUENCE: 548

Lys Val Glu Ser Leu Gln Glu Glu Ile Ala Phe Leu Lys Lys
1               5                   10
```

-continued

<210> SEQ ID NO 549
<211> LENGTH: 10
<212> TYPE: PRT
<213> ORGANISM: HUMAN

<400> SEQUENCE: 549

Leu Gly Asp Leu Tyr Glu Glu Glu Met Arg
1               5                   10

<210> SEQ ID NO 550
<211> LENGTH: 19
<212> TYPE: PRT
<213> ORGANISM: HUMAN

<400> SEQUENCE: 550

Leu Leu Gln Asp Ser Val Asp Phe Ser Leu Ala Asp Ala Ile Asn Thr
1               5                   10                  15

Glu Phe Lys

<210> SEQ ID NO 551
<211> LENGTH: 14
<212> TYPE: PRT
<213> ORGANISM: HUMAN

<400> SEQUENCE: 551

Leu Gln Asp Glu Ile Gln Asn Met Lys Glu Glu Met Ala Arg
1               5                   10

<210> SEQ ID NO 552
<211> LENGTH: 8
<212> TYPE: PRT
<213> ORGANISM: HUMAN

<400> SEQUENCE: 552

Leu Gln Glu Glu Met Leu Gln Arg
1               5

<210> SEQ ID NO 553
<211> LENGTH: 13
<212> TYPE: PRT
<213> ORGANISM: HUMAN

<400> SEQUENCE: 553

Asn Leu Asp Ser Leu Pro Leu Val Asp Thr His Ser Lys
1               5                   10

<210> SEQ ID NO 554
<211> LENGTH: 10
<212> TYPE: PRT
<213> ORGANISM: HUMAN

<400> SEQUENCE: 554

Asn Leu Gln Glu Ala Glu Glu Trp Tyr Lys
1               5                   10

<210> SEQ ID NO 555
<211> LENGTH: 10
<212> TYPE: PRT
<213> ORGANISM: HUMAN

<400> SEQUENCE: 555

Gln Asp Val Asp Asn Ala Ser Leu Ala Arg
1               5                   10

<210> SEQ ID NO 556
<211> LENGTH: 9
<212> TYPE: PRT
<213> ORGANISM: HUMAN

<400> SEQUENCE: 556

Gln Gln Tyr Glu Ser Val Ala Ala Lys
1               5

<210> SEQ ID NO 557
<211> LENGTH: 9
<212> TYPE: PRT
<213> ORGANISM: HUMAN

<400> SEQUENCE: 557

Gln Val Asp Gln Leu Thr Asn Asp Lys
1               5

<210> SEQ ID NO 558
<211> LENGTH: 13
<212> TYPE: PRT
<213> ORGANISM: HUMAN

<400> SEQUENCE: 558

Gln Val Gln Ser Leu Thr Cys Glu Val Asp Ala Leu Lys
1               5                   10

<210> SEQ ID NO 559
<211> LENGTH: 10
<212> TYPE: PRT
<213> ORGANISM: HUMAN

<400> SEQUENCE: 559

Arg Gln Val Asp Gln Leu Thr Asn Asp Lys
1               5                   10

<210> SEQ ID NO 560
<211> LENGTH: 21
<212> TYPE: PRT
<213> ORGANISM: HUMAN

<400> SEQUENCE: 560

Thr Val Glu Thr Arg Asp Gly Gln Val Ile Asn Glu Thr Ser Gln His
1               5                   10                  15

His Asp Asp Leu Glu
            20

<210> SEQ ID NO 561
<211> LENGTH: 9
<212> TYPE: PRT
<213> ORGANISM: HUMAN

<400> SEQUENCE: 561

Val Glu Leu Gln Glu Leu Asn Asp Arg
1               5

<210> SEQ ID NO 562
<211> LENGTH: 14
<212> TYPE: PRT
<213> ORGANISM: HUMAN

<400> SEQUENCE: 562

Val Glu Val Glu Arg Asp Asn Leu Ala Glu Asp Ile Met Arg

```
1               5                   10
```

<210> SEQ ID NO 563
<211> LENGTH: 16
<212> TYPE: PRT
<213> ORGANISM: HUMAN

<400> SEQUENCE: 563

```
Asp Asp Glu Val Asp Val Asp Gly Thr Val Glu Glu Asp Leu Gly Lys
1               5                   10                  15
```

<210> SEQ ID NO 564
<211> LENGTH: 10
<212> TYPE: PRT
<213> ORGANISM: HUMAN

<400> SEQUENCE: 564

```
Glu Phe Glu Pro Leu Leu Asn Trp Met Lys
1               5                   10
```

<210> SEQ ID NO 565
<211> LENGTH: 10
<212> TYPE: PRT
<213> ORGANISM: HUMAN

<400> SEQUENCE: 565

```
Glu Gly Val Lys Phe Asp Glu Ser Glu Lys
1               5                   10
```

<210> SEQ ID NO 566
<211> LENGTH: 12
<212> TYPE: PRT
<213> ORGANISM: HUMAN

<400> SEQUENCE: 566

```
Glu Leu Ile Ser Asn Ala Ser Asp Ala Leu Asp Lys
1               5                   10
```

<210> SEQ ID NO 567
<211> LENGTH: 19
<212> TYPE: PRT
<213> ORGANISM: HUMAN

<400> SEQUENCE: 567

```
Phe Gln Ser Ser His His Pro Thr Asp Ile Thr Ser Leu Asp Gln Tyr
1               5                   10                  15

Val Glu Arg
```

<210> SEQ ID NO 568
<211> LENGTH: 9
<212> TYPE: PRT
<213> ORGANISM: HUMAN

<400> SEQUENCE: 568

```
Gly Leu Phe Asp Glu Tyr Gly Ser Lys
1               5
```

<210> SEQ ID NO 569
<211> LENGTH: 14
<212> TYPE: PRT
<213> ORGANISM: HUMAN

<400> SEQUENCE: 569

```
Gly Val Val Asp Ser Asp Asp Leu Pro Leu Asn Val Ser Arg
```

-continued

```
1               5                   10

<210> SEQ ID NO 570
<211> LENGTH: 13
<212> TYPE: PRT
<213> ORGANISM: HUMAN

<400> SEQUENCE: 570

Lys Ile Ala Asp Asp Lys Tyr Asn Asp Thr Phe Trp Lys
1               5                   10

<210> SEQ ID NO 571
<211> LENGTH: 10
<212> TYPE: PRT
<213> ORGANISM: HUMAN

<400> SEQUENCE: 571

Leu Gly Val Ile Glu Asp His Ser Asn Arg
1               5                   10

<210> SEQ ID NO 572
<211> LENGTH: 19
<212> TYPE: PRT
<213> ORGANISM: HUMAN

<400> SEQUENCE: 572

Leu Ile Ser Leu Thr Asp Glu Asn Ala Leu Ser Gly Asn Glu Glu Leu
1               5                   10                  15

Thr Val Lys

<210> SEQ ID NO 573
<211> LENGTH: 14
<212> TYPE: PRT
<213> ORGANISM: HUMAN

<400> SEQUENCE: 573

Asn Leu Leu His Val Thr Asp Thr Gly Val Gly Met Thr Arg
1               5                   10

<210> SEQ ID NO 574
<211> LENGTH: 14
<212> TYPE: PRT
<213> ORGANISM: HUMAN

<400> SEQUENCE: 574

Arg Val Phe Ile Thr Asp Asp Phe His Asp Met Met Pro Lys
1               5                   10

<210> SEQ ID NO 575
<211> LENGTH: 11
<212> TYPE: PRT
<213> ORGANISM: HUMAN

<400> SEQUENCE: 575

Ser Ile Leu Phe Val Pro Thr Ser Ala Pro Arg
1               5                   10

<210> SEQ ID NO 576
<211> LENGTH: 13
<212> TYPE: PRT
<213> ORGANISM: HUMAN

<400> SEQUENCE: 576

Val Phe Ile Thr Asp Asp Phe His Asp Met Met Pro Lys
```

```
<210> SEQ ID NO 577
<211> LENGTH: 9
<212> TYPE: PRT
<213> ORGANISM: HUMAN

<400> SEQUENCE: 577

Glu Leu Pro Ser Phe Val Gly Glu Lys
1               5

<210> SEQ ID NO 578
<211> LENGTH: 16
<212> TYPE: PRT
<213> ORGANISM: HUMAN

<400> SEQUENCE: 578

Glu Leu Pro Ser Phe Val Gly Glu Lys Val Asp Glu Glu Gly Leu Lys
1               5                   10                  15

<210> SEQ ID NO 579
<211> LENGTH: 17
<212> TYPE: PRT
<213> ORGANISM: HUMAN

<400> SEQUENCE: 579

Glu Leu Pro Ser Phe Val Gly Glu Lys Val Asp Glu Glu Gly Leu Lys
1               5                   10                  15

Lys

<210> SEQ ID NO 580
<211> LENGTH: 10
<212> TYPE: PRT
<213> ORGANISM: HUMAN

<400> SEQUENCE: 580

Gly Glu Lys Val Asp Glu Glu Gly Leu Lys
1               5                   10

<210> SEQ ID NO 581
<211> LENGTH: 8
<212> TYPE: PRT
<213> ORGANISM: HUMAN

<400> SEQUENCE: 581

Val Asp Glu Glu Gly Leu Lys Lys
1               5

<210> SEQ ID NO 582
<211> LENGTH: 10
<212> TYPE: PRT
<213> ORGANISM: HUMAN

<400> SEQUENCE: 582

Tyr Ser Cys Gln Glu Gly Asp Lys Phe Lys
1               5                   10

<210> SEQ ID NO 583
<211> LENGTH: 19
<212> TYPE: PRT
<213> ORGANISM: HUMAN

<400> SEQUENCE: 583

Cys Leu Thr Thr Asp Glu Tyr Asp Gly His Ser Thr Tyr Pro Ser His
```

```
1               5                   10                  15

Gln Tyr Gln

<210> SEQ ID NO 584
<211> LENGTH: 9
<212> TYPE: PRT
<213> ORGANISM: HUMAN

<400> SEQUENCE: 584

His Asp Leu Gly His Phe Met Leu Arg
1               5

<210> SEQ ID NO 585
<211> LENGTH: 24
<212> TYPE: PRT
<213> ORGANISM: HUMAN

<400> SEQUENCE: 585

Leu Pro Ser Glu Gly Pro Arg Pro Ala His Val Val Gly Asp Val
1               5                   10                  15

Leu Gln Ala Ala Asp Val Asp Lys
            20

<210> SEQ ID NO 586
<211> LENGTH: 10
<212> TYPE: PRT
<213> ORGANISM: HUMAN

<400> SEQUENCE: 586

Leu Gln Ala Val Thr Asp Asp His Ile Arg
1               5                   10

<210> SEQ ID NO 587
<211> LENGTH: 14
<212> TYPE: PRT
<213> ORGANISM: HUMAN

<400> SEQUENCE: 587

Asn Asp Leu Ser Pro Thr Thr Val Met Ser Glu Gly Ala Arg
1               5                   10

<210> SEQ ID NO 588
<211> LENGTH: 17
<212> TYPE: PRT
<213> ORGANISM: HUMAN

<400> SEQUENCE: 588

Pro Ala His Val Val Gly Asp Val Leu Gln Ala Ala Asp Val Asp
1               5                   10                  15

Lys

<210> SEQ ID NO 589
<211> LENGTH: 15
<212> TYPE: PRT
<213> ORGANISM: HUMAN

<400> SEQUENCE: 589

Thr Val Ala Gly Gln Asp Ala Val Ile Val Leu Leu Gly Thr Arg
1               5                   10                  15

<210> SEQ ID NO 590
<211> LENGTH: 13
<212> TYPE: PRT
```

```
<213> ORGANISM: HUMAN

<400> SEQUENCE: 590

Glu Asn Phe Pro Asn Phe Leu Ser Ala Cys Asp Lys Lys
1               5                   10

<210> SEQ ID NO 591
<211> LENGTH: 11
<212> TYPE: PRT
<213> ORGANISM: HUMAN

<400> SEQUENCE: 591

Gly Thr Asn Tyr Leu Ala Asp Val Phe Glu Lys
1               5                   10

<210> SEQ ID NO 592
<211> LENGTH: 12
<212> TYPE: PRT
<213> ORGANISM: HUMAN

<400> SEQUENCE: 592

Gly Thr Asn Tyr Leu Ala Asp Val Phe Glu Lys Lys
1               5                   10

<210> SEQ ID NO 593
<211> LENGTH: 11
<212> TYPE: PRT
<213> ORGANISM: HUMAN

<400> SEQUENCE: 593

Ile Asp Lys Pro Ser Leu Leu Thr Met Met Lys
1               5                   10

<210> SEQ ID NO 594
<211> LENGTH: 13
<212> TYPE: PRT
<213> ORGANISM: HUMAN

<400> SEQUENCE: 594

Lys Gly Thr Asn Tyr Leu Ala Asp Val Phe Glu Lys Lys
1               5                   10

<210> SEQ ID NO 595
<211> LENGTH: 13
<212> TYPE: PRT
<213> ORGANISM: HUMAN

<400> SEQUENCE: 595

Gln Ser His Gly Ala Ala Pro Cys Ser Gly Gly Ser Gln
1               5                   10

<210> SEQ ID NO 596
<211> LENGTH: 11
<212> TYPE: PRT
<213> ORGANISM: HUMAN

<400> SEQUENCE: 596

Ser Ile Ile Gly Met Ile Asp Met Phe His Lys
1               5                   10

<210> SEQ ID NO 597
<211> LENGTH: 17
<212> TYPE: PRT
<213> ORGANISM: HUMAN
```

```
<400> SEQUENCE: 597

Ala Asp Asn Ala Gly Glu Glu Gly Gly Glu Ala Pro Gln Glu Pro Gln
1               5                   10                  15

Ser

<210> SEQ ID NO 598
<211> LENGTH: 23
<212> TYPE: PRT
<213> ORGANISM: HUMAN

<400> SEQUENCE: 598

Asp Asn Leu Thr Leu Trp Gly Ala Asp Asn Ala Gly Glu Glu Gly Gly
1               5                   10                  15

Glu Ala Pro Gln Glu Pro Gln
            20

<210> SEQ ID NO 599
<211> LENGTH: 24
<212> TYPE: PRT
<213> ORGANISM: HUMAN

<400> SEQUENCE: 599

Asp Asn Leu Thr Leu Trp Gly Ala Asp Asn Ala Gly Glu Glu Gly Gly
1               5                   10                  15

Glu Ala Pro Gln Glu Pro Gln Ser
            20

<210> SEQ ID NO 600
<211> LENGTH: 10
<212> TYPE: PRT
<213> ORGANISM: HUMAN

<400> SEQUENCE: 600

Asp Ser Thr Leu Ile Met Gln Leu Leu Arg
1               5                   10

<210> SEQ ID NO 601
<211> LENGTH: 9
<212> TYPE: PRT
<213> ORGANISM: HUMAN

<400> SEQUENCE: 601

Glu Met Pro Pro Thr Asn Pro Ile Arg
1               5

<210> SEQ ID NO 602
<211> LENGTH: 14
<212> TYPE: PRT
<213> ORGANISM: HUMAN

<400> SEQUENCE: 602

Gly Ala Val Glu Lys Gly Glu Glu Leu Ser Cys Glu Glu Arg
1               5                   10

<210> SEQ ID NO 603
<211> LENGTH: 9
<212> TYPE: PRT
<213> ORGANISM: HUMAN

<400> SEQUENCE: 603

Gly Glu Glu Leu Ser Cys Glu Glu Arg
1               5
```

<210> SEQ ID NO 604
<211> LENGTH: 7
<212> TYPE: PRT
<213> ORGANISM: HUMAN

<400> SEQUENCE: 604

Leu Ala Glu Gln Ala Glu Arg
1               5

<210> SEQ ID NO 605
<211> LENGTH: 8
<212> TYPE: PRT
<213> ORGANISM: HUMAN

<400> SEQUENCE: 605

Asn Leu Leu Ser Val Ala Tyr Lys
1               5

<210> SEQ ID NO 606
<211> LENGTH: 12
<212> TYPE: PRT
<213> ORGANISM: HUMAN

<400> SEQUENCE: 606

Arg Tyr Leu Ala Glu Val Ala Thr Gly Asp Asp Lys
1               5                   10

<210> SEQ ID NO 607
<211> LENGTH: 11
<212> TYPE: PRT
<213> ORGANISM: HUMAN

<400> SEQUENCE: 607

Ser Ala Tyr Gln Glu Ala Met Asp Ile Ser Lys
1               5                   10

<210> SEQ ID NO 608
<211> LENGTH: 12
<212> TYPE: PRT
<213> ORGANISM: HUMAN

<400> SEQUENCE: 608

Ser Ala Tyr Gln Glu Ala Met Asp Ile Ser Lys Lys
1               5                   10

<210> SEQ ID NO 609
<211> LENGTH: 14
<212> TYPE: PRT
<213> ORGANISM: HUMAN

<400> SEQUENCE: 609

Ser Asn Glu Glu Gly Ser Glu Lys Gly Pro Glu Val Arg
1               5                   10

<210> SEQ ID NO 610
<211> LENGTH: 9
<212> TYPE: PRT
<213> ORGANISM: HUMAN

<400> SEQUENCE: 610

Ser Thr Leu Ile Met Gln Leu Leu Arg
1               5

<210> SEQ ID NO 611

-continued

```
<211> LENGTH: 19
<212> TYPE: PRT
<213> ORGANISM: HUMAN

<400> SEQUENCE: 611

Ser Val Phe His Tyr Glu Ile Ala Asn Ser Pro Glu Glu Ala Ile Ser
1               5                   10                  15

Leu Ala Lys

<210> SEQ ID NO 612
<211> LENGTH: 18
<212> TYPE: PRT
<213> ORGANISM: HUMAN

<400> SEQUENCE: 612

Thr Ala Asp Asn Ala Gly Glu Glu Gly Gly Glu Ala Pro Gln Glu Pro
1               5                   10                  15

Gln Ser

<210> SEQ ID NO 613
<211> LENGTH: 17
<212> TYPE: PRT
<213> ORGANISM: HUMAN

<400> SEQUENCE: 613

Thr Thr Phe Asp Glu Ala Met Ala Asp Leu His Thr Leu Ser Glu Asp
1               5                   10                  15

Ser

<210> SEQ ID NO 614
<211> LENGTH: 19
<212> TYPE: PRT
<213> ORGANISM: HUMAN

<400> SEQUENCE: 614

Thr Thr Phe Asp Glu Ala Met Ala Asp Leu His Thr Leu Ser Glu Asp
1               5                   10                  15

Ser Tyr Lys

<210> SEQ ID NO 615
<211> LENGTH: 8
<212> TYPE: PRT
<213> ORGANISM: HUMAN

<400> SEQUENCE: 615

Val Leu Ser Ser Ile Glu Gln Lys
1               5

<210> SEQ ID NO 616
<211> LENGTH: 9
<212> TYPE: PRT
<213> ORGANISM: HUMAN

<400> SEQUENCE: 616

Tyr Glu Asp Met Ala Ala Phe Met Lys
1               5

<210> SEQ ID NO 617
<211> LENGTH: 11
<212> TYPE: PRT
<213> ORGANISM: HUMAN

<400> SEQUENCE: 617
```

```
Tyr Leu Ala Glu Val Ala Thr Gly Asp Asp Lys
1               5                   10

<210> SEQ ID NO 618
<211> LENGTH: 12
<212> TYPE: PRT
<213> ORGANISM: HUMAN

<400> SEQUENCE: 618

Tyr Leu Ala Glu Val Ala Thr Gly Asp Asp Lys Lys
1               5                   10

<210> SEQ ID NO 619
<211> LENGTH: 9
<212> TYPE: PRT
<213> ORGANISM: HUMAN

<400> SEQUENCE: 619

Asp Gly Tyr Asn Tyr Thr Leu Ser Lys
1               5

<210> SEQ ID NO 620
<211> LENGTH: 9
<212> TYPE: PRT
<213> ORGANISM: HUMAN

<400> SEQUENCE: 620

Ile Ser Ser Pro Thr Glu Thr Glu Arg
1               5

<210> SEQ ID NO 621
<211> LENGTH: 16
<212> TYPE: PRT
<213> ORGANISM: HUMAN

<400> SEQUENCE: 621

Thr Glu Phe Leu Ser Phe Met Asn Thr Glu Leu Ala Ala Phe Thr Lys
1               5                   10                  15

<210> SEQ ID NO 622
<211> LENGTH: 10
<212> TYPE: PRT
<213> ORGANISM: HUMAN

<400> SEQUENCE: 622

Ala Thr Ala Val Val Asp Gly Ala Phe Lys
1               5                   10

<210> SEQ ID NO 623
<211> LENGTH: 17
<212> TYPE: PRT
<213> ORGANISM: HUMAN

<400> SEQUENCE: 623

Glu Gly Gly Leu Gly Pro Leu Asn Ile Pro Leu Leu Ala Asp Val Thr
1               5                   10                  15

Arg

<210> SEQ ID NO 624
<211> LENGTH: 8
<212> TYPE: PRT
<213> ORGANISM: HUMAN

<400> SEQUENCE: 624
```

```
Gly Leu Phe Ile Ile Asp Gly Lys
1               5
```

<210> SEQ ID NO 625
<211> LENGTH: 9
<212> TYPE: PRT
<213> ORGANISM: HUMAN

<400> SEQUENCE: 625

```
Ile Gly Lys Pro Ala Pro Asp Phe Lys
1               5
```

<210> SEQ ID NO 626
<211> LENGTH: 18
<212> TYPE: PRT
<213> ORGANISM: HUMAN

<400> SEQUENCE: 626

```
Lys Glu Gly Gly Leu Gly Pro Leu Asn Ile Pro Leu Leu Ala Asp Val
1               5                   10                  15

Thr Arg
```

<210> SEQ ID NO 627
<211> LENGTH: 9
<212> TYPE: PRT
<213> ORGANISM: HUMAN

<400> SEQUENCE: 627

```
Leu Ser Glu Asp Tyr Gly Val Leu Lys
1               5
```

<210> SEQ ID NO 628
<211> LENGTH: 27
<212> TYPE: PRT
<213> ORGANISM: HUMAN

<400> SEQUENCE: 628

```
Leu Val Gln Ala Phe Gln Tyr Thr Asp Glu His Gly Glu Val Cys Pro
1               5                   10                  15

Ala Gly Trp Lys Pro Gly Ser Asp Thr Ile Lys
            20                  25
```

<210> SEQ ID NO 629
<211> LENGTH: 11
<212> TYPE: PRT
<213> ORGANISM: HUMAN

<400> SEQUENCE: 629

```
Gln Ile Thr Val Asn Asp Leu Pro Val Gly Arg
1               5                   10
```

<210> SEQ ID NO 630
<211> LENGTH: 27
<212> TYPE: PRT
<213> ORGANISM: HUMAN

<400> SEQUENCE: 630

```
Gln Tyr Thr Asp Glu His Gly Glu Val Cys Pro Ala Gly Trp Lys Pro
1               5                   10                  15

Gly Ser Asp Thr Ile Lys Pro Asn Val Asp Cys
            20                  25
```

```
<210> SEQ ID NO 631
<211> LENGTH: 10
<212> TYPE: PRT
<213> ORGANISM: HUMAN

<400> SEQUENCE: 631

Arg Leu Ser Glu Asp Tyr Gly Val Leu Lys
1               5                   10

<210> SEQ ID NO 632
<211> LENGTH: 8
<212> TYPE: PRT
<213> ORGANISM: HUMAN

<400> SEQUENCE: 632

Thr Asp Glu Gly Ile Ala Tyr Arg
1               5

<210> SEQ ID NO 633
<211> LENGTH: 8
<212> TYPE: PRT
<213> ORGANISM: HUMAN

<400> SEQUENCE: 633

Phe Asn Ala Leu Gln Tyr Leu Arg
1               5

<210> SEQ ID NO 634
<211> LENGTH: 9
<212> TYPE: PRT
<213> ORGANISM: HUMAN

<400> SEQUENCE: 634

Ile Leu Gly Pro Leu Ser Tyr Ser Lys
1               5

<210> SEQ ID NO 635
<211> LENGTH: 15
<212> TYPE: PRT
<213> ORGANISM: HUMAN

<400> SEQUENCE: 635

Ile Ser Glu Thr Ser Leu Pro Pro Asp Met Tyr Glu Cys Leu Arg
1               5                   10                  15

<210> SEQ ID NO 636
<211> LENGTH: 10
<212> TYPE: PRT
<213> ORGANISM: HUMAN

<400> SEQUENCE: 636

Ile Ser Asn Ile Pro Asp Glu Tyr Phe Lys
1               5                   10

<210> SEQ ID NO 637
<211> LENGTH: 11
<212> TYPE: PRT
<213> ORGANISM: HUMAN

<400> SEQUENCE: 637

Leu Lys Glu Asp Ala Val Ser Ala Ala Phe Lys
1               5                   10

<210> SEQ ID NO 638
<211> LENGTH: 18
```

```
<212> TYPE: PRT
<213> ORGANISM: HUMAN

<400> SEQUENCE: 638

Leu Pro Ser Gly Leu Pro Val Ser Leu Leu Thr Leu Tyr Leu Asp Asn
1               5                   10                  15

Asn Lys

<210> SEQ ID NO 639
<211> LENGTH: 21
<212> TYPE: PRT
<213> ORGANISM: HUMAN

<400> SEQUENCE: 639

Asn Ile Pro Thr Val Asn Glu Asn Leu Glu Asn Tyr Tyr Leu Glu Val
1               5                   10                  15

Asn Gln Leu Glu Lys
            20

<210> SEQ ID NO 640
<211> LENGTH: 10
<212> TYPE: PRT
<213> ORGANISM: HUMAN

<400> SEQUENCE: 640

Asn Asn Gln Ile Asp His Ile Asp Glu Lys
1               5                   10

<210> SEQ ID NO 641
<211> LENGTH: 9
<212> TYPE: PRT
<213> ORGANISM: HUMAN

<400> SEQUENCE: 641

Arg Phe Asn Ala Leu Gln Tyr Leu Arg
1               5

<210> SEQ ID NO 642
<211> LENGTH: 11
<212> TYPE: PRT
<213> ORGANISM: HUMAN

<400> SEQUENCE: 642

Ser Leu Glu Asp Leu Gln Leu Thr His Asn Lys
1               5                   10

<210> SEQ ID NO 643
<211> LENGTH: 14
<212> TYPE: PRT
<213> ORGANISM: HUMAN

<400> SEQUENCE: 643

Ser Leu Glu Tyr Leu Asp Leu Ser Phe Asn Gln Ile Ala Arg
1               5                   10

<210> SEQ ID NO 644
<211> LENGTH: 10
<212> TYPE: PRT
<213> ORGANISM: HUMAN

<400> SEQUENCE: 644

Ser Val Pro Met Val Pro Pro Gly Ile Lys
1               5                   10
```

```
<210> SEQ ID NO 645
<211> LENGTH: 8
<212> TYPE: PRT
<213> ORGANISM: HUMAN

<400> SEQUENCE: 645

Val Ala Asn Glu Val Thr Leu Asn
1               5

<210> SEQ ID NO 646
<211> LENGTH: 10
<212> TYPE: PRT
<213> ORGANISM: HUMAN

<400> SEQUENCE: 646

Ala Gly Phe Ala Gly Asp Asp Ala Pro Arg
1               5                   10

<210> SEQ ID NO 647
<211> LENGTH: 19
<212> TYPE: PRT
<213> ORGANISM: HUMAN

<400> SEQUENCE: 647

Ala Leu Asp Phe Glu Gln Glu Met Ala Thr Ala Ala Ser Ser Ser
1               5                   10                  15

Leu Glu Lys

<210> SEQ ID NO 648
<211> LENGTH: 9
<212> TYPE: PRT
<213> ORGANISM: HUMAN

<400> SEQUENCE: 648

Ala Val Phe Pro Ser Ile Val Gly Arg
1               5

<210> SEQ ID NO 649
<211> LENGTH: 11
<212> TYPE: PRT
<213> ORGANISM: HUMAN

<400> SEQUENCE: 649

Ala Val Phe Pro Ser Ile Val Gly Arg Pro Arg
1               5                   10

<210> SEQ ID NO 650
<211> LENGTH: 28
<212> TYPE: PRT
<213> ORGANISM: HUMAN

<400> SEQUENCE: 650

Cys Pro Glu Ala Leu Phe Gln Pro Ser Phe Leu Gly Met Glu Ser Cys
1               5                   10                  15

Gly Ile His Glu Thr Thr Phe Asn Ser Ile Met Lys
            20                  25

<210> SEQ ID NO 651
<211> LENGTH: 17
<212> TYPE: PRT
<213> ORGANISM: HUMAN

<400> SEQUENCE: 651
```

Asp Asp Asp Ile Ala Ala Leu Val Val Asp Asn Gly Ser Gly Met Cys
1               5                   10                  15

Lys

<210> SEQ ID NO 652
<211> LENGTH: 16
<212> TYPE: PRT
<213> ORGANISM: HUMAN

<400> SEQUENCE: 652

Asp Asp Ile Ala Ala Leu Val Val Asp Asn Gly Ser Gly Met Cys Lys
1               5                   10                  15

<210> SEQ ID NO 653
<211> LENGTH: 8
<212> TYPE: PRT
<213> ORGANISM: HUMAN

<400> SEQUENCE: 653

Asp Leu Thr Asp Tyr Leu Met Lys
1               5

<210> SEQ ID NO 654
<211> LENGTH: 21
<212> TYPE: PRT
<213> ORGANISM: HUMAN

<400> SEQUENCE: 654

Asp Leu Tyr Ala Asn Thr Val Leu Ser Gly Gly Thr Thr Met Tyr Pro
1               5                   10                  15

Gly Ile Ala Asp Arg
            20

<210> SEQ ID NO 655
<211> LENGTH: 11
<212> TYPE: PRT
<213> ORGANISM: HUMAN

<400> SEQUENCE: 655

Asp Ser Tyr Val Gly Asp Glu Ala Gln Ser Lys
1               5                   10

<210> SEQ ID NO 656
<211> LENGTH: 12
<212> TYPE: PRT
<213> ORGANISM: HUMAN

<400> SEQUENCE: 656

Asp Ser Tyr Val Gly Asp Glu Ala Gln Ser Lys Arg
1               5                   10

<210> SEQ ID NO 657
<211> LENGTH: 11
<212> TYPE: PRT
<213> ORGANISM: HUMAN

<400> SEQUENCE: 657

Glu Ile Thr Ala Leu Ala Pro Ser Thr Met Lys
1               5                   10

<210> SEQ ID NO 658
<211> LENGTH: 9
<212> TYPE: PRT
<213> ORGANISM: HUMAN

```
<400> SEQUENCE: 658

Gly Phe Ala Gly Asp Asp Ala Pro Arg
1               5

<210> SEQ ID NO 659
<211> LENGTH: 12
<212> TYPE: PRT
<213> ORGANISM: HUMAN

<400> SEQUENCE: 659

Gly Ile His Glu Thr Thr Phe Asn Ser Ile Met Lys
1               5                   10

<210> SEQ ID NO 660
<211> LENGTH: 11
<212> TYPE: PRT
<213> ORGANISM: HUMAN

<400> SEQUENCE: 660

Gly Ile Val Thr Asn Trp Asp Asp Met Glu Lys
1               5                   10

<210> SEQ ID NO 661
<211> LENGTH: 14
<212> TYPE: PRT
<213> ORGANISM: HUMAN

<400> SEQUENCE: 661

Gly Gln Lys Asp Ser Tyr Val Gly Asp Glu Ala Gln Ser Lys
1               5                   10

<210> SEQ ID NO 662
<211> LENGTH: 10
<212> TYPE: PRT
<213> ORGANISM: HUMAN

<400> SEQUENCE: 662

Gly Tyr Ser Phe Thr Thr Thr Ala Glu Arg
1               5                   10

<210> SEQ ID NO 663
<211> LENGTH: 11
<212> TYPE: PRT
<213> ORGANISM: HUMAN

<400> SEQUENCE: 663

His Gln Gly Val Met Val Gly Met Gly Gln Lys
1               5                   10

<210> SEQ ID NO 664
<211> LENGTH: 22
<212> TYPE: PRT
<213> ORGANISM: HUMAN

<400> SEQUENCE: 664

His Gln Gly Val Met Val Gly Met Gly Gln Lys Asp Ser Tyr Val Gly
1               5                   10                  15

Asp Glu Ala Gln Ser Lys
            20

<210> SEQ ID NO 665
<211> LENGTH: 7
<212> TYPE: PRT
```

<213> ORGANISM: HUMAN

<400> SEQUENCE: 665

Ile Ile Ala Pro Pro Glu Arg
1               5

<210> SEQ ID NO 666
<211> LENGTH: 8
<212> TYPE: PRT
<213> ORGANISM: HUMAN

<400> SEQUENCE: 666

Ile Ile Ala Pro Pro Glu Arg Lys
1               5

<210> SEQ ID NO 667
<211> LENGTH: 11
<212> TYPE: PRT
<213> ORGANISM: HUMAN

<400> SEQUENCE: 667

Ile Trp His His Thr Phe Tyr Asn Glu Leu Arg
1               5                   10

<210> SEQ ID NO 668
<211> LENGTH: 22
<212> TYPE: PRT
<213> ORGANISM: HUMAN

<400> SEQUENCE: 668

Lys Asp Leu Tyr Ala Asn Thr Val Leu Ser Gly Gly Thr Thr Met Tyr
1               5                   10                  15

Pro Gly Ile Ala Asp Arg
            20

<210> SEQ ID NO 669
<211> LENGTH: 14
<212> TYPE: PRT
<213> ORGANISM: HUMAN

<400> SEQUENCE: 669

Lys Gln Glu Tyr Asp Glu Ser Gly Pro Ser Ile Val His Arg
1               5                   10

<210> SEQ ID NO 670
<211> LENGTH: 17
<212> TYPE: PRT
<213> ORGANISM: HUMAN

<400> SEQUENCE: 670

Lys Tyr Pro Ile Glu His Gly Ile Val Thr Asn Trp Asp Asp Met Glu
1               5                   10                  15

Lys

<210> SEQ ID NO 671
<211> LENGTH: 23
<212> TYPE: PRT
<213> ORGANISM: HUMAN

<400> SEQUENCE: 671

Leu Cys Tyr Val Ala Leu Asp Phe Glu Gln Glu Met Ala Thr Ala Ala
1               5                   10                  15

Ser Ser Ser Ser Leu Glu Lys

20

<210> SEQ ID NO 672
<211> LENGTH: 10
<212> TYPE: PRT
<213> ORGANISM: HUMAN

<400> SEQUENCE: 672

Leu Leu Thr Glu Ala Pro Leu Asn Pro Lys
1               5                   10

<210> SEQ ID NO 673
<211> LENGTH: 15
<212> TYPE: PRT
<213> ORGANISM: HUMAN

<400> SEQUENCE: 673

Pro Ile Glu His Gly Ile Val Thr Asn Trp Asp Asp Met Glu Lys
1               5                   10                  15

<210> SEQ ID NO 674
<211> LENGTH: 13
<212> TYPE: PRT
<213> ORGANISM: HUMAN

<400> SEQUENCE: 674

Gln Glu Tyr Asp Glu Ser Gly Pro Ser Ile Val His Arg
1               5                   10

<210> SEQ ID NO 675
<211> LENGTH: 19
<212> TYPE: PRT
<213> ORGANISM: HUMAN

<400> SEQUENCE: 675

Arg Val Ala Pro Glu Glu His Pro Val Leu Leu Thr Glu Ala Pro Leu
1               5                   10                  15

Asn Pro Lys

<210> SEQ ID NO 676
<211> LENGTH: 13
<212> TYPE: PRT
<213> ORGANISM: HUMAN

<400> SEQUENCE: 676

Ser Gly Gly Thr Thr Met Tyr Pro Gly Ile Ala Asp Arg
1               5                   10

<210> SEQ ID NO 677
<211> LENGTH: 15
<212> TYPE: PRT
<213> ORGANISM: HUMAN

<400> SEQUENCE: 677

Ser Lys Gln Glu Tyr Asp Glu Ser Gly Pro Ser Ile Val His Arg
1               5                   10                  15

<210> SEQ ID NO 678
<211> LENGTH: 10
<212> TYPE: PRT
<213> ORGANISM: HUMAN

<400> SEQUENCE: 678

Ser Tyr Glu Leu Pro Asp Gly Gln Val Ile

```
1               5                   10

<210> SEQ ID NO 679
<211> LENGTH: 12
<212> TYPE: PRT
<213> ORGANISM: HUMAN

<400> SEQUENCE: 679

Ser Tyr Glu Leu Pro Asp Gly Gln Val Ile Thr Ile
1               5                   10

<210> SEQ ID NO 680
<211> LENGTH: 16
<212> TYPE: PRT
<213> ORGANISM: HUMAN

<400> SEQUENCE: 680

Ser Tyr Glu Leu Pro Asp Gly Gln Val Ile Thr Ile Gly Asn Glu Arg
1               5                   10                  15

<210> SEQ ID NO 681
<211> LENGTH: 14
<212> TYPE: PRT
<213> ORGANISM: HUMAN

<400> SEQUENCE: 681

Thr Thr Gly Ile Val Met Asp Ser Gly Asp Gly Val Thr His
1               5                   10

<210> SEQ ID NO 682
<211> LENGTH: 22
<212> TYPE: PRT
<213> ORGANISM: HUMAN

<400> SEQUENCE: 682

Thr Thr Gly Ile Val Met Asp Ser Gly Asp Gly Val Thr His Thr Val
1               5                   10                  15

Pro Ile Tyr Glu Gly Tyr
            20

<210> SEQ ID NO 683
<211> LENGTH: 26
<212> TYPE: PRT
<213> ORGANISM: HUMAN

<400> SEQUENCE: 683

Thr Thr Gly Ile Val Met Asp Ser Gly Asp Gly Val Thr His Thr Val
1               5                   10                  15

Pro Ile Tyr Glu Gly Tyr Ala Leu Pro His
            20                  25

<210> SEQ ID NO 684
<211> LENGTH: 29
<212> TYPE: PRT
<213> ORGANISM: HUMAN

<400> SEQUENCE: 684

Thr Thr Gly Ile Val Met Asp Ser Gly Asp Gly Val Thr His Thr Val
1               5                   10                  15

Pro Ile Tyr Glu Gly Tyr Ala Leu Pro His Ala Ile Leu
            20                  25

<210> SEQ ID NO 685
```

```
<211> LENGTH: 16
<212> TYPE: PRT
<213> ORGANISM: HUMAN

<400> SEQUENCE: 685

Thr Val Leu Ser Gly Gly Thr Thr Met Tyr Pro Gly Ile Ala Asp Arg
1               5                   10                  15

<210> SEQ ID NO 686
<211> LENGTH: 8
<212> TYPE: PRT
<213> ORGANISM: HUMAN

<400> SEQUENCE: 686

Val Ala Pro Glu Glu His Pro Val
1               5

<210> SEQ ID NO 687
<211> LENGTH: 9
<212> TYPE: PRT
<213> ORGANISM: HUMAN

<400> SEQUENCE: 687

Val Ala Pro Glu Glu His Pro Val Leu
1               5

<210> SEQ ID NO 688
<211> LENGTH: 10
<212> TYPE: PRT
<213> ORGANISM: HUMAN

<400> SEQUENCE: 688

Val Ala Pro Glu Glu His Pro Val Leu Leu
1               5                   10

<210> SEQ ID NO 689
<211> LENGTH: 13
<212> TYPE: PRT
<213> ORGANISM: HUMAN

<400> SEQUENCE: 689

Val Ala Pro Glu Glu His Pro Val Leu Leu Thr Glu Ala
1               5                   10

<210> SEQ ID NO 690
<211> LENGTH: 16
<212> TYPE: PRT
<213> ORGANISM: HUMAN

<400> SEQUENCE: 690

Val Ala Pro Glu Glu His Pro Val Leu Leu Thr Glu Ala Pro Leu Asn
1               5                   10                  15

<210> SEQ ID NO 691
<211> LENGTH: 18
<212> TYPE: PRT
<213> ORGANISM: HUMAN

<400> SEQUENCE: 691

Val Ala Pro Glu Glu His Pro Val Leu Leu Thr Glu Ala Pro Leu Asn
1               5                   10                  15

Pro Lys

<210> SEQ ID NO 692
```

```
<211> LENGTH: 21
<212> TYPE: PRT
<213> ORGANISM: HUMAN

<400> SEQUENCE: 692

Val Ala Pro Glu Glu His Pro Val Leu Leu Thr Glu Ala Pro Leu Asn
1               5                   10                  15

Pro Lys Ala Asn Arg
            20

<210> SEQ ID NO 693
<211> LENGTH: 16
<212> TYPE: PRT
<213> ORGANISM: HUMAN

<400> SEQUENCE: 693

Tyr Pro Ile Glu His Gly Ile Val Thr Asn Trp Asp Asp Met Glu Lys
1               5                   10                  15

<210> SEQ ID NO 694
<211> LENGTH: 21
<212> TYPE: PRT
<213> ORGANISM: HUMAN

<400> SEQUENCE: 694

Tyr Val Ala Leu Asp Phe Glu Gln Glu Met Ala Thr Ala Ala Ser Ser
1               5                   10                  15

Ser Ser Leu Glu Lys
            20

<210> SEQ ID NO 695
<211> LENGTH: 18
<212> TYPE: PRT
<213> ORGANISM: HUMAN

<400> SEQUENCE: 695

Lys Pro Leu Thr Ser Ser Ser Ala Ala Pro Gln Arg Pro Ile Ser Thr
1               5                   10                  15

Gln Arg

<210> SEQ ID NO 696
<211> LENGTH: 12
<212> TYPE: PRT
<213> ORGANISM: HUMAN

<400> SEQUENCE: 696

Ala Ala Gln Gln Gln Gln Pro Ser Ala Ser Pro Arg
1               5                   10

<210> SEQ ID NO 697
<211> LENGTH: 12
<212> TYPE: PRT
<213> ORGANISM: HUMAN

<400> SEQUENCE: 697

Arg Pro Asn Glu Thr Phe His Leu Ala Thr Arg Lys
1               5                   10

<210> SEQ ID NO 698
<211> LENGTH: 23
<212> TYPE: PRT
<213> ORGANISM: HUMAN

<400> SEQUENCE: 698
```

```
Asp Asn Leu Thr Leu Trp Thr Ser Asp Thr Gln Gly Asp Glu Ala Glu
1               5                   10                  15

Ala Gly Glu Gly Gly Glu Asn
            20
```

<210> SEQ ID NO 699
<211> LENGTH: 10
<212> TYPE: PRT
<213> ORGANISM: HUMAN

<400> SEQUENCE: 699

```
Asp Ser Thr Leu Ile Met Gln Leu Leu Arg
1               5                   10
```

<210> SEQ ID NO 700
<211> LENGTH: 8
<212> TYPE: PRT
<213> ORGANISM: HUMAN

<400> SEQUENCE: 700

```
Glu Lys Ile Glu Thr Glu Leu Arg
1               5
```

<210> SEQ ID NO 701
<211> LENGTH: 18
<212> TYPE: PRT
<213> ORGANISM: HUMAN

<400> SEQUENCE: 701

```
Gly Ile Val Asp Gln Ser Gln Gln Ala Tyr Gln Glu Ala Phe Glu Ile
1               5                   10                  15

Ser Lys
```

<210> SEQ ID NO 702
<211> LENGTH: 19
<212> TYPE: PRT
<213> ORGANISM: HUMAN

<400> SEQUENCE: 702

```
Gly Ile Val Asp Gln Ser Gln Gln Ala Tyr Gln Glu Ala Phe Glu Ile
1               5                   10                  15

Ser Lys Lys
```

<210> SEQ ID NO 703
<211> LENGTH: 7
<212> TYPE: PRT
<213> ORGANISM: HUMAN

<400> SEQUENCE: 703

```
Leu Ala Glu Gln Ala Glu Arg
1               5
```

<210> SEQ ID NO 704
<211> LENGTH: 9
<212> TYPE: PRT
<213> ORGANISM: HUMAN

<400> SEQUENCE: 704

```
Met Asp Lys Asn Glu Leu Val Gln Lys
1               5
```

<210> SEQ ID NO 705

```
<211> LENGTH: 8
<212> TYPE: PRT
<213> ORGANISM: HUMAN

<400> SEQUENCE: 705

Asn Leu Leu Ser Val Ala Tyr Lys
1               5

<210> SEQ ID NO 706
<211> LENGTH: 16
<212> TYPE: PRT
<213> ORGANISM: HUMAN

<400> SEQUENCE: 706

Ser Asp Thr Gln Gly Asp Glu Ala Glu Ala Gly Glu Gly Gly Glu Asn
1               5                   10                  15

<210> SEQ ID NO 707
<211> LENGTH: 9
<212> TYPE: PRT
<213> ORGANISM: HUMAN

<400> SEQUENCE: 707

Ser Thr Leu Ile Met Gln Leu Leu Arg
1               5

<210> SEQ ID NO 708
<211> LENGTH: 14
<212> TYPE: PRT
<213> ORGANISM: HUMAN

<400> SEQUENCE: 708

Ser Val Thr Glu Gln Gly Ala Glu Leu Ser Asn Glu Glu Arg
1               5                   10

<210> SEQ ID NO 709
<211> LENGTH: 19
<212> TYPE: PRT
<213> ORGANISM: HUMAN

<400> SEQUENCE: 709

Thr Ala Phe Asp Glu Ala Ile Ala Glu Leu Asp Thr Leu Ser Glu Glu
1               5                   10                  15

Ser Tyr Lys

<210> SEQ ID NO 710
<211> LENGTH: 8
<212> TYPE: PRT
<213> ORGANISM: HUMAN

<400> SEQUENCE: 710

Val Val Ser Ser Ile Glu Gln Lys
1               5

<210> SEQ ID NO 711
<211> LENGTH: 9
<212> TYPE: PRT
<213> ORGANISM: HUMAN

<400> SEQUENCE: 711

Tyr Asp Asp Met Ala Ala Cys Met Lys
1               5

<210> SEQ ID NO 712
```

```
<211> LENGTH: 12
<212> TYPE: PRT
<213> ORGANISM: HUMAN

<400> SEQUENCE: 712

Tyr Leu Ala Glu Val Ala Ala Gly Asp Asp Lys Lys
1               5                   10

<210> SEQ ID NO 713
<211> LENGTH: 10
<212> TYPE: PRT
<213> ORGANISM: HUMAN

<400> SEQUENCE: 713

Ala Glu Ser Met Leu Gln Gln Ala Asp Lys
1               5                   10

<210> SEQ ID NO 714
<211> LENGTH: 14
<212> TYPE: PRT
<213> ORGANISM: HUMAN

<400> SEQUENCE: 714

His Val Ile Pro Met Asn Pro Asn Thr Asp Asp Leu Phe Lys
1               5                   10

<210> SEQ ID NO 715
<211> LENGTH: 16
<212> TYPE: PRT
<213> ORGANISM: HUMAN

<400> SEQUENCE: 715

Ile Asp Ile Asn Met Ser Gly Phe Asn Glu Thr Asp Asp Leu Lys Arg
1               5                   10                  15

<210> SEQ ID NO 716
<211> LENGTH: 9
<212> TYPE: PRT
<213> ORGANISM: HUMAN

<400> SEQUENCE: 716

Ile Lys Val Pro Val Asp Trp Ser Lys
1               5

<210> SEQ ID NO 717
<211> LENGTH: 13
<212> TYPE: PRT
<213> ORGANISM: HUMAN

<400> SEQUENCE: 717

Met Ile Asn Leu Ser Val Pro Asp Thr Ile Asp Glu Arg
1               5                   10

<210> SEQ ID NO 718
<211> LENGTH: 14
<212> TYPE: PRT
<213> ORGANISM: HUMAN

<400> SEQUENCE: 718

Ser Gly Asn Leu Thr Glu Asp Asp Lys His Asn Asn Ala Lys
1               5                   10

<210> SEQ ID NO 719
<211> LENGTH: 25
<212> TYPE: PRT
```

```
<213> ORGANISM: HUMAN

<400> SEQUENCE: 719

Thr Ile Ser Ser Ser Leu Ala Trp Asp Leu Ile Asp Ala Ile Gln Pro
1               5                   10                  15

Gly Cys Ile Asn Tyr Asp Leu Val Lys
            20                  25

<210> SEQ ID NO 720
<211> LENGTH: 8
<212> TYPE: PRT
<213> ORGANISM: HUMAN

<400> SEQUENCE: 720

Val Asn Lys Pro Pro Tyr Pro Lys
1               5

<210> SEQ ID NO 721
<211> LENGTH: 14
<212> TYPE: PRT
<213> ORGANISM: HUMAN

<400> SEQUENCE: 721

Val Tyr Ala Leu Pro Glu Asp Leu Val Glu Val Lys Pro Lys
1               5                   10

<210> SEQ ID NO 722
<211> LENGTH: 15
<212> TYPE: PRT
<213> ORGANISM: HUMAN

<400> SEQUENCE: 722

Ala Leu Thr Val Pro Glu Leu Thr Gln Gln Met Phe Asp Ala Lys
1               5                   10                  15

<210> SEQ ID NO 723
<211> LENGTH: 15
<212> TYPE: PRT
<213> ORGANISM: HUMAN

<400> SEQUENCE: 723

Ala Val Leu Val Asp Leu Glu Pro Gly Thr Met Asp Ser Val Arg
1               5                   10                  15

<210> SEQ ID NO 724
<211> LENGTH: 17
<212> TYPE: PRT
<213> ORGANISM: HUMAN

<400> SEQUENCE: 724

Glu Ile Val His Leu Gln Ala Gly Gln Cys Gly Asn Gln Ile Gly Ala
1               5                   10                  15

Lys

<210> SEQ ID NO 725
<211> LENGTH: 18
<212> TYPE: PRT
<213> ORGANISM: HUMAN

<400> SEQUENCE: 725

Gly His Tyr Thr Glu Gly Ala Glu Leu Val Asp Ser Val Leu Asp Val
1               5                   10                  15

Val Arg
```

```
<210> SEQ ID NO 726
<211> LENGTH: 12
<212> TYPE: PRT
<213> ORGANISM: HUMAN

<400> SEQUENCE: 726

Ile Met Asn Thr Phe Ser Val Val Pro Ser Pro Lys
1               5                   10

<210> SEQ ID NO 727
<211> LENGTH: 8
<212> TYPE: PRT
<213> ORGANISM: HUMAN

<400> SEQUENCE: 727

Ile Arg Glu Glu Tyr Pro Asp Arg
1               5

<210> SEQ ID NO 728
<211> LENGTH: 14
<212> TYPE: PRT
<213> ORGANISM: HUMAN

<400> SEQUENCE: 728

Leu His Phe Phe Met Pro Gly Phe Ala Pro Leu Thr Ser Arg
1               5                   10

<210> SEQ ID NO 729
<211> LENGTH: 25
<212> TYPE: PRT
<213> ORGANISM: HUMAN

<400> SEQUENCE: 729

Leu Thr Thr Pro Thr Tyr Gly Asp Leu Asn His Leu Val Ser Ala Thr
1               5                   10                  15

Met Ser Gly Val Thr Thr Cys Leu Arg
            20                  25

<210> SEQ ID NO 730
<211> LENGTH: 26
<212> TYPE: PRT
<213> ORGANISM: HUMAN

<400> SEQUENCE: 730

Ser Gly Pro Phe Gly Gln Ile Phe Arg Pro Asp Asn Phe Val Phe Gly
1               5                   10                  15

Gln Ser Gly Ala Gly Asn Asn Trp Ala Lys
            20                  25

<210> SEQ ID NO 731
<211> LENGTH: 9
<212> TYPE: PRT
<213> ORGANISM: HUMAN

<400> SEQUENCE: 731

Thr Ala Val Cys Asp Ile Pro Pro Arg
1               5

<210> SEQ ID NO 732
<211> LENGTH: 15
<212> TYPE: PRT
<213> ORGANISM: HUMAN
```

-continued

```
<400> SEQUENCE: 732

His His Ala Ala Tyr Val Asn Asn Leu Asn Val Thr Glu Glu Lys
1               5                  10                  15

<210> SEQ ID NO 733
<211> LENGTH: 14
<212> TYPE: PRT
<213> ORGANISM: HUMAN

<400> SEQUENCE: 733

Ala Ser Ala Glu Thr Val Asp Pro Ala Ser Leu Trp Glu Tyr
1               5                  10

<210> SEQ ID NO 734
<211> LENGTH: 18
<212> TYPE: PRT
<213> ORGANISM: HUMAN

<400> SEQUENCE: 734

Asp Val Pro Trp Gly Val Asp Ser Leu Ile Thr Leu Ala Phe Gln Asp
1               5                  10                  15

Gln Arg

<210> SEQ ID NO 735
<211> LENGTH: 8
<212> TYPE: PRT
<213> ORGANISM: HUMAN

<400> SEQUENCE: 735

Glu Val Pro Gly Pro Asp Cys Arg
1               5

<210> SEQ ID NO 736
<211> LENGTH: 10
<212> TYPE: PRT
<213> ORGANISM: HUMAN

<400> SEQUENCE: 736

Phe Leu Ile Val Ala His Asp Asp Gly Arg
1               5                  10

<210> SEQ ID NO 737
<211> LENGTH: 10
<212> TYPE: PRT
<213> ORGANISM: HUMAN

<400> SEQUENCE: 737

Lys Val Thr Gly Thr Leu Asp Ala Asn Arg
1               5                  10

<210> SEQ ID NO 738
<211> LENGTH: 16
<212> TYPE: PRT
<213> ORGANISM: HUMAN

<400> SEQUENCE: 738

Leu Val Ala Arg Pro Glu Pro Ala Thr Gly Tyr Thr Leu Glu Phe Arg
1               5                  10                  15

<210> SEQ ID NO 739
<211> LENGTH: 9
<212> TYPE: PRT
<213> ORGANISM: HUMAN
```

<400> SEQUENCE: 739

Trp Ser Leu Gln Ser Glu Ala His Arg
1               5

<210> SEQ ID NO 740
<211> LENGTH: 14
<212> TYPE: PRT
<213> ORGANISM: HUMAN

<400> SEQUENCE: 740

Tyr Leu Ala Ala Asp Lys Asp Gly Asn Val Thr Cys Glu Arg
1               5                   10

<210> SEQ ID NO 741
<211> LENGTH: 20
<212> TYPE: DNA
<213> ORGANISM: HUMAN

<400> SEQUENCE: 741
atgtacttgg aaaaaggccg                                       20

<210> SEQ ID NO 742
<211> LENGTH: 20
<212> TYPE: DNA
<213> ORGANISM: HUMAN

<400> SEQUENCE: 742
ccctgctctt gaggagctta                                       20

<210> SEQ ID NO 743
<211> LENGTH: 23
<212> TYPE: DNA
<213> ORGANISM: HUMAN

<400> SEQUENCE: 743
agagacacag agtccggcat tgg                                   23

<210> SEQ ID NO 744
<211> LENGTH: 24
<212> TYPE: DNA
<213> ORGANISM: HUMAN

<400> SEQUENCE: 744
tccaccttct cccggtactc acgc                                  24

<210> SEQ ID NO 745
<211> LENGTH: 24
<212> TYPE: DNA
<213> ORGANISM: HUMAN

<400> SEQUENCE: 745
cttccttagt gcctgtgaca aaaa                                  24

<210> SEQ ID NO 746
<211> LENGTH: 28
<212> TYPE: DNA
<213> ORGANISM: HUMAN

<400> SEQUENCE: 746
aaggacagaa actcagaaaa atcaatct                              28

<210> SEQ ID NO 747
<211> LENGTH: 25

<212> TYPE: DNA
<213> ORGANISM: HUMAN

<400> SEQUENCE: 747
atgtcagacg cagccgtaga cacca                                      25

<210> SEQ ID NO 748
<211> LENGTH: 24
<212> TYPE: DNA
<213> ORGANISM: HUMAN

<400> SEQUENCE: 748
ctagtcatcc tcgtcggtct tctg                                       24

<210> SEQ ID NO 749
<211> LENGTH: 24
<212> TYPE: DNA
<213> ORGANISM: HUMAN

<400> SEQUENCE: 749
agcagagctc ggaatcttcc tctt                                       24

<210> SEQ ID NO 750
<211> LENGTH: 24
<212> TYPE: DNA
<213> ORGANISM: HUMAN

<400> SEQUENCE: 750
atcagcactg aaaccaacca tgcc                                       24

<210> SEQ ID NO 751
<211> LENGTH: 23
<212> TYPE: DNA
<213> ORGANISM: HUMAN

<400> SEQUENCE: 751
cagccatgta cgttgctatc cag                                        23

<210> SEQ ID NO 752
<211> LENGTH: 21
<212> TYPE: DNA
<213> ORGANISM: HUMAN

<400> SEQUENCE: 752
gtttcgtgga tgccacagga c                                          21

<210> SEQ ID NO 753
<211> LENGTH: 98
<212> TYPE: PRT
<213> ORGANISM: HUMAN

<400> SEQUENCE: 753

Met Met Cys Ser Ser Leu Glu Gln Ala Leu Ala Val Leu Val Thr Thr
1               5                   10                  15

Phe His Lys Tyr Ser Cys Gln Glu Gly Asp Lys Phe Lys Leu Ser Lys
                20                  25                  30

Gly Glu Met Lys Glu Leu Leu His Lys Glu Leu Pro Ser Phe Val Gly
            35                  40                  45

Glu Lys Val Asp Glu Glu Gly Leu Lys Lys Leu Met Gly Ser Leu Asp
        50                  55                  60

Glu Asn Ser Asp Gln Gln Val Asp Phe Gln Glu Tyr Ala Val Phe Leu
65                  70                  75                  80

-continued

```
Ala Leu Ile Thr Val Met Cys Asn Asp Phe Phe Gln Gly Cys Pro Asp
                85                  90                  95
Arg Pro

<210> SEQ ID NO 754
<211> LENGTH: 500
<212> TYPE: PRT
<213> ORGANISM: HUMAN

<400> SEQUENCE: 754

Ser Ala Ser Ser Thr Ala Thr Met Thr Ala Asn Gly Thr Ala Glu Ala
1               5                   10                  15

Val Gln Ile Gln Phe Gly Leu Ile Asn Cys Gly Asn Lys Tyr Leu Thr
                20                  25                  30

Ala Glu Ala Phe Gly Phe Lys Val Asn Ala Ser Ala Ser Ser Leu Lys
                35                  40                  45

Lys Lys Gln Ile Trp Thr Leu Glu Gln Pro Pro Asp Glu Ala Gly Ser
            50                  55                  60

Ala Ala Val Cys Leu Arg Ser His Leu Gly Arg Tyr Leu Ala Ala Asp
65                  70                  75                  80

Lys Asp Gly Asn Val Thr Cys Glu Arg Glu Val Pro Gly Pro Asp Cys
                85                  90                  95

Arg Phe Leu Ile Val Ala His Asp Asp Gly Arg Trp Ser Leu Gln Ser
                100                 105                 110

Glu Ala His Arg Arg Tyr Phe Gly Gly Thr Glu Asp Arg Leu Ser Cys
                115                 120                 125

Phe Ala Gln Thr Val Ser Pro Ala Glu Lys Trp Ser Val His Ile Ala
            130                 135                 140

Met His Pro Gln Val Asn Ile Tyr Ser Val Thr Arg Lys Arg Tyr Ala
145                 150                 155                 160

His Leu Ser Ala Arg Pro Ala Asp Glu Ile Ala Val Asp Arg Asp Val
                165                 170                 175

Pro Trp Gly Val Asp Ser Leu Ile Thr Leu Ala Phe Gln Asp Gln Arg
                180                 185                 190

Tyr Ser Val Gln Thr Ala Asp His Arg Phe Leu Arg His Asp Gly Arg
                195                 200                 205

Leu Val Ala Arg Pro Glu Pro Ala Thr Gly Tyr Thr Leu Glu Phe Arg
            210                 215                 220

Ser Gly Lys Val Ala Phe Arg Asp Cys Glu Gly Arg Tyr Leu Ala Pro
225                 230                 235                 240

Ser Gly Pro Ser Gly Thr Leu Lys Ala Gly Lys Ala Thr Lys Val Gly
                245                 250                 255

Lys Asp Glu Leu Phe Ala Leu Glu Gln Ser Cys Ala Gln Val Val Leu
                260                 265                 270

Gln Ala Ala Asn Glu Arg Asn Val Ser Thr Arg Gln Gly Met Asp Leu
            275                 280                 285

Ser Ala Asn Gln Asp Glu Glu Thr Asp Gln Glu Thr Phe Gln Leu Glu
            290                 295                 300

Ile Asp Arg Asp Thr Lys Lys Cys Ala Phe Arg Thr His Thr Gly Lys
305                 310                 315                 320

Tyr Trp Thr Leu Thr Ala Thr Gly Gly Val Gln Ser Thr Ala Ser Ser
                325                 330                 335

Lys Asn Ala Ser Cys Tyr Phe Asp Ile Glu Trp Arg Asp Arg Arg Ile
                340                 345                 350
```

-continued

```
Thr Leu Arg Ala Ser Asn Gly Lys Phe Val Thr Ser Lys Asn Gly
            355                 360                 365

Gln Leu Ala Ala Ser Val Glu Thr Ala Gly Asp Ser Glu Leu Phe Leu
370                 375                 380

Met Lys Leu Ile Asn Arg Pro Ile Ile Val Phe Arg Gly Glu His Gly
385                 390                 395                 400

Phe Ile Gly Cys Arg Lys Val Thr Gly Thr Leu Asp Ala Asn Arg Ser
                405                 410                 415

Ser Tyr Asp Val Phe Gln Leu Glu Phe Asn Asp Gly Ala Tyr Asn Ile
                420                 425                 430

Lys Asp Ser Thr Gly Lys Tyr Trp Thr Val Gly Ser Asp Ser Ala Val
                435                 440                 445

Thr Ser Ser Gly Asp Thr Pro Val Asp Phe Phe Phe Glu Phe Cys Asp
                450                 455                 460

Tyr Asn Lys Val Ala Ile Lys Val Gly Gly Arg Tyr Leu Lys Gly Asp
465                 470                 475                 480

His Ala Gly Val Leu Lys Ala Ser Ala Glu Thr Val Asp Pro Ala Ser
                485                 490                 495

Leu Trp Glu Tyr
            500

<210> SEQ ID NO 755
<211> LENGTH: 375
<212> TYPE: PRT
<213> ORGANISM: HUMAN

<400> SEQUENCE: 755

Met Asp Ala Leu Gln Leu Ala Asn Ser Ala Phe Ala Val Asp Leu Phe
1               5                   10                  15

Lys Gln Leu Cys Glu Lys Glu Pro Leu Gly Asn Val Leu Phe Ser Pro
                20                  25                  30

Ile Cys Leu Ser Thr Ser Leu Ser Leu Ala Gln Val Gly Ala Lys Gly
                35                  40                  45

Asp Thr Ala Asn Glu Ile Gly Gln Val Leu His Phe Glu Asn Val Lys
50                  55                  60

Asp Ile Pro Phe Gly Phe Gln Thr Val Thr Ser Asp Val Asn Lys Leu
65                  70                  75                  80

Ser Ser Phe Tyr Ser Leu Lys Leu Ile Lys Arg Leu Tyr Val Asp Lys
                85                  90                  95

Ser Leu Asn Leu Ser Thr Glu Phe Ile Ser Ser Thr Lys Arg Pro Tyr
                100                 105                 110

Ala Lys Glu Leu Glu Thr Val Asp Phe Lys Asp Lys Leu Glu Glu Thr
                115                 120                 125

Lys Gly Gln Ile Asn Asn Ser Ile Lys Asp Leu Thr Asp Gly His Phe
                130                 135                 140

Glu Asn Ile Leu Ala Asp Asn Ser Val Asn Asp Gln Thr Lys Ile Leu
145                 150                 155                 160

Val Val Asn Ala Ala Tyr Phe Val Gly Lys Trp Met Lys Lys Phe Pro
                165                 170                 175

Glu Ser Glu Thr Lys Glu Cys Pro Phe Arg Leu Asn Lys Thr Asp Thr
                180                 185                 190

Lys Pro Val Gln Met Met Asn Met Glu Ala Thr Phe Cys Met Gly Asn
                195                 200                 205

Ile Asp Ser Ile Asn Cys Lys Ile Ile Glu Leu Pro Phe Gln Asn Lys
```

```
                210                 215                 220
His Leu Ser Met Phe Ile Leu Pro Lys Asp Val Glu Asp Glu Ser
225                 230                 235                 240

Thr Gly Leu Glu Lys Ile Glu Lys Gln Leu Asn Ser Glu Ser Leu Ser
                245                 250                 255

Gln Trp Thr Asn Pro Ser Thr Met Ala Asn Ala Lys Val Lys Leu Ser
                260                 265                 270

Ile Pro Lys Phe Lys Val Glu Lys Met Ile Asp Pro Lys Ala Cys Leu
            275                 280                 285

Glu Asn Leu Gly Leu Lys His Ile Phe Ser Glu Asp Thr Ser Asp Phe
        290                 295                 300

Ser Gly Met Ser Glu Thr Lys Gly Val Ala Leu Ser Asn Val Ile His
305                 310                 315                 320

Lys Val Cys Leu Glu Ile Thr Glu Asp Gly Gly Asp Ser Ile Glu Val
                325                 330                 335

Pro Gly Ala Arg Ile Leu Gln His Lys Asp Glu Leu Asn Ala Asp His
                340                 345                 350

Pro Phe Ile Tyr Ile Ile Arg His Asn Lys Thr Arg Asn Ile Ile Phe
            355                 360                 365

Phe Gly Lys Phe Cys Ser Pro
370                 375

<210> SEQ ID NO 756
<211> LENGTH: 327
<212> TYPE: PRT
<213> ORGANISM: HUMAN

<400> SEQUENCE: 756

Met Ala Trp Trp Lys Ala Trp Ile Glu Gln Glu Gly Val Thr Val Lys
1               5                   10                  15

Ser Ser Ser His Phe Asn Pro Asp Pro Asp Ala Glu Thr Leu Tyr Lys
                20                  25                  30

Ala Met Lys Gly Ile Gly Thr Asn Glu Gln Ala Ile Ile Asp Val Leu
            35                  40                  45

Thr Lys Arg Ser Asn Thr Gln Arg Gln Gln Ile Ala Lys Ser Phe Lys
        50                  55                  60

Ala Gln Phe Gly Lys Asp Leu Thr Glu Thr Leu Lys Ser Glu Leu Ser
65                  70                  75                  80

Gly Lys Phe Glu Arg Leu Ile Val Ala Leu Met Tyr Pro Pro Tyr Arg
                85                  90                  95

Tyr Glu Ala Lys Glu Leu His Asp Ala Met Lys Gly Leu Gly Thr Lys
                100                 105                 110

Glu Gly Val Ile Ile Glu Ile Leu Ala Ser Arg Thr Lys Asn Gln Leu
            115                 120                 125

Arg Glu Ile Met Lys Ala Tyr Glu Glu Asp Tyr Gly Ser Ser Leu Glu
        130                 135                 140

Glu Asp Ile Gln Ala Asp Thr Ser Gly Tyr Leu Glu Arg Ile Leu Val
145                 150                 155                 160

Cys Leu Leu Gln Gly Ser Arg Asp Asp Val Ser Ser Phe Val Asp Pro
                165                 170                 175

Gly Leu Ala Leu Gln Asp Ala Gln Asp Leu Tyr Ala Ala Gly Glu Lys
            180                 185                 190

Ile Arg Gly Thr Asp Glu Met Lys Phe Ile Thr Ile Leu Cys Thr Arg
        195                 200                 205
```

```
Ser Ala Thr His Leu Leu Arg Val Phe Glu Glu Tyr Glu Lys Ile Ala
    210                 215                 220

Asn Lys Ser Ile Glu Asp Ser Ile Lys Ser Glu Thr His Gly Ser Leu
225                 230                 235                 240

Glu Glu Ala Met Leu Thr Val Val Lys Cys Thr Gln Asn Leu His Ser
                245                 250                 255

Tyr Phe Ala Glu Arg Leu Tyr Tyr Ala Met Lys Gly Ala Gly Thr Arg
                260                 265                 270

Asp Gly Thr Leu Ile Arg Asn Ile Val Ser Arg Ser Glu Ile Asp Leu
                275                 280                 285

Asn Leu Ile Lys Cys His Phe Lys Lys Met Tyr Gly Lys Thr Leu Ser
290                 295                 300

Ser Met Ile Met Glu Asp Thr Ser Gly Asp Tyr Lys Asn Ala Leu Leu
305                 310                 315                 320

Ser Leu Val Gly Ser Asp Pro
                325

<210> SEQ ID NO 757
<211> LENGTH: 210
<212> TYPE: PRT
<213> ORGANISM: HUMAN

<400> SEQUENCE: 757

Met Pro Pro Tyr Thr Val Val Tyr Phe Pro Val Arg Gly Arg Cys Ala
1               5                   10                  15

Ala Leu Arg Met Leu Leu Ala Asp Gln Gly Gln Ser Trp Lys Glu Glu
                20                  25                  30

Val Val Thr Val Glu Thr Trp Gln Glu Gly Ser Leu Lys Ala Ser Cys
            35                  40                  45

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Val Ser Leu Ile Tyr Thr Asn Tyr
                100                 105                 110

Glu Val Gly Lys Asp Asp Tyr Val Lys Ala Leu Pro Gly Gln Leu Lys
            115                 120                 125

Pro Phe Glu Thr Leu Leu Ser Gln Asn Gln Gly Gly Lys Thr Phe Ile
    130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
                180                 185                 190

Phe Leu Ala Ser Pro Glu Tyr Val Asn Leu Pro Ile Asn Gly Asn Gly
            195                 200                 205

Lys Gln
    210

<210> SEQ ID NO 758
<211> LENGTH: 466
<212> TYPE: PRT
<213> ORGANISM: HUMAN
```

<400> SEQUENCE: 758

| | | | | | | | | | | | | | | |
|---|---|---|---|---|---|---|---|---|---|---|---|---|---|---|
|Met|Ser|Thr|Arg|Ser|Val|Ser|Ser|Ser|Tyr|Arg|Arg|Met|Phe|Gly|
|1| | | |5| | | | |10| | | | |15|

Gly Pro Gly Thr Ala Ser Arg Pro Ser Ser Ser Arg Ser Tyr Val Thr
            20            25            30

Thr Ser Thr Arg Thr Tyr Ser Leu Gly Ser Ala Leu Arg Pro Ser Thr
        35            40            45

Ser Arg Ser Leu Tyr Ala Ser Ser Pro Gly Gly Val Tyr Ala Thr Arg
50                55            60

Ser Ser Ala Val Arg Leu Arg Ser Ser Val Pro Gly Val Arg Leu Leu
65                70            75            80

Gln Asp Ser Val Asp Phe Ser Leu Ala Asp Ala Ile Asn Thr Glu Phe
            85            90            95

Lys Asn Thr Arg Thr Asn Glu Lys Val Glu Leu Gln Glu Leu Asn Asp
        100           105          110

Arg Phe Ala Asn Tyr Ile Asp Lys Val Arg Phe Leu Glu Gln Gln Asn
     115            120          125

Lys Ile Leu Leu Ala Glu Leu Glu Gln Leu Lys Gly Gln Gly Lys Ser
130               135            140

Arg Leu Gly Asp Leu Tyr Glu Glu Glu Met Arg Glu Leu Arg Arg Gln
145              150            155          160

Val Asp Gln Leu Thr Asn Asp Lys Ala Arg Val Glu Val Glu Arg Asp
            165          170          175

Asn Leu Ala Glu Asp Ile Met Arg Leu Arg Glu Lys Leu Gln Glu Glu
        180           185          190

Met Leu Gln Arg Glu Glu Ala Glu Asn Thr Leu Gln Ser Phe Arg Gln
     195            200          205

Asp Val Asp Asn Ala Ser Leu Ala Arg Leu Asp Leu Glu Arg Lys Val
210               215            220

Glu Ser Leu Gln Glu Glu Ile Ala Phe Leu Lys Lys Leu His Glu Glu
225              230            235          240

Glu Ile Gln Glu Leu Gln Ala Gln Ile Gln Glu Gln His Val Gln Ile
            245          250          255

Asp Val Asp Val Ser Lys Pro Asp Leu Thr Ala Ala Leu Arg Asp Val
        260           265          270

Arg Gln Gln Tyr Glu Ser Val Ala Ala Lys Asn Leu Gln Glu Ala Glu
     275            280          285

Glu Trp Tyr Lys Ser Lys Phe Ala Asp Leu Ser Glu Ala Ala Asn Arg
290               295            300

Asn Asn Asp Ala Leu Arg Gln Ala Lys Gln Glu Ser Thr Glu Tyr Arg
305               310            315          320

Arg Gln Val Gln Ser Leu Thr Cys Glu Val Asp Ala Leu Lys Gly Thr
            325          330          335

Asn Glu Ser Leu Glu Arg Gln Met Arg Glu Met Glu Glu Asn Phe Ala
        340           345          350

Val Glu Ala Ala Asn Tyr Gln Asp Thr Ile Gly Arg Leu Gln Asp Glu
     355            360          365

Ile Gln Asn Met Lys Glu Glu Met Ala Arg His Leu Arg Glu Tyr Gln
            370          375          380

Asp Leu Leu Asn Val Lys Met Ala Leu Asp Ile Glu Ile Ala Thr Tyr
385               390            395          400

Arg Lys Leu Leu Glu Gly Glu Glu Ser Arg Ile Ser Leu Pro Leu Pro

-continued

```
                405                 410                 415
Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
        450                 455                 460

Leu Glu
465

<210> SEQ ID NO 759
<211> LENGTH: 206
<212> TYPE: PRT
<213> ORGANISM: HUMAN

<400> SEQUENCE: 759

Met Ala Val Lys Lys Ile Ala Ile Phe Gly Ala Thr Gly Gln Thr Gly
1               5                   10                  15

Leu Thr Thr Leu Ala Gln Ala Val Gln Ala Gly Tyr Glu Val Thr Val
            20                  25                  30

Leu Val Arg Asp Ser Ser Arg Leu Pro Ser Glu Gly Pro Arg Pro Ala
        35                  40                  45

His Val Val Val Gly Asp Val Leu Gln Ala Ala Asp Val Asp Lys Thr
    50                  55                  60

Val Ala Gly Gln Asp Ala Val Ile Val Leu Leu Gly Thr Arg Asn Asp
65                  70                  75                  80

Leu Ser Pro Thr Thr Val Met Ser Glu Gly Ala Arg Asn Ile Val Ala
                85                  90                  95

Ala Met Lys Ala His Gly Val Asp Lys Val Val Ala Cys Thr Ser Ala
            100                 105                 110

Phe Leu Leu Trp Asp Pro Thr Lys Val Pro Pro Arg Leu Gln Ala Val
        115                 120                 125

Thr Asp Asp His Ile Arg Met His Lys Val Leu Arg Glu Ser Gly Leu
    130                 135                 140

Lys Tyr Val Ala Val Met Pro Pro His Ile Gly Asp Gln Pro Leu Thr
145                 150                 155                 160

Gly Ala Tyr Thr Val Thr Leu Asp Gly Arg Gly Pro Ser Arg Val Ile
                165                 170                 175

Ser Lys His Asp Leu Gly His Phe Met Leu Arg Cys Leu Thr Thr Asp
            180                 185                 190

Glu Tyr Asp Gly His Ser Thr Tyr Pro Ser His Gln Tyr Gln
        195                 200                 205

<210> SEQ ID NO 760
<211> LENGTH: 472
<212> TYPE: PRT
<213> ORGANISM: HUMAN

<400> SEQUENCE: 760

Met Thr Thr Cys Ser Arg Gln Phe Thr Ser Ser Ser Ser Met Lys Gly
1               5                   10                  15

Ser Cys Gly Ile Gly Gly Gly Ile Gly Gly Ser Ser Arg Ile Ser
            20                  25                  30

Ser Val Leu Ala Gly Gly Ser Cys Arg Ala Pro Ser Thr Tyr Gly Gly
        35                  40                  45

Gly Leu Ser Val Ser Ser Ser Arg Phe Ser Ser Gly Gly Ala Tyr Gly
```

```
                50              55              60
Leu Gly Gly Tyr Gly Gly Phe Ser Ser Ser Ser Ser Phe
 65              70              75              80

Gly Ser Gly Phe Gly Gly Tyr Gly Gly Leu Gly Ala Gly Leu
                85              90              95

Gly Gly Gly Phe Gly Gly Phe Ala Gly Gly Asp Gly Leu Leu Val
            100             105             110

Gly Ser Glu Lys Val Thr Met Gln Asn Leu Asn Asp Arg Leu Ala Ser
            115             120             125

Tyr Leu Asp Lys Val Arg Ala Leu Glu Glu Ala Asn Ala Asp Leu Glu
            130             135             140

Val Lys Ile Arg Asp Trp Tyr Gln Arg Gln Arg Pro Ala Glu Ile Lys
145             150             155             160

Asp Tyr Ser Pro Tyr Phe Lys Thr Ile Glu Asp Leu Arg Asn Lys Ile
                165             170             175

Leu Thr Ala Thr Val Asp Asn Ala Asn Val Leu Leu Gln Ile Asp Asn
                180             185             190

Ala Arg Leu Ala Ala Asp Asp Phe Arg Thr Lys Tyr Glu Thr Glu Leu
            195             200             205

Asn Leu Arg Met Ser Val Glu Ala Asp Ile Asn Gly Leu Arg Arg Val
            210             215             220

Leu Asp Glu Leu Thr Leu Ala Arg Ala Asp Leu Glu Met Gln Ile Glu
225             230             235             240

Ser Leu Lys Glu Glu Leu Ala Tyr Leu Lys Lys Asn His Glu Glu Glu
                245             250             255

Met Asn Ala Leu Arg Gly Gln Val Gly Gly Asp Val Asn Val Glu Met
            260             265             270

Asp Ala Ala Pro Gly Val Asp Leu Ser Arg Ile Leu Asn Glu Met Arg
            275             280             285

Asp Gln Tyr Glu Lys Met Ala Glu Lys Asn Arg Lys Asp Ala Glu Glu
            290             295             300

Trp Phe Phe Thr Lys Thr Glu Glu Leu Asn Arg Glu Val Ala Thr Asn
305             310             315             320

Ser Glu Leu Val Gln Ser Gly Lys Ser Glu Ile Ser Glu Leu Arg Arg
                325             330             335

Thr Met Gln Asn Leu Glu Ile Glu Leu Gln Ser Gln Leu Ser Met Lys
            340             345             350

Ala Ser Leu Glu Asn Ser Leu Glu Glu Thr Lys Gly Arg Tyr Cys Met
            355             360             365

Gln Leu Ala Gln Ile Gln Glu Met Ile Gly Ser Val Glu Glu Gln Leu
    370             375             380

Ala Gln Leu Arg Cys Glu Met Glu Gln Gln Asn Gln Glu Tyr Lys Ile
385             390             395             400

Leu Leu Asp Val Lys Thr Arg Leu Glu Gln Glu Ile Ala Thr Tyr Arg
                405             410             415

Arg Leu Leu Glu Gly Glu Asp Ala His Leu Ser Ser Ser Gln Phe Ser
            420             425             430

Ser Gly Ser Gln Ser Ser Arg Asp Val Thr Ser Ser Arg Gln Ile
            435             440             445

Arg Thr Lys Val Met Asp Val His Asp Gly Lys Val Val Ser Thr His
        450             455             460

Glu Gln Val Leu Arg Thr Lys Asn
465             470
```

<210> SEQ ID NO 761
<211> LENGTH: 346
<212> TYPE: PRT
<213> ORGANISM: HUMAN

<400> SEQUENCE: 761

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 762
<211> LENGTH: 153
<212> TYPE: PRT

<213> ORGANISM: HUMAN

<400> SEQUENCE: 762

```
Ala Thr Lys Ala Val Cys Val Leu Lys Gly Asx Gly Pro Val Glx Gly
1               5                   10                  15

Ile Ile Asx Phe Glx Glx Lys Glu Ser Asn Gly Pro Val Lys Val Trp
            20                  25                  30

Gly Ser Ile Lys Gly Leu Thr Glu Gly Leu His Gly Phe His Val His
            35                  40                  45

Glu Phe Gly Asp Asn Thr Ala Gly Cys Thr Ser Ala Gly Pro His Phe
50                  55                  60

Asn Pro Leu Ser Arg Lys His Gly Gly Pro Lys Asp Glu Glu Arg His
65                  70                  75                  80

Val Gly Asx Leu Gly Asx Val Thr Ala Asx Lys Asx Gly Val Ala Asx
                85                  90                  95

Val Ser Ile Glx Asx Ser Val Ile Ser Leu Ser Gly Asx His Cys Ile
                100                 105                 110

Ile Gly Arg Thr Leu Val Val His Glu Lys Ala Asp Asp Leu Gly Lys
            115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150
```

<210> SEQ ID NO 763
<211> LENGTH: 320
<212> TYPE: PRT
<213> ORGANISM: HUMAN

<400> SEQUENCE: 763

```
Arg Pro Leu Pro Ser Pro Ser Ala Ala Pro Ser Phe Pro Ser Pro Ser
1               5                   10                  15

Arg Ser Leu Arg Ala Gly Arg Cys Gly Gly Thr Arg Pro Ser Pro
            20                  25                  30

Thr Pro Gly Gly Gly Gly Ala Ala Gly Arg Gly Arg Gly Pro Arg Gly
            35                  40                  45

Pro Lys Arg Glu Gly Lys Ala Trp Pro Arg Ala Gly Arg Ser Pro Gly
50                  55                  60

Leu Ala Arg Arg Arg Pro Pro Glu His Pro Val Met Asp Lys Asn Glu
65                  70                  75                  80

Leu Val Gln Lys Ala Lys Leu Ala Glu Gln Ala Glu Arg Tyr Asp Asp
                85                  90                  95

Met Ala Ala Cys Met Lys Ser Val Thr Glu Gln Gly Ala Glu Leu Ser
                100                 105                 110

Asn Glu Glu Arg Asn Leu Leu Ser Val Ala Tyr Lys Asn Val Val Gly
            115                 120                 125

Ala Arg Arg Ser Ser Trp Arg Val Val Ser Ser Ile Glu Gln Lys Thr
    130                 135                 140

Glu Gly Ala Glu Lys Lys Gln Gln Met Ala Arg Glu Tyr Arg Glu Lys
145                 150                 155                 160

Ile Glu Thr Glu Leu Arg Asp Ile Cys Asn Asp Val Leu Ser Leu Leu
                165                 170                 175

Glu Lys Phe Leu Ile Pro Asn Ala Ser Gln Ala Glu Ser Lys Val Phe
            180                 185                 190

Tyr Leu Lys Met Lys Gly Asp Tyr Tyr Arg Tyr Leu Ala Glu Val Ala
```

-continued

```
            195                 200                 205
Ala Gly Asp Asp Lys Lys Gly Ile Val Asp Gln Ser Gln Gln Ala Tyr
    210                 215                 220

Gln Glu Ala Phe Glu Ile Ser Lys Lys Glu Met Gln Pro Thr His Pro
225                 230                 235                 240

Ile Arg Leu Gly Leu Ala Leu Asn Phe Ser Val Phe Tyr Tyr Glu Ile
                245                 250                 255

Leu Asn Ser Pro Glu Lys Ala Cys Ser Leu Ala Lys Thr Ala Phe Asp
            260                 265                 270

Glu Ala Ile Ala Glu Leu Asp Thr Leu Ser Glu Glu Ser Tyr Lys Asp
        275                 280                 285

Ser Thr Leu Ile Met Gln Leu Leu Arg Asp Asn Leu Thr Leu Trp Thr
    290                 295                 300

Ser Asp Thr Gln Gly Asp Glu Ala Glu Ala Gly Glu Gly Gly Glu Asn
305                 310                 315                 320
```

BIOMARKERS FOR HEAD-AND-NECK CANCERS AND PRECANCERS

RELATED APPLICATIONS

This application is a continuation in part of U.S. application Ser. No. 12/866,567, filed Nov. 17, 2010, now U.S. Pat. No. 8,921,053, which is a national stage application of International Patent Application No. PCT/CA2009/000154, filed Feb. 6, 2009, which claims priority to Canadian Patent Application No. 2,643,611, filed Nov. 10, 2008 and Canadian Patent Application No. 2,618,163, filed on Feb. 7, 2008 all of which are incorporated herein by reference, as if set forth in their entirety.

FIELD OF THE INVENTION

The invention relates to markers for head-and-neck cancers, including oral cancers, and head-and-neck precancers, including, for example, oral leukoplakia with hyperplasia or dysplasia. The invention further relates to methods for assessing the status of head-and-neck tissue and oral tissue, and methods for the detection, diagnosis and prediction of head-and-neck disease. In one aspect, the invention relates to biomarkers of head-and-neck squamous cell carcinoma and biomarkers of head-and-neck precancers (including, but not limited to, oral leukoplakia with hyperplasia or dysplasia), and methods for detecting, diagnosing and predicting these and related conditions. In a further aspect, the invention relates to biomarkers of oral leukoplakia with hyperplasia or dysplasia, and methods for detecting, diagnosing and predicting same. In another aspect, the invention relates to a method for predicting risk of malignant transformation in oral lesions.

BACKGROUND OF THE INVENTION

Annually, about 500,000 cancer-related deaths are estimated in the United States alone. Of these, approximately 13,000 are attributed to head-and-neck including oral squamous-cell carcinoma (HNOSCC), making it the sixth most common cause of cancer deaths and the fourth most prevalent cancer in men worldwide (1).

A lack of biomarkers for early detection and risk assessment is clearly reflected by the fact that more than 50% of all patients with head-and-neck squamous-cell carcinoma (HNSCC) have advanced disease at the time of diagnosis (2). The five-year survival rate of HNSCC patients is less than 50%, and the prognosis of advanced HNSCC cases has not changed much over the past three decades, except in a few advanced centers (2). Conceivably, improvement in understanding of the steps leading to tumorigenesis will provide the ability to identify and predict malignant progression at an earlier stage of HNSCC lesions, in turn leading to more effective treatment and reduction of morbidity and mortality.

The precancerous lesions, potentially malignant lesions, premalignant lesions, and squamous intraepithelial lesions (SILs) of the head and neck (oral cavity, oropharynx, and larynx)—which are clinically usually defined as "leukoplakia"—remain the main controversial topic in head and neck pathology as regards classification, histological diagnosis, and treatment (3-5). The transition from a normal epithelium to squamous cell carcinoma (SCC) of the head and neck is a lengthy, comprehensive and multistage process, causally related to progressive accumulation of genetic changes leading to the selection of a clonal population of transformed epithelial cells (6). The whole spectrum of histological changes occurring in this process has been recently cumulatively designated potentially malignant lesions or SILs, ranging from squamous hyperplasia to carcinoma in situ (CIS) (3). In their evolution, some cases of potentially malignant lesions and SILs are self-limiting and reversible, some persist, and some progress to SCC in spite of careful follow-up and treatment.

Oral squamous-cell carcinoma (OSCC), the most common form of HNOSCC, is often preceded by clinically-well-defined lesions, such as leukoplakia, causally linked with chronic exposure of the oral mucosa to carcinogens or growth promoters in tobacco and alcohol; leukoplakias with dysplasia are termed "oral premalignant lesions" (OPLs) (3, 6).

Currently, there are no clinically-established biomarkers to facilitate the diagnosis or prognosis of head-and-neck cancer and/or oral leukoplakia. It is expected that identification of novel protein markers or therapeutic targets will ultimately improve patient care and survival. It is hoped that these biomarkers will transform clinical practice by including cancer screening and diagnosis based on molecular markers as a complement to histopathology.

In the post-genomics era, proteomics combined with mass spectrometry (MS) has become a powerful paradigm for the examination of proteins in a global manner, and the consequent discovery of cancer risk markers and drug targets. While transcriptomics provides a tool for unraveling gene-expression networks, proteomics links these networks to protein products and provides further insight into post-translational modifications that regulate cellular functions, thereby complementing genomic analyses (reviewed in Ralhan (8)). Identification of differentially expressed proteins in HNSCCs using proteomics revealed that expression patterns of proteins may have some predictive power for clinical outcome and personalized risk assessment (8-16)

Differential tagging with isotopic reagents, such as isotope-coded affinity tags (ICAT) (17) or the more recent variation that uses isobaric tagging reagents, iTRAQ (Applied Biosystems, Foster City, Calif.), followed by multidimensional liquid chromatography (LC) and tandem mass spectrometry (MS/MS) analysis, is emerging as one of the more powerful methodologies in the search for disease biomarkers. Recent studies using iTRAQ reagents resulted in identification and relative quantification of proteins leading to a discovery of potential cancer markers (PCMs) for human cancers (17-23).

The presence of dysplastic areas in the oral epithelium is associated with a likely progression to cancer; however, it is not an accurate predictor of cancer risk (6, 7). The major challenge in oral tumorigenesis is the identification of proteins that may serve as markers to differentiate the high-risk leukoplakic lesions, including OPLs, from more benign lesions for early intervention to reduce the morbidity associated with this devastating disease. Rapid advances in treatment modalities and improvements in the early detection of head-and-neck cancers have not significantly impacted the overall survival rates of cancer patients. Thus, much effort has been focused on genomics- and proteomics-based identification of biomarkers that can detect the disease in early stages, predict the risk of malignant transformation in patients with oral leukoplakia, including OPLs, and/or predict the clinical outcome in HNOSCC patients after treatment of primary tumors.

Increased levels of S100A7 transcripts have been identified by microarray analysis in oral dysplasia relative to normal oral mucosa (63). Winter et al., (125) showed by RT-PCR S100A7 overexpression and DOC1 downregulation in 15 leukoplakia biopsies and proposed that the combined investigation of both genes may be a marker for estimating the risk of cancer development in intraoral lesions. However, major limitations of the Winter et al. study were the limited sample size and no data on correlation with clinical outcome in a follow up study or in a longitudinal study. Further, the majority of studies examining markers for oral lesions are cross-sectional analyses and do not provide data on these lesions over time, thus rendering them unsuitable for identifying patients with dysplasia that is at high risk of transformation. Longitudinal long term follow-up studies of OPLs are required to determine the robust signature of markers for predicting fate of dysplastic lesions.

SUMMARY OF THE INVENTION

As discussed herein, the inventors used iTRAQ labeling in combination with multidimensional LC-MS/MS analysis of head-and-neck cancer in order to compare protein profiles of HNSCC and non-cancerous head-and-neck tissues. The inventors also used iTRAQ labeling in combination with multidimensional LC-MS/MS analysis of oral leukoplakia with dysplasia (oral premalignant lesions, or OPLs) in order to compare protein profiles of OPLs and normal head-and-neck tissues. These studies were designed to identify potential biomarkers, and to identify, in a global fashion, molecular pathways that are deregulated in head-and-neck and oral cancer, thereby aiding in drug-target discovery.

The iTRAQ experiments were performed on resected HNSCC, excised OPLs, and non-cancerous tissue homogenates. The rationale for using whole tissue homogenates as opposed to laser-capture-microdissection (LCM)-procured tumor cells has been discussed previously (21, 23). There are at least two major advantages in the analysis of tissue homogenates: the relevant proteins are much more abundant in the tissues of interest than in bodily fluids, and there is an automatic link between a protein that is differentially expressed and the tumor itself. Such a link would need to be demonstrated if the differentially expressed proteins were to be discovered in a bodily fluid (e.g., blood), as every tissue or organ can potentially discharge into blood. Furthermore, the tumor microenvironment plays an important role in cancer progression (24); examination of protein expression in tissues from a homogenate of different cell types takes into account the contributions of the tumor microenvironment.

The protein expression profiles of HNSCCs and OPLs were compared with non-cancerous head-and-neck tissues (controls) using the iTRAQ-labelling technique in combination with multidimensional LC-MS/MS analysis. In the iTRAQ technology, primary amines are tagged, thereby potentially allowing the tagging of most tryptic peptides. The multiplexing ability afforded by the iTRAQ reagents, which are available in four different tags, was ideally suited for the present study, as it provided a means to perform a proteomic analysis of both paired and non-paired non-cancerous (histologically normal) head-and-neck tissues, while simultaneously comparing them against the cancer samples. This strategy helps to identify proteins that might be differentially expressed due to manifestation of field cancerization (25-27) in clinically normal mucosa, and may be useful in designing strategies for risk prediction of disease recurrence or second primary tumor development.

Some of the overexpressed proteins that were identified in the tissues by the iTRAQ technology and LC MS/MS analysis were confirmed by immunohistochemistry and Western blotting. These approaches ensured that the selected proteins demonstrated a consistent pattern of overexpression in HNSCCs and OPLs, and greatly increased confidence in the observations stemming from iTRAQ analysis. Apart from their potential utility as biomarkers for HNSCC and OPLs, these proteins also provide valuable insight into previously unknown molecular networks and mechanisms that govern the normal-to-malignant conversion of epithelium.

Using the above techniques, the inventors identified markers associated with head-and-neck tissues, including oral tissues. Thus, the invention relates to novel markers for head-and-neck including oral tissues, including markers of head-and-neck including oral disease, and compositions comprising same.

In one aspect, the invention provides marker sets that distinguish head-and-neck cells, including oral cells, or tissue, diseases, or phases thereof. Also provided are uses of these marker sets. In specific aspects, the markers include at least 2, 3, 4, or 5 polypeptides listed in Table 5. In another aspect, the protein marker set includes protein clusters or proteins in pathways including markers listed in Table 5 and Table 2. In yet another aspect, the invention provides markers in Table 1 that are up-regulated or down-regulated or expressed in cancer samples as compared to the non-cancer samples. In yet another aspect, the invention provides markers in 5 and optionally Table 8 including 13, 14, 15, 16, 17, 18, 19, 20, 21, 22, 23, 24, 25, 26, 27, 28, 29, 30, 31, or 32 of the markers listed therein that are up-regulated or down-regulated or expressed in OPL samples as compared to the normal samples. In specific aspects, the OPL markers include at least 2, 3, 4, or 5 polypeptides listed in Table 6 and 13, 14, 15, 16, 17, 18, 19, 20, 21, 22, 23, 24, 25, 26, 27, 28, 29, 30, 31, or 32 listed in Table 5. In another aspect, the protein marker set includes protein clusters or proteins in pathways including markers listed in Table 5 (13, 14, 15, 16, 17, 18, 19, 20, 21, 22, 23, 24, 25, 26, 27, 28, 29, 30, 31, or 32).

Up-regulated markers identified in Table 1 (up-regulated in cancer samples versus non-cancer samples), and Table 6 (up-regulated in OPL samples versus non-cancer samples), including but not limited to native-sequence polypeptides, isoforms, chimeric polypeptides, all homologs, fragments, and precursors of the markers, including modified forms of the polypeptides and derivatives are referred to and defined herein as "head-and-neck cancer marker(s) and OPL marker(s)".

Up-regulated head-and-neck cancer markers listed in Table 1 (in cancer sample versus non-cancer sample), those listed in Table 1 or 2, have application in the determination of the status of the head-and-neck cell or tissue and in the detection of a head-and-neck disease such as head-and-neck cancer. Thus, the markers can be used for diagnosis, monitoring (i.e., monitoring progression), prognosis, or classification of a head-and-neck disease (e.g., head-and-neck cancer), HNSCC or related conditions or as markers before surgery or after relapse. The invention also contemplates methods for assessing the status of a head-and-neck tissue.

Up-regulated OPL markers listed in Table 6 (in OPL sample versus normal sample), those listed in Table 6 or Table 7, have application in the determination of the status or phase of the head-and-neck/oral cell or tissue and in the detection of a head-and-neck disease such as oral leukoplakia with hyperplasia or dysplasia or head-and-neck cancer. Thus, the markers can be used for diagnosis, monitoring (i.e., monitoring progression), prognosis, or classification of a head-and-neck disease (e.g., oral leukoplakia with hyperplasia or dysplasia or OPLs), HNSCC or related conditions or as markers before surgery or after relapse. The invention also contemplates methods for assessing the status of a head-and-neck tissue.

In an aspect, a method is provided for characterizing a head-and-neck tissue by detecting OPL markers/head-and-neck cancer markers associated with a head-and-neck tissue stage or phase, or head-and-neck disease in a subject including:
(a) obtaining a sample from a subject;
(b) detecting or identifying in the sample OPL markers/head-and-neck cancer markers; and
(c) comparing the detected amount with an amount detected for a standard.

In an embodiment of the invention, a method is provided for detecting OPL markers or head-and-neck cancer markers associated with OPL or head-and-neck cancer in a patient including:
(a) obtaining a sample from a patient;
(b) detecting in the sample OPL markers or head-and-neck cancer markers; and
(c) comparing the detected amount with an amount detected for a standard.

The term "detect" or "detecting" includes assaying, imaging or otherwise establishing the presence or absence of the target OPL markers or head-and-neck cancer markers, subunits thereof, or combinations of reagent bound targets, and the like, or assaying for, imaging, ascertaining, establishing, or otherwise determining one or more factual characteristics of a head-and-neck tissue phase or head-and-neck disease including OPL, cancer, metastasis, stage, or similar conditions. The term encompasses diagnostic, prognostic, and monitoring applications for the OPL markers or head-and-neck cancer markers.

The invention also provides a method of assessing whether a patient is afflicted with or has a pre-disposition for head-and-neck disease, in particular OPL or head-and-neck cancer, the method including comparing:
(a) levels of OPL or head-and-neck cancer markers
(b) or head-and-neck cancer markers associated with the head-and-neck disease in a sample from the patient; and
(c) normal levels of OPL or head-and-neck cancer markers
(d) or head-and-neck cancer markers associated with the head-and-neck disease in samples of the same type obtained from control patients not afflicted with the disease, wherein altered levels of the OPL or head-and-neck cancer markers relative to the corresponding normal levels of OPL or head-and-neck cancer markers is an indication that the patient is afflicted with head-and-neck disease.

In an aspect of a method of the invention for assessing whether a patient is afflicted with or has a pre-disposition for head-and-neck cancer, higher levels of head-and-neck cancer markers (e.g., YWHAZ, stratifin, S100A7) in a sample relative to the corresponding normal levels is an indication that the patient is afflicted with head-and-neck cancer.

In an aspect of a method of the invention for assessing whether a patient is afflicted with or has a pre-disposition for OPL/head-and-neck cancer, higher levels of OPL markers (e.g., YWHAZ, stratifin, hnRNPK) in a sample relative to the corresponding normal levels is an indication that the patient is afflicted with OPL.

In another aspect of a method of the invention for assessing whether a patient is afflicted with or has a pre-disposition for head-and-neck cancer, lower levels of head-and-neck cancer markers (e.g., alpha-1-antitrypsin, KPSG lumican) in a sample relative to the corresponding normal levels is an indication that the patient is afflicted with head-and-neck cancer.

In another aspect of a method of the invention for assessing whether a patient is afflicted with or has a pre-disposition for OPL/head-and-neck cancer, lower levels of OPL/head-and-neck cancer markers (e.g., alpha-1-antitrypsin, peroxiredoxin 2) in a sample relative to the corresponding normal levels is an indication that the patient is afflicted with OPL (oral leukoplakia with dysplasia).

In a further aspect, a method for screening a subject for head-and-neck disease is provided including (a) obtaining a biological sample from a subject; (b) detecting the amount of OPL or head-and-neck cancer markers associated with the disease in said sample; and (c) comparing said amount of OPL or head-and-neck cancer markers detected to a predetermined standard, where detection of a level of OPL or head-and-neck cancer markers that differs significantly from the standard indicates head-and-neck disease.

In an embodiment, a significant difference between the levels of OPL or head-and-neck cancer marker levels in a patient and normal levels is an indication that the patient is afflicted with or has a predisposition to head-and-neck disease.

In a particular embodiment the amount of head-and-neck cancer marker(s) (e.g., prothymosin alpha, APC-binding protein EB1) detected is greater than that of a standard and is indicative of head-and-neck disease, in particular head-and-neck cancer. In another particular embodiment the amount of head-and-neck cancer marker(s) (e.g., alpha-1-antitrypsin, KPSG lumican) detected is lower than that of a standard and is indicative of head-and-neck disease, in particular head-and-neck cancer.

In a particular embodiment the amount of OPL/head-and-neck marker(s) (e.g., YWHAZ, stratifin, hnRNPK) detected is greater than that of a standard and is indicative of head-and-neck disease, in particular OPL (oral leukoplakia with hyperplasia or dysplasia)/head-and-neck cancer. In another particular embodiment the amount of OPL/head-and-neck marker(s) (e.g., alpha-1-antitrypsin, peroxiredoxin 2) detected is lower than that of a standard and is indicative of head-and-neck disease, in particular OPL/head-and-neck cancer.

In aspects of the methods of the invention, the methods are non-invasive for detecting head-and-neck disease which in turn allow for diagnosis of a variety of conditions or diseases associated with the head-and-neck.

In particular, the invention provides a non-invasive non-surgical method for detection, diagnosis or prediction of head-and-neck disease (e.g., OPL or oral leukoplakia with hyperplasia or dysplasia and head-and-neck cancer or HNSCC) in a subject including: obtaining a sample of blood, plasma, serum, urine or saliva or a tissue sample from the subject; subjecting the sample to a procedure to detect OPL markers and head-and-neck cancer markers in the blood, plasma, serum, urine, saliva or tissue; detecting, diagnosing, and predicting head-and-neck disease by comparing the levels of OPL markers and head-and-neck cancer markers to the levels of marker(s) obtained from a control subject with no head-and-neck disease.

In an embodiment, head-and-neck disease is detected, diagnosed, or predicted by determination of increased levels of markers (e.g., one or more Table 1 or 6 up-regulated markers, preferable Table 5 up-regulated markers and more preferably one or more Table 2 or 7 up-regulated markers) when compared to such levels obtained from the control.

In another embodiment, head-and-neck disease is detected, diagnosed, or predicted by determination of decreased levels of markers (e.g., one or more Table 1 or 6 down-regulated markers) when compared to such levels obtained from the control.

The invention also provides a method for assessing the aggressiveness or indolence of a head-and-neck disease in particular OPL (e.g., staging hyperplasia or dysplasia or degree of differentiation—mild dysplasia or severe dysplasia) or cancer (e.g., staging), the method including comparing:
(a) levels of OPL or head-and-neck cancer markers or head-and-neck cancer markers associated with the head-and-neck disease in a patient sample; and
(b) normal levels of the OPL or head-and-neck cancer markers in a control sample.

In an embodiment, a significant difference between the levels in the sample and the normal levels is an indication that the head-and-neck disease, in particular OPL or cancer, is aggressive or indolent. In a particular embodiment, the levels of OPL or head-and-neck cancer markers are higher than normal levels. In another particular embodiment, the levels of OPL or head-and-neck cancer markers are lower than normal levels.

In an embodiment, a method is provided for diagnosing and/or monitoring OPL and HNSCC including comparing:
(a) levels of YWHAZ in a sample from the patient; and
(b) normal levels of YWHAZ in samples of the same type obtained from control patients not afflicted with OPL or head-and-neck cancer or having a different stage of OPL or head-and-neck cancer, wherein altered levels of YWHAZ compared with the corresponding normal levels is an indication that the patient is afflicted with OPL or HNSCC.

In an embodiment, a method is provided for diagnosing and/or monitoring OPL or HNSCC including comparing:
(a) levels of S100A7 in a sample from the patient; and
(b) normal levels of S100A7 in samples of the same type obtained from control patients not afflicted with head-and-neck cancer or having a different stage of head-and-neck cancer, wherein altered levels of S100A7 compared with the corresponding normal levels is an indication that the patient is afflicted with HNSCC.

In an embodiment, a method is provided for diagnosing and/or monitoring oral leukoplakia with hyperplasia or dysplasia (OPL)/HNSCC including comparing:
(a) levels of hnRNPK in a sample from the patient; and
(b) normal levels of hnRNPK in samples of the same type obtained from control patients not afflicted with leukoplakia with hyperplasia or dysplasia (OPL)/head-and-neck cancer or having a different stage of leukoplakia with hyperplasia or dysplasia (OPL) or head-and-neck cancer, wherein altered levels of hnRNPK compared with the corresponding normal levels is an indication that the patient is afflicted with leukoplakia with hyperplasia or dysplasia (OPL)/HNSCC.

In an embodiment, a method is provided for diagnosing and/or monitoring HNSCC and leukoplakia with hyperplasia or dysplasia (OPL) including comparing
(a) levels of stratifin in a sample from the patient; and
(b) normal levels of stratifin in samples of the same type obtained from control patients not afflicted with head-and-neck cancer or leukoplakia with hyperplasia or dysplasia (OPL) or having a different stage of leukoplakia with hyperplasia or dysplasia (OPL) or head-and-neck cancer, wherein altered levels of stratifin compared with the corresponding normal levels is an indication that the patient is afflicted with HNSCC.

In an aspect, the invention provides a method for determining whether a cancer has metastasized or is likely to metastasize in the future, the method including comparing:
(a) levels of OPL or head-and-neck cancer markers or head-and-neck cancer markers in a patient sample; and
(b) normal levels (or non-metastatic levels) of the OPL or head-and-neck cancer markers in a control sample.

In an embodiment, a significant difference between the levels in the patient sample and the normal levels is an indication that the cancer has metastasized or is likely to metastasize in the future.

In another aspect, the invention provides a method for monitoring the progression of head-and-neck disease, in particular OPL or head-and-neck cancer in a patient the method including:
(a) detecting OPL or head-and-neck cancer markers associated with the disease in a sample from the patient at a first time point;
(b) repeating step (a) at a subsequent point in time; and
(c) comparing the levels detected in (a) and (b), thereby monitoring the progression of the head-and-neck disease.

The invention contemplates a method for determining the effect of an environmental factor on the head-and-neck tissue, or head-and-neck disease including comparing OPL or head-and-neck cancer markers in the presence and absence of the environmental factor.

The invention also provides a method for assessing the potential efficacy of a test agent for inhibiting head-and-neck disease, and a method of selecting an agent for inhibiting head-and-neck disease.

The invention contemplates a method of assessing the potential of a test compound to contribute to a head-and-neck disease including:
(a) maintaining separate aliquots of head-and-neck diseased cells in the presence and absence of the test compound; and
(b) comparing the levels of OPL or head-and-neck cancer markers associated with the disease in each of the aliquots.

A significant difference between the levels of OPL or head-and-neck cancer markers in an aliquot maintained in the presence of (or exposed to) the test compound relative to the aliquot maintained in the absence of the test compound, indicates that the test compound potentially contributes to head-and-neck disease.

The invention further relates to a method of assessing the efficacy of a therapy for inhibiting head-and-neck disease in a patient. A method of the invention includes comparing: (a) levels of OPL or head-and-neck cancer markers associated with disease in a first sample from the patient obtained from the patient prior to providing at least a portion of the therapy to the patient; and (b) levels of OPL or head-and-neck cancer markers associated with disease in a second sample obtained from the patient following therapy.

In an embodiment, a significant difference between the levels of OPL or head-and-neck cancer markers in the second sample relative to the first sample is an indication that the therapy is efficacious for inhibiting head-and-neck disease.

In a particular embodiment, the method is used to assess the efficacy of a therapy for inhibiting head-and-neck disease (e.g., OPL or head-and-neck cancer), where lower levels of OPL or head-and-neck cancer markers in the second sample relative to the first sample, is an indication that the therapy is efficacious for inhibiting the disease.

The "therapy" may be any therapy for treating head-and-neck disease, in particular OPL or head-and-neck cancer, including but not limited to therapeutics, radiation, immunotherapy, gene therapy, and surgical removal of tissue. Therefore, the method can be used to evaluate a patient before, during, and after therapy.

Certain methods of the invention employ binding agents (e.g., antibodies) that specifically recognize OPL or head-and-neck cancer markers.

In an embodiment, the invention provides methods for determining the presence or absence of head-and-neck disease, in particular OPL or head-and-neck cancer, in a patient, including the steps of (a) contacting a biological sample obtained from a patient with one or more binding agent that specifically binds to one or more OPL or head-and-neck cancer markers associated with the disease; and (b) detecting in the sample an amount of marker that binds to the binding agent, relative to a predetermined standard or cut-off value (e.g., a control), thereby determining the presence or absence of head-and-neck disease in the patient.

In another embodiment, the invention relates to a method for diagnosing and monitoring a head-and-neck disease, in particular OPL or head-and-neck cancer, in a subject by quantifying one or more OPL or head-and-neck cancer markers associated with the disease in a biological sample from the subject including (a) reacting the biological sample with one or more binding agent specific for the OPL or head-and-neck cancer markers (e.g., an antibody) that are directly or indirectly labelled with a detectable substance; and (b) detecting the detectable substance.

In another aspect the invention provides a method of using an antibody to detect expression of one or more head-and-neck marker in a sample, the method including: (a) combining antibodies specific for one or more head-and-neck marker with a sample under conditions which allow the formation of antibody:marker complexes; and (b) detecting complex formation, wherein complex formation indicates expression of the marker in the sample. Expression may be compared with standards and is diagnostic of a head-and-neck disease, in particular OPL or HNSCC.

Embodiments of the methods of the invention involve (a) reacting a biological sample from a subject with antibodies specific for one or more OPL or head-and-neck cancer markers which are directly or indirectly labelled with an enzyme; (b) adding a substrate for the enzyme wherein the substrate is selected so that the substrate, or a reaction product of the enzyme and substrate forms fluorescent complexes; (c) quantifying one or more OPL or head-and-neck cancer markers in the sample by measuring fluorescence of the fluorescent complexes; and (d) comparing the quantified levels to levels obtained for other samples from the subject patient, or control subjects.

In another embodiment the quantified levels are compared to levels quantified for control subjects (e.g., normal or benign) without a head-and-neck disease (e.g., OPL or cancer) wherein an increase in head-and-neck marker levels compared with the control subjects is indicative of head-and-neck disease.

In a further embodiment the quantified levels are compared to levels quantified for control subjects (e.g., normal or benign) without a head-and-neck disease (e.g., OPL or cancer) wherein a decrease in head-and-neck marker levels compared with the control subjects is indicative of head-and-neck disease.

A particular embodiment of the invention includes the following steps (a) incubating a biological sample with first antibodies specific for one or more OPL or head-and-neck cancer markers which are directly or indirectly labelled with a detectable substance, and second antibodies specific for one or more head-and-neck cancer markers which are immobilized;

(b) detecting the detectable substance thereby quantifying OPL or head-and-neck cancer markers in the biological sample; and (c) comparing the quantified OPL or head-and-neck cancer markers with levels for a predetermined standard.

The standard may correspond to levels quantified for samples from control subjects without OPL or head-and-neck cancer (normal or benign), with a different disease stage, or from other samples of the subject. In an embodiment, increased levels of OPL or head-and-neck cancer markers as compared to the standard may be indicative of head-and-neck precancer or cancer. In another embodiment, lower levels of OPL or head-and-neck cancer markers as compared to a standard may be indicative of head-and-neck precancer or cancer.

OPL or HNSCC marker levels can be determined by constructing an antibody microarray in which binding sites include immobilized, preferably monoclonal, antibodies specific to a substantial fraction of marker-derived OPL or HNSCC marker proteins of interest.

The invention also relates to kits for carrying out the methods of the invention. In an embodiment, a kit is for assessing whether a patient is afflicted with a head-and-neck disease (e.g., or leukoplakia with hyperplasia or dysplasia (OPL) or head-and-neck cancer or HNSCC or related conditions) and it includes reagents for assessing one or more head-and-neck cancer markers.

The invention also provides a diagnostic composition including an OPL or HNSCC marker. A composition is also provided including an antibody specific for OPL or HNSCC markers or a fragment thereof. The antibodies can be labeled with a detectable substance.

Still further the invention relates to therapeutic applications for head-and-neck diseases, in particular OPL or head-and-neck cancer, employing OPL or head-and-neck cancer markers, and/or binding agents for the markers.

In an aspect, the invention provides antibodies specific for OPL or HNSCC markers associated with a disease (e.g., leukoplakia with hyperplasia or dysplasia or HNSCC) that can be used therapeutically to destroy or inhibit the disease (e.g., the growth of OPL or HNSCC marker expressing cancer cells), or to block OPL or HNSCC marker activity associated with a disease. In an aspect, OPL or HNSCC markers may be used in various immunotherapeutic methods to promote immune-mediated destruction or growth inhibition of tumors expressing OPL or HNSCC markers.

The invention contemplates the methods and kits described herein using additional markers associated with a head-and-neck disease (e.g., OPL or head-and-neck cancer, HNSCCm or related conditions). The methods described herein may be modified by including reagents to detect the additional markers.

In particular, the invention contemplates the methods described herein using multiple markers for OPL or HNSCC cancer. Therefore, the invention contemplates a method for analyzing a biological sample for the presence of OPL or HNSCC markers, and other markers that are specific indicators of cancer, in particular head-and-neck cancer. The methods described herein may be modified by including reagents to detect the additional markers, or nucleic acids for the additional markers.

In embodiments of the invention the methods and kits use one or more of the markers listed in Table 5, in particular those listed in Table 2 and Table 7. In another embodiment, the method uses a panel of markers selected from the markers listed in Table 5, and in one embodiment of those listed in Table 2 and Table 7 in particular a panel including two, three or four or more of the markers in Table 5.

In an aspect, the present invention provides a method for diagnosing an increased risk for development of oral cancer in a subject having oral dysplasia. The method comprises measuring the level of S100A7 in a biological sample from the subject; and comparing the level of S100A7 in the biological sample with the level of S100A7 in a control, wherein a measured level of S100A7 higher than the control level is indicative of an increased risk for developing oral cancer. In some embodiments of this aspect, the biological sample comprises epithelial cells. In some embodiments, the biological sample is a cytosmear. In preferred embodiments, the epithelial cells are dysplastic.

In some embodiments of the invention, the control level is the level of S100A7 in a biological sample comprising dysplastic epithelial cells known not to progress to oral cancer for at least 3.5 years following measurement of the control level. In some embodiments, the biological sample known not to progress to cancer is known not to progress to cancer for at least 10 years following measurement of the control level.

In another aspect, the present invention provides a method for diagnosing an increased risk for development of oral cancer in a subject having oral dysplasia, the method comprising measuring the level of nuclear PTMA in a biological sample from the subject. In some embodiments, the measured level of nuclear PTMA is compared to the level of nuclear PTMA in a control. In some embodiments, a measured level of nuclear PTMA higher than the control level is indicative of an increased risk for developing oral cancer.

In some embodiments, the method further comprises measuring the level of cytoplasmic S100A7 in a biological sample from the subject; and comparing the level of cytoplasmic S100A7 in the biological sample with the level of cytoplasmic S100A7 in a control. In some embodiments, a measured level of cytoplasmic S100A7 higher than the control level is indicative of an increased risk for developing oral cancer.

In some embodiments of this aspect, the biological sample comprises epithelial cells. In some embodiments, the biological sample is a cytosmear. In some embodiments, the epithelial cells are dysplastic. In some embodiments, the control is a biological sample comprising dysplastic epithelial cells known not to progress to oral cancer for at least 3.5 years following measurement of the control level. In some embodiments, the biological sample known not to progress to cancer is known not to progress to cancer for at least 10 years following measurement of the control level.

In some embodiments of this aspect, the method further comprises measuring the degree of dysplasia in the biological sample obtained from the subject, wherein a moderate or severe degree of dysplasia is indicative of an increased risk for developing oral cancer relative to a corresponding control sample having a mild degree of dysplasia.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE TABLES AND DRAWINGS

Tables

Table 1. iTRAQ ratios for HNSCC and non-cancerous head-and-neck tissue samples. HNSCC samples (C1-05, cancer of the buccal mucosa; C6-C10, cancer of the tongue), non-paired non-cancerous samples (N1, N4, N5), and paired non-cancerous samples (N2, N3) versus the pooled non-paired non-cancerous control. Grey boxes, not detected; NQ, not quantified; 9999, no expression observed in the pooled sample Table 2. Receiver-operating characteristics from the iTRAQ ratios of a panel of three best-performing biomarkers-YWHAZ, stratifin, and S100A7-individually and as a panel.

Table 3. Receiver-operating characteristics from the IHC scores of a panel of three best-performing biomarkers-YWHAZ, stratifin, and S100A7-individually and as a panel.

Table 4. Comparison of receiver-operating characteristics from the iTRAQ ratios of the panel of three best-performing biomarkers. Non-paired non-cancerous tissues give better sensitivity and specificity as comparators than do paired non-cancerous tissues.

Table 5. Differentially-expressed proteins not previously described in OPLs and head-and-neck malignancies and cancer.

Table 6. Average iTRAQ ratios for OPLs and histologically-normal control oral tissue samples. Ratios are from the comparison between OPLs (D1-D6) and the pooled normal sample, and the comparison between histologically-normal oral tissues (N1-N3) and the pooled normal sample. N4-N6 are histologically-normal oral tissues analyzed in an earlier iTRAQ analysis using the same pooled normal control to demonstrate consistent iTRAQ ratios in different experiments analyzed over different time periods. ND, not detected; NQ, not quantified Table 7. Receiver-operating characteristics from (A) the iTRAQ ratios and (B) IHC scores of a panel of three best-performing biomarkers-YWHAZ, stratifin, and hnRNPK-individually and as a panel.

Table 8. Analysis of Stratifin and YWHAZ in HNOSCCs: correlation with clinicopathological parameters.

Table 9a. Analysis of overexpression of hnRNPK protein in oral lesions and correlation with clinicopathological parameters.

Table 9b. Biomarker analysis of hnRNPK (nuclear/cytoplasmic) in oral lesions.

Table 10. Alternate accession numbers for OPL proteins.

Table 11. Peptide sequences and coverage for HNSCC and OPL.

Table 12. Clinicopathological parameters of patients with oral premalignant lesions (OPLs).

Table 13. Antibodies used for immunohistochemistry and Western Blotting: sources and dilutions.

Table 14. RT-PCR analysis primers and PCR conditions.

Table 15. Molecules identified in the Networks and their cellular functions.

Table 16. Analysis of clinical parameters with transformation potential of Oral Dysplasia patients.

Table 17. Correlation of candidate protein markers expression with transformation in Oral Dysplasia patients.

Table 18. Evaluation of association of degree of dysplasia with candidate protein markers expression.

Table 19. Evaluation of correlation between p16 expression and protein markers.

Table 20. Evaluation of clinical parameters and S100A7 overexpression for determining oral cancer free survival (OCFS) in dysplasia patients.

Table 21: Multivariate Cox Regression analysis of cytoplasmic S100A7, nuclear PTMA and degree of dysplasia in patients having oral dysplastic lesions.

FIGURES

FIG. 1 provides a flow diagram for online 2D LC-MS/MS analysis. In position 1, ports 1-2, 3-4, 5-6, 7-8, and 9-10 are connected; in position 2, ports 2-3, 4-5, 6-7, 8-9, and 10-1 are connected. In the diagram, the valves are shown at the initial (Time=0 min) positions.

FIG. 2 shows a receiver-operating-characteristic curves of a panel of three best-performing biomarkers, YWHAZ, stratifin, and S100A7: (a) iTRAQ ratios, and (b) IHC scores.

FIG. 3 presents an immunohistochemical verification of iTRAQ-discovered potential cancer markers, YWHAZ, stratifin, and S100A7 in HNSCCs and non-cancerous head-and-neck tissues. Positive staining is brown and is intense in HNSCCs. The left panel shows the noncancerous (histologically normal) tissues and the right panel depicts the HNSCC tissue sections. Panel A: the HNSCC sample shows intense cytoplasmic and nuclear staining for YWHAZ, while the normal mucosa shows no detectable immunostaining. Panel B: the HNSCC tissue section shows cytoplasmic staining for stratifin in tumor cells, while the normal mucosa shows no detectable immunostaining. Panel C: the HNSCC tissue section shows intense cytoplasmic staining for S100A7 in tumor cells, while the normal mucosa shows no detectable immunoreactivity. All panels show ×200 magnifications.

FIG. 4 depicts Western blot analyses of YWHAZ, Stratifin and S100A7 in HNSCCs and paired noncancerous head-and-neck tissues. Equal amounts of protein lysates from HNSCCs and paired non-cancerous head-and-neck tissues were employed. See the text for details. The Panels show increased expression of (i) YWHAZ, (ii) stratifin, and (iii) S100A7 in HNSCCs (C1-C3) as compared to paired non-cancerous head-and-neck tissues (N1-N3). Alpha-tubulin (Panel 4) was used as the loading control.

FIG. 5 shows RT-PCR analyses of YWHAZ, stratifin, and S100A7 in HNSCCs and non-cancerous head-and-neck tissues: Panel (i) shows increased levels of YWHAZ transcripts in HNSCCs (C1-C3) as compared to the non-cancerous head-and-neck tissues that show basal levels (N2 and N3) and no detectable level (N1) of YWHAZ transcripts. Panel (ii) shows increased levels of stratifin transcripts in HNSCCs (C1-C3) as compared to the non-cancerous head-and-neck tissues that show basal level (N3) and no detectable level (N1 and N2) of stratifin transcripts. Panel (iii) shows increased levels of S100A7 transcripts in HNSCCs (C1-C3) as compared to the non-cancerous head-and-neck tissues that show basal level (N3) and no detectable level (N1 and N2) of S100A7 transcripts. β-Actin (Panel iv) was used as a control for normalizing the quantity of RNA used.

FIG. 6 provides receiver-operating-characteristic curves of a panel of three best-performing biomarkers, YWHAZ, stratifin, and hnRNPK: (A) iTRAQ ratios, and (B) IHC scores.

FIG. 7 presents an immunohistochemical verification of iTRAQ-discovered potential biomarkers, YWHAZ, stratifin, hnRNPK, S100A7, and PTHA in OPLs and histologically normal oral tissues. Verification of the panel of these 5 potential biomarkers was carried out using an independent set of 30 OPLs and 21 histological normal oral tissues. Representative photomicrographs are shown here. Positive staining is brown and is intense in OPLs. The upper panel shows the normal tissues and the lower panel the OPL tissue sections. Panel A: the OPL sample shows intense cytoplasmic and nuclear staining for YWHAZ, while the normal mucosa shows no detectable immunostaining. Panel B: the OPL tissue section exhibits cytoplasmic staining for stratifin in epithelial cells, while the normal mucosa shows no detectable immunostaining. Panel C: the OPL tissue section shows nuclear staining for hnRNPK in epithelial cells, while no detectable immunostaining is evident in the normal mucosa. Panel D: the OPL sample shows intense cytoplasmic staining for S100A7 in epithelial cells, while the normal mucosa displays no detectable immunoreactivity. Panel E: the OPL sample exhibits intense nuclear staining for PTHA in epithelial cells, while no detectable immunostaining is evident in the normal sample. All panels show ×100 magnifications.

FIG. 8A illustrates Western blot analyses of YWHAZ, stratifin, hnRNPK, S100A7 and PTHA in representative OPLs and histologically normal oral tissues. The OPLs and histologically normal oral tissues (n=3) were selected randomly from the same cohort of tissues as used for IHC analysis and the results shown are representative of 3 independent experiments. Equal amounts of protein lysates from OPLs (D1-D3) and histologically normal oral tissues (N1-N3) were used. The panels show increased expression of (i) YWHAZ, (ii) stratifin, (iii) hnRNPK, (iv) S100A7, and (v) PTHA in OPLs (D1-D3) as compared to the histologically normal oral tissues (N1-N3). α-tubulin (Panel (vi)) was used as the loading control.

FIG. 8B depicts RT-PCR analyses of YWHAZ, stratifin, hnRNPK, S100A7, and PTHA in representative OPLs and histologically normal oral tissues selected randomly, as used for IHC and Western blot analysis and the results shown are representative of 3 independent experiments: Panel (i) shows increased levels of YWHAZ transcripts in OPLs (D1-D3) as compared to the histologically normal oral tissues (N1-N3) that did not show detectable levels of YWHAZ transcripts. Panel (ii) demonstrates increased levels of stratifin transcripts in OPLs (D1-D3) as compared to the histologically normal oral tissues (N1-N3) that show basal level (N1) and no detectable level (N2 and N3) of stratifin transcripts. Panel (iii) shows increased levels of hnRNPK transcripts in OPLs (D1-D3) as compared to the histologically normal oral tissues (N1-N3), in which no detectable levels of hnRNPK transcripts are evident. Panel (iv) exhibits increased levels of S100A7 transcripts in OPLs (D1-D3) as compared to no detectable levels in the histologically normal oral tissues (N1-N3). Panel (v) shows increased levels of PTHA transcripts in OPLs (D1-D3) as compared to the histologically normal oral tissues (N1-N3) in which no detectable levels of PTHA transcripts are evident. β-Actin (Panel iv) was used as a control for normalizing the quantity of RNA used.

FIG. 8C shows network analysis using ingenuity pathways analysis (IPA) software. Differentially expressed proteins identified in OPLs in comparison with normal oral tissues were analyzed using the IPA software. Network analysis classified proteins into 2 networks on the basis of function cited previously in literature. Above panel shows merged network of the pathways identified using IPA software. Bold lines (—) show direct interactions/regulation while dashed lines (---) show indirect interactions/regulation of proteins at the ends of line. Proteins shown in red color are upregulated and in green color are down-regulated in OPLs in comparison with normal tissues.

FIGS. 9A and 9B illustrate identification of stratifin (9A) and YWHAZ (9B) in HNOSCCs by mass spectrometry. The peptides for which MS/MS spectra are shown are colored red and in a larger font. Those that are common between stratifin and YWHAZ are shown in purple. Other peptides observed are in blue. The matched b ions are shown in green, and the matched y ions in red.

FIG. 10 provides an immunohistochemical analysis of stratifin in head-and-neck cancer tissues. Paraffin-embedded HNOSCC tissue sections and non-malignant mucosa were stained using anti-stratifin antibody (all ×100 magnifications): Panel a shows normal oral mucosa with no detectable stratifin immunostaining; Panel b shows HNOSCC with strong cytoplasmic and nuclear stratifin immunostaining in the tumor cells; Panel c shows HNOSCC negative control with lack of staining in the tumor cells.

FIG. 11 shows a box-plot analysis. The box plot shows distribution of total scores of stratifin in HNOSCCs and non-malignant head-and-neck tissues.

FIG. 12 sets forth a co-immunoprecipitation assay and Western blot analysis. Immunoprecipitation assays of stratifin, YWHAZ, NFκB, Bcl-2, and β-catenin proteins were carried out using specific antibodies in head-and-neck cancer cells, HSC2. FIG. 12a shows immunoblot analysis for stratifin, demonstrating the binding of stratifin with YWHAZ, NFκB, Bcl-2, and β-catenin, and the lack of binding in the negative control. Similarly, reverse immunoprecipitation assays were carried out using specific antibodies for YWHAZ, NFκB, Bcl-2, and β-catenin. FIG. 12b shows immunoblot analysis for: (i) YWHAZ, (ii) NFκB, (iii) Bcl-2, and (iv) β-catenin confirming the binding of these proteins with stratifin.

FIG. 13 illustrates a Kaplan-Meier estimation of cumulative proportion of disease-free survival: 13a, stratifin protein expression; the median time for disease-free survival (no recurrence/metastasis) in patients with stratifin-positive tumors was 19 months, whereas in those with stratifin-negative tumors it was 38 months (p=0.06). 13b, YWHAZ protein expression; the median time for disease-free survival (no recurrence/metastasis) in patients with YWHAZ-positive tumors was 23 months, whereas in those with YWHAZ-negative tumors it was 35 months (p=0.08). 13c, concomitant stratifin and YWHAZ expressions; the median time for disease-free survival of patients with HNOSCCs showing concomitant expressions of stratifin and YWHAZ (Stratifin+/YWHAZ+) was 13 months, as compared to patients with tumors that did not show increased expression of either of these proteins with the median time for disease-free survival being 38 months (p=0.019).

FIG. 14 shows an immunohistochemical analysis of hnRNPK in head-and-neck cancer tissues. Paraffin-embedded sections of histologically normal mucosa, leukoplakia with no evidence of dysplasia or with dysplasia and HNOSCCs were stained using anti-hnRNPK monoclonal antibody as described herein. (a) Normal oral mucosa with no detectable hnRNPK immunostaining. (b) Leukoplakic lesion with no dysplasia showing nuclear hnRNPK immunostaining. (c) Leukoplakic lesion with no dysplasia showing nuclear and cytoplasmic hnRNPK immunostaining. (d) Dysplasia depicting nuclear hnRNPK immunostaining in epithelial cells. (e) Dysplasia depicting nuclear and cytoplasmic hnRNPK immunostaining in epithelial cells. (f) HNOSCC section illustrating only nuclear hnRNPK immunostaining in the tumor cells. (g) HNOSCC section showing both cytoplasmic and nuclear staining in tumor cells. (h) HNOSCC section showing no immunostaining in tumor cells for hnRNPK protein serving as a negative control. Arrow shows nuclear staining of hnRNPK in panels b, d, and f, and nuclear and cytoplasmic staining in panel c, e, and g. a-h, original magnification×200

FIG. 15 presents receiver-operating characteristic curves of hnRNPK (nuclear/cytoplasmic) in (a) normal vs. leukoplakia with no evidence of dysplasia; (b) normal vs. dysplasia; and (c) normal vs. HNOSCCs. Bold line shows ROC analysis for nuclear hnRNPK. Dashed line shows ROC analysis for cytoplasmic hnRNPK.

FIG. 16 depicts an evaluation of hnRNPK expression (nuclear/cytoplasmic) as a biomarker for risk prediction of oral leukoplakia and prognosis of HNOSCCs. The figure shows estimated (a) positive predictive value (PPV) and (b) negative predictive value (NPV) for nuclear/cytoplasmic hnRNPK expression as prognostic biomarkers for disease progression of leukoplakia. Panels c and d show PPV and NPV for recurrence in HNOSCC patients, respectively.

FIG. 17 illustrates a Kaplan-Meier estimation of cumulative proportion of disease-free survival showing: (a) significantly reduced time for disease progression (p<0.001; median time=17 months) in leukoplakia patients showing increased cytoplasmic expression of hnRNPK as compared to median time of 35 months in the patients showing no/faint immunostaining of hnRNPK in cytoplasm; (b) median time for disease progression (34 months) was observed in leukoplakia patients showing intense nuclear expression of hnRNPK (n=78) as compared to patients who did not show increased nuclear hnRNPK; and (c) Median time for disease-free survival (no recurrence/metastasis) in HNOSCC patients showing cytoplasmic immunostaining of hnRNPK was 11 months, whereas in those patients showing no/faint hnRNPK-immunostaining in cytoplasm it was 41 months (p=0.004). In patients showing increased nuclear expression disease (d), free survival was 14 months as compared to HNOSCCs that showed mild or moderate nuclear immunostaining (median disease-free survival=57 months, p=0.07).

FIG. 18 depicts validation of hnRNPK expression in oral lesions. (a) Western blot analysis of hnRNPK in normal mucosa, leukoplakia and HNOSCC tissues. Equal amount of protein lysates from these tissues were electrophoresced on 12% SDS-PAGE and transferred to PVDF membrane. The membrane was incubated with respective primary antibodies and secondary antibodies as described herein, and the signal detected by enhanced chemiluminescence method. Panel (a) shows increased expression of hnRNPK in leukoplakia (L) and HNOSCCs (T) as compared to paired non-malignant head-and-neck tissues (N). Actin was used as control for equal loading of protein in SDS-PAGE (lower panel). (b) RT-PCR analysis of hnRNPK in normal mucosa, leukoplakia and HNOSCC tissues. Panel shows increased levels of hnRNPK transcripts in leukoplakia (L) and HNOSCCs (T) as compared to the non-malignant head-and-neck tissues that showed basal levels (N) of hnRNPK transcripts. β-actin, used as a control to normalize the quantity of RNA used for each RT-PCR reaction, is shown in the lower panel.

FIG. 19A-E presents CID spectra of the single-peptide identifications in the HNSCC and OPL.

Figure 22:
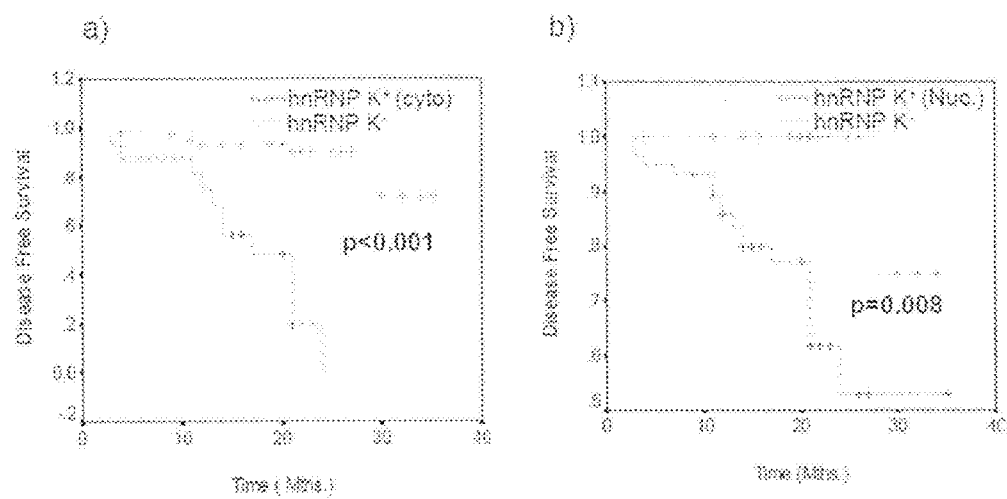

FIG. 22 sets forth a Kaplan-Meier analysis of OPLs with no evidence of dysplasia showing overexpression of hnRNPK.

Figure 23:
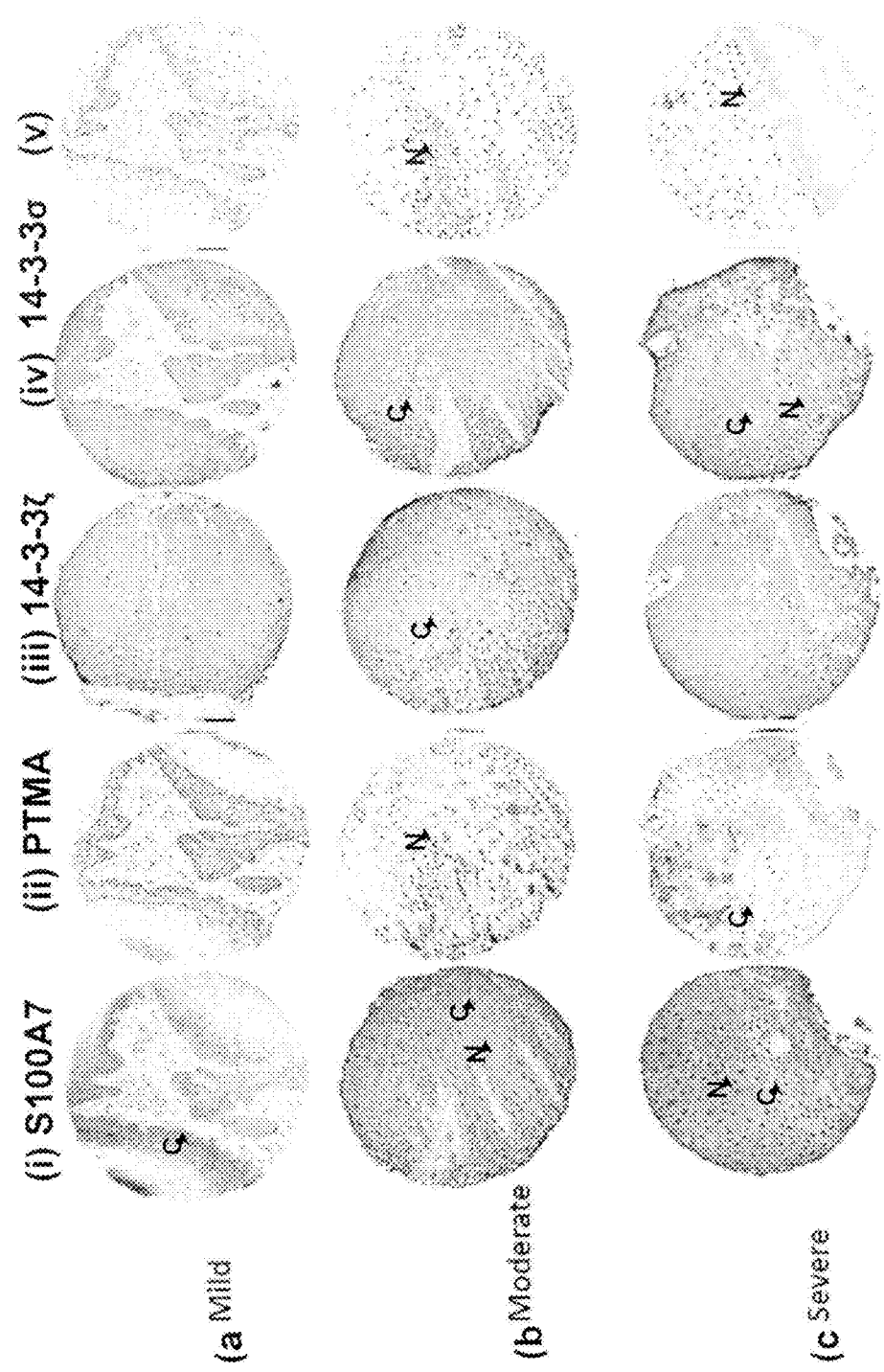

FIG. 23 depicts immunohistochemical analysis of five candidate markers in oral lesions with dysplasia. Immunohistochemistry was carried out in tissue sections from oral lesions with dysplasia using specific antibodies for S100A7, prothymosin alpha (PTMA), 14-3-3ζ, 14-3-3σ and heterogeneous nuclear ribonucleoprotein K (hnRNP K) as described in Materials and Methods. Panel shows cytoplasmic and/or nuclear immunostaining of (i) S100A7; (ii) PTMA; (iii) 14-3-3ζ and (iv) 14-3-3σ in (a) mild; (b) moderate and (c) severe dysplasia. Panel (v) shows nuclear hnRNP K in (a) mild; (b) moderate and (c) severe dysplasia; No detectable cytoplasmic expression of hnRNPK was observed in dysplasia sections used in this study. Arrows show cytoplasmic (C) or nuclear (N) staining in cells (Original magnification×200).

Figure 24:
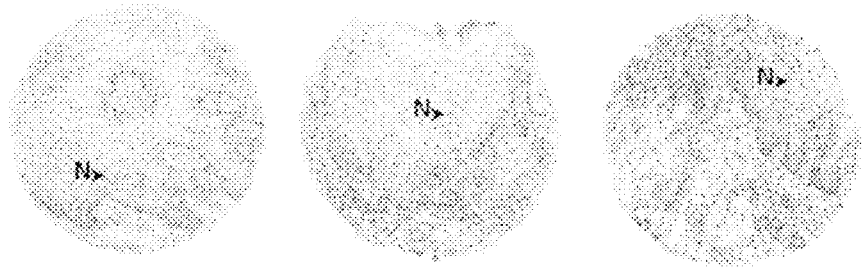
Figure 24:
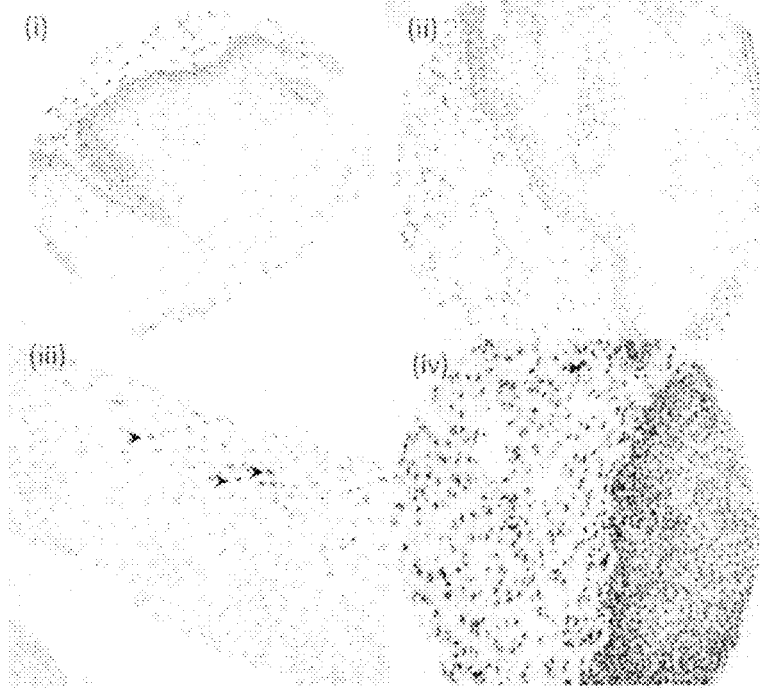

FIG. 24 depicts analysis of p16 and HPV 16/18 status in oral lesions with dysplasia. (A) Nuclear immunostaining of nuclear p16 in (i) mild; (ii) moderate and (iii) severe dysplasia; No detectable cytoplasmic expression of p16 was observed in dysplasia sections used in this study. Arrows show nuclear (N) staining in cells (original magnification× 200); (B) (i) a representative dysplasia section showing no staining for HPV 16/18; (ii) dysplasia section used as a negative control; (iii) cervical cancer tissue section showing positive staining for HPV16/18 in epithelial cells and (iv) dysplasia section used as positive control showing integrity of genomic DNA in tissue sections Arrow shows presence of HPV 16/18 in epithelial cells in cervical cancer section (original magnification×200).

Figure 25:
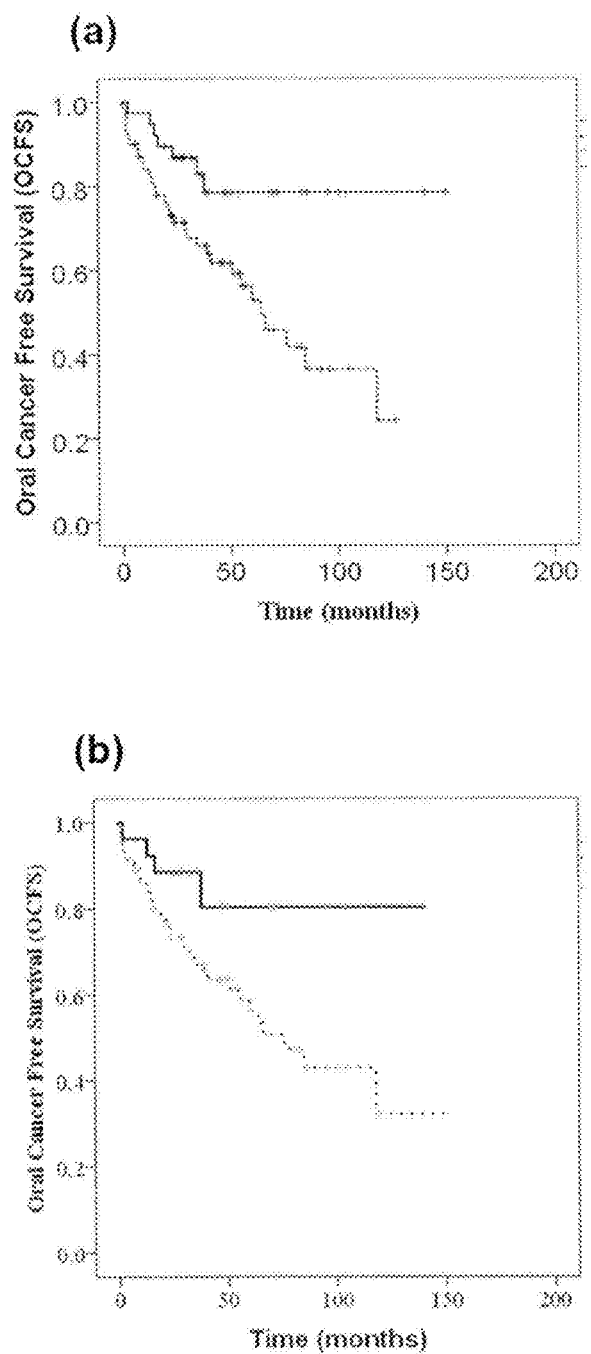

FIG. 25 depicts Kaplan-Meier survival analysis for evaluation of oral cancer-free survival (OCFS). Kaplan-Meier survival curves for (A) cytoplasmic S100A7 expression showing reduced OCFS (p=0.007) and (B) nuclear S100A7 expression (p=0.041).

Figure 26:
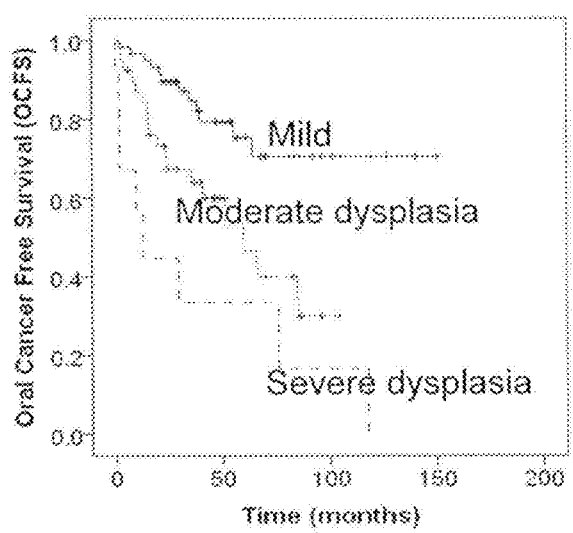

FIG. 26 depicts Kaplan-Meier survival analysis for evaluation of oral cancer-free survival (OCFS). Kaplan-Meier survival curves for mild, moderate and severe dysplasia. Patients with moderate dysplasia demonstrated low mean OCFS=58.59 months (p=0.004) while in severe dysplasia cases, patients showed mean OCFS=38.9 months, (p<0.001) as compared to mild dysplasia (mean OCFS=116.25 months).

Figure 27:
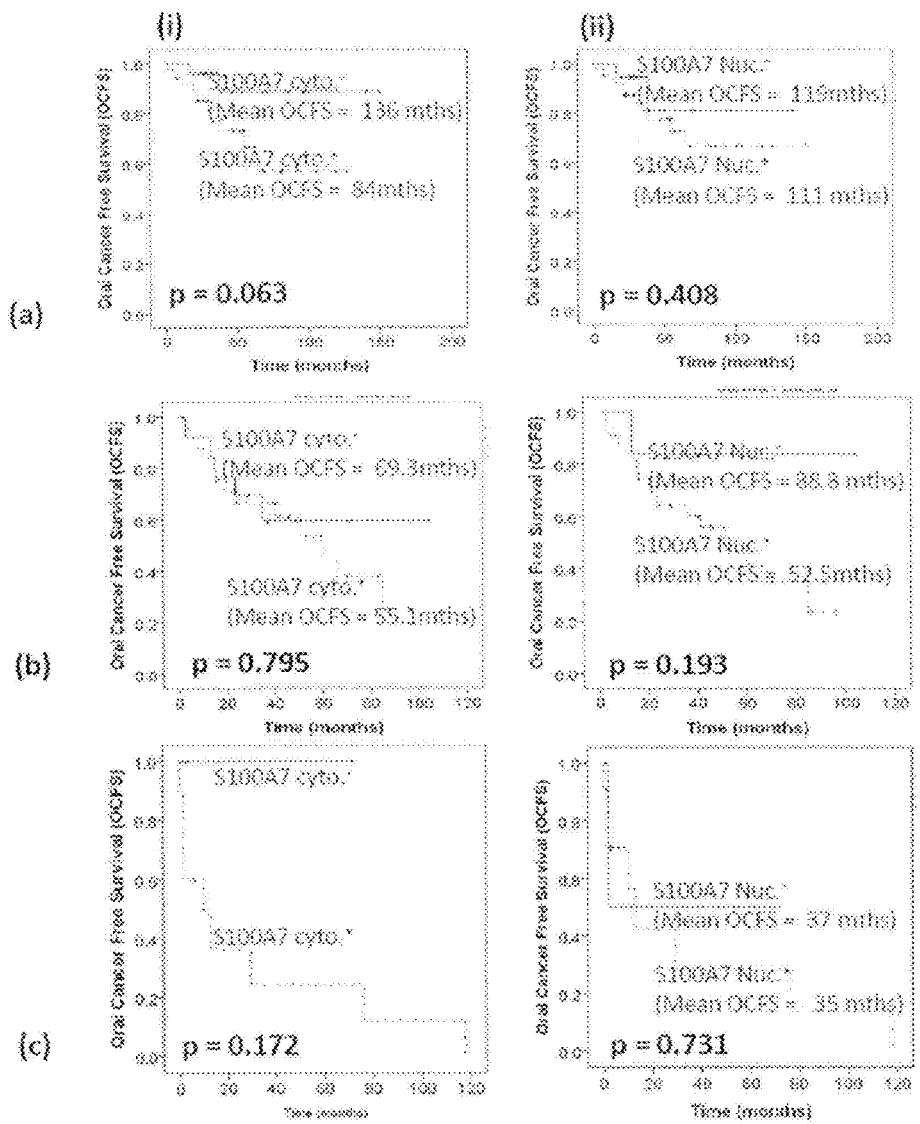

FIG. 27 depicts Kaplan-Meier survival analysis for evaluation of S100A7 overexpression with degree of dysplasia. Kaplan-Meier survival curves for S100A7 overexpression in (i) cytoplasm and (ii) nucleus in (a) mild dysplasia, (b) moderate dysplasia and (c) severe dysplasia.

Figure 28:
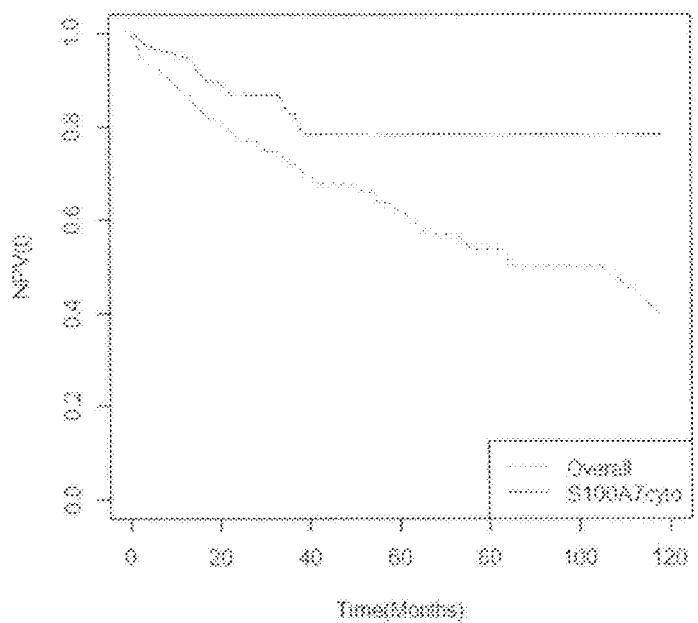
Figure 28:
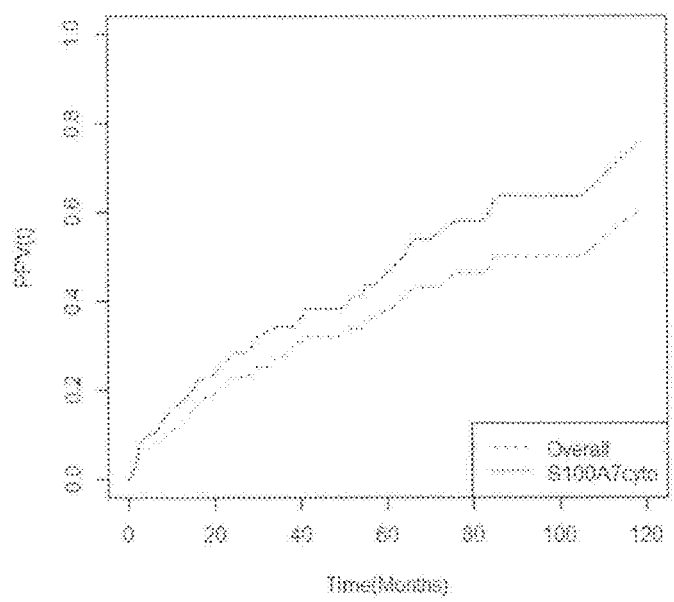

FIG. 28 depicts positive and negative predictive values for time to malignant transformation. (a) Positive Predictive Values [PPV(t)] for time to malignant transformation for 39 oral dysplasia patients with S100A7 expression and for all 110 dysplasia patients with survival data (overall); (b) Negative Predictive Values [NPV(t)] for time to malignant transformation for 39 patients with S100A7 overexpression, and for all 110 patients (overall).

Figure 29:
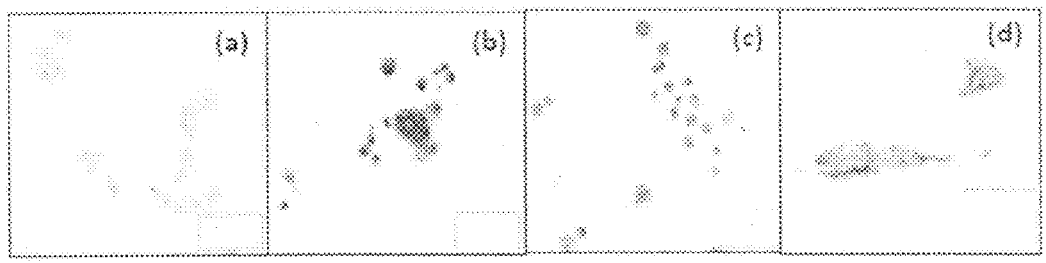

FIG. 29 depicts representative photomicrographs of S100A7 immunostaining in cytosmears. (a) stained oral epithelial cells obtained by scraping a patient's oral lesion; (b) stained oral cancer cells (positive control); (c) stained oral cancer cells (negative control); and (d) stained oral squamous cell carcinoma cells, depicting S100A7 immunostaining in both cytoplasm and nuclei.

Figure 30:
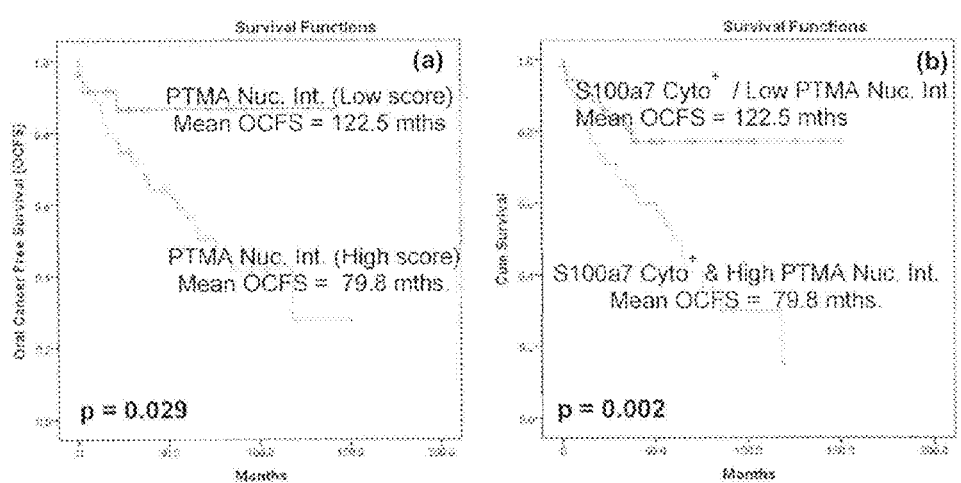

FIG. 30 depicts Kaplan-Meier survival analysis for evaluation of PTMA and S100A7 intensity scores with oral cancer free survival time in months. A. Kaplan-Meier survival curves for PTMA nuclear intensity scores (low and high). B. Kaplan-Meier survival curves for PTMA nuclear intensity scores (low and high) in combination with S100A7 cytoplasmic intensity scores.

Figure 31A:
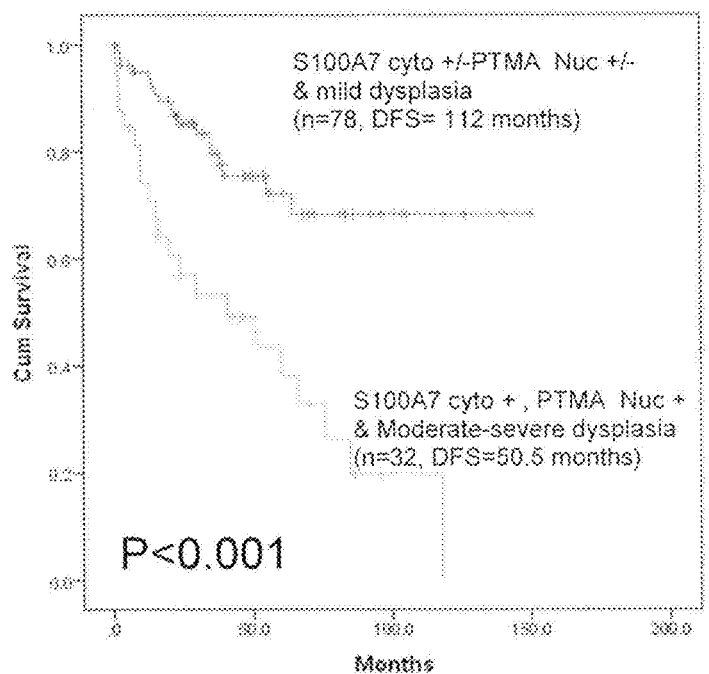

FIGS. 31a and b depict Kaplan-Meier survival analyses of combination of cytoplasmic S100A7, nuclear PTMA and degree of dysplasia.

DETAILED DESCRIPTION OF THE INVENTION

Multidimensional liquid chromatography-mass spectrometry (LC-MS/MS) has been used for the analysis of biological samples labeled with isobaric mass tags (iTRAQ) to identify proteins that are differentially expressed in human head-and-neck squamous-cell carcinomas (HNSCCs) in relation to non-cancerous head-and-neck tissues (control) for cancer biomarker discovery. Fifteen individual samples (cancer and non-cancerous tissues) were compared against a pooled non-cancerous control (prepared by pooling equal amounts of proteins from six noncancerous tissues) in five sets by online and offline separation. Eight hundred and eleven (811) non-redundant proteins in HNSCCs were identified, including structural proteins, signaling components, enzymes, receptors, transcription factors and chaperones.

A panel of proteins showing consistent differential expression in HNSCC relative to the non-cancerous controls was discovered. Some of the proteins include stratifin (14-3-3 sigma), YWHAZ (14-3-3 zeta), three calcium-binding proteins of the S100 family, S100A 2, S100A 7 (psoriasin) and S100A 11 (calgizarrin), prothymosin alpha (PTMA or PTHA), L-lactate dehydrogenase A chain (LDH-A), glutathione S transferase-Pi, APC binding protein EB1, and fascin. Peroxiredoxin2, carbonic anhydrase I, flavin reductase, histone H3, and polybromo-1D (BAF180) were underexpressed in HNSCCs.

A panel of the three best performing biomarkers—YWHAZ, stratifin, and S100A7—achieved a sensitivity of 0.92 and a specificity of 0.91 in discriminating cancerous from non-cancerous head-and-neck tissues (Table 7A). Verification of differential expression of YWHAZ, stratifin and S100A7 proteins in clinical samples of HNSCCs and paired and non-paired non-cancerous tissues by immunohistochemistry (Table 7B), immunoblotting, and RT-PCR confirmed their overexpression in head-and-neck cancer. Verification of YWHAZ, stratifin and S100A7 in an independent set of HNSCCs achieved a sensitivity of 0.92 and a specificity of 0.87 in discriminating cancerous from non-cancerous head-and-neck tissues, thereby confirming their overexpressions and utility as credible cancer biomarkers.

The inventors also used iTRAQ labeling in combination with multidimensional LC-MS/MS analysis of oral leukoplakia with dysplasia (oral premalignant lesions, or OPLs) in order to compare protein profiles of OPLs and normal head-and-neck tissues. Nine individual samples (6 OPLs and 3 normal tissues) were compared against a pooled normal control (prepared by pooling equal amounts of proteins from six noncancerous tissues) in five sets by online and offline separation.

The LC-MS/MS analyses collectively resulted in identification of 459 non-redundant proteins; 216 were identified as single hits with more than 95% confidence. Of all the proteins identified, only 17 were differentially expressed in OPLs relative to normal control (observed in ≥3 out of the 6 samples and with >50% showing differential expression). Of these, 15 proteins were confidently identified with a minimum of two peptide matches in each case. Two proteins, parathymosin and DLC1 were identified by single peptides. All these 17 proteins are given in Table 6, along with two structural proteins: β-actin and gelsolin precursor as controls. The heat map in Table 6 also depicts the variations in the levels of overexpressed and underexpressed proteins in individual OPL and histological normal tissues versus the pooled normal control. These differential expression levels were averages of the replicate analyses: 56.4% of the ratios varied by less than 10% from their respective averages shown, and 82.0% varied by less than 20%.

Thirteen proteins that did not meet the aforementioned initial criteria—IGL2, P37AUF1 (HNRPD), SOD2, PKM2, ROA1HNRNPA1, HSP27, cofilin, glyceraldehyde-3-phosphate dehydrogenase, NDP kinase B, elongation factor 2, CALM3, PEBP, and S100A7—were also included in Table 5 for further analysis, as these proteins are of biological relevance in cancer development. Of these, 11 proteins were confidently identified with a minimum of two peptide matches in each case. p37AUF1 (hnRNP D) was identified by a single peptide with a confidence of 99%. SOD2 was identified by more than one unique peptides, however, the best matching peptide was identified with a confidence of 93%. Although, individually this peptide did not meet the inventors' stipulated criteria for acceptance, manual verification of the spectrum showed good sequence coverage for this peptide. Furthermore, the cumulative score which included the lower confidence peptide matches was >2.0 and corresponded with a confidence of 99%.

The best-performing proteins that can differentiate between OPLs and normal tissues were identified by determining the individual receiver-operating characteristic (ROC) curves of the proteins in Table 7. The three proteins with the highest AUC values—YWHAZ, stratifin and hnRNPK—are listed in Table 7A together with their individual and collective figures-of-merit, including sensitivity and specificity. As a panel, these three biomarkers achieved a sensitivity of 0.83 and a specificity of 0.74 in discriminating OPLs from histological normal oral tissues (Table 7A and FIG. 6A).

Figure 8A:
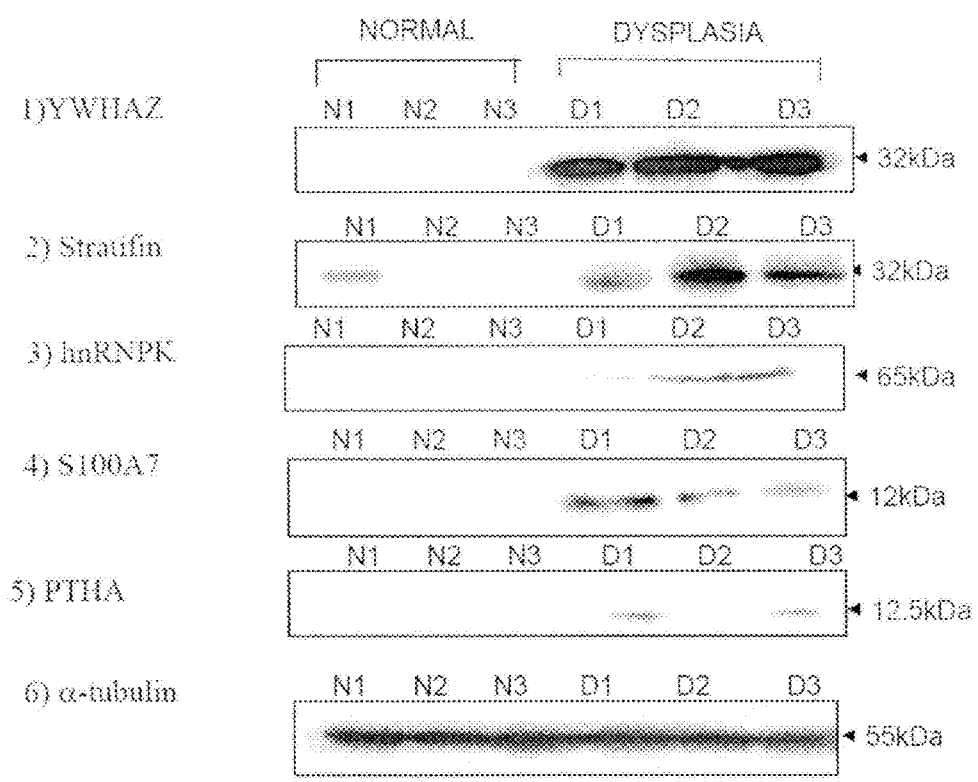
Figure 8B:
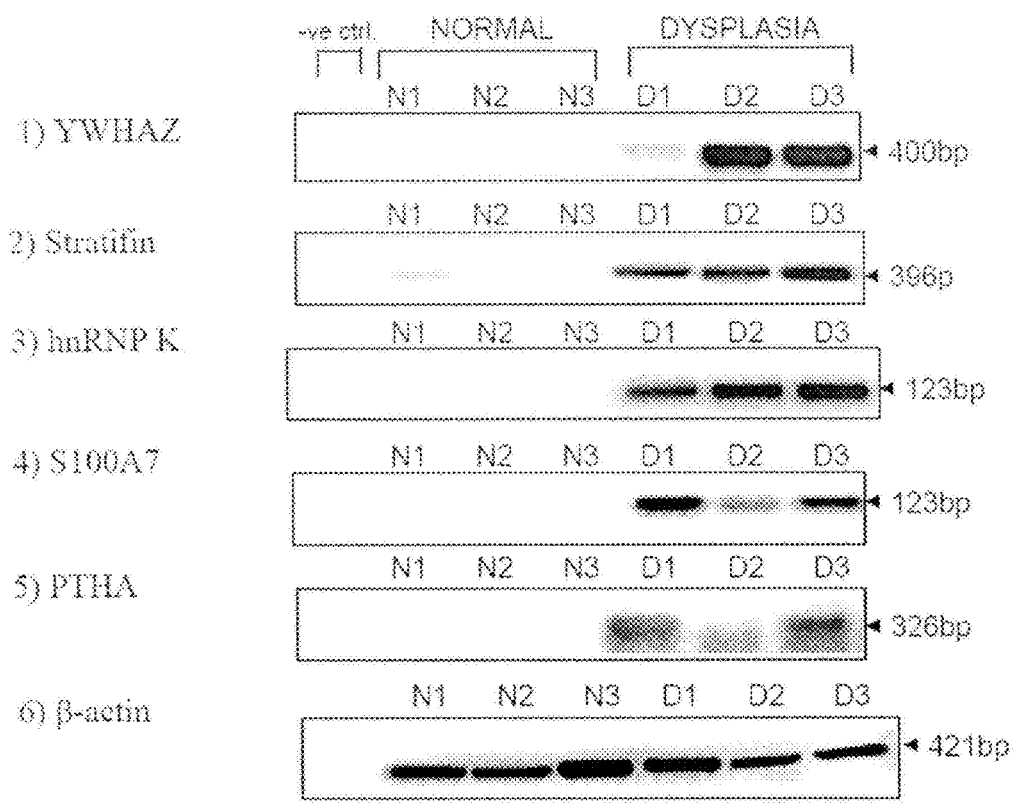

The panel of three potential biomarkers, YWHAZ, stratifin and hnRNPK, and two other proteins with high AUC values, S100A7 (0.56) and PTHA (0.56), were chosen for verification in an independent set of OPLs (30 cases) and normal tissues (21 cases) by IHC. Representative levels of expression and subcellular localizations of all the five proteins in oral dysplastic tissues in comparison with normal tissues are shown in FIG. 7A-E. These data were further verified by Western blot analysis (FIG. 8A) at the protein level, as well as RT-PCR analysis at the mRNA level (FIG. 8B). The differential expression suggested by iTRAQ ratios tended to be moderate, while the results of Western and RT-PCR analyses tended to show more extreme differential expression. Thus, Western and RT-PCR analyses, verified the differential expression reported by the iTRAQ analysis in trend but not in scale. This discrepancy of scale has also been noted in other studies ascribed to compression of the dynamic range of iTRAQ ratios (21). Importantly, in IHC analysis, the biomarker panel of YWHAZ, stratifin, and hnRNPK achieved a sensitivity of 0.91, specificity of 0.95, and predictive value of 0.96 (Table 7B and FIG. 7B) in discriminating OPLs from histological normal oral tissues.

Figure 8C:
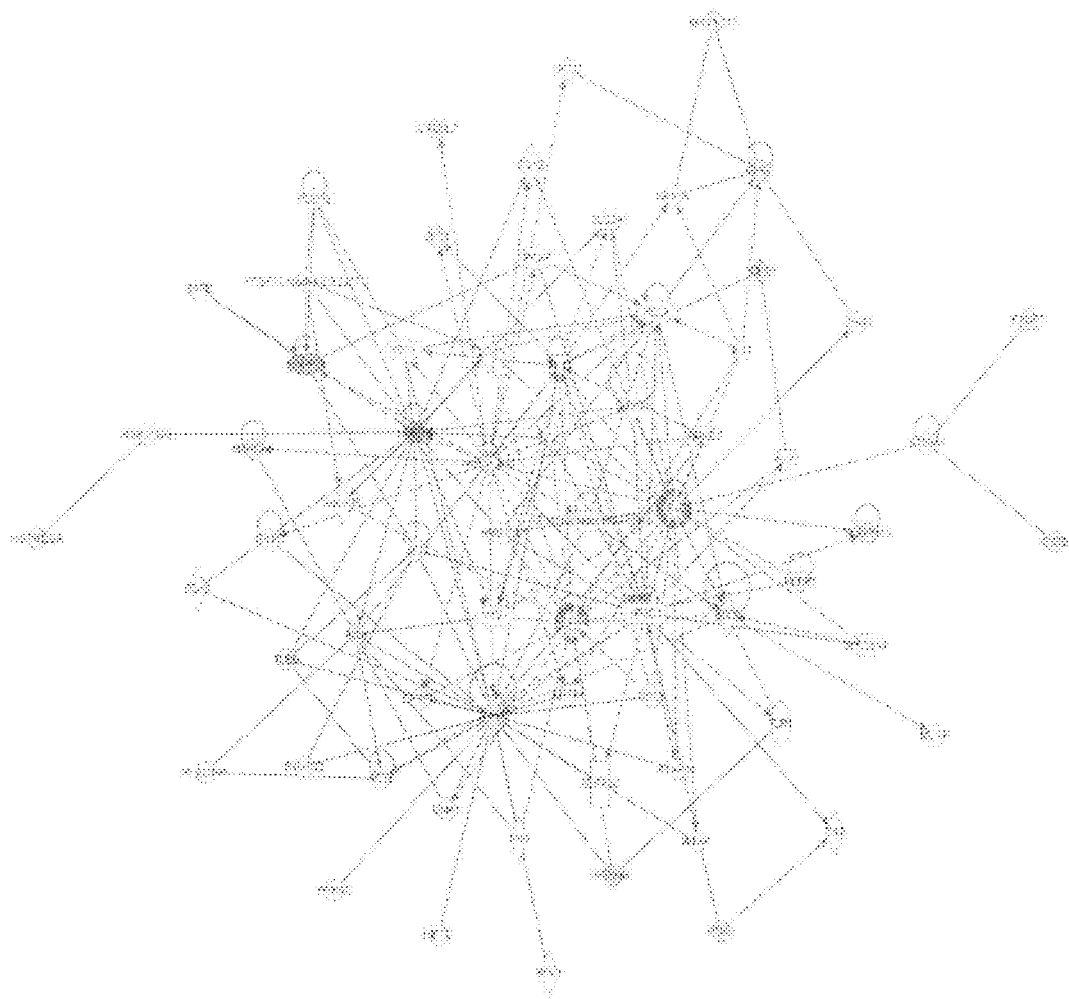

To gain insight into the plausible biological processes in which these proteins might be involved, the inventors used the Ingenuity pathway analysis tools (Ingenuity Systems, Inc. software) and discovered two major networks in OPLs (FIG. 8C). The network comprised of 23 proteins identified in this study that are primarily involved in inflammation, molecular transport, cellular movement, cellular signaling, proliferation, gene expression and cancer. To the best of the inventors' knowledge, this is the first study reporting differential expressions of p37AUF1 (HNRPD) and histone H2B.1 in OPLs.

Accordingly, the inventors describe herein methods for detecting the presence of a head-and-neck disease (e.g., OPL or head-and-neck cancer) in a sample, the absence of a disease (e.g., OPL or head-and-neck cancer) in a sample, the stage or grade of the disease, and other characteristics of head-and-neck diseases that are relevant to prevention, diagnosis, characterization, and therapy of head-and-neck diseases such as OPL or cancer in a patient, for example, the benign, premalignant or malignant nature of a head-and-neck cancer, the metastatic potential of a head-and-neck cancer, assessing the histological type of neoplasm associated with a head-and-neck cancer, the indolence or aggressiveness of a leukoplakia with hyperplasia or dysplasia or head-and-neck cancer, and other characteristics of head-and-neck diseases that are relevant to prevention, diagnosis, characterization, and therapy of head-and-neck diseases such as OPL or cancer in a patient. Methods are also provided for assessing the efficacy of one or more test agents for inhibiting a head-and-neck disease, assessing the efficacy of a therapy for a head-and-neck disease, monitoring the progression of a head-and-neck disease, selecting an agent or therapy for inhibiting a head-and-neck disease, and assessing the disease (e.g., carcinogenic) potential of a test compound.

In some embodiments of the present invention, a method for diagnosing an increased risk for development of oral cancer in a subject having oral dysplasia is provided. In such a method, the level of S100A7 protein in a biological sample from the subject is measured using an assay suitable for protein detection, as set forth above.

The measured level of S100A7 in the biological sample is then compared with the level of S100A7 in a control, wherein a measured level of S100A7 higher than the control level is indicative of an increased risk or a "high" or "higher" risk for developing oral cancer. In some embodiments, the biological sample from the subject comprises oral epithelial cells. In some embodiments, the biological sample is a cytosmear. In preferred embodiments, at least some of the oral epithelial cells in the biological sample are dysplastic.

In some embodiments, the control is a biological sample comprising dysplastic epithelial cells that are known not to progress to oral cancer for at least 3.5 years following measurement of S100A7 in the control biological sample. In preferred embodiments, the biological sample known not to progress to cancer is known not to progress to cancer for at least 10 years following measurement of S100A7 in the control biological sample.

As is apparent from the foregoing embodiments, the presently disclosed methods are useful for managing the treatment of patients with potential oral cancer or with known oral cancer. For example, in some embodiments, S100A7 can be useful for screening patients to identify patients at high risk or higher risk for oral cancer. Other known methods of identifying oral cancer might not identify the same patients as being at high or higher risk for oral cancer. In this manner, only those patients with a test result indicating a high or higher probability of malignant transformation of an oral lesion can be sent on to have one or more anti-cancer therapies. Patients whose test results suggest a low probability of cancer can be re-evaluated using S100A7 during their routine follow-up.

In some aspects of the present invention, a method for diagnosing an increased risk for development of oral cancer in a subject having oral dysplasia comprising measuring the level of nuclear PTMA in a biological sample from the subject is provided. The measured level of nuclear PTMA is then compared with the level of nuclear PTMA in a control, wherein a measured level of nuclear PTMA higher than the control level is indicative of an increased risk for developing oral cancer.

In some embodiments of this aspect, the method further comprises measuring the level of cytoplasmic S100A7 in a biological sample from the subject; and comparing the level of cytoplasmic S100A7 in the biological sample with the level of cytoplasmic S100A7 in a control, wherein a measured level of cytoplasmic S100A7 higher than the control level is indicative of an increased risk for developing oral cancer.

In some embodiments of this aspect, the biological sample comprises epithelial cells. In some embodiments, the biological sample is a cytosmear. In some embodiments, the epithelial cells are dysplastic.

In some embodiments of this aspect, the control is a biological sample comprising dysplastic epithelial cells known not to progress to oral cancer for at least 3.5 years following measurement of the control level. In some embodiments, the biological sample known not to progress to cancer is known not to progress to cancer for at least 10 years following measurement of the control level.

In some embodiments of this aspect, the method further comprises measuring the degree of dysplasis in the sample obtained from the subject. In some embodiments a moderate or severe degree of dysplasia is indicative of an increased risk for developing oral cancer relative to a corresponding control sample having a mild degree of dysplasia.

In some embodiments, the presently disclosed methods comprise detecting a level of S100A7 expression in epithelial cells. In some embodiments of these methods, cytosmear can be used to obtain the epithelial cells. The cytosmear can be stained, as described herein, and examined by light microscopy to determine cytopathology and S100A7 expression levels.

Abbreviation Index.

For convenience, certain abbreviations used in the description, tables, figures, and appended claims are defined here: iTRAQ, isobaric tags for relative and absolute quantification; LC, liquid chromatography; MS/MS, tandem mass spectrometry; PCM, potential cancer marker; HNSCC, head-and-neck squamous cell carcinoma; LCM, laser capture microdissection; PBS, phosphate-buffered saline; SCX, strong cation exchange; ID, internal diameter; RP, reverse phase; IDA, information-dependent acquisition; TBS, tris-buffered saline; SFN, stratifin or 14-3-3 sigma; YWHAZ, 14-3-3 zeta; LDH-A, L-lactate dehydrogenase A; SD, standard deviation; ROC, receiver-operating characteristics; PPIA, peptidyl prolyl isomerase A; PV, predictive values; PPV, positive predictive values; PTHA, prothymosin alpha; PTMA, prothymosin appha; PKM2, pyruvate kinase isozyme M2; AUC, area under the curve; RSD, relative standard deviation; TMA, tissue microarray.

Glossary.

For convenience, certain terms employed in the specification, examples, and appended claims are collected here.

The recitation of numerical ranges by endpoints herein includes all numbers and fractions subsumed within that range (e.g., 1 to 5 includes 1, 1.5, 2, 2.75, 3, 3.90, 4, and 5).

It is also to be understood that all numbers and fractions thereof are presumed to be modified by the term "about." Furthermore, it is to be understood that "a", "an," and "the" include plural referents unless the content clearly dictates otherwise. Thus, for example, reference to a method comprising "a head-and-neck marker" includes two or more OPL or head-and-neck cancer markers. The term "about" means plus or minus 0.1 to 50%, 5-50%, or 10-40%, preferably 10-20%, more preferably 10% or 15%, of the number to which reference is being made.

"Head-and-neck disease" refers to any disorder, disease, condition, syndrome or combination of manifestations or symptoms recognized or diagnosed as a disorder of the head and neck, including but not limited to hyperplasia, dysplasia and cancer precursors, head-and-neck cancer or carcinoma.

"Head-and-neck cancer" or "head-and-neck carcinoma" includes malignant head-and-neck disease including but not limited to squamous cell and adenocarcinomas.

Biomarkers of head-and-neck precancers includes OPL markers including but not limited to oral leukoplakia with hyperplasia or dysplasia.

The terms "sample", "biological sample", and the like mean a material known or suspected of expressing or containing one or more OPL or head-and-neck cancer markers. A test sample can be used directly as obtained from the source or following a pretreatment to modify the character of the sample. The sample can be derived from any biological source, such as tissues, extracts, or cell cultures, including cells (e.g., tumor cells), cell lysates, and physiological fluids, such as, for example, whole blood, plasma, serum, saliva, ocular lens fluid, cerebral spinal fluid, sweat, urine, milk, ascites fluid, synovial fluid, peritoneal fluid, lavage fluid, and the like. The sample can be obtained from animals, preferably mammals, most preferably humans. The sample can be treated prior to use, such as preparing plasma from blood, diluting viscous fluids, and the like. Methods of treatment can involve filtration, distillation, extraction, concentration, inactivation of interfering components, the addition of reagents, and the like.

In embodiments of the invention the sample is a mammalian tissue sample. In a particular embodiment, the tissue is head-and-neck tissue. In some embodiments, the sample comprises oral dysplastic epithelial cells.

In another embodiment the sample is a human physiological fluid. In a particular embodiment, the sample is human serum.

The terms "subject", "individual", and "patient" refer to a mammal. In particular, the terms refer to a human. A subject, individual or patient may be afflicted with or suspected of having or being pre-disposed to head-and-neck disease or a condition as described herein.

The term "head-and-neck marker" refers to a marker associated with normal or diseased head-and-neck tissue and includes or consists of one or more of the polypeptides that are up-regulated in cancer samples as compared to normal samples in Table 1 and Table 7, those listed in Table 5, in particular The term includes native-sequence polypeptides, isoforms, chimeric polypeptides, complexes, all homologs, fragments, precursors, and modified forms and derivatives of the markers.

A head-and-neck marker may be associated with a head-and-neck disease, in particular it may be an OPL or head-and-neck cancer marker. The term "OPL or head-and-neck cancer marker" includes a marker associated with OPL or head-and-neck cancer, in particular a marker listed in Table 5.

The terms "YWHAZ", "YWHAZ polypeptide", and "YWHAZ protein" include human YWHAZ, in particular the native-sequence polypeptide, isoforms, chimeric polypeptides, all homologs, fragments, precursors, complexes, and modified forms and derivatives of human YWHAZ. The amino acid sequence for native human YWHAZ includes the amino acid sequences referenced in NCBI Gene ID: Q86V33, including GenBank Accession Nos. P29213, P29312, Q32P43, Q5XJ08, Q6GPI2, Q6IN74, Q6NUR9, Q6P3U9, and the exemplary sequences shown in SEQ ID NO: 24 (GenBank Accession No. P63104). Corresponding terms for "S100A7", "stratifin", and "hnRNPK" have similar meanings. The amino acid sequence for native human S100A7 includes the amino acid sequences referenced in NCBI Gene ID: P31151, including GenBank Accession Nos. Q6FGE3, Q9H1E2, and the exemplary sequences shown in SEQ ID NO: 13 (GenBank Accession No. P31151). The amino acid sequence for native human stratifin includes the amino acid sequences referenced in NCBI Gene ID: P31947, including GenBank Accession Nos. Q6FH30, Q6FH51, Q96DH0, and the exemplary sequences shown in SEQ ID NO: 23 (GenBank Accession No. P31947). The amino acid sequence for native human hnRNPK includes the amino acid sequences referenced in NCBI Gene ID: gi|48429103, NP_002131.2, P61978.1 including GenBank Accession Nos. S74678.1, NP_112552.1, AAB20770.1, NP_112553.1, X72727.1, 1J5K_A, CAA51267.1, 1KHM_A, AB209562.1, IZZI_A, BAD92799.1, IZZI_B, BC000355.2, IZZJ_A, AAH00355.1, IZZJ_B, BC014980.1, IZZJ_C, AAH14980.1, 1ZZK_A, and the exemplary sequences shown in SEQ ID NO: 25 (GenBank Accession No. P61978.1).

A "native-sequence polypeptide" includes a polypeptide having the same amino acid sequence of a polypeptide derived from nature. Such native-sequence polypeptides can be isolated from nature or can be produced by recombinant or synthetic means. The term specifically encompasses naturally occurring truncated or secreted forms of a polypeptide, polypeptide variants including naturally occurring variant forms (e.g., alternatively spliced forms or splice variants), and naturally occurring allelic variants.

The term "polypeptide variant" means a polypeptide having at least about 45%, 50%, 55%, 60%, 65%, 70%, 75%, 80%, 85%, 90%, 95%, 97%, 98%, or 99% amino acid sequence identity, particularly at least about 70-80%, more particularly at least about 85%, still more particularly at least about 90%, most particularly at least about 95% amino acid sequence identity with a native-sequence polypeptide. Particular polypeptide variants have at least 70-80%, 85%, 90%, 95% amino acid sequence identity to the sequences identified in Table 5 or 2 or 7. Such variants include, for instance, polypeptides wherein one or more amino acid residues are added to, or deleted from, the N- or C-terminus of the full-length or mature sequences of the polypeptide, including variants from other species, but excludes a native-sequence polypeptide. In aspects of the invention variants retain the immunogenic activity of the corresponding native-sequence polypeptide.

Percent identity of two amino acid sequences, or of two nucleic acid sequences is defined as the percentage of amino acid residues or nucleotides in a candidate sequence that are identical with the amino acid residues in a polypeptide or nucleic acid sequence, after aligning the sequences and introducing gaps, if necessary, to achieve the maximum percent sequence identity, and not considering any conservative substitutions as part of the sequence identity. Skilled artisans can determine appropriate parameters for measuring alignment, including any algorithms needed to achieve maximal alignment over the full length of the sequences being compared. Methods to determine identity and similarity are codified in publicly-available computer programs.

An allelic variant may also be created by introducing substitutions, additions, or deletions into a polynucleotide encoding a native polypeptide sequence such that one or more amino acid substitutions, additions, or deletions are introduced into the encoded protein. Mutations may be introduced by standard methods, such as site-directed mutagenesis and PCR-mediated mutagenesis. In an embodiment, conservative substitutions are made at one or more predicted non-essential amino acid residues. A "conservative amino acid substitution" is one in which an amino acid residue is replaced with an amino acid residue with a similar side chain. Amino acids with similar side chains are known in the art and include amino acids with basic side chains (e.g., Lys, Arg, His), acidic side chains (e.g., Asp, Glu), uncharged polar side chains (e.g., Gly, Asp, Glu, Ser, Thr, Tyr, and Cys), non-polar side chains (e.g., Ala, Val, Leu, Iso, Pro, Trp), beta-branched side chains (e.g., Thr, Val, Iso), and aromatic side chains (e.g., Tyr, Phe, Trp, His). Mutations can also be introduced randomly along part or all of the native sequence, for example, by saturation mutagenesis. Following mutagenesis the variant polypeptide can be recombinantly expressed and the activity of the polypeptide may be determined.

Polypeptide variants include polypeptides comprising amino acid sequences sufficiently identical to or derived from the amino acid sequence of a native polypeptide which include fewer amino acids than the full length polypeptides. A portion of a polypeptide can be a polypeptide which is for example, 10, 15, 20, 25, 30, 35, 40, 45, 50, 60, 70, 80, 90, 100 or more amino acids in length. Portions in which regions of a polypeptide are deleted can be prepared by recombinant techniques and can be evaluated for one or more functional activities such as the ability to form antibodies specific for a polypeptide.

A naturally occurring allelic variant may contain conservative amino acid substitutions from the native polypeptide sequence or it may contain a substitution of an amino acid from a corresponding position in a polypeptide homolog, for example, a murine polypeptide.

A modified form of a polypeptide referenced herein includes modified forms of the polypeptides and derivatives of the polypeptides, including post-translationally modified forms such as glycosylated, phosphorylated, acetylated, methylated or lapidated forms of the polypeptides. For example, an N-terminal methionine may be cleaved from a polypeptide, and a new N-terminal residue may or may not be acetylated. In particular, for chaperonin 10 the first residue, methionine, can be cleaved and the second first residue, alanine can be N-acetylated.

Oral premalignant lesions (OPL) or head-and-neck cancer markers may be prepared by recombinant or synthetic methods, or isolated from a variety of sources, or by any combination of these and similar techniques.

"Statistically different levels", "significantly altered levels", or "significant difference" in levels of markers in a patient sample compared to a control or standard (e.g., normal levels or levels in other samples from a patient) may represent levels that are higher or lower than the standard error of the detection assay. In particular embodiments, the levels may be 1.5, 2, 3, 4, 5, or 6 times higher or lower than the control or standard.

"Microarray" and "array" refer to nucleic acid or nucleotide arrays or protein or peptide arrays that can be used to detect biomolecules associated with head and neck cell or tissue phase and head-and-neck disease, for instance to measure gene or protein expression. A variety of arrays are made in research and manufacturing facilities worldwide, some of which are available commercially.

"Binding agent" refers to a substance such as a polypeptide or antibody that specifically binds to one or more OPL or head-and-neck cancer markers. A substance "specifically binds" to one or more OPL or head-and-neck cancer markers if is reacts at a detectable level with one or more OPL or head-and-neck cancer markers, and does not react detectably with peptides containing an unrelated or different sequence. Binding properties may be assessed using an ELISA, which may be readily performed by those skilled in the art (see, for example, Newton et al., Develop. Dynamics 197: 1-13, 1993).

A binding agent may be a ribosome, with or without a peptide component, an aptamer, an RNA molecule, or a polypeptide. A binding agent may be a polypeptide that includes one or more OPL or head-and-neck marker sequence, a peptide variant thereof, or a non-peptide mimetic of such a sequence. By way of example, a YWHAZ sequence may be a peptide portion of a YWHAZ that is capable of modulating a function mediated by YWHAZ.

Antibodies for use in the present invention include but are not limited to monoclonal or polyclonal antibodies, immunologically active fragments (e.g., a Fab or (Fab)2 fragments), antibody heavy chains, humanized antibodies, antibody light chains, genetically engineered single chain Fv molecules (Ladner et al., U.S. Pat. No. 4,946,778), chimeric antibodies, for example, antibodies which contain the binding specificity of murine antibodies, but in which the remaining portions are of human origin, or derivatives, such as enzyme conjugates or labeled derivatives.

Antibodies, including monoclonal and polyclonal antibodies, fragments and chimeras, may be prepared using methods known to those skilled in the art. Isolated native or recombinant OPL or head-and-neck cancer markers may be utilized to prepare antibodies. Antibodies specific for an OPL or head-and-neck marker may also be obtained from scientific or commercial sources.

In an embodiment of the invention, antibodies are reactive against an OPL or head-and-neck marker if they bind with a Ka of greater than or equal to 10-7 M.

Markers.

The invention provides a set of markers correlated with head-and-neck disease. In an aspect, the invention provides a set of markers identified as useful for detection, diagnosis, prevention and therapy of head-and-neck disease including or consisting of one or more of the markers listed in Table 5. In another aspect, the invention provides the head-and-neck or OPL cancer markers in Table 2 and Table 7 for detection, diagnosis and prognosis of a head-and-neck disease. The invention also provides a method of using OPL or head-and-neck cancer markers listed in Table 5 or Table 2 or Table 7, to distinguish head-and-neck disease.

In an embodiment, the markers include or consist of 1, 2, 3, 4 or more other markers listed in Table 5, Table 2, and Table 7.

In embodiments of the invention, a marker is provided which is selected from the group consisting of the polypeptides set forth in Table 5 which polypeptides are up-regulated biomarkers in OPL or head-and-neck cancer and optionally at least 2, 3, 4, 5, 6, 7, 8, 9, or 10 polypeptides set forth in Table 5 and/or 2 or polypeptides in Table 1 and Table 5 and/or 6 or polypeptides in Table 7 that are up-regulated biomarkers in OPL or head-and-neck cancer.

In embodiments of the invention, a marker is provided which is selected from the group consisting of at least one marker of Table 2 or 7 and at least 2, 3, 4, 5, 6, 7, 8, 9, or 10 polypeptides set forth in Table 5.

The invention provides marker sets that distinguish head-and-neck disease and uses therefor. In an aspect, the invention provides a method for classifying a head-and-neck disease including detecting a difference in the expression of a first plurality of OPL or head-and-neck cancer markers relative to a control, the first plurality of OPL or head-and-neck cancer markers or OPL. In specific aspects, the plurality of markers consists of the markers listed in Table 2 and optionally at least 5 to 10 of the markers listed in Table 5. In specific aspects, the plurality of markers consists of the markers listed in Table 7 and optionally at least 5 to 10 of the markers listed in Table 5. In specific aspects, a control includes markers derived from a pool of samples from individual patients with no head-and-neck disease.

Any of the markers provided herein may be used alone or with other markers of head-and-neck disease, or with markers for other phenotypes or conditions. Additionally, all of the sequences provided herein are representative only; there may be other sequences for particular protein or coding sequences or related sequences. The invention is not intended to be limited to the sequences herein provided.

Detection Methods.

A variety of methods can be employed for the diagnostic and prognostic evaluation of head-and-neck disease or head-and-neck cancer markers, and the identification of subjects with a predisposition to head-and-neck diseases or that are receptive to in vitro fertilization and embryo transfer procedures. Such methods may, for example, utilize head-and-neck cancer markers, and fragments thereof, and binding agents (e.g., antibodies) against one or more OPL or head-and-neck cancer markers, including peptide fragments. In particular, the antibodies may be used, for example, for the detection of either an over- or an under-abundance of one or more OPL or head-and-neck cancer markers relative to a non-disorder state or a different head and neck cell or tissue phase or the presence of a modified (e.g., less than full length) OPL or head-and-neck marker which correlates with a disorder state or a progression toward a disorder state.

The invention contemplates a method for detecting the phase of a head-and-neck tissue, in particular a secretory head-and-neck tissue, including producing a profile of levels of one or more OPL or head-and-neck marker associated with a known head and/or neck cell or tissue phase and/, and optionally other markers associated with the phase in cells from a patient, and comparing the profile with a reference to identify a profile for the test cells indicative of the phase. In an aspect, the head-and-neck cancer markers include those of Table 5, preferably Table 2 or fragments thereof. In an aspect, the OPL markers include those of Table 5, preferably Table 7 or fragments thereof.

The invention also contemplates a method for detecting a head-and-neck disease, in particular an OPL or head-and-neck cancer, including producing a profile of levels of one or more head-and-neck marker associated with a head-and-neck disease and/, and other markers associated with head-and-neck disease in cells from a patient, and comparing the profile with a reference to identify a profile for the test cells indicative of disease. In an aspect, the head-and-neck cancer markers are one or more of those listed in Table 5 or Table 2. In an aspect, the OPL markers are one or more of those listed in Table 5 or Table 7.

The methods described herein may be used to evaluate the probability of the presence of malignant or pre-malignant cells, for example, in a group of cells freshly removed from a host. Such methods can be used to detect tumors, quantify their growth, and help in the diagnosis and prognosis of head-and-neck disease. The methods can be used to detect the presence of cancer metastasis, as well as confirm the absence or removal of all tumor tissue following surgery, cancer chemotherapy, and/or radiation therapy. They can further be used to monitor cancer chemotherapy and tumor reappearance.

The methods described herein can be adapted for diagnosing and monitoring head-and-neck tissue status or a head-and-neck disease by detecting one or more OPL or head-and-neck cancer markers in biological samples from a subject. These applications require that the amount of markers quantified in a sample from a subject being tested be compared to a predetermined standard or cut-off value. The standard may correspond to levels quantified for another sample or an earlier sample from the subject, or levels quantified for a control sample. Levels for control samples from healthy subjects, different head-and-neck tissue phases, or subjects with a head-and-neck disease may be established by prospective and/or retrospective statistical studies. Healthy subjects who have no clinically evident disease or abnormalities may be selected for statistical studies. Diagnosis may be made by a finding of statistically different levels of detected head-and-neck cancer markers associated with disease, compared to a control sample or previous levels quantified for the same subject.

The methods described herein may also use multiple markers for a head-and-neck disease, in particular OPL and head-and-neck cancer. The methods described herein may be modified by including reagents to detect the additional markers.

Oral premalignant lesion (OPL) or head-and-neck cancer marker-positive samples or alternatively higher levels in patients compared to a control (e.g., non-cancerous tissue) may be indicative of late stage disease, and/or that the patient is not responsive to chemotherapy. Alternatively, negative samples or lower levels compared to a control (e.g., non-cancerous tissue or negative samples) may be indicative of progressive disease and shorter overall survival.

Protein Methods.

Binding agents may be used for a variety of diagnostic and assay applications. There are a variety of assay formats known to the skilled artisan for using a binding agent to detect a target molecule in a sample. In general, the presence or absence of a head-and-neck disease (e.g., cancer) in a subject may be determined by (a) contacting a sample from the subject with a binding agent; (b) detecting in the sample a level of polypeptide that binds to the binding agent; and (c) comparing the level of polypeptide with a predetermined standard or cut-off value.

In particular embodiments of the invention, the binding agent is an antibody. Antibodies specifically reactive with one or more head-and-neck marker, or derivatives, such as enzyme conjugates or labeled derivatives, may be used to detect one or more head-and-neck marker in various samples (e.g., biological materials). They may be used as diagnostic or prognostic reagents and they may be used to detect abnormalities in the level of expression of one or more head-and-neck marker, or abnormalities in the structure, and/or temporal, tissue, cellular, or subcellular location of one or more head-and-neck marker. Antibodies may also be used to screen potentially therapeutic compounds in vitro to determine their effects on disorders (e.g., OPL or head-and-neck cancer) involving one or more OPL or head-and-neck cancer markers, and other conditions. In vitro immunoassays may also be used to assess or monitor the efficacy of particular therapies.

In an aspect, the invention provides a method for monitoring or diagnosing a head-and-neck disease (e.g., OPL or cancer) in a subject by quantifying one or more OPL or head-and-neck cancer markers in a biological sample from the subject including reacting the sample with antibodies specific for one or more OPL or head-and-neck cancer markers, which are directly or indirectly labeled with detectable substances and detecting the detectable substances. In a particular embodiment of the invention, OPL or head-and-neck cancer markers are quantified or measured.

In an aspect of the invention, a method for detecting a head-and-neck disease (e.g., OPL or cancer) is provided including:
(a) obtaining a sample suspected of containing one or more OPL or head-and-neck cancer markers associated with a head-and-neck disease;
(b) contacting said sample with antibodies that specifically bind to the OPL or head-and-neck cancer markers under conditions effective to bind the antibodies and form complexes;
(c) measuring the amount of OPL or head-and-neck cancer markers present in the sample by quantifying the amount of the complexes; and
(d) comparing the amount of OPL or head-and-neck cancer markers present in the samples with the amount of OPL or head-and-neck cancer markers in a control, wherein a change or significant difference in the amount of OPL or head-and-neck cancer markers in the sample compared with the amount in the control is indicative of a head-and-neck disease.

In an embodiment, the invention contemplates a method for monitoring the progression of a head-and-neck disease (e.g., OPL or cancer) in an individual, including:
(a) contacting antibodies which bind to one or more OPL or head-and-neck cancer markers with a sample from the individual so as to form complexes including the antibodies and one or more OPL or head-and-neck cancer markers in the sample;
(b) determining or detecting the presence or amount of complex formation in the sample;
(c) repeating steps (a) and (b) at a point later in time; and
(d) comparing the result of step (b) with the result of step (c), wherein a difference in the amount of complex formation is indicative of disease, disease stage, and/or progression of the disease in said individual.

The amount of complexes may also be compared to a value representative of the amount of the complexes from an individual not at risk of, or afflicted with, a head-and-neck disease at different stages. A significant difference in complex formation may be indicative of advanced disease (e.g., advanced head-and-neck cancer, or an unfavourable prognosis).

In aspects of the invention for diagnosis and monitoring of OPL or head-and-neck cancer, the OPL or head-and-neck cancer markers are one or more of those upregulated in cancer samples as compared to normal samples in Table 1, those listed in Table 5, and/or YWHAZ, S100A7, and/or stratifin, and/or hnRNPK.

In embodiments of the methods of the invention, YWHAZ, S100A7, hnRNPK and/or stratifin is detected in samples and higher levels, in particular significantly higher levels compared to a control (normal or benign) is indicative of the prognosis of OPL or head-and-neck cancer patient outcome.

In aspects of the invention for characterizing head-and-neck disease the OPL or head-and-neck cancer markers include YWHAZ, S100A7, hnRNPK and/or stratifin and fragments thereof.

Antibodies may be used in any known immunoassays that rely on the binding interaction between antigenic determinants of one or more head-and-neck marker and the antibodies. Examples of immunoassays are radioimmunoassays (RIA), enzyme immunoassays (e.g., ELISA), munofluorescence, immunoprecipitation, latex agglutination, hemagglutination, histochemical tests, and sandwich (immunometric) assays.

According to an embodiment of the invention, an immunoassay for detecting one or more OPL or head-and-neck cancer markers in a biological sample includes contacting binding agents that specifically bind to OPL or head-and-neck cancer markers in the sample under conditions that allow the formation of first complexes including a binding agent and OPL or head-and-neck cancer markers and determining the presence or amount of the complexes as a measure of the amount of OPL or head-and-neck cancer markers contained in the sample. In a particular embodiment, the binding agents are labeled differently or are capable of binding to different labels.

Antibodies may be used to detect and quantify one or more OPL or head-and-neck cancer markers in a sample in order to diagnose pathological states. In particular, the antibodies may be used in immunohistochemical analyses, for example, at the cellular and sub-subcellular level, to detect one or more OPL or head-and-neck cancer markers, to localize them to particular head-and-neck cells and tissues (e.g., tumor cells and tissues), and to specific subcellular locations, and to quantify the level of expression.

Immunohistochemical methods for the detection of antigens in tissue samples are well known in the art. Briefly, in the context of the present invention, a tissue sample obtained from a subject suspected of having a head-and-neck-related problem is contacted with antibodies, preferably monoclonal antibodies recognizing one or more head-and-neck cancer markers. The site at which the antibodies are bound is determined by selective staining of the sample by standard immunohistochemical procedures. The same procedure may be repeated on the same sample using other antibodies that recognize one or more OPL or head-and-neck cancer markers. Alternatively, a sample may be contacted with antibodies against one or more OPL or head-and-neck cancer markers simultaneously, provided that the antibodies are labeled differently or are able to bind to a different label. The tissue sample may be normal head-and-neck tissue, an OPL, or a cancer tissue or a benign tissue.

An antibody microarray in which binding sites include immobilized, preferably monoclonal, antibodies specific to a substantial fraction of marker-derived OPL or head-and-neck cancer markers of interest can be utilized in the present invention. Antibody arrays can be prepared using methods known in the art (see, for example, Zhu et al., Science 293:2101 (2001) and reference 20).

Antibodies specific for one or more OPL or head-and-neck marker may be labelled with a detectable substance and localised in biological samples based upon the presence of the detectable substance. Examples of detectable substances include, but are not limited to, the following: radioisotopes (e.g., 3H, 14C, 35s, 125I, 131I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin (e.g., streptavidin containing a fluorescent marker or enzymatic activity that can be detected by optical or colorimetric methods)), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

One of the ways an antibody can be detectably labeled is to link it directly to an enzyme. The enzyme when later exposed to its substrate will produce a product that can be detected. Examples of detectable substances that are enzymes are horseradish peroxidase, beta-galactosidase, luciferase, alkaline phosphatase, acetylcholinesterase, malate dehydrogenase, ribonuclease, urease, catalase, glucose-6-phosphate, staphylococcal nuclease, delta-5-steroid isomerase, yeast alcohol dehydrogenase, alpha-glycerophosphate, triose phosphate isomerase, asparaginase, glucose oxidase, and acetylcholine esterase.

For increased sensitivity in an immunoassay system a fluorescence-emitting metal atom such as Eu (europium) and other lanthanides can be used. These can be attached to the desired molecule by means of metal-chelating groups such as DTPA or EDTA.

A bioluminescent compound may also be used as a detectable substance. Examples of bioluminescent detectable substances are luciferin, luciferase and aequorin.

Indirect methods may also be employed in which the primary antigen-antibody reaction is amplified by the introduction of a second antibody, having specificity for the antibody reactive against one or more head-and-neck cancer markers. By way of example, if the antibody having specificity against one or more OPL or head-and-neck marker is a rabbit IgG antibody, the second antibody may be goat anti-rabbit gamma-globulin labelled with a detectable substance as described herein.

Methods for conjugating or labelling the antibodies discussed above may be readily accomplished by one of ordinary skill in the art.

Cytochemical techniques known in the art for localizing antigens using light and electron microscopy may be used to detect one or more head-and-neck cancer markers. Generally, antibodies may be labeled with detectable substances and one or more head-and-neck cancer markers may be localised in tissues and cells based upon the presence of the detectable substances.

In the context of the methods of the invention, the sample, binding agents (e.g., antibodies specific for one or more OPL or head-and-neck cancer markers), or one or more OPL or head-and-neck cancer markers may be immobilized on a carrier or support. Examples of suitable carriers or supports are agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, ethylene-maleic acid copolymer, nylon, silk, etc. The support material may have any possible configuration including spherical (e.g., bead), cylindrical (e.g., inside surface of a test tube or well, or the external surface of a rod), or flat (e.g., sheet, test strip). Thus, the carrier may be in the shape of, for example, a tube, test plate, well, beads, disc, sphere, etc. The immobilized antibody may be prepared by reacting the material with a suitable insoluble carrier using known chemical or physical methods, for example, cyanogen bromide coupling. An antibody may be indirectly immobilized using a second antibody specific for the antibody. For example, mouse antibody specific for a head-and-neck marker may be immobilized using sheep anti-mouse IgG Fc fragment specific antibody coated on the carrier or support.

Where a radioactive label is used as a detectable substance, one or more OPL or head-and-neck marker may be localized by radioautography. The results of radioautography may be quantified by determining the density of particles in the radioautographs by various optical methods, or by counting the grains.

Time-resolved fluorometry may be used to detect a signal. For example, the method described by Christopoulos T K and Diamandis E P in Anal Chem 1992:64:342-346 may be used with a conventional time-resolved fluorometer.

In accordance with an embodiment of the invention, a method is provided wherein one or more OPL or head-and-neck marker antibodies are directly or indirectly labelled with enzymes, substrates for the enzymes are added wherein the substrates are selected so that the substrates, or a reaction product of an enzyme and substrate, form fluorescent complexes with a lanthanide metal (e.g., europium, terbium, samarium, and dysprosium, preferably europium and terbium). A lanthanide metal is added and one or more OPL or head-and-neck cancer markers are quantified in the sample by measuring fluorescence of the fluorescent complexes. Enzymes are selected based on the ability of a substrate of the enzyme, or a reaction product of the enzyme and substrate, to complex with lanthanide metals such as europium and terbium. Suitable enzymes and substrates that provide fluorescent complexes are described in U.S. Pat. No. 5,312,922 to Diamandis. Examples of suitable enzymes include alkaline phosphatase and β-galactosidase. Preferably, the enzyme is alkaline phosphatase.

One or more OPL or head-and-neck marker antibodies may also be indirectly labelled with an enzyme. For example, the antibodies may be conjugated to one partner of a ligand binding pair, and the enzyme may be coupled to the other partner of the ligand binding pair. Representative examples include avidin-biotin, and riboflavin-riboflavin binding protein. In an embodiment, the antibodies are biotinylated, and the enzyme is coupled to streptavidin. In another embodiment, an antibody specific for OPL or head-and-neck marker antibody is labeled with an enzyme.

In accordance with an embodiment, the present invention provides means for determining one or more OPL or head-and-neck cancer markers in a sample by measuring one or more head-and-neck cancer markers by immunoassay. It will be evident to a skilled artisan that a variety of immunoassay methods can be used to measure one or more head-and-neck cancer markers. In general, an immunoassay method may be competitive or non-competitive. Competitive methods typically employ an immobilized or immobilizable antibody to one or more OPL or head-and-neck marker and a labeled form of one or more OPL or head-and-neck marker. Sample OPL or head-and-neck cancer markers and labeled OPL or head-and-neck cancer markers compete for binding to antibodies to OPL or head-and-neck cancer markers. After separation of the resulting labeled OPL or head-and-neck cancer markers that have become bound to antibodies (bound fraction) from that which has remained unbound (unbound fraction), the amount of the label in either bound or unbound fraction is measured and may be correlated with the amount of OPL or head-and-neck cancer markers in the test sample in any conventional manner (e.g., by comparison to a standard curve).

In an aspect, a non-competitive method is used for the determination of one or more OPL or head-and-neck cancer markers, with the most common method being the "sandwich" method. In this assay, two antibodies to OPL or head-and-neck cancer markers are employed. One of the antibodies to OPL or head-and-neck cancer markers is directly or indirectly labeled (sometimes referred to as the "detection antibody") and the other is immobilized or immobilizable (sometimes referred to as the "capture antibody"). The capture and detection antibodies can be contacted simultaneously or sequentially with the test sample. Sequential methods can be accomplished by incubating the capture antibody with the sample, and adding the detection antibody at a predetermined time thereafter (sometimes referred to as the "forward" method); or the detection antibody can be incubated with the sample first and then the capture antibody added (sometimes referred to as the "reverse" method). After the necessary incubation(s) have occurred, to complete the assay, the capture antibody is separated from the liquid test mixture, and the label is measured in at least a portion of the separated capture antibody phase or the remainder of the liquid test mixture. Generally, it is measured in the capture antibody phase since it includes OPL or head-and-neck cancer markers bound by ("sandwiched" between) the capture and detection antibodies. In an embodiment, the label may be measured without separating the capture antibodies and liquid test mixture.

In a typical two-site immunometric assay for OPL or head-and-neck cancer markers, one or both of the capture and detection antibodies are polyclonal antibodies or one or both of the capture and detection antibodies are monoclonal antibodies (i.e. polyclonal/polyclonal, monoclonal/monoclonal, or monoclonal/polyclonal). The label used in the detection antibody can be selected from any of those known conventionally in the art. The label may be an enzyme or a chemiluminescent moiety, but it can also be a radioactive isotope, a fluorophor, a detectable ligand (e.g., detectable by a secondary binding by a labeled binding partner for the ligand), and the like. In a particular aspect, the antibody is labelled with an enzyme which is detected by adding a substrate that is selected so that a reaction product of the enzyme and substrate forms fluorescent complexes. The capture antibody may be selected so that it provides a means for being separated from the remainder of the test mixture. Accordingly, the capture antibody can be introduced to the assay in an already immobilized or insoluble form, or can be in an immobilizable form, that is, a form which enables immobilization to be accomplished subsequent to introduction of the capture antibody to the assay. An immobilized capture antibody may include an antibody covalently or non-covalently attached to a solid phase such as a magnetic particle, a latex particle, a microtiter plate well, a bead, a cuvette, or other reaction vessel. An example of an immobilizable capture antibody is antibody which has been chemically modified with a ligand moiety, e.g., a hapten, biotin, or the like, and which can be subsequently immobilized by contact with an immobilized form of a binding partner for the ligand, e.g., an antibody, avidin, or the like. In an embodiment, the capture antibody may be immobilized using a species specific antibody for the capture antibody that is bound to the solid phase.

The above-described immunoassay methods and formats are intended to be exemplary and are not limiting.

Screening Methods.

The invention also contemplates methods for evaluating test agents or compounds for their ability to inhibit a head-and-neck disease (e.g., OPL or cancer), potentially contribute to a head-and-neck disease (e.g., OPL or cancer). Test agents and compounds include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies (e.g., polyclonal, monoclonal, humanized, anti-idiotypic, chimeric, single chain antibodies, fragments (e.g., Fab, F(ab)2, and Fab expression library fragments, and epitope-binding fragments thereof), and small organic or inorganic molecules. The agents or compounds may be endogenous physiological compounds or natural or synthetic compounds.

The invention provides a method for assessing the potential efficacy of a test agent for inhibiting a head-and-neck disease (e.g., OPL or cancer) in a patient, the method including comparing:
(a) levels of one or more OPL or head-and-neck cancer markers, and optionally other markers in a first sample obtained from a patient and exposed to the test agent; and
(b) levels of one or more OPL or head-and-neck cancer markers, and optionally other markers, in a second sample obtained from the patient, wherein the sample is not exposed to the test agent, wherein a significant difference in the levels of expression of one or more head-and-neck cancer markers, and optionally the other markers, in the first sample, relative to the second sample, is an indication that the test agent is potentially efficacious for inhibiting a head-and-neck disease (e.g., OPL or cancer) in the patient.

The first and second samples may be portions of a single sample obtained from a patient or portions of pooled samples obtained from a patient.

In an aspect, the invention provides a method of selecting an agent for inhibiting a head-and-neck disease (e.g., OPL or cancer) in a patient including:
(a) obtaining a sample from the patient;
(b) separately maintaining aliquots of the sample in the presence of a plurality of test agents;
(c) comparing one or more OPL or head-and-neck cancer markers, and optionally other markers, in each of the aliquots; and
(d) selecting one of the test agents which alters the levels of one or more OPL or head-and-neck cancer markers and optionally other markers in the aliquot containing that test agent, relative to other test agents.

In a further aspect, the invention provides a method of selecting an agent for inhibiting or enhancing a OPL or head and neck cell or tissue phase in a patient including:
(a) obtaining a sample of OPL or head and neck cell or tissue in a selected phase;
(b) separately maintaining aliquots of the sample in the presence of a plurality of test agents;
(c) comparing one or more OPL or head-and-neck cancer markers, and optionally other markers, in each of the aliquots; and
(d) selecting one of the test agents which alters the levels of one or more OPL or head-and-neck cancer markers, and optionally other markers in the aliquot containing that test agent, relative to other test agents.

Still another aspect of the present invention provides a method of conducting a drug discovery business including:

(a) providing one or more methods or assay systems for identifying agents that inhibit a head-and-neck disease (e.g., OPL or head-and-neck cancer) or affect a OPL or head and neck cell or tissues phase in a patient;
(b) conducting therapeutic profiling of agents identified in step (a), or further analogs thereof, for efficacy and toxicity in animals; and
(c) formulating a pharmaceutical preparation including one or more agents identified in step (b) as having an acceptable therapeutic profile.

In certain embodiments, the subject method can also include a step of establishing a distribution system for distributing the pharmaceutical preparation for sale, and may optionally include establishing a sales group for marketing the pharmaceutical preparation.

The invention also contemplates a method of assessing the potential of a test compound to contribute to a head-and-neck disease (e.g., OPL or head-and-neck cancer) including:
(a) maintaining separate aliquots of cells or tissues from a patient with a head-and-neck disease (e.g., OPL or cancer) in the presence and absence of the test compound; and
(b) comparing one or more OPL or head-and-neck cancer markers, and optionally other markers in each of the aliquots.

A significant difference between the levels of the markers in the aliquot maintained in the presence of (or exposed to) the test compound relative to the aliquot maintained in the absence of the test compound, indicates that the test compound possesses the potential to contribute to a head-and-neck disease (e.g., OPL or head-and-neck cancer).

Kits.

The invention also contemplates kits for carrying out the methods of the invention. Kits may typically include two or more components required for performing a diagnostic assay. Components include but are not limited to compounds, reagents, containers, and/or equipment.

The methods described herein may be performed by utilizing pre-packaged diagnostic kits including one or more specific OPL or head-and-neck marker antibody described herein, which may be conveniently used, e.g., in clinical settings to screen and diagnose patients and to screen and identify those individuals exhibiting a predisposition to developing a head-and-neck disease.

In an embodiment, a container with a kit includes a binding agent as described herein. By way of example, the kit may contain antibodies or antibody fragments which bind specifically to epitopes of one or more OPL or head-and-neck cancer markers and optionally other markers, antibodies against the antibodies labelled with an enzyme; and a substrate for the enzyme. The kit may also contain microtiter plate wells, standards, assay diluent, wash buffer, adhesive plate covers, and/or instructions for carrying out a method of the invention using the kit.

In an aspect of the invention, the kit includes antibodies or fragments of antibodies which bind specifically to an epitope of one or more polypeptide listed in Table 1 that is upregulated in cancer samples as compared to normal samples, or those listed in Table 5 or Table 2 and means for detecting binding of the antibodies to their epitope associated with tumor cells, either as concentrates (including lyophilized compositions), which may be further diluted prior to use or at the concentration of use, where the vials may include one or more dosages. Where the kits are intended for in vivo use, single dosages may be provided in sterilized containers, having the desired amount and concentration of agents. Containers that provide a formulation for direct use, usually do not require other reagents, as for example, where the kit contains a radiolabelled antibody preparation for in vivo imaging.

In an aspect of the invention, the kit includes antibodies or fragments of antibodies which bind specifically to an epitope of one or more polypeptide listed in Table 6 that is upregulated in OPL samples as compared to normal samples, or those listed in Table 5 or Table 7 and means for detecting binding of the antibodies to their epitope associated with OPL cells, either as concentrates (including lyophilized compositions), which may be further diluted prior to use or at the concentration of use, where the vials may include one or more dosages. Where the kits are intended for in vivo use, single dosages may be provided in sterilized containers, having the desired amount and concentration of agents. Containers that provide a formulation for direct use, usually do not require other reagents, as for example, where the kit contains a radiolabelled antibody preparation for in vivo imaging.

The reagents suitable for applying the screening methods of the invention to evaluate compounds may be packaged into convenient kits described herein providing the necessary materials packaged into suitable containers.

The invention contemplates a kit for assessing the presence of head-and-neck cells, wherein the kit includes antibodies specific for one or more OPL or head-and-neck cancer markers, and optionally antibodies specific for other markers associated with a head-and-neck disease (e.g., OPL or cancer).

The invention relates to a kit for assessing the suitability of each of a plurality of test compounds for inhibiting a head-and-neck disease (e.g., OPL or head-and-neck cancer) in a patient. The kit includes reagents for assessing one or more OPL or head-and-neck cancer markers, and optionally a plurality of test agents or compounds.

Additionally the invention provides a kit for assessing the potential of a test compound to contribute to a head-and-neck disease (e.g., OPL or cancer). The kit includes head-and-neck diseased cells (e.g., OPL or cancer cells) and reagents for assessing one or more OPL or head-and-neck cancer markers and optionally other markers associated with a head-and-neck disease.

The inventors' study lays a major thrust on determining the clinical impact of a proteomics based biomarkers in predicting the high risk leukoplakia, as early as hyperplasia, and clinical outcome in HNOSCC patients after treatment of primary tumors. The unique features of the inventors' study are its prospective nature, the large number of patients in this type of disease setting, and the length of follow-up of leukoplakia and HNOSCC patients. Furthermore, in support of the proposed role of hnRNPK, S100A7 and nuclear PTMA as malignant transformation-related proteins, their overexpression in early oral lesions is a very important unique finding of this study and herein the inventors present clinical evidence to establish its link with progression potential of leukoplakia. To the inventors' knowledge, this is the first investigation to demonstrate the clinical application of a candidate biomarker identified using MS-based tissue proteomics in identifying early oral premalignant lesions that may be at high risk of disease progression.

Most studies on leukoplakia focus on dysplastic lesions, while knowledge of molecular alterations in oral hyperplasias is meager. As per the existing literature, the malignant transformation potential is often linked to the severity of dysplasia; in comparison the hyperplastic lesions have received less attention, primarily because lesions undergo spontaneous regression. However, the lesions that do not regress need identification and biomarkers to predict the risk of malignant transformation. In this context the inventors' study assumes importance, because not only does it show aberrant hnRNPK expression as early as in hyperplasia, but the follow-up study also points to the relevance of cytoplasmic hnRNPK in predicting the risk of disease progression in leukoplakia patients with hyperplasia and HNOSCCs. Further, S100A7 and/or nuclear PTMA overexpression in oral dysplastic lesions are shown to predict a high risk of malignant transformation.

It is noteworthy that studies on molecular analysis of leukoplakia with hyperplasia are very limited, because these patients often do not come to the clinics since their lesions are small and do not pose any overt clinical problem. However, it is extremely important to target this patient population for risk assessment and early intervention for cancer prevention in high risk cases. Hence, the inventors' findings are important and warrant further validation in larger independent studies on oral hyperplastic lesions. Furthermore, the cytoplasmic expression of hnRNPK protein observed in epithelial cells of a subset of hyperplastic and dysplastic lesions points to a potential role in development and progression during early stages of oral tumorigenesis, while the overexpression in HNOSCCs and association with poor prognosis suggests a sustained involvement in frank malignancy as well.

The present invention is described in the following non-limiting Examples, which are set forth to illustrate and to aid in an understanding of the invention, and should not be construed to limit in any way the scope of the invention as defined in the claims which follow thereafter.

EXAMPLES

In Examples 1-13, the inventors demonstrate the identification of a consistently increased expression of a panel of proteins, including stratifin (14-3-3σ) and YWHAZ (14-3-3ζ), that may serve as cancer biomarkers. In Examples 14-20, the prognostic utility of these two candidate biomarkers for head-and-neck/oral squamous cell carcinoma (HNOSCC) is described. In Examples 21-27, the clinical significance and utility of one of the OPL markers, hnRNPK, in early premalignant stages and in development, progression, and prognosis of premalignant lesions and confirmed/frank head-and-neck malignancies, is described. In Example 28, the inventors demonstrate that S100A7 is a biomarker that can be used to predict the malignant transformation in oral dysplastic lesions.

Example 1—Samples and Reagents

Head-and-neck cancer and oral leukoplakia tissues were retrieved from an in-house, dedicated, research head-and-neck tissue bank, with approval from the Human Ethics Committee of All India Institute of Medical Sciences, New Delhi, India. With patient consent, biopsies/excised tissue specimens of oral leukoplakia and surgically resected specimens of HNSCCs, and paired non-cancerous tissues (each taken from a distant site) were collected and banked from patients undergoing treatment at the Department of Otorhinolaryngology, All India Institute of Medical Sciences. Normal tissues with no evidence of cancer (non-paired noncancerous controls) were collected from patients attending the Dental Outpatient Department of All India Institute of Medical Sciences for tooth extraction, after consent of the patients. After excision, tissues were flash-frozen in liquid nitrogen within 20 min of devitalization and stored at −80°

C. until further use; one tissue piece was collected in 10% formalin and embedded in paraffin for histopathological analysis. The clinical and pathological data were recorded in a pre-designed proforma. These included clinical TNM staging (tumor, node, metastasis based on International Union Against Cancer's classification of malignant tumors, 1988), site of the lesion, histopathological differentiation, age, and gender of the patients.

The histologic diagnosis (dysplasia for OPLs and histological normal oral epithelium for controls) was rendered using microscopic examination of hematoxylin-and-eosin-stained frozen section of each research tissue block. The histologic diagnosis for each HNSCC sample was reconfirmed using microscopic examination of a hematoxylin-and-eosin-stained frozen section of each research tissue block. The tissue from the mirror face of the histologic section was then washed three times in approximately 1 ml of phosphate-buffered saline (PBS) with a cocktail of protease inhibitors as described previously (1 mM 4-(2-aminoethyl)benzenesulfonyl fluoride, 10 µM leupeptin, 1 µg/ml aprotinin, and 1 µM pepstatin) (21). The washed tissue was then homogenized in 0.5 ml PBS with protease inhibitors, using a handheld homogenizer. These homogenates were then flash frozen in liquid nitrogen and stored at −80° C. until use. Samples were thawed and clarified by centrifugation and the protein concentration determined by a Bradford-type assay using Bio-Rad protein quantification reagent (Bio-Rad, Mississauga, ON, Canada).

The iTRAQ experiments were performed in five sets of four samples each for the HNSCC samples. A pool of non-paired non-cancerous head-and-neck tissue homogenates was used as a control in each set of experiments: equal amounts of total protein from the lysates of six non-cancerous samples (non-paired controls) were pooled to generate a common reference "control sample" against which all the HNSCC samples were compared. Each sample contained 200 µg of proteins. Trypsin digestion and labeling were performed according to the manufacturer's (Applied Biosystems') protocol; however, as double the manufacturer's recommended amounts were used, two individual vials of each reagent were used for labeling each sample. iTRAQ labeling was performed as follows: control (non-paired non-cancerous pool), iTRAQ reagent 114; two cancer samples, iTRAQ 115 and 117; individual non-cancerous tissue sample (paired or non-paired sample), iTRAQ 116. A total of five iTRAQ sets were analyzed resulting in ten cancer (five buccal mucosa and five tongue) samples and two paired non-cancerous plus three non-paired noncancerous samples being compared to the control sample. The paired non-cancerous samples originated from patients with cancer that were resected from sites a minimum of 2 cm away from the advancing edge of the cancer. Each iTRAQ set was analyzed with one run each of online 2D LC-MS/MS and offline 2D LC-MS/MS analyses.

The experiments with OPLs were performed in three sets of four samples; the same pool of non-cancerous oral-tissue homogenates was used as a control in each set of experiments. Each analytical set comprised 4×100 µg of each sample labeled as follows: control (normal pool) was labeled with one iTRAQ tag; two OPL samples were labeled with two other iTRAQ tags; and an individual histological normal tissue sample was labeled with the fourth iTRAQ tag. Thus a total of six OPLs and three histological normal samples were compared to the control sample in three iTRAQ sets. The order in which the samples were labeled within each of these three sets was randomized to minimize any systematic error and bias. The iTRAQ analysis of these samples was performed with one run of online reverse phase LC-MS/MS for preliminary examinations, and three replicate runs per set of online two-dimensional LC-MS/MS analyses.

Example 2—Strong Cation Exchange (SCX) Separation Conditions

For the offline 2D LC-MS/MS analysis, each set of labeled samples was first separated by SCX fractionation using an HP1050 high-performance liquid chromatograph (Agilent, Palo Alto, Calif., U.S.) with a 2.1-mm internal diameter (ID)×100-mm length polysulfoethyl A column packed with 5-µm beads with 300 Å pores (The Nest Group, Southborough, Mass.) as described previously (21). A 2.1-mm ID×10-mm length guard column of the same material was fitted immediately upstream of the analytical column. Separation was performed as previously described (21). Briefly, each pooled sample set was diluted with the loading buffer (15 mM KH2PO4 in 25% acetonitrile, pH 3.0) to a total volume of 2 ml and the pH adjusted to 3.0 with phosphoric acid. Samples were then filtered using a 0.45-µm syringe filter (Millipore, Cambridge, ON, Canada) before loading onto the column. Separation was performed using a linear binary gradient over one hour. Buffer A was identical in composition to the loading buffer, while Buffer B was Buffer A containing 350 mM KCl. Fractions were collected every two minutes using an SF-2120 Super Fraction Collector (Advantec MFs, Dublin, Calif.), after an initial wait of 2 minutes to accommodate the void volume. This resulted in a total of 30 SCX fractions per sample set. These fractions were dried by speed vacuuming (Thermo Savant SC110 A, Holbrook, N.Y.) and resuspended in 30 µl of 0.1% formic acid each.

Figure 1:
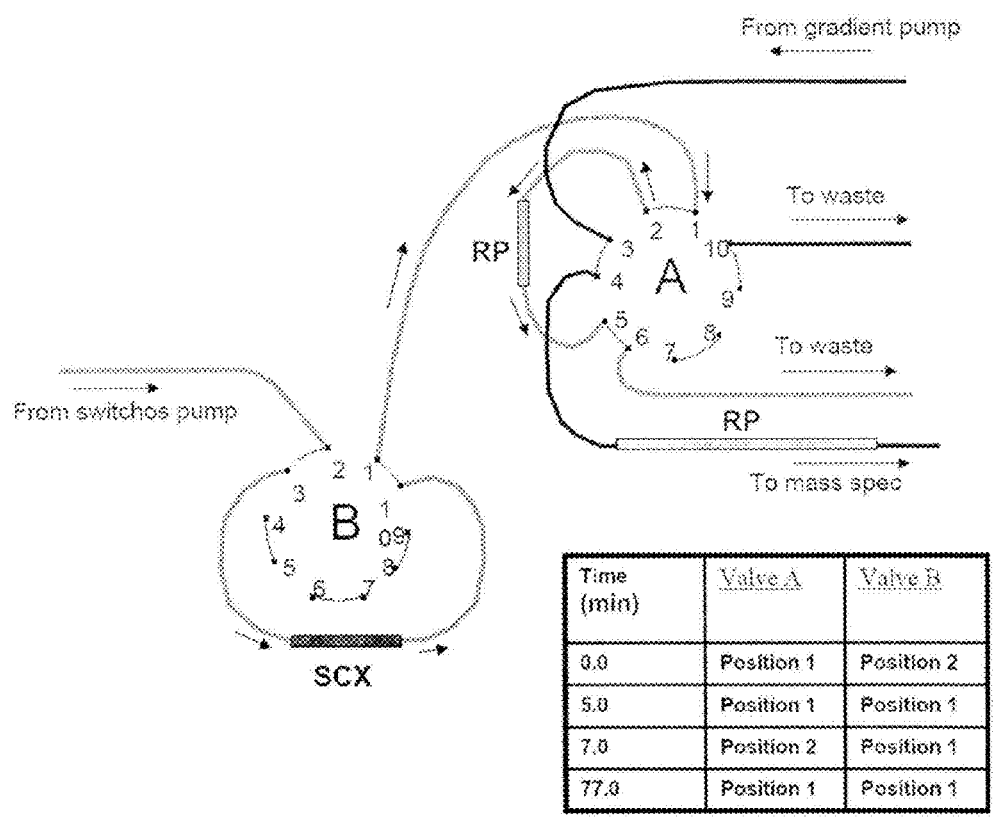

For the online 2D LC-MS/MS analysis, an SCX cartridge (BioX-SCX, LC Packings, The Netherlands) was plumbed upstream of the reverse phase (RP) desalting cartridge and analytical column. This SCX cartridge was connected through a second valve on the Switchos unit as shown in FIG. 1. Samples were separated on this SCX cartridge using 10 µl step elutions with increasing concentration of ammonium acetate (10 mM, 50 mM, 100 mM, 150 mM, 200 mM, 250 mM, 300 mM, 350 mM, 500 mM and 1M). Each step elution was loaded onto the RP desalting column using the switching program as shown in FIG. 1, where the eluting peptides were desalted before loading onto the analytical column that was subsequently brought inline with the desalting column. The flow path used for these steps was designed to ensure that there was never any flow reversal through either of the cartridges (SCX or RP). Separation on the RP analytical column was effected as described for the second stage of the offline LC-MS/MS analysis described below.

Example 3—LC-MS/MS Run Conditions

The SCX fractions from 6 to 30 were analyzed by nanoLC-MS/MS using the LC Packings Ultimate instrument (Amsterdam, The Netherlands) fitted with a 10-µl sample loop. Samples were loaded, using a µl pick-up mode, onto a 5-mm RP C18 precolumn (LC Packings) at 50 µl/min and washed for 4 min before switching the precolumn inline with the separation column. The separation column used was either a 75-µm ID×150-mm length PepMap RP column from LC Packings packed with 3 µm C18 beads with 100 Å pores, or an in-house equivalent packed with similar beads (Kromasil; The Nest Group, Southborough, Mass.). The flow rate used for separation on the RP column was 200 nl/min with the following gradient:

| Time (min) | 0 | 10 | 15 | 125 | 145 | 150 | 160 | 162 | 188 |
|---|---|---|---|---|---|---|---|---|---|
| % B | | 5 | 5 | 15 | 35 | 60 | 80 | 80 | 5 Stop |

Samples were analyzed on a QSTAR Pulsar i mass spectrometer (Applied Biosystems/MDS SCIEX, Foster City, Calif.) in information-dependent acquisition (IDA) mode with the scan cycles set up to perform a 1-s MS scan followed by five MS/MS scans of the five most abundant peaks for 2 s each. Every fourth scan the peak that was closest in intensity to the threshold of 10 counts was selected for MS/MS. Data acquisition was performed without any repetitions and with a dynamic exclusion of 30 s. Relative protein abundances were determined using the MS/MS scans of iTRAQ-labeled peptides (17). The iTRAQ-labeled peptides fragmented under collision-induced dissociation (CID) conditions to give reporter ions at 114.1, 115.1, 116.1, and 117.1 Th.

The ratios of peak areas of the iTRAQ reporter ions reflect the relative abundances of the peptides and, consequently, the proteins in the samples. Larger, sequence-information-rich fragment ions were also produced under these conditions and gave the identity of the protein from which the peptide was derived.

The OPL samples were analyzed on a Q-STAR Pulsar-i hybrid quadrupole/time-of-flight tandem mass spectrometer (Applied Biosystems/MDS SCIEX, Foster City, Calif.) in information-dependent acquisition (IDA) mode with the scan cycles set up to perform a 1-s MS scan followed by five MS/MS scans of the five most abundant ions for 2 s each. The method was also set up to select the least abundant ions in the MS scan that are nearest to a threshold of 10 counts on every fourth scan. Data acquisition was performed without any repetitions and with a dynamic exclusion of 30 s. Relative protein abundances were determined using the 114.1, 115.1, 116.1 and 117.1 Th reporter ions in the MS/MS scans of the iTRAQ-labeled peptides (23). The ratios of the peak areas of the iTRAQ reporter ions reflect the relative abundances of the peptides and the relative concentrations of the proteins in the samples. Larger, sequence-information-rich fragment ions were also produced under these MS/MS conditions and gave the identity of the protein from which the peptide originated.

Example 4—Data Analysis

The software used for data acquisition was Analyst QS 1.1 (Applied Biosystems/MDS SCIEX). Data were analyzed using ProteinPilot (21, 28) and the database searched was the Celera human database (human KBMS 20041109) with a total of 178, 243 entries, both provided by Applied Biosystems Inc. Identified proteins were grouped by the software to minimize redundancy. All peptides used for the calculation of protein ratios were unique to the given protein or proteins within the group; peptides that were common to other isoforms or proteins of the same family that were reported separately were ignored. The ProteinPilot cutoff score used was 1.3, which corresponds to a confidence limit of 95%.

Example 5—Statistical Analysis

The average iTRAQ ratios from different runs were calculated for each protein in the offline and online analyses. Thereafter, the iTRAQ ratios for each protein in the two analyses were averaged. Proteins that were selected for further analysis met the following criteria: (1) detection in ≥6 out of the 10 cancer samples, ≥50% of which showed differential expression≥1.5-fold relative to the control sample, and/or (2) known to be of interest from other studies. These proteins are listed in Table 1 along with two housekeeping proteins (to contrast the performance of the potential biomarkers).

For the OPL samples, the average iTRAQ ratios from the replicates were calculated for each protein. Proteins selected for further statistical analysis met the following criteria: (1) detection in ≥3 of 6 OPLs, and ≥50% of which showed differential expression≥50% higher than the control sample, and/or (2) known to be of interest based on their biological functions or associations with tumorigenesis. These proteins are listed in Table 6 along with two housekeeping proteins (to contrast the performance of the potential biomarkers).

Example 6—Biomarker Panel Analysis

To identify a panel of best-performing proteins that can distinguish between HNSCC and non-cancerous tissues, each protein in Table 1 was individually assessed for its ability to discriminate between normal and cancer samples by evaluating its receiver operator characteristic (ROC) curve based on the iTRAQ ratios. Plotting ROC curves and calculating the area-under-the-curve (AUC) and other attributes were performed using the ROCR package within the R statistical computing environment (29). Proteins giving the highest AUC values were selected for biomarker panel analysis and used as input variables into a Naïve Bayes model, implemented in JAVA (30) using the WEKA package (31). Given a sample i that has iTRAQ ratios (or IHC scores, see later) in the vector x(i), the Naïve Bayes model has the form:

$$P(i=cancer|x(i))=P(cancer) \times P(x(i)|i=cancer)/P(x(i))$$

where P(i=cancer|x(i)) is the probability that i is a cancer sample given its x(i) values. This is the posterior probability and is calculated using Bayes theorem. A value≥0.5 is considered a positive hit. P(x(i)|i=cancer) is the probability that within the cancer samples, x(i) exists within them. P(cancer) is the probability of i being a cancer sample; this is the prior probability. P(x(i)) is the probability of i occurring and is a normalization factor. Nine trials of three-fold cross validation were used for each biomarker panel input into the Naïve Bayes model. Sensitivity, specificity, positive predictive value (PPV), and negative predictive value (NPV) were calculated for each trial.

Figure 6:
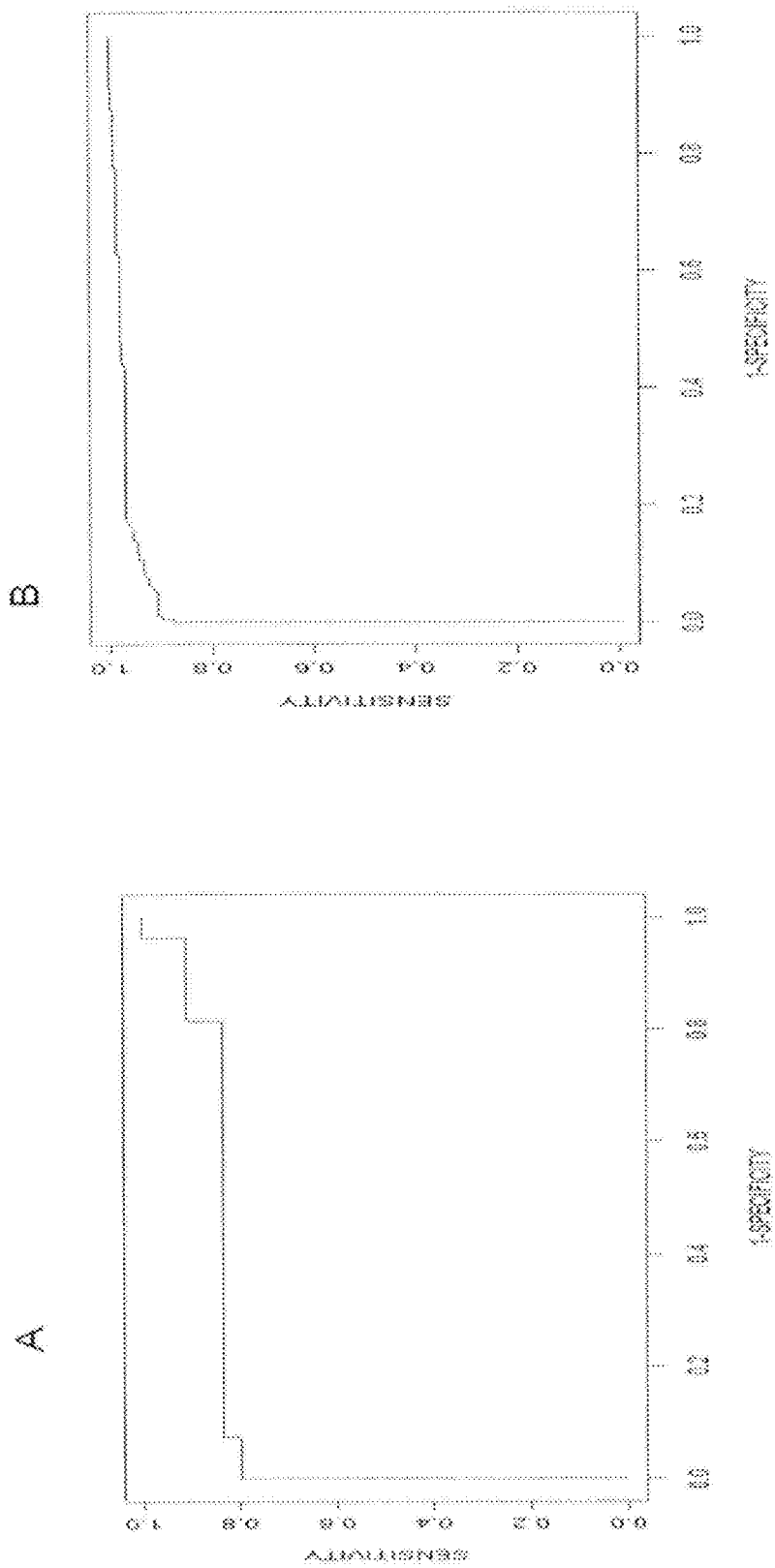
Figure 7:
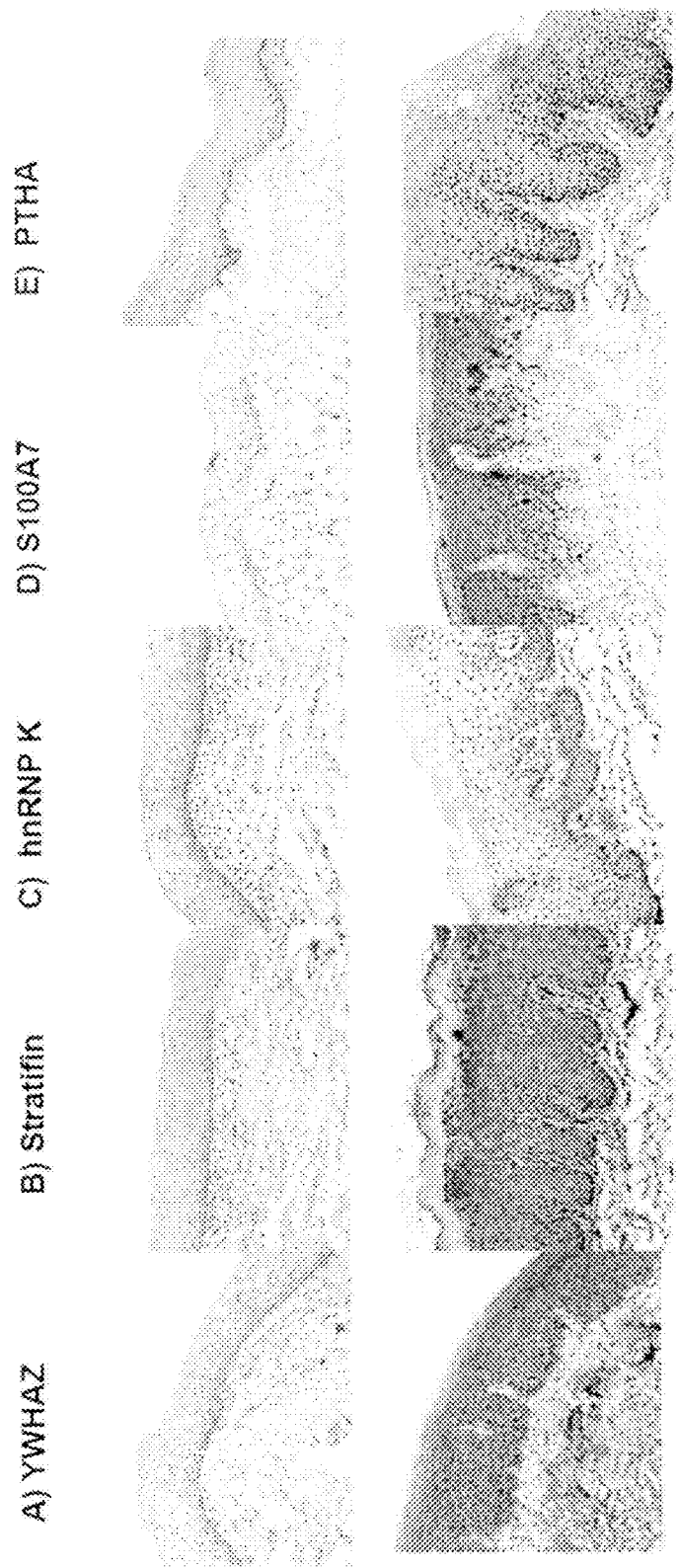

To identify a panel of best-performing proteins that can distinguish between OPL and normal tissues, each protein in Table 6 was individually assessed for its ability to discriminate between histological normal and OPL samples by evaluating its receiver-operating characteristic (ROC) performance based on the iTRAQ ratio values in terms of sensitivity and specificity using the ROCR package within the R statistical computing environment (29, 30). Proteins giving the highest AUC values were selected for biomarker panel analysis and used as input variables into a Naïve Bayes model, implemented in JAVA (30) using the WEKA package (31). Nine trials of three-fold cross-validation were used for each biomarker panel input into the Naïve Bayes model. Sensitivity, specificity, PPV, and NPV were calculated for each trial and the averages are shown in Table 7A. The ROC curve for the panel of the three-best biomarkers—stratifin, YWHAZ, and hnRNPK—is depicted in FIG. 6A.

Example 7—Verification of Candidate Potential Cancer Markers (PCMS) by Immunohistochemistry The three best-performing proteins from the above biomarker panel analysis were selected for immunohistochemical verification using an independent, larger sample set (Table 12). Antibodies against these three biomarkers were available commercially (Santa Cruz Biotechnology Inc., Santa Cruz, Calif., Table 13). Each antibody was first optimized with respect to dilution and the use of microwave heating in citrate buffer (0.01 M, pH 6.0) to expose the antigen ("antigen retrieval"). Paraffin-embedded sections (5 µm) of human HNSCCs (25 cases) and paired head-and-neck non-cancerous tissues from these patients (25 samples), as well as non-paired non-cancerous head-and-neck tissues (10 samples) were collected on gelatin-coated slides. For histopathological analysis, representative sections were stained with hematoxylin and eosin; immunostaining was done on serial sections as previously described (32). Following the application of a protein blocker for 10 min, deparaffinized tissue sections were first incubated with the primary antibodies for 1 h at room temperature or for 16 h at 4° C., followed by the respective secondary antibody conjugated with biotin. The primary antibody was detected using the streptavidin-biotin complex (DAKO LSAB plus kit, DAKO Cytomation, Denmark) and diaminobenzidine as chromogen. Slides were washed with 3× Tris-buffered saline (TBS, 0.1 M, pH=7.4) after every step. Finally, the sections were counterstained with Mayer's hematoxylin and mounted with DPX mountant. In the negative controls, the primary antibody was replaced by non-immune mouse IgG of the same isotype to ensure specificity. HNSCC tissue sections with known immunopositivity for specific proteins were used as positive controls in each batch of sections analyzed (32).

Example 8—Evaluation of Immunohistochemical Staining

The immunopositive staining was evaluated in five areas. Sections were scored as positive if epithelial cells showed immunopositivity in the cytoplasm, plasma membrane and/or nucleus when judged independently by two scorers who were blinded to the clinical outcome, i.e., the slides were coded and the pathologists did not have prior knowledge of the local tumor burden, lymphonodular spread, and grading of the tissue samples, while scoring the immunoreactivity. First, a quantitative score was performed by estimating the percentage of immunopositive-stained cells: 0<10% cells, 1=10-30% cells, 2=30-50% cells, 3=50-70% cells, and 4=>70% cells. Second, the intensity of staining was scored by evaluating the average staining intensity of the positive cells (0, none; 1, weak; 2, intermediate; and 3, strong). Finally, a total score (ranging from 0 to 7) was obtained by adding the quantitative score and the intensity score for each of the 60 sections. The immunohistochemical data were subjected to statistical analysis as described above for the MS results.

Example 9—Western Blot Analysis of Proteins in HNSCCS and Normal Tissues

Whole-cell lysates were prepared from five HNSCCs and five non-cancerous head-and-neck tissues. Frozen tissue samples were homogenized and lysed in a buffer containing 50 mM Tris-Cl (pH 7.5), 150 mM NaCl, 10 mM MgCl2, 1 mM ethylenediamine tetraacetate (pH 8.0), 1% Nonidet P-40, 100 mM sodium fluoride, 1 mM phenylmethylenesulfonyl fluoride, and 2 µl/ml protease inhibitor cocktail (Sigma). Protein concentrations were determined using the Bradford reagent (Sigma), and equal amounts of proteins (80 µg/lane) from the HNSCCs and non-cancerous tissues were resolved on 12% sodium dodecyl sulphate (SDS)-polyacrylamide gel. The proteins were then electro-transferred onto polyvinylidene-difluoride (PVDF) membranes. After blocking with 5% non-fat powdered milk in TBS (0.1 M, pH=7.4), blots were incubated with the respective primary antibodies (1:200 dilution) at 4° C. overnight. The protein abundance of alpha-tubulin was used as a control for protein loading, and was determined with mouse monoclonal anti-alpha-tubulin antibody (Clone B7, Santa Cruz Biotechnology Inc.). Membranes were incubated with the respective secondary antibody, HRP-conjugated rabbit/goat/mouse anti-IgG (goat anti-rabbit IgG, 1:5000; rabbit anti-goat IgG, 1:4000; or rabbit anti-mouse IgG, 1:2000, DAKO Cytomation, Denmark), and diluted with 1% bovine serum albumin for 2 h at room temperature. After each step, blots were washed three times with Tween (0.2%)-TBS. Protein bands were detected by the enhanced chemiluminescence method (Santa Cruz Biotechnology Inc.) on XO-MAT film.

The panel of the three-best biomarkers for OPLs-stratifin, YWHAZ and hnRNPK-together with two additionally promising proteins-S100A7 and PTHA-were evaluated for their performances using IHC on an independent set of 30 OPLs and 21 histological normal oral tissues. The inventors included S100A7 because it had high individual AUC value and was identified as one of the best-performing PCMs in the inventors' earlier iTRAQ analysis of HNOSCCs (23); it is important to determine whether overexpression of S100A7 occurs in early stages in the development of HNOSCC. PTHA was included because it also had high individual AUC value and had been reported to be important in other cancers (33-36). The sources of the antibodies and dilutions used for IHC are given in Table 13. After histological confirmations of dysplasia in OPLs and normal oral mucosa in the control tissues, paraffin-embedded tissue sections were processed for immunohistochemistry (23).

Figure 20:
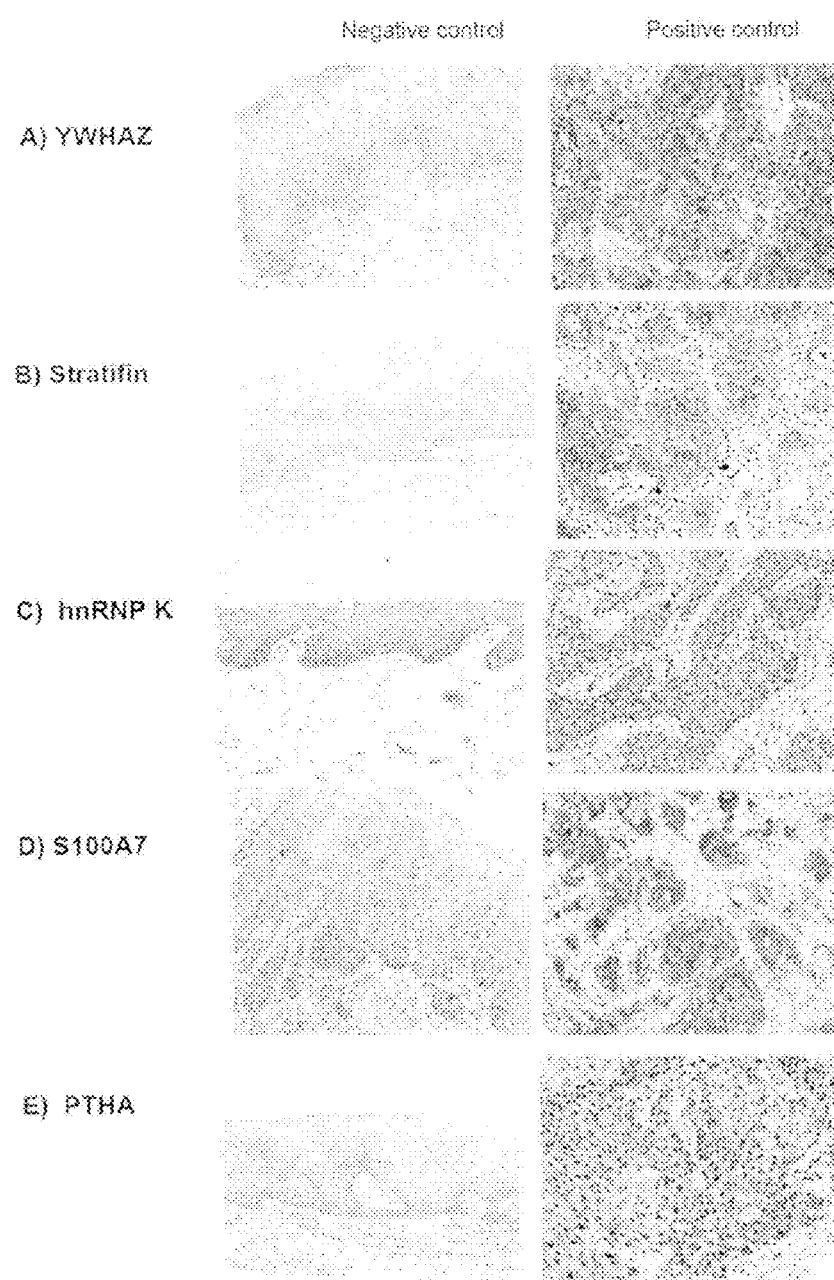
FIG. 20 illustrates negative and positive controls for IHC in OPLs.

Briefly, after antigen retrieval, tissue sections were incubated with the primary antibodies (See Table 13 for details) for 16 h at 4° C., followed by the respective biotin conjugated secondary antibodies and detected using streptavidin-biotin complex (DAKO LSAB plus kit, DAKO Cytomation, Glostrup, Denmark) and diaminobenzidine as the chromogen. In the negative controls, the primary antibody was replaced by isotype specific non-immune mouse IgG to ensure specificity. HNOSCC sections with known immunopositivity for respective proteins as reported earlier (23) were used as positive control in each batch of sections analyzed (FIG. 20).

Example 10—Evaluation of Immunohistochemical Staining

Immunopositive staining was evaluated in five areas of the tissue sections as described (32). Sections were scored as positive if epithelial cells showed immunopositivity in the cytoplasm, plasma membrane, and/or nucleus when observed by two evaluators who were blinded to the clinical outcome. These sections were scored as follows: 0, <10% cells; 1, 10-30% cells; 2, 30-50% cells; 3, 50-70% cells; and 4, >70% cells showed immunoreactivity. Sections were also scored semi-quantitatively on the basis of intensity as follows: 0, none; 1, mild; 2, moderate; and 3, intense. Finally, a total score (ranging from 0 to 7) was obtained by adding the scores of percentage positivity and intensity for each of the 51 sections (30 OPLs and 21 histologically normal tissues). The immunohistochemical data were subjected to statistical analysis as described above for the iTRAQ ratios.

Example 11—Western Blot Analysis of 14-3-3 Proteins in OPLS and Normal Tissues Whole-cell lysates were prepared from 3 OPLs and 3 normal oral tissues using lysis buffer containing 50 mM Tris-Cl (pH 7.5), 150 mM sodium chloride, 10 mM magnesium chloride, 1 mM EDTA (pH 8.0), 1% Nonidet P-40, 100 mM sodium fluoride, 1 mM phenylmethylene sulphonylfluoride, and 2 µl/ml protease inhibitor cocktail (23). Equal amounts of proteins (80 µg/lane) from OPLs and normal tissues were resolved on 12% SDS-polyacrylamide gels. The proteins were then electro-transferred onto polyvinylidene difluoride (PVDF) membranes. After blocking with 5% non-fat milk in TBS (0.1 M, pH 7.4), blots were incubated at 4° C. overnight with the respective antibodies (details given in Table 13). The sources of the antibodies and dilutions used for IHC for OPL markers are given in Table 13. Protein abundance of α-tubulin served as a control for protein loading. Membranes were incubated with the respective secondary antibodies, horseradish peroxidase-conjugated rabbit/goat/mouse anti-IgG diluted at the appropriate dilution in 1% BSA for 2 h at room temperature. After each step, blots were washed three times with Tween (0.2%)-Tris-buffer saline (TTBS). Protein bands were detected by the enhanced chemiluminescence method (ECL, Santa Cruz Biotechnology Inc.) on XO-MAT film.

Example 12—Reverse Transcription-Polymerase Chain Reaction (RT-PCR) Analysis To determine if overexpression of the five proteins in OPLs were due to increase in the transcript levels, RT-PCR analysis was performed using total RNA isolated from OPLs and normal oral mucosa (3 each), using gene-specific primers for YWHAZ, stratifin, hnRNPK, S100A7 and PTHA, and beta actin as a control (See Table 14 for gene-specific primer sequences (synthesized by Microsynth, Switzerland) and PCR conditions used). Synthesis of complementary DNAs (cDNAs) were carried out by reverse transcription of 2.0 µg of total RNA using MMLV reverse transcriptase. PCR amplification was carried out in a total volume of 20 µl containing 3 µl reverse transcribed cDNA, 10×PCR buffer, 10 mM dNTPs, 20 µM of each primer and 1 U of Taq polymerase. After 5 min of initial denaturation, 32 amplification cycles of 1 min at 94° C.—1 min at specific annealing temperature and 1 min at 72° C.—were carried out, followed by a 10-min elongation at 72° C. β-actin was used as a control to optimize the amounts of cDNAs generated. PCR products were separated on 1.5% agarose gel, stained with ethidium bromide, and visualized with Chemilmager IS-4400 (Alpha Innotech Corp., CA) (23).

Example 13—Network Analysis

The 30 proteins listed in Table 6 were used for network analysis. HUGO or SwissProt accession numbers were imported into the Ingenuity Pathway Analysis (IPA) Software (Ingenuity Systems, Mountain View, Calif.). The IPA database consists of proprietary ontology representing 300 000 biologic objects ranging from genes, proteins, and molecular and cellular processes. More than 11 200 human genes are currently represented in the database. The proteins were categorized based on location, cellular components, and reported or suggested biochemical, biologic, and molecular functions using the software. The identified proteins were mapped to networks that were generated based on evidence from existing literature available in the Ingenuity database and then ranked by score. A score of 3 or higher has a 99.9% confidence level of not being generated by random chance alone and was used as the cutoff for identifying protein networks. The molecules identified in the networks and their cellular functions are given in Table 15.

Figure 19A:
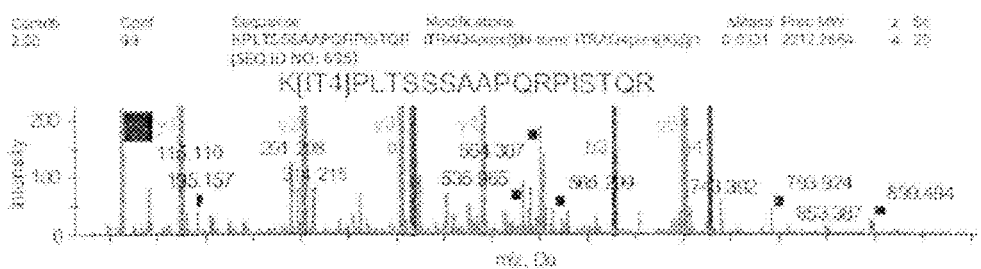
Figure 19D:
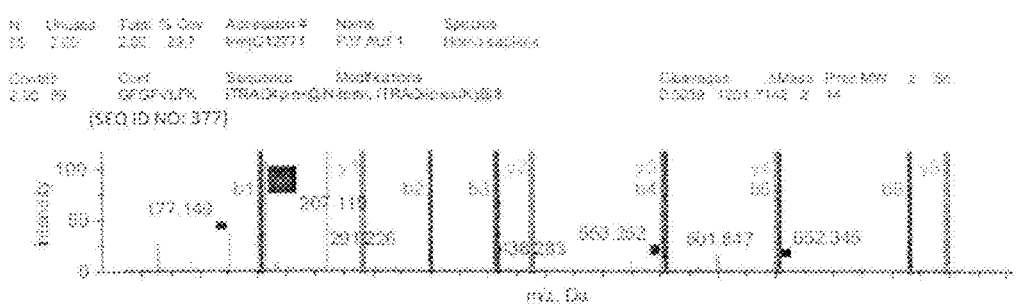

Provided below is a summary of the results obtained by the inventors in connection with the experiments of Examples 1-13:

The offline and online 2D LC-MS/MS analyses collectively resulted in the identification of a total of 811 non-redundant proteins. Only a few of these proteins displayed consistent differential expression in the HNSCC samples (measured in ≥6 out of the 10 samples and with ≥50% showing ≥1.5-fold differential expression relative to the control sample) that warranted further analysis. These proteins, all confidently identified with ≥two peptide matches (except APC-binding protein EB1 and superoxide dismutase [Mn]) are given in Table 1 along with two structural proteins, actin and β-2-tubulin, as controls. (See Table 11 for peptide sequences and coverage, and FIG. 19A for the CID spectra of the single-peptide identifications.) As the nanoLC analyses were performed on 25 SCX fractions, the acquired data files were searched in two groups out of necessity (the version of ProteinPilot software available at that time was incapable of handling a large number of data files each with a large amount of data). Fractions 6-15 were, therefore, searched in one group, while fractions 16-30 were searched in a second group.

The ProteinPilot result files from these two halves were then exported into an Excel spreadsheet where the proteins of interest from the two searches were combined by averaging the ratios for the protein in each sample. It is noteworthy that each of the ratios reported by searching either half of the fractions is itself comprised of the ratios from multiple peptides identified in the given protein. ProteinPilot automatically only includes unique and high-confidence matches of peptides for any particular protein in the ratios reported (i.e., it excludes those that are shared between different isoforms of any protein or low-confidence matches to peptides). These averaged ratios from the offline and online analyses were then again averaged and reported in Table 1. Of all the individual expression ratios (two offline and two online), 56.4% varied by less than 10% from their respective average shown, and 82.0% varied by less than 20%. It is reassuring that the expression ratios from different analyses and separate handling were comparable.

Figure 2:
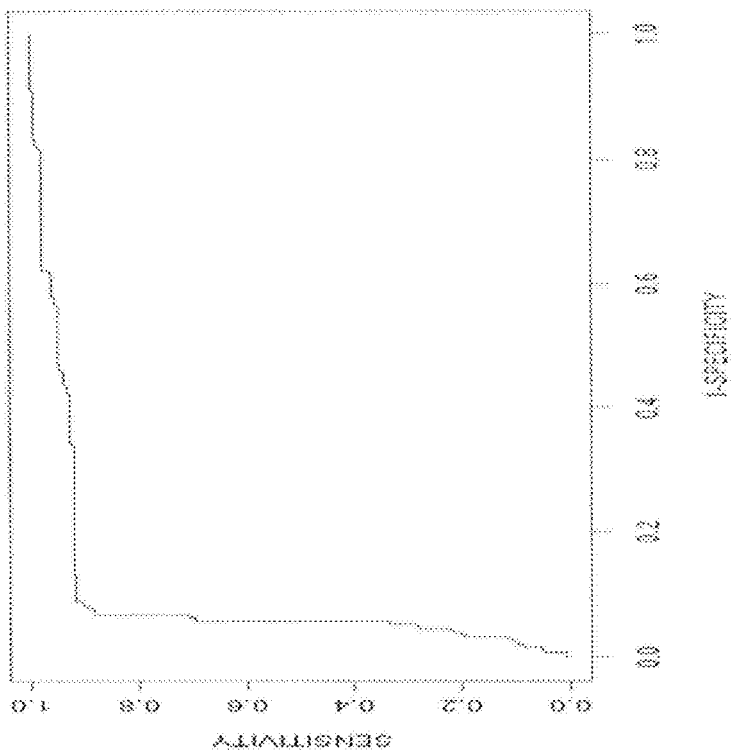
Figure 2:
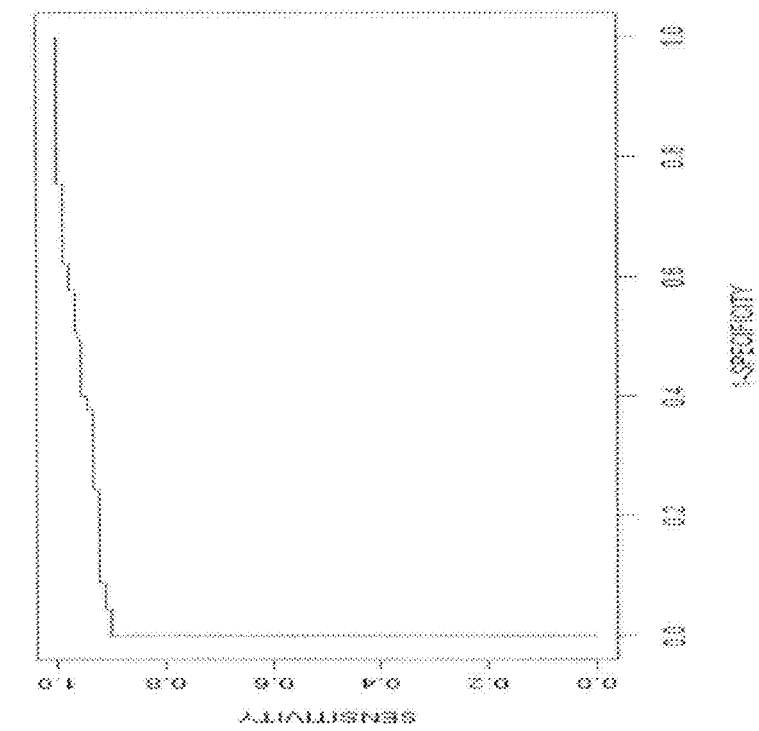

Nine proteins that did not meet the cutoff criteria stated above—cytokeratin 14, polybromo 1D, PKM2, annexin A1, nucleophosmin 1, Hsp27, cystatin B, GRP 94, and MARCKS—were also included in Table 1 for further analysis, as these had been reported in head-and-neck cancer or are of biological relevance in cancer. The HNSCCs analyzed included five squamous-cell carcinomas (SCCs) of buccal mucosa and five SCCs of the tongue. The rationale for the choice of these two SCC types was to determine if there are site-specific protein expressions or not. The best-performing proteins that can differentiate between HNSCC and non-cancerous tissues were identified by determining the individual ROC curves of the proteins in Table 1 (as described in the Experimental section). The three proteins with the highest AUC values-YWHAZ, stratifin and S100A7—are listed in Table 2 together with their individual and collective figures-of-merit, including sensitivity (cancer samples correctly identified as cancer samples) and specificity (normal samples correctly identified as normal samples). As a panel, the three best-performing biomarkers achieved a sensitivity of 0.92 and a specificity of 0.91 in discriminating HNSCC from non-cancerous head-and-neck tissues (Table 2 and FIG. 2a).

A number of proteins, e.g., prothymosin alpha and APC-binding protein EB1, were predominantly overexpressed in SCCs of buccal mucosa (Table 1) and showed some promise in differentiating between SCCs of buccal mucosa and the tongue; however, as the number of samples are small, this possibility will need to be fully investigated in a future study involving more samples of both types.

Figure 3:
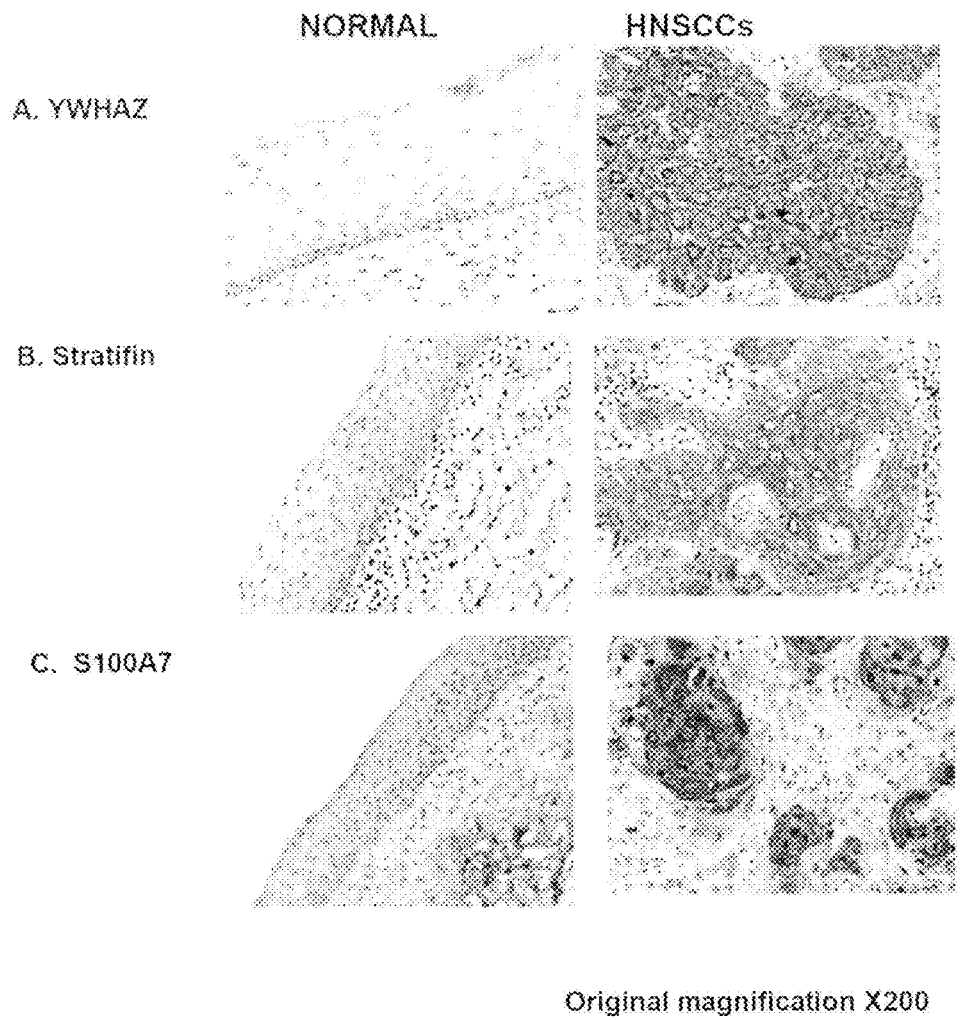
Figure 4:
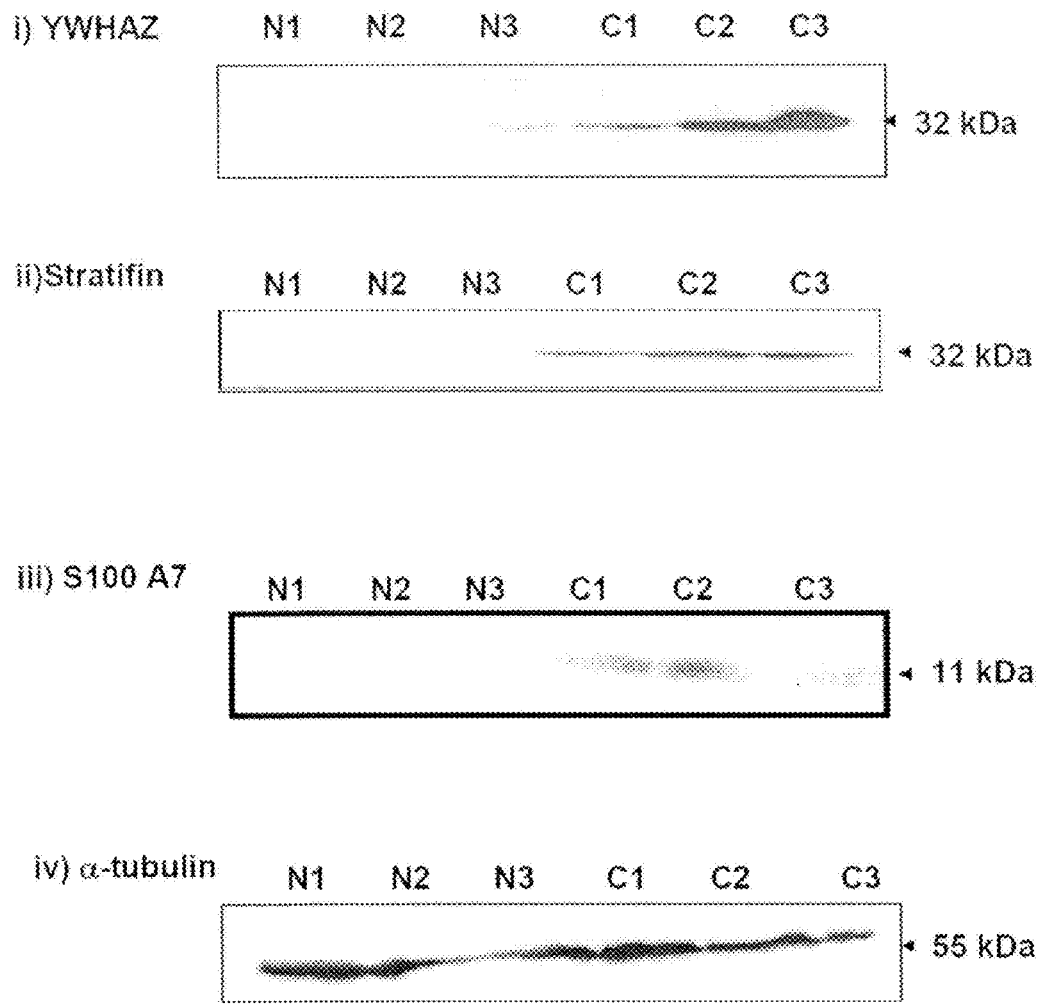
Figure 5:
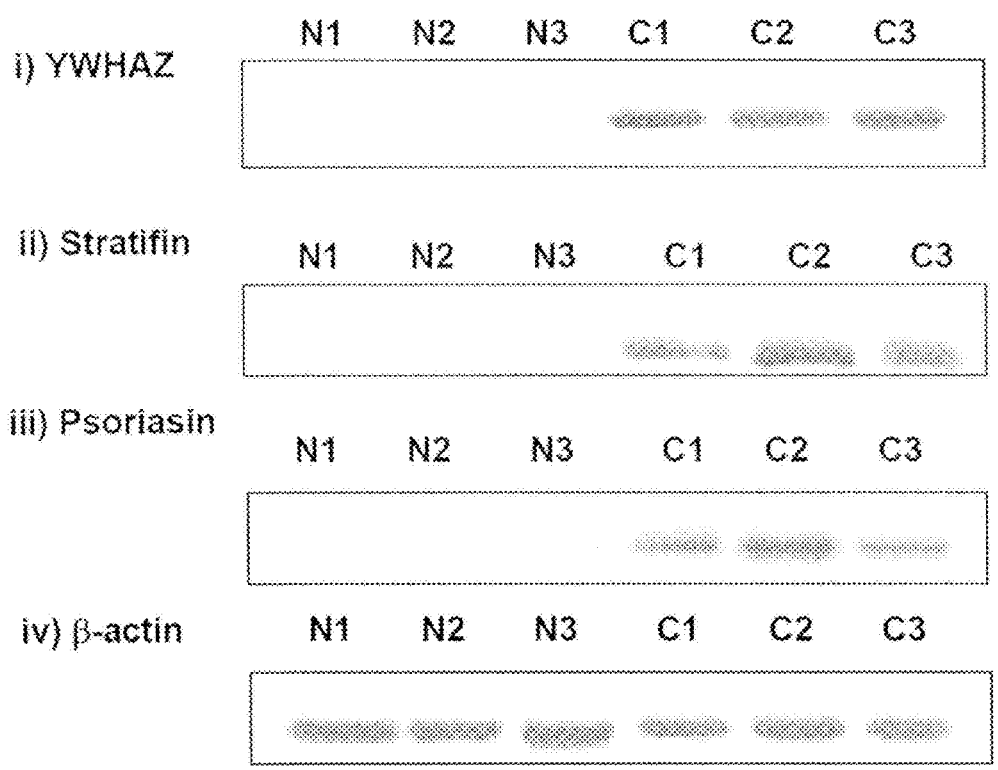

Verification of candidate protein biomarkers is a necessary step in moving from the initial discovery to possible application. The panel of three best-performing biomarkers identified by MS analysis—YWHAZ, stratifin and S100A7—were chosen for verification in a different and larger set of HNSCCs and non-cancerous head-and-neck tissues. Verification exercises included immunohistochemical (FIG. 3) and Western blot analyses (FIG. 4) at the protein level, as well as RT-PCR analysis (FIG. 5) at the mRNA level. All verification results support the above MS findings. In the immunohistochemical analysis, the biomarker panel of YWHAZ, stratifin and S100A7 achieved a sensitivity of 0.92 and a specificity of 0.87 (Table 3 and FIG. 2b) in discriminating HNSCCs from non-cancerous head-and-neck tissues. The paired non-cancerous head-and-neck tissues obtained from HNSCC patients might have altered protein expressions prior to histological changes.

To investigate this possibility, the noncancerous tissues were segregated into paired and non-paired groups and evaluated separately with the HNSCCs. Significantly, the panel of the three biomarkers—YWHAZ, Stratifin and S100A7—appears to perform better in discriminating HNSCC tissues against the non-paired non-cancerous head-and-neck tissues (sensitivity, 0.96; specificity, 0.96) than against the paired non-cancerous tissues (sensitivity, 0.92; specificity, 0.83) (see Table 4). These results appear to support the notion of protein-expression alterations prior to histological changes and caution the use of only paired samples.

The LC-MS/MS analyses of OPLs collectively resulted in identification of 439 non-redundant proteins; 216 were identified as single hits with more than 95% confidence. Of all the proteins identified, only 17 passed the inventors' criteria for further statistical analysis (vide supra). Of this subset, 15 proteins were confidently identified with a minimum of two peptide matches in each case (See Table 11 for peptide sequences and coverage). Two proteins, parathymosin and DLC1 were identified by single peptides (See FIG. 19B-E for the CID spectra of the single-peptide identifications). These 17 proteins are given in Table 6, along with two structural proteins, β-actin and gelsolin precursor, as controls. Table 6 also depicts the variations in the levels of overexpressed and underexpressed proteins in individual OPL and histological normal tissues versus the pooled normal control. These differential expression levels were averages of the replicate injections: 56.4% of the ratios varied by less than 10% from their respective averages shown, and 82.0% varied by less than 20%.

Figure 19E:
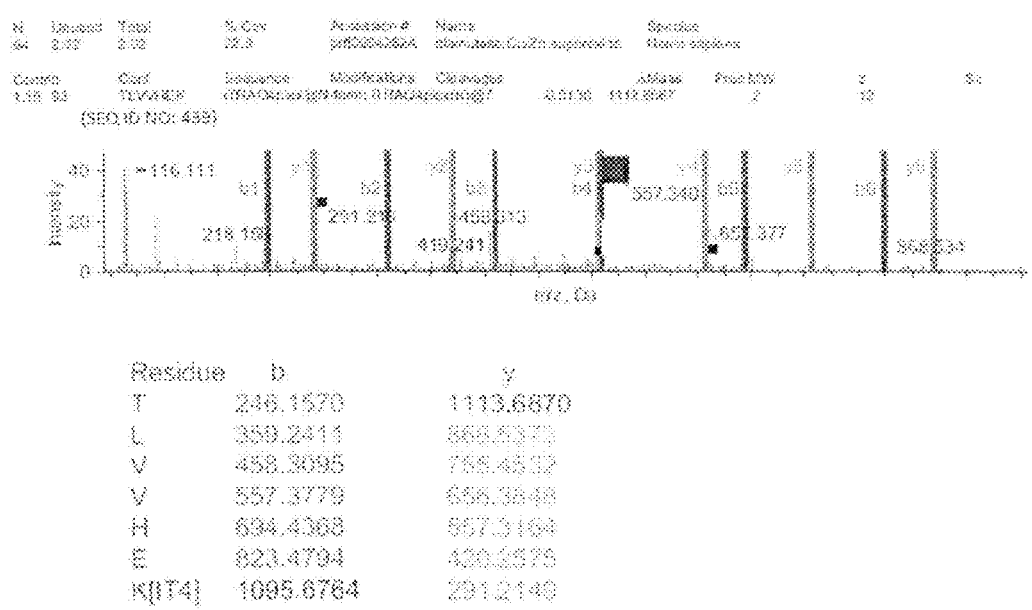

Thirteen proteins that did not meet the aforementioned initial criteria—IGL2, p37AUF1 (hnRNPD), SOD2, PKM2, hnRNPA1, HSP27, cofilin, glyceraldehyde-3-phosphate dehydrogenase, NDP kinase B, elongation factor 2, CALM3, PEBP and S100A7—were also included in Table 6 for further analysis, as they are of biological relevance in cancer development. Of these, 11 proteins were confidently identified with a minimum of two peptide matches in each case (see Table 11B-E for peptide sequences and coverage). p37AUF1 (hnRNPD) was identified by a single peptide with a confidence of 99% (see FIG. 19D for the CID spectra of the single-peptide identification). SOD2 was identified by more than one unique peptide; however, the best-matching peptide was identified with a confidence of only 93%. Although this peptide did not meet the inventors' stipulated criteria for acceptance, manual verification of the spectrum showed good sequence coverage for this peptide (FIG. 19E). Furthermore, the cumulative score, which included the lower confidence peptide matches, was >2.0 and corresponded to a confidence of 99%.

The best-performing proteins that can differentiate between OPLs and normal tissues were identified by determining the individual ROC curves of the proteins in Table 7. The three proteins with the highest AUC values-YWHAZ, stratifin and hnRNPK—are listed in Table 7A together with their individual and collective figures-of-merit, including sensitivity and specificity. As a panel, these three biomarkers achieved a sensitivity of 0.83 and a specificity of 0.74 in discriminating OPLs from histological normal oral tissues (Table 7A and FIG. 6A).

Verification of Candidate Biomarkers by Immunohistochemistry, Western Blot, and RT-PCR Analyses.

The panel of three potential biomarkers, YWHAZ, stratifin and hnRNPK, and two other proteins with high AUC values, S100A7 (0.56) and PTHA (0.56), were chosen for verification in an independent set of OPLs (30 cases) and normal tissues (21 cases) by IHC. Representative levels of expression and subcellular localizations of all five proteins in oral dysplastic tissues in comparison with normal tissues are shown in FIG. 7A-E. (FIG. 20 depicts the positive and negative controls used for each protein analyzed by IHC.) These data were further verified by Western blot analysis (FIG. 8A) at the protein level, as well as RT-PCR analysis at the mRNA level (FIG. 8B).

The differential expression suggested by iTRAQ ratios tended to be moderate, whereas the results of Western and RT-PCR analyses tended to show more extreme differential expression. Thus, Western and RT-PCR analyses, verified the differential expression reported by the iTRAQ analysis in trend, but not in scale. This discrepancy of scale has also been noted in other studies and has been ascribed to compression of the dynamic range of iTRAQ ratios (21). Specifically, in that study the inventors determined that a two-fold differential expression as determined by iTRAQ analysis was in reality closer to a four-fold differential expression in an absolute quantification study that was performed on the same samples. Importantly, in IHC analysis, the biomarker panel of YWHAZ, stratifin, and hnRNPK achieved a sensitivity of 0.91 and a specificity of 0.95 (Table 8B and FIG. 6B) in discriminating OPLs from histological normal oral tissues.

Network Analysis.

To gain insight into the plausible biological processes in which these proteins might be involved, the inventors used the Ingenuity Pathway Analysis tools (Ingenuity Systems, Inc. software) and discovered two major networks (Table 15) in OPLs (the merged network is shown in FIG. 8C). To the best of the inventors' knowledge, ours is the first study reporting differential expressions of p37AUF1 and histone H2B.1 in OPLs. These proteins and their cellular functions are listed in Table 11.

Without being bound by theory, the results obtained in the experiments of Examples 1-13 are discussed below:

Multidimensional LC-MS/MS has been used for the analysis of clinical samples of HNSCCs labeled with isobaric mass tags (iTRAQ) to identify proteins that are differentially expressed in head-and-neck cancer in relation to non-cancerous head-and-neck tissues. The expression ratios were consistent between the online and offline 2D LC-MS/MS methods used, demonstrating that the methodologies were rugged and reproducible, even though the conditions and details used in peptide elution from the SCX columns in the two methods were different. Expectedly, the numbers of proteins identified by the online analysis (431) was lower than those identified by the offline analysis (580), due to the lower capacity of the SCX cartridge used in the former (50 ng of total peptides versus up to 1 mg in the latter). However, the online analysis was advantageous in terms of shorter data acquisition time and lower amounts of total sample required.

Development of HNSCC is a multistep process that often involves field cancerization, a phenomenon in which not only the site of the primary tumor, but the entire mucosa of the upper aerodigestive tract, is prone to undergoing malignant transformation or progression at multiple sites (37). It is now evident that molecular changes underlying field cancerization are not localized to areas with altered histology, but may persist beyond the histological border of precancerous lesions; a large fraction of the carcinogen-exposed field may harbor molecular aberrations without presenting clinical or morphological symptoms (6 and references therein). Identification of proteins with altered expression as a manifestation of field cancerization is important in identification of biomarkers for prediction of risk of recurrence, as well as for development of second primary tumors in patients treated for HNSCC. Thus, the selection of normal controls for HNSCCs in a differential expression analysis, including the current study, is non-straightforward and requires careful planning.

To address this issue, the inventors have included two types of non-cancerous histologically confirmed normal tissues in the inventors' analysis: (1) noncancerous tissues obtained from HNSCC patients from a site distant to the tumor, and (2) normal tissues obtained from individuals with no evidence of cancer or pre-cancerous lesions. In a recent proteomic study, Roesch-Ely et al. (12) investigated changes in protein expressions occurring in different stages of tumorigenesis and field cancerization in HNSCCs. A number of reported differentially expressed proteins, including calgizarrin, stratifin, histone H4, and cystatin A, are also identified in this current study. This study appears to be the first reporting differential expression of calmodulin-like protein 5, polybromo-1D, APC-binding protein EB1, α-1-antitrypsin precursor, carbonic anhydrase I, mast cell tryptase β-III, histone H2B.1, L-plastin, and peptidylprolyl isomerase A (PPIA) in HNSCC.

Among the differentially expressed proteins identified, no single protein emerged as a unique marker for HNSCC. However, a panel of three best-performing biomarkers YWHAZ, Stratifin and S100A7 performed satisfactorily, as determined by both MS and immunohistochemistry on independent sets of samples. Significantly, YWHAZ has previously been identified by the inventors to be overexpressed in oral cancer at the mRNA level and has subsequently been verified using immunohistochemical analysis (38, 39). This serves as an independent validation of and complements the current results. Furthermore, YWHAZ has also been reported to be overexpressed in stomach cancer (40), and in breast and prostate tumor model systems (41, 42). More importantly, YWHAZ is not overexpressed in lung-cancer tissue samples (43), thus illustrating the fact that this protein can provide some selectivity in discriminating among different cancer types.

Stratifin has been reported to be overexpressed in HNSCC. A recent proteomic study reported a 3.6-fold straffin overexpression (44), thus corroborating the results obtained in this study. A second independent study also showed stratifin overexpression in the range of 2.8-9.1-fold in cancer samples (45). In addition, a study of 300 patients with pancreatic ductal adenocarcinoma showed stratifin overexpression in 82% of primary infiltrating adenocarcinomas, while another 15% showed weak immunopositivity. Overexpression of stratifin correlated with poor prognosis (46). Interestingly and significantly, stratifin was reported to be down-regulated in HNSCCs by Roesch-Ely et al. (12), whereas the inventors observed consistent overexpression of stratifin in iTRAQ and in IHC verification analysis. The HNSCCs in the study of Roesch-Ely et al. (12) are from the German population with tobacco smoking and alcohol consumption being the major risk factors, while the clinical samples in this study, and in Lo et al. (15, 44) and Chen et al. (45) are from Asian populations, where in addition, chewing tobacco and/or betel quid, and bidi smoking are important risk factors. These differences in the risk factors may account for the observed variations in stratifin expression and warrant in-depth investigation in a larger study.

14-3-3 proteins recognize phosphoserine/threonine (pS/T)-containing motifs used by a variety of signal transduction pathways to bind over 200 target proteins that play important roles in the regulation of various cellular processes, including mitogenic and cell-survival signaling, cell-cycle control and apoptotic cell death, epithelial-mesenchymal transition, and cell adhesion, invasion and metastasis (46). The involvement of 14-3-3 proteins in the regulation of oncogenes and tumor suppressor genes points to a potential role in tumorigenesis (47); multiple pathways can be targeted by modulation of these proteins, underscoring their potential as candidate drug targets. Although it might be argued that 14-3-3 proteins are, therefore, too pleiotropic to be targets for therapeutic inhibition, it has been shown that simultaneous inactivation of all 14-3-3 proteins sensitizes cancer cells to DNA-damaging agents. Selective inactivation of stratifin leads to an increased sensitivity towards cancer chemotherapeutic agents. Recent studies have shown that stratifin forms homodimers, while YWHAZ forms homodimers and also heterodimers with other isoforms (48-50). Stratifin has been extensively investigated; by contrast, YWHAZ remains largely unexplored. It is noteworthy that the potential success of strategies aimed at modulating 14-3-3 availability in the cell for cancer therapy is provided in studies showing that reducing cellular 14-3-3 increases chemosensitivity (51, 52).

Cytokeratin 14 has also been demonstrated to be overexpressed in many squamous cell carcinomas. A study using immunohistochemical analysis demonstrated that 67 of 74 cases of squamous cell carcinomas showed immunoreactivity regardless of origin, suggesting cytokeratin to be a useful marker for squamous cell carcinoma (53). Another study, comparing mRNA levels of cytokeratin 14 between oral squamous cell carcinoma and leukoplakia samples reported that the former showed a higher amount of cytokeratin 14 (54).

Prothymosin alpha, found to be overexpressed here in HNSCC, has recently been proposed to be a potential marker of proliferation in patients with thyroid cancer (55). This protein was implicated in various other cancers, including gastric, lung, liver, colon, and breast cancers (33-36, 56, 57).

Prothymosin alpha was proposed to be a surrogate marker for the diagnosis of estrogen-negative breast-cancer cases (56), and a urinary marker for the detection and monitoring of bladder cancer (58). Prothymosin alpha expression has been observed in lymph nodes and tonsils (59). This expression in lymph nodes of HNSCC patients would correlate with locoregional spread of the disease and may be a determinant of disease prognosis. Prothymosin alpha is a small, highly acidic, nuclear protein that has been proposed to play a role in cell proliferation and immune regulation (60).

Protein changes related to cytoskeletal reorganization, cellular metabolism, and protein-protein interactions have been observed, based on which a model for its immunological mode of action has been proposed (60). Interestingly, some of the proteins identified in that study, such as L-plastin, HSP90, vinculin, aldolaseA, meosin, and galectin 3 are found to be overexpressed in the present study as well, although not all of them are included in Table 1.

L-plastin is expressed by hematopoetic cells and by most human cancer cell lines, including human submandibular gland cell lines (61, 62); yet, its functional importance in tumor tissues is controversial: its expression correlates with tumor progression in colon cancer, but not in breast cancer; in melanoma, L-plastin phosphorylation promotes tumor cell invasion (reviewed in 61). Intriguingly, L-plastin has also been proposed to represent a novel target for cancer therapy, and the constitutive activity of its promoter in non-hematopoetic tumors presents novel perspectives for cancer gene therapy using L-plastin promoter-driven viral vectors (61).

S100A7, a small calcium-binding protein of the S100 protein family, originally identified in psoriatic keratinocytes, is up-regulated in abnormally differentiating keratinocytes, squamous carcinomas of different organs, and in a subset of breast tumors (62-66). Incidentally, S100A7 was also identified in oral premalignant epithelia by microarray analysis and proposed to be a marker for invasion (63). It has been hypothesized to play a role in breast-tumor progression by promoting angiogenesis and enhancing the selection of cells that overcome their anti-invasive function (64). This hypothesis has also been suggested to explain why S100A7 expression is high in high-grade or estrogen-receptor negative tumors, as these are associated with increased hypoxia and reactive oxygen species (ROS), a scenario in which the angiogenic effects of S100A7 are most important.

It is noteworthy that increased hypoxia and ROS also occur in head-and-neck tumors and might explain the observed changes in S100A7 expression here. Another study in breast cancer showed that BRCA1 is a transcriptional repressor of S100A7. BRCA1 and c-Myc form a complex on S100A7 promoter, and BRCA1-mediated repression is dependent on a functional c-Myc (68). Furthermore, BRCA1 mutations in tumors abrogate the repression of S100A7. In the absence of BRCA1, S100A7 is induced by topoisomerase II poison and etoposide, as well as increases the cellular sensitivity to etoposide, suggesting a mechanism for BRCA1-mediated resistance to etoposide (68). Incidentally, BRCA1 alterations have been reported in head-and-neck cancer (69, 70). However, a correlation, if any, between BRCA1 alterations and S100A7 expression in head-and-neck cancer remains to be demonstrated.

Calgizzarin (S100 A11) has also been previously linked with cancer and was reported as a potential marker for head-and-neck cancer (18). Likewise, S100 A2, which shows overexpression in HNSCC is also known to be overexpressed in other forms of cancer, such as non-small cell lung cancer and uterine leiomyoma (71, 72). It has been demonstrated that calgizzarin plays an anti-apoptotic role in uterine leiomyosarcoma cell line (72). Fascin has been discovered to be an early marker for esophageal squamous cell carcinoma (73). The inventors have previously reported pyruvate kinase M2 to be overexpressed in head-and-neck cancers (17, 21). Several studies suggest that PKM2 is present primarily in a dimeric form in tumors, and is useful as a biomarker in their early detection (74-78). PKM2 overexpression in tumor cells is explained on the basis of its key role in the generation of ATP in the glycolytic pathway. Under hypoxic conditions that are typical for tumors, this pathway is a critical route by which tumors satisfy the higher energy requirements needed for proliferation (reviewed in 79, 80).

Two of the more interesting proteins discovered in this current HNSCC study are the APC-binding protein EB1 and polybromo-1D. End-binding protein 1 (EB1) was initially discovered as a protein that binds adenomatous polyposis coli protein (APC) at its C-terminal region (81). More recently, however, it has also been shown to bind tubulin and has been detected to associate with the microtubules that form the mitotic spindle during mitosis (82).

The EB1 interaction with APC is of particular interest as APC is a tumor suppressor whose inactivation leads to a significantly enhanced level of susceptibility for malignant transformation in colorectal cancer (82). Among others, APC binds to β-catenin and possibly controls β-catenin's availability in the cytoplasm (82). By virtue of APC's binding to tubulin, EB1 participates in microtubule-dependent processes, including intracellular vesicle trafficking, organization of organelles within the cell, and even cell migration (82).

One possible proposed explanation for the mechanism of action of EB1, is that overexpression of EB1, at least in esophageal squamous cell carcinoma, affects the interaction between APC and β-catenin, and that this overexpression correlates with the nuclear accumulation of β-catenin (82). Normally, APC in combination with glycogen synthase kinase 3β (GSK 3β) and axin forms a destruction complex that phosphorylates free β-catenin in the cytoplasm, which in turn targets it for ubiquitination and degradation (82). Disruption of APC interaction with β-catenin by EB1 overexpression leads to increased levels of β-catenin in the nucleus, which in turn binds to T-cell factor/lymphoid-enhancing factor (TCF/LEF) and activates transcription of target genes such as c-myc and cyclin D1. Thus, the overexpression of EB1 is thought to play a role in the development of esophageal squamous cell carcinoma by indirectly causing the activation of the β-catenin/TCF pathway (83). It is, therefore, possible that overexpression of EB1 in this study could be the first evidence for the same process occurring in HNSCC.

Polybromo 1D (PB1), also known as BRG1-associated factor 180 (BAF180), is a relatively new member of the SWI/SNF-B (PBAF) chromatin remodeling complex that is a homolog of the yeast rsc protein complex, which is required for progression through mitosis (84). In fact, antibodies against BAF180 localize to the kinetochores during mitosis (84). The fact that both PB1 and EB1 are known to be involved with mitosis is also noteworthy, but requires further investigation to ascertain if a direct relationship between the two exists. Other studies have shown that in yeast, rsc can act as an activator as well as a suppressor of transcription, and that it can be functionally linked with the PKC pathway (85, 86).

Additionally, it was shown that temperature-sensitive mutants of one of the proteins (nps1) in the rsc complex, when placed at the restrictive temperature, can be rescued by the overexpression of not only the yeast homolog of PKC, PKC1 (as well as other proteins downstream of the PKC1 signal pathway), but also by Bim1p, which is the yeast homolog of EB1 (85). It was further demonstrated that there is no direct interaction between Pkc1p and Bim1p, or any activation of BIM1 transcription or post-transcriptional regulation by Pkc1p, but that suppression of the activity of overexpressed Pkc1p requires a functional Bim1p (85).

In addition to the possibility of this potentially significant link between PB1 and EB1, there is also independent evidence suggesting that PB1 is a tumor suppressor and that this activity is found in lung cancer but not in breast cancer (86). This was verified when transfection of BAF180 gene into breast tumor cell lines, possessing a truncated version of the same gene, resulted in growth inhibition (86). Other members of this complex that have been associated with cancer include hSNF5/INI1 and BRG1 itself. HSNF5/INI1 mutations have been found in malignant rhabdoid tumors, while mutations in BRG1 have been noted in various cell lines including carcinomas of the breast, lung, pancreas and prostate. Implication of other members of the PBAF complex in suppression of various cancers, in addition to the above evidence which suggests that PB1 may be a tumor suppressor itself, makes PB1 an exciting discovery in the inventors' study. In light of PB1's suggested tumor suppressor role, the presently observed lower expression of this protein in the HNSCC samples is consistent with expectations and warrants in-depth investigation of its role in head-and-neck tumorigenesis.

Thus, the use of iTRAQ-labeling of head-and-neck cancers combined with LCMS/MS has led to the discovery of several novel, differentially expressed proteins in these tumors. A panel of the three best-performing biomarkers achieved a sensitivity of 0.92 and a specificity of 0.91. This performance was verified using immunohistochemistry on a larger, independent set of clinical samples of HNSCCs.

The unique features of the OPL study are its prospective nature, the large number of patients in this type of disease setting, and the length of follow-up of leukoplakia and HNOSCC patients. Table 7 also shows the analysis of three histological normal samples used in a previous exercise to demonstrate consistency and validity over a period of six months (23). The number of OPLs examined in this study—six for the LC-MS/MS and 30 for subsequent verifications—was relatively modest, but was necessitated by the small number and size of OPL samples available. Nevertheless, the inventors successfully demonstrated the utility of iTRAQ-labeling of small OPL biopsy specimens and detection of a large number of expressed proteins that led to the discovery of a panel of candidate OPL biomarkers.

Replicate analyses demonstrated that the expression ratios were reproducible-82% were within 20% of the averages shown in Table 6. Differential expressions analyses of the proteomes between OPLs and histological normal oral tissues revealed 30 proteins that merit further examination and verification. A panel of three potential biomarkers selected by ROC analyses and two other biologically relevant proteins that had high AUC values were successfully verified to be overexpressed using an independent and larger set of OPLs and histological normal tissues by IHC and Western analyses, thus confirming findings of the iTRAQ analyses. In addition, RT-PCR analyses showed increased levels of transcripts for all five proteins, suggesting that the increased protein expressions were due to upregulation at the transcriptional level.

The inventors' approach enabled identifying in oral premalignant lesions a large number of proteins, including mediators of inflammatory response, redox system, proteases, chaperones, transcriptional regulators, calcium binding proteins, metabolic enzymes, and proteins involved in cell proliferation and growth, intermediary metabolism, signal transduction, cell cycle regulation, cell death, cell motility and cell morphology. Pathway analyses unraveled important novel links between inflammation and cancer. Importantly, it showed direct interaction between all the three proteins-YWHAZ, stratifin and hnRNPK—that constitute the panel of OPL biomarkers (87). The mechanism involved in upregulation of YWHAZ and stratifin in OPLs remains unknown.

hnRNPK is an RNA-binding protein that regulates gene expression at both transcriptional and translational levels (88, 89). Therefore, the inventors speculate that hnRNPK may be involved in regulation of YWHAZ and stratifin in OPLs. The data analysis also suggests that hnRNPK directly regulates the expression of COX2, enzyme implicated in the synthesis of prostaglandins, which are mediators of the inflammatory response. The inventors' earlier in vitro and in vivo studies demonstrated that COX-2 activation and NF-kB overexpression are parallel events occurring in early precancerous stages of tobacco-associated oral carcinogenesis and these events remain elevated down the tumorigenic pathway (90), while others demonstrated a role for 14-3-3 proteins in the nuclear export of p65-Iκβ-alpha complexes (91) and the role of 14-3-3 in phosphorylation of beta-catenin by AKT that promotes beta-catenin transcriptional activity (92) as well as in apoptosis and cell adhesion emphasizing the oncogenic character of 14-3-3 zeta (YWHAZ) (93). Tobacco carcinogens, including tobacco specific nitrosamines (TSNA), 4-(methylnitrosamino)-1-(3-pyridyl)-1-butanone (NNK), appear to activate these proteins involved in the inflammatory response of epithelial cells and initiation of the carcinogenic cascade.

The other important links identified are regulation of NF-kB by SERPINA1 and phosphatidyl ethanolamine binding protein 1 (PEBP1). SERPINA1 has been shown to reduce the activation of NF-kB; decrease in SERPINA1 levels in OPLs may partly account for activated NF-kB in OPLs. Pathway analyses also showed, for the first time, that deregulation of calcium-associated proteins (cystatin B, FABP5, and S100A7) and mitochondrial dysfunction (SOD2) may play an important role in the development of OPLs. Importantly, YWHAZ was found to directly interact with nucleophosmin (NPM1), an important protein involved in increased cellular proliferation, and with HSP90B1, which has been reported to increase the activity of ERK. HSP90B1, YWHAZ, nucleophosmin1, parathymosin (PTMS), SOD2, and PEBP1 are all involved in the inhibition of apoptosis.

Furthermore, HSP90B1, SOD2, and stratifin are associated with increased cell viability. Increased expressions of hnRNPK, PTHA, stratifin, SOD2 and nucleophosmin1, and reduced expression of DLC1, play a role in hyperproliferation of cells. Increased cell proliferation and inhibition of apoptosis are two hallmarks of cancer, and the inventors' data suggest that both events are occurring in early, premalignant stages. Alterations in cytoskeleton are important events in tumorigenesis; deregulation of YWHAZ and its interaction with MARCKS, beta actin and tubulin identified herein suggest the implication of cytoskeletal reorganization in development of oral dysplasias.

It is noteworthy that invasion is an important event in the progression of dysplasia as well as of cancer, and five proteins identified in the inventors' study—underexpressions of DLC1, IGHG1 and FABP5, and overexpressions of S100A7 and PEBP1—are all involved in cell invasion. Significantly, this is the first report of p37AUF1 (hnRNPD) expression in OPLs, and pathway analyses suggest its potential interaction with stratifin and scaffold protein b (SAFB). PEBP1 is oncogenic, while FABP5 and SERPINA1 are metastatic. Taken together, the discovery of these alterations in OPLs suggests that these proteins may be associated with the potential of malignant transformation. The findings herein certainly warrant additional validation; elucidation of functional significance in future studies will provide further insight into the biology of development and progression of OPLs.

None of the aforementioned proteins can be classified individually as specific biomarkers for OPLs. However, a panel of the three best-performing biomarkers: YWHAZ, stratifin, and hnRNPK confer satisfactory performance. The current study clearly demonstrates overexpression of YWHAZ in OPLs, suggesting its involvement in early stages of oral carcinogenesis. Mechanistically, YWHAZ overexpression increases p53 protein degradation via hyperactivation of the phosphoinositide 3-kinase (PI3K)-Akt signaling pathway that phosphorylates MDM2 (92-95). Replacement of p53 leads to luminal cell apoptosis. YWHAZ is known to be involved in diverse cellular processes, many of which are deregulated in HNOSCCs (39). The inventors' ongoing studies on functional analysis of YWHAZ in oral cancer cells have also shown its involvement in the activation of PI3K-Akt signaling pathway and cytoskeletal reorganization (data not shown).

Stratifin, another member of the 14-3-3 protein family, was overexpressed in OPLs and emerged as one of the best-performing potential biomarkers. The inventors' present data suggest that the increase in stratifin expression is an early event in the development of cancer. Importantly, their recent proteomic analysis showed overexpression of stratifin in HNOSCCs (23); underscoring its importance in head-and-neck tumorigenesis (87). Interestingly and significantly, stratifin was reported to be down-regulated in HNSCCs by Roesch-Ely et al., (12), whereas the inventors observed consistent overexpression of stratifin in iTRAQ and in IHC verification analyses. The HNSCCs in the study of Roesch-Ely et al. (12) were from the German population with tobacco smoking and alcohol consumption being the major risk factors; while the clinical samples in this study, and in Lo et al. (44), were from Asian populations, where in addition, chewing tobacco and/or betel quid, bidi smoking and HPV infection are important risk factors. In support of these observations, Bhawal et al., (96) reported that hypermethylation of stratifin promoter is not a frequent event in HNSCC. Moreover, IKK alpha, a catalytic subunit of the IKK complex, has been shown to protect the stratifin locus from hypermethylation; this function serves to maintain genomic stability in keratinocytes.

Heterogeneous nuclear ribonucleoprotein K protein (hnRNPK), identified by iTRAQ analysis and verified by IHC in OPLs, is an interesting protein that has been strongly implicated as a key player of tumorigenesis (87). hnRNPK is overexpressed, aberrantly localized, and associated with poor prognosis in colorectal cancer (88), while its transcriptional upregulation was reported in OSCC (89). In view of a role of hnRNPK as a transformation-related protein, its overexpression in OPLs is an important finding; in-depth studies are warranted to establish its link, if any, with transformation potential of OPLs.

Prothymosin alpha, overexpressed in a subset of OPLs, has been proposed to be a proliferation marker in patients with thyroid cancer (55). This protein was implicated in various other cancers, including gastric, lung, liver, colon, and breast cancers (33-36, 55-60). S100A7, a small calcium-binding protein, is upregulated in abnormally differentiating keratinocytes, squamous carcinomas of different organs, and in a subset of breast tumors (65, 67). S100A7 has been identified in oral premalignant epithelia by microarray analysis and proposed to be a marker for invasion (66). It is postulated to play a role in breast-tumor progression in association with increased hypoxia and ROS by promoting angiogenesis (67). Increased hypoxia and ROS also occur in OPLs and HNOSCCs, and might explain the observed changes in S100A7 expression here. Reciprocal negative regulation between S100A7 and β-catenin signaling has been shown to play an important role in tumor progression of OSCC.

Thus, proteomic analyses of OPLs revealed the integrated importance of alterations in multiple cellular processes and suggested novel links between inflammation and premalignancy, some of which may serve as potential chemopreventive/therapeutic targets. Validation of the panel of OPL biomarkers in larger studies will ascertain its clinical utility and long-term patient follow up will evaluate the potential of these biomarkers for predicting the risk of malignant transformation in OPLs.

Example 14—Tissues

Following institutional human ethics committee approval, 51 anonymized HNOSCCs and 39 non-malignant head-and-neck tissues dating from 2002 and 2006 were retrieved from the Research Tissue Bank at All India Institute of Medical Sciences, New Delhi, India. The tissue specimens, surgically resected human HNOSCCs and non-malignant tissues (taken from a distant site) had been collected from patients undergoing curative surgery (with prior written patient consents). After excision, tissues were immediately snap-frozen in liquid nitrogen and stored at −80° C. in the Research Tissue Bank. One piece from each patient was collected in 10% formalin and embedded in paraffin for histopathological analysis; the rest was banked. Clinical and pathological data were recorded in a pre-designed performa; these included clinical TNM staging (tumor, node, and metastasis classification of malignant tumors of the International Union Against Cancer (UICC)) (97), site of the lesion, histopathological differentiation, age, and gender.

Example 15—Follow-Up Study

Fifty-one HNOSCC patients who underwent treatment of primary HNOSCC between 2002 and 2006 were investigated and evaluated in the head-and-neck cancer follow-up clinic. Survival status of the patients was verified and regularly updated from the records of the Tumor Registry, Institute Rotary Cancer Hospital, as of May, 2007. Patients were monitored for a maximum period of 42 months. As per the hospital protocol, HNOSCC patients with T1 and T2 tumors were treated with radical radiotherapy or surgery alone, whereas the majority of patients with T3 and T4 diseases were treated using a combination of radical surgery followed by postoperative radical radiotherapy. The patients were revisited clinically on a regular basis and the time to recurrence was recorded. If a patient died, the survival time was censored at the time of death; the medical history, clinical examination, and radiological evaluation were used to determine whether the death had resulted from recurrent cancer (relapsing patients) or from any other cause.

Disease-free survivors were defined as patients free from clinical and radiological evidence of local, regional, or distant relapse at the time of the last follow-up. Loco-regional relapse/death was observed in 17 of 51 (30%) patients monitored in this study. Thirty-four patients who did not show recurrence were alive until the end of the follow-up period. Only disease-free survival was evaluated in the present study, as the number of deaths due to disease progression did not allow a reliable statistical analysis. Disease-free survival was expressed as the number of months from the date of surgery to the loco-regional relapse.

Example 16—Immunohistochemistry

Paraffin-embedded sections (5 μm thick) of human oral normal tissues (n=39) and HNOSCCs (n=51) were collected on gelatin-coated slides. For histopathological analysis, representative sections were stained with hematoxylin and eosin, whereas immunostaining was performed on serial sections as described previously (23, 98). Briefly, the sections were deparaffinized in xylene, hydrated, and pretreated in a microwave oven in citrate buffer (0.01 M (pH=6.0)) for antigen retrieval. The sections were incubated with hydrogen peroxide (0.3% v/v) in methanol for 20 min to quench the endogenous peroxidase activity. Non-specific binding was blocked with 1% bovine serum albumin (BSA) in phosphate-buffered saline (PBS, 0.01 M, pH=7.2) for 1 h. Thereafter, slides were incubated with the primary antibody, (1 μg/ml) (anti-14-3-3a, goat polyclonal antibody, Santa Cruz Biotechnology Inc., Santa Cruz, Calif.) for 16 h at 4° C. and washed with PBS. The primary antibody was detected using the streptavidin-biotin complex (Dako LSAB plus kit, Dako, Copenhagen, Denmark) and diaminobenzidine as the chromogen. All incubations were performed at room temperature in a moist chamber. Slides were washed with 3× Tris-buffered saline (TBS, 0.1 M, pH=7.4) after every step. Finally, the sections were counterstained with Mayer's hematoxylin and mounted with DPX mountant. In negative controls, the primary antibody was replaced by non-immune mouse IgG of the same isotype to ensure specificity.

Example 17—Positive Criteria for Immunohistochemical Staining

Immunopositive staining was evaluated in five areas of the tissue section. For stratifin expression, sections were scored as positive if epithelial cells showed immunopositivity in the cytoplasm, plasma membrane, and/or nucleus as evaluated by two independent scorers blinded to the clinical outcome (the slides were coded and the scorers did not have prior knowledge of the local tumor burden, lymphonodular spread, and grading of the tissue samples). These sections were rated based on the percentage of cells showing immunopositivity as follows: 0, <10%; 1, 10-30%; 2, 30-50%; 3, 50-70%; and 4, >70%. Sections were also rated on the basis of stain intensity as follows: 0, none; 1, mild; 2, moderate; 3, intense, as described by Perathoner et al. (99). Finally, a total score (ranging from 0 to 7) was obtained by adding the scores of percentage positivity and intensity. The sections were considered positive if the total score was ≥5 (23).

Example 18—Cell Culture

Human oral squamous carcinoma cell line, HSC2, was used in this study. Cells were grown in monolayer cultures in Dulbecco's modified eagle medium (DMEM-F12) supplemented with 10% fetal bovine serum (FBS, Sigma-Aldrich, MO), 100 g/ml streptomycin and 100 U/ml Penicillin in a humidified incubator (5% carbon-dioxide, 95% air) at 37° C. as described (23).

Example 19—Co-Immunoprecipitation

Co-immunoprecipitation (Co-IP) assays were carried out as described earlier (100). Briefly, oral cancer cells, HSC2, were rinsed in ice-cold PBS and lysed in lysis buffer. Lysates were incubated on ice for 30 min and cell debris was removed by centrifugation. Lysates were pre-cleared by adding 20:1 of Protein A-Sepharose (GE Healthcare Biosciences, Sweden), followed by overnight incubation with polyclonal stratifin, YWHAZ, and NFκB antibodies, or monoclonal β-catenin and Bcl-2 antibodies (1:200 dilution) (Santa Cruz Biotechnology, CA) on a rocker at 4° C. Immunocomplexes were pulled down by incubating with Protein A-Sepharose for 2 h at 4° C., followed by washing with 4× ice-cold lysis buffer to eliminate non-specific interactions. In negative controls, the primary antibody was replaced by non-immune mouse IgG of the same isotype to ensure specificity. Protein A-Sepharose-bound immunocomplexes were then resuspended in Laemelli sample buffer (10 mM Tris, 10% v/v glycerol, 2% w/v SDS, 5 mM EDTA, 0.02% bromophenol blue, and 6% β-mercaptoethanol, pH=7.4), boiled for 5 min, and analyzed by Western blotting using specific antibodies.

The proteins were electro-transferred onto polyvinylidenedifluoride (PVDF) membrane. After blocking with 5% non-fat powdered milk in TBS (0.1 M, pH=7.4), blots were incubated with anti-14-3-3σ antibody (1:200 dilution) at 4° C. overnight. alpha-Tubulin served as a control for protein loading and was determined with mouse monoclonal anti-alpha-tubulin antibody (Santa Cruz Biotechnology, Santa Cruz, Calif.). Membranes were incubated with secondary antibody, HRP-conjugated goat/mouse anti-IgG (Dako CYTOMATION, Denmark), diluted at an appropriate dilution in 1% BSA, for 2 h at room temperature. After each step, blots were washed with 3× Tween (0.2%)-TBS (TTBS). Protein bands were detected by the enhanced chemiluminescence method (Santa Cruz Biotechnology, CA) on XO-MAT film.

Example 20—Statistical Analysis

The immunohistochemical data were subjected to statistical analysis using SPSS 10.0 software. The relationship between the protein expression and clinicopathological parameters were tested by Chi-Square and Fischer's exact test. Two sided p-values were calculated and p≤0.05 was considered to be significant. Box plots were prepared to determine the distribution of total score of stratifin expression in HNOSCCs and non-malignant tissues. The correlation of stratifin and or YWHAZ staining with patient survival was evaluated using life tables constructed from survival data with Kaplan-Meier plots.

Figure 9A:
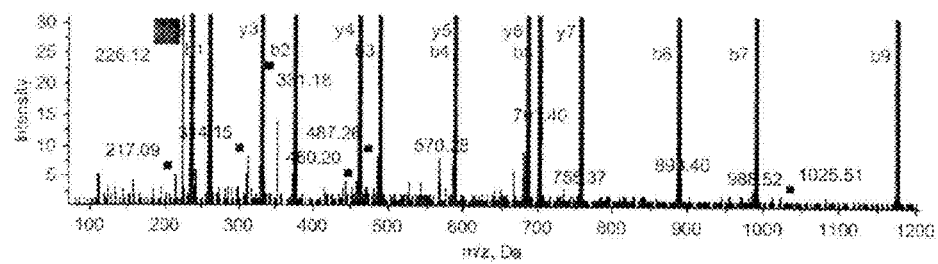
Figure 9B:
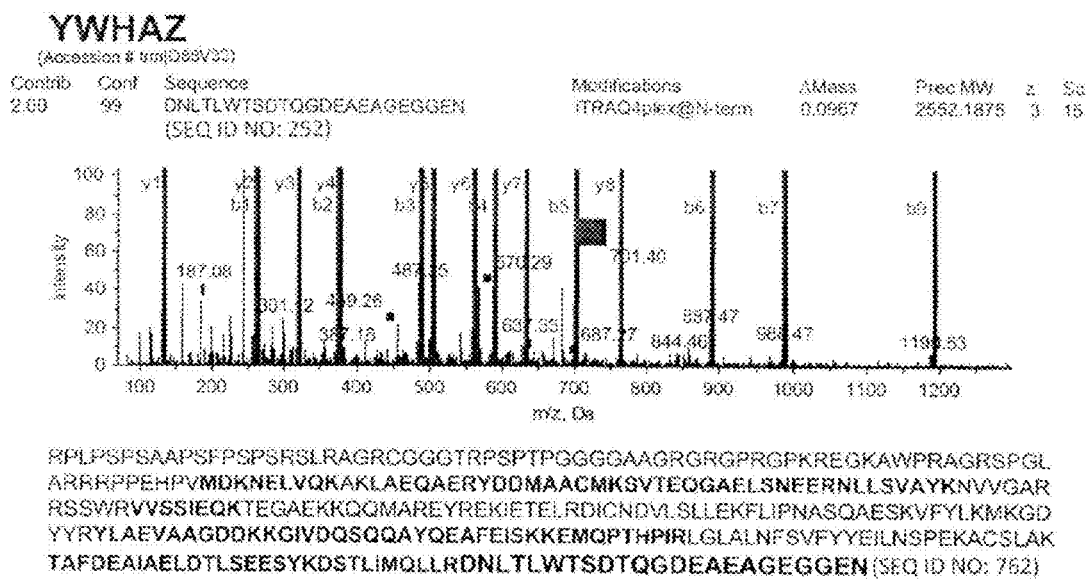

Provided below is a summary of the results obtained by the inventors in connection with the experiments of Examples 14-20:

To determine the clinical significance of stratifin and YWHAZ in head-and-neck tumorigenesis, their expressions were analyzed in HNOSCCs (51 cases) and non-malignant tissues (39 cases) using immunohistochemistry. Significant increase in stratifin expression was observed in the HNOSCCs as compared to the non-malignant mucosa (p=0.03, Odd's Ratio (OR)=3.8, 95% CI=1.6-9.2). Kaplan-Meier survival analysis reveals correlation of stratifin overexpression with reduced disease-free survival of HNOSCC patients (p=0.06). The most intriguing finding is the significant decrease in median disease-free survival (13 months) in HNOSCC patients showing overexpression of both stratifin and YWHAZ proteins, as compared to patients that did not show overexpression of these proteins (median disease-free survival=38 months, p=0.019), underscoring their utility as adverse prognosticators for HNOSCCs. Co-immunoprecipitation assays show the formation of stratifin-YWHAZ heterodimers in HNOSCC and interactions with NFκB, β-catenin, and Bcl-2 proteins. These results indicate the involvement of these proteins in the development of head-and-neck cancer and their association with adverse disease outcome. The amino acid sequences of stratifin and YWHAZ with peptides identified by MS and MS/MS are given in FIGS. 9A and 9B, respectively.

Immunohistochemical Analysis of Stratifin in HNOSCCs and Non-Malignant Tissues.

Figure 10:
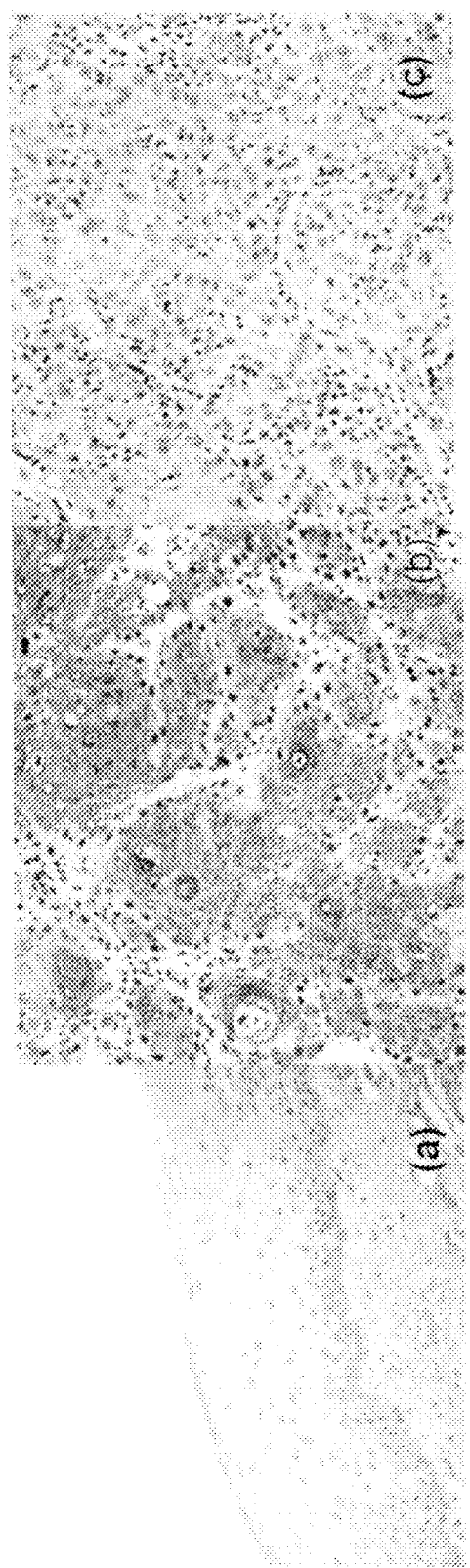
Figure 11:
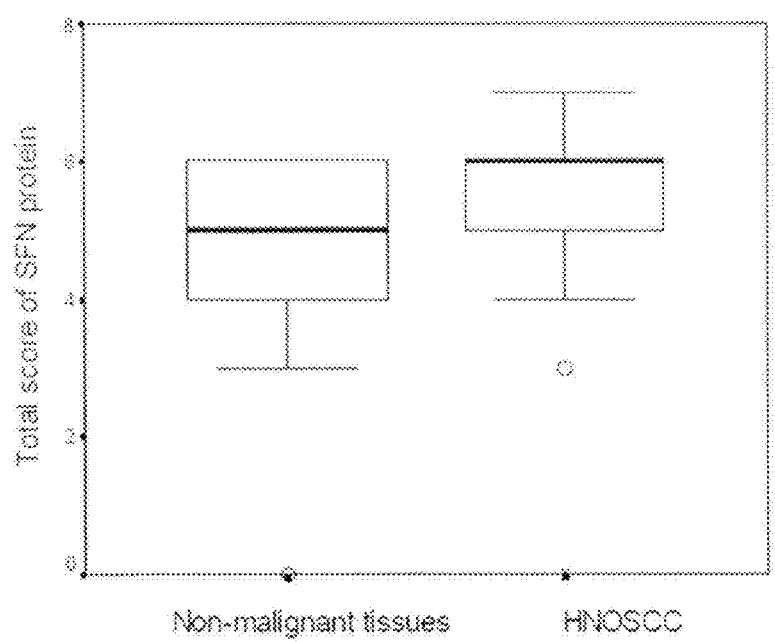

Results of the immunohistochemical analysis of stratifin expression in HNOSCCs and non-malignant mucosa, and the relationship with clinicopathological parameters are summarized in Table 8. Chi-Square analysis shows significant increase in stratifin expression in HNOSCCs as compared to non-malignant mucosa (p=0.03, OR=3.8, 95% CI=1.6-9.2). In histologically normal oral tissues, 31% of the cases show weak immunostaining of stratifin (FIG. 10a). Increased stratifin expression was observed in 63% of HNOSCCs. Intense nuclear/membranous staining, in addition to cytoplasmic staining, was observed in the epithelial cells of HNOSCCs (FIG. 10b). No immunostaining was observed in tissue sections used as negative controls where the primary antibody was replaced by isotype specific IgG (FIG. 10c). No significant correlation was observed between stratifin overexpression and clinicopathological parameters including age, gender, histological differentiation, tumor stage, and nodal status of HNOSCCs (Table 8). Increased expressions of stratifin were observed in HNOSCCs with a median score of 6 (range 4-7) as compared to non-malignant (histologically normal) oral tissues median score of 5 (range 4-6) shown in the box plot analysis in FIG. 11.

Co-Immunoprecipitation.

Figure 12:
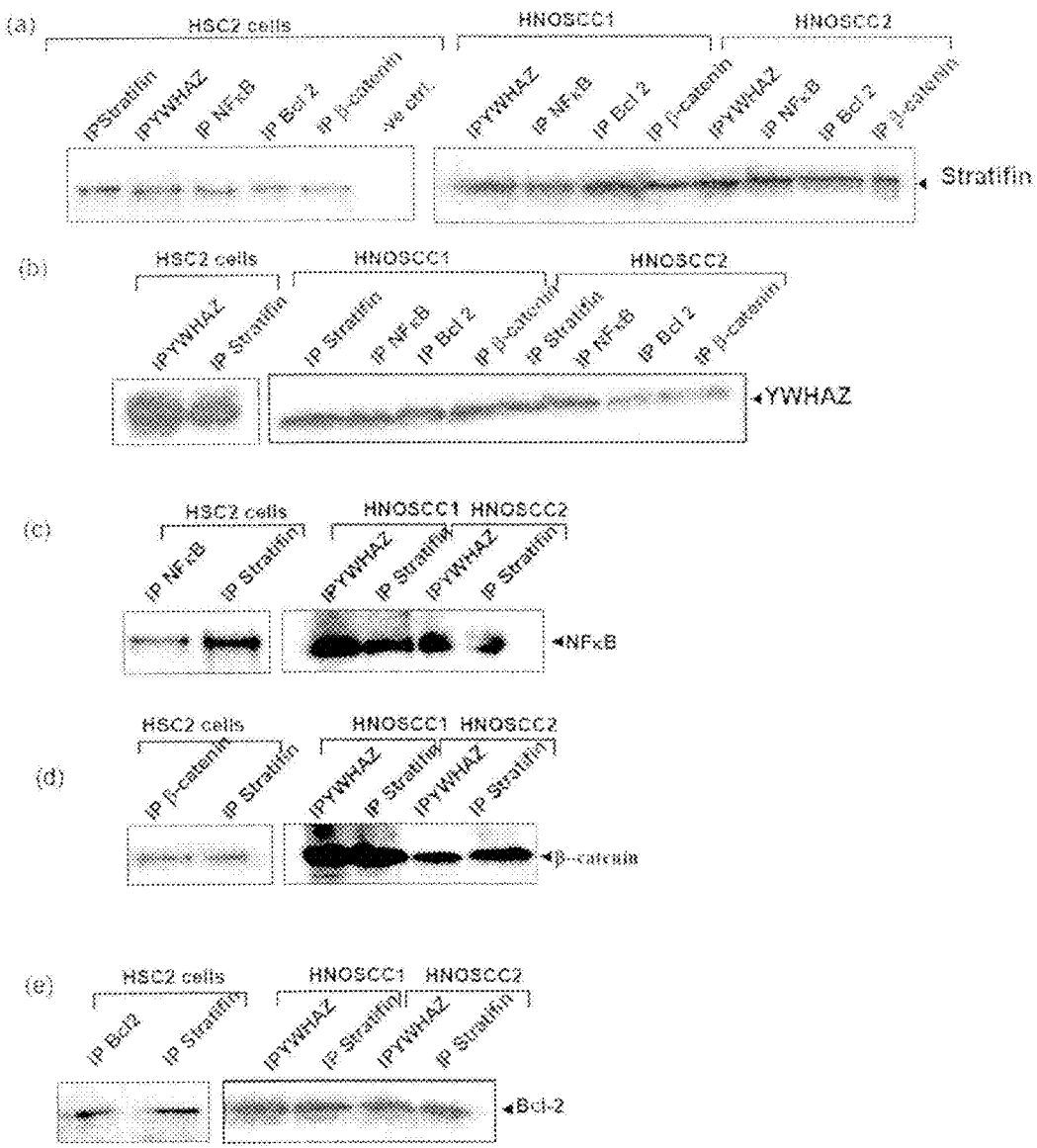

To determine the functional significance of stratifin in head-and-neck carcinogenesis, the inventors identified its binding partners in oral cancer cells, HSC2, using co-IP assays followed by Western blotting. IP of stratifin reveals its binding to YWHAZ NFκB, β-catenin, and Bcl-2 proteins as shown in FIG. 12a. Reverse IP assay using specific antibodies for these proteins followed by Western blotting confirmed their binding to stratifin (FIG. 12b). No band was observed in the immunoblot analysis of the negative controls. It is noteworthy that all these proteins—stratifin, YWHAZ, NFκB, β-catenin and Bcl-2—have 14-3-3 binding motif, Mode 1, as previously reported by the inventors (39).

Association of Stratifin and YWHAZ Expression with Disease Outcome.

Figure 13:
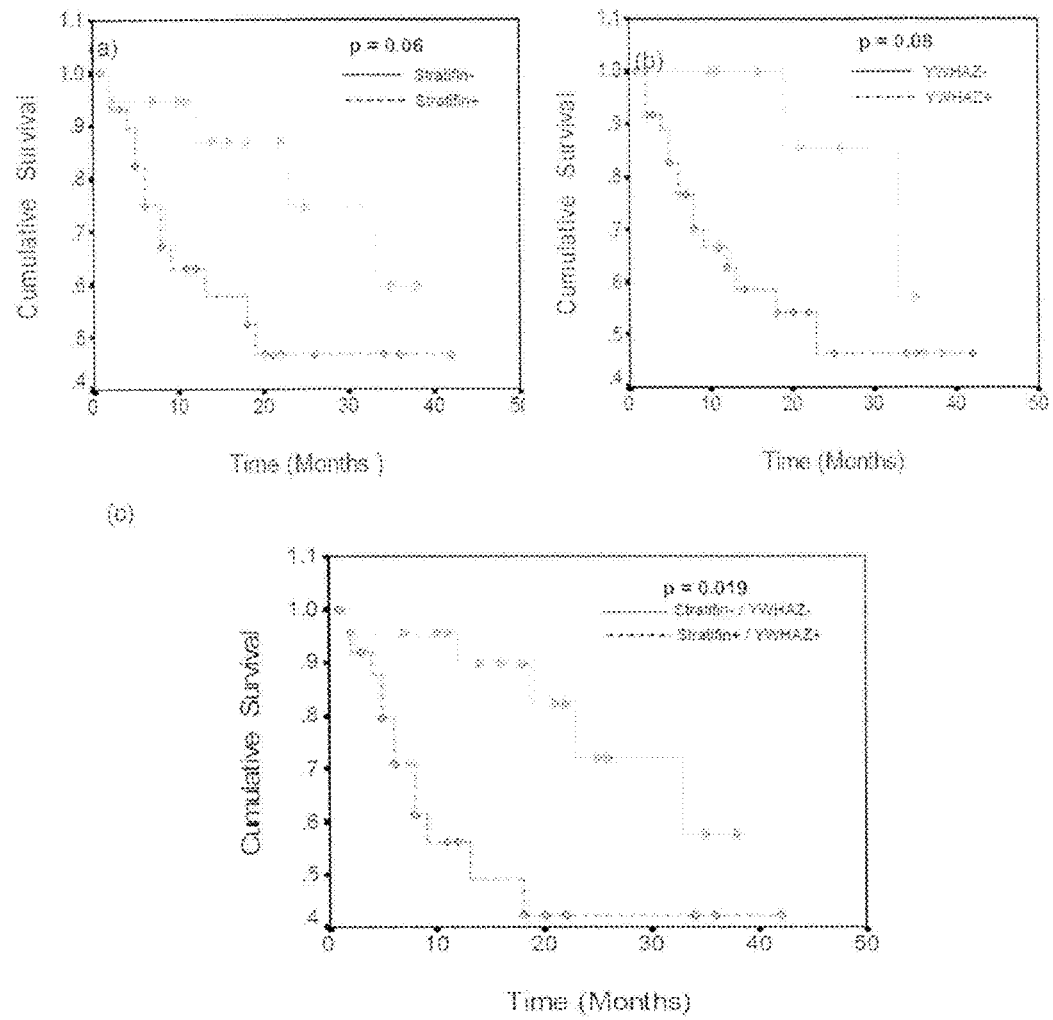

Kaplan-Meier Survival analysis reveals reduced disease-free survival for HNOSCC patients overexpressing stratifin (p=0.06, FIG. 13a). The median disease-free survival was 19 months in HNOSCC patients showing stratifin overexpression as compared to 38 months in HNOSCC patients who did not. Patients with YWHAZ-positive tumors had a shorter disease-free survival (median=23 months) than YWHAZ-negative tumors (median=35 months; p=0.08, FIG. 13b). Most remarkably, HNOSCC patients showing overexpressions of both stratifin and YWHAZ have a significantly decreased median disease-free survival of 13 months (p=0.019, FIG. 13c) in HNOSCCs, as compared to patients showing no overexpression of these two proteins (median=38 months), underscoring the utility of these proteins as adverse prognosticators for HNOSCCs.

Without being bound by theory, the results obtained in the experiments of Examples 14-20 are discussed below:

This investigation is one of the very few studies that demonstrate the prognostic utility of candidate biomarkers identified using MS-based proteomics. Recently, a comparison of protein profiles in tumor-distant head-and-neck tissues with clinical outcomes was reported to reveal a significant association between aberrant profiles and tumor-relapse events, suggesting that proteomic profiling in conjunction with protein identification may have significant predictive power for clinical outcome (12). The concept of using a panel of biomarkers for the purpose of improved diagnostics has taken hold in recent years. For example, DeSouza et al. (21) and Dubé et al. (101) demonstrated that the use of a panel of three biomarkers-chaperonin 10, pyruvate kinase M2, and α-1-antitrypsin-markedly increases the sensitivity and specificity for differentiating between endometrial carcinoma and non-malignant endometrial tissues. For head-and-neck cancers, Example 1 determined that a panel of biomarkers-stratifin, YWHAZ, and S100A7-performs better than any of the individual biomarkers for the detection of HNOSCC (23). In this current study, it is found that a panel of two biomarkers-stratifin and YWHAZ-shows promise as prognostic markers for HNOSCCs. Although not wishing to be bound by any particular theory, the enhanced performance of the combination of stratifin and YWHAZ versus either protein individually, in prognosing the clinical outcome of HNOSCCs, can be understood on the basis of their biological functions detailed below.

Results of in vitro studies demonstrate the formation of stratifin-YWHAZ heterodimers and binding of stratifin to NFκB, β-catenin, and Bcl-2, implicating stratifin's involvement in many cellular processes associated with tumorigenesis. Similar to the present invention, Bhawal et al. (96) have very recently reported increased expression of the stratifin transcript and protein in OSCCs. These results are in accordance with findings of Chen et al. (45) and Lo et al. (15, 44) who reported overexpression of stratifin in OSCCs. In addition, Lo et al. (15) demonstrated ten-fold increases in stratifin expression in HPV18-positive OSCCs in comparison with HPV18-negative OSCCs. It is of note that all these studies are on Asian populations. By contrast, studies on European populations reported decreased expression of stratifin in HNSCCs (12). If this geographical difference stands up to further scrutiny, it points to the importance of genetic and/or risk factors in developing HNOSCCs. Furthermore, epigenetic inactivation of stratifin has been shown to be associated with p16 gene silencing and HPV negativity in OSCCs (102). Thus these results suggest different mechanisms at work in HNOSCC tumorigenesis exhibiting overexpression of stratifin and tumorigenesis that does not. Whether these different mechanisms can be attributed to the presence or absence of HPV infection and/or differences in risk factors, such as smoking and drinking in the European and Western populations, and chewing of betel quid and/or tobacco in the Asian population, remains to be determined.

Overexpression of stratifin has been observed in other human cancers. Perathoner et al. (99) suggested that stratifin overexpression promotes tumor proliferation and/or prevents apoptotic signal transduction in colorectal carcinoma. Samuel et al. (103) demonstrated the role of stratifin in prevention of apoptosis by influencing the sub-cellular distribution of the pro-apoptotic protein, Bax, in colorectal cancer cells. Deletion of stratifin has been correlated with increased sensitivity of colorectal cells to doxorubicin. Similarly, Guweidhi et al. (104) proposed an anti-apoptotic role for stratifin in pancreatic cancer cells by inhibiting bad-mediated apoptosis. Liu et al. (105) showed that elevated stratifin expression contributes considerably to the observed drug resistance in MCF7/AdVp3000 cells. Stratifin has been shown to be a pivotal MDM2 regulator, involved in blocking a variety of MDM2 activities, including MDM2-mediated cytoplasmic localization of p53. Stratifin overexpression leads to destabilization of MDM2 by enhancing its self-ubiquitination and, thereby, stabilizing the cellular p53 (106). In previous studies, the inventors reported that p53 mutations are infrequent in OSCCs in the Indian population, despite stratifin overexpression; a currently unknown mechanism must be involved in stabilizing p53 in these OSCC patients (107, 108). The present inventors have also reported overexpression of MDM2 and cyclinD1 in OSCCs (109). Investigation of the relationship between stratifin overexpression, p53 stabilization, MDM2 and cyclinD1 expressions in HNOSCCs is currently underway.

The inventors, in a recent study aimed at delineation of early changes in expression of proteins in hyperplasia, demonstrated increased expressions of NFκB and COX-2 in early pre-malignant stages of the development of oral cancer and sustained elevation along the tumorigenic pathway (90). Furthermore, increased expression of YWHAZ in different stages of the development of OSCC and YWHAZ's involvement in cell signaling pathways involved in inflammation, cell proliferation and abrogation of apoptosis during oral carcinogenesis (39) was shown. Herein the inventors extend these findings by demonstrating the binding of stratifin with YWHAZ, thus suggesting the formation of stratifin-YWHAZ heterodimers and binding to NF-kB in oral cancer. These findings are supported by the study of Aguilera et al. (91) which showed the requirement of 14-3-3 proteins for efficient export of the p65 sub-unit of NF-kB. Taken together with the inventors' earlier findings of YWHAZ it is hypothesized that 14-3-3 proteins may be an important link between chronic inflammation and cancer that warrants further investigation.

The Co-IP results show stratifin binding also with β-catenin and Bcl-2 proteins. Earlier, the inventors showed that these proteins interact with YWHAZ thereby supporting the hypothesis that these complexes may be responsible for altered functions of stratifin. Fang et al. (92) recently showed that AKT, which is activated downstream from epidermal growth factor receptor signaling, phosphorylates β-catenin at Ser-552 in vitro and in vivo, causing its dissociation from cell-cell contacts and accumulation in both the cytosol and nucleus, and enhancing its interaction with YWHAZ via a binding motif containing Ser-552. This phosphorylation of β-catenin by AKT increases β-catenin's transcriptional activity and promotes tumor cell invasion, indicating that AKT-dependent regulation of β-catenin plays a critical role in tumor invasion and development. The oncogenic role of YWHAZ has been proposed in a recent study using siRNA for knocking down its expression in cancer cells (93). Down-regulation of YWHAZ sensitizes cells to stress-induced apoptosis and JNK/p38 signaling; in addition, it enforces cell-cell contacts and expression of adhesion proteins. YWHAZ's oncogenic properties is also supported by a Web-based meta-analysis (Onco-mine) that reveals its overexpression in various types of carcinomas (39, 93). To unravel the functional significance of 14-3-3 proteins in tumor development, the present inventors have investigated the functional significance of the interactions between stratifin and YWHAZ, and their respective roles in the development and progression of HNOSCC. All indications are that targeting specific 14-3-3 isoforms may serve as a plausible strategy for cancer therapy.

Hence, stratifin is overexpressed in HNOSCCs relative to normal tissues. Increased concomitant expression of stratifin and YWHAZ serves as adverse prognosticator in HNOSCCs and underscores the importance of these proteins in head-and-neck tumorigenesis. Increased expression of stratifin forming stratifin-YWHAZ heterodimers and binding to NFκB, β-catenin, and Bcl-2 proteins suggest the implication of these complexes in diverse cellular processes in head-and-neck carcinogenesis. It is submitted that targeting the stratifin-YWHAZ heterodimer, using small molecule modulator/peptide inhibitor that intervenes with 14-3-3 client protein interactions, would serve as a plausible therapeutic strategy for head-and-neck cancer.

Example 21—Patients and Clinicopathological Data Collection and Tumor and Biopsy Specimens The Institutional Human Ethics Committee of the All India Institute of Medical Sciences (AIIMS), New Delhi, India, approved this study prior to its commencement. Tissue specimens were obtained from diagnostic or therapeutic procedures from 199 patients with oral leukoplakia (with no dysplasia (n=115) or with dysplasia (n=84) (Table 9A)) attending the Outpatient Clinic of the Departments of Surgical Disciplines and Otolaryngology, AIIMs, and from 100 HNOSCC patients undergoing curative cancer surgery during the period 2002-2007, after obtaining patient consents. Wherever possible non-malignant tissues (n=30) were taken from a site distant from the surgically resected HNOSCC patients. Non-malignant normal oral tissues (n=25) were also collected from the patients attending the Outpatient Department of Dental Surgery for tooth extraction. Taken together, these 55 non-malignant oral tissues with histological evidence of normal epithelium constituted the normal group. After excision, tissues were immediately snap-frozen in liquid nitrogen and stored at −80° C. in the Research Tissue Bank till further use; one part of the tissue was collected in 10% formalin and embedded in paraffin for histopathological and immunohistochemical analyses.

The histopathological assessment scoring was based on the architectural and cytological changes of grading epithelial dysplasia described in the WHO classification and recently reviewed (3). For each case, the pathologist recorded the grade and details of the criteria on which the decision was based. Leukoplakic lesions were classified into two groups: (a) lesions with no dysplasia, (b) lesions with dysplasia.

Histologically confirmed oral normal epithelia, leukoplakia with evidence of no dysplasia or with dysplasia, and HNOSCCs as revealed by H&E staining were used for immunohistochemistry (32). Patient demographic, clinical, and pathological data were recorded in a pre-designed form as described previously (32). The information documented included clinical TNM staging (tumor, node, metastasis based on the Union International Center le Cancer TNM classification of malignant tumors 1998), site of the lesion, histopathological differentiation, age, gender, and tobacco consumption habits.

Example 22—Follow-Up Study

One hundred patients with oral leukoplakia who underwent treatment between 2002-2005 were followed up in the head-and-neck follow-up clinic at regular time intervals with the maximum follow-up period included in this study being 36 months. All small leukoplakic lesions (size< or =4×4 cm) were completely excised, while incisional biopsy was done for the large diffuse lesions (size>4×4 cm). The patients were followed every six months, and the status of each lesion was defined and recorded using following the criteria: (a) static: if it was within ±2 mm size on the largest diameter; (B) progressed: if it had grown more than 2 mm from the original (size of the residuam, if partially excised); and (c) regressed: if it was reduced in size by more than 2 mm from the original residuam. For the lesions that were excised completely-disease progression was defined as development of a new lesion after excision of the primary lesion at the same site, or at another site in the oral cavity. The lesions that had progressed as per the above mentioned criteria were re-biopsied and leukoplakic lesions with dysplasia were excised.

Seventy-seven HNOSCC patients who underwent treatment from 2002-2007 were also investigated and evaluated in the head-and-neck cancer follow-up clinic at regular time intervals. Survival status of the HNOSCC patients was verified and updated from the records of the Tumor Registry, Institute Rotary Cancer Hospital, AIIMs, as of May 2008. HNOSCC patients were monitored for a maximum period of 76 months. As per the hospital protocol, HNOSCC patients with T1 and T2 tumors were treated with radical radiotherapy or surgery alone, whereas the majority of patients with T3 and T4 diseases were treated by radical surgery followed by postoperative radical radiotherapy. The patients were revisited clinically on a regular basis and the time to recurrence was recorded.

If a patient died, the survival time was censored at the time of death; the medical history, clinical examination, and radiological evaluation were used to determine whether the death had resulted from recurrent cancer (relapsing patients) or from any other causes. Disease-free survivors were defined as patients free from clinical and radiological evidence of local, regional, or distant relapse at the time of the last follow-up. Loco-regional relapse/death was observed in 61 of 77 (79%) patients monitored during the follow-up. Sixteen patients who did not show recurrence were alive until the end of the follow-up period. Only disease-free survival was evaluated in the present study, as the number of deaths due to disease progression did not allow a reliable statistical analysis. Disease-free survival was expressed as the number of months from the date of surgery to loco-regional relapse.

Example 23—Immunohistochemistry

Paraffin-embedded sections (5 μm) of human oral non-malignant tissues (n=55), leukoplakic lesions (with no dysplasia (n=115) or with dysplasia (n=84)) and HNOSCCs (n=100) were collected on gelatin-coated slides. Immunohistochemistry conditions were optimized and evaluated by three of the inventors. In brief, the sections were deparaffinized in xylene, hydrated in gradient alcohol, and pre-treated in a microwave oven for 10 min in Tris-EDTA buffer (0.01 M, pH=9) for antigen retrieval. The sections were incubated with hydrogen peroxide (0.3% v/v) in methanol for 30 min to quench the endogenous peroxidase activity, followed by blocking with 1% bovine serum albumin (BSA) to preclude nonspecific binding. Thereafter, the slides were incubated with mouse monoclonal anti-hnRNPK antibody (1 μg/ml, ab23644, Abcam Inc., Cambridge, Mass.) for 16 h at 4° C. The primary antibody was detected using the streptavidin-biotin complex with the Dako LSAB plus kit (Dako CYTOMATION, Glostrup, Denmark) and diaminobenzidine as the chromogen (25). All procedures were carried out at room temperature unless otherwise specified. Slides were washed with Tris-buffered saline (TBS, 0.1 M, pH=7.4), 3-5 times after every step. Finally, the sections were counterstained with Mayer's hematoxylin and mounted with D.P.X. mountant. In the negative control tissue sections, the primary antibody was replaced by isotype-specific non-immune mouse IgG. A section from colorectal cancer tissue was used as a positive control in each batch of immunohistochemistry. The sections were evaluated by light microscopic examination.

Example 24—Evaluation of Immunohistochemical Staining

Each slide was evaluated for hnRNPK immunoreactivity using a semiquantitative scoring system for both staining intensity and the percentage of positive epithelial cells. Immunopositive staining was evaluated in randomly selected five areas of the tissue section. For hnRNPK protein expression, sections were scored as positive if epithelial cells showed immunopositivity in the nucleus/cytoplasm when observed independently by three of the inventors, who were blinded to the clinical outcome. (The slides were coded and the scorers did not have prior knowledge of the local tumor burden, lymphonodular spread, and grading of the tissue samples.) The tissue sections were scored based on the % of immunostained cells as: 0-10%=0; 10-30%=1; 30-50%=2; 50-70%=3 and 70-100%=4. Sections were also scored semi-quantitatively on the basis of staining intensity as negative=0; mild=1; moderate=2; intense=3 (17). Finally, a total score was obtained by adding the score of percentage positivity and intensity.

Example 25—Statistical Analyses

The immunohistochemical data were subjected to statistical analyses using the SPSS 10.0 software (Chicago). Sensitivity and specificity were calculated and quantified using ROC analyses. The PV describes the proportion of correctly classified cases. Based on sensitivity and specificity values for hnRNPK, a cutoff≥5 was defined as positive criterion for hnRNPK immunopositivity for statistical analyses. The relationships between hnRNPK protein expression and clinicopathologic parameters were tested using Chi-Square and Fischer's exact test. Two-sided p values were calculated and p<0.05 was considered to be significant.

For the follow-up study of 100 leukoplakia cases, let T denote the failure time, i.e., the first time the progression is diagnosed after excision of the leukoplakic lesions. For these data, the positive and negative predictive values as functions of time are defined as follows:

$PV_{nuclear}(t) = \text{Prob}(T \leq t \text{ AND Progression}|\text{hnRNPK (nuclear)} \geq 5)$;

$PV_{nuclear}(t) = \text{Prob}(T > t \text{ OR No Progression}|\text{hnRNPK (nuclear)} < 5)$;

$0 \leq t \leq 36$, and, analogously, for cytoplasmic hnRNPK. Similarly, PPV and NPV were calculated for recurrence in HNOSCCs (where t runs from 0 to 76 months). These probabilities are estimated from the observed accumulated incidences over the respective time periods. The correlation of hnRNPK staining with patient survival was evaluated using life tables constructed from survival data with Kaplan-Meier plots.

Example 26—Immunoblot Analysis of HNRNPK in Oral Tissues

Whole-cell lysates were prepared from oral non-malignant, leukoplakia and HNOSCC tissues by homogenization in lysis buffer containing 50 mM Tris-Cl (pH=7.5), 150 mM NaCl, 10 mM MgCl2, 1 mM ethylenediamine tetraacetate (EDTA, pH=8.0), 1% Nonidet P-40, 100 mM sodium fluoride, 1 mM phenylmethylene sulfonylfluoride (PMSF) and 2 µl/ml protease inhibitor cocktail (Sigma) as previously described (32). Protein concentration was determined using the Bradford reagent (Sigma) and equal amounts of proteins (80 µg/lane) were resolved on 10% sodium dodecyl sulfate (SDS)-polyacrylamide gel. The proteins were then electro-transferred onto polyvinylidenedifluoride (PVDF) membrane. After blocking with 5% non-fat powdered milk in Tris-buffered saline (TBS, 0.1 M, pH=7.4), blots were incubated with anti-hnRNPK monoclonal antibody (1 µl/ml, Abcam Inc., Cambridge, Mass.) at 4° C. overnight. Protein abundance of actin (goat polyclonal antibody, Santa Cruz Biotechnology, CA) served as a control for protein loading in each lane. Membranes were incubated with HRP-conjugated anti-mouse/goat secondary antibody, G (DAKO Cytomation, Glostrup, Denmark), diluted at an appropriate dilution in 1% BSA, for 2 h at room temperature. After each step, blots were washed three times with Tween (0.1%)-Tris-buffer saline (TTBS). Protein bands were detected by the enhanced chemiluminescence method (ECL, Santa Cruz Biotechnology, CA) on XO-MAT film.

Example 27—Reverse Transcription—PCT

Representative frozen tissue specimens of histologically confirmed oral normal tissues, leukoplakia and HNOSCCs were used for extraction of total RNA using the TRI reagent (Sigma, MO) as previously described (29). First-strand cDNA was synthesized using 2 µg RNA with oligo dT as the primer with MMLV reverse transcriptase. PCR was carried out using hnRNPK specific primers forward-(5'AGCA-GAGCTCGGAATCTTCCTCTT3' SEQ ID NO: 749) and reverse-(5'ATCAGCACTGAAACC AAC CA TGCC3' SEQ ID NO: 750) (Accession No. NM_002140). 20 µl of each PCR product was used for electrophoresis on a 1.2% agarose gel stained with ethidium bromide. The gel was visualized with UV light and photographed.

Provided below is a summary of the results obtained by the inventors in connection with the experiments of Examples 21-27:

Identification of hnRNP K in Oral Premalignant Lesions by Mass Spectrometry.

Figure 21A:
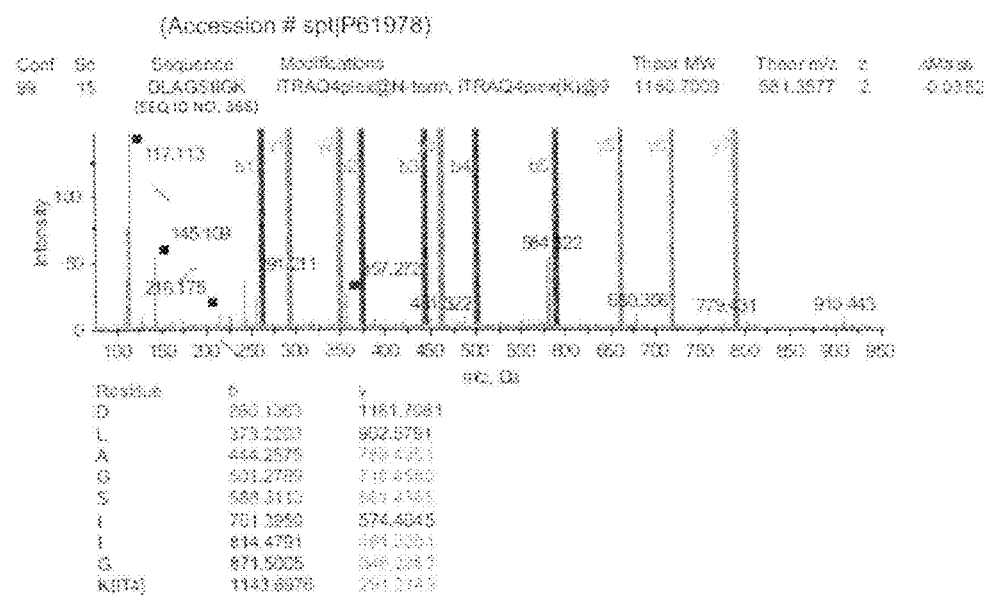
FIGS. 21A and 21B depict CID spectra of two peptides, A: DLAGSIIGK (SEQ ID NO: 368) and B: IDEPLEGSEDR (SEQ ID NO: 369), identified from hnRNPK in iTRAQ-labeled oral leukoplakia with dysplasia.
Figure 21B:
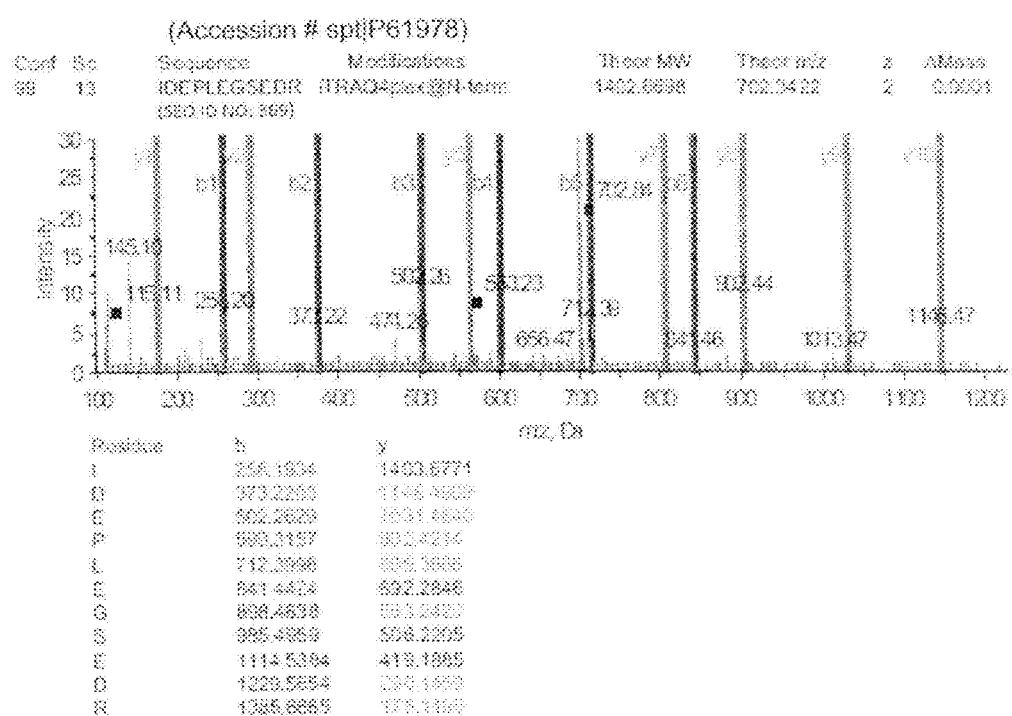

The tandem MS spectra for the two peptides, A: DLAG-SIIGK (SEQ ID NO: 368) and B: IDEPLEGSEDR (SEQ ID NO: 369), identified from hnRNPK in iTRAQ-labeled oral leukoplakia with dysplasia by LC-MS are given in FIGS. 21A and 21B, respectively. In each case, the topmost panel shows the confidence and score for each peptide, the sequence, theoretical mass, theoretical mass/charge ratio, charge state and difference between experimental and theoretical mass of the peptide. The expected product ion masses highlighted in the table in the middle are matched with the detected peaks in each spectrum. The lowermost panel in each case shows the location of the peptide within the context of the intact protein sequence.

Immunohistochemical Analysis of hnRNP K Expression in Oral Lesions.

To determine the clinical significance of hnRNPK protein in head-and-neck tumorigenesis, its expression was analyzed in different stages of HNOSCC development by means of immunohistochemistry using a specific monoclonal antibody. Of the 55 normal tissues analyzed, 51 cases (93%) showed faint or no detectable hnRNPK immunostaining in the nucleus/cytoplasm of the epithelial cells (Table 9a, FIG. 14a). However, four normal tissues showed nuclear expression of hnRNPK, as per positivity criteria defined in the Methods section; all these four tissues were obtained from a site adjacent to the tumor from HNOSCC patients, and thus the increased hnRNPK expression in these histological normal tissues may be a manifestation of field cancerization.

Chi square trend analysis showed significant increase in nuclear staining of hnRNPK in different stages of head-and-neck/oral tumorigenesis (normal, leukoplakia and HNOSCCs; Table 9a, ptrend<0.001). Of the 199 leukoplakias analyzed, 141 cases (71%) showed significant increase in nuclear hnRNPK immunostaining in comparison with the normal tissues (p<0.001, Odds ratio (OR)=30.9, 95% CI=10.7-89.7, Table 9a). Oral leukoplakia is a clinical terminology and histologically these lesions are classified into leukoplakia with no dysplasia or with dysplasia for disease management. Of the 199 leukoplakias, 115 cases showed no histological evidence of dysplasia; 78/115 (68%) cases showed significant increase in nuclear hnRNPK immunoreactivity in comparison with the normal tissues (p<0.001, OR=26.8, 95% CI=9.1-79.9, Table 1a and FIG. 14b). Importantly, progressive increase in nuclear expression of hnRNPK was observed in 75% dysplasias (63 of 84 cases, FIG. 14d) in comparison with normal tissues (p<0.001, OR=38.2, 95% CI=11.7-113.1).

Figure 14:
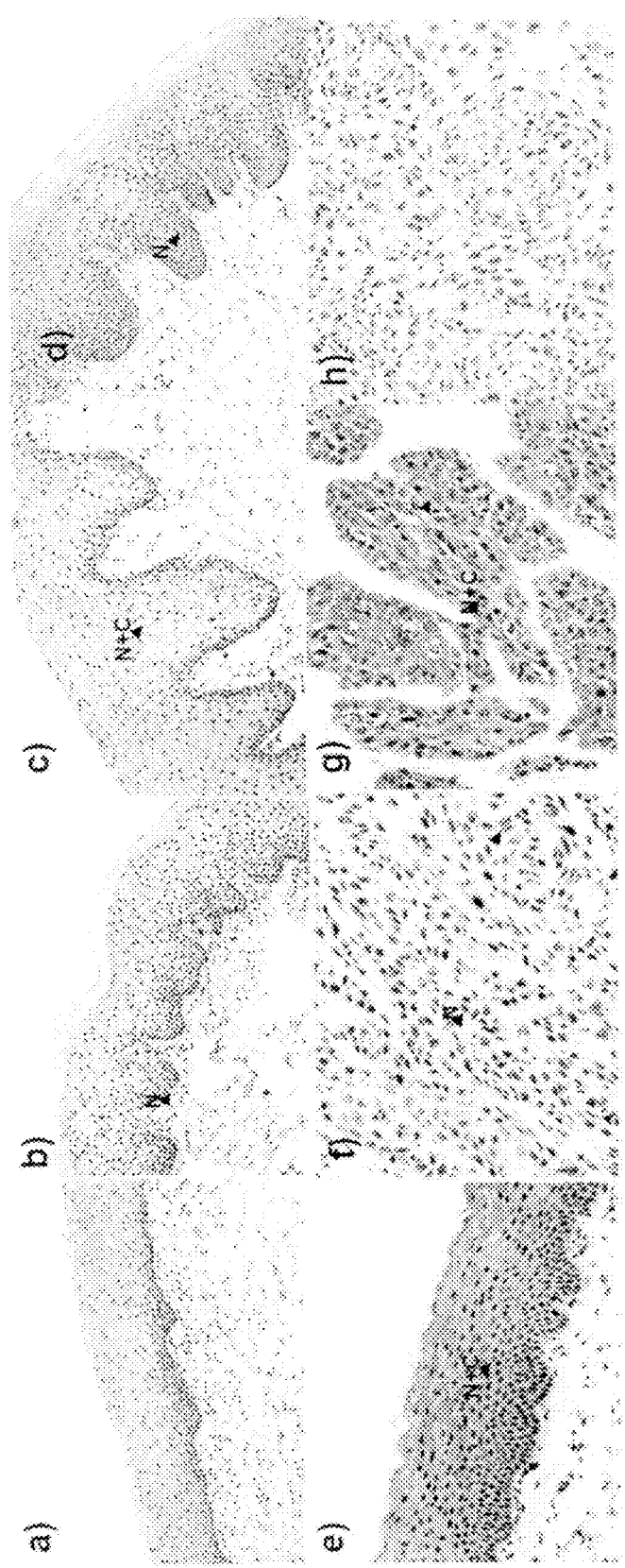

It is noteworthy that 26 of 199 leukoplakia cases showed cytoplasmic localization of hnRNPK, in addition to its nuclear expression, as shown in FIGS. 14c and 14e, respectively. Chi square analysis revealed that leukoplakias showing cytoplasmic hnRNPK staining are at 4.3-fold higher risk for cancer development (p<0.001, 95% CI=2.2-7.2, Table 9a). The majority of HNOSCCs (78%) showed nuclear localization of hnRNPK in tumor cells (FIG. 14f). In addition to nuclear staining, intense hnRNPK staining was also observed in the cytoplasm of tumors cells in 38 of 100 HNOSCCs analyzed (FIG. 14g).

The clinicopathological parameters of HNOSCCs patients and their correlation with nuclear/cytoplasmic expression of hnRNPK are shown in Table 9a. Increased cytoplasmic staining of hnRNPK showed a significant association with de-differentiation of HNOSCCs (p=0.001). Furthermore, no significant correlation between nuclear/cytoplasmic hnRNPK and other clinicopathological parameter, including gender, tumor size, nodal status or tobacco consumption of HNOSCC patients was found. No immunostaining was observed in tissue sections used as negative controls where the primary antibody was replaced by isotype specific IgG (FIG. 14h), while the positive control (colorectal cancer) showed nuclear expression of hnRNPK protein (data not shown).

Evaluation of hnRNP K as Potential Biomarker for Diagnosis and/or Prognosis.

Figure 15:
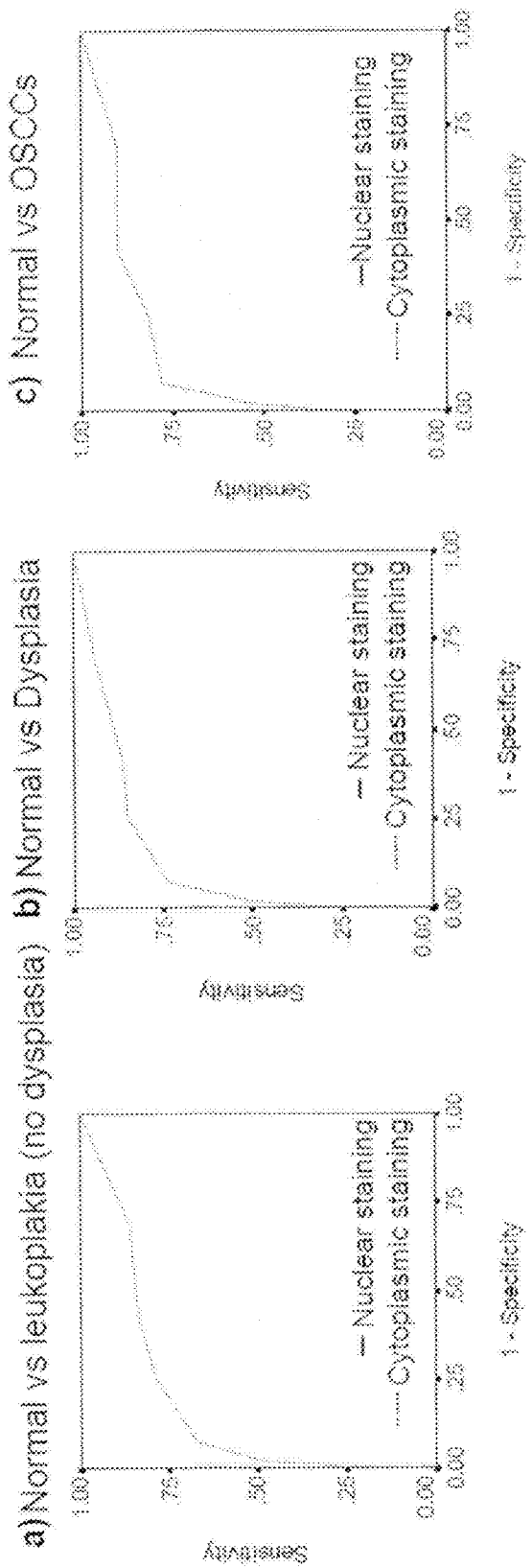

Receiver-operating characteristic (ROC) curve analysis was used to determine the potential of hnRNPK as a biomarker to distinguish leukoplakia and HNOSCCs from normal oral epithelium. The values for AUC were 0.822, 0.872 and 0.869 for leukoplakia without dysplasia (FIG. 15a), with dysplasia (FIG. 15b), and cancer (FIG. 15c), respectively, with respect to normal oral tissues based on the total score for nuclear immunostaining (Table 9b). The PPVs were 92.7, 92.3, and 92.3, respectively, for nuclear immunostaining in the three groups. Similarly, ROC analysis was used for determination of AUC and PPV for cytoplasmic hnRNPK staining in all these three groups as shown in Table 9b and FIG. 16a-c.

hnRNP K Expression as a Predictor of Disease Progression and Prognosis.

Significantly, the follow-up data sets of 100 leukoplakia patients for three years and 77 HNOSCC cases for seven years were used to assess the prognostic value of hnRNPK for predicting disease progression in patients with leukoplakia and cancer recurrence in HNOSCC patients after completion of primary treatment. Both PPVs NPVs of the prognostic test are of paramount importance in this context, with the former to correctly identify cases that need early intervention, and with the latter to gauge, in the most accurate way, where such intervention with its monumental personal impacts can and should be avoided.

Figure 16:
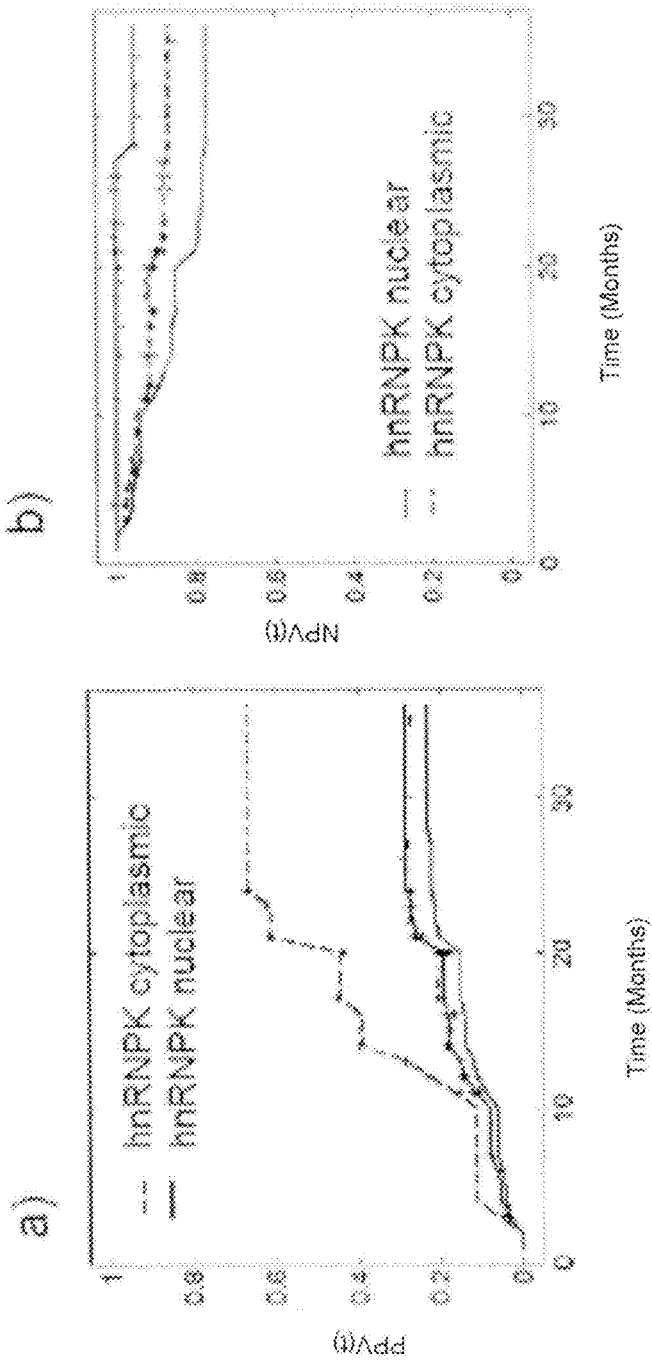
Figure 16:
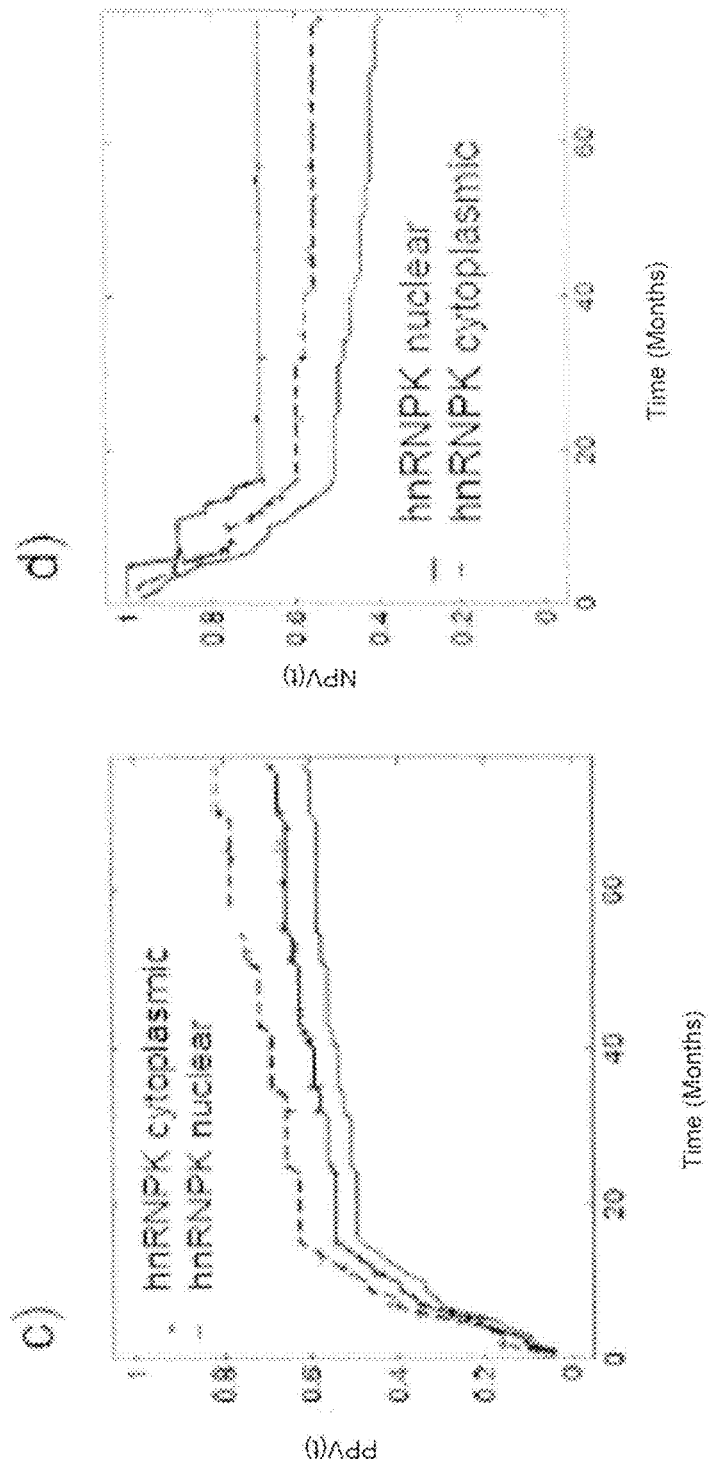

FIG. 16 shows the estimated PPVs and NPVs for nuclear and cytoplasmic hnRNPK expression as prognostic biomarkers. FIGS. 16a and 16b for disease progression of leukoplakia; and for cancer recurrence in HNOSCC patients (FIGS. 16c and 16d). Even though the absolute numbers that give rise to these estimates are only moderate (23 cases), cytoplasmic hnRNPK expression in leukoplakias (12 cases) appears to be a promising biomarker for disease progression, with PPVcyto (18 months)=44.4 and PPVcyto (36 months)= 66.7 (12 disease progressions). These values are compared with the PPVs of overall hnRNPK expression (both nuclear and cytoplasmic immunopositivity–PPVoverall), PPVoverall (18 months)=15.0 and PPVoverall (36 months)=23.0. These result in estimated ratios or relative positive predictive values of cytoplasmic hnRNPK expression for disease progression of 2.96 and 2.90 for 18 and 36 months, respectively.

On the other hand, high nuclear hnRNPK expression (22 cases) appears not, by itself, to define a biomarker of high prognostic value (PPV nuc (36 months)=28.2, compared with PPVoverall (36 months)=23). Of note, the negative predictive value of cytoplasmic hnRNPK expression in leukoplakias is very high (NPVcyto (36 months)=86.6). Based on the inventors' data, the additional prognostic value which hnRNPK, in either its nuclear or cytoplasmic expression, provides for predicting (PPV) or excluding (NPV) cancer recurrence in HNOSCC patients is: PPVnuc (76 months)/PPVoverall(76 months)=68.9/61.0; PPVcyto (76 months)/PPVoverall(76 months)=81.3/61.0; NPVnuc (76 months)/NPVoverall (76 months)=68.9/39.0; and NPVcyto (76 months)/NPVoverall (76 months)=53.3/39.0. Based on these analyses, the most significant improvement over clinicopathological criteria that cytoplasmic hnRNPK appears to offer as a marker is in predicting disease progression in leukoplakia patients and prognosis of HNOSCCs.

Figure 17:
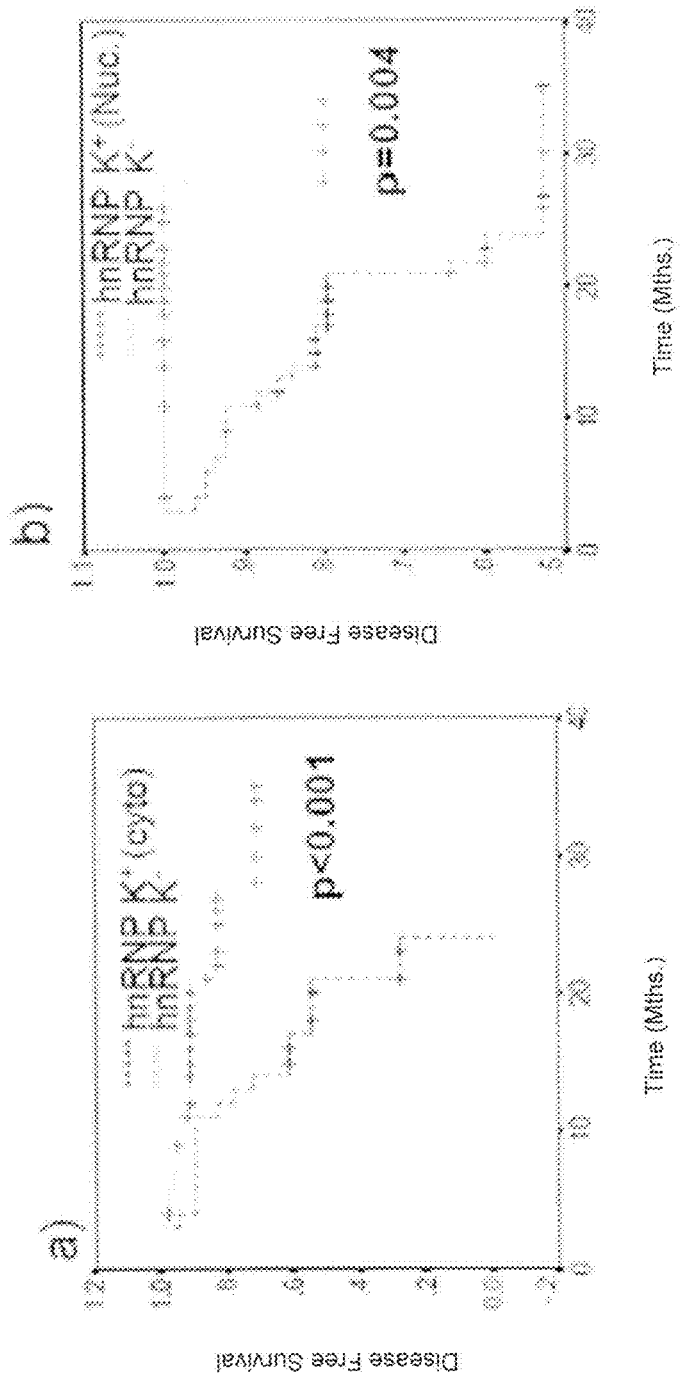
Figure 17:
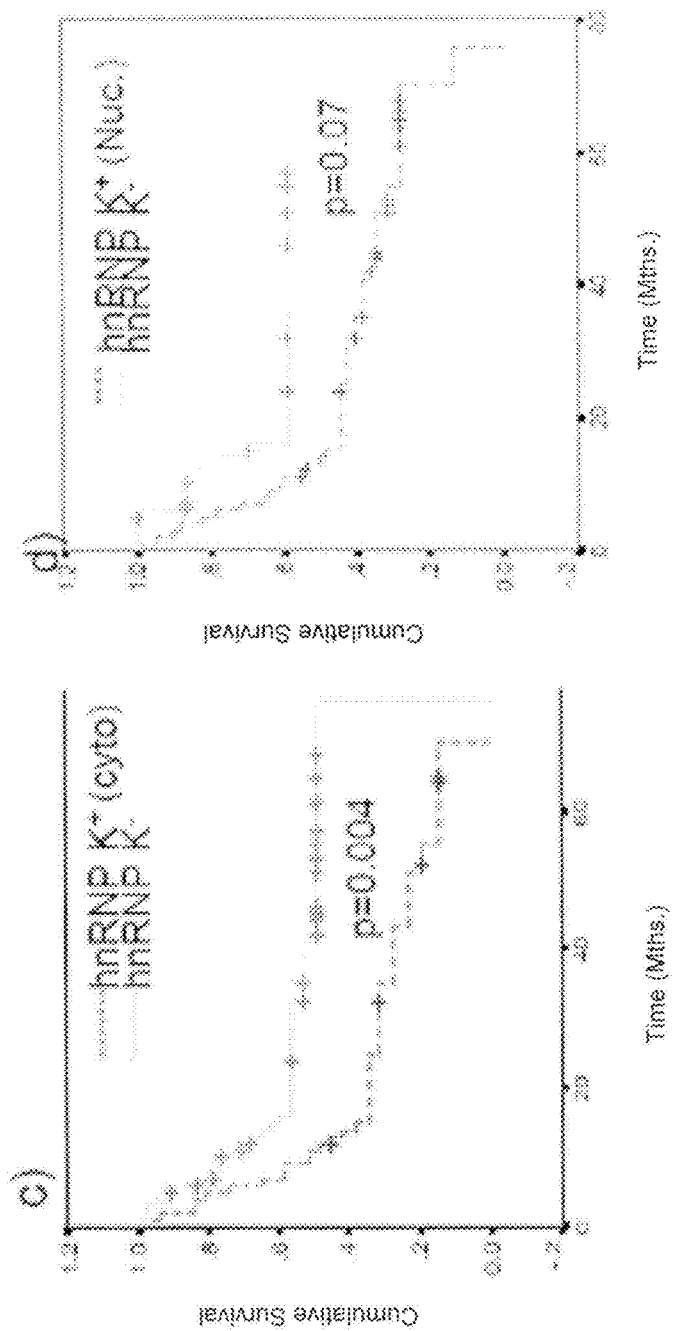

While PPVs. and NPVs. quantify the estimated predictive power of the marker, the strength of the statistical association of hnRNPK expression with poor prognosis was assessed by Kaplan-Meier survival analysis. Log-rank test showed significantly reduced time for disease progression (p<0.001; median time=17 months) in leukoplakia patients showing increased cytoplasmic expression of hnRNPK (18 cases), as compared to the median time of 35 months in the patients showing no/faint immunostaining of hnRNPK in the cytoplasm (FIG. 17a). Leukoplakia patients showing intense nuclear hnRNPK expression (78 cases) had poor prognosis, as compared to patients who did not show increased nuclear hnRNPK (p=0.004, FIG. 17b), though there was no significant difference in median time for disease progression. The inventors' findings clearly underscore the potential of cytoplasmic hnRNPK as a marker for predicting disease progression in leukoplakia patients. Of the 100 leukoplakia patients, 83 cases showed no histological evidence of dysplasia and similar correlations of cytoplasmic and nuclear expression were observed with disease progression for these leukoplakias (FIGS. 4a and 4b, respectively). However, similar statistical analysis could not be carried out for dysplasias due to the small number of cases in this group (17 cases).

In addition, Kaplan-Meier survival analysis showed significantly reduced disease free survival (p=0.004; median survival 11 months) in HNOSCC patients harboring increased cytoplasmic expression of hnRNPK, as compared to median disease-free survival of 41 months in the patients showing no/faint cytoplasmic hnRNPK immunostaining (FIG. 17c). Similarly, reduced disease-free survival of 14 months was observed in HNOSCC patients showing intense nuclear expression of hnRNPK, as compared to patients who did not show increased nuclear hnRNPK (median survival of 57 months); although this could not reach a statistically significant value of p≤0.05 (FIG. 17d). These findings clearly demonstrate the potential of nuclear hnRNPK as a biomarker for diagnosis, and cytoplasmic hnRNPK as a potential marker for predicting poor prognosis of HNOSCCs.

Immunoblotting and RT-PCR.

Figure 18:
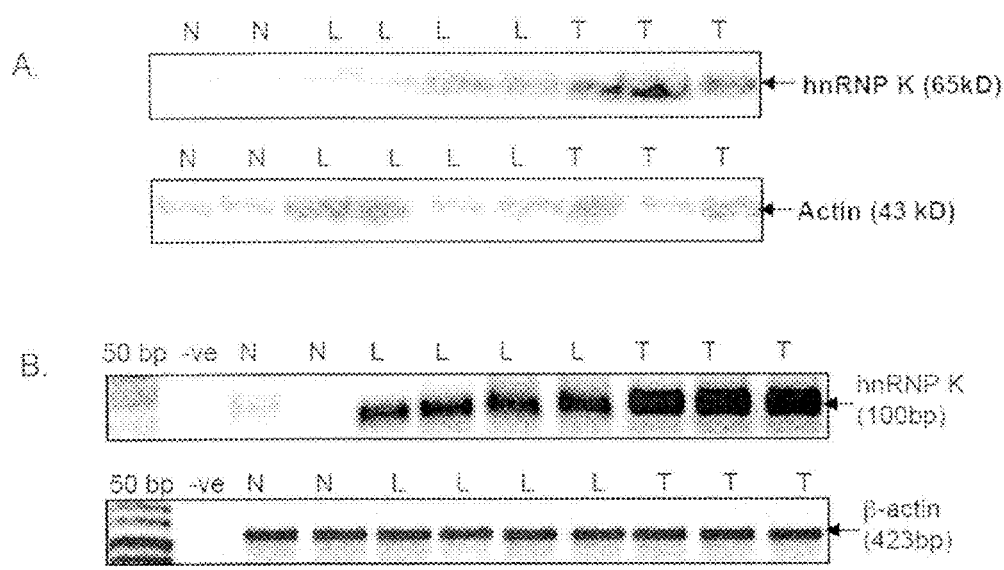

The overexpression of hnRNPK in oral lesions was further validated by immunoblotting and RT-PCR analyses in the same tissue samples as used for immunohistochemical analysis. Immunoblot analysis showed a single intense band of 64 kDa, confirming the increased expression of hnRNPK in oral leukoplakias and HNOSCCs, as compared to the normal tissues (FIG. 18A). RT-PCR analysis demonstrated increased levels of hnRNPK transcripts in the same tissue specimens of leukoplakias and HNOSCCs in comparison with normal tissues (FIG. 18B), thus supporting the immunohistochemical findings and suggesting transcriptional upregulation of hnRNPK in these tissues.

Without being bound by theory, the results obtained in the experiments of Examples 21-27 are discussed below:

hnRNPK overexpression in early oral lesions is a very important unique finding of this study, providing clinical evidence to establish its link with progression potential of leukoplakia in support of its proposed role as a transformation-related protein. To the inventors' knowledge, this is the first investigation to demonstrate the clinical application of a candidate biomarker identified using MS-based tissue proteomics in identifying early oral premalignant lesions that may be at high risk of disease progression. The salient findings of the inventors' study are: i) nuclear hnRNPK expression increases progressively from oral normal tissues to hyperplasia, dysplasia and frank malignancy and may serve as a plausible diagnostic marker for HNOSCCs; ii) cytoplasmic accumulation of hnRNPK is significantly increased from leukoplakia to cancer; (iii) aberrant subcellular localization (cytoplasmic accumulation) of hnRNPK is a predictor of disease progression in leukoplakia patients and disease recurrence in HNOSCC patients; iv) cytoplasmic hnRNPK is associated with poor prognosis of HNOSCCs; and v) hnRNPK is transcriptionally upregulated in head and neck tumorigenesis.

Expression profiling of different cancer types and mechanistic studies have strongly implicated hnRNPK as a key player in human cancers. To the inventors' knowledge, this study is the first report demonstrating increased expression of hnRNPK in oral leukoplakia by immunohistochemistry. The significantly increased nuclear expression of hnRNPK in oral hyperplastic lesions points to this alteration being an early event in the development of premalignant lesions and is in accord with its role as a transcriptional regulator of growth promoting genes such as myc and src and promoter of cell proliferation (111-117).

The major challenge in oral tumorigenesis is the identification of proteins that may serve as markers to predict high risk leukoplakias for early intervention. Most studies on leukoplakia focus on dysplastic lesions, while knowledge of molecular alterations in oral hyperplasia is meager. As per the existing literature, the malignant transformation potential is often linked to the severity of dysplasia; in comparison the hyperplastic lesions have received less attention, primarily because these lesions often undergo spontaneous regression. However, the lesions that do not regress need identification and biomarkers to predict the risk of malignant transformation.

In this context, the study assumes importance, because not only does it show aberrant hnRNPK expression as early as in hyperplasia, but the follow-up study also points to the relevance of cytoplasmic hnRNPK in predicting the risk of disease progression in leukoplakia patients with hyperplasia and HNOSCCs. It is noteworthy that studies on molecular analysis of leukoplakia with hyperplasia are very limited, because these patients often do not come to the clinics since their lesions are small and do not pose any overt clinical problem. However, it is extremely important to target this patient population for risk assessment and early intervention for cancer prevention in high risk cases. Hence, the inventors' findings are important and warrant further validation in larger independent studies on oral hyperplastic lesions. Furthermore, the cytoplasmic expression of hnRNPK protein observed in epithelial cells of a subset of hyperplastic and dysplastic lesions points to a potential role in development and progression during early stages of oral tumorigenesis, while the overexpression in HNOSCCs and association with poor prognosis suggests a sustained involvement in frank malignancy as well.

In this context, the aberrant cytoplasmic accumulation of hnRNPK protein in a small subset of leukoplakias (26/199, 13% cases) and larger proportion of HNOSCCs (38%) and its potential of risk prediction is noteworthy. The cumulative risk of leukoplakia to transform into OSCC range from 3.6 to 19.8%, 0.4 to 38%, 3 to 33%, and 0 to 20% in different studies; the calculated average amounted to 3% to 8.1% (35). Based on meta-analysis of several follow-up studies of leukoplakia patients an overall rate of 5% transformations in 5 years, resulting in an average annual transformation rate of 1% has been reported by Hunter et al. (2). This 3 year follow-up study showed disease progression in 23/100 leukoplakia patients, 12/23 showed cytoplasmic accumulation of hnRNPK. Long-term follow-up of these leukoplakia patients is needed to establish the link between cytoplasmic hnRNPK and risk of cancer development.

Kaplan-Meier survival analysis revealed association of cytoplasmic hnRNPK with disease progression of leukoplakia and poor prognosis of HNOSCC. Furthermore, analysis of the predictive potential of hnRNPK revealed its utility as a marker to identify high risk leukoplakia and aggressive HNOSCCs, supporting the association observed by Kaplan Meier analysis. These findings also suggest that leukoplakic lesions with cytoplasmic hnRNPK protein expression are at high risk of disease progression and warrant early intervention as well. The potential mechanistic link between cytoplasmic hnRNPK expression and potential of malignant transformation remains to be established. Efforts are currently underway to demonstrate the role of hnRNPK in malignant transformation of cell cultures established from oral hyperplastic lesions in vitro.

The poor prognosis of HNOSCC patients showing aberrant cytoplasmic hnRNPK protein expression also supports a role for this protein in progression of HNOSCCs. Interestingly, aberrant cytoplasmic hnRNPK protein expression has also been observed in colorectal cancers (88). Importantly, nasopharyngeal carcinoma patients showing cytoplasmic hnRNPK were reported to have significantly reduced distant metastasis free survival (118). The cytoplasmic hnRNPK expression may be attributed to the presence of a N-terminal bipartite nuclear localization signal and a hnRNPK-specific nuclear shuttling signal that confer the capacity for bidirectional transport across the nuclear envelope (114). Recently, the K nuclear shuttling (KNS) domain, a well-known signal for nuclear import and export, has also been shown to be responsible for the transactivation activity of hnRNPK protein (119). The cytoplasmic accumulation of hnRNPK is controlled by extracellular signal-regulated kinase (ERK)-dependent serine phosphorylation (Ser284 and Ser353) (120). In the cytoplasm, hnRNPK functions as a translational regulator of specific mRNAs, such as c-myc mRNA, renin mRNA, human papillomavirus type 16 L2 capsid protein mRNA, and reticulocyte-15-lipoxygenase (r15-LOX) mRNA (121-124). HPV 16 and 18 have been associated with a large proportion of HNOSCCs, especially among non-consumers of tobacco, though the molecular mechanisms underlying the development of HPV associated HNOSCCS are under intense investigation. Recent proteomic analysis of HPV positive and HPV negative OSCCs have revealed differences in protein expression patterns; whether hnRNPK plays different roles in these tumor subtypes remains to be investigated (15). In the cytoplasm, hnRNPK functions as a specific activator of c-Src and is a substrate of this tyrosine kinase. c-Src-dependent phosphorylation modulates the r15-LOX mRNA-binding activity of hnRNPK and its function in the control of mRNA translation during erythroid cell maturation (113, 114, 124). Taken together with the diverse influence of hnRNPK on gene expression and mechanisms regulating hnRNPK subcellular localization, it is speculated that gene dysregulation resulting from cytoplasmic accumulation of hnRNPK may play an important role in tumorigenesis.

Hence, hnRNPK has herein been shown to be overexpressed in oral lesions—early premalignant stages of tumorigenesis and in frank tumors in comparison with normal oral tissues both at protein and transcript levels. Furthermore, its subcellular localization—predominantly nuclear in hyperplasias, but present in both cytoplasm and nucleus in a subset of hyperplasias and dysplasias and increasing cytoplasmic expression in tumor cells, suggests that nuclear-cytoplasmic translocation may have an important role in malignant transformation of oral cancer cells. The most important finding is that cytoplasmic hnRNPK is a predictor of disease progression in leukoplakia patients and poor prognostic marker for HNOSCCs, hence targeting hnRNPK might be a new chemopreventive/therapeutic strategy in head and neck/oral cancer. Large scale studies are warranted to further evaluate hnRNPK's potential as an indicator of risk of progression of leukoplakia and role in development and progression during early stages of head and neck/oral tumorigenesis.

Example 28—S100A7 Overexpression is a Predictive Marker for High Risk of Malignant Transformation in Oral Dysplasia In this example, 5 candidate protein biomarkers were evaluated for their potential use in assessing the risk of cancer development from oral dysplasias. In particular, the results of this example support the use of S100A7 overexpression as a biomarker for identifying oral dysplastic lesions at high risk of cancer development.

Materials and Methods.

Study Population Characteristics and Criteria.

This study was approved by the research ethics board of Mount Sinai Hospital, Toronto, Canada, prior to commencement. Patient charts from 2000 to 2010 containing clinicopathological diagnosis of dysplasia were retrospectively reviewed in the Department of Pathology at Mount Sinai Hospital to obtain clinical information and follow-up data. Information regarding gender, age, site of lesions at the time of initial dysplasia diagnosis and smoking history was documented in a clinical database. Patients with oral lesions having histopathological evidence of dysplasia and a known clinical outcome were included in this study. Patients with oral lesions with dysplasia but with no available follow-up data and patients diagnosed with oral lesions with dysplasia concomitant with OSCC at the first visit were excluded from this study.

Based on the aforementioned inclusion/exclusion criteria, an independent set of 110 patients with dysplasia were selected for further analysis. There was no overlap of dysplasia cases used in the present study with the samples used in the discovery set published previously (87). In cases where patients with oral lesions underwent multiple biopsies, the first biopsy section with histological evidence of dysplasia was used for immunostaining.

All patients with oral lesions had an initial biopsy. The patients with histopathological evidence of mild dysplasia were monitored at six-month intervals. A repeat biopsy was performed if the lesion changed in appearance. Patients with moderate or higher grades of dysplasia had excision of the lesions wherever feasible clinically. When excision was not feasible, the patient was continually monitored with repeat biopsies for clinically suspicious areas for cancer development.

Histopathology.

The histopathologic diagnosis in all cases was re-examined and confirmed by oral pathologists at Mount Sinai Hospital according to the World Health Organization (WHO) criteria. Dysplastic areas were selected from a hematoxylin and eosin (H&E) stained section of each tissue sample. Dysplastic lesions were classified as mild, moderate or severe dysplasia based on WHO standard criteria (3). These cases included mild (n=58), moderate (n=39) and severe (n=13) dysplasia. Of 110 tissue blocks reviewed for inclusion in this study, 86 dysplasia cases were used for construction of tissue microarrays (TMAs) and 24 cases were used for immunohistochemistry using whole tissue sections.

Construction of Tissue Microarrays (TMAs).

The TMA blocks were constructed by relocating small cylindrical tissue cores (2 cores per tissue block representing the dysplasia sections) from individual donor blocks and placing them in a recipient block with defined array coordinates. Arrays were constructed from formalin-fixed paraffin embedded (FFPE) tissues by the removal of 0.6 mm diameter tissue cores from donor blocks. A total of two morphologically representative areas of interest from each donor block were identified under the microscope by a pathologist using a stained H&E section as a guide. Using a precise spacing pattern on a manual TMA instrument, 150-200 cores could be transferred to the recipient paraffin block in a grid like fashion, retaining a link to the original block and its pathology. Consecutive 4 µm sections were cut from the recipient block and used for immunohistochemical staining for p16, five candidate protein biomarkers and HPV 16/18 status using chromogenic in situ hybridization (cISH) as described below.

Immunhistochemistry (IHC) of Candidate Markers in Oral Lesions Using TMA.

TMA slides were immunostained using Vectastain Elite ABC kit (PK-6100) rapid protocol as described by the manufacturers (Vectastain Laboratories, CA). Antigen retrieval was performed using microwave in Tris-EDTA buffer pH=9.0 containing 0.05% Tween-20 for 15 minutes at 450 watts followed by 5 minutes at 900 watts. Slides were immunostained with the respective mouse monoclonal antibodies; anti-p16 (sc-1661, Santa Cruz Biotechnology, CA) at 1:100 dilution, anti-S100A7 (sc-52948, Santa Cruz Biotechnology, CA) at 1:500 dilution; anti-PTMA (LS-B2322, Lifespan Biosciences, WA) at 1:3500 dilution; anti-hnRNPK (ab23644, Abcam, MA) at 1:5000 dilution; anti-14-3-3σ (ab14116-50, Abcam, MA) at 1:2500 dilution; 14-3-3ζ (IMG-6664A, Imgenex, CA) at 1:100 dilution. Tissue sections of liver were used as positive control in the TMA slides. The sections were evaluated by light microscopic examination. Images were captured using the Visiopharm Integrator System (Horsholm, Denmark).

Evaluation of Immunohistochemical Staining.

Immunopositive staining was evaluated in five areas of the tissue sections as previously described (87, 100, 126, 127, 128). Sections were scored as positive if epithelial cells showed immunopositivity in the cytoplasm, and/or nucleus when observed by evaluators who were blinded to the clinical outcome. These sections were scored as follows: 0, <10% cells; 1, 11-30% cells; 2, 31-50% cells; 3, 51-70% cells; and 4, >70% cells showed immunoreactivity. Sections were also scored semi-quantitatively on the basis of intensity as follows: 0, none; 1, mild; 2, moderate; and 3, intense. Finally, a total score (ranging from 0 to 7) was obtained by adding the scores of percentage positivity and intensity for each of the tissue sections. The immunohistochemical data were subjected to statistical analysis as described below. Scoring by 2 observers was discrepant in about 2% of cases, wherein a consensus on the final result was reached by re-evaluation of these slides and discussion. An inter-rater reliability analysis using the K-statistic was performed to determine consistency among evaluators. The inter-rater reliability for the evaluators was found to be K=0.921 ($p<0.001$, 95% C.I.=0.83-1.01).

cISH for HPV16/18 Detection.

HPV 16/18 status was determined in formalin-fixed oral dysplasia tissue sections in TMA using a known cISH protocol. Briefly, formalin-fixed paraffin embedded oral dysplasia tissue sections in TMA were deparaffinized in xylene. Sections were treated by digestion with proteinase K, followed by hybridization with biotinylated DNA probes for HR-HPV genotypes 16/18 or human embryonic DNA used as a control for determining genomic DNA integrity as previously described (129). Cervical cancer tissue section was used as a positive control for detection of HPV 16/18 infection. For determining HPV 16/18 status, diffuse nuclear staining was considered as indicative of episomal HPV, while point-form nuclear staining was characteristic of integrated HPV16/18 DNA (129).

Follow-Up Data and Statistical Analysis.

Statistical analysis was performed using the software packages SPSS version 20.0 for Windows (SPSS Inc., Chicago Ill.) and R-statistical software version 2.12.2 (R Foundation, Vienna, Austria). Malignant transformation versus no transformation of oral dysplastic lesions was considered to be the clinical outcome of the patients in this study. A descriptive analysis was performed on clinical and pathological factors. Based on our earlier studies, a pre-defined cut-off value for each candidate protein biomarker was chosen for defining positivity (low/high score). The $\chi 2$ test and Fischer exact test were used to assess associations among categorical variables. Significance of our null hypothesis was verified using the Mann-Whitney test.

Follow-up period of dysplasia patients for oral cancer free survival (OCFS) was defined as the interval from the date when the patient underwent first biopsy to the date of malignant transformation (i.e. events) or no transformation at last consultation (for censored observations). Dysplasia patients were monitored for a maximum period of 150 months (mean 43 months and median 36.5 months). Notably, malignant transformation of oral dysplasia was observed in 39 of 110 (35.4%) patients. However, seventy-one patients (64.5%) showed no histological evidence of malignant transformation until the end of the follow-up period. Life tables were created to determine the median OCFS among patients with mild, moderate and severe dysplasia. Oral cancer free survival was determined using time-to-event analysis, the Kaplan-Meier method and the log-rank test. Cox proportional hazards models were utilized to evaluate clinicopathological factors including age, gender, degree of dysplasia, smoking habits, p16 immunostaining and overexpression of candidate markers in predicting risk of cancer development. Hazard ratios (H.R.) with 95% confidence intervals (95% C.I.) and significant p-values were reported. All tests were two-sided, and p-values<0.05 were considered statistically significant. The systematic and rigorous assessment of PPVs and NPVs for prognostic markers was carried out as previously described earlier (100, 126, 1727, 128).

Results.

Patient Characteristics.

Of the 110 patients with dysplasia included in the current study, follow-up data were available for up to a maximum of 150 months with a mean follow-up period of 43 months. 39 patients (35.4%) developed invasive squamous cell carcinoma of the oral cavity with a mean time for malignant transformation of 27.9 months (range 2-118 months). The baseline clinico-pathological characteristics of patients with dysplastic lesions including age, site of lesion, histopathological grade and smoking history are presented in Table 1. The average age at diagnosis was 59 years (range, 30 years-88 years). On the basis of histopathological characteristics, these lesions were sub-classified as mild (58 cases, 52.7%), moderate (39 cases, 35.4%) or severe dysplasia (13 cases, 11.8%). No significant differences were observed in age, gender, site of lesion or smoking history between patients with dysplasia that showed malignant transformation (i.e. developed oral cancer) relative to those with untransformed dysplasia (Table 16). Notably, 12 of 58 (20.7%) cases with mild dysplasia, 18 of 39 (46.1%) cases with moderate dysplasia (p=0.008, odd's ratio, O.R.=3.286, 95% C.I.=1.3-8.1, Table 16) and 9 of 13 (69.2%) severe dysplasia developed malignancy (p=0.001, O.R.=8.625, 95% C.I.=2.3-32.8, Table 16).

Analysis of Candidate Marker Overexpression and Clinicopathological Parameters.

Our immunohistochemical analysis revealed 79.1% (87 of 110) dysplastic lesions exhibited increased expression of S100A7 protein in either the cytoplasm and/or nucleus of epithelial cells (FIG. 23(*i, a-c*); Table 17). The intensity of S100A7 expression in dysplasia sections ranged from weak to strongly positive among different grades of dysplasia (FIG. 23(*i, a-c*)). Thirty four of 58 (58.6%) cases with mild dysplasia, 26 of 39 (66.7%) cases with moderate dysplasia and 10 of 13 (76.9%) cases with severe dysplasia exhibited cytoplasmic S100A7 overexpression (Table 18). Notably, 32 of the 70 dysplasia cases (45.7%) exhibiting S100A7 overexpression in cytoplasm transformed to cancer (p=0.003, O.R.=3.97, 95% C.I.=1.5-10.2, Table 17). Nuclear S100A7 expression was observed in 40 of 58 cases with mild dysplasia (68.9%), 33 of 39 (84.6%) cases with moderate dysplasia and 11 of 13 (84.6%) cases with severe dysplasia (Table 18). Thirty five of the 84 (41.6%) dysplasia cases exhibiting nuclear S100A7 developed malignancy (p=0.018, O.R.=3.929, 95% C.I.=1.2-12.4, Table 17). However, no significant correlation was observed between S100A7 overexpression (cytoplasm/nucleus) and degree of dysplasia (p>0.05, Table 18).

IHC analysis showed PTMA expression in either cytoplasm (25 of 39 cases, 64.1%) or nuclei (36 of 39 cases, 92.3%) of epithelial cells of dysplasia that progressed to cancer (FIG. 23(*ii, a-c*); Table 2). Similarly, increased expression of both the 14-3-3ζ and 14-3-3σ isoforms were observed in cytoplasm and/or nuclei of epithelial cells in mild, moderate and severe dysplasia cases (FIGS. 23(*iii, a-c*) and (*iv, a-c*); Table 17). Among dysplasia cases that transformed to cancer, 79.5% (31 of 39 cases) exhibited cytoplasmic expression of 14-3-3ζ, while 21 cases (53.8%) exhibited 14-3-3ζ expression in nuclei of epithelial cells (Table 17). 64.1% of dysplasia cases exhibited 14-3-3a expression in cytoplasm while 46.2% of dysplasia cases exhibited nuclear expression in addition to cytoplasmic staining (Table 17). Nuclear hnRNP K was observed in tissue samples obtained from all dysplasia patients studied, but no detectable expression of nuclear hnRNPK was observed in cytoplasm (FIG. 23(*v, a-c*); Table 17). No significant difference was observed for expression of cytoplasmic or nuclear PTMA, 14-3-3ζ, 14-3-3a and hnRNP K in dysplasia that transformed to cancer as compared to those that did not progress to cancer (Table 17). Mann-Whitney tests also showed significant association of S100A7 overexpression in cytoplasm (p=0.002) and nucleus (p=0.008) in dysplasia cells among patients with oral lesions who progressed to cancer relative to patients who did not progress to cancer, thereby providing an independent evaluation of association of protein markers with dysplasia.

Evaluation of p16 Expression and HPV 16/18 Status.

Expression of p16 was evaluated in all oral dysplasia cases analyzed in this study. Nuclear p16 was observed in 85 of 110 cases (77.3%), while 25 cases (22.7%) exhibited low or no detectable expression of nuclear p16 in oral dysplasia cells (FIG. 24). Thirty two of 39 (82.1%) dysplasia cases that transformed to cancer exhibited nuclear p16 expression (Table 17). Nuclear p16 expression was observed in 49 of 58 (84.4%) mild, 28 of 39 (71.7%) moderate, and 8 of 13 (61.3%) severe dysplasia (Table 18). However, no significant correlation was observed between nuclear p16 and any of the five candidate protein biomarkers exhibiting overexpression in oral dysplasia cases analyzed in this study (Table 19).

Our study revealed no detectable levels of HPV 16/18 in the dysplasia cases analyzed, irrespective of their p16 status (positive/negative) (FIG. 24, i, Table 17). Oral dysplasia tissue sections used as negative controls showed no detectable levels of HPV 16/18 (FIG. 24, ii). Cervical cancer tissue sections used as positive controls showed strong positivity for HPV 16/18 (FIG. 24, iii). TMA tissue sections used as control to determine genomic DNA integrity showed strong positive staining (FIG. 24, iv). No significant correlation was observed between nuclear p16 and HPV16/18 in oral dysplasia cases. Together, these data clearly suggest lack of association of p16 or HPV 16/18 with S100A7 expression and transformation of oral dysplasia.

Evaluation of S100A7 Overexpression as a Marker for Oral Cancer Free Survival (OCFS).

Among the five candidate protein biomarkers analyzed in our study, S100A7 overexpression in cytoplasm or nuclei showed significant association with malignant transformation of dysplastic lesions (Table 17). Hence, we further determined the potential of S100A7 overexpression in identifying patients having OLs with dysplasia at high risk of cancer development using Kaplan-Meier survival analysis to determine the probability of OCFS for these dysplasia patients. The association between S100A7 overexpression in cytoplasm or nuclei of dysplasia, loss of p16 expression and other potential risk factors including dysplasia grade (mild, moderate & severe), smoking history, age, gender and site of lesion with OCFS was analyzed by univariate analysis (Table 20). Notably, dysplasia patients showing cytoplasmic S100A7 had significantly reduced OCFS (mean OCFS=68.6 months, p=0.007) as compared to patients with weak or no cytoplasmic S100A7 immunostaining (mean OCFS=122.8 months; FIG. 25a; Table 20). Similarly, dysplasia patients showing nuclear S100A7 had reduced OCFS (mean OCFS=81.5 months, p=0.041) in comparison with patients with weak or no nuclear S100A7 immunostaining (mean OCFS=117.2 months; FIG. 25b; Table 20). Among clinical parameters, degree of dysplasia (moderate or severe) showed a significant correlation with OCFS (p<0.05, Table 3). Patients with moderate dysplasia demonstrated a low mean OCFS of 58.59 months (p=0.004) while in severe dysplasia cases, patients showed a mean OCFS of 38.9 months, (p<0.001, FIG. 26) compared to mild dysplasia (mean OCFS=116.25 months; FIG. 26). None of the other clinical parameters including age, gender, site of lesion or smoking history showed any significant correlation with OCFS (p>0.05, Table 3).

The life table and Kaplan Meier analysis clearly showed the low mean OCFS in moderate and severe dysplasia patients exhibiting S100A7 overexpression in cytoplasm or nuclei of dysplasia cells. 13 of 18 (72.2%) moderate dysplasia cases and 9 of 9 (100%) severe dysplasia cases that developed oral carcinoma exhibited cytoplasmic S100A7 overexpression, while 17 of 18 (94.4%) moderate and 8 of 9 (88.8%) severe dysplasia cases exhibited nuclear overexpression of S100A7. However, no significant correlation was observed for differences in OCFS in moderate/severe dysplasia patients exhibiting S100A7 overexpression in cytoplasm or nuclei (p>0.05) as revealed by Kaplan Meier analysis (FIG. 27a-c).

Analysis of risk factors for transformation of dysplasia into cancer was performed using the Cox proportional hazards model (Table 20). Cytoplasmic S100A7 overexpression (p=0.041, H.R.=2.36) and degree of dysplasia (moderate dysplasia, p=0.013 and severe dysplasia, p<0.001) emerged as an independent factor for identifying high risk dysplasia (Table 20). This clearly demonstrated the significance of cytoplasmic S100A7 overexpression in predicting malignant transformation of dysplasia.

Based on these data, the additional prognostic value that S100A7 overexpression in cytoplasm provided for predicting (Positive Predictive Value, PPV) or excluding (Negative Predictive Value, NPV) malignant transformation in oral dysplasia patients was measured by the ratios: PPVtransformation/dysplasia (118 months|S100A7 cyto+)/PPVtransformation/dysplasia (118 months)=75.6/60.0; NPVtransformation/dysplasia (118 months|S100A7 cyto+)/NPVtransformation/dysplasia (118 months)=78.5/40.0 (FIGS. 24a and 24b). Increase in PPV and NPV for S100A7 in comparison to dysplasia grade underscores the potential of S100A7 as a marker for predicting malignant transformation in dysplastic lesions.

Discussion of Results.

Early prediction for malignant potential of oral epithelial dysplasia is desired for clinical management of patients with the disease. In the present study, the expression of five candidate protein biomarkers, namely, S100A7, PTMA, 14-3-3ζ, 14-3-3σ and hnRNP K was verified in oral dysplasia and correlated with p16 expression as well as HPV 16/18 status. The majority of the dysplasia (mild/moderate/severe) that progressed to malignancy exhibited S100A7 overexpression (cytoplasm/nuclear). These data support the potential of S100A7 overexpression for use in distinguishing dysplasia patients at higher risk of cancer development. Of the five candidate protein biomarkers analyzed, S100A7 overexpression in cytoplasm emerged as the most significant risk factor of cancer development in patients having oral lesions with dysplasia with PPV (75.6%) and NPV (78.5%), regardless of age, gender, site of lesion, smoking habits and grade of dysplasia. Unlike S100A7, there was no significant difference in the expression of nuclear p16 among dysplasia patients who transformed to cancer relative to those who did not transform to cancer. Moreover, HPV 16/18 was not detected in any of the dysplasia cases analyzed in this study using cISH, irrespective of their p16 status or transformation to malignancy. Reports regarding the use of p16 expression as a surrogate marker for high risk (HR)-HPV infection or as a marker for progression in dysplasia are controversial (130-136). Moreover, involvement of both p16 and HR-HPV in development of oral epithelial dysplasia and their roles in transformation to malignancy have not been shown unequivocally as demonstrated in squamous cell carcinomas of pharynx (137-139).

Example 29—Combined Cytoplasmic S100A7 and Nuclear PTMA Overexpression is a Predictive Marker for High Risk of Malignant Transformation in Oral Dysplasia In this example, PTMA was further evaluated for its potential use in assessing the risk of cancer development from oral dysplasias. In particular, the results of this example support the use of cytoplasmic S100A7 overexpression combined with nuclear PTMA overexpression as a biomarker for identifying oral dysplastic lesions at high risk of cancer development.

Materials and Methods.

Study population characteristics and criteria, histopathology, IHC and statistical analyses were consistent with those described in Example 28. Tissue sections analyzed were serial sections used for S100A7 immunostaining in Example 28.

Results.

Immunohistochemical analysis revealed that 78.2% (86 of 110) of dysplastic lesions exhibited increased nuclear expression of PTMA (FIG. 30). Thirty eight of 39 cases (92.3%) that transformed into cancer exhibited a high nuclear PTMA score relative to 50 of 71 (70.4%) cases that did not transform into cancer and had low nuclear PTMA scores (p=0.008). Kaplan Meier survival analysis demonstrated a significant correlation between high nuclear PTMA intensity score and poor prognosis in oral dysplasia patients (i.e., a high nuclear PTMA score indicated a high likelihood of malignant transformation). Oral dysplasia patients exhibiting increased nuclear PTMA had a mean oral cancer free survival (OCFS)=79.8 months. In contrast, patients exhibiting low expression of nuclear PTMA had a mean OCFS=122.5 months (p=0.029, FIG. 30a). Combination of cytoplasmic S100A7 and nuclear PTMA intensity scores emerged also as an indicator of poor prognosis in oral dysplasia patients (p=0.002, FIG. 30b).

Further, in Cox multivariate regression analysis, subjects having cytoplasmic S100A7 positive, nuclear PTMA positive moderate to severe dysplastic lesions are at higher risk for cancer development relative to other groups (Table 21).

Patients having cytoplasmic S100A7 positive, nuclear PTMA positive, moderate or severe grade oral dysplasia had significantly reduced disease free survival (mean DFS=50.5 months) compared to patients having S100A7 positive, nuclear PTMA positive, mild grade oral dysplasia (mean DFS=112 months; p<0.001; FIG. 31a).

Figure 31B:
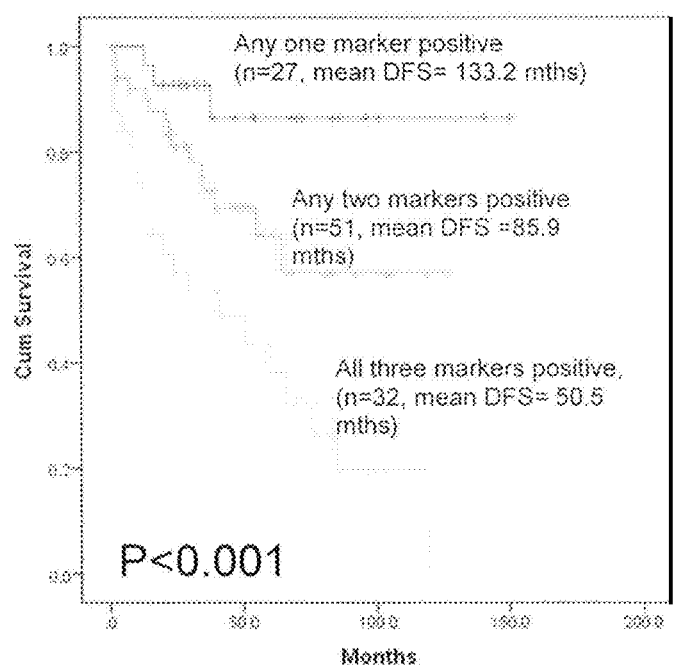

Patients having cytoplasmic S100A7 positive, nuclear PTMA positive moderate or severe grade oral dysplasia had significantly reduced disease free survival (mean DFS=50.5 months) compared to any two of these markers being positive (mean DFS=85.9 months) or any one of these markers being positive (mean DFS=133.2 months; p<0.001; FIG. 31b).

Example 30—Oral Cytosmears can be Used to Assess S100A7 Expression Levels in Oral Epithelial Cells In this example, cytosmear samples were evaluated for their potential use in assessing S100A7 expression in oral lesions. In particular, the results of this example support the use of cytosmear samples in methods that comprise detecting S100A7 overexpression as a biomarker for i) identifying oral dysplastic lesions at high risk of cancer development and ii) diagnosing and prognosing head and neck cancers, as set forth herein above.

Materials and Methods.

Oral cytosmears (n=20) were obtained from patients with oral lesions in the Dentistry Clinic at MSH, Toronto. To obtain the smear of exfoliated cells from the oral cavity of patients, a wooden spatula was used for scraping over the oral lesion. Cells collected were spread over a glass slide and fixed with a cytofixative. These cytomears were used for S100A7 immunostaining as described above. Briefly, cytomears were hydrated by dipping in Tris-buffered saline (TBS, 0.1M, pH=7.2), permeabilized with 0.025% of Triton-X 100 followed by blocking with 5% bovine serum albumin for 30 min. at room temperature in a moist chamber. Thereafter, slides were incubated with mouse monoclonal S100A7 antibody (sc-52948, Santa Cruz Biotechnology, CA) for 1 h at room temperature in a moist chamber. Slides will be washed with Tris-buffered saline (TBS, 0.1M, pH=7.2) followed by incubation with biotinylated secondary antibodies for 20 minutes. The sections were then incubated with VECTASTAIN Elite ABC Reagent (Vector labs, Burlingame, Calif.) and diaminobenzidine, which was used as the chromogen. Finally, the sections were counterstained with Mayer's hematoxylin and mounted with D.P.X mountant. Cytosmears prepared from oral cancer cells were used as controls. In negative controls, primary antibody was replaced by isotype-specific non-immune mouse IgG. The sections were evaluated by light microscopy using a Nanozoomer Scanner for cytopathology and scored for S100A7 immunostaining.

Results.

Cytosmears obtained from patients with oral lesions exhibited weak or no immunostaining for S100A7 in cytoplasm or nuclei of oral epithelial cells (FIG. 29a). Cytosmears prepared from oral cancer cells, which were used as a positive control, exhibited moderate S100A7 immunostaining in both cytoplasm and nuclei (FIG. 29b). No immunostaining was observed in negative control cytosmear samples (FIG. 29c). Cytosmears prepared from subjects having oral squamous cell carcinoma exhibited S100A7 immunostaining in both cytoplasm and nuclei (FIG. 29d).

While the foregoing invention has been described in some detail for purposes of clarity and understanding, it will be appreciated by one skilled in the art, from a reading of the disclosure, that various changes in form and detail can be made without departing from the true scope of the invention in the appended claims The present invention is not to be limited in scope by the specific embodiments described herein, since such embodiments are intended as but single illustrations of one aspect of the invention, and any functionally equivalent embodiments are within the scope of thereof. Indeed, various modifications of the invention, in addition to those shown and described herein, will become apparent to those skilled in the art from the foregoing description and accompanying drawings. Such modifications are intended to fall within the scope of the appended claims.

All publications, patents, and patent applications referred to herein are incorporated by reference in their entirety to the same extent as if each individual publication, patent, or patent application were specifically and individually indicated to be incorporated by reference in its entirety. Nothing herein is to be construed as an admission that the invention is not entitled to antedate the cited references by virtue of prior invention.

Set out below are full citations for the references cited herein.

1. Jemal A, Siegel R, Ward E, Hao Y, Xu J et al. (2008) Cancer statistics, 2008. CA Cancer J Clin 58: 71-96.
2. Hunter K D, Parkinson E K, Harrison P R (2005) Profiling early head-and-neck cancer. Nat Rev Cancer 5:127-35.
3. Warnakulasuriya s, Reibel J, Bouquot J, Dabelsteen E (2008) Oral epithelial dysplasia classification systems: predictive value, utility, weaknesses and scope for improvement. J Oral Pathol Med 37: 127-33.
4. Gale N, Michaels L, Luzar B, Poljak M, Zidar N, Fischinger J, Cardesa A. (2008) Current review on squamous intraepithelial lesions of the larynx. Histopathology. 2008 Aug. 25. [Epub ahead of print]
5. Mahajan M, Hazarey V K. An assessment of oral epithelial dysplasia using criteria of Smith and Pindborg's grading system and Ljubljiana Grading system in oral precancer lesions. J Oral Maxillofac Pathol 2004; 8: 73-81.

6. Warnakulasuriya K A, Ralhan R (2007) Clinical, pathological, cellular and molecular lesions caused by oral smokeless tobacco. J Oral Pathol Med 36: 63-77.
7. Brennan M, Migliorati C A, Lockhart P B, Wray D, Al-Hashimi I et al. (2007) Management of oral epithelial dysplasia: a review. Oral Surg Oral Med Oral Pathol Oral Radiol Endod 103:1-12.
8. Ralhan R. (2007) Diagnostic potential of Genomic and Proteomic signatures in Oral cancer. Review. Int J of Human Genetics. 7, 57-66.
9. Linkov, F., Lisovich, A., Yurkovetsky, Z., Marrangoni, A., Velikokhatnaya, L., Nolen, B., Winans, M., Bigbee, W., Siegfried, J., Lokshin, A., Ferris, R L. (2007) Early detection of head-and-neck cancer: development of a novel screening tool using multiplexed immunobead-based biomarker profiling. Cancer Epidemiol Biomarkers Prev. 16, 102-7.
10. Koike, H., Uzawa, K., Nakashima, D., Shimada, K., Kato, Y., Higo, M., Kouzu, Y., Endo, Y., Kasamatsu, A., Tanzawa, H. (2005) Identification of differentially expressed proteins in oral squamous cell carcinoma using a global proteomic approach. Int J Oncol. 27, 59-67.
11. Melle, C., Ernst, G., Schimmel, B., Bleul, A., Koscielny, S., Wiesner, A., Bogumil, R., Moller, U., Osterloh, D., Halbhuber, K. J., von Eggeling, F. (2003) Biomarker discovery and identification in laser microdissected head-and-neck squamous cell carcinoma with ProteinChip technology, two-dimensional gel electrophoresis, tandem mass spectrometry, and immunohistochemistry. Mol Cell Proteomics. 2, 443-52.
12. Roesch-Ely, M., Nees, M., Karsai, S., Ruess, A., Bogumil, R., Warnken, U., Schnolzer, M., Dietz, A., Plinkert, P. K., Hofele, C., Bosch, F. X. (2007) Proteomic analysis reveals successive aberrations in protein expression from healthy mucosa to invasive head-and-neck cancer. Oncogene 26, 54-64.
13. Drake, R. R., Cazare, L. H., Semmes, O. J., Wadsworth, J. T. (2005) Serum, salivary and tissue proteomics for discovery of biomarkers for head-and-neck cancers. Expert Rev. Mol Diagn. 5, 93-100.
14. Balys, R., Alaoui-Jamali, M., Hier, M., Black, M., Domanowski, G., Rochon, L., Jie, S. (2006) Clinically relevant oral cancer model for serum proteomic eavesdropping on the tumour microenvironment. J Otolaryngol. 35, 157-66.
15. Lo, W. Y., Lai, C. C., Hua, C. H., Tsai, M. H., Huang, S. Y., Tsai, C. H., Tsai, F. J. (2007) S100A8 is identified as a biomarker of HPV18-infected oral squamous cell carcinomas by suppression subtraction hybridization, clinical proteomics analysis, and immunohistochemistry staining. J Proteome Res. 6(6), 2143-51.
16. Gygi, S. P., Rist, B., Gerber, S. A., Turecek, F., Gelb, M. H., Aebersold, R. (1999) Quantitative analysis of complex protein mixtures using isotope-coded affinity tags. Nat Biotechnol. 17, 994-99.
17. DeSouza, L., Diehl, G., Rodrigues, M. J., Guo, J., Romaschin, A. D., Colgan, T. J., Siu, K. W. M. (2005) Search for cancer markers from endometrial tissues using differentially labeled tags iTRAQ and cICAT with multidimensional liquid chromatography and tandem mass spectrometry. J Proteome Res. 4, 377-86.
18. DeSouza, L., Diehl, G., Yang, E. C. C., Guo, J., Rodrigues, M. J., Romaschin, A. D., Colgan, T. J., Siu, K. W. M. (2005) Proteomic Analysis of the Proliferative and Secretory Phases of the Human Endometrium: Protein Identification and Differential Protein Expression. Proteomics. 5, 270-81.
19. Li, H., Desouza, L. V., Ghanny, S., Li, W., Romaschin, A. D., Colgan, T. J., Siu, K. W. M. (2007) Identification of Candidate Biomarker Proteins Released by Human Cervical Cancer Cells Using Two-Dimensional Liquid Chromatography/Tandem Mass Spectrometry. J Proteome Res. 6, 2648-55.
20. Guo, J., Colgan, T. J., DeSouza, L., Rodrigues, M. J., Romaschin, A D., Siu, K. W. M. (2005) Direct analysis of laser capture microdissected endometrial carcinoma and epithelium by matrix-assisted laser desorption/ionization mass spectrometry. Rapid Commun Mass Spectrom. 19, 2762-66.
21. DeSouza, L. V., Grigull, J., Ghanny, S., Dubé, V., Romaschin, A. D., Colgan, T. J., Siu, K. W. M. (2007) Endometrial carcinoma biomarker discovery and verification using differentially tagged clinical samples with multidimensional liquid chromatography and tandem mass spectrometry. Mol Cell Proteomics (2007) 6:1170-82.
22. DeSouza L V, et al. Multiple reaction monitoring of mTRAQ labeled peptides enables absolute quantification of endogenous levels of a potential cancer marker in cancerous and normal endometrial tissues. J Proteome Res (2008).
23. Ralhan R, et al. Discovery and verification of head-and-neck cancer biomarkers by differential protein expression analysis using iTRAQ-labeling and multidimensional liquid chromatography and tandem mass spectrometry. Mol Cell Proteomics (2008); 7:1162-73
24. Ariztia, E. V., Lee, C. J., Gogoi, R., Fishman, D. A. (2006) The tumor microenvironment: key to early detection. Crit Rev Clin Lab Sci. 43, 393-425.
25. Slaughter D P, Southwick H. W., Smejkal, W. 'Field cancerisation' in oral stratified squamous epithelium. Cancer (1953) 6:963-8.
26. Braakhuis B J, et al. Expanding fields of genetically altered cells in head-and-neck squamous carcinogenesis. Semin Cancer Biol (2005) 15:113-20.
27. Garcia S B, et al. Field cancerization, clonality, and epithelial stem cells: the spread of mutated clones in epithelial sheets. J Pathol (1999) 187:61-81.
28. Shilov, I. V., Seymour, S. L., Patel, A. A., Loboda, A., Tang, W. H., Keating, S. P., Hunter, C. L., Nuwaysir, L. M., Schaeffer, D. A. (2007) The Paragon Algorithm: A next generation search engine that uses sequence temperature values and feature probabilities to identify peptides from tandem mass spectra. Mol Cell Proteomics. May 27, [Epub ahead of print].
29. The R Development Core Team. The R Project for Statistical Computing. http://www.rproject.org.
30. Sun Developer Network (SDN). Java.sun.com: The Source for Java Developers. http://java.sun.com.
31. Witten, I. H. and Frank, E. (2005) Data Mining: Practical machine learning tools and techniques. 2nd Edition. Morgan Kaufmann. San Francisco.
32. Arora, S., Kaur, J., Sharma, C., Mathur, M., Bahadur, S., Shukla, N. K., Deo, S. V., Ralhan, R. (2005) Stromelysin 3, Ets-1, and vascular endothelial growth factor expression in oral precancerous and cancerous lesions: correlation with microvessel density, progression, and prognosis. Clin Cancer Res. 11, 2272-84.
33. Leys, C. M., Nomura, S., LaFleur, B. J., Ferrone, S., Kaminishi, M., Montgomery, E., Goldenring. J. R. (2007) Expression and prognostic significance of prothymosin-alpha and ERp57 in human gastric cancer. Surgery. 141, 41-50.

34. Sasaki, H., Nonaka, M., Fujii, Y., Yamakawa, Y., Fukai, I., Kiriyama, M. and Sasaki, M. (2001) Expression of the prothymosin-a gene as a prognostic factor in lung cancer. Surg Today. 31, 936-938.

35. Wu, C. G., Habib, N. A., Mitry, R. R., Reitsma, P. H., van Deventer, S. J. and Chamuleau, R. A. (1997) Overexpression of hepatic prothymosin alpha, a novel marker for human hepatocellular carcinoma. Br J Cancer. 76, 1199-1204.

36. Mori, M., Barnard, G. F., Staniunas. R. J., Jessup. J. M., Steele. G. D. Jr and Chen, L. B. (1993) Prothymosin-alpha mRNA expression correlates with that of c-myc in human colon cancer. Oncogene. 8, 2821-2826.

37. Slaughter, D. P., Southwick H. W., Smejkal, W. (1953) Cancer 6, 963-968.

38. Arora, S., Matta, A., Shukla, N. K., Deo, S. V. and Ralhan R. (2005) Identification of differentially expressed genes in oral squamous cell carcinoma. Mol Carcinog. 42, 97-108.

39. Matta, A.; Bahadur, S.; Duggal, R.; Gupta, S. D.; Ralhan, R. Over-expression of 14-3-3zeta is an early event in oral cancer. BMC Cancer 2007, 7, 169.

40. Jang, J. S., Cho, H. Y., Lee, Y. J., Ha, W. S. and Kim, H. W. (2004) The differential proteome profile of stomach cancer: identification of the biomarker candidates. Oncol Res. 14, 491-499.

41. Meehan, K. L., Sadar, M. D. (2004) Quantitative profiling of LNCaP prostate cancer cells using isotope-coded affinity tags and mass spectrometry. Proteomics. 4, 1116-34.

42. Li, D. Q, Wang, L., Fei, F., Hou, Y. F., Luo, J. M., Wei-Chen, Zeng, R., Wu, J., Lu, J. S., Di, G. H., Ou, Z. L., Xia, Q. C, Shen, Z. Z., Shao, Z. M. (2006) Identification of breast cancer metastasis-associated proteins in an isogenic tumor metastasis model using two dimensional gel electrophoresis and liquid chromatography-ion trap-mass spectrometry. Proteomics. 6(11): 3352-68.

43. Qi, W., Liu, X., Qiao, D. and Martinez, J. D. (2005) Isoform-specific expression of 14-3-3 proteins in human lung cancer tissues. Int J Cancer. 113, 359-363.

44. Lo, W. Y., Tsai, M. H., Tsai, Y., Hua, C. H., Tsai, F. J., Huang, S. Y., Tsai, C. H. and Lai, C. C. (2007) Identification of over-expressed proteins in oral squamous cell carcinoma (OSCC) patients by clinical proteomic analysis. Clin Chim Acta. 376, 101-107.

45. Chen, J., He, Q. Y., Yuen, A. P. and Chiu J. F. (2004) Proteomics of buccal squamous cell carcinoma: the involvement of multiple pathways in tumorigenesis. Proteomics. 4: 2465-2475.

46. Hustinx, S. R., Fukushima, N., Zahurak, M. L., Riall, T. S., Maitra, A., Brosens, L., Cameron, J. L., Yeo, C. J., Offerhaus, G. J., Hruban, R. H. and Goggins, M. (2005) Expression and prognostic significance of 14-3-3sigma and ERM family protein expression in periampullary neoplasms. Cancer Biol Ther. 4, 596-601.

47. Hermeking, H., Benzinger, A. (2006) 14-3-3 proteins in cell cycle regulation. Semin Cancer Biol. 16, 183-92.

48. Tzivion, G., Gupta, V. S., Kaplunm L., Balan, V. (2006) 14-3-3 proteins as potential oncogenes. Semin Cancer Biol. 16, 203-13.

49. Verdoodt, B., Benzinger, A., Popowicz, G. M., Holak, T. A., Hermeking, H. (2006) Characterization of 14-3-3 sigma dimerization determinants: requirement of homodimerization for inhibition of cell proliferation. Cell Cycle. 5, 2920-6.

50. Gardino, A. K., Smerdon, S. J., Yaffe, M. B. (2006) Structural determinants of 14-3-3 binding specificities and regulation of subcellular localization of 14-3-3-ligand complexes: a comparison of the X-ray crystal structures of all human 14-3-3 isoforms. Semin Cancer Biol. 16, 173-82.

51. Rosell, R., Cecere, F., Santarpia, M., Reguart, N., Taron, M. (2006) Predicting the outcome of chemotherapy for lung cancer. Curr Opin Pharmacol. 6, 323-31.

52. Qi, W., Martinez, J. D. (2003) Reduction of 14-3-3 proteins correlates with increased sensitivity to killing of human lung cancer cells by ionizing radiation. Radiat. Res. 160, 217-23.

53. Chu, P. G., Lyda, M. H. and Weiss, L. M. (2001) Cytokeratin 14 expression in epithelial neoplasms: a survey of 435 cases with emphasis on its value in differentiating squamous cell carcinomas from other epithelial tumours. Histopathology. 39, 9-16.

54. Ohkura, S., Kondoh, N., Hada, A., Arai, M., Yamazaki, Y., Sindoh, M., Takahashi, M., Matsumoto, I. and Yamamoto, M. (2005) Differential expression of the keratin-4, -13, -14, -17 and transglutaminase 3 genes during the development of oral squamous cell carcinoma from leukoplakia. Oral Oncol. 41, 607-613.

55. Letsas, K. P., Vartholomatos, G., Tsepi, C., Tsatsoulis, A., Frangou-Lazaridis, M. (2007) Fine-needle aspiration biopsy-RT-PCR expression analysis of prothymosin alpha and parathymosin in thyroid: novel proliferation markers? Neoplasma. 54, 57-62.

56. Traub, F., Jost, M., Hess, R., Schorn, K., Menzel, C., Budde, P., Schulz-Knappe, P., Lamping, N., Pich, A., Kreipe, H. and Tammen, H. (2006) Peptidomic analysis of breast cancer reveals a putative surrogate marker for estrogen receptor-negative carcinomas. Lab Invest. 86, 246-53.

57. Tsitsiloni, O. E., Stiakakis, J., Koutselinis, A., Gogas, J., Markopoulos, C., Yialouris, P., Bekris, S., Panoussopoulos, D., Kiortsis, V., Voelter, W. and Haritos, A. A. (1993) Expression of alpha-thymosins in human tissues in normal and abnormal growth. Proc Natl Acad Sci. 90, 9504-9507.

58. Tzai, T S., Tsai, Y. S., Shiau, A L, Wu, C. L., Shieh, G. S., Tsai, H. T. (2006) Urine prothymosin-alpha as novel tumor marker for detection and follow-up of bladder cancer. Urology. 67, 294-9.

59. Gallego, R., Roson, E., Garcia-Caballero, T., Fraga, M., Forteza, J., Dominguez, F., Beiras, A. (1992) Prothymosin alpha expression in lymph nodes and tonsils: an optical and ultrastructural study. Acta Anat (Basel). 43, 219-22

60. Skopeliti, M., Kratzer, U., Altenberend, F., Panayotou, G., Kalbacher, H., Stevanovic, S., Voelter, W., Tsitsilonis, O. E. (2007) Proteomic exploitation on prothymosin alpha induced mononuclear cell activation. Proteomics. 7, 1814-1824.

61. Samstag, Y., Klemke, M. (2007) Ectopic expression of L-plastin in human tumor cells: Diagnostic and therapeutic implications. Adv Enzyme Regul. February 28, [Epub ahead of print].

62. Kasamatsu, A., Uzawa, K., Nakashima, D., Kouzu, Y., Endo, Y., Koike, H., Yokoe, H., Harada, K., Sato, M., Tanzawa, H. (2006) A proteomics approach to characterizing human submandibular gland cell lines by fluorescent two-dimensional differential in-gel electrophoresis. Int. J. Mol. Med. 17, 253-60.

63. Banerjee, A. G., Bhattacharyya, I., Vishwanatha, J. K. (2005) Identification of genes and molecular pathways involved in the progression of premalignant oral epithelia. Mol. Cancer. Ther. 4, 865-75.

64. Moubayed, N., Weichenthal, M., Harder, J., Wandel, E., Sticherling, M., Glaser, R. (2007) Psoriasin (S100A7) is significantly up-regulated in human epithelial skin tumours. *J Cancer Res Clin Oncol.* 133, 253-61.

65. Skliris, G. P., Lewis, A., Emberley, E., Peng, B., Weebadda, W. K., Kemp, A., Davie, J. R., Shiu, R. P., Watson, P. H., Murphy, L. C. (2007) Estrogen receptor-beta regulates psoriasin (S100A7) in human breast cancer. *Breast Cancer Res Treat.* 104, 75-85.

66. Fukuzawa, H., Kiyoshima, T., Kobayashi, I., Ozeki, S., Sakai, H. (2006) Transcription promoter activity of the human S100A7 gene in oral squamous cell carcinoma cell lines. *Biochem. Biophys. Acta.* 1759, 171-6.

67. Krop, I., Marz, A., Carlsson, H., Li, X., Bloushtain-Qimron, N., Hu, M., Gelman, R., Sabel, M. S., Schnitt, S., Ramaswamy, S., Kleer, C. G., Enerback, C., Polyak, K. (2005) A putative role for psoriasin in breast tumor progression. *Cancer Res.* 65, 11326-34.

68. Kennedy, R. D., Gorski, J. J., Quinn, J. E., Stewart, G. E., James, C. R., Moore, S., Mulligan, K., Emberley, E. D., Lioe, T. F., Morrison, P. J., Mullan, P. B., Reid, G., Johnston, P. G., Watson, P. H., Harkin, D. P. (2005) BRCA1 and c-Myc associate to transcriptionally repress psoriasin, a DNA damage-inducible gene. *Cancer Res.* 65, 10265-72.

69. Sparano, A., Quesnelle, K. M., Kumar, M. S., Wang, Y., Sylvester, A. J., Feldman, M., Sewell, D. A., Weinstein, G. S., Brose, M. S. (2006) Genome-wide profiling of oral squamous cell carcinoma by array-based comparative genomic hybridization. *Laryngoscope.* 116, 735-41.

70. Vora, H. H., Shah, N. G., Patel, D. D., Trivedi, T. I., Choksi, T. J. (2003) BRCA1 expression in leukoplakia and carcinoma of the tongue. *J Surg Oncol.* 83, 232-40.

71. Zech, V. F., Dlaska, M., Tzankov, A. and Hilbe, W. (2006) Prognostic and diagnostic relevance of hnRNP A2/B1, hnRNP B1 and S100 A2 in non-small cell lung cancer. *Cancer Detect Prev.* 30, 395-402.

72. Kanamori, T., Takakura, K., Mandai, M., Kariya, M., Fukuhara, K., Sakaguchi, M., Huh, N. H., Saito, K., Sakurai, T., Fujita, J. and Fujii, S. (2004) Increased expression of calcium-binding protein S100 in human uterine smooth muscle tumors. *Mol Hum Reprod.* 10, 735-42.

73. Zhang, H., Xu, L., Xiao, D., Xie, J., Zeng, H., Cai, W., Niu, Y., Yang, Z., Shen, Z. and Li, E. (2006) Fascin is a potential biomarker for early-stage oesophageal squamous cell carcinoma. *J Clin Pathol.* 59, 958-964.

74. Zhang, B., Chen, J. Y., Chen, D. D., Wang, G. B., Shen, P. (2004) Tumor type M2 pyruvate kinase expression in gastric cancer, colorectal cancer and controls. *World J Gastroenterol.* 10, 1643-6.

75. Ahmed, A. s, Dew, T., Lawton, F. G., Papadopoulos, A. J., Devaja, O., Raju, K. S., Sherwood, R. A. (2007) M2-PK as a novel marker in ovarian cancer. A prospective cohort study. *Eur J Gynaecol Oncol.* 28, 83-8.

76. Goonetilleke, K. S., Mason, J. M., Siriwardana, P., King, N. K., France, M. W., Siriwardena, A. K. (2007) Diagnostic and prognostic value of plasma tumor M2 pyruvate kinase in periampullary cancer: evidence for a novel biological marker of adverse prognosis. *Pancreas.* 34, 318-24.

77. Kumar, Y., Tapuria, N., Kirmani, N., Davidson, B. R. (2007) Tumor, M2-pyruvate kinase: a gastrointestinal cancer marker. *Eur J Gastroenterol Hepatol.* 19, 265-76.

78. Stetak, A., Veress, R., Ovadi, J., Csermely, P., Keri, G., Ullrich, A. (2007) Nuclear translocation of the tumor marker pyruvate kinase M2 induces programmed cell death. *Cancer Res.* 67, 1602-8.

79. Kim, J. W., Dang, C. V. (2006) Cancer's molecular sweet tooth and the Warburg effect. *Cancer Res.* 66, 8927-30.

80. Shaw, R. J. (2006) Glucose metabolism and cancer. *Curr Opin Cell Biol.* 18, 598-608.

81. Juwana, J. P., Henderikx, P., Mischo, A., Wadle, A., Fadle, N., Gerlach, K., Arends, J. W., Hoogenboom, H., Pfreundschuh, M. and Renner, C. (1999) EB/RP gene family encodes tubulin binding proteins. *Int J Cancer.* 81, 275-284.

82. Wang, Y., Zhou, X., Zhu, H., Liu, S., Zhou, C., Zhang, G., Xue, L., Lu, N., Quan, L., Bai, J., Zhan, Q. and Xu, N. (2005) Overexpression of EB1 in human esophageal squamous cell carcinoma (ESCC) may promote cellular growth by activating beta-catenin/TCF pathway. *Oncogene.* 24, 6637-6645.

83. Xue, Y., Canman, J. C., Lee, C. S., Nie, Z., Yang, D, Moreno, G. T., Young, M. K., Salmon, E. D. and Wang, W. (2000) The human SWI/SNF-B chromatin-remodeling complex is related to yeast Rsc and localizes at kinetochores of mitotic chromosomes. *Proc Natl Acad Sci.* 97, 13015-13020.

84. Martens, J. A. and Winston, F. (2003) Recent advances in understanding chromatin remodeling by Swi/Snf complexes. *Curr Opin Genet Dev.* 13, 136-142.

85. Hosotani, T., Koyama, H., Uchino, M., Iyakawa/T. and Tsuchiya/E. (2001) PKC1, a protein kinase C homologue of *Saccharomyces cerevisiae*, participates in microtubule function through the yeast EB1 homologue, BIM1. *Genes Cells.* 6, 775-788.

86. Sekine, I., Sato, M., Sunaga, N., Toyooka, S., Peyton, M., Parsons, R., Wang, W., Gazdar, A. F. and Minna., J. D. (2005) The 3p21 candidate tumor suppressor gene BAF180 is normally expressed in human lung cancer. *Oncogene.* 24, 2735-2738.

87. Ralhan R, Leroi V. DeSouza, Ajay Matta, Satyendra Chandra Tripathi, Shaun Ghanny, Siddartha DattaGupta, Alok Thakar and Siu K W M. iTRAQ-Multidimensional Liquid Chromatography and Tandem Mass Spectrometry based Identification of Potential Biomarkers of Oral Epithelial Dysplasia and Novel Networks between Inflammation and Premalignancy. Journal of Proteome Research. 2009; 8:300-9.

88. Carpenter B, et al. Heterogeneous nuclear ribonucleoprotein K is over expressed aberrantly localized and is associated with poor prognosis in colorectal cancer. Br J Cancer (2006) 95:921-7.

89. Roychoudhury P, et al. Evidence for heterogeneous nuclear ribonucleoprotein K overexpression in oral squamous cell carcinoma. Br J Cancer (2007) 97:574-5.

90. Sawhney, M.; Rohatgi, N.; Kaur, J.; Shishodia, S.; Sethi, G.; Gupta, S. D.; Deo, S. V.; Shukla, N. K.; Aggarwal, B. B.; Ralhan, R. Expression of NF-kappaB parallels COX-2 expression in oral precancer and cancer: association with smokeless tobacco. *Int. J. Cancer* 2007, 120, 2545-56.

91. Aguilera, C.; Fernandez-Majada, V.; Ingles-Esteve, J.; Rodilla, V.; Bigas, A.; Espinosa, L. Efficient nuclear export of p65-IkappaBalpha complexes requires 14-3-3 proteins. *J. Cell. Sci.* 2006, 119, 3695-704.

92. Fang, D.; Hawke, D.; Zheng, Y.; Xia, Y.; Meisenhelder, J.; Nika, H.; Mills, G. B.; Kobayashi, R.; Hunter, T.; Lu, Z.; Phosphorylation of beta-catenin by AKT promotes beta-catenin transcriptional activity. *J. Biol. Chem.* 2007, 82, 11221-9.

93. Niemantsverdriet, M.; Wagner, K.; Visser, M.; Backendorf, C. Cellular functions of 14-3-3zeta in apoptosis and cell adhesion emphasize its oncogenic character. *Oncogene* 2007, (Epub ahead of print)
94. Danes, C. G., Wyszomierski, S. L.; Lu, J.; Neal, C. L.; Yang, W.; Yu, D. 14-3-3 zeta down-regulates p53 in mammary epithelial cells and confers luminal filling. *Cancer. Res.* 2008, 68, 1760-7.
95. Wilker, E.; Yaffe, M. B. 14-3-3 Proteins-a focus on cancer and human disease. *J. Mol. Cell. Cardiol.* 2004, 37, 633-42.
96. Bhawal, U. K.; Tsukinoki, K.; Sasahira, T.; Sato, F.; Mori, Y.; Muto, N.; Sugiyama, M.; Kuniyasu, H. Methylation and intratumoural heterogeneity of 14-3-3 sigma in oral cancer. *Oncol Rep.* 2007, 18, 817-24.
97. http://www.uicc.org.
98. Cregger, M.; Berger, A. J.; Rimm, D. L. Immunohistochemistry and quantitative analysis of protein expression. *Arch. Pathol. Lab. Med.* 2006, 130, 1026-30.
99. Perathoner, A.; Pirkebner, D.; Brandacher, G.; Spizzo, G.; Stadlmann, S.; Obrist, P.; Margreiter, R.; Amberger, A. 14-3-3sigma expression is an independent prognostic parameter for poor survival in colorectal carcinoma patients. *Clin. Cancer Res.* 2005, 11, 3274-9.
100. Matta, A.; DeSouza, L. V.; Bahadur, S.; Gupta, S. D.; Ralhan, R.; Siu, K. W. Prognostic Significance of Head-and-neck cancer Biomarkers Previously Discovered Using iTRAQ-Multidimensional Liquid Chromatography and Tandem Mass Spectrometry. *J. Proteome. Research.* 2008, 7, 2078-87.
101. Dubé V, Grigull J, DeSouza L, Ghanny s, Colgan T J, Romaschin A D, Siu K W M. Verification of head-and-neck tissue biomarkers previously discovered using mass-tagging and multidimensional liquid chromatography/tandem mass spectrometry by means of immunohistochemistry in a tissue microarray format. J. Proteome Res. 2007; July; 6(7):2648-55.
102. Gasco, M.; Bell, A. K.; Heath, V.; Sullivan, A.; Smith, P.; Hiller, L.; Yulug, I.; Numico, G.; Merlano, M.; Farrell, P. J.; Tavassoli, M.; Gusterson, B.; Crook, T. Epigenetic inactivation of 14-3-3 sigma in oral carcinoma: association with p16(INK4a) silencing and human papilloma virus negativity. *Cancer Res.* 2002, 62, 2072-6.
103. Samuel, T.; Weber, H. O.; Rauch, P.; Verdoodt, B.; Eppel, J. T.; McShea, A.; Hermeking, H.; Funk, O. The G2/M regulator 14-3-3sigma prevents apoptosis through sequestration of Bax. *J. Biol. Chem.* 2001, 276, 45201-6.
104. Guweidhi, A.; Kleeff, J.; Giese, N.; El, Fitori. J; Ketterer, K.; Giese, T.; Buchler, M. W.; Korc, M.; Friess, H. Enhanced expression of 14-3-3sigma in pancreatic cancer and its role in cell cycle regulation and apoptosis. *Carcinogenesis* 2004, 25, 1575-85.
105. Liu, Y.; Liu, H.; Han, B.; Zhang, J. T. Identification of 14-3-3sigma as a contributor to drug resistance in human breast cancer cells using functional proteomic analysis. *Cancer Res.* 2006, 66, 3248-55.
106. Yang, H. Y.; Wen, Y. Y.; Lin, Y. L.; Pham, L.; Su, C. H.; Yang, H.; Chen, J.; Lee, M. H. Roles for negative cell regulator 14-3-3sigma in control of MDM2 activities. *Oncogene* 2007.
107. Ralhan, R.; Agarwal, S.; Nath, N.; Mathur, M.; Wasylyk, B.; Srivastava, A. Correlation between p53 gene mutations and circulating antibodies in betel- and tobacco-consuming North Indian population. *Oral Oncol.* 2001, 37, 243-50.
108. Ralhan, R.; Sandhya, A.; Meera, M.; Bohdan, W.; Nootan, S. K. Induction of MDM2-P2 transcripts correlates with stabilized wild-type p53 in betel- and tobacco-related human oral cancer. *Am. J. Pathol.* 2000, 157, 587-96.
109. Soni, S.; Kaur, J.; Kumar, A.; Chakravarti, N.; Mathur, M.; Bahadur, S.; Shukla, N. K.; Deo, S. V.; Ralhan, R. Alterations of Rb pathway components are frequent events in patients with oral epithelial dysplasia and predict clinical outcome in patients with squamous cell carcinoma. *Oncology* 2005, 68, 314-25.
110. Matta A, Tripathi S C, DeSouza L V, Bahadur s, DattaGupta S, Ralhan R* and Siu K W M. Clinical Significance of Heterogenous ribonucleoprotein K in Head and Neck Tumorigenesis: A Potential Biomarker Previously Discovered Using iTRAQ-Multidimensional Liquid Chromatography and Tandem Mass Spectrometry. Clinical Cancer Research, submitted.
111. Evans J R, Mitchell S A, Spriggs K A et al. Members of the poly (rC) binding protein family stimulate the activity of the c-myc internal ribosome entry segment in vitro and in vivo. Oncogene 2003; 22:8012-20.
112. Adolph D, Flach N, Mueller K, Ostareck D H, Ostareck-Lederer A. Deciphering the cross talk between hnRNPK and c-Src: the c-Src activation domain in hnRNPK is distinct from a second interaction site. Mol Cell Biol 2007; 27:1758-70.
113. Naarmann Is, Harnisch C, Flach N et al. mRNA silencing in human erythroid cell maturation: hnRNPK controls the expression of its regulator c-Src. J Biol Chem 2008; 283:18461-72
114. Ostrowski J, Bomsztyk K. Nuclear shift of hnRNPK protein in neoplasms and other states of enhanced cell proliferation. Br J Cancer 2003; 89:1493-501.
115. Bomsztyk K, Denisenko O, Ostrowski J. hnRNPK: one protein multiple processes. Bioessays 2004; 26:629-38.
116. He Y, Brown M A, Rothnagel J A, Saunders N A, Smith R. Roles of heterogeneous nuclear ribonucleoproteins A and B in cell proliferation. J Cell Sci 2005; 118:3173-83.
117. Michael W M, Eder Ps, Dreyfuss G. The K nuclear shuttling domain: a novel signal for nuclear import and nuclear export in the hnRNPK protein. EMBO J 1997; 16: 3587-98.
118. Sun Y, Yi H, Zhang P F et al. Identification of differential proteins in nasopharyngeal carcinoma cells with p53 silence by proteome analysis. FEBS Lett 2007; 581:131-9.
119. Chan J Y, Huang S M, Liu S T, Huang C H. The transactivation domain of heterogeneous nuclear ribonucleoprotein K overlaps its nuclear shuttling domain. Int J Biochem Cell Biol 2008; 40:2078-89.
120. Habelhah H, Shah K, Huang L et al. ERK phosphorylation drives cytoplasmic accumulation of hnRNP-K and inhibition of mRNA translation. Nat Cell Biol 2001; 3:325-30.
121. Evans J R, Mitchell S A, Spriggs K A et al. Members of the poly (rC) binding protein family stimulate the activity of the c-myc internal ribosome entry segment in vitro and in vivo. Oncogene 2003; 22:8012-20.
122. Skalweit A, Doller A, Huth A et al. Posttranscriptional control of renin synthesis: identification of proteins interacting with renin mRNA 3'-untranslated region. Circ Res 2003; 92:419-27.
123. Collier B, Goobar-Larsson L, Sokolowski M, Schwartz S. Translational inhibition in vitro of human papillomavirus type 16 L2 Mrna mediated through interaction with heterogenous ribonucleoprotein K and poly(rC)-binding proteins 1 and 2. J Biol Chem 1998; 273:22648-56.

124. Reimann I, Huth A, Thiele H, Thiele B J. Suppression of 15-lipoxygenase synthesis by hnRNP E1 is dependent on repetitive nature of LOX mRNA 3'-UTR control element DICE. *J Mol Biol* 2002; 315: 965-74.
125. Winter J, Pantelis A, Reich R, Jepsen S, Allam J P, Novak N, Wenghoefer M. Risk estimation for a malignant transformation of oral lesions by S100A7 and Doc-1 gene expression. *Cancer Invest* 2011; 29:478-84.
126. Matta A, Tripathi S C, DeSouza L V, Grigull J, Kaur J, Chauhan S S, et al. Matta A, Tripathi S C, DeSouza L V, Grigull J, Kaur J, Chauhan S S, Srivastava A, Thakar A, Shukla N K, Duggal R, DattaGupta S, Ralhan R, et al. Heterogeneous ribonucleoprotein K is a marker of oral leukoplakia and correlates with poor prognosis of squamous cell carcinoma. *Int J Cancer* 2009; 125:1398-406.
127. Tripathi S C, Matta A, Kaur J, Grigull J, Chauhan S S, Thakar A, Shukla N K, Duggal R, DattaGupta S, Ralhan R, Siu K W. Nuclear S100A7 is associated with poor prognosis in head and neck cancer. *PLoS One* 2010; 5:e11939.
128. Tripathi S C, Matta A, Kaur J, Grigull J, Chauhan S S, Thakar A, Shukla N K, Duggal R, Choudhary A R, Dattagupta S, Sharma M C, Ralhan R, et al. Overexpression of prothymosin alpha predicts poor disease outcome in head and neck cancer. *PLoS One* 2011; 6:e19213.
129. McLachlin C M, Kandel R A, Colgan T J, Swanson D B, Witterick U, Ngan B Y. Prevalence of human papillomavirus in sinonasal papillomas: a study using polymerase chain reaction and in situ hybridization. *Mod Pathol* 1992; 5:406-9.
130. Fregonesi P A, Teresa D B, Duarte R A, Neto C B, de Oliveira M R, Soares C P. p16(INK4A) immunohistochemical overexpression in premalignant and malignant oral lesions infected with human papillomavirus. *J Histochem Cytochem* 2003; 51:1291-7.
131. Nemes J A, Deli L, Nemes Z, Marton U. Expression of p16 (INK4A), p53, and Rb proteins are independent from the presence of human papillomavirus genes in oral squamous cell carcinoma. *Oral Surg Oral Med Oral Pathol Oral Radiol Endod* 2006; 102:344-52.
132. Cunningham L L Jr, Pagano G M, Li M, Tandon R, Holm S W, White D K, Lele S M. Overexpression of p16INK4 is a reliable marker of human papillomavirus-induced oral high-grade squamous dysplasia. *Oral Surg Oral Med Oral Pathol Oral Radiol Endod* 2006; 102:77-81.
133. König F, Krekeler G, Hönig J F, Cordon-Cardo C, Fischer G, Korabiowska M. Relation between human papillomavirus positivity and p16 expression in head and neck carcinomas—a tissue microarray study. *Anticancer Res* 2007; 27:283-8.
134. Angiero F, Gatta L B, Seramondi R, Berenzi A, Benetti A, Magistro S, Ordesi P, Grigolato P, Dessy E. Frequency and role of HPV in the progression of epithelial dysplasia to oral cancer. *Anticancer Res* 2010; 30:3435-40
135. Geißler C, Tahtali A, Diensthuber M, Gassner D, Stöver T, Wagenblast J. The role of p16 expression as a predictive marker in HPV-positive oral SCCHN—a retrospective single-center study. *Anticancer Res* 2013; 33:913-6.
136. Stokes A, Guerra E, Bible J, Halligan E, Orchard G, Odell E, Thavaraj S. Human papillomavirus detection in dysplastic and malignant oral verrucous lesions. *J Clin Pathol* 2012; 65:283-6.
137. Tahtali A, Hey C, Geissler C, Filman N, Diensthuber M, Leinung M, Stöver T, Wagenblast J. HPV Status and Overall Survival of Patients with Oropharyngeal Squamous Cell Carcinoma—A Retrospective Study of a German Head and Neck Cancer Center. *Anticancer Res* 2013; 33:3481-5.
138. Nichols A C, Dhaliwal S S, Palma D A, Basmaji J, Chapeskie C, Dowthwaite S, Franklin J H, Fung K, Kwan K, Wehrli B, Howlett C, Siddiqui I, Salvadori M I, Winquist E, Ernst S, Kuruvilla S, Read N, Venkatesan V, Todorovic B, Hammond J A, Koropatnick J, Mymryk J S, Yoo J, Barrett J W. Does HPV type affect outcome in oropharyngeal cancer? *J Otolaryngol Head Neck Surg* 2013; 42:9.
139. Woo S B, Cashman E C, Lerman M A. Human papillomavirus-associated oral intraepithelial neoplasia. *Mod Pathol* 2013, Apr. 19 [In press].

TABLE 1

| iTRAQ ratios for HNSCC and non-cancerous head-and-neck tissue samples | | | | | | | | | |
|---|---|---|---|---|---|---|---|---|---|
| Accession # | Protein name | C1 | C2 | C3 | C4 | C5 | C6 | C7 | C8 |
| spt\|P31947 | Stratifin | 3.6 | 2.48 | 1.73 | 2.23 | 2.09 | 3.44 | 3.15 | 2.05 |
| trm\|Q86V33 | YWHAZ | 2.58 | 2.34 | 1.45 | 1.54 | 1.23 | 1.85 | 10.27 | 1.58 |
| spt\|P29034 | S100A 2 | 4.1 | 3.48 | 1.85 | 1.5 | 3.58 | 1.95 | 32.17 | 4.8 |
| spt\|P31151 | S100A 7 | 2.35 | 2.33 | 3.04 | 2.9 | 3.78 | 2.65 | NQ | 2.82 |
| spt\|P06454 | Prothymosin Alpha | 2.72 | 3.63 | 2.85 | 2.37 | 1.43 | 1.05 | NQ | 1.25 |
| trm\|Q96IH1 | Fascin | 3.51 | 2.35 | NQ | 0.85 | 2.33 | 1.89 | 12.1 | NQ |
| spt\|P31949 | Calgizzarin | 2.38 | NQ | 2.35 | 2.75 | 2.13 | 1.83 | NQ | 2.37 |
| spt\|P36952 | Maspin Precursor | 2.03 | NQ | 1.76 | 1.76 | 1.02 | 2.2 | NQ | 1.98 |
| spt\|P13928 | Annexin A8 | 1.3 | NQ | NQ | 1.58 | 1.6 | 1.33 | NQ | NQ |
| spt\|Q9NZT1 | Calmodulin-like protein 5 | 1.61 | 1.19 | NQ | 1.72 | 0.76 | 1.54 | 1.77 | NQ |
| gb\|AAC13869.1 | Glutathione S Transferase-P | 1.99 | 1.68 | 1.23 | 1.1 | 1.73 | 1.71 | 0.92 | 1.38 |
| spt\|P00338 | LDH A | 2.07 | 1.74 | 1.27 | 1.02 | 1.36 | 1.77 | 2.33 | 1.56 |
| spt\|P62937 | PPIA | 1.69 | 1.89 | 1.18 | 0.99 | 1.76 | 1.34 | 2.86 | 1.65 |
| spt\|Q15691 | APC-binding protein EB1 | 2.15 | 2.62 | 3.02 | 3.45 | 9999 | 1.39 | NQ | 2.02 |
| gb\|AAH16934 | Superoxide dismutase [Mn] | 2.38 | 1.81 | NQ | 1 | 0.81 | 7.96 | NQ | NQ |
| trm\|Q86YI6 | L Plastin | 1.78 | 1 | NQ | 0.88 | 1.36 | 1.68 | NQ | NQ |
| spt\|P60709 | Beta Actin | 1.11 | 1.04 | 1.06 | 0.86 | 1.14 | 0.86 | 0.82 | 1.3 |
| trm\|Q81Z29 | Tubulin beta2 | 1.2 | 0.91 | 1.02 | 0.88 | 1.18 | 1.13 | NQ | 1.05 |
| trm\|Q8WU39 | PACAP | 0.3 | 0.72 | 0.65 | 0.71 | 0.61 | 0.48 | 0.13 | 0.52 |

TABLE 1-continued iTRAQ ratios for HNSCC and non-cancerous head-and-neck tissue samples

| Accession # | Protein name | | | | | | | |
|---|---|---|---|---|---|---|---|---|
| trm|Q71DI3 | Histone H3 | 0.38 | NQ | 0.57 | 0.58 | 0.69 | 0.36 | NQ | 0.6 |
| spt|P62805 | Histone H4 | 0.66 | 0.69 | 0.52 | 0.69 | NQ | 0.68 | 0.67 | 0.54 |
| spt|P01009 | Alpha 1 Anti-Trypsin Precursor | 0.97 | 0.29 | 0.35 | 0.65 | 0.5 | 0.62 | 0.22 | 0.35 |
| spt|P51884 | KSPG Lumican | 0.51 | 0.65 | 0.7 | 0.71 | 0.51 | 0.53 | 0.65 | 0.65 |
| trm|Q96RZ7 | Mast cell tryptase beta III | 0.51 | 0.76 | 0.7 | 0.76 | 0.64 | 0.54 | 0.62 | 0.65 |
| trm|Q9UE88 | Histone H2B.1 | 0.58 | 0.6 | 0.61 | 0.87 | 0.62 | 0.58 | 1.9 | 0.48 |
| spt|P08670 | Vimentin | 0.26 | 0.4 | 0.62 | 0.61 | 0.55 | 0.33 | 0.38 | 0.45 |
| spt|P32119 | Peroxiredoxin 2 | 0.43 | 0.85 | 0.56 | 0.66 | 0.71 | 0.46 | 0.55 | 0.89 |
| spt|P00915 | Carbonic Anhydrase I | 0.34 | 0.78 | 0.48 | 0.57 | 0.37 | 0.37 | 0.88 | 0.67 |
| spt|P30043 | Flavin reductase | 0.54 | 0.74 | 0.54 | NQ | 0.8 | 0.59 | 0.1 | 0.86 |
| pir|KRHUE | Cytokeratin 14 | 1.27 | 1.31 | 1.84 | 3.83 | 1.46 | 1.29 | 0.24 | 2.06 |
| trm|Q86U86 | Polybromo-1D | NQ | NQ | 0.54 | NQ | 0.58 | NQ | NQ | NQ |
| spt|P14618 | PK M2 | 1.51 | 1.48 | 1.18 | 1.04 | 1.18 | 1.34 | 2.26 | 1.61 |
| spt|P04083 | Annexin A1 | 0.96 | 1.63 | 1.2 | 2.36 | 1.4 | 1.68 | 0.63 | 1.24 |
| gb|AAH16768.1 | Nucleophosmin 1 | 1.37 | NQ | 1.69 | 1.46 | 1.4 | 1.8 | NQ | 1.19 |
| spt|P04792 | Hsp27 | 1.2 | 1.3 | 1.25 | 1.68 | 1.25 | 1.49 | 1.69 | 1.82 |
| spt|P04080 | Cystatin B | 1.04 | 0.75 | 0.58 | 0.77 | 0.76 | 1.21 | 0.67 | 0.76 |
| spt|P14625 | GRP 94 | 0.5 | 0.86 | NQ | 0.8 | 0.77 | 0.55 | 0.59 | NQ |
| gb|AAA59555 | MARCKS | 0.86 | 1.57 | 1.26 | 9999 | 0.54 | 1.09 | 5.47 | 1.3 |

| | Accession # | Protein name | C9 | C10 | N2 | N3 | N1 | N4 | N5 |
|---|---|---|---|---|---|---|---|---|---|
| | spt|P31947 | Stratifin | 1.93 | 1.04 | 0.84 | 0.52 | 0.82 | 0.86 | 1.06 |
| | trm|Q86V33 | YWHAZ | 1.58 | 1.02 | 0.95 | 0.81 | 0.98 | 0.93 | 0.93 |
| | spt|P29034 | S100A 2 | 2.34 | 2.27 | 1.37 | 1.28 | 0.95 | 1.35 | 1.88 |
| | spt|P31151 | S100A 7 | 1.71 | 1.44 | 0.69 | 1.01 | 0.81 | 1.08 | 1.26 |
| | spt|P06454 | Prothymosin Alpha | 1.79 | 1.29 | 0.88 | 1.53 | 1.04 | 1.16 | 1.66 |
| | trm|Q96IH1 | Fascin | 1.43 | 1.76 | 1.16 | NQ | 1.14 | 1.02 | 1.01 |
| | spt|P31949 | Calgizzarin | 2.5 | 2.23 | NQ | 1 | 1.59 | 1.3 | 1.19 |
| | spt|P36952 | Maspin Precursor | 1.98 | 0.94 | NQ | 1.09 | 0.86 | 1.09 | 0.88 |
| | spt|P13928 | Annexin A8 | 1.71 | 1.53 | 0.83 | NQ | 1.84 | 1.18 | 1.12 |
| | spt|Q9NZT1 | Calmodulin-like protein 5 | 1.17 | 0.98 | 0.92 | NQ | 0.88 | 0.58 | 1.06 |
| | gb|AAC13869.1 | Glutathione S Transferase-P | 1.73 | 1.13 | 1.08 | 0.97 | 0.59 | 1.01 | 0.92 |
| | spt|P00338 | LDH A | 1.84 | 1.26 | 1.03 | 0.75 | 0.96 | 0.94 | 0.93 |
| | spt|P62937 | PPIA | 1.17 | 1.06 | 0.86 | 0.48 | 0.86 | 0.92 | 0.97 |
| | spt|Q15691 | APC-binding protein EB1 | 1.94 | NQ | 0.93 | 0.87 | 1.36 | 1.40 | NQ |
| | gb|AAH16934 | Superoxide dismutase [Mn] | NQ | 0.91 | NQ | NQ | NQ | 0.81 | 1.13 |
| | trm|Q86YI6 | L Plastin | 1.25 | 1.52 | NQ | NQ | 0.98 | 0.68 | 1.08 |
| | spt|P60709 | Beta Actin | 1.06 | 0.87 | 0.83 | 0.71 | 1.07 | 0.81 | 1.1 |
| | trm|Q81Z29 | Tubulin beta2 | 1.2 | 1.02 | 0.99 | 0.88 | 1.18 | 1 | NQ |
| | trm|Q8WU39 | PACAP | 0.72 | 0.62 | 0.39 | 0.31 | 1.66 | 1.44 | 1.02 |
| | trm|Q71DI3 | Histone H3 | 0.62 | 2.47 | NQ | 1.86 | 1.73 | 1.24 | 1.84 |
| | spt|P62805 | Histone H4 | 1.24 | NQ | 1.2 | 2.36 | 1.89 | 2.72 | NQ |
| | spt|P01009 | Alpha 1 Anti-Trypsin Precursor | 0.71 | 0.28 | 1 | 0.31 | 0.73 | 0.85 | 0.82 |
| | spt|P51884 | KSPG Lumican | 0.6 | 0.93 | 2.03 | 1.84 | 0.68 | 1.02 | 0.8 |
| | trm|Q96RZ7 | Mast cell tryptase beta III | 0.7 | 0.83 | 1.36 | 1.84 | 0.93 | 0.92 | 0.79 |
| | trm|Q9UE88 | Histone H2B.1 | 0.43 | 1.09 | 2 | 1.3 | 1.45 | 1.38 | 1.79 |
| | spt|P08670 | Vimentin | 0.43 | 0.73 | 0.91 | 0.77 | 1.03 | 0.55 | 0.78 |
| | spt|P32119 | Peroxiredoxin 2 | 0.63 | 0.51 | 0.94 | 0.43 | 0.64 | 0.55 | 0.77 |
| | spt|P00915 | Carbonic Anhydrase I | 0.59 | 0.56 | 0.63 | 0.36 | 0.51 | 0.67 | 0.93 |
| | spt|P30043 | Flavin reductase | NQ | 0.72 | 0.67 | 0.5 | 0.64 | NQ | 0.81 |
| | pir|KRHUE | Cytokeratin 14 | 1.01 | 1.7 | 0.61 | 0.98 | 0.91 | 1.04 | 1.18 |
| | trm|Q86U86 | Polybromo-1D | NQ | 0.58 | 1.69 | NQ | NQ | 1.07 | NQ |
| | spt|P14618 | PK M2 | 1.4 | 1.21 | 0.9 | 0.84 | 0.95 | 0.94 | 0.97 |
| | spt|P04083 | Annexin A1 | 0.91 | 1.52 | 0.86 | 0.94 | 1.05 | 1.27 | 1.4 |
| | gb|AAH16768.1 | Nucleophosmin 1 | 1.15 | 1.36 | NQ | 0.84 | 1.19 | 1.48 | 0.98 |
| | spt|P04792 | Hsp27 | 1.42 | 1.01 | 1.21 | 1.01 | 0.9 | 1.32 | 1.12 |
| | spt|P04080 | Cystatin B | 0.78 | 0.52 | 0.95 | 0.37 | 0.72 | 0.83 | 0.72 |
| | spt|P14625 | GRP 94 | 0.8 | 0.73 | 0.68 | NQ | 1.17 | 0.81 | 0.77 |
| | gb|AAA59555 | MARCKS | 0.56 | 0.54 | 1.19 | 1.1 | 0.98 | 0.54 | 0.83 |

NQ—Not Quantifiable.

TABLE 2

Receiver-operating characteristics from the iTRAQ ratios of a panel of three best-performing biomarkers - YWHAZ, stratifin, and S100A7 - individually and as a panel.

| BIOMARKER PANEL | SENS | SPEC | PPV | NPV | AUC |
|---|---|---|---|---|---|
| YWHAZ | 0.30 | 1.00 | 1.00 | 0.42 | 1.00 |
| SFN | 0.80 | 1.00 | 1.00 | 0.71 | 0.98 |
| S100 CBP A7 | 0.70 | 1.00 | 1.00 | 0.63 | 0.90 |
| YWHAZ, STRATIFIN, S100A7 | 0.92 | 0.91 | 0.95 | 0.85 | 0.96 |

TABLE 3

Receiver-operating characteristics from the IHC scores of a panel of three best-performing biomarkers - YWHAZ, stratifin, and S100A7 - individually and as a panel.

| BIOMARKER PANEL | SENS | SPEC | PPV | NPV | AUC |
|---|---|---|---|---|---|
| YWHAZ | 1.00 | 0.71 | 0.71 | 1.00 | 0.90 |
| SFN | 0.92 | 0.60 | 0.62 | 0.91 | 0.85 |
| S100 CBP A7 | 0.96 | 0.71 | 0.71 | 0.96 | 0.90 |
| YWHAZ, STRATIFIN, S100A7 | 0.92 | 0.87 | 0.83 | 0.94 | 0.91 |

TABLE 4

Comparison of receiver-operating characteristics from the iTRAQ ratios of the panel of three best-performing biomarkers.

| COMPARISON | SENS | SPEC | PPV | NPV | AUC |
|---|---|---|---|---|---|
| Cancer vs. Paired Normal | 0.92 | 0.83 | 0.85 | 0.92 | 0.89 |
| Cancer vs. Non-Paired Normal | 0.96 | 0.96 | 0.98 | 0.90 | 0.97 |

TABLE 5

Differentially-expressed proteins not previously described in OPLs and head-and-neck malignancies and cancer.

| SEQ ID. No. | Protein Name | Gene Name | Accession No. | Expression in Head-and-Neck Cancer | Expression in OPLs |
|---|---|---|---|---|---|
| 1. | Calmodulin-like protein 5 | CALML5 | Peptide: spt\|Q9NZT1<br>mRNA/DNA coding: NM_017422 | Up-regulated | |
| 2. | Polybromo-1D | PBRM1 | Peptide: trm\|Q86U86<br>mRNA/DNA coding: NM_181042 | Down-regulated | |
| 3. | APC-binding protein EB1 | MAPRE1 | Peptide: spt\|Q15691<br>mRNA/DNA coding: NM_012325 | Up-regulated | |
| 4. | Carbonic anhydrase I | CA1 | Peptide: spt\|P00915<br>mRNA/DNA coding: NM_001738 | Down-regulated | |
| 5. | Mast cell tryptase beta III | tryptaseB | Peptide: trm\|Q96RZ7<br>mRNA/DNA coding: NM_024164 | Down-regulated | |
| 6. | Histone H3 | HIST2H3A | Peptide: trm\|Q71DI3<br>mRNA/DNA coding: NM_021059 | Down-regulated | |
| 7. | Plastin 3 | PLS3 | Peptide: spt\|P13797<br>mRNA/DNA coding: NM_005032 | Up-regulated | |
| 8. | Histone H4 | HIST1H4A | Peptide: spt\|P62805<br>mRNA/DNA coding: NM_003495 | Down-regulated | |
| 9. | Cyclophilin A | PPIA | Peptide: trm\|Q6NTE9<br>mRNA/DNA coding: NM_021130 | Up-regulated | |
| 10. | PACAP (proapoptotic caspase adaptor protein) | MGC29506 | Peptide: trm\|Q8WU39<br>mRNA/DNA coding: NM_016459 | Down-regulated | |
| 11. | LDH A | LDHA | Peptide: spt\|P00338<br>mRNA/DNA coding: NM_005566 | Up-regulated | |
| 12. | KSPG Luminican | LUM | Peptide: spt\|P51884<br>mRNA/DNA coding: NM_002345 | Down-regulated | |
| 13. | S100 CBP A7 | S100A7 | Peptide: spt\|P31151<br>mRNA/DNA coding: NM_002963.3 | Up-regulated | *Up-regulated |
| 14. | Peroxiredoxin 2 | PRDX2 | Peptide: spt\|P32119<br>mRNA/DNA coding: NM_181738 | Down-regulated | Down-regulated |
| 15. | Superoxide dismutase 2 (SOD2 protein) | SOD2 | Peptide: trm\|AAH16934<br>mRNA/DNA coding: BC016934 | Up-regulated | *Up-regulated |
| 16. | Alpha 1 Anti-Trypsin Precursor | SERPINA1 or AAT | Peptide: spt\|P01009<br>mRNA/DNA coding: NM_001002236 | Down-regulated | Down-regulated |
| 17. | MARCKS | MACS | Peptide: gb\|AAA59555.1<br>mRNA/DNA coding: M68956 | Up-regulated | Down-regulated |
| 18. | GRP-94 | HSP90B1 | Peptide: spt\|P14625<br>mRNA/DNA coding: NM_003299 | Down-regulated | Up-regulated |
| 19. | Prothymosin Alpha | PTMA (also referred to as PTHA) | Peptide: spt\|P06454<br>mRNA/DNA coding: NM_001099285 | Up-regulated | Up-regulated |
| 20. | Histone H2B.1 | HIST2H2BE | Peptide: spt\|Q16778<br>mRNA/DNA coding: NM_003528 | Down-regulated | Up-regulated |
| 21. | Nucleophosmin 1 | NPM1 | Peptide: gb\|AAH16768.1<br>mRNA/DNA coding: BC016768 | Up-regulated | Up-regulated |
| 22. | PK M2 | PKM2 | Peptide: spt\|P14618<br>mRNA/DNA coding: NM_182471 | | Up-regulated |

TABLE 5-continued

Differentially-expressed proteins not previously described in OPLs and head-and-neck malignancies and cancer.

| SEQ ID. No. | Protein Name | Gene Name | Accession No. | Expression in Head-and-Neck Cancer | Expression in OPLs |
|---|---|---|---|---|---|
| 23. | Stratifin | SFN | spt\|P31947 mRNA/DNA coding: | | Up-regulated |
| 24. | YWHAZ | | trm\|Q86V33 mRNA/DNA coding: | | Up-regulated |
| 25. | hnRNPK | | spt\|P61978 mRNA/DNA coding: | | Up-regulated |
| 18. | HSP90B1 | | spt\|P14625 mRNA/DNA coding: | | Up-regulated |
| 26. | Parathymosin | PTHM | trm\|O15256 mRNA/DNA coding: | | Up-regulated |
| 27. | Cystatin B | | spt\|P04080 mRNA/DNA coding: P04080 | | Down-regulated |
| 28. | DLC1 | | trm\|Q6NSB4 mRNA/DNA coding: | | Down-regulated |
| 29. | FABP5 | | spt\|Q01469 mRNA/DNA coding: | | Down-regulated |
| 30. | IGHG1 protein | | gb\|AAH25314.1 mRNA/DNA coding: | | Down-regulated |
| 31. | Calgizzarin | | spt\|P31949 mRNA/DNA coding: | | Down-regulated |
| 32. | IGL 2* | | trm\|Q8N5F4 mRNA/DNA coding: | | Up-regulated |
| 33. | P37AUF1* | | trm\|Q12771 mRNA/DNA coding: | | Up-regulated |
| 22. | PKM2* | | spt\|P14618 mRNA/DNA coding: | | Up-regulated |
| 34. | ROA1HNRNPA1* | | sptIP09651 mRNA/DNA coding: | | Up-regulated |
| 35. | Hsp27* | | sptIP04792 mRNA/DNA coding: P04792 | | Up-regulated |
| 36. | Cofilin* | | spt\|P23528 mRNA/DNA coding: | | Up-regulated |
| 37. | Glyceraldehyde-3-phosphate Dehydrogenase* | | emb\|CAA25833.1 mRNA/DNA coding: | | Up-regulated |
| 38. | NDP Kinase B* | | spt\|P22392 mRNA/DNA coding: | | Up-regulated |
| 39. | Elongation Factor 2* | | spt\|P13639 mRNA/DNA coding: | | Up-regulated |
| 40. | PE Binding protein* | | spt\|P30086 mRNA/DNA coding: | | Up-regulated |
| 41. | CALM 3* | | spt\|P27482 mRNA/DNA coding: | | Up-regulated |

TABLE 6

Average iTRAQ ratios for OPLs aNQ histologically-normal control oral tissue samples

| Accession # | Protein Name | D1 | D2 | D3 | D4 | D5 | D6 |
|---|---|---|---|---|---|---|---|
| spt\|P31947 | Stratifin | 0.74 | 2.15 | 1.94 | 1.53 | 1.77 | 1.63 |
| trm\|Q86V33 | YWHAZ | 1.02 | 3.07 | 1.19 | 1.88 | 0.81 | 1.5 |
| spt\|P61978 | hnRNPK | 9.86 | 1.14 | 1.13 | 1.71 | 1.25 | 1.5 |
| spt\|P06454 | PTHA | 0.64 | 0.61 | 1.19 | 1.53 | 3.91 | 3.54 |
| spt\|P14625 | HSP90B1 | 2.86 | 1.65 | 1.46 | 3.38 | 0.8 | 0.99 |
| trm\|O15256 | Parathymosin | NQ | NQ | NQ | 3.97 | 2.35 | 2.89 |
| trm\|Q9UE88 | Histone H2B.1 | 2.97 | 1.25 | 1.73 | 0.87 | 1.96 | 1.52 |
| spt\|P14625 | GRP 94 | 2.86 | 1.65 | 1.19 | 3.38 | 0.8 | 0.99 |
| gb\|AAH16768.1 | Nucleophosmin 1 | 1.2 | 0.96 | 1.56 | 1.66 | NQ | NQ |
| spt\|P04080 | Cystatin B | 0.78 | 1.14 | 0.36 | 0.39 | 0.54 | 0.78 |
| gb\|AAA59555.1 | MARCKS | 0.67 | 0.5 | 0.57 | 0.61 | 0.72 | 0.6 |
| trm\|Q6NSB4 | DLC1 | 1.63 | 0.29 | NQ | NQ | 0.5 | 0.53 |
| spt\|P01009 | Alpha 1 Anti-Trypsin Precursor | 0.45 | 0.57 | 0.67 | 0.85 | 1.36 | 0.99 |
| spt\|P32119 | Peroxiredoxin 2 | 0.89 | 0.72 | 0.62 | 0.63 | 0.64 | 0.47 |
| spt\|Q01469 | FABP5 | 0.78 | 1.43 | 0.79 | 0.67 | 0.58 | 0.66 |

TABLE 6-continued

Average iTRAQ ratios for OPLs aNQ histologically-normal control oral tissue samples

| | | | | | | | |
|---|---|---|---|---|---|---|---|
| gb|AAH25314.1 | IGHG1 protein | 1.13 | 0.58 | 1.15 | 0.67 | NQ | NQ |
| spt|P31949 | Calgizzarin | 0.48 | 0.45 | NQ | NQ | 0.84 | 1.18 |
| trm|Q8N5F4 | IGL 2* | NQ | NQ | NQ | NQ | 4.09 | 1.77 |
| trm|Q12771 | p37AUF1* | 7.77 | 4.35 | NQ | NQ | NQ | NQ |
| prf|0904262A | SOD2* | NQ | NQ | NQ | NQ | 1.34 | 1.51 |
| spt|P14618 | PKM2* | 1.04 | 1.37 | 1.26 | 1.66 | 1.09 | 1.12 |
| spt|P09651 | ROA1HNRNPA1* | 1.3 | 1.7 | 1.16 | 1.25 | 0.9 | 1.87 |
| spt|P04792 | Hsp27* | 1.17 | 1.88 | 0.78 | 1.27 | 1.13 | 2.35 |
| spt|P23528 | Cofilin* | 1.13 | 1.27 | 1.45 | 2.06 | 1.17 | 1.17 |
| emb|CAA25833.1 | Glyceraldehyde-3-phosphate Dehydrogenase | 1.37 | 1.55 | 0.75 | 1.5 | 1.13 | 1.12 |
| spt|P13639 | Elongation Factor 2* | 1.26 | 1.47 | NQ | NQ | 1.35 | 1.28 |
| spt|P31151 | S100 A7* | NQ | NQ | 1.3 | 1.4 | NQ | NQ |
| spt|P30086 | PE BiNQing protein | NQ | NQ | NQ | NQ | 1.4 | 1.57 |
| spt|P27482 | CALM 3* | 1.25 | 0.97 | 1.15 | 1.15 | 4.55 | 1.08 |
| spt|P06396 | Gelsolin Precursor | 1.04 | 1 | 0.95 | 1.03 | 1.04 | 1.15 |

| Accession # | Protein Name | N1 | N2 | N3 | N4 | N5 | N6 |
|---|---|---|---|---|---|---|---|
| spt|P31947 | Stratifin | 0.88 | 0.74 | 0.75 | 0.84 | 0.78 | 1.03 |
| trm|Q86V33 | YWHAZ | 1.18 | 0.84 | 0.99 | 1 | 0.8 | 0.97 |
| spt|P61978 | hnRNPK | 1.04 | 1.24 | 1.1 | 1.23 | 0.9 | NQ |
| spt|P06454 | PTHA | 0.69 | 0.91 | 1.57 | 0.88 | 1.16 | 1.66 |
| spt|P14625 | HSP90B1 | 1.16 | 1.19 | 0.61 | 0.98 | 1.05 | 1.02 |
| trm|O15256 | Parathymosin | NQ | NQ | 0.81 | NQ | NQ | NQ |
| trm|Q9UE88 | Histone H2B.1 | 1.2 | 0.82 | 1.83 | 1.2 | 1.38 | 1.5 |
| spt|P14625 | GRP 94 | 1.16 | 0.61 | 1.46 | 1 | 0.81 | 0.85 |
| gb|AAH16768.1 | Nucleophosmin 1 | 0.77 | 0.97 | NQ | 1.17 | 1.05 | NQ |
| spt|P04080 | Cystatin B | 0.96 | 0.29 | 0.82 | 0.87 | 0.77 | 0.73 |
| gb|AAA59555.1 | MARCKS | 0.56 | 0.57 | 0.83 | NQ | 0.54 | 0.83 |
| trm|Q6NSB4 | DLC1 | 0.43 | NQ | 0.75 | 0.68 | NQ | 0.99 |
| spt|P01009 | Alpha 1 Anti-Trypsin Precursor | 0.92 | 0.77 | 0.79 | 0.81 | 0.69 | 1.06 |
| spt|P32119 | Peroxiredoxin 2 | 0.99 | 0.7 | 0.69 | 0.6 | 0.75 | NQ |
| spt|Q01469 | FABP5 | 0.89 | 0.97 | 0.87 | 0.83 | 0.93 | 0.93 |
| gb|AAH25314.1 | IGHG1 protein | 1.11 | 1.24 | NQ | NQ | NQ | NQ |
| spt|P31949 | Calgizzarin | 0.51 | NQ | 1.19 | 1.23 | NQ | 1.19 |
| trm|Q8N5F4 | IGL 2* | NQ | NQ | 0.95 | NQ | NQ | NQ |
| trm|Q12771 | p37AUF1* | 0.97 | NQ | NQ | NQ | NQ | NQ |
| prf|0904262A | SOD2* | NQ | NQ | 1.23 | NQ | 0.81 | 1.13 |
| spt|P14618 | PKM2* | 1.12 | 0.94 | 1.09 | 1.01 | 0.87 | 0.97 |
| spt|P09651 | ROA1HNRNPA1* | 0.81 | 1.33 | 1.04 | 1.23 | 0.88 | 1.07 |
| spt|P04792 | Hsp27* | 0.96 | 1.17 | 0.83 | 0.89 | 1.23 | 0.95 |
| spt|P23528 | Cofilin* | 0.73 | 0.93 | 1.05 | 1.04 | 0.9 | NQ |
| emb|CAA25833.1 | Glyceraldehyde-3-phosphate Dehydrogenase | 1.39 | 0.62 | 1.36 | 1.17 | 0.71 | 0.97 |
| spt|P13639 | Elongation Factor 2* | 1.03 | NQ | 1.34 | 1.22 | 1.07 | 0.93 |
| spt|P31151 | S100 A7* | NQ | 0.88 | NQ | 0.81 | 1.03 | 1.09 |
| spt|P30086 | PE BiNQing protein | NQ | NQ | 1.05 | NQ | NQ | NQ |
| spt|P27482 | CALM 3* | 0.89 | 1 | 0.89 | 0.51 | 1.02 | 1.06 |
| spt|P06396 | Gelsolin Precursor | 0.9 | 1.05 | 1.02 | 0.91 | 1.05 | 1.02 |

NQ—Not Quantifiable.

TABLE 7

Receiver-operating characteristics from (A) the iTRAQ ratios and (B) IHC scores of a panel of three best-performing biomarkers - YWHAZ, stratifin, and hnRNPK - individually and as a panel.

| Biomarker | Sensitivity | Specificity | PPV | NPV | AUC |
|---|---|---|---|---|---|
| A. iTRAQ analysis | | | | | |
| YWHAZ | 0.33 | 1.0 | 1.0 | 0.43 | 0.78 |
| Stratifin | 0.81 | 1.0 | 1.0 | 0.75 | 0.82 |
| hnRNPK | 0.17 | 1.0 | 1.0 | 0.38 | 0.78 |
| Panel of the three | 0.83 | 0.74 | 0.87 | 0.69 | 0.85 |
| B. IHC analysis | | | | | |
| YWHAZ | 0.90 | 0.95 | 0.96 | 0.87 | 0.93 |
| Stratifin | 0.77 | 0.95 | 0.96 | 0.74 | 0.93 |
| hnRNPK | 0.80 | 0.91 | 0.92 | 0.76 | 0.89 |
| Panel of the three | 0.91 | 0.95 | 0.96 | 0.88 | 0.97 |

TABLE 8

Analysis of Stratifin and YWHAZ in HNOSCCs: correlation with clinicopathological parameters.

| Clinicopathological Features | Total Cases N | STRATIFIN+ n | (%) | STRATIFIN+-YWHAZ+ n | (%) | STRATIFIN+/YWHAZ+ n | (%) |
|---|---|---|---|---|---|---|---|
| Non-malignant tissue | 39 | 12 | (31) | 8 | (20) | 25 | (64) |
| HNOSCC# | 51 | 32 | (63) | 28 | (55) | 43 | (84) |
| Differentiation* | | | | | | | |
| WDSCC | 29 | 18 | (62) | 16 | (55) | 26 | (90) |
| MDSCC | 19 | 12 | (63) | 10 | (53) | 15 | (79) |
| PDSCC | 3 | 2 | (67) | 2 | (67) | 2 | (67) |
| Tumor Stage | | | | | | | |
| $T_1$ | 6 | 5 | (83) | 5 | (83) | 6 | (100) |
| $T_2$ | 15 | 6 | (40) | 4 | (27) | 11 | (73) |
| $T_3$ | 13 | 9 | (69) | 8 | (61) | 12 | (92) |
| $T_4$ | 17 | 12 | (71) | 11 | (65) | 14 | (82) |
| Nodal Status | | | | | | | |
| $N^-$ | 28 | 17 | (61) | 15 | (54) | 23 | (82) |
| $N^+$ | 23 | 15 | (65) | 13 | (56) | 20 | (87) |

*WDSCC, well differentiated squamous cell carcinoma; MDSCC, moderately differentiated squamous cell carcinoma; PDSCC, poorly differentiated squamous cell carcinoma
For HNOSCCs vs. Non-malignant tissues:
a) Stratifin+ (p = 0.03, OR = 3.8, 95% CI = 1.6-9.2);
b) YWHAZ+ (p = 0.024, OR = 2.8, 95% CI = 1.2-6.8);
c) Stratifin+-YWHAZ+ (p = 0.001, OR = 4.7, 95% CI = 1.8-12.2);
d) SFN+/YWHAZ+ (p = 0.027, OR = 3.1, 95% CI = 1.1-8.2).

TABLE 9a

Analysis of overexpression of hnRNP K protein in oral lesions and correlation with clinicopathological parameters.

| Clinicopathological Features | Total Cases | Nuclear N | Positivity (%) | p-value | OR (95% CI) | Cytoplasmic N | Positivity (%) | p-value | OR (95% CI) |
|---|---|---|---|---|---|---|---|---|---|
| NORMAL | 55 | 4 | (7) | | | — | — | | |
| LEUKOPLAKIA | 199 | 141 | (71) | <0.001[a] | 30.9 (10.7-89.7) | 26 | (13) | <0.001[b] | 4.3 (2.2-7.2) |
| NO DYSPLASIA | 115 | 78 | (68) | <0.001[c] | 26.8 (9.1-79.9) | 18 | (16) | <0.001[d] | 4.3 (1.8-6.3) |
| DYSPLASIA | 84 | 63 | (75) | <0.001[e] | 38.2 (11.7-113.1) | 8 | (10) | <0.001[f] | 5.8 (2.5-13.4) |
| HNOSCC | 100 | 78 | (78) | <0.001[g] | 45.2 (14.7-138.8) | 38 | (38) | | |
| Age (Median, 53 yrs) | | | | | | | | | |
| <53 | 49 | 34 | (69) | 0.05 | 2.7 (1.1-7.5) | 16 | (33) | 0.28 | — |
| ≥53 | 51 | 44 | (86) | | | 22 | (43) | | |
| Gender | | | | | | | | | |
| Male | 75 | 59 | (78) | 0.78 | — | 28 | (37) | 0.81 | — |
| Female | 25 | 19 | (76) | | | 10 | (40) | | |
| Differentiation | | | | | | | | 0.001 | |
| WDSCC | 45 | 33 | (73) | 0.31 | — | 9 | (20) | | — |
| MDSCC | 49 | 39 | (79) | | | 24 | (49) | | |
| PDSCC | 6 | 6 | (100) | | | 5 | (83) | | |
| Tumor Stage | | | | | | | | 0.19 | |
| $T_1$ | 4 | 4 | (100) | 0.42 | — | 3 | (75) | | — |
| $T_2$ | 35 | 28 | (80) | | | 15 | (43) | | |
| $T_3$ | 25 | 17 | (68) | | | 6 | (24) | | |
| $T_4$ | 36 | 29 | (81) | | | 14 | (39) | | |
| Nodal Status | | | | | | | | 0.52 | |
| $N_0$ | 33 | 24 | (73) | 0.37 | — | 14 | (42) | | — |
| $N_{1-4}$ | 67 | 54 | (81) | | | 24 | (36) | | |
| Habits | | | | | | | | 0.41 | |
| Non consumer | 22 | 19 | (86) | 0.28 | — | 10 | (45) | | — |
| Tobacco consumer | 78 | 59 | (75) | | | 28 | (36) | | |

Nuclear staining:
[a]Normal vs. Leukoplakia;
[c]Normal vs. Leukoplakia with no evidence of dysplasia;
[e]Normal vs. Dysplasia;
[g]Normal vs. HNOSCCs; N/L/HNOSCCs: p < 0.001;
Cytoplasmic staining:
[b]Leukoplakia vs. HNOSCCs;
[d]Leukoplakia with no evidence of dysplasia vs. HNOSCCs;
[f]Dysplasia vs. HNOSCCs; N/L/HNOSCCs: p < 0.001

TABLE 9b

Biomarker analysis of hnRNP K (nuclear/cytoplasmic) in oral lesions.

| hnRNP K | Sensitivity | Specificity | PPV | AUC |
|---|---|---|---|---|
| I) Nuclear staining | | | | |
| Normal vs. Leukoplakia (No Dysplasia) | 67.0 | 92.7 | 94.8 | 0.822 |
| Normal vs. Leukoplakia (Dysplasia) | 74.1 | 92.3 | 93.7 | 0.872 |
| Normal vs. OSCCs | 78.0 | 92.3 | 95.1 | 0.869 |
| II) Cytoplasmic staining | | | | |
| Normal vs. Leukoplakia (No Dysplasia) | 15.3 | 100 | 100 | 0.577 |
| Normal vs. Leukoplakia (Dysplasia) | 8.3 | 100 | 100 | 0.543 |
| Normal vs. OSCCs | 38.1 | 100 | 100 | 0.709 |

TABLE 10

Alternate accession numbers for OPL proteins.

| Accession # | Protein Name | Alternate Accession #s |
|---|---|---|
| spt\|P61978 | hnRNPK | gi\|48429103, NP_002131.2, S74678.1, NP_112552.1, AAB20770.1, NP_112553.1, X72727.1, 1J5K_A, CAA51267.1, 1KHM_A, AB209562.1, 1ZZI_A, BAD92799.1, 1ZZI_B, BC000355.2, 1ZZJ_A, AAH00355.1, 1ZZJ_B, BC014980.1, 1ZZJ_C, AAH14980.1, 1ZZK_A, S43363 |
| spt\|P14625 | HSP90B1 | gi\|119360, AAH66656.1, X15187.1, M26596.1, CAA33261.1, AAA58621.1, M33716.1, AY040226.1, AAA68201.1, AAK74072.1, BC066656.1, NP_003290.1 |
| trm\|O15256 | Parathymosin | gi\|74705500, Y13586.1, CAA73913.1 |
| trm\|Q6NSB4 | DLC1 | gi\|74758095, BC070299.1, AAH70299.1 |
| spt\|Q01469 | FABP5 | gi\|232081, AAH70303.1, M94856.1, I56326, AAA58467.1, NP_001435.1, BT007449.1, XP_001127657.1, AAP36117.1, XP_001128089.1, BC019385.2, XP_001718427.1, AAH19385.1, 1B56_A, BC070303.1, 1JJJ_A |
| gb\|AAH25314.1 | IGHG1 protein | gi\|19263707 |
| trm\|Q8N5F4 | IGL 2* | gi\|74728989, BC032452.1, AAH32452.1 |
| trm\|Q12771 | P37AUF1* | gi\|74754454, U02019.1, AAC50056.1, A54601 |
| prf\|0904262A | SOD2* | gi\|223632 |
| spt\|P14618 | PKM2* | gi\|20178296, BC007952.2, M23725.1, AAH07952.3, AAA36449.1, BC012811.2, M26252.1, AAH12811.3, AAA36672.1, BC035198.1, X56494.1, AAH35198.1, CAA39849.1, AF025439.1, AY352517.1, AAC39559.1, AAQ15274.1, S30038, AK222927.1, S64635, BAD96647.1, NP_002645.3, AC020779.10, NP_872270.1, CH471082.1, 1T5A_A, EAW77884.1, 1T5A_B, BC000481.2, 1T5A_C, AAH00481.3, 1T5A_D, BC007640.1, 1ZJH_A, AAH07640.1 |
| spt\|P09651 | ROA1HNRNPA1* | gi\|133254, AAH74502.1, X12671.1, BC103707.1, CAA31191.1, AAI03708.1, X06747.1, NZ_SHDD041214211, |

TABLE 10-continued

Alternate accession numbers for OPL proteins.

| Accession # | Protein Name | Alternate Accession #s |
|---|---|---|
| | | CAA29922.1, NP_002127.1, X04347.1, 1HA1_A, CAA27874.1, 1L3K_A, X79536.1, 1PGZ_A, CAA56072.1, 1PO6_A, BC002355.2, 1U1K_A, AAH02355.1, 1U1L_A, BC009600.1, 1U1M_A, AAH09600.1, 1U1N_A, BC012158.1, 1U1O_A, AAH12158.1, 1U1P_A, BC033714.1, 1U1Q_A, AAH33714.1, 1U1R_A, BC052296.1, 1UP1_A, AAH52296.1, 2H4M_C, BC070315.1, 2H4M_D, AAH70315.1, 2UP1_A, BC074502.1 |
| spt\|P23528 | Cofilin* | gi\|116848, AAH11005.1, D00682.1, BC012265.1, BAA00589.1, AAH12265.1, U21909.1, BC012318.1, AAA64501.1, AAH12318.1, X95404.1, BC018256.2, CAA64685.1, AAH18256.1, BT006846.1, NP_005498.1, AAP35492.1, 1Q8G_A, BC011005.2, 1Q8X_A |
| emb\|CAA25833.1 | Glyceraldehyde-3-Phosphate Dehydrogenase* | gi\|31645, 1U8F, 1ZNQ |
| spt\|P22392 | NDP Kinase B* | gi\|127983, NP_002503.1, X58965.1, 1NSK_L, CAB37870.1, 1NSK_N, M36981.1, 1NSK_O, AAA36369.1, 1NSK_R, L16785.1, 1NSK_T, AAA60228.1, 1NSK_U, BC002476.2, 1NUE_A, AAH02476.1, 1NUE_B, A49798, 1NUE_C, NP_001018146.1, 1NUE_D, NP_001018147.1, 1NUE_E, NP_001018148.1, 1NUE_F, NP_001018149.1 |
| spt\|P13639 | Elongation Factor 2* | gi\|119172, BC126259.1, X51466.1, AAI26260.1, CAA35829.1, M19997.1, Z11692.1, AAA50388.1, CAA77750.1, EFHU2, AY942181.1, NP_001952.1, AAX34409.1 |
| spt\|P30086 | PE Binding protein | gi\|1352726, BC031102.1, D16111.1, AAH31102.1, BAA03684.1, S76773.1, X75252.1, AAD14234.1, CAA53031.1, I53745, X85033.1, NP_002558.1, CAA59404.1, 1BD9_A, BC008714.2, 1BD9_B, AAH08714.1, 1BEH_A, BC017396.1, 1BEH_B, AAH17396.1 |
| spt\|P27482 | CALM 3* | gi\|115502, CAI11029.1, M58026.1, BC031889.1, AAA36356.1, AAH31889.1, X13461.1, AAA21893.1, CAA31809.1, NP_005176.1, AL732437.12, 1GGZ_A |

TABLE 11

| ACCESSION | PROTEIN | SEQUENCE COVERAGE | # PEPTIDES | PEPTIDE |
|---|---|---|---|---|
| gb\|AAC13869.1 | Glutathione S Transferase-P | 38.27751279 | 6 | AFLASPEYVNLPINGNGKQ<br>DQQEAALVDMVNDGVEDLR<br>FQDGDLTLYQSNTILR<br>MLLADQGQSWK<br>PPYTVVYFPVR<br>TLGLYGKDQQEAALVDMVNDGVEDLR |
| spt\|P00338 | LDH A | 20.54380625 | 7 | DQLIYNLLK<br>FIIPNVVK<br>GEMMDLQHGSLFLR<br>LVIITAGAR<br>QVVESAYEVIK<br>VIGSGCNLDSAR<br>VTLTSEEEAR |
| spt\|P01009 | Alpha 1 Anti-Trypsin Precursor | 29.90430593 | 9 | AVLTIDEK<br>DTEEEDFHVDQVTTVK<br>FLENEDRR<br>GTEAAGAMFLEAIPM<br>GTEAAGAMFLEAIPMSIPPEVK<br>LQHLENELTHDIITK<br>SVLGQLGITK<br>TDTSHHDQDHPTFNK<br>VFSNGADLSGVTEEAPLK |
| spt\|P04080 | Cystatin B | 54.08163071 | 6 | CGAPSATQPATAETQHIADQVR<br>GAPSATQPATAETQHIADQVR<br>MMCGAPSATQPATAETQHIADQVR<br>PSATQPATAETQHIADQVR<br>SQVVAGTNYFIK<br>VHVGDEDFVHLR |
| spt\|P04083 | Annexin A1 | 34.49275494 | 9 | ALYEAGER<br>DITSDTSGDFR<br>GLGTDEDTLIEILASR<br>GTDVNVFNTILTTR<br>GVDEATIIDILTK<br>KGTDVNVFNTILTTR<br>NALLSLAK<br>QAWFIENEEQEYVQTVK<br>TPAQFDADELR |
| spt\|P06454 | Prothymosin Alpha | 35.45454443 | 5 | AAEDDEDDDVDTK<br>AAEDDEDDDVDTKK<br>EVVEEAENGR<br>KEVVEEAENGR<br>SDAAVDTSSEITTK |
| spt\|P07585 | Decorin Precursor | 5.013927445 | 4 | DFEPSLGPVCPFR<br>DLPPDTTLLDNLQNNK<br>ELHLDNNK<br>VSPGAFTPLVK |
| spt\|P08670 | Vimentin | 58.81057382 | 28 | ADLSEAANR<br>DGQVINETSQHHDDLE<br>DNLAEDIMR<br>EEAENTLQSFR<br>EKLQEEMLQR<br>EMEENFAVEAANYQDTIGR<br>ETNLDSLPLVDTHSK<br>EYQDLLNVK<br>FADLSEAANR<br>ILLAELEQLK<br>ISLPLPNFSSLNLR<br>KLLEGEESR<br>LGDLYEEEMR<br>LLEGEESR<br>LLQDSVDFSLADAINTEFK<br>LQDEIQNMK<br>LQDEIQNMKEEMAR<br>LQEEMLQR<br>NLDSLPLVDTHSK<br>NLQEAEEWYK<br>ODVDNASLAR<br>QQYESVAAK<br>QVDQLTNDK<br>QVQSLTCEVDALK |

TABLE 11-continued

|  |  |  |  |  |
|---|---|---|---|---|
|  |  |  |  | RQVDQLTNDK |
|  |  |  |  | TNEKVELQELNDR |
|  |  |  |  | VELQELNDR |
|  |  |  |  | VEVERDNLAEDIMR |
| spt\|P13928 | Annexin A8 | 17.4311921 | 6 | AYEEDYGSSLEEDIQADTSGYLER |
|  |  |  |  | EGVIIEILASR |
|  |  |  |  | GIGTNEQAIIDVLTK |
|  |  |  |  | NALLSLVGSDP |
|  |  |  |  | SSSHFNPDPDAETLYK |
|  |  |  |  | TLSSMIMEDTSGDYK |
| spt\|P14618 | PK M2 | 39.81132209 | 18 | AEGSDVANAVLDGADCIMLSGETAK |
|  |  |  |  | APIIAVTR |
|  |  |  |  | EAEAAIYHLQLFEELR |
|  |  |  |  | EAEAAIYHLQLFEELRR |
|  |  |  |  | FDEILEASDGIMVAR |
|  |  |  |  | GADFLVTEVENGGSLGSK |
|  |  |  |  | GDLGIEPAEK |
|  |  |  |  | GDYPLEAVR |
|  |  |  |  | GSGTAEVELK |
|  |  |  |  | GVNLPGAAVDLPAVSEK |
|  |  |  |  | IYVDDGLISLQVK |
|  |  |  |  | KASDVHEVR |
|  |  |  |  | LAPITSDPTEATAVGAVEASFK |
|  |  |  |  | LDIDSPPITAR |
|  |  |  |  | NTGIICTIGPASR |
|  |  |  |  | RFDEILEASDGIMVAR |
|  |  |  |  | TATESFASDPILYRPVAVALDTK |
|  |  |  |  | VNFAMNVGK |
| spt\|P14625 | GRP 94 | 16.31382257 | 6 | FAFQAEVNR |
|  |  |  |  | GVVDSDDLPLNVSR |
|  |  |  |  | IYMAGSSR |
|  |  |  |  | LGVIEDHSNR |
|  |  |  |  | LISLTDENALSGNEELTVK |
|  |  |  |  | NLLHVTDTGVGMTR |
| spt\|P26038 | Meosin | 31.25 | 17 | ALELEQER |
|  |  |  |  | ALTSELANAR |
|  |  |  |  | APDFVFYAPR |
|  |  |  |  | AQQELEEQTR |
|  |  |  |  | EALLQASR |
|  |  |  |  | EKEELMER |
|  |  |  |  | FYPEDVSEELIQDITQR |
|  |  |  |  | IGFPWSEIR |
|  |  |  |  | IQVWHEEHR |
|  |  |  |  | ISQLEMAR |
|  |  |  |  | KAQQELEEQTR |
|  |  |  |  | KTQEQLALEMAELTAR |
|  |  |  |  | QLFDQVVK |
|  |  |  |  | TAMSTPHVAEPAENEQDEQDENGAEAS |
|  |  |  |  | TANDMIHAENMR |
|  |  |  |  | TQEQLALEMAELTAR |
|  |  |  |  | VTTMDAELEFAIQPNTTGK |
| spt\|P29034 | S100A 2 | 17.52577275 | 2 | ELPSFVGEK |
|  |  |  |  | ELPSFVGEKVDEEGLK |
| spt\|P31151 | S100A 7 | 33.00000131 | 3 | GTNYLADVFEK |
|  |  |  |  | GTNYLADVFEKK |
|  |  |  |  | SIIGMIDMFHK |
| spt\|P31947 | SFN | 75.4629612 | 16 | ADLHTLSEDSYK |
|  |  |  |  | DNLTLWTADNAGEEGGEAPQEPQS |
|  |  |  |  | DSTLIMQLLR |
|  |  |  |  | EEKGPEVR |
|  |  |  |  | EMPPTNPIR |
|  |  |  |  | GAVEKGEELSCEER |
|  |  |  |  | GEELSCEER |
|  |  |  |  | LAEQAER |
|  |  |  |  | NLLSVAYK |
|  |  |  |  | SAYQEAMDISK |
|  |  |  |  | SAYQEAMDISKK |
|  |  |  |  | SNEEGSEEKGPEVR |
|  |  |  |  | TTFDEAMADLHTLSEDSYK |
|  |  |  |  | VLSSIEQK |
|  |  |  |  | YEDMAAFMK |
|  |  |  |  | YLAEVATGDDK |

TABLE 11-continued

| | | | | |
|---|---|---|---|---|
| spt\|P31949 | Calgizzarin | 36.19047701 | 2 | ISSPTETER<br>TEFLSFMNTELAAFTK |
| spt\|P36952 | Maspin Precursor | 11.4666631 | 2 | GDTANEIGQVLHFENVK<br>VCLEITEDGGDSIEVPGAR |
| spt\|P51884 | KSPG Lumican | 23.66863936 | 6 | FNALQYLR<br>ISNIPDEYFK<br>NIPTVMENLENYYLEVNQLEK<br>NNQIDHIDEK<br>SLEDLQLTHNK<br>SLEYLDLSFNQIAR |
| spt\|P60709 | Beta Actin | 72.5333333 | 34 | AALVVDNGSGMCK<br>AGFAGDDAPR<br>ALDFEQEMATAASSSSLEK<br>AVRPSIVGR<br>AVRPSIVGRPR<br>DDDIAALVVDNGSGMCK<br>DESGPSIVHR<br>DLTDYLMK<br>DLYANTVLSGGTTMYPGIADR<br>DSYVGDEAQSK<br>DSYVGDEAQSKR<br>EITALAPSTMK<br>GFAGDDAPR<br>GYSFTTTAER<br>HQGVMVGMGQK<br>IWHHTFYNELR<br>KDLYANTVLSGGTTMYPGIADR<br>LCYVALDFEQEMATAASSSSLEK<br>LLTEAPLNPK<br>QEYDESGPSIVHR<br>SGGTTMYPGIADR<br>SYELPDGQVIYIGNER<br>TALAPSTMK<br>TEAPLNPK<br>TTGIVMDSGDGVTHTVPIYEGY<br>TTGIVMDSGDGVTHTVPIYEGYALPH<br>TTGIVMDSGDGVTHTVPIYEGYALPHAIL<br>VALDFEQEMATAASSSSLEK<br>VAPEEHPV<br>VAPEEHPVL<br>VAPEEHPVLL<br>VAPEEHPVLLTEAPLNPK<br>VLSGGTTMYPGIADR<br>YPIEHGIVTNWDDMEK |
| spt\|P62805 | Histone H4 | 48.0392158 | 5 | DAVTYTEHAK<br>DNIQGITKPAIR<br>ISGLIYEETR<br>TVTAMDVVYALK<br>VFLENVIR |
| spt\|Q9NZT1 | Calmodulin-like protein 5 | 58.21917653 | 6 | AFDQDGDGHITVDELR<br>AFSAVDTDGNGTINAQELGAALK<br>AGLEDLQVAFR<br>AMAGLGQPLPQEELDAMIR<br>NLSEAQLR<br>VNYEEFAR |
| trm\|O60744 | Thioredoxin Delta 3 | 39.28571343 | 3 | EKLEATINELV<br>TAFQEALDAAGDK<br>VGEFSGANK |
| trm\|Q6NTE9 | PPIA | 52.38095522 | 8 | EGMNIVEAMER<br>FEDENFILK<br>IIPGFMCQGGDFTR<br>ITIADCGQLE<br>KITIADCGQLE<br>SIYGEKFEDENFILK<br>VNPTVFFDIAVDGEPLGR<br>VSFELFADK |
| trm\|Q71DI3 | Histone H3 | 30.14705777 | 2 | EIAQDFKTDLR<br>SAPATGGVK |
| trm\|Q86V33 | YWHAZ | 39.37500119 | 13 | DNLTLWTSDTQGDEAEAGEGGEN<br>DSTLIMQLLR<br>EMQPTHPIR |

TABLE 11-continued

|  |  |  |  | GIVDQSQQAYQEAFEISK |
|---|---|---|---|---|
|  |  |  |  | GIVDQSQQAYQEAFEISKK |
|  |  |  |  | LAEQAER |
|  |  |  |  | MDKNELVQK |
|  |  |  |  | NLLSVAYK |
|  |  |  |  | SVTEQGAELSNEER |
|  |  |  |  | TAFDEAIAELDTLSEESYK |
|  |  |  |  | VVSSIEQK |
|  |  |  |  | YDDMAACMK |
|  |  |  |  | YLAEVAAGDDKK |
| trm\|Q8WU39 | PACAP | 26.98412836 | 3 | ELSELVYTDVLDR |
|  |  |  |  | NWQDYGVR |
|  |  |  |  | TCLHYLGEFGEDQIYEAHQQGR |
| trm\|Q96IH1 | FSCN1 | 5.200000107 | 5 | ASAETVDPASLWEY |
|  |  |  |  | DVPWGVDSLITLAFQDQR |
|  |  |  |  | FLIVAHDDGR |
|  |  |  |  | KVTGTLDANR |
|  |  |  |  | YLAADKDGNVTCER |
| trm\|Q96RZ7 | Mast cell tryptase beta III | 18.02575141 | 5 | DDMLCAGNTR |
|  |  |  |  | EQHLYYQDQLLPVSR |
|  |  |  |  | IVGGQEAPR |
|  |  |  |  | VPIMENHICDAK |
|  |  |  |  | YHLGAYTGDDVR |
| trm\|Q9UE88 | Histone H2B.1 | 19.80198026 | 3 | AMGIMNSFVNDIFER |
|  |  |  |  | LLLPGELAK |
|  |  |  |  | QVHPDTGISSK |
| OPLs |
| spt\|P29966 | MARCKS | 9.64 | 2 | AAEEPSKVEEK |
|  |  |  |  | EAPAEGEAAEPGSPTAAEGEAASAASS |
| spt\|P06748 | Nucleophosmin 1 | 6.18 | 2 | GPSSVEDIK |
|  |  |  |  | VTLATLK |
| gb\|AAH25314.1 | IGHG1 protein | 21.49 | 12 | ALPAPIEK |
|  |  |  |  | DYFPEPVTV |
|  |  |  |  | FNWYVDGVEVHNAK |
|  |  |  |  | GFYPSDIAVEWESNGQPENNYK |
|  |  |  |  | GPSVFPLAPSSK |
|  |  |  |  | NQVSLTCLVK |
|  |  |  |  | QVQLVQSGAEVK |
|  |  |  |  | STSGGTAALGCLVK |
|  |  |  |  | THTCPPCPAPELLGGPSVFLFPPKPK |
|  |  |  |  | TPEVTCVVVDVSHEDPEVK |
|  |  |  |  | TTPPVLDSDGSFFLYSK |
|  |  |  |  | VVSVLTVLHQDWLNGK |
| spt\|P01009 | Alpha 1 Anti-Trypsin Precursor | 8.13 | 3 | AVLTIDEK |
|  |  |  |  | DTEEEDFHVDQVTTVK |
|  |  |  |  | LSITGTYDLK |
| spt\|P04080 | Cystatin B | 36.73 | 4 | GAPSATQPATAETQHIADQVR |
|  |  |  |  | MMCGAPSATQPATAETQHIADQVR |
|  |  |  |  | SQVVAGTNYFIK |
|  |  |  |  | VFQSLPHENKPLTLSNYQTNK |
| spt\|P06454 | PTHA | 25.45 | 5 | AAEDDEDDDVDTK |
|  |  |  |  | AAEDDEDDDVDTKK |
|  |  |  |  | EVVEEAENGR |
|  |  |  |  | RAAEDDEDDDVDTK |
|  |  |  |  | SDAAVDTSSEITTK |
| spt\|P14625 | GRP 94 | 3.74 | 10 | DDEVDVDGTVEEDLGK |
|  |  |  |  | EFEPLLNWMK |
|  |  |  |  | EVEEDEYK |
|  |  |  |  | FAFQAEVNR |
|  |  |  |  | KEASESSPFVER |
|  |  |  |  | LGVIEDHSNR |
|  |  |  |  | LISLTDENALSGNEELTVK |
|  |  |  |  | TDDEVVQREEEAIQLDGLNASQIR |
|  |  |  |  | TVLDLAVVLFETATLR |
|  |  |  |  | VFITDDFHDMMPK |
| spt\|P27482 | Calmodulin related | 20.27 | 5 | AADTDGDGQVNYEEFVR |
|  |  |  |  | ADQLTEEQVTEFK |

TABLE 11-continued

| | | | | |
|---|---|---|---|---|
| | protein-NB1 | | | LSDEEVDEMIR |
| | CALM3 | | | SLGQNPTEAELR |
| | | | | VFDKDGNGFVSAAELR |
| spt\|P30086 | PE Binding protein PEBP | 15.05 | 3 | GNDISSGTVLSDYVGSGPPK<br>LYTLVLTDPDAPSR<br>VLTPTQVK |
| spt\|P31151 | S100A7 | 24.00 | 4 | GTNYLADVFEK<br>KIDFSEFLSLLGDIATDYHK<br>QSHGAAPCSGGSQ<br>SIIGMIDMFHK |
| spt\|P31947 | Stratifin | 28.24 | 16 | DSTLIMQLLR<br>EKVETELQGCDTVLGLLDSHLIK<br>EKVETELQGCDTVLGLLDSHLIKEAGD<br>EMPPTNPIR<br>GAVEKGEELSCEER<br>GEELSCEER<br>GSEEKGPEVR<br>LAEQAER<br>NLLSVAYK<br>SAYQEAMDISKK<br>SNEEGSEEKGPEVR<br>TTFDEAMADLHTLSEDSYK<br>VETELQGVCDTVLGLLDSHLIK<br>VLSSIEQK<br>YEDMAAFMK<br>YLAEVATGDDK |
| spt\|P60709 | Beta Actin | 27.47 | 21 | AGFAGDDAPR<br>AVFPSIVGR<br>AVFPSIVGRPR<br>DDDIAALVVDNGSGMCK<br>DLYANTVLSGGTTMYPGIADR<br>DSYVGDEAQSK<br>DSYVGDEAQSKR<br>EITALAPSTMK<br>GYSFTTTAER<br>HQGVMVGMGQK<br>IIAPPER<br>IWHHYFYNELR<br>LCYVALDFEQEMATAASSSSLEK<br>LDLAGRDLTDYLMKILTERGYSFTTTAER<br>QEYDEYGPSIVHR<br>SYELPDGQVITIGNER<br>TEAPLNPK<br>TTGIVMDSGDGVTHTVPIYEGYALPHAIL<br>VAPEEHPVLL<br>VAPEEHPVLLTEAPLNPK<br>YPIEHGIVTNWDDMEK |
| spt\|P61978 | heterogeneous nuclear protein K | 2.38 | 3 | DLAGSIIGK<br>IDEPLEGSEDR<br>ILSISADIETIGEILK |
| spt\|Q01469 | FABP5 | 28.15 | 5 | ATVQQLEGR<br>ELGVGIALR<br>FEETTADGR<br>GFDEYMK<br>TTQFSCTLGEKFEETTADGR |
| trm\|O15256 | Parathymosin | 19.05 | 1 | AAEEEDEADPKR |
| trm\|Q12771 | P37AUF1* | 2.80 | 1 | GFGFVLFK |
| trm\|Q6NSB4 | Hp Protein, DLC1 | 3.20 | 1 | VGYVSGWGR |
| spt\|P63104 | YWHAZ | 13.75 | 8 | DSTLIMQLLR<br>GIVDQSQQAYQEAFEISK<br>LAEQAER<br>NLLSVYK<br>SVTEQGAELSNEER<br>TAFDEAIAELDTLSEESYK<br>VVSSIEQK<br>YLAEVAAGDDKK |

TABLE 11-continued

| | | | | |
|---|---|---|---|---|
| trm\|Q8N5F4 | IGL2* | 23.61 | 4 | AGVETTTPSK<br>DTERPSGIPER<br>SYELTQPPSVSVSPGQTAR<br>SYSCQVTHEGSTVEK |
| spt\|P06396 | Gelsolin Precursor | 2.30 | 2 | AQPVQVAEGSEPDGFWEALGGK<br>TPSAAYLWVGTGASEAEK |
| emb\|CAA25833.1 | eraldehyde3-phosphate Dehydrogen | 16.72 | 8 | AGAHLQGGAK<br>GALQNIIPASTGAAK<br>LTGMAFR<br>QASEGPLK<br>TVDGPSGK<br>VIPELDGK<br>VPTANVSVVDLTCR<br>VVDLMAHMASKE |
| spt\|P14618 | PKM2* | 9.04 | 8 | APIIAVTR<br>GADFLVTEVENGGSLGSK<br>GDLGIEPAEK<br>GDYPLEAVR<br>IENHEGVR<br>KASDVHEVR<br>LDIDSPPITAR<br>NTGIICTIGPASR |
| spt\|P04792 | Hsp27* | 18.85 | 5 | AQLGGPEAAK<br>LATQSNEITIPVTFESR<br>QDEHGYISR<br>QLSSGVSEIR<br>VSLDVNHFAPDELTVK |
| spt\|P09651 | ROA1HNRNPA1* | 7.50 | 2 | EDSQRPGAHLTVK<br>SESPKEPEQLR |
| spt\|P13639 | Elongation Factor 2* | 1.17 | 2 | GEGQLGPAER<br>SDPVVSYR |
| spt\|P14625 | HSP90B1 | 3.74 | 10 | DDEVDVDGTVEEDLGK<br>EFEPLLNWMK<br>EVEEDEYK<br>FAFQAEVNR<br>KEAESSPFVER<br>LGVIEDHSNR<br>LISLTDENALSGNEELTVK<br>TDDEVVQREEEAIQLDGLNASQIR<br>TVLDLAVVLFETATLR<br>VFITDDFHDMMPK |
| spt\|P22392 | NDP Kinase B* | 11.84 | 2 | GLVGEIIK<br>NIIHGSDSVK |
| spt\|P23528 | Cohlin* | 4.82 | 4 | ASGVAVSDGVIK |
| spt\|P31949 | Calgizzanin | 8.57 | 2 | ISSPTETER<br>NQKDPGVLDR |
| spt\|P32119 | Peroxiredoxin 2 | 4.04 | 6 | ATAVVDGAFK<br>GLFIIDGK<br>KEGGLGPLNIPLLADVTR<br>LSEDYGVLK<br>QITVNDLPVGR<br>TDEGIAYR |
| pf\|0904262A | SOD2* | 13.73 | 1 | TLVVHEK |
| spt\|Q16778 | Histone H2B.1 | 15.87 | 3 | AMGIMNSFVNDIFER<br>LLLPGELAK<br>QVHPDTGISSK |

OFFLINE

| ACCESSION | PROTEIN | SEQUENCE COVERAGE | # PEPTIDES | PEPTIDE |
|---|---|---|---|---|
| gb\|AAA59555.1 | MARCKS | 59.33734775 | 11 | AAEEPSKVEEK<br>AEDGATPSPSNETPK<br>AEDGATPSPSNETPKK<br>AVAPEKPPASDETK<br>EAGEGGEAEAPAAEGGK |

TABLE 11-continued

| | | | | |
|---|---|---|---|---|
| | | | | EAPAEGEAAEPGSPTAAEGEAASAASS |
| | | | | EELQANGSAPAADKEEPAAAGSGAASP |
| | | | | GEAAAERPGEAAVASSPSK |
| | | | | GEPAAAAAPEAGASPVEK |
| | | | | GSAPAADKEEPAAGSGAASPSAAEK |
| | | | | VNGDASPAAAESGAK |
| gb\|AAC13869.1 | Glutathione S Transferase-P | 61.90476418 | 4 | AFLASPEYVNLPINGNGKQ |
| | | | | ALPGQLKPFETLLSQNQGGK |
| | | | | ASCLYGQLPK |
| | | | | FQDGDLTLYQSNTILR |
| gb\|AAH16768.1 | Nucleophosmin 1 | 12.24489808 | 3 | GPSSVEDIK |
| | | | | MSVQPTVSLGGFEITPPVVLR |
| | | | | MTDQEAIQDLWQWR |
| pir\|KRHUE | Cytokeratin 14 | 69.4915235 | 5 | ASLENSLEETK |
| | | | | DAEEWFFTK |
| | | | | ILTATVDNANVLLQIDNAR |
| | | | | KVVSTHEQVLR |
| | | | | VVSTHEQVLR |
| spt\|P00338 | LDH A | 52.56797671 | 14 | ATLKDQLITNLLKEEQTPQNIK |
| | | | | DQLIYNLLK |
| | | | | DQLIYNLLKEEQTPQNK |
| | | | | FIIPNVVK |
| | | | | GEMMDLQHGSLFLR |
| | | | | KSADTLWGIQK |
| | | | | LVIITAGAR |
| | | | | QVVESAYEVIK |
| | | | | RVHPVSTMIK |
| | | | | SADTLWGIQK |
| | | | | TLHPDLGTDKDKEQWK |
| | | | | VHPVSTMIK |
| | | | | VIGSGCNLDSAR |
| | | | | VTLTSEEEAR |
| spt\|P00915 | Carbonic anhydraseI | 66.15384817 | 13 | ASPDWGYDDK |
| | | | | ASPDWGYDDKNGPEQWSK |
| | | | | EIINVGHSFHVNFEDNDNR |
| | | | | GGPFSDSYR |
| | | | | HDTSLKPISV |
| | | | | HDTSLKPISVSYNPATAK |
| | | | | LYPIANGNNQSPVDIK |
| | | | | SAELHVAHWNSAK |
| | | | | SLLSNVEGDNAVPMQHNNRPTQPLK |
| | | | | SSEQLAQFR |
| | | | | VLDALQAIK |
| | | | | YSAELHVAHWNSAK |
| | | | | YSSLAEAASK |
| spt\|P01009 | Alpha 1 Anti-Trypsin Precursor | 55.74162602 | 9 | DTEEEDFHVDQVTTVK |
| | | | | EDPQGDAAQK |
| | | | | GTEAAGAMFLEAIPM |
| | | | | KLSSWVLLMK |
| | | | | LGMFNIQHCK |
| | | | | LQHLENELTHDIITK |
| | | | | LSITGTYDLK |
| | | | | LVDKFLEDVK |
| | | | | VFSNGADLSGVTEEAPLK |
| spt\|P04083 | Annexin A1 | 75.36231875 | 14 | AAYLQETGKPLDETLK |
| | | | | AAYLQETGKPLDETLKK |
| | | | | ALYEAGER |
| | | | | CATSKPAFFAEK |
| | | | | DITSDTSGDFR |
| | | | | GGPGSAVSPYPTFNPSSDVAALHK |
| | | | | GLGTDEDTLIEILASR |
| | | | | GTDVNVFNTILTTR |
| | | | | GVDEATIIDILTK |
| | | | | KGTDVNVFNTIKTTR |
| | | | | NALLSLAK |
| | | | | SEDFGVNEDLADSDAR |
| | | | | SEIDMNDIK |
| | | | | TPAQFDADELR |
| spt\|P04792 | Hsp27 | 34.55497324 | 7 | DGVVEITGK |
| | | | | KYTLPPGVDPTQVSSSLSPEGTLTVEAP |
| | | | | LATQSNEITIPVTFESR |
| | | | | QDEHGYISR |

TABLE 11-continued

|  |  |  |  | QLSSGVSEIR<br>TKDGVVEITGK<br>VSLDVNHFAPDELTVK |
|---|---|---|---|---|
| spt\|P06454 | Prothymosin alpha | 23.63636345 | 6 | AAEDDEDDDVDTK<br>AAEDDEDDDVDTKK<br>EVVEEAENGR<br>EVVEEAENGRDAPAN<br>KEVVEEAENGR<br>SDAAVDTSSEITTK |
| spt\|P07585 | Deconin Precursor | 38.16156089 | 5 | DLPPDTTLLDLQNNK<br>NLHALILVNNK<br>SSGIENGAFQGMK<br>VSPGAFTPLVK<br>VVQCSDLGLDKVPK |
| spt\|P08670 | Vimentin | 63.21585774 | 29 | ADLSEAANR<br>DGQVINETSQHHDDLE<br>DNLAEDIMR<br>EEAENTLQSFR<br>EKLQEEMLQR<br>EMEENFAVEAANYQDTIGR<br>ETNLDSLPLVDTHSK<br>EYQDLLNVK<br>FADLSEAANR<br>ILLAELEQLK<br>ILLAELEQLKGQGK<br>ISLPLPNFSSLNLR<br>KLLEGEESR<br>KVESLQEEIAFLK<br>KVESLQEEIAFLKK<br>LGDLYEEEMR<br>LLQDSVDFSLADAINTEFK<br>LQDEIQNMKEEMAR<br>LQEEMLQR<br>NLDSLPLVDTHSK<br>NLQEAEEWYK<br>QDVDNASLAR<br>QQYESVAAK<br>QVDQLTNDK<br>QVQSLTCEVDALK<br>RQVDQLTNDK<br>TVETRDGQVINETSQHHDDLE<br>VELQELNDR<br>VEVERDNLAEDIMR |
| spt\|P14625 | GRP 94 | 26.40099525 | 14 | DDEVDVDGTVEEDLGK<br>EFEPLLNWMK<br>EGVKFDESEK<br>ELISNASDALDK<br>FQSSHHPTDITSLDQYVER<br>GLFDEYGSK<br>GVVDSDDLPLNVSR<br>KIADDKYNDTFWK<br>LGVIEDHSNR<br>LISTDENALSGNEELTVK<br>NLLHVTDTGVGMTR<br>RVFITDDFHDMMPK<br>SILFVPTSAPR<br>VFITDDFHDMMPK |
| spt\|P29034 | S100A 2 | 27.83505023 | 6 | ELPSFVGEK<br>ELPSFVGEKVDEEGLK<br>ELPSFVGEKVDEEGLKK<br>GEKVDEEGLK<br>VDEEGLKK<br>YSCQEGDKFK |
| spt\|P30043 | Flavin reductase | 39.51219618 | 7 | CLTTDEYDGHSTYPSHQYQ<br>HDLGHFMLR<br>LPSEGPRPAHVVVGDVLQAADVDK<br>LQAVTDDHIR<br>NDLSPTTVMSEGAR<br>PAHVVVGDVLQAADVDK<br>TVAGQDAVIVLLGTR |
| spt\|P31151 | S100A 7 | 98.00000191 | 7 | ENFPNFLSACDKK<br>GTNYLADVFEK<br>GTNYLADVFEKK |

TABLE 11-continued

|  |  |  |  |  |
|---|---|---|---|---|
|  |  |  |  | IDKPSLLTMMK |
|  |  |  |  | KGTNYLADVFEKK |
|  |  |  |  | QSHGAAPCSGGSQ |
|  |  |  |  | SIIGMIDMFHK |
| spt\|P31947 | SFN | 89.35185075 | 22 | ADNAGEEGGEAPQEPQS |
|  |  |  |  | DNLTLWTADNAGEEGGEAPQEPQ |
|  |  |  |  | DNLTLWTADNAGEEGGEAPQEPQS |
|  |  |  |  | DSTLIMQLLR |
|  |  |  |  | EMPPTNPIR |
|  |  |  |  | GAVEKGEELSCEER |
|  |  |  |  | GEELSCEER |
|  |  |  |  | LAEQAER |
|  |  |  |  | NLLSVAYK |
|  |  |  |  | RYLAEVATGDDK |
|  |  |  |  | SAYQEAMDISK |
|  |  |  |  | SAYQEAMDISKK |
|  |  |  |  | SNEEGSEEKGPEVR |
|  |  |  |  | STLIMQLLR |
|  |  |  |  | SVFHYEIANSPEEAISLAK |
|  |  |  |  | TADNAGEEGGEAPQEPQS |
|  |  |  |  | TTFDEAMADLHTLSEDS |
|  |  |  |  | TTFDEAMADLHTLSEDSYK |
|  |  |  |  | VLSSIEQK |
|  |  |  |  | YEDMAAFMK |
|  |  |  |  | YLAEVATGDDK |
|  |  |  |  | YLAEVATGDDKK |
| spt\|P31949 | Calgizzarin | 23.80952388 | 3 | DGYNYTLSK |
|  |  |  |  | ISSPTETER |
|  |  |  |  | TEFLSFMNTELAAFTK |
| spt\|P32119 | Peroxiredoxin 2 | 64.64646459 | 11 | ATAVVDGAFK |
|  |  |  |  | EGGLGPLNIPLLADVTR |
|  |  |  |  | GLFIIDGK |
|  |  |  |  | IGKPAPDFK |
|  |  |  |  | KEGGLGPLNIPLLADVTR |
|  |  |  |  | LSEDYGVLK |
|  |  |  |  | LVQAFQYTDEHGEVCPAGWKPGSDTIK |
|  |  |  |  | QITVNDLPVGR |
|  |  |  |  | QYTDEHGEVCPAGWKPGSDTIKPNVDC |
|  |  |  |  | RLSEDYGVLK |
|  |  |  |  | TDEGIAYR |
| spt\|P51884 | KSPG Lumican | 56.80473447 | 13 | FNALQYLR |
|  |  |  |  | ILGPLSYSK |
|  |  |  |  | ISETSLPPDMYECLR |
|  |  |  |  | ISNIPDEYFK |
|  |  |  |  | LKEDAVSAAFK |
|  |  |  |  | LPSGLPVSLLTLYLDNNK |
|  |  |  |  | NIPTVNENLENYYLEVNQLEK |
|  |  |  |  | NNQIDHIDEK |
|  |  |  |  | RFNALQYLR |
|  |  |  |  | SLEDLQLTHNK |
|  |  |  |  | SLEYLDLSFNQIAR |
|  |  |  |  | SVPMVPPGIK |
|  |  |  |  | VANEVTLN |
| spt\|P60709 | Beta Actin | 83.46656694 | 49 | AGFAGDDAPR |
|  |  |  |  | ALDFEQEMATAASSSSLEK |
|  |  |  |  | AVFPSIVGR |
|  |  |  |  | AVFPSIVGRPR |
|  |  |  |  | CPEALFQPSFLGMESCGIHETTFNSIMK |
|  |  |  |  | DDDIAALVVDNGSGMCK |
|  |  |  |  | DDIAALVVDNGSGMCK |
|  |  |  |  | DLTDYLMK |
|  |  |  |  | DLYANTVLSGGTTMYPGIADR |
|  |  |  |  | DSYVGDEAQSK |
|  |  |  |  | DSYVGDEAQSKR |
|  |  |  |  | EITALAPSTMK |
|  |  |  |  | GFAGDDAPR |
|  |  |  |  | GIHETTFNSIMK |
|  |  |  |  | GIVTNWDDMEK |
|  |  |  |  | GQKDSYVGDEAQSK |
|  |  |  |  | GYSFTTTAER |
|  |  |  |  | HQGVMVGMGQK |
|  |  |  |  | HQGVMVGMGQKDSYVGDEAQSK |
|  |  |  |  | IIAPPER |
|  |  |  |  | IIAPPERK |
|  |  |  |  | IWHHTFYNELR |

TABLE 11-continued

| | | | | |
|---|---|---|---|---|
| | | | | KDLYANTVLSGGTTMYPGIADR |
| | | | | KQEYDESGPSIVHR |
| | | | | KYPIEHGIVTNWDDMEK |
| | | | | LCYVALDFEQEMATAASSSSLEK |
| | | | | LLTEAPLNPK |
| | | | | PIEHGIVTNWDDMEK |
| | | | | QEYDESGPSIVHR |
| | | | | RVAPEEHPVLLTEAPLNPK |
| | | | | SGGTTMYPGIADR |
| | | | | SKQEYDESGPSIVHR |
| | | | | SYELPDGQVI |
| | | | | SYELPDGQVITI |
| | | | | SYELPDGQVITIGNER |
| | | | | TTGIVMDSGDGVTH |
| | | | | TTGIVMDSGDGVTHTVPIYEGY |
| | | | | TTGIVMDSGDGVTHTVPIYEGYALPH |
| | | | | TTGIVMDSGDGVTHTVPIYEGYALPHAIL |
| | | | | TVLSGGTTMYPGIADR |
| | | | | VAPEEHPV |
| | | | | VAPEEHPVL |
| | | | | VAPEEHPVLL |
| | | | | VAPEEHPVLLTEA |
| | | | | VAPEEHPVLLTEAPLN |
| | | | | VAPEEHPVLLTEAPLNPK |
| | | | | VAPEEHPVLLTEAPLNPKANR |
| | | | | YPIEHGIVTNWDDMEK |
| | | | | YVALDFEQEMATAASSSSLEK |
| spt\|Q15691 | APC-binding protein EB1 | 8.955223858 | 1 | KPLTSSSAAPQRPISTQR |
| trm\|Q86U86 | Polybromo-1D | 29.01124954 | 2 | AAQQQQPSASPR |
| | | | | RPNETFHLATRK |
| trm\|Q86V33 | YWHAZ | 77.49999762 | 15 | DNLTLWTSDTQGDEAEAGEGGEN |
| | | | | DSTLIMQLLR |
| | | | | EKIETELR |
| | | | | GIVDQSQQAYQEAFEISK |
| | | | | GIVDQSQQAYQEAFEISKK |
| | | | | LAEQAER |
| | | | | MDKNELVQK |
| | | | | NLLSVAYK |
| | | | | SDTQGDEAEAGEGGEN |
| | | | | STLIMQLLR |
| | | | | SVTEQGAELSNEER |
| | | | | TAFDEAIAELDTLSEESYK |
| | | | | VVSSIEQK |
| | | | | YDDMAACMK |
| | | | | YLAEVAAGDDKK |
| trm\|Q86YI6 | L Plastin | 52.53968239 | 9 | AESMLQQADK |
| | | | | HVIPMNPNTDDLFK |
| | | | | IDINMSGFNETDDLKR |
| | | | | IKPVDWSK |
| | | | | MINLSVPDTIDER |
| | | | | SGNLTEDDKHNNAK |
| | | | | TISSSLAVVDLIDAIQPGCINYDLVK |
| | | | | VNKPPYPK |
| | | | | VYALPEDLVEVKPK |
| trm\|Q8IZ29 | Tubulin, beta, 2 | 40.67415595 | 10 | ALTVPELTQQMFDAK |
| | | | | AVLVDLEPGTMDSVR |
| | | | | EIVHLQAGQCGNQIGAK |
| | | | | GHYTEGAELVDSVLDVVR |
| | | | | IMNTFSVVPSPK |
| | | | | IREEYPDR |
| | | | | LHFFMPGFAPLTSR |
| | | | | LTTPTYGDLNHLVSATMSGVTTCLR |
| | | | | SGPFGQOFRPDNFVFGQSGAGNNWAK |
| | | | | TAVCDIPPR |
| trm\|Q96AM7 | Superoxide dismutase [Mn] | 52.85714269 | 1 | HHAAYVNNLNVTEEK |
| trm\|Q96IH1 | FSCN1 | 66.60000086 | 8 | ASAETVDPASLWEY |
| | | | | DVPWGVDSLITLAFQDQR |
| | | | | EVPGPDCR |
| | | | | FLIVAHDDGR |
| | | | | KVTGTLDANR |
| | | | | LVARPEPATGYTLEFR |

TABLE 11-continued

| | | WSLQSEAHR<br>YLAADKDGNVTCER | | |
|---|---|---|---|---|
| | ACCESSION | MAX<br>Confidence | Seq<br>ID | #<br>Times<br>Seen |
| | gb\|AAC13869.1 | 98.99999499 | 42 | 17 |
| | | 98.99999499 | 43 | 17 |
| | | 98.99999499 | 44 | 11 |
| | | 98.99999499 | 45 | 2 |
| | | 98.99999499 | 46 | 1 |
| | | 98.99999499 | 47 | 2 |
| | spt\|P00338 | 98.99999499 | 48 | 2 |
| | | 98.99999499 | 49 | 3 |
| | | 98.99999499 | 50 | 2 |
| | | 98.99999499 | 51 | 11 |
| | | 98.99999499 | 52 | 5 |
| | | 98.99999499 | 53 | 7 |
| | | 98.99999499 | 54 | 12 |
| | spt\|P01009 | 98.99999499 | 55 | 2 |
| | | 98.99999499 | 56 | 2 |
| | | 97.99999595 | 57 | 1 |
| | | 98.99999499 | 58 | 3 |
| | | 98.99999499 | 59 | 1 |
| | | 98.99999499 | 60 | 1 |
| | | 98.99999499 | 61 | 2 |
| | | 98.99999499 | 62 | 1 |
| | | 98.99999499 | 63 | 5 |
| | spt\|P04080 | 98.99999499 | 64 | 2 |
| | | 98.99999499 | 65 | 2 |
| | | 98.99999499 | 66 | 21 |
| | | 98.99999499 | 67 | 4 |
| | | 98.99999499 | 68 | 14 |
| | | 98.99999499 | 69 | 10 |
| | spt\|P04083 | 98.99999499 | 70 | 7 |
| | | 98.99999499 | 71 | 6 |
| | | 98.99999499 | 72 | 50 |
| | | 98.99999499 | 73 | 9 |
| | | 98.99999499 | 74 | 4 |
| | | 98.99999499 | 75 | 8 |
| | | 98.99999499 | 76 | 6 |
| | | 98.99999499 | 77 | 1 |
| | | 98.99999499 | 78 | 6 |
| | spt\|P06454 | 98.99999499 | 79 | 1 |
| | | 98.99999499 | 80 | 2 |
| | | 98.99999499 | 81 | 3 |
| | | 98.99999499 | 82 | 5 |
| | | 98.99999499 | 83 | 6 |
| | spt\|P07585 | 94.99999881 | 84 | 1 |
| | | 98.99999499 | 85 | 1 |
| | | 97.99999499 | 86 | 1 |
| | | 98.99999499 | 87 | 1 |
| | spt\|P08670 | 98.99999499 | 88 | 2 |
| | | 98.99999499 | 89 | 5 |
| | | 98.99999499 | 90 | 10 |
| | | 98.99999499 | 91 | 4 |
| | | 98.99999499 | 92 | 6 |
| | | 98.99999499 | 93 | 17 |
| | | 98.99999499 | 94 | 8 |
| | | 98.99999499 | 95 | 2 |
| | | 98.99999499 | 96 | 10 |
| | | 98.99999499 | 97 | 3 |
| | | 98.99999499 | 98 | 5 |
| | | 98.99999499 | 99 | 7 |
| | | 98.99999499 | 100 | 13 |
| | | 94.99999881 | 101 | 1 |
| | | 98.99999499 | 102 | 2 |
| | | 98.99999499 | 103 | 3 |
| | | 98.99999499 | 104 | 9 |
| | | 98.99999499 | 105 | 10 |
| | | 98.99999499 | 106 | 1 |
| | | 98.99999499 | 107 | 3 |

TABLE 11-continued

|  |  |  |  |
|---|---|---|---|
|  | 98.99999499 | 108 | 1 |
|  | 98.99999499 | 109 | 5 |
|  | 98.99999499 | 110 | 2 |
|  | 98.99999499 | 111 | 7 |
|  | 96.9999969 | 112 | 1 |
|  | 98.99999499 | 113 | 5 |
|  | 98.99999499 | 114 | 7 |
|  | 98.99999499 | 115 | 2 |
| spt\|P13928 | 98.99999499 | 116 | 1 |
|  | 97.99999595 | 117 | 1 |
|  | 97.99999595 | 118 | 1 |
|  | 96.9999969 | 119 | 1 |
|  | 98.99999499 | 120 | 1 |
|  | 98.99999499 | 121 | 2 |
| spt\|P14618 | 98.99999499 | 122 | 14 |
|  | 98.99999499 | 123 | 17 |
|  | 98.99999499 | 124 | 3 |
|  | 98.99999499 | 125 | 1 |
|  | 98.99999499 | 126 | 3 |
|  | 98.99999499 | 127 | 17 |
|  | 98.99999499 | 128 | 3 |
|  | 98.99999499 | 129 | 10 |
|  | 98.99999499 | 130 | 1 |
|  | 98.99999499 | 131 | 5 |
|  | 98.99999499 | 132 | 7 |
|  | 98.99999499 | 133 | 1 |
|  | 98.99999499 | 134 | 3 |
|  | 98.99999499 | 135 | 21 |
|  | 98.99999499 | 136 | 10 |
|  | 98.99999499 | 137 | 17 |
|  | 98.99999499 | 138 | 6 |
|  | 98.99999499 | 139 | 2 |
| spt\|P14625 | 98.99999499 | 140 | 1 |
|  | 98.99999499 | 141 | 2 |
|  | 98.99999499 | 142 | 1 |
|  | 98.99999499 | 143 | 4 |
|  | 98.99999499 | 144 | 1 |
|  | 98.99999499 | 145 | 11 |
| spt\|P26038 | 98.99999499 | 146 | 5 |
|  | 98.99999499 | 147 | 8 |
|  | 98.99999499 | 148 | 5 |
|  | 98.99999499 | 149 | 3 |
|  | 96.9999969 | 150 | 4 |
|  | 98.99999499 | 151 | 4 |
|  | 98.99999499 | 152 | 2 |
|  | 96.9999969 | 153 | 1 |
|  | 98.99999499 | 154 | 3 |
|  | 98.99999499 | 155 | 6 |
|  | 98.99999499 | 156 | 10 |
|  | 98.99999499 | 157 | 1 |
|  | 96.9999969 | 158 | 1 |
|  | 96.9999969 | 159 | 1 |
|  | 98.99999499 | 160 | 3 |
|  | 98.99999499 | 161 | 1 |
|  | 98.99999499 | 162 | 2 |
| spt\|P29034 | 98.99999499 | 163 | 13 |
|  | 98.99999499 | 164 | 1 |
| spt\|P31151 | 98.99999499 | 165 | 4 |
|  | 98.99999499 | 166 | 2 |
|  | 98.99999499 | 167 | 32 |
| spt\|P31947 | 96.9999969 | 168 | 1 |
|  | 98.99999499 | 169 | 4 |
|  | 98.99999499 | 170 | 180 |
|  | 97.99999595 | 171 | 1 |
|  | 98.99999499 | 172 | 9 |
|  | 98.99999499 | 173 | 20 |
|  | 98.99999499 | 174 | 10 |
|  | 98.99999499 | 175 | 3 |
|  | 98.99999499 | 176 | 56 |
|  | 98.99999499 | 177 | 4 |
|  | 98.99999499 | 178 | 10 |
|  | 98.99999499 | 179 | 56 |
|  | 98.99999499 | 180 | 50 |

TABLE 11-continued

| | | | |
|---|---|---|---|
| | 98.99999499 | 181 | 47 |
| | 98.99999499 | 182 | 9 |
| | 98.99999499 | 183 | 9 |
| spt\|P31949 | 98.99999499 | 184 | 6 |
| | 98.99999499 | 185 | 6 |
| spt\|P36952 | 98.99999499 | 186 | 1 |
| | 98.99999881 | 187 | 1 |
| spt\|P51884 | 97.99999595 | 188 | 1 |
| | 96.9999969 | 189 | 1 |
| | 98.99999499 | 190 | 3 |
| | 98.99999499 | 191 | 13 |
| | 98.99999499 | 192 | 11 |
| | 98.99999499 | 193 | 10 |
| spt\|P60709 | 98.99999499 | 194 | 5 |
| | 98.99999499 | 195 | 66 |
| | 98.99999499 | 196 | 6 |
| | 98.99999499 | 197 | 36 |
| | 98.99999499 | 198 | 68 |
| | 98.99999499 | 199 | 88 |
| | 98.99999499 | 200 | 2 |
| | 98.99999499 | 201 | 24 |
| | 98.99999499 | 202 | 16 |
| | 98.99999499 | 203 | 32 |
| | 98.99999499 | 204 | 8 |
| | 98.99999499 | 205 | 38 |
| | 98.99999499 | 206 | 1 |
| | 98.99999499 | 207 | 10 |
| | 98.99999499 | 208 | 1 |
| | 98.99999499 | 209 | 4 |
| | 98.99999499 | 210 | 7 |
| | 98.99999499 | 211 | 1 |
| | 98.99999499 | 212 | 2 |
| | 98.99999499 | 213 | 6 |
| | 98.99999499 | 214 | 2 |
| | 98.99999499 | 215 | 101 |
| | 98.99999499 | 216 | 3 |
| | 98.99999499 | 217 | 16 |
| | 98.99999499 | 218 | 6 |
| | 98.99999499 | 219 | 1 |
| | 98.99999499 | 220 | 15 |
| | 98.99999499 | 221 | 2 |
| | 97.99999595 | 222 | 2 |
| | 95.99999785 | 223 | 2 |
| | 98.99999499 | 224 | 5 |
| | 96.9999969 | 225 | 1 |
| | 98.99999499 | 226 | 3 |
| | 98.99999499 | 227 | 33 |
| spt\|P62805 | 98.99999499 | 228 | 15 |
| | 98.99999499 | 229 | 2 |
| | 98.99999499 | 230 | 10 |
| | 98.99999499 | 231 | 1 |
| | 97.99999595 | 232 | 7 |
| spt\|Q9NZT1 | 98.99999499 | 233 | 3 |
| | 98.99999499 | 234 | 1 |
| | 98.99999499 | 235 | 4 |
| | 98.99999499 | 236 | 2 |
| | 98.99999499 | 237 | 1 |
| | 98.99999499 | 238 | 1 |
| trm\|O60744 | 98.99999499 | 239 | 1 |
| | 98.99999499 | 240 | 4 |
| | 98.99999499 | 241 | 10 |
| trm\|Q6NTE9 | 98.99999499 | 242 | 14 |
| | 98.99999499 | 243 | 3 |
| | 98.99999499 | 244 | 21 |
| | 96.9999969 | 245 | 1 |
| | 98.99999499 | 246 | 2 |
| | 98.99999499 | 247 | 8 |
| | 98.99999499 | 248 | 54 |
| | 98.99999499 | 249 | 1 |

TABLE 11-continued

| | | | |
|---|---|---|---|
| trm\|Q71DI3 | 94.99999481 | 250 | 1 |
| | 98.99999499 | 251 | 4 |
| trm\|Q86V33 | 98.99999499 | 252 | 3 |
| | 98.99999499 | 253 | 180 |
| | 98.99999499 | 254 | 8 |
| | 98.99999499 | 255 | 6 |
| | 98.99999499 | 256 | 2 |
| | 98.99999499 | 257 | 3 |
| | 98.99999499 | 258 | 4 |
| | 98.99999499 | 259 | 56 |
| | 98.99999499 | 260 | 8 |
| | 98.99999499 | 261 | 45 |
| | 98.99999499 | 262 | 9 |
| | 98.99999499 | 263 | 7 |
| | 98.99999499 | 264 | 9 |
| trm\|Q8WU39 | 98.99999499 | 265 | 11 |
| | 98.99999499 | 266 | 5 |
| | 98.99999499 | 267 | 1 |
| trm\|Q96IH1 | 98.99999499 | 268 | 1 |
| | 98.99999499 | 269 | 1 |
| | 98.99999499 | 270 | 7 |
| | 98.99999499 | 271 | 3 |
| | 98.99999499 | 272 | 2 |
| trm\|Q96RZ7 | 96.9999969 | 273 | 1 |
| | 98.99999499 | 274 | 2 |
| | 98.99999499 | 275 | 9 |
| | 98.99999499 | 276 | 2 |
| | 98.99999499 | 277 | 6 |
| trm\|Q9UE88 | 98.99999499 | 278 | 4 |
| | 98.99999499 | 279 | 2 |
| | 98.99999499 | 280 | 11 |
| OPLs | | | |
| spt\|P29966 | 99.00 | 281 | 2 |
| | 99.00 | 282 | 1 |
| spt\|P06748 | 99.00 | 283 | 5 |
| | 96.00 | 284 | 1 |
| gb\|AAH25314.1 | 99.00 | 285 | 12 |
| | 98.00 | 286 | 1 |
| | 99.00 | 287 | 5 |
| | 99.00 | 288 | 4 |
| | 99.00 | 289 | 2 |
| | 99.00 | 290 | 1 |
| | 99.00 | 291 | 3 |
| | 99.00 | 292 | 2 |
| | 98.00 | 293 | 2 |
| | 99.00 | 294 | 3 |
| | 99.00 | 295 | 24 |
| | 99.00 | 296 | 2 |
| spt\|P01009 | 99.00 | 297 | 4 |
| | 99.00 | 298 | 2 |
| | 99.00 | 299 | 1 |
| spt\|P04080 | 99.00 | 300 | 1 |
| | 99.00 | 301 | 12 |
| | 99.00 | 302 | 3 |
| | 99.00 | 303 | 2 |
| spt\|P06454 | 99.00 | 304 | 9 |
| | 99.00 | 305 | 14 |
| | 99.00 | 306 | 6 |
| | 99.00 | 307 | 1 |
| | 99.00 | 308 | 17 |
| spt\|P14625 | 99.00 | 309 | 5 |
| | 99.00 | 310 | 4 |
| | 99.00 | 311 | 3 |
| | 99.00 | 312 | 1 |
| | 99.00 | 313 | 4 |
| | 99.00 | 314 | 3 |

TABLE 11-continued

|  |  |  |  |
|---|---|---|---|
|  | 99.00 | 315 | 4 |
|  | 99.00 | 316 | 1 |
|  | 96.00 | 317 | 1 |
|  | 99.00 | 318 | 2 |
| spt\|P27482 | 99.00 | 319 | 3 |
|  | 99.00 | 320 | 4 |
|  | 99.00 | 321 | 1 |
|  | 99.00 | 322 | 2 |
|  | 99.00 | 323 | 5 |
| spt\|P30086 | 99.00 | 324 | 1 |
|  | 99.00 | 325 | 1 |
|  | 99.00 | 326 | 1 |
| spt\|P31151 | 99.00 | 327 | 1 |
|  | 99.00 | 328 | 3 |
|  | 99.00 | 329 | 1 |
|  | 99.00 | 330 | 2 |
| spt\|P31947 | 99.00 | 331 | 52 |
|  | 99.00 | 332 | 13 |
|  | 99.00 | 333 | 2 |
|  | 99.00 | 334 | 4 |
|  | 99.00 | 335 | 38 |
|  | 99.00 | 336 | 7 |
|  | 97.00 | 337 | 1 |
|  | 98.00 | 338 | 2 |
|  | 99.00 | 339 | 62 |
|  | 99.00 | 340 | 1 |
|  | 99.00 | 341 | 42 |
|  | 99.00 | 342 | 4 |
|  | 99.00 | 343 | 2 |
|  | 99.00 | 344 | 26 |
|  | 98.00 | 345 | 2 |
|  | 99.00 | 346 | 9 |
| spt\|P60709 | 99.00 | 347 | 83 |
|  | 99.00 | 348 | 14 |
|  | 99.00 | 349 | 73 |
|  | 99.00 | 350 | 20 |
|  | 99.00 | 351 | 8 |
|  | 99.00 | 352 | 29 |
|  | 99.00 | 353 | 36 |
|  | 99.00 | 354 | 34 |
|  | 99.00 | 355 | 5 |
|  | 99.00 | 356 | 4 |
|  | 97.00 | 357 | 7 |
|  | 98.00 | 358 | 4 |
|  | 99.00 | 359 | 12 |
|  | 97.00 | 360 | 2 |
|  | 99.00 | 361 | 1 |
|  | 99.00 | 362 | 199 |
|  | 99.00 | 363 | 37 |
|  | 99.00 | 364 | 3 |
|  | 99.00 | 365 | 2 |
|  | 99.00 | 366 | 48 |
|  | 99.00 | 367 | 7 |
| spt\|P61978 | 99.00 | 368 | 2 |
|  | 99.00 | 369 | 1 |
|  | 96.00 | 370 | 2 |
| spt\|Q01469 | 99.00 | 371 | 7 |
|  | 99.00 | 372 | 17 |
|  | 99.00 | 373 | 3 |
|  | 96.00 | 374 | 4 |
|  | 99.00 | 375 | 1 |
| trm\|O15256 | 99.00 | 376 | 8 |
| trm\|Q12771 | 99.00 | 377 | 5 |
| trm\|Q6NSB4 | 99.00 | 378 | 2 |
| spt\|P63104 | 99.00 | 379 | 50 |
|  | 99.00 | 380 | 1 |
|  | 98.00 | 381 | 2 |
|  | 99.00 | 382 | 59 |
|  | 99.00 | 383 | 7 |

TABLE 11-continued

| | | | |
|---|---|---|---|
| | 99.00 | 384 | 4 |
| | 99.00 | 385 | 10 |
| | 99.00 | 386 | 2 |
| trm\|Q8N5F4 | 99.00 | 387 | 21 |
| | 98.00 | 388 | 1 |
| | 99.00 | 389 | 2 |
| | 99.00 | 390 | 17 |
| spt\|P06396 | 99.00 | 391 | 1 |
| | 99.00 | 392 | 6 |
| emb\|CAA25833.1 | 99.00 | 393 | 11 |
| | 99.00 | 394 | 19 |
| | 98.00 | 395 | 3 |
| | 99.00 | 396 | 9 |
| | 99.00 | 397 | 4 |
| | 99.00 | 398 | 16 |
| | 99.00 | 399 | 10 |
| | 99.00 | 400 | 2 |
| spt\|P14618 | 99.00 | 401 | 10 |
| | 99.00 | 402 | 1 |
| | 99.00 | 403 | 6 |
| | 99.00 | 404 | 2 |
| | 99.00 | 405 | 5 |
| | 99.00 | 406 | 1 |
| | 99.00 | 407 | 9 |
| | 99.00 | 408 | 4 |
| spt\|P04792 | 99.00 | 409 | 21 |
| | 99.00 | 410 | 9 |
| | 99.00 | 411 | 6 |
| | 99.00 | 412 | 1 |
| | 99.00 | 413 | 8 |
| spt\|P09651 | 99.00 | 414 | 3 |
| | 99.00 | 415 | 4 |
| spt\|P13639 | 99.00 | 416 | 1 |
| | 99.00 | 417 | 1 |
| spt\|P14625 | 99.00 | 418 | 5 |
| | 99.00 | 419 | 4 |
| | 99.00 | 420 | 3 |
| | 99.00 | 421 | 1 |
| | 99.00 | 422 | 4 |
| | 99.00 | 423 | 3 |
| | 99.00 | 424 | 4 |
| | 99.00 | 425 | 1 |
| | 96.00 | 426 | 1 |
| | 99.00 | 427 | 2 |
| spt\|P22392 | 99.00 | 428 | 4 |
| | 99.00 | 429 | 1 |
| spt\|P23528 | 99.00 | 430 | 24 |
| spt\|P31949 | 98.00 | 431 | 1 |
| | 99.00 | 432 | 2 |
| spt\|P32119 | 99.00 | 433 | 18 |
| | 99.00 | 434 | 2 |
| | 99.00 | 435 | 2 |
| | 99.00 | 436 | 1 |
| | 99.00 | 437 | 10 |
| | 99.00 | 438 | 6 |
| pf\|0904262A | 93.00 | 439 | 1 |
| spt\|Q16778 | 99.00 | 440 | 4 |
| | 99.00 | 441 | 7 |
| | 99.00 | 442 | 68 |

| OFFLINE ACCESSION | MAX Confidence | Seq ID | # Times Seen |
|---|---|---|---|
| gb\|AAA59555.1 | 98.99999499 | 443 | 2 |
| | 99.00000095 | 444 | 3 |

TABLE 11-continued

|  |  |  |  |
|---|---|---|---|
|  | 94.99999881 | 445 | 1 |
|  | 99.00000095 | 446 | 1 |
|  | 99.00000095 | 447 | 1 |
|  | 98.99999499 | 448 | 3 |
|  | 99.00000095 | 449 | 3 |
|  | 99.00000095 | 450 | 6 |
|  | 99.00000095 | 451 | 9 |
|  | 98.99999499 | 452 | 1 |
|  | 99.00000095 | 453 | 7 |
| gb\|AAC13869.1 | 99.00000095 | 454 | 2 |
|  | 99.00000095 | 455 | 27 |
|  | 99.00000095 | 456 | 1 |
|  | 98.00000191 | 457 | 1 |
| gb\|AAH16768.1 | 99.00000095 | 458 | 1 |
|  | 98.99999499 | 459 | 1 |
|  | 98.99999499 | 460 | 2 |
| pir\|KRHUE | 99.00000095 | 461 | 2 |
|  | 99.00000095 | 462 | 2 |
|  | 98.99999499 | 463 | 2 |
|  | 99.00000095 | 464 | 2 |
|  | 99.00000095 | 465 | 6 |
| spt\|P00338 | 98.99999499 | 466 | 8 |
|  | 98.99999499 | 467 | 2 |
|  | 99.00000095 | 468 | 2 |
|  | 94.99999881 | 469 | 2 |
|  | 98.99999499 | 470 | 2 |
|  | 97.99999595 | 471 | 2 |
|  | 99.00000095 | 472 | 20 |
|  | 99.00000095 | 473 | 32 |
|  | 99.00000095 | 474 | 8 |
|  | 99.00000095 | 475 | 3 |
|  | 98.99999499 | 476 | 2 |
|  | 99.00000095 | 477 | 2 |
|  | 99.00000095 | 478 | 31 |
|  | 99.00000095 | 479 | 55 |
| spt\|P00915 | 99.00000095 | 480 | 2 |
|  | 99.00000095 | 481 | 3 |
|  | 99.00000095 | 482 | 71 |
|  | 99.00000095 | 483 | 2 |
|  | 99.00000095 | 484 | 1 |
|  | 99.00000095 | 485 | 49 |
|  | 99.00000095 | 486 | 31 |
|  | 99.00000095 | 487 | 3 |
|  | 99.00000095 | 488 | 73 |
|  | 99.00000095 | 489 | 2 |
|  | 99.00000095 | 490 | 6 |
|  | 99.00000095 | 491 | 22 |
|  | 99.00000095 | 492 | 3 |
| spt\|P01009 | 99.00000095 | 493 | 7 |
|  | 98.00000191 | 494 | 1 |
|  | 95.99999785 | 495 | 1 |
|  | 96.9999969 | 496 | 1 |
|  | 99.00000095 | 497 | 1 |
|  | 98.99999499 | 498 | 3 |
|  | 99.00000095 | 499 | 2 |
|  | 98.99999499 | 500 | 1 |
|  | 99.00000095 | 501 | 15 |
| spt\|P04083 | 99.00000095 | 502 | 10 |
|  | 99.00000095 | 503 | 35 |
|  | 99.00000095 | 504 | 8 |
|  | 99.00000095 | 505 | 4 |
|  | 99.00000095 | 506 | 40 |
|  | 99.00000095 | 507 | 14 |
|  | 99.00000095 | 508 | 427 |
|  | 99.00000095 | 509 | 25 |
|  | 99.00000095 | 510 | 75 |
|  | 99.00000095 | 511 | 14 |
|  | 98.00000191 | 512 | 2 |
|  | 99.00000095 | 513 | 25 |
|  | 99.00000095 | 514 | 1 |
|  | 99.00000095 | 515 | 12 |

TABLE 11-continued

| | | | | |
|---|---|---|---|---|
| spt\|P04792 | 99.00000095 | 516 | 4 | |
| | 99.00000095 | 517 | 5 | |
| | 98.99999499 | 518 | 14 | |
| | 95.99999785 | 519 | 2 | |
| | 98.99999499 | 520 | 2 | |
| | 99.00000095 | 521 | 6 | |
| | 99.00000095 | 522 | 15 | |
| spt\|P06454 | 98.00000191 | 523 | 1 | |
| | 98.99999499 | 524 | 1 | |
| | 99.00000095 | 525 | 13 | |
| | 98.99999499 | 526 | 1 | |
| | 99.00000095 | 527 | 1 | |
| | 99.00000095 | 528 | 54 | |
| spt\|P07585 | 99.00000095 | 529 | 7 | |
| | 99.00000095 | 530 | 3 | |
| | 99.00000095 | 531 | 3 | |
| | 99.00000095 | 532 | 3 | |
| | 99.00000095 | 533 | 3 | |
| spt\|P08670 | 98.00000191 | 534 | 1 | |
| | 98.99999499 | 535 | 6 | |
| | 99.00000095 | 536 | 9 | |
| | 99.00000095 | 537 | 6 | |
| | 98.99999499 | 538 | 1 | |
| | 98.99999499 | 539 | 16 | |
| | 98.99999499 | 540 | 4 | |
| | 98.99999499 | 541 | 2 | |
| | 99.00000095 | 542 | 7 | |
| | 98.99999499 | 543 | 18 | |
| | 98.99999499 | 544 | 14 | |
| | 98.99999499 | 545 | 55 | |
| | 98.99999499 | 546 | 1 | |
| | 98.99999499 | 547 | 15 | |
| | 98.99999499 | 548 | 1 | |
| | 99.00000095 | 549 | 7 | |
| | 98.99999499 | 550 | 18 | |
| | 98.99999499 | 551 | 4 | |
| | 99.00000095 | 552 | 4 | |
| | 98.99999499 | 553 | 2 | |
| | 98.99999499 | 554 | 4 | |
| | 99.00000095 | 555 | 78 | |
| | 97.99999595 | 556 | 2 | |
| | 98.00000191 | 557 | 2 | |
| | 98.99999499 | 558 | 6 | |
| | 97.99999595 | 559 | 1 | |
| | 98.99999499 | 560 | 2 | |
| | 98.99999499 | 561 | 5 | |
| | 98.99999499 | 562 | 2 | |
| spt\|P14625 | 98.99999499 | 563 | 2 | |
| | 96.9999969 | 564 | 2 | |
| | 98.99999499 | 565 | 2 | |
| | 99.00000095 | 566 | 1 | |
| | 99.00000095 | 567 | 2 | |
| | 99.00000095 | 568 | 1 | |
| | 99.00000095 | 569 | 21 | |
| | 98.99999499 | 570 | 2 | |
| | 99.00000095 | 571 | 1 | |
| | 98.99999499 | 572 | 6 | |
| | 98.99999499 | 573 | 6 | |
| | 99.00000095 | 574 | 3 | |
| | 98.99999499 | 575 | 9 | |
| | 98.99999499 | 576 | 2 | |
| spt\|P29034 | 99.00000095 | 577 | 6 | |
| | 99.00000095 | 578 | 14 | |
| | 99.00000095 | 579 | 13 | |
| | 94.99999881 | 580 | 1 | |
| | 98.99999499 | 581 | 6 | |
| | 99.00000095 | 582 | 7 | |
| spt\|P30043 | 99.00000095 | 583 | 1 | |
| | 99.00000095 | 584 | 2 | |
| | 99.00000095 | 585 | 9 | |
| | 99.00000095 | 586 | 1 | |
| | 99.00000095 | 587 | 14 | |

TABLE 11-continued

|  |  |  |  |
|---|---|---|---|
|  | 98.99999499 | 588 | 4 |
|  | 98.99999499 | 589 | 4 |
| spt\|P31151 | 99.00000095 | 590 | 9 |
|  | 99.00000095 | 591 | 22 |
|  | 99.00000095 | 592 | 7 |
|  | 99.00000095 | 593 | 2 |
|  | 95.99999785 | 594 | 2 |
|  | 99.00000095 | 595 | 3 |
|  | 99.00000095 | 596 | 300 |
| spt\|P31947 | 99.00000095 | 597 | 13 |
|  | 96.9999969 | 598 | 2 |
|  | 99.00000095 | 599 | 53 |
|  | 99.00000095 | 600 | 515 |
|  | 99.00000095 | 601 | 14 |
|  | 99.00000095 | 602 | 26 |
|  | 99.00000095 | 603 | 16 |
|  | 99.00000095 | 604 | 9 |
|  | 99.00000095 | 605 | 35 |
|  | 98.00000191 | 606 | 1 |
|  | 99.00000095 | 607 | 9 |
|  | 99.00000095 | 608 | 29 |
|  | 99.00000095 | 609 | 9 |
|  | 98.99999499 | 610 | 1 |
|  | 98.99999499 | 611 | 1 |
|  | 98.99999499 | 612 | 6 |
|  | 98.99999499 | 613 | 1 |
|  | 99.00000095 | 614 | 396 |
|  | 99.00000095 | 615 | 6 |
|  | 99.00000095 | 616 | 12 |
|  | 99.00000095 | 617 | 19 |
|  | 98.99999499 | 618 | 2 |
| spt\|P31949 | 99.00000095 | 619 | 1 |
|  | 99.00000095 | 620 | 13 |
|  | 99.00000095 | 621 | 15 |
| spt\|P32119 | 99.00000095 | 622 | 3 |
|  | 99.00000095 | 623 | 4 |
|  | 99.00000095 | 624 | 14 |
|  | 99.00000095 | 625 | 22 |
|  | 99.00000095 | 626 | 21 |
|  | 99.00000095 | 627 | 7 |
|  | 99.00000095 | 628 | 52 |
|  | 99.00000095 | 629 | 41 |
|  | 97.00000286 | 630 | 1 |
|  | 99.00000095 | 631 | 5 |
|  | 99.00000095 | 632 | 13 |
| spt\|P51884 | 99.00000095 | 633 | 7 |
|  | 99.00000095 | 634 | 3 |
|  | 99.00000095 | 635 | 4 |
|  | 99.00000095 | 636 | 4 |
|  | 99.00000095 | 637 | 8 |
|  | 99.00000095 | 638 | 17 |
|  | 99.00000095 | 639 | 5 |
|  | 99.00000095 | 640 | 2 |
|  | 99.00000095 | 641 | 2 |
|  | 99.00000095 | 642 | 10 |
|  | 99.00000095 | 643 | 8 |
|  | 99.99999881 | 644 | 1 |
|  | 95.99999785 | 645 | 1 |
| spt\|P60709 | 99.00000095 | 646 | 77 |
|  | 99.00000095 | 647 | 13 |
|  | 99.00000095 | 648 | 61 |
|  | 99.00000095 | 649 | 303 |
|  | 98.99999499 | 650 | 30 |
|  | 99.00000095 | 651 | 172 |
|  | 99.00000095 | 652 | 3 |
|  | 99.00000095 | 653 | 29 |
|  | 99.00000095 | 654 | 64 |
|  | 99.00000095 | 655 | 39 |
|  | 99.00000095 | 656 | 3 |
|  | 99.00000095 | 657 | 46 |
|  | 99.00000095 | 658 | 1 |
|  | 99.00000095 | 659 | 3 |
|  | 99.00000095 | 660 | 1 |
|  | 99.00000095 | 661 | 8 |

TABLE 11-continued

| | | | |
|---|---|---|---|
| | 99.00000095 | 662 | 33 |
| | 98.99999499 | 663 | 14 |
| | 98.00000191 | 664 | 1 |
| | 97.00000286 | 665 | 8 |
| | 99.00000095 | 666 | 3 |
| | 99.00000095 | 667 | 512 |
| | 99.00000095 | 668 | 99 |
| | 99.00000095 | 669 | 2 |
| | 99.00000095 | 670 | 1 |
| | 98.99999499 | 671 | 12 |
| | 99.00000095 | 672 | 2 |
| | 98.99999499 | 673 | 2 |
| | 99.00000095 | 674 | 36 |
| | 98.99999499 | 675 | 2 |
| | 99.00000095 | 676 | 6 |
| | 99.00000095 | 677 | 2 |
| | 99.00000095 | 678 | 5 |
| | 98.99999499 | 679 | 6 |
| | 99.00000095 | 680 | 702 |
| | 98.99999499 | 681 | 4 |
| | 99.00000095 | 682 | 5 |
| | 99.00000095 | 683 | 1 |
| | 99.00000095 | 684 | 69 |
| | 99.00000095 | 685 | 3 |
| | 99.00000095 | 686 | 9 |
| | 97.00000286 | 687 | 4 |
| | 99.00000095 | 688 | 8 |
| | 98.99999499 | 689 | 4 |
| | 98.99999499 | 690 | 8 |
| | 99.00000095 | 691 | 509 |
| | 99.00000095 | 692 | 3 |
| | 99.00000095 | 693 | 120 |
| | 94.99999881 | 694 | 2 |
| spt\|Q15691 | 99.00000095 | 695 | 12 |
| trm\|Q86U86 | 98.00000191 | 696 | 2 |
| | 99.00000095 | 697 | 1 |
| trm\|Q86V33 | 99.00000095 | 698 | 10 |
| | 99.00000095 | 699 | 753 |
| | 96.9999969 | 700 | 1 |
| | 99.00000095 | 701 | 21 |
| | 99.00000095 | 702 | 32 |
| | 99.00000095 | 703 | 10 |
| | 98.00000191 | 704 | 1 |
| | 99.00000095 | 705 | 38 |
| | 99.00000095 | 706 | 3 |
| | 98.99999499 | 707 | 2 |
| | 99.00000095 | 708 | 113 |
| | 99.00000095 | 709 | 899 |
| | 99.00000095 | 710 | 7 |
| | 99.00000095 | 711 | 3 |
| | 99.00000095 | 712 | 11 |
| trm\|Q86YI6 | 99.00000095 | 713 | 1 |
| | 98.99999499 | 714 | 2 |
| | 98.99999499 | 715 | 2 |
| | 98.99999499 | 716 | 2 |
| | 94.99999881 | 717 | 1 |
| | 99.00000095 | 718 | 4 |
| | 98.99999499 | 719 | 2 |
| | 99.00000095 | 720 | 1 |
| | 95.99999785 | 721 | 2 |
| trm\|Q8IZ29 | 98.99999499 | 722 | 1 |
| | 98.99999499 | 723 | 6 |
| | 98.99999499 | 724 | 2 |
| | 98.99999499 | 725 | 4 |
| | 98.99999499 | 726 | 1 |
| | 97.99999595 | 727 | 1 |
| | 98.99999499 | 728 | 7 |
| | 98.99999499 | 729 | 4 |
| | 98.99999499 | 730 | 34 |
| | 98.99999499 | 731 | 2 |

TABLE 11-continued

| | | | |
|---|---|---|---|
| trm\|Q96AM7 | 99.00000095 | 732 | 1 |
| trm\|Q96IH1 | 99.00000095 | 733 | 3 |
| | 98.99999499 | 734 | 4 |
| | 99.00000095 | 735 | 1 |
| | 99.00000095 | 736 | 3 |
| | 98.99999499 | 737 | 1 |
| | 98.99999499 | 738 | 2 |
| | 94.99999881 | 739 | 1 |
| | 99.00000095 | 740 | 5 |

TABLE 12

Clinicopathological parameters of patients with Oral Premalignant Lesions (OPLs)

| Age/Gender | Site | Tissue | Histopathology | Tobacco habits |
|---|---|---|---|---|
| A) ITRAQ Analysis: Discovery of Biomarkers ||||||
| 1. 35/F | GBS | Leukoplakia | Dysplasia | *Areca* nut chewing (×5-6 yrs) |
| 2. 42/M | BM | Leukoplakia | Dysplasia | Bidi smoking (×10 yrs) |
| 3. 50/M | BM | Leukoplakia | Dysplasia | Pan masala and bidi smoking (×15-18 yrs) |
| 4. 42/M | GBS | Leukoplakia | Dysplasia | Gutkha chewing (×20 yrs) and Bidi smoking (×6 yrs) |
| 5. 42/M | T | Leukoplakia | Dysplasia | Gutkha chewing and bidi smoking (×5 yrs) |
| 6. 50/M | SP | Leukoplakia | Dysplasia | Gutkha chewing and bidi smoking (×35 yrs) |
| B) Immunohistochemical Analysis: Verification of Biomarkers ||||||
| 1. 23/M | BM | Leukoplakia | Dysplasia | Khaini chewing (×4 yrs) |
| 2. 36/M | LIP | Leukoplakia | Dysplasia | Khaini chewing (×10-12 yrs) |
| 3. 40/F | GBS | Leukoplakia | Dysplasia | Khaini chewing (×14 yrs) |
| 4. 22/M | GBS | Leukoplakia | Dysplasia | Khaini chewing (×5 yrs) |
| 5. 45/F | BM | Leukoplakia | Dysplasia | Gutkha chewing (×8 yrs) |
| 6. 22/M | BM | Leukoplakia | Dysplasia | Gutkha chewing (×3-4 yrs) |
| 7. 50/F | GBS | Leukoplakia | Dysplasia | Gutkha chewing (×5 yrs) |
| 8. 18/M | GBS | Leukoplakia | Dysplasia | Gutkha and khaini chewing (×5 yrs) |
| 9. 35/M | BM | Leukoplakia | Dysplasia | Gutkha and khaini chewing (×10 yrs) |
| 10. 40/F | T | Leukoplakia | Dysplasia | Gutkha and khaini chewing (×6 yrs) |
| 11. 31/M | BM | Leukoplakia | Dysplasia | Betel quid with khaini chewing (×8 yrs) |
| 12. 42/M | BM | Leukoplakia | Dysplasia | Bidi smoking (×18 yrs) |
| 13. 50/M | BM | Leukoplakia | Dysplasia | Bidi smoking (×30 yrs) |
| 14. 46/M | BM | Leukoplakia | Dysplasia | Bidi smoking (×18 yrs) |
| 15. 54/M | BM | Leukoplakia | Dysplasia | Bidi smoking (×27 yrs) |
| 16. 45/M | BM | Leukoplakia | Dysplasia | Bidi smoking (×12 yrs) |
| 17. 50/M | BM | Leukoplakia | Dysplasia | Bidi smoking (×20 yrs) |
| 18. 35/M | T | Leukoplakia | Dysplasia | Bidi smoking (×8 yrs) |
| 19. 55/M | T | Leukoplakia | Dysplasia | Bidi smoking (×45 yrs) |
| 20. 43/M | BM | Leukoplakia | Dysplasia | Cigarette smoking (×21 yrs) |
| 21. 50/M | BM | Leukoplakia | Dysplasia | Cigarette smoking (×11 yrs) |
| 22. 27/M | BM | Leukoplakia | Dysplasia | Gutkha chewing (×2 yrs) and cigarette smoking (×5 yrs) |
| 23. 35/M | BM | Leukoplakia | Dysplasia | Gutkha and cigarette smoking (×10 yrs) |
| 24. 24/M | BM | Leukoplakia | Dysplasia | Gutkha chewing (×3 yrs) and cigarette smoking (×1 yrs) |
| 25. 54/M | BM | Leukoplakia | Dysplasia | Ghutka, khaini chewing (×15-16 yrs) and hookah smoking (×15-16 yrs) |
| 26. 36/M | BM | Leukoplakia | Dysplasia | Gutkha and pan masala chewing (×8 yrs); bidi smoking (×10-12 yrs) |
| 27. 66/M | BM | Leukoplakia | Dysplasia | Gutkha and khaini (×8 yrs) and bidi smoking (5 yrs) |
| 28. 39/M | BM | Leukoplakia | Dysplasia | Betel quid with khaini (×2 yrs) and cigarette smoking (×5 yrs) |
| 29. 45/M | A | Leukoplakia | Dysplasia | Betel quid with khaini (×20 yrs) and cigarette smoking (×25 yrs) |
| 30. 70/M | BM | Leukoplakia | Dysplasia | No habit of addiction (NHA) |

All the patients were from India. Abbreviations: M: Male; F: Female; Site: A; Alveolus, BM: Buccal Mucosa, GBS: Gigivo-buccal sulcus, T: Tongue; SP: Soft palate; 'Khaini' is a mixture of tobacco, lime and menthol or aromatic spices; 'Gutkha' usually contains powdered tobacco, betel nut, catechu, lime and flavors; Pan masala is a mixture of spices such as cardamom, lime, menthol, catechu and betel nuts; 'Bidi' is tobacco hand rolled in Temburini leaf.

TABLE 13

Antibodies used for immunohistochemistry and Western Blotting: sources and dilutions.

| Antibody | Company | Clone ID | Dilution used for IHC | Dilution used for Western Blot |
|---|---|---|---|---|
| Anti-14-3-3ζ (YWHAZ) Rabbit polyclonal antibody | Santa Cruz | C-16 | 1:200 | 1:500 |
| Anti-14-3-3σ (Stratifin) Goat polyclonal antibody | Santa Cruz | N-14 | 1:200 | 1:200 |
| Anti-Psoriasin (S100A7) mouse monoclonal antibody | Santa Cruz | 47C1068 | 1:100 | 1:200 |
| Anti-Pro-thymosinα (PTHA) Goat polyclonal antibody | Santa Cruz | N-18 | 1:75 | 1:100 |
| Anti-hnRNPK mouse monoclonal antibody | Abcam | ab23644 | 1:400 | 1:400 |
| Anti-Tubulin α mouse monoclonal antibody | Santa Cruz | B7 | — | 1:200 |
| Secondary Antibody: | | | | |
| Goat Anti-rabbit IgG | DAKO | — | 1:5000 | 1:5000 |
| Rabbit Anti-Goat IgG | DAKO | — | 1:4000 | 1:4000 |
| Rabbit Anti-Mouse IgG | DAKO | — | 1:2000 | 1:2000 |

TABLE 14

RT-PCR Analysis Primers and PCR conditions:

| Gene (Accession #) | Primer Sequence (SEQ ID NO:) | Annealing Temperature (° C.) | No. of amplification cycles | Product size (bp) |
|---|---|---|---|---|
| 14-3-3ζ (NM_001135699) | 5'-ATGTACTTGGAAAAAGGCCG-3' (SEQ ID NO: 741) 5'-CCCTGCTCTTGAGGAGCTTA-3' (SEQ ID NO: 742) | 54 | 32 | 400 |
| Stratifin (NM_006142) | 5'-AGAGACACAGAGTCCGGCATTGG-3' (SEQ ID NO: 743) 5'-TCCACCTTCTCCCGGTACTCACGC-3' (SEQ ID NO: 744) | 57 | 32 | 396 |
| S100A7 (Psoriasin) (NM_002963) | 5'-CTTCCTTAGTGCCTGTGACAAAAA-3' (SEQ ID NO: 745) 5'-AAGGACAGAAACTCAGAAAAATCAATCT-3' (SEQ ID NO: 746) | 57 | 32 | 121 |
| Prothymosin Alpha (NP_001092755.1) | 5'-ATGTCAGACGCAGCCGTAGACACCA-3' (SEQ ID NO: 747) 5'CTAGTCATCCTCGTCGGTCTTCTG-3' (SEQ ID NO: 748) | 65 | 32 | 326 |
| HnRNPK (NM_002140) | 5'AGCAGAGCTCGGAATCTTCCTCTT-3' (SEQ ID NO: 749) 5'ATCAGCACTGAAACCAACCATGCC-3' (SEQ ID NO: 750) | 54 | 32 | 123 |
| Beta actin (NM_001101.3) | 5'-CAGCCATGTACGTTGCTATCCAG-3' (SEQ ID NO: 751) 5'-GTTTCGTGGATGCCACAGGAC-3' (SEQ ID NO: 752) | 62 | 32 | 421 |

TABLE 15

Molecules identified in the Networks and their cellular functions

| ID | Molecules in Network | Score | Focus genes | Top Functions |
|---|---|---|---|---|
| 1 | ↑ACTB, Actin, ADRA2C, ALOX15, ANG, COX2, ↓CSTB, DDX1, ERK, ↓ FABP5, ↑HNRPD, ↑ HNRPK, ↑ HSP90B1, KIF1C, LIMA1, LOX, ↓ MARCKS, MLXIP, NFkB, ↑ NPM1 (includes EG: 4869), PCBP2, PCBP1 (includes EG: 29371), ↑PEBP1, PHACTR1, REM1, ↑S100A7, SAFB, ↓SERPINA1, ↑ SFN, ↑ SOD2, SYNPO2, ↑TUBB, WTAP, YWHAD, ↑YWHAZ | 39 | 15 | Molecular Transport, Cancer, Cellular Movement |
| 2 | AKAP13, AKT1, AKT2, ↑ CALML3, COX2, ↓ DLC1, ERRFI1, HMG1L1, ↑HNRPD, IGH-1A, ↓IGHG1, IGHG3, IGKV1-117, IL33, KRT19, KRT72, LCK, LOX, ↑NPM1 | 15 | 7 | Cancer, Cell-To-Cell Signalling and Interaction, |

TABLE 15-continued

Molecules identified in the Networks and their cellular functions

| ID | Molecules in Network | Score | Focus genes | Top Functions |
|---|---|---|---|---|
| | (includes EG: 4869), NR3C1, PCAF, PRKDC, ↑PTMS, RELA, retinoic acid, RGS3, SLC25A4, SLC2A1, SUMO1, TAT, TCL1B, ↑TLR1, TPD52, VAV1, YBX1 | | | Hematological System Development and Function |

TABLE 16

Analysis of clinical parameters with transformation potential of Oral Dysplasia patients.

| Characteristics | | Transformed N | (%) | Untransformed N | (%) | p-value | O.R. | (95% C.I.)¶ |
|---|---|---|---|---|---|---|---|---|
| Dysplasia (110 cases) | | 39 | (35.4) | 71 | (64.5) | | | |
| Age (Years) | ≤59 | 15 | (38.5) | 37 | (52.1) | | | |
| | >59 | 24 | (61.5) | 34 | (47.9) | 0.170 | 1.741 | (0.7-3.85) |
| Gender | Female | 21 | (53.8) | 30 | (42.2) | | | |
| | Male | 18 | (46.2) | 41 | (57.8) | 0.243 | 0.627 | (0.3-1.4) |
| Site | Tongue | 26 | (66.7) | 53 | (74.6) | | | |
| | Others§ | 13 | (33.3) | 18 | (25.4) | 0.373 | 0.679 | (0.3-1.6) |
| Histopathological Grade | Mild | 12 | (30.8) | 46 | (64.8) | | | |
| | Moderate | 18 | (46.2) | 21 | (29.6) | 0.008* | 3.286 | (1.3-8.1) |
| | Severe | 9 | (23.1) | 4 | (5.6) | 0.001** | 8.625 | (2.3-32.8) |
| Smoking history§§ | Yes | 15 | (51.7) | 31 | (52.5) | | | |
| | No | 14 | (48.3) | 28 | (47.5) | 0.942 | 0.968 | (0.4-2.4) |

¶O.R. Odd's ratio, 95% C.I., 95% Confidence Interval
§Others included buccal mucosa (n = 18), floor of mouth (n = 12) and lip (n = 1)
§§Smoking history available for 88 cases only;
*p-value obtained from Chi-square analysis for Mild vs. Moderate dysplasia
**p-value obtained from Chi-square analysis for Mild vs. Severe dysplasia

TABLE 17

Correlation of candidate protein markers expression with transformation in Oral Dysplasia patients.

| Characteristics | | Transformed N | (%) | Untransformed N | (%) | p-value | O.R.¶ | (95% C.I.)¶ |
|---|---|---|---|---|---|---|---|---|
| Dysplasia (n = 110) | | 39 | | 71 | | — | — | — |
| p16 expression | Nuclear positive | 32 | (82.1) | 53 | (74.6) | 0.375 | 1.553 | (0.5-4.1) |
| HPV 16/18+ | | 0 | — | 0 | — | — | — | — |
| S100A7+ | Overexpression (cytoplasm/nuclear) | 36 | (92.3) | 51 | (71.8) | 0.014 | 4.706 | (1.3-17.1) |
| | Cytoplasm | 32 | (82.1) | 38 | (53.5) | 0.003 | 3.970 | (1.5-10.2) |
| | Nuclear | 35 | (89.7) | 49 | (69.0) | 0.018 | 3.929 | (1.2-12.4) |
| PTMA+ | Overexpression (cytoplasm/nuclear) | 37 | (94.9) | 67 | (94.4) | 0.911 | 1.104 | (0.2-6.3) |
| | Cytoplasm | 25 | (64.1) | 36 | (50.7) | 0.176 | 1.736 | (0.8-3.8) |
| | Nuclear | 36 | (92.3) | 63 | (88.7) | 0.743 | 1.524 | (0.4-6.1) |
| 14-3-3ζ+ | Overexpression (cytoplasm/nuclear) | 37 | (94.9) | 69 | (97.2) | 0.536 | 0.536 | (0.1-5.3) |
| | Cytoplasm | 31 | (79.5) | 62 | (87.3) | 0.277 | 0.563 | (0.2-1.6) |
| | Nuclear | 21 | (53.8) | 38 | (53.5) | 0.974 | 1.013 | (0.4-2.2) |
| 14-3-3σ+ | Overexpression (cytoplasm/nuclear) | 27 | (69.2) | 62 | (87.3) | 0.040 | 0.327 | (0.1-0.8) |
| | Cytoplasm | 25 | (64.1) | 57 | (80.3) | 0.062 | 0.439 | (0.2-1.1) |
| | Nuclear | 18 | (46.2) | 46 | (64.8) | 0.071 | 0.466 | (0.2-1.1) |
| hnRNP K+ | *Nuclear | 39 | (100) | 70 | (98.6) | 1.000 | 0.986 | (0.9-1.1) |

¶O.R. Odd's ratio, 95% C.I., 95% Confidence Interval
*No cytoplasmic staining was observed for p16 and hnRNP K in tissue sections used in this study

TABLE 18

Evaluation of association of degree of dysplasia with candidate protein markers expression.

| Characteristics | | Mild dysplasia N | (%) | Moderate dysplasia N | (%) | Severe dysplasia N | (%) | p-value |
|---|---|---|---|---|---|---|---|---|
| Dysplasia (n = 110) | | 58 | (52.7) | 39 | (35.4) | 13 | (11.8) | |
| Disease Outcome | Transformed | 12 | (20.7) | 18 | (46.2) | 9 | (69.2) | |
| | Untransformed | 46 | (79.3) | 21 | (53.8) | 4 | (30.8) | 0.001 |
| p16 expression | *Nuclear | 49 | (84.4) | 28 | (71.7) | 8 | (61.3) | 0.121 |
| S100A7+ | Cytoplasm | 34 | (58.6) | 26 | (66.7) | 10 | (76.9) | 0.411 |
| | Nuclear | 40 | (68.9) | 33 | (84.6) | 11 | (84.6) | 0.156 |
| PTMA+ | Cytoplasm | 30 | (51.7) | 22 | (56.4) | 9 | (69.2) | 0.512 |
| | Nuclear | 53 | (91.4) | 34 | (87.2) | 12 | (92.3) | 0.762 |
| 14-3-3ζ+ | Cytoplasm | 47 | (81.0) | 34 | (87.2) | 12 | (92.3) | 0.508 |
| | Nuclear | 24 | (41.4) | 26 | (66.7) | 9 | (69.2) | 0.024 |
| 14-3-3σ+ | Cytoplasm | 46 | (79.3) | 27 | (69.2) | 9 | (69.2) | 0.480 |
| | Nuclear | 38 | (65.5) | 18 | (46.2) | 8 | (61.5) | 0.160 |
| hnRNP K+ | *Nuclear | 58 | (100) | 38 | (97.4) | 13 | (100) | 0.399 |

*No cytoplasmic staining was observed for p16 and hnRNP K in tissue sections used in this study.

TABLE 19

Evaluation of correlation between p16 expression and protein markers.

| Characteristics | | p16 expression N (%) | p-value |
|---|---|---|---|
| Dysplasia(n = 110) | | 85 (77.3) | |
| Untransformed Dysplasia | | 53 (74.3) | |
| Transformed Dysplasia | | 32 (82.1) | 0.375 |
| S100A7+ | Overexpression (cytoplasm/nuclear) | 67 (78.8) | 0.899 |
| | Cytoplasm | 55 (64.7) | 0.667 |
| | Nuclear | 66 (77.6) | 0.559 |
| PTMA+ | Overexpression (cytoplasm/nuclear) | 82 (96.5) | 0.101 |
| | Cytoplasm | 51 (60.0) | 0.077 |
| | Nuclear | 79 (92.9) | 0.058 |
| 14-3-3ζ+ | Overexpression (cytoplasm/nuclear) | 81 (95.3) | 0.572 |
| | Cytoplasm | 70 (82.4) | 0.241 |
| | Nuclear | 44 (51.8) | 0.468 |
| 14-3-3σ+ | Overexpression (cytoplasm/nuclear) | 66 (77.6) | 0.108 |
| | Cytoplasm | 62 (72.9) | 0.476 |
| | Nuclear | 47 (55.3) | 0.258 |
| hnRNPK+ | *Nuclear | 84 (98.8) | 0.586 |

*No cytoplasmic staining was observed for hnRNP K in tissue sections used in this study.

TABLE 20

Evaluation of clinical parameters and S100A7 overexpression for determining OCFS in dysplasia patients.

| | Kaplan Meier Survival analysis Un-adjusted p-value | Multi-variate Cox regression analysis Adjusted p-value | Hazard's Ratio (H.R.) | 95% C.I. |
|---|---|---|---|---|
| Age | 0.411 | 0.771 | — | — |
| Gender | 0.391 | 0.612 | — | — |
| Site | 0.740 | 0.284 | — | — |
| Smoking history | 0.755 | 0.124 | — | — |
| Dysplasia | | | | |
| Grade | | | | |
| Mild* | — | — | — | — |
| Moderate | 0.004 | 0.013 | 2.54 | (1.6-10.8) |
| Severe | <0.001 | <0.001 | 5.42 | (2.6-23.2) |
| p16 expression | 0.995 | 0.892 | — | — |
| S100A7 overexpression | | | | |
| Cytoplasm+ | 0.007 | 0.041 | 2.36 | (0.9-8.4) |
| Nuclear+ | 0.041 | 0.570 | — | — |

TABLE 21

Multivariate Cox regression analysis indicating that patients with cytoplasmic S100A7 positive, nuclear PTMA positive and moderate or severe grade of dysplasia are at at higher risk of cancer development compared to other patients exhibiting 0, 1 or 2 of the same variables.

| | Kaplan Meier Survival analysis Un-adjusted p-value | Multi-variate Cox regression analysis Adjusted p-value | Hazard's Ratio (HR) | 95% C.I. |
|---|---|---|---|---|
| S100A7 Cytoplasm+ | 0.007 | 0.269 | — | — |
| PTMA Nuclear+ | 0.690 | 0.618 | — | — |
| S100A7 Cyto+ + PTMA Nuc+ | 0.006 | 0.295 | — | — |
| Degree of Dysplasia | <0.001 | 0.127 | — | — |

TABLE 21-continued

Multivariate Cox regression analysis indicating that patients with cytoplasmic S100A7 positive, nuclear PTMA positive and moderate or severe grade of dysplasia are at at higher risk of cancer development compared to other patients exhibiting 0, 1 or 2 of the same variables.

| | Kaplan Meier Survival analysis Un-adjusted p-value | Multi-variate Cox regression analysis Adjusted p-value | Hazard's Ratio (HR) | 95% C.I. |
|---|---|---|---|---|
| S100A7 Cyto⁺ + PTMA Nuc⁺ + Mild Dysplasia | 0.368 | 0.295 | — | — |
| S100A7 Cyto⁺ + PTMA Nuc⁺ + Moderate/Severe Dysplasia | <0.001 | <0.001 | 3.47 | 1.85-6.53 |

We claim:

1. A method of concurrently detecting levels of nuclear prothymosin alpha, PTMA, and cytoplasmic psoriasin, S100A7, in a biological sample obtained from a subject having moderate or severe grade oral dysplasia, the method comprising:

concurrently contacting the biological sample with a first binding agent that specifically binds to prothymosin alpha, PTMA, and a second binding agent that specifically binds to psoriasin, S100A7, wherein the biological sample is an oral tissue sample, a cytosmear, saliva or a combination thereof; and, detecting the level of nuclear PTMA and the level of cytoplasmic S100A7 in the sample by measuring the amount of PTMA and S100A7 bound to the first and second binding agents, respectively.

2. The method of claim 1, wherein the biological sample comprises epithelial cells.

3. The method of claim 2, wherein the epithelial cells are dysplastic.

4. The method of claim 3, wherein at least one of the first binding agent and the second binding agent is an antibody.

5. The method of claim 1, wherein the step of detecting the level of nuclear PTMA and the level of cytoplasmic S100A7 is conducted using immunohistochemistry (IHC).

6. The method of claim 4, wherein the step of detecting the level of nuclear PTMA and the level of cytoplasmic S100A7 is conducted using immunohistochemistry (IHC).

* * * * *